US012220455B2

(12) United States Patent
Sullivan et al.

(10) Patent No.: US 12,220,455 B2
(45) **Date of Patent: *Feb. 11, 2025**

(54) CORONAVIRUS VACCINE COMPOSITIONS AND METHODS

(71) Applicant: Arcturus Therapeutics, Inc., San Diego, CA (US)

(72) Inventors: Sean Michael Sullivan, Escondido, CA (US); Daiki Matsuda, San Diego, CA (US); Kiyoshi Tachikawa, San Diego, CA (US); Padmanabh Chivukula, San Diego, CA (US); Priya Prakash Karmali, San Diego, CA (US); Jared Henry Davis, Poway, CA (US); Yanjie Bao, San Diego, CA (US); Amit Sagi, San Diego, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/345,893

(22) Filed: Jun. 30, 2023

(65) Prior Publication Data

US 2024/0115691 A1 Apr. 11, 2024

Related U.S. Application Data

(63) Continuation of application No. 17/196,889, filed on Mar. 9, 2021, now Pat. No. 11,744,887.

(60) Provisional application No. 63/073,900, filed on Sep. 2, 2020, provisional application No. 62/987,191, filed on Mar. 9, 2020.

(51) Int. Cl.

| | |
|---|---|
| ***A61K 39/215*** | (2006.01) |
| ***A61K 9/51*** | (2006.01) |
| ***A61K 38/00*** | (2006.01) |
| ***A61K 39/00*** | (2006.01) |
| ***A61K 39/12*** | (2006.01) |
| ***A61K 47/10*** | (2017.01) |
| ***A61K 47/20*** | (2006.01) |
| ***A61K 47/26*** | (2006.01) |
| ***C07K 14/005*** | (2006.01) |
| ***C07K 14/18*** | (2006.01) |
| ***C12N 7/00*** | (2006.01) |
| ***C12N 15/86*** | (2006.01) |

(52) U.S. Cl.

CPC .......... *A61K 39/215* (2013.01); *A61K 9/5123* (2013.01); *A61K 39/12* (2013.01); *A61K 47/10* (2013.01); *A61K 47/20* (2013.01); *A61K 47/26* (2013.01); *C07K 14/005* (2013.01); *C07K 14/1808* (2013.01); *C12N 7/00* (2013.01); *C12N 15/86* (2013.01); *A61K 38/00* (2013.01); *A61K 2039/53* (2013.01); *C12N 2770/20022* (2013.01); *C12N 2770/20034* (2013.01); *C12N 2770/36122* (2013.01); *C12N 2770/36134* (2013.01); *C12N 2830/42* (2013.01); *C12N 2830/50* (2013.01)

(58) Field of Classification Search

CPC .... A61K 39/215; A61K 9/5123; A61K 39/12; A61K 47/10; A61K 47/20; A61K 47/26; A61K 38/00; A61K 2039/53; A61K 39/395; A61K 2039/507; A61K 2039/884; A61K 2039/55555; A61K 2039/572; A61K 2039/575; C07K 14/005; C07K 14/1808; C07K 2317/76; C07K 16/2818; C07K 16/2827; C12N 7/00; C12N 15/86; C12N 2770/20022; C12N 2770/20034; C12N 2770/36122; C12N 2770/36134; C12N 2830/42; C12N 2830/50; C12N 2740/13071; C12N 2760/16134; C12N 2760/16171; C12N 2740/13034; A61P 35/00; A61P 31/14; A61P 31/16; Y02A 50/30

See application file for complete search history.

(56) References Cited

U.S. PATENT DOCUMENTS

| | | | |
|---|---|---|---|
| 7,332,322 | B2 | 2/2008 | Frolov et al. |
| 7,425,337 | B2 | 9/2008 | Smith et al. |
| 7,442,381 | B2 | 10/2008 | Smith et al. |
| 8,093,367 | B2 | 1/2012 | Kore et al. |
| 8,158,601 | B2 | 4/2012 | Chen et al. |
| 8,304,529 | B2 | 11/2012 | Kore et al. |
| 8,961,995 | B2 | 2/2015 | Frolov et al. |
| 9,254,265 | B2 | 2/2016 | Geall et al. |
| 9,295,646 | B2 | 3/2016 | Brito et al. |

(Continued)

FOREIGN PATENT DOCUMENTS

| | | |
|---|---|---|
| EP | 2591114 B1 | 6/2016 |
| EP | 3471778 A2 | 4/2019 |

(Continued)

OTHER PUBLICATIONS

Apr. 27, 2019) "Cloning Vector pCMV-VEE-GFP", Complete Sequence, GenBank ID: MH891622.1, 7 pages.

(Continued)

*Primary Examiner* — Rachel B Gill

(74) *Attorney, Agent, or Firm* — Mintz, Levin, Cohn, Ferris, Glovsky and Popeo, P.C.

(57) ABSTRACT

Provided herein are nucleic acid molecules encoding viral replication proteins and antigenic coronavirus proteins or fragments thereof. Also provided herein are compositions that include nucleic acid molecules encoding viral replication and antigenic proteins, and lipids. Nucleic acid molecules provided herein are useful for inducing immune responses.

33 Claims, 54 Drawing Sheets

Specification includes a Sequence Listing.

(56) References Cited

U.S. PATENT DOCUMENTS

| | | | |
|---|---|---|---|
| 9,730,997 B2 | 8/2017 | Perri et al. | |
| 9,770,463 B2 | 9/2017 | Geall et al. | |
| 10,238,733 B2 | 3/2019 | Brito et al. | |
| 10,487,105 B2 | 11/2019 | Chivukula et al. | |
| 11,135,283 B2 | 10/2021 | Berglund et al. | |
| 11,744,887 B2 | 9/2023 | Sullivan et al. | |
| 2009/0075384 A1 | 3/2009 | Kamrud et al. | |
| 2009/0155301 A1 | 6/2009 | Mason et al. | |
| 2011/0171255 A1 | 7/2011 | Kliver et al. | |
| 2011/0207223 A1 | 8/2011 | Tang et al. | |
| 2011/0256175 A1 | 10/2011 | Hope et al. | |
| 2012/0027803 A1 | 2/2012 | Manoharan et al. | |
| 2012/0128760 A1 | 5/2012 | Manoharan et al. | |
| 2012/0156251 A1 | 6/2012 | Brito et al. | |
| 2013/0171241 A1 | 7/2013 | Geall | |
| 2013/0195968 A1 | 8/2013 | Geall et al. | |
| 2014/0227346 A1 | 8/2014 | Geall et al. | |
| 2014/0242152 A1 | 8/2014 | Geall et al. | |
| 2015/0024002 A1 | 1/2015 | Perri et al. | |
| 2016/0074500 A1 | 3/2016 | Pushko et al. | |
| 2016/0348132 A1 | 12/2016 | Rayner et al. | |
| 2018/0036398 A1 | 2/2018 | Hagen et al. | |
| 2018/0104359 A1 | 4/2018 | Kamrud | |
| 2018/0169268 A1 | 6/2018 | Payne et al. | |
| 2018/0171340 A1 | 6/2018 | Kamrud et al. | |
| 2018/0273576 A1 | 9/2018 | Hogrefe et al. | |
| 2018/0327471 A1 | 11/2018 | Limphong et al. | |
| 2019/0091329 A1 | 3/2019 | Brito et al. | |
| 2019/0224299 A1 | 7/2019 | Kamrud et al. | |
| 2019/0321458 A1 | 10/2019 | Sahin et al. | |
| 2019/0374650 A1 | 12/2019 | Moon et al. | |
| 2020/0010849 A1 | 1/2020 | Blair et al. | |
| 2020/0113830 A1 | 4/2020 | Geall et al. | |
| 2020/0113831 A1 | 4/2020 | Geall et al. | |
| 2020/0222332 A1 | 7/2020 | Irvine et al. | |
| 2020/0230058 A1 | 7/2020 | Geall et al. | |
| 2020/0230225 A1 | 7/2020 | Vogels et al. | |
| 2020/0297634 A1 | 9/2020 | Karmali et al. | |
| 2020/0330585 A1 | 10/2020 | Mogler et al. | |
| 2021/0030859 A1 | 2/2021 | Bucala et al. | |
| 2021/0284974 A1 | 9/2021 | Chivukula et al. | |
| 2021/0290752 A1 | 9/2021 | Sullivan et al. | |
| 2021/0290756 A1 | 9/2021 | Sullivan et al. | |
| 2022/0347298 A1 | 11/2022 | Sullivan et al. | |
| 2022/0395570 A1 | 12/2022 | Rauch et al. | |
| 2022/0401550 A1* | 12/2022 | Simon-Loriere | A61K 39/12 |
| 2023/0219996 A1 | 7/2023 | Matsuda et al. | |
| 2024/0115692 A1 | 4/2024 | Sullivan et al. | |

FOREIGN PATENT DOCUMENTS

| | | |
|---|---|---|
| EP | 3433369 B1 | 3/2020 |
| EP | 2729126 B1 | 12/2020 |
| WO | 2008119827 A1 | 10/2008 |
| WO | 2009079185 A2 | 6/2009 |
| WO | 2009086558 A1 | 7/2009 |
| WO | 2009127060 A1 | 10/2009 |
| WO | 2010048536 A2 | 4/2010 |
| WO | 2010054406 A1 | 5/2010 |
| WO | 2010088537 A2 | 8/2010 |
| WO | 2010129709 A1 | 11/2010 |
| WO | 2011153493 A2 | 12/2011 |
| WO | 2012006369 A2 | 1/2012 |
| WO | 2012006380 A2 | 1/2012 |
| WO | 2012170431 A2 | 12/2012 |
| WO | 2014170493 A2 | 10/2014 |
| WO | 2015051169 A2 | 4/2015 |
| WO | 2015061491 A1 | 4/2015 |
| WO | 2016184822 A1 | 11/2016 |
| WO | 2017083356 A1 | 5/2017 |
| WO | 2017223085 A2 | 12/2017 |
| WO | 2018078053 A1 | 5/2018 |
| WO | 2018208856 A1 | 11/2018 |
| WO | 2018222890 A1 | 12/2018 |
| WO | 2018222926 A1 | 12/2018 |
| WO | 2019023566 A1 | 1/2019 |
| WO | 2020014654 A1 | 1/2020 |
| WO | 2020035609 A2 | 2/2020 |
| WO | 2020254535 A1 | 12/2020 |
| WO | 2020254804 A1 | 12/2020 |
| WO | 2020255055 A1 | 12/2020 |
| WO | 2021067181 A1 | 4/2021 |
| WO | 2021183563 A1 | 9/2021 |
| WO | 2021183564 A1 | 9/2021 |
| WO | 2023010128 A2 | 2/2023 |

OTHER PUBLICATIONS

International Search Report and Written Opinion for Application No. PCT/US21/21572, mailed on Jul. 20, 2021, 11 pages.

International Search Report and Written Opinion for Application No. PCT/US21/21573, mailed on Jul. 1, 2021, 12 pages.

International Search Report and Written Opinion for Application No. PCT/US22/74337, mailed on Dec. 30, 2022, 16 pages.

(Jul. 18, 2020) "Surface Glycoprotein [Severe Acute Respiratory Syndrome Coronavirus 2]", GenBank ID: YP_009724390, 3 pages.

Altschul et al. (Oct. 5, 1990) "Basic Local Alignment Search Tool", Journal of Molecular Biology, 215(3):403-410.

Altschul et al. (Sep. 1, 1997) "Gapped BLAST and PSI-BLAST: A New Generation of Protein Database Search Programs", Nucleic Acids Research, 25(17):3389-3402.

Baden et al. (Feb. 4, 2021) "Efficacy and Safety of the mRNA-1273 SARS-CoV-2 Vaccine", The New England Journal of Medicine, 384(5):403-416.

Bochicchio et al. (2014) "Liposomes as siRNA Delivery Vectors", Current Drug Metabolism, 15(9):882-892.

Boles et al. (2017) "Synthetic Construct H7N9 HA Gene, Complete CDS", GenBank KY199425.1, National Library of Medicine, 4 pages.

Both et al. (Mar. 1, 1975) "Methylation-Dependent Translation Of Viral Messenger RNAs In Vitro", Proceedings of the National Academy of Sciences, 72(3): 1189-1193.

Bouloy et al. (Jul. 1, 1980) "Both The 7-Methyl and The 2'-O-Methyl Groups In The Cap Of mRNA Strongly Influence Its Ability To Act As Primer For Influenza Virus RNA Transcription", Proceedings of the National Academy of Sciences, 77(7):3952-3956.

Chan et al. (Sep. 19, 2016) "Cross-reactive antibodies enhance live attenuated virus infection for increased immunogenicity", Nature Microbiology, 1(12):16164 (10 pages).

Chan et al. (Oct. 5, 2017) "Early Molecular Correlates of Adverse Events Following Yellow Fever Vaccination", JCI Insight, 2(19):e96031 (12 pages).

Chan et al. (Aug. 2019) "Metabolic Perturbations and Cellular Stress Underpin Susceptibility to Symptomatic Live-attenuated Yellow Fever Infection", Nature Medicine, 25(8):1218-1224 (21 pages).

Chu et al. (Aug. 1978) "Paradoxical Observations on the 5' Terminus of Ovalbumin Messenger Ribonucleic Acid", Journal of Biological Chemistry, 253(15):5228-5231.

Cirelli et al. (May 16, 2019) "Slow Delivery Immunization Enhances Hiv Neutralizing Antibody and Germinal Center Responses via Modulation of Immunodominance", Cell, 177(5):1153-1171.e28 (57 pages).

Conticello et al. (Aug. 22, 2008) "Interaction Between Antibody-diversification Enzyme Aid and Spliceosome-associated Factor CTNNBL1", Molecular Cell, 31(4):474-484.

Corbett et al. (Oct. 22, 2020) "SARS-CoV-2 mRNA Vaccine Design Enabled by Prototype Pathogen Preparedness", Nature, 586(7830):567-571.

Corbett et al. (Jun. 11, 2020) "SARS-CoV-2 mRNA Vaccine Development Enabled by Prototype Pathogen Preparedness", bioRxiv., 39 pages.

Dabkowska et al. (Mar. 7, 2012) "The Effect Of Neutral Helper Lipids On The Structure Of Cationic Lipid Monolayers", Journal of the Royal Society Interface, 9(68):548-561.

Dua et al. (Apr.-Jun. 2012) "Liposome: Methods of Preparation and Applications", International Journal of Pharmaceutical Studies and Research, 3(3):14-20.

(56) References Cited

OTHER PUBLICATIONS

Dupuis et al. (Sep. 1, 2000) "Distribution of Dna Vaccines Determines Their Immunogenicity After Intramuscular Injection in Mice", The Journal of Immunology, 165(5):2850-2858.
Ehrchen et al. (Sep. 2009) "The Endogenous Toll-like Receptor 4 Agonist S1OOA8/S1OOA9 (Calprotectin) as Innate Amplifier of Infection, Autoimmunity, and Cancer", Journal of Leukocyte Biology, 86(3):557-566.
Enright et al. (Dec. 12, 2003) "MicroRNA targets in *Drosophil*", Genome Biology, 5:R1 (14 pages).
Geall et al. (Sep. 4, 2012) "Nonviral Delivery of Self-amplifying Rna Vaccines", Proceedings of the National Academy of Sciences, 109(36):14604-14609.
Groom et al. (Mar. 10, 2011) "CXCR3 in T Cell Function", Experimental Cell Research, 317(5):620-631.
Gustafsson et al. (Jul. 2004) "Codon Bias and Heterologous Protein Expression", Trends in Biotechnoloov, 22(7):346-353.
Hashem et al. (Oct. 8, 2019) "A Highly Lmmunogenic, Protective, and Safe Adenovirus-based Vaccine Expressing Middle East Respiratory Syndrome Coronavirus S1-cd40l Fusion Protein in a Transgenic Human Dipeptidyl Peptidase 4 Mouse Model", The Journal of Infectious Diseases, 220(10):1558-1567.
Hassett et al. (Apr. 15, 2019) "Optimization of Lipid Nanoparticles for Intramuscular Administration of mRNA Vaccines", Molecular Therapy—Nucleic Acids, 15:1-11.
Higgins et al. (Apr. 2019) "Programming Isotype-specific Plasma Cell Function", Trends Immunology, 40(4):345-357.
Honda-Okubo et al. (Mar. 2015) "Severe Acute Respiratory Syndrome-associated Coronavirus Vaccines Formulated with Delta Inulin Adjuvants Provide Enhanced Protection While Ameliorating Lung Eosinophilic Immunopathology", Journal of Virological Methods, 89(6):2995-3007.
Hsieh et al. (Sep. 18, 2020) "Structure-based design of prefusion-stabilized SARS-CoV-2 spikes", Science, 369(6510):1501-1505 (10 pages).
Huang et al. (Aug. 15, 2011) "In Vivo Delivery of RNAi with Lipid-Based Nanoparticles", Annual Review of Biomedical Engineering, 13:507-530.
Hyde et al. (Aug. 3, 2015) "The 5' and 3' Ends of Alphavirus RNAs-non-coding Is Not Non-functional", Virus Research, 206:99-107 (8 pages).
Ishikawa et al. (Sep. 27, 2009) "Preparation of Eukaryotic mRNA having Differently Methylated Adenosine at the 5'-Terminus and the Effect of the Methyl Group in Translation", Nucleic Acids Symposium, 53(1):129-130.
Jackson et al. (Feb. 4, 2020) "The Promise of mRNA Vaccines: a Biotech and Industrial Perspective", NPJ Vaccines, 5:11 (6 pages).
Jin et al. (Jul. 5, 2010) "Immunomodulatory Effects of dsRNA and Its Potential as Vaccine Adjuvant", Journal of Biomedicine and Biotechnology, 2010:690438.
Jokerst et al. (Jun. 2011) "Nanoparticle PEGylation for Imaging and Therapy", Nanomedicine (Lond), 6(4):715-728.
Kalnin et al. (2021) "Immunogenicity and efficacy of mRNA COVID-19 vaccine MRT5500 in preclinical animal models", NPJ Vaccines, 6(61):12 pages.
Karlin et al. (Jun. 1993) "Applications and Statistics for Multiple High-Scoring Segments in Molecular Sequences", Proceedings of the National Academy of Sciences, 90(12):5873-5877.
Karlin et al. (Mar. 1990) "Methods for Assessing the Statistical Significance of Molecular Sequence Features by Using General Scoring Schemes", Proceedings of the National Academy of Sciences, 87(6):2264-2268.
Kasturi et al. (Feb. 24, 2011) "Programming the Magnitude and Persistence of Antibody Responses with Innate Immunity", Nature, 470(7335):543-547 (20 pages).
Kawabata et al. (1995) "The Fate of Plasmid DNA After Intravenous Injection in Mice: Involvement of Scavenger Receptors in Its Hepatic Uptake", Pharmaceutical Research, 12:825-830.
Keech et al. (Dec. 10, 2020) "Phase 1-2 Trial of a SARS-CoV-2 Recombinant Spike Protein Nanoparticle Vaccine", The New England Journal of Medicine, 383:2320-2332.
Kirchdoerfer et al. (Oct. 24, 2018) "Stabilized Coronavirus Spikes Are Resistant to Conformational Changes Induced by Receptor Recognition or Proteolysis", Science Reports. 8(1):15701 (11 pages).
Kowalski et al. (Apr. 2019) "Delivering the Messenger: Advances in Technologies for Therapeutic mRNA Delivery", Molecular Therapy, 27(4):710-728.
Kozak Marilyn. (Nov. 1990) "Downstream Secondary Structure Facilitates Recognition of Initiator Codons by Eukaryotic Ribosomes", Proceedings of the National Academy of Sciences, 87(21):8301-8305.
Kozak Marilyn. (Jul. 1988) "Leader Length and Secondary Structure Modulate mRNA Function Under Conditions Of Stress.", Molecular and Cellular Biology, 8(7):2737-2744.
Kozak Marilyn. (Oct. 25, 1991) "Structural Features In Eukaryotic mRNAs That Modulate The Initiation Of Translation", Journal of Biological Chemistry, 266(30):19867-19870.
Kozak Marilyn. (Feb. 1989) "The Scanning Model for Translation: An Update", Journal of Cell Biology, 108(2):229-241.
Kreiter et al. (Jan. 1, 2008) "Increased Antigen Presentation Efficiency by Coupling Antigens to MHC Class I Trafficking Signals", Journal of Immunology, 180(1):309-318.
Kulasegaran-Shylini et al. (Apr. 25, 2009) "The 5'UTR-specific Mutation in Veev TC-83 Genome Has a Strong Effect on RNA Replication and Subgenomic RNA Synthesis, but Not on Translation of the Encoded Proteins", Virology, 387(1):211-221 (24 pages).
Kulkarni et al. (Jun. 2018) "Lipid Nanoparticles Enabling Gene Therapies: From Concepts to Clinical Utility", Nucleic Acid Therapeutics, 28(3):146-157.
Lasic Dand. (Jul. 1, 1998) "Novel Applications of Liposomes", Trends in Biotechnology, 16(7):307-321.
Li et al. (Jan. 2011) "Biosynthesis of Nanoparticles by Microorganisms and Their Applications", Journal of Nanomaterials, Article ID 270974, 2011:17 Pages.
Li et al. (Aug. 3, 2010) "Stealth Nanoparticles: High Density but Sheddable PEG is a Key for Tumor Targeting", Journal of Controlled Release, 145(3):178-181.
Lin et al. (Jan. 2014) "Lipid-based Nanoparticles in the Systemic Delivery of siRNA", Nanomedicine, 9(1):105-120.
Love et al. (Feb. 2, 2010) "Lipid-like materials for low-dose, In Vivo Gene Silencing", Proceedings of the National Academy of Sciences, 107(5):1864-1869.
Magini et al. (Aug. 15, 2016) "Self-amplifying mRNA Vaccines Expressing Multiple Conserved Influenza Antigens Confer Protection Against Homologous and Heterosubtypic Viral Challenge", PLoS one, 11(8):e0161193 (25 pages).
Maruggi et al. (Dec. 2013) "Engineered Alphavirus Replicon Vaccines Based on Known Attenuated Viral Mutants Show Limited Effects on Immunogenicity", Virology, 447(1-2):254-264.
Maruggi et al. (Apr. 10, 2019) "mRNA as a Transformative Technology for Vaccine Development to control Infectious Diseases", Molecular Therapy, 27(4):757-772.
Muthukrishnan et al. (May 1, 1975) "5'-Terminal 7-Methylguanosine in Eukaryotic mRNA is Required for Translation", Nature, 255:33-37.
Olmedillas et al. (May 6, 2021) "Structure-based design of a highly stable, covalently-linked SARS-CoV-2 spike trimer with improved structural properties and immunogenicity", bioRxiv, 51 pages.
Patil et al. (Jan. 2014) "Novel Methods for Liposome Preparation", Chemistry and Physics of Lipids, 177:8-18.
Pearson et al. (2013) "An Introduction to Sequence Similarity ("Homology") Searching", Current Protocols in Bioinformatics Book, 42:3.1.1-3.1.8.
Pearson et al. (Apr. 1988) "Improved Tools for Biological Sequence Comparison", Proceedings of the National Academy of Sciences, 85:2444-2448.
Pepini et al. (May 15, 2017) "Induction of an IFN-mediated Antiviral Response by a Self-amplifying RNA Vaccine: Implications for Vaccine Design", The Journal of Immunology, 198(10):4012-4024 (13 pages).

(56) References Cited

OTHER PUBLICATIONS

Petkov et al. (Jun. 4, 2018) "DNA Immunization Site Determines the Level of Gene Expression and the Magnitude, but Not the Type of the Induced Immune Response", PLoS One, 13(6): e0197902 (22 pages).
Polack et al. (Dec. 31, 2020) "Safety and Efficacy of the BNT162b2 mRNA Covid-19 Vaccine", The New England Journal of Medicine, 383:2603-2615.
Querec et al. (Jan. 2009) "Systems Biology Approach Predicts Immunogenicity of the Yellow Fever Vaccine in Humans", National Immunology, 10(1):116-125 (26 pages).
Querec et al. (2007) "Understanding the Role of Innate Immunity in the Mechanism of Action of the Live Attenuated Yellow Fever Vaccine 17D", Advances in Experimental Medicine and Biology, 590:43-53.
Ramanathan et al. (Sep. 19, 2016) "mRNA Capping: Biological Functions and Applications", Nucleic Acids Research, 44(16):7511-7526.
Rodriguez-Gascon et al., (Apr. 10, 2014) "Development Of Nucleic Acid Vaccines: Use Of Self-Amplifying RNA In Lipid Nanoparticles", International Journal of Nanomedicine, 9:1833-1843.
Sahin et al. (Dec. 11, 2020) "BNT162b2 Induces SARS-CoV-2-Neutralising Antibodies and T cells in Humans", medRxiv, 49 pages.
Sahin et al. (May 27, 2021) "BNT162b2 vaccine induces neutralizing antibodies and poly-specific T cells in humans", Nature, 595:572-577.
Saltl et al. (Dec. 15, 2011) "Granzyme B Regulates Antiviral CD8+ T Cell Responses", Journal of Immunology, 187(12):6301-6309 (19 pages).
Sercombe et al. (Dec. 1, 2015) "Advances and Challenges of Liposome Assisted Drug Delivery", Frontiers in Pharmacology, 6(286):13 Pages.
Slansky et al. (Oct. 2000) "Enhanced Antigen-Specific Antitumor Immunity with Altered Peptide Ligands that Stabilize the MHC-Peptide-TCR Complex", Immunity, 13(4):529-538.
Tam et al. (Oct. 4, 2016) "Sustained Antigen Availability During Germinal Center Initiation Enhances Antibody Responses to Vaccination", Proceedings of the National Academy of Sciences, 113(43):e6639-e6648.
Taverniti et al. (Jan. 9, 2015) "Elimination of Cap Structures Generated by mRNA Decay Involves the New Scavenger mRNA Decapping Enzyme Aph1/FHIT Together with DcpS", Nucleic Acids Research, 43(1):482-492.
Thompson et al. (Mar. 7, 2006) "Mucosal and Systemic Adjuvant Activity of Alphavirus Replicon Particles", Proceedings of the National Academy of Sciences, 103(10):3722-3727.
Villalobos et al. (Jun. 6, 2006) "Gene Designer: A Synthetic Biology Tool For Constructing Artificial DNA Segments", BMC Bioinformatics, 7:285 (8 pages).
Von Herrath et al. (Jun. 2003) "Immune Responsiveness, Tolerance and dsRNA: Implications for Traditional Paradigms", Trends in Immunology, 24(6):289-293 (4 pages).
Wootton et al. (Jun. 1993) "Statistics of Local Complexity in Amino Acid Sequences and Sequence Databases", Computers & Chemistry, 17(2):149-163.
Wrapp et al. (Mar. 13, 2020) "Cryo-EM Structure of the 2019-nCoV Spike in the Prefusion Conformation", Science, 367(6483):1260-1263.
Wu et al. (Mar. 12, 2020) "A New Coronavirus Associated with Human Respiratory Disease in China", Nature, 579(7798):265-269.
Yu et al. (Sep. 2000) "APRIL and TALL-I and Receptors BCMA and TACI: System for Regulating Humoral Immunity", Nature Immunology, 1(3):252-256.
Extended European Search Report for Application No. EP 21767978.6, mailed on Apr. 30, 2024, 11 pages.
Extended European Search Report for Application No. EP 21768525.4, mailed on Mar. 22, 2024, 10 pages.
(Retrieved date Aug. 28, 2024) "Tris", Retrieved from https://www.sigmaaldrich.com/US/en/products/chemistry-and-biochemicals/biochemicals/biological-buffers/tris, 7 Pages.
Keyer et al. (2019) "Non-structural Polyprotein [Cloning Vector pCMV-VEE-GFP]", GenBank: QCD25069.1, 2 pages.
Kim et al. (2014) "Enhancement of Protein Expression by Alphavirus Replicons by Designing Self-replicating Subgenomic RNAs", Proceedings of the National Academy of Sciences of the United States of America, 111(29):10708-10713.
Lundstrom, Kenneth (2016) "Replicon RNA Viral Vectors as Vaccines", Vaccines, 4(4):39.
Lundstrom, Kenneth (2018) "Self-Replicating RNA Viruses for RNA Therapeutics", Molecules, 23(12):3310.
Shustov et al. (2006) "VEEV Replicon Vector YFV-C1, Complete Sequence", GenBank: DQ322637.1, 4 pages.

* cited by examiner

Lipid nano particle (LNP) formulations

| | Particle diameter | Polydispersity index (PDI) | RNA trapping efficiency |
|---|---|---|---|
| mRNA | 67 nm | 0.09 | 92% |
| ARCT-021 | 69 nm | 0.09 | 91% |

SEQUENCE LISTING

```
Sequence total quantity: 129
SEQ ID NO: 1            moltype = DNA  length = 18
FEATURE                 Location/Qualifiers
misc_feature            1..18
                        note = Synthetic polynucleotide
source                  1..18
                        mol_type = other DNA
                        organism = synthetic construct
modified_base           15
                        mod_base = OTHER
                        note = uracil
SEQUENCE: 1
gaggaaactt aagatggg                                          18

SEQ ID NO: 2            moltype =   length =
```

```
SEQUENCE: 2
000

SEQ ID NO: 3           moltype =   length =
SEQUENCE: 3
000

SEQ ID NO: 4           moltype =   length =
SEQUENCE: 4
000

SEQ ID NO: 5           moltype = RNA  length = 129
FEATURE                Location/Qualifiers
misc_feature           1..129
                       note = Synthetic polynucleotide
source                 1..129
                       mol_type = other RNA
                       organism = synthetic construct
SEQUENCE: 5
tcaacacaac atatacaaaa caaacgaatc tcaagcaatc aagcattcta cttctattgc  60
agcaatttaa atcatttctt ttaaagcaaa agcaattttc tgaaaatttt caccatttac  120
gaacgatag                                                          129

SEQ ID NO: 6           moltype = RNA  length = 28
FEATURE                Location/Qualifiers
misc_feature           1..28
                       note = Synthetic polynucleotide
source                 1..28
                       mol_type = other RNA
                       organism = synthetic construct
SEQUENCE: 6
attattacat caaaacaaaa agccgcca                                     28

SEQ ID NO: 7           moltype = RNA  length = 245
FEATURE                Location/Qualifiers
misc_feature           1..245
                       note = Synthetic polynucleotide
source                 1..245
                       mol_type = other RNA
                       organism = synthetic construct
SEQUENCE: 7
cttaaggggg cgctgcctac ggaggtggca gccatctcct tctcggcatc aagcttacca  60
tggtgcccca ggccctgctc ttggtcccgc tgctggtgtt ccccctctgc ttcggcaagt  120
tccccatcta caccatcccc gacaagctgg ggccgtggag ccccatcgac atccaccacc  180
tgtcctgccc caacaacctc gtggtcgagg acgagggctg caccaacctg agcgggttct  240
cctac                                                              245

SEQ ID NO: 8           moltype = RNA  length = 177
FEATURE                Location/Qualifiers
misc_feature           1..177
                       note = Synthetic polynucleotide
source                 1..177
                       mol_type = other RNA
                       organism = synthetic construct
SEQUENCE: 8
tgagtgtcgt acagcctcca ggcccccccc tcccgggaga gccatagtgg tctgcggaac  60
cggtgagtac accggaattg ccgggaagac tgggtccttt cttggataaa cccactctat  120
gcccggccat ttgggcgtgc ccccgcaaga ctgctagccg agtagtgttg ggttgcg     177

SEQ ID NO: 9           moltype = RNA  length = 89
FEATURE                Location/Qualifiers
misc_feature           1..89
                       note = Synthetic polynucleotide
source                 1..89
                       mol_type = other RNA
                       organism = synthetic construct
SEQUENCE: 9
aattattggt taaagaagta tattagtgct aatttccctc cgtttgtcct agcttttctc  60
ttctgtcaac cccacacgcc tttggcaca                                    89

SEQ ID NO: 10          moltype = RNA  length = 569
FEATURE                Location/Qualifiers
misc_feature           1..569
                       note = Synthetic polynucleotide
source                 1..569
                       mol_type = other RNA
                       organism = synthetic construct
SEQUENCE: 10
ctccctcccc ccccccctaac gttactggcc gaagccgctt ggaataaggc cggtgtgcgt  60
```

```
ttgtctatat gttattttcc accatattgc cgtcttttgg caatgtgagg gcccggaaac  120
ctggccctgt cttcttgacg agcattccta ggggtctttc ccctctcgcc aaaggaatgc  180
aaggtctgtt gaatgtcgtg aaggaagcag ttcctctgga agcttcttga agacaaacaa  240
cgtctgtagc gaccctttgc aggcagcgga acccccccacc tggcgacagg tgcctctgcg  300
gccaaaagcc acgtgtataa gatacacctg caaaggcggc acaaccccag tgccacgttg  360
tgagttggat agttgtggaa agagtcaaat ggctctcctc aagcgtattc aacaaggggc  420
tgaaggatgc ccagaaggta ccccattgta tgggatctga tctggggcct cggtgcacat  480
gctttacgtg tgtttagtcg aggttaaaaa acgtctaggc cccccgaacc acggggacgt  540
ggttttcctt tgaaaaacac gatgataat                                    569

SEQ ID NO: 11          moltype = RNA  length = 44
FEATURE                Location/Qualifiers
misc_feature           1..44
                       note = Synthetic polynucleotide
source                 1..44
                       mol_type = other RNA
                       organism = synthetic construct
SEQUENCE: 11
gtcagctttc aaactctttg tttcttgttt gttgattgag aata                   44

SEQ ID NO: 12          moltype = RNA  length = 54
FEATURE                Location/Qualifiers
misc_feature           1..54
                       note = Synthetic polynucleotide
source                 1..54
                       mol_type = other RNA
                       organism = synthetic construct
SEQUENCE: 12
ctctcgcctg agaaaaaaaa tccacgaacc aatttctcag caaccagcag cacg         54

SEQ ID NO: 13          moltype = RNA  length = 52
FEATURE                Location/Qualifiers
misc_feature           1..52
                       note = Synthetic polynucleotide
source                 1..52
                       mol_type = other RNA
                       organism = synthetic construct
SEQUENCE: 13
acctgtgagg gttcgaagga agtagcagtg ttttttgttc ctagaggaag ag           52

SEQ ID NO: 14          moltype = RNA  length = 71
FEATURE                Location/Qualifiers
misc_feature           1..71
                       note = Synthetic polynucleotide
source                 1..71
                       mol_type = other RNA
                       organism = synthetic construct
SEQUENCE: 14
acacagaaac attcgcaaaa acaaaatccc agtatcaaaa ttcttctctt tttttcatat  60
ttcgcaaaga c                                                        71

SEQ ID NO: 15          moltype = RNA  length = 52
FEATURE                Location/Qualifiers
misc_feature           1..52
                       note = Synthetic polynucleotide
source                 1..52
                       mol_type = other RNA
                       organism = synthetic construct
SEQUENCE: 15
cagaaaaatt tgctacattg tttcacaaac ttcaaatatt attcatttat tt           52

SEQ ID NO: 16          moltype = RNA  length = 158
FEATURE                Location/Qualifiers
misc_feature           1..158
                       note = Synthetic polynucleotide
source                 1..158
                       mol_type = other RNA
                       organism = synthetic construct
SEQUENCE: 16
ctagtgactg actaggatct ggttaccact aaaccagcct caagaacacc cgaatggagt  60
ctctaagcta cataatacca acttacactt acaaaatgtt gtcccccaaa atgtagccat  120
tcgtatctgc tcctaataaa aagaaagttt cttcacat                          158

SEQ ID NO: 17          moltype = RNA  length = 166
FEATURE                Location/Qualifiers
misc_feature           1..166
                       note = Synthetic polynucleotide
source                 1..166
                       mol_type = other RNA
```

```
                         organism = synthetic construct
SEQUENCE: 17
tgcaaggctg gccggaagcc cttgcctgaa agcaagattt cagcctggaa gagggcaaag  60
tggacgggag tggacaggag tggatgcgat aagatgtggt ttgaagctga tgggtgccag  120
ccctgcattg ctgagtcaat caataaagag ctttcttttg acccat                 166

SEQ ID NO: 18            moltype = RNA  length = 143
FEATURE                  Location/Qualifiers
misc_feature             1..143
                         note = Synthetic polynucleotide
source                   1..143
                         mol_type = other RNA
                         organism = synthetic construct
SEQUENCE: 18
acgccgaagc ctgcagccat gcgaccccac gccaccccgt gcctcctgcc tccgcgcagc  60
ctgcagcggg agaccctgtc cccgccccag ccgtcctcct ggggtggacc ctagtttaat  120
aaagattcac caagtttcac gca                                          143

SEQ ID NO: 19            moltype = RNA  length = 220
FEATURE                  Location/Qualifiers
misc_feature             1..220
                         note = Synthetic polynucleotide
source                   1..220
                         mol_type = other RNA
                         organism = synthetic construct
SEQUENCE: 19
tagagcggca aaccctagct acactccata gctagtttct tttttttttg tttttttttt  60
tttttttttt tttttttttt tttttttttc ctttcttttc cttctttttt tcctcttttc  120
ttggtggctc catcttagcc ctagtcacgg ctagctgtga aaggtccgtg agccgcatga  180
ctgcagagag tgccgtaact ggtctctctg cagatcatgt                        220

SEQ ID NO: 20            moltype = RNA  length = 170
FEATURE                  Location/Qualifiers
misc_feature             1..170
                         note = Synthetic polynucleotide
source                   1..170
                         mol_type = other RNA
                         organism = synthetic construct
SEQUENCE: 20
acacatcaca accacaacct tctcaggcta ccctgagaaa aaaagacatg aagactcagg  60
actcatcttt tctgttggtg taaaatcaac accctaagga acacaaattt ctttaaacat  120
ttgacttctt gtctctgtgc tgcaattaat aaaaaatgga aagaatctac             170

SEQ ID NO: 21            moltype = RNA  length = 110
FEATURE                  Location/Qualifiers
misc_feature             1..110
                         note = Synthetic polynucleotide
source                   1..110
                         mol_type = other RNA
                         organism = synthetic construct
SEQUENCE: 21
gctggagcct cggtagccgt tcctcctgcc cgctgggcct cccaacgggc cctcctcccc  60
tccttgcacc ggcccttcct ggtctttgaa taaagtctga gtgggcagca             110

SEQ ID NO: 22            moltype = RNA  length = 123
FEATURE                  Location/Qualifiers
misc_feature             1..123
                         note = Synthetic polynucleotide
source                   1..123
                         mol_type = other RNA
                         organism = synthetic construct
SEQUENCE: 22
tagtgcagtc actggcacaa cgcgttgccc ggtaagccaa tcgggtatac acggtcgtca  60
tactgcagac agggttcttc tactttgcaa gatagtctag agtagtaaaa taaatagtat  120
aag                                                                123

SEQ ID NO: 23            moltype =   length =
SEQUENCE: 23
000

SEQ ID NO: 24            moltype =   length =
SEQUENCE: 24
000

SEQ ID NO: 25            moltype = RNA  length = 21
FEATURE                  Location/Qualifiers
misc_feature             1..21
                         note = Synthetic polynucleotide
source                   1..21
```

```
                         mol_type = other RNA
                         organism = synthetic construct
SEQUENCE: 25
cacaaagagt aaagaagaac a                                                21

SEQ ID NO: 26            moltype = RNA  length = 21
FEATURE                  Location/Qualifiers
misc_feature             1..21
                         note = Synthetic polynucleotide
source                   1..21
                         mol_type = other RNA
                         organism = synthetic construct
SEQUENCE: 26
aacactaaaa gtagaagaaa a                                                21

SEQ ID NO: 27            moltype = RNA  length = 21
FEATURE                  Location/Qualifiers
misc_feature             1..21
                         note = Synthetic polynucleotide
source                   1..21
                         mol_type = other RNA
                         organism = synthetic construct
SEQUENCE: 27
ctcagaaaga taagatcagc c                                                21

SEQ ID NO: 28            moltype = RNA  length = 21
FEATURE                  Location/Qualifiers
misc_feature             1..21
                         note = Synthetic polynucleotide
source                   1..21
                         mol_type = other RNA
                         organism = synthetic construct
SEQUENCE: 28
aaccaatcga aagaaaccaa a                                                21

SEQ ID NO: 29            moltype = RNA  length = 21
FEATURE                  Location/Qualifiers
misc_feature             1..21
                         note = Synthetic polynucleotide
source                   1..21
                         mol_type = other RNA
                         organism = synthetic construct
SEQUENCE: 29
ctctaatcac caggagtaaa a                                                21

SEQ ID NO: 30            moltype = RNA  length = 21
FEATURE                  Location/Qualifiers
misc_feature             1..21
                         note = Synthetic polynucleotide
source                   1..21
                         mol_type = other RNA
                         organism = synthetic construct
SEQUENCE: 30
gagagagatc ttaacaaaaa a                                                21

SEQ ID NO: 31            moltype = RNA  length = 21
FEATURE                  Location/Qualifiers
misc_feature             1..21
                         note = Synthetic polynucleotide
source                   1..21
                         mol_type = other RNA
                         organism = synthetic construct
SEQUENCE: 31
tgtgtaacaa caacaacaac a                                                21

SEQ ID NO: 32            moltype = RNA  length = 21
FEATURE                  Location/Qualifiers
misc_feature             1..21
                         note = Synthetic polynucleotide
source                   1..21
                         mol_type = other RNA
                         organism = synthetic construct
SEQUENCE: 32
ccgcagtagg aagagaaagc c                                                21

SEQ ID NO: 33            moltype = RNA  length = 21
FEATURE                  Location/Qualifiers
misc_feature             1..21
                         note = Synthetic polynucleotide
```

```
source                  1..21
                        mol_type = other RNA
                        organism = synthetic construct
SEQUENCE: 33
aaaaaaaaaa gaaatcataa a                                              21

SEQ ID NO: 34           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 34
gagagaagaa agaagaagac g                                              21

SEQ ID NO: 35           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 35
caattaaaaa tacttaccaa a                                              21

SEQ ID NO: 36           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 36
gcaaacagag taagcgaaac g                                              21

SEQ ID NO: 37           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 37
gcgaagaaga cgaacgcaaa g                                              21

SEQ ID NO: 38           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 38
ttaggactgt attgactggc c                                              21

SEQ ID NO: 39           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 39
atcatcggaa ttcggaaaaa g                                              21

SEQ ID NO: 40           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 40
aaaacaaaag ttaaagcaga c                                              21

SEQ ID NO: 41           moltype = RNA  length = 21
FEATURE                 Location/Qualifiers
misc_feature            1..21
```

-continued

```
                        note = Synthetic polynucleotide
source                  1..21
                        mol_type = other RNA
                        organism = synthetic construct
SEQUENCE: 41
tttatctcaa ataagaaggc a                                          21

SEQ ID NO: 42           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 42
ggtggggagg tgagatttct t                                          21

SEQ ID NO: 43           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 43
tgattaggaa actacaaagc c                                          21

SEQ ID NO: 44           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 44
catttttcaa tttcataaaa c                                          21

SEQ ID NO: 45           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 45
ttacttttaa gcccaacaaa a                                          21

SEQ ID NO: 46           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 46
ggcgtgtgtg tgtgttgttg a                                          21

SEQ ID NO: 47           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 47
gtggtgaagg ggaaggttta g                                          21

SEQ ID NO: 48           moltype = RNA  length = 21
FEATURE                 Location/Qualifiers
misc_feature            1..21
                        note = Synthetic polynucleotide
source                  1..21
                        mol_type = other RNA
                        organism = synthetic construct
SEQUENCE: 48
ttgttttttt ttggtttggt t                                          21

SEQ ID NO: 49           moltype = DNA  length = 44
FEATURE                 Location/Qualifiers
```

```
misc_feature            1..44
                        note = Synthetic polynucleotide
source                  1..44
                        mol_type = other DNA
                        organism = synthetic construct
SEQUENCE: 49
atgggcggcg catgagagaa gcccagacca attacctacc caaa                 44

SEQ ID NO: 50           moltype = DNA  length = 7482
FEATURE                 Location/Qualifiers
misc_feature            1..7482
                        note = Synthetic polynucleotide
source                  1..7482
                        mol_type = other DNA
                        organism = synthetic construct
SEQUENCE: 50
atggagaaag ttcacgttga catcgaggaa gacagcccat tcctcagagc tttgcagcgg  60
agcttcccgc agtttgaggt agaagccaag caggtcactg ataatgacca tgctaatgcc  120
agagcgtttt cgcatctggc ttcaaaactg atcgaaacgg aggtggaccc atccgacacg  180
atccttgaca ttggaagtgc gcccgcccgc agaatgtatt ctaagcacaa gtatcattgt  240
atctgtccga tgagatgtgc ggaagatccg gacagattgt ataagtatgc aactaagctg  300
aagaaaaact gtaaggaaat aactgataag gaattggaca agaaaatgaa ggagctggcc  360
gccgtcatga gcgaccctga cctggaaact gagactatgt gcctccacga cgacgagtcg  420
tgtcgctacg aagggcaagt cgctgtttac caggatgtat acgccgtcga cggcccaccc  480
agcctgtacc accaggccaa caagggcgtg agggtggcct actggatcgg cttcgacacc  540
acacccttca tgttcaagaa cctggccggc gcctacccca gctacagcac caactgggcc  600
gacgagaccg tgctgaccgc caggaacatc ggcctgtgca gcagcgacgt gatggagagg  660
agccggagag gcatgagcat cctgaggaag aaatacctga agcccagcaa caacgtgctg  720
ttcagcgtgg gcagcaccat ctaccacgag aagagggacc tgctcaggag ctggcacctg  780
cccagcgtgt tccacctgag gggcaagcag aactacacct gcaggtgcga gaccatcgtg  840
agctgcgacg gctacgtggt gaagaggatc gccatcagcc ccggcctgta cggcaagccc  900
agcggctacg ccgctacaat gcacagggag ggcttcctgt gctgcaaggt gaccgacacc  960
ctgaacggcg agagggtgag cttccccgtg tgcacctacg tgcccgccac cctgtgcgac  1020
cagatgaccg gcatcctggc caccgacgtg agcgccgacg acgcccagaa gctgctcgtg  1080
ggcctgaacc agaggatcgt ggtcaacggc aggacccaga ggaacaccaa cacaatgaag  1140
aactacctgc tgcccgtggt ggcccaggct ttcgccaggt gggccaagga gtacaaggag  1200
gaccaggaag acgagaggcc cctgggcctg agggacaggc agctggtgat gggctgctgc  1260
tgggccttca ggcggcacaa gatcaccagc atctacaaga ggcccgacac ccagaccatc  1320
atcaaggtga acagcgactt ccacagcttc gtgctgccca ggatcggcag caacaccctg  1380
gagatcggcc tgaggacccg gatcaggaag atgctggagg aacacaagga gcccagccca  1440
ctgatcaccg ccgaggacgt gcaggaggcc aagtgcgctg ccgacgaggc caaggaggtg  1500
agggaggccg aggaactgag ggccgccctg ccacccctgg ctgccgacgt ggaggaaccc  1560
accctggaag ccgacgtgga cctgatgctg caggaggccg gcgccggaag cgtggagaca  1620
cccaggggcc tgatcaaggt gaccagctac gacggcgagg acaagatcgg cagctacgcc  1680
gtgctgagcc cacaggccgt gctgaagtcc gagaagctga gctgcatcca cccactggcc  1740
gagcaggtga tcgtgatcac ccacagcggc aggaagggca ggtacgccgt ggagccctac  1800
cacggcaagg tggtcgtgcc cgagggccac gccatccccg tgcaggactt ccaggccctg  1860
agcgagagcg ccaccatcgt gtacaacgag agggagttcg tgaacaggta cctgcaccat  1920
atcgccaccc acggcggagc cctgaacacc gacgaggaat actacaagac cgtgaagccc  1980
agcgagcacg acggcgagta cctgtacgac atcgacagga agcagtgcgt gaagaaagag  2040
ctggtgaccg gcctgggact gaccggcgag ctggtggacc caccccttcca cgagttcgcc  2100
tacgagagcc tgaggaccag acccgccgct ccctaccagg tgcccaccat cggcgtgtac  2160
ggcgtgcccg gcagcggaaa gagcggcatc atcaagagcg ccgtgaccaa gaaagacctg  2220
gtggtcagcg ccaaggaaaga gaactgcgcc gagatcatca gggacgtgaa gaagatgaaa  2280
ggcctggacg tgaacgcgcg caccgtggac agcgtgctgc tgaacggctg caagcacccc  2340
gtggagaccc tgtacatcga cgaggccttc gcttgccacg ccggcaccct gagggccctg  2400
atcgccatca tcaggcccaa gaaagccgtg ctgtgcggcg accccaagca gtgcggcttc  2460
ttcaacatga tgtgcctgaa ggtgcacttc aaccacgaga tctgcaccca ggtgttccac  2520
aagagcatca gcaggcggtg caccaagagc gtgaccagcg tcgtgagcac cctgttctac  2580
gacaagaaaa tgaggaccac caaccccaag gagaccaaaa tcgtgatcga caccacaggc  2640
agcaccaagc ccaagcagga cgacctgatc ctgacctgct tcaggggctg ggtgaagcag  2700
ctgcagatcg actacaaggg caacgagatc atgaccgccg ctgccagcca gggcctgacc  2760
aggaagggcg tgtacgccgt gaggtacaag gtgaacgaga acccactgta cgctcccacc  2820
agcgagcacg tgaacgtgct gctgaccagg accgaggaca ggatcgtgtg gaagaccctg  2880
gccggcgacc cctggatcaa gaccctgacc gccaagtacc ccggcaactt caccgccacc  2940
atcgaagagt ggcaggccga gcacgacgcc atcatgaggc acatcctgga gaggcccgac  3000
cccaccgacg tgttccagaa caaggccaac gtgtgctggg ccaaggccct ggtgcccgtg  3060
ctgaagaccg ccggcatcga catgaccaca gagcagtgga acaccgtgga ctacttcgag  3120
accgacaagg cccacagcgc cgagatcgtg ctgaaccagc tgtgcgtgag gttcttcggc  3180
ctggacctgg acagcggcct gttcagcgcc cccaccgtgc cactgagcat caggaacaac  3240
cactgggaca acagccccag cccaaacatg tacggcctga acaaggaggt ggtcaggcag  3300
ctgagcaggc ggtacccaca gctgcccagg gccgtggcca ccggcagggt gtacgacatg  3360
aacaccggca ccctgaggaa ctacgacccc aggatcaacc tggtgcccgt gaacaggcgg  3420
ctgccccacg ccctggtgct gcaccacaac gagcacccac agagcgactt cagctccttc  3480
gtgagcaagc tgaaaggcag gaccgtgctg gtcgtgggcg agaagctgag cgtgcccggc  3540
aagatggtgg actggctgag cgacaggccc gaggccacct tccgggccag gctggacctc  3600
ggcatccccg gcgacgtgcc caagtacgac atcatcttcg tgaacgtcag gaccccatac  3660
aagtaccacc attaccagca gtgcgaggac cacgccatca agctgagcat gctgaccaag  3720
aaggcctgcc tgcacctgaa ccccggaggc acctgcgtga gcatcggcta cggctacgcc  3780
```

```
gacagggcca gcgagagcat cattggcgcc atcgccaggc tgttcaagtt cagcagggtg  3840
tgcaaaccca agagcagcct ggaggaaacc gaggtgctgt tcgtgttcat cggctacgac  3900
cggaaggcca ggacccacaa cccctacaag ctgagcagca ccctgacaaa catctacacc  3960
ggcagcaggc tgcacgaggc cggctgcgcc cccagctacc acgtggtcag gggcgatatc  4020
gccaccgcca ccgagggcgt gatcatcaac gctgccaaca gcaagggcca gcccggaggc  4080
ggagtgtgcg gcgccctgta caagaagttc cccgagagct tcgacctgca gcccatcgag  4140
gtgggcaagg ccaggctggt gaagggcgcc gctaagcaca tcatccacgc cgtgggcccc  4200
aacttcaaca aggtgagcga ggtggaaggc gacaagcagc tggccgaagc ctacgagagc  4260
atcgccaaga tcgtgaacga caataactac aagagcgtgg ccatccccact gctcagcacc  4320
ggcatcttca gcggcaacaa ggacaggctg acccagagcc tgaaccacct gctcaccgcc  4380
ctggacacca ccgatgccga cgtggccatc tactgcaggg acaagaagtg ggagatgacc  4440
ctgaaggagg ccgtggccag gcgggaggcc gtggaagaga tctgcatcag cgacgactcc  4500
agcgtgaccg agcccgacgc cgagctggtg agggtgcacc ccaagagctc cctggccggc  4560
aggaagggct acagcaccag cgacggcaag accttcagct acctggaggg caccaagttc  4620
caccaggccg ctaaggacat cgccgagatc aacgctatgt ggcccgtggc caccgaggcc  4680
aacgagcagg tgtgcatgta catcctgggc gagagcatgt ccagcatcag gagcaagtgc  4740
cccgtggagg aaagcgaggc cagcacacca cccagcaccc tgccctgcct gtgcatccac  4800
gctatgacac ccgagagggt gcagcggctg aaggccagca ggcccgagca gatcaccgtg  4860
tgcagctcct tcccactgcc caagtacagg atcaccggcg tgcagaagat ccagtgcagc  4920
cagcccatcc tgttcagccc aaaggtgccc gcctacatcc accccaggaa gtacctggtg  4980
gagaccccac ccgtggacga gacacccgag ccaagcgccg agaaccagag caccgagggc  5040
acacccgagc agccacccct gatcaccgag gacgagacaa ggacccggac cccagagccc  5100
atcattatcg aggaagagga agaggacagc atcagcctgc tgagcgacgg ccccacccac  5160
caggtgctgc aggtggaggc cgacatccac ggcccaccca gcgtgtccag ctccagctgg  5220
agcatcccac acgccagcga cttcgacgtg gacagcctga gcatcctgga caccctggag  5280
ggcgccagcg tgacctccgg cgccaccagc gccgagacca acagctactt cgccaagagc  5340
atggagttcc tggccaggcc cgtgccagct cccaggaccg tgttcaggaa cccaccccac  5400
ccagctccca ggaccaggac cccaagcctg gctcccagca gggcctgcag caggaccagc  5460
ctggtgagca ccccacccgg cgtgaacagg gtgatcacca gggaggaact ggaggccctg  5520
acacccagca ggacccccag caggtccgtg agcaggacta gtctggtgtc caacccaccc  5580
ggcgtgaaca gggtgatcac cagggaggaa ttcgaggcct tcgtggccca gcaacagaga  5640
cggttcgacg ccggcgccta catcttcagc agcgacaccg gccagggaca cctgcagcaa  5700
aagagcgtga ggcagaccgt gctgagcgag gtggtgctgg agaggaccga gctggaaatc  5760
agctacgccc ccaggctgga ccaggagaag gaggaactgc tcaggaagaa actgcagctg  5820
aaccccaccc cagccaacag gagcaggtac cagagcagga aggtggagaa catgaaggcc  5880
atcaccgcca ggcggatcct gcagggcctg ggacactacc tgaaggccga gggcaaggtg  5940
gagtgctaca ggaccctgca ccccgtgcca ctgtacagct ccagcgtgaa cagggccttc  6000
tccagcccca aggtggccgt ggaggcctgc aacgctatgc tgaaggagaa cttccccacc  6060
gtggccagct actgcatcat ccccgagtac gacgcctacc tggacatggt ggacggcgcc  6120
agctgctgcc tggacaccgc cagcttctgc cccgccaagc tgaggagctt ccccaagaaa  6180
cacagctacc tggagcccac catcaggagc gccgtgccca gcgccatcca gaacaccctg  6240
cagaacgtgc tggccgctgc caccaagagg aactgcaacg tgacccagat gagggagctg  6300
cccgtgctgg acagcgctgc cttcaacgtg gagtgcttca agaaatacgc ctgcaacaac  6360
gagtactggg agaccttcaa ggagaacccc atcaggctga ccgaagagaa cgtggtgaac  6420
tacatcacca agctgaaggg ccccaaggcc gctgccctgt tcgctaagac ccacaacctg  6480
aacatgctgc aggacatccc aatggacagg ttcgtgatgg acctgaagag ggacgtgaag  6540
gtgacacccg gcaccaagca caccgaggag aggcccaagg tgcaggtgat ccaggccgct  6600
gacccactgg ccaccgccta cctgtgcggc atccacaggg agctggtgag gcggctgaac  6660
gccgtgctgc tgcccaacat ccacaccctg ttcgacatga gcgccgagga cttcgacgcc  6720
atcatcgccg agcacttcca gcccggcgac tgcgtgctgg agaccgacat cgccagcttc  6780
gacaagagcg aggatgacgc tatggccctg accgctctga tgatcctgga ggacctgggc  6840
gtggacgccg agctgctcac cctgatcgag gctgccttcg gcgagatcag ctccatccac  6900
ctgcccacca agaccaagtt caagttcggc gctatgatga aaagcggaat gttcctgacc  6960
ctgttcgtga acaccgtgat caacattgtg atcgccagca gggtgctgcg ggagaggctg  7020
accggcagcc cctgcgctgc cttcatcggc gacgacaaca tcgtgaaggg cgtgaaaagc  7080
gacaagctga tggccgacag gtgcgccacc tggctgaaca tggaggtgaa gatcatcgac  7140
gccgtggtgg gcgagaaggc cccctacttc tgcggcggat tcatcctgtg cgacagcgtg  7200
accggcaccg cctgcagggt ggccgacccc ctgaagaggc tgttcaagct gggcaagcca  7260
ctggccgctg acgatgagca cgacgatgac aggcggaggg ccctgcacga ggaaagcacc  7320
aggtggaaca gggtgggcat cctgagcgag ctgtgcaagg ccgtggagag caggtacgag  7380
accgtgggca ccagcatcat cgtgatggct atgaccacac tggccagctc cgtcaagagc  7440
ttctcctacc tgaggggggc ccctataact ctctacggct aa                       7482

SEQ ID NO: 51            moltype = AA  length = 2493
FEATURE                  Location/Qualifiers
REGION                   1..2493
                         note = Synthetic polypeptide
source                   1..2493
                         mol_type = protein
                         organism = synthetic construct
SEQUENCE: 51
MEKVHVDIEE DSPFLRALQR SFPQFEVEAK QVTDNDHANA RAFSHLASKL IETEVDPSDT  60
ILDIGSAPAR RMYSKHKYHC ICPMRCAEDP DRLYKYATKL KKNCKEITDK ELDKKMKELA  120
AVMSDPDLET ETMCLHDDES CRYEGQVAVY QDVYAVDGPT SLYHQANKGV RVAYWIGFDT  180
TPFMFKNLAG AYPSYSTNWA DETVLTARNI GLCSSDVMER SRRGMSILRK KYLKPSNNVL  240
FSVGSTIYHE KRDLLRSWHL PSVFHLRGKQ NYTCRCETIV SCDGYVVKRI AISPGLYGKP  300
SGYAATMHRE GFLCCKVTDT LNGERVSFPV CTYVPATLCD QMTGILATDV SADDAQKLLV  360
GLNQRIVVNG RTQRNTNTMK NYLLPVVAQA FARWAKEYKE DQEDERPLGL RDRQLVMGCC  420
WAFRRHKITS IYKRPDTQTI IKVNSDFHSF VLPRIGSNTL EIGLRTRIRK MLEEHKEPSP  480
```

-continued

```
LITAEDVQEA KCAADEAKEV REAEELRAAL PPLAADVEEP TLEADVDLML QEAGAGSVET  540
PRGLIKVTSY DGEDKIGSYA VLSPQAVLKS EKLSCIHPLA EQVIVITHSG RKGRYAVEPY  600
HGKVVVPEGH AIPVQDFQAL SESATIVYNE REFVNRYLHH IATHGGALNT DEEYYKTVKP  660
SEHDGEYLYD IDRKQCVKKE LVTGLGLTGE LVDPPFHEFA YESLRTRPAA PYQVPTIGVY  720
GVPGSGKSGI IKSAVTKKDL VVSAKKENCA EIIRDVKKMK GLDVNARTVD SVLLNGCKHP  780
VETLYIDEAF ACHAGTLRAL IAIIRPKKAV LCGDPKQCGF FNMMCLKVHF NHEICTQVFH  840
KSISRRCTKS VTSVVSTLFY DKKMRTTNPK ETKIVIDTTG STKPKQDDLI LTCFRGWVKQ  900
LQIDYKGNEI MTAAASQGLT RKGVYAVRYK VNENPLYAPT SEHVNVLLTR TEDRIVWKTL  960
AGDPWIKTLT AKYPGNFTAT IEEWQAEHDA IMRHILERPD PTDVFQNKAN VCWAKALVPV  1020
LKTAGIDMTT EQWNTVDYFE TDKAHSAEIV LNQLCVRFFG LDLDSGLFSA PTVPLSIRNN  1080
HWDNSPSPNM YGLNKEVVRQ LSRRYPQLPR AVATGRVYDM NTGTLRNYDP RINLVPVNRR  1140
LPHALVLHHN EHPQSDFSSF VSKLKGRTVL VVGEKLSVPG KMVDWLSDRP EATFRARLDL  1200
GIPGDVPKYD IIFVNVRTPY KYHHYQQCED HAIKLSMLTK KACLHLNPGG TCVSIGYGYA  1260
DRASESIIGA IARLFKFSRV CKPKSSLEET EVLFVFIGYD RKARTHNPYK LSSTLTNIYT  1320
GSRLHEAGCA PSYHVVRGDI ATATEGVIIN AANSKGQPGG GVCGALYKKF PESFDLQPIE  1380
VGKARLVKGA AKHIIHAVGP NFNKVSEVEG DKQLAEAYES IAKIVNDNNY KSVAIPLLST  1440
GIFSGNKDRL TQSLNHLLTA LDTTDADVAI YCRDKKWEMT LKEAVARREA VEEICISDDS  1500
SVTEPDAELV RVHPKSSLAG RKGYSTSDGK TFSYLEGTKF HQAAKDIAEI NAMWPVATEA  1560
NEQVCMYILG ESMSSIRSKC PVEESEASTP PSTLPCLCIH AMTPERVQRL KASRPEQITV  1620
CSSFPLPKYR ITGVQKIQCS QPILFSPKVP AYIHPRKYLV ETPPVDETPE PSAENQSTEG  1680
TPEQPPLITE DETRTRTPEP IIIEEEEDS ISLLSDGPTH QVLQVEADIH GPPSVSSSSW  1740
SIPHASDFDV DSLSILDTLE GASVTSGATS AETNSYFAKS MEFLARPVPA PRTVFRNPPH  1800
PAPRTRTPSL APSRACSRTS LVSTPPGVNR VITREELEAL TPSRTPSRSV SRTSLVSNPP  1860
GVNRVITREE FEAFVAQQQR RFDAGAYIFS SDTGQGHLQQ KSVRQTVLSE VVLERTELEI  1920
SYAPRLDQEK EELLRKKLQL NPTPANRSRY QSRKVENMKA ITARRILQGL GHYLKAEGKV  1980
ECYRTLHPVP LYSSSVNRAF SSPKVAVEAC NAMLKENFPT VASYCIIPEY DAYLDMVDGA  2040
SCCLDTASFC PAKLRSFPKK HSYLEPTIRS AVPSAIQNTL QNVLAAATKR NCNVTQMREL  2100
PVLDSAAFNV ECFKKYACNN EYWETFKENP IRLTEENVVN YITKLKGPKA AALFAKTHNL  2160
NMLQDIPMDR FVMDLKRDVK VTPGTKHTEE RPKVQVIQAA DPLATAYLCG IHRELVRRLN  2220
AVLLPNIHTL FDMSAEDFDA IIAEHFQPGD CVLETDIASF DKSEDDAMAL TALMILEDLG  2280
VDAELLTLIE AAFGEISSIH LPTKTKFKFG AMMKSGMFLT LFVNTVINIV IASRVLRERL  2340
TGSPCAAFIG DDNIVKGVKS DKLMADRCAT WLNMEVKIID AVVGEKAPYF CGGFILCDSV  2400
TGTACRVADP LKRLFKLGKP LAADDEHDDD RRRALHEEST RWNRVGILSE LCKAVESRYE  2460
TVGTSIIVMA MTTLASSVKS FSYLRGAPIT LYG                              2493

SEQ ID NO: 52           moltype = DNA  length = 44
FEATURE                 Location/Qualifiers
misc_feature            1..44
                        note = Synthetic polynucleotide
source                  1..44
                        mol_type = other DNA
                        organism = synthetic construct
SEQUENCE: 52
cctgaatgga ctacgacata gtctagtccg ccaaggccgc cacc                  44

SEQ ID NO: 53           moltype = DNA  length = 468
FEATURE                 Location/Qualifiers
misc_feature            1..468
                        note = Synthetic polynucleotide
source                  1..468
                        mol_type = other DNA
                        organism = synthetic construct
SEQUENCE: 53
actcgagtat gttacgtgca aaggtgattg tcaccccccg aaagaccata ttgtgacaca  60
ccctcagtat cacgcccaaa catttacagc cgcggtgtca aaaaccgcgt ggacgtggtt  120
aacatccctg ctgggaggat cagccgtaat tattataatt ggcttggtgc tggctactat  180
tgtggccatg tacgtgctga ccaaccagaa acataattga atacagcagc aattggcaag  240
ctgcttacat agaactcgcg gcgattggca tgccgcctta aaatttttat tttatttttt  300
cttttctttt ccgaatcgga ttttgttttt aatatttcaa aaaaaaaaaa aaaaaaaaaa  360
aaatctagaa aaaaaaaaaa aaaaaaaaaa aaaaaaaaaa aaaaaaaaaa aaaaaaaaaa  420
aaaaaaaaaa aaaaaaaaaa aaaaaaaaaa aaaaaaaaaa aaaaaaaa              468

SEQ ID NO: 54           moltype = DNA  length = 7485
FEATURE                 Location/Qualifiers
misc_feature            1..7485
                        note = Synthetic polynucleotide
source                  1..7485
                        mol_type = other DNA
                        organism = synthetic construct
SEQUENCE: 54
atgcccgaga aggtgcacgt ggacatcgag gaggacagcc ccttcctgag ggccctgcag  60
aggagcttcc cacagttcga agtggaggcc aagcaggtga ccgacaacga ccacgccaac  120
gccagggcct tcagccacct ggccagcaag ctgatcgaga ccgaggtgga ccccagcgac  180
accatcctgg acatcggcag cgcccccagcc aggagaatgt acagcaagca caagtaccac  240
tgcatctgcc ccatgaggtg cgccgaggac cccgacaggc tgtacaagta cgccaccaaa  300
ctgaagaaga actgcaagga gatcaccgac aaggagctgg acaagaaaat gaaggagctg  360
gccgccgtga tgagcgaccc cgacctggag accgagacaa tgtgcctgca cgacgacgag  420
agctgcaggt acgagggcca ggtggccgtc taccaggacg tgtacgccgt cgacggcccc  480
accagcctgt accaccaggc caacaagggc gtgagggtgg cctactggat cggcttcgac  540
```

-continued

```
accacaccct tcatgttcaa gaacctggcc ggcgcctacc ccagctacag caccaactgg  600
gccgacgaga ccgtgctgac cgccaggaac atcggcctgt gcagcagcga cgtgatggag  660
aggagccgga gaggcatgag catcctgagg aagaaatacc tgaagcccag caacaacgtg  720
ctgttcagcg tgggcagcac catctaccac gagaagaggg acctgctcag gagctggcac  780
ctgcccagcg tgttccacct gaggggcaag cagaactaca cctgcaggtg cgagaccatc  840
gtgagctgcg acggctacgt ggtgaagagg atcgccatca gccccggcct gtacggcaag  900
cccagcggct acgccgctac aatgcacagg gagggcttcc tgtgctgcaa ggtgaccgac  960
accctgaacg gcgagagggt gagcttcccc gtgtgcacct acgtgcccgc caccctgtgc  1020
gaccagatga ccggcatcct ggccaccgac gtgagcgccg acgacgccca gaagctgctc  1080
gtgggcctga accagaggat cgtggtcaac ggcaggaccc agaggaacac caacacaatg  1140
aagaactacc tgctgcccgt ggtggcccag gctttcgcca ggtgggccaa ggagtacaag  1200
gaggaccagg aagacgagag gcccctgggc ctgagggaca ggcagctggt gatgggctgc  1260
tgctgggcct tcaggcggca caagatcacc agcatctaca agaggcccga cacccagacc  1320
atcatcaagg tgaacagcga cttccacagc ttcgtgctgc ccaggatcgg cagcaacacc  1380
ctggagatcg gcctgaggac ccggatcagg aagatgctgg aggaacacaa ggagcccagc  1440
ccactgatca ccgccgagga cgtgcaggag gccaagtgcg ctgccgacga ggccaaggag  1500
gtgagggagg ccgaggaact gagggccgcc ctgccacccc tggctgccga cgtggaggaa  1560
cccaccctgg aagccgacgt ggacctgatg ctgcaggagg ccggcgccgg aagcgtggag  1620
acacccaggg gcctgatcaa ggtgaccagc tacgacggcg aggacaagat cggcagctac  1680
gccgtgctga gcccacaggc cgtgctgaag tccgagaagc tgagctgcat ccacccactg  1740
gccgagcagg tgatcgtgat cacccacagc ggcaggaagg gcaggtacgc cgtggagccc  1800
taccacggca aggtggtcgt gcccgagggc cacgccatcc ccgtgcagga cttccaggcc  1860
ctgagcgaga gcgccaccat cgtgtacaac gagagggagt tcgtgaacag gtacctgcac  1920
catatcgcca cccacggcgg agccctgaac accgacgagg aatactacaa gaccgtgaag  1980
cccagcgagc acgacggcga gtacctgtac gacatcgaca ggaagcagtg cgtgaagaaa  2040
gagctggtga ccggcctggg actgaccggc gagctggtgg acccaccctt ccacgagttc  2100
gcctacgaga gcctgaggac cagacccgcc gctccctacc aggtgcccac catcggcgtg  2160
tacggcgtgc ccggcagcgg aaagagcggc atcatcaaga gcgccgtgac caagaaagac  2220
ctggtggtca gcgccaagaa agagaactgc gccgagatca tcagggacgt gaagaagatg  2280
aaaggcctgg acgtgaacgc gcgcaccgtg gacagcgtgc tgctgaacgg ctgcaagcac  2340
cccgtggaga ccctgtacat cgacgaggcc ttcgcttgcc acgccggcac cctgagggcc  2400
ctgatcgcca tcatcaggcc caagaaagcc gtgctgtgcg gcgaccccaa gcagtgcggc  2460
ttcttcaaca tgatgtgcct gaaggtgcac ttcaaccacg agatctgcac ccaggtgttc  2520
cacaagagca tcagcaggcg gtgcaccaag agcgtgacca gcgtcgtgag caccctgttc  2580
tacgacaaga aaatgaggac caccaacccc aaggagacca aaatcgtgat cgacaccaca  2640
ggcagcacca agcccaagca ggacgacctg atcctgacct gcttcagggg ctgggtgaag  2700
cagctgcaga tcgactacaa gggcaacgag atcatgaccg ccgctgccag ccagggcctg  2760
accaggaagg gcgtgtacgc cgtgaggtac aaggtgaacg agaacccact gtacgctccc  2820
accagcgagc acgtgaacgt gctgctgacc aggaccgagg acaggatcgt gtggaagacc  2880
ctggccggcg accccctggat caagaccctg accgccaagt accccggcaa cttcaccgcc  2940
accatcgaag agtggcaggc cgagcacgac gccatcatga ggcacatcct ggagaggccc  3000
gaccccaccg acgtgttcca gaacaaggcc aacgtgtgct gggccaaggc cctggtgccc  3060
gtgctgaaga ccgccggcat cgacatgacc acagagcagt ggaacaccgt ggactacttc  3120
gagaccgaca aggcccacag cgccgagatc gtgctgaacc agctgtgcgt gaggttcttc  3180
ggcctggacc tggacagcgg cctgttcagc gcccccaccg tgccactgag catcaggaac  3240
aaccactggg acaacagccc cagcccaaac atgtacggcc tgaacaagga ggtggtcagg  3300
cagctgagca ggcggtaccc acagctgccc agggccgtgg ccaccggcag ggtgtacgac  3360
atgaacaccg gcaccctgag gaactacgac cccaggatca acctggtgcc cgtgaacagg  3420
cggctgcccc acgccctggt gctgcaccac aacgagcacc cacagagcga cttcagctcc  3480
ttcgtgagca agctgaaagg caggaccgtg ctggtcgtgg gcgagaagct gagcgtgccc  3540
ggcaagatgg tggactggct gagcgacagg cccgaggcca ccttccgggc caggctggac  3600
ctcggcatcc ccggcgacgt gcccaagtac gacatcatct tcgtgaacgt caggacccca  3660
tacaagtacc accattacca gcagtgcgag gaccacgcca tcaagctgag catgctgacc  3720
aagaaggcct gcctgcacct gaaccccgga ggcacctgcg tgagcatcgg ctacggctac  3780
gccgacaggg ccagcgagag catcattggc gccatcgcca ggctgttcaa gttcagcagg  3840
gtgtgcaaac ccaagagcag cctggaggaa accgaggtgc tgttcgtgtt catcggctac  3900
gaccggaagg ccaggaccca caacccctac aagctgagca gcaccctgac aaacatctac  3960
accggcagca ggctgcacga ggccggctgc gcccccagct accacgtggt caggggcgat  4020
atcgccaccg ccaccgaggg cgtgatcatc aacgctgcca acagcaaggg ccagcccgga  4080
ggcggagtgt gcggcgccct gtacaagaag ttccccgaga gcttcgacct gcagcccatc  4140
gaggtgggca aggccaggct ggtgaagggc gccgctaagc acatcatcca cgccgtgggc  4200
cccaacttca acaaggtgag cgaggtggaa ggcgacaagc agctggccga agcctacgag  4260
agcatcgcca agatcgtgaa cgacaataac tacaagagcg tggccatccc actgctcagc  4320
accggcatct tcagcggcaa caaggacagg ctgacccaga gcctgaacca cctgctcacc  4380
gccctggaca ccaccgatgc cgacgtggcc atctactgca gggacaagaa gtgggagatg  4440
accctgaagg aggccgtggc caggcgggag gccgtggaag agatctgcat cagcgacgac  4500
tccagcgtga ccgagcccga cgccgagctg gtgagggtgc accccaagag ctccctggcc  4560
ggcaggaagg gctacagcac cagcgacggc aagaccttca gctacctgga gggcaccaag  4620
ttccaccagg ccgctaagga catcgccgag atcaacgcta tgtggcccgt ggccaccgag  4680
gccaacgagc aggtgtgcat gtacatcctg ggcgagagca tgtccagcat caggagcaag  4740
tgccccgtgg aggaaagcga ggccagcaca ccacccagca ccctgccctg cctgtgcatc  4800
cacgctatga cacccgagag ggtgcagcgg ctgaaggcca gcaggcccga gcagatcacc  4860
gtgtgcagct ccttcccact gcccaagtac aggatcaccg gcgtgcagaa gatccagtgc  4920
agccagccca tcctgttcag cccaaaggtg cccgcctaca tccaccccag gaagtacctg  4980
gtggagaccc cacccgtgga cgagacaccc gagccaagcg ccgagaacca gagcaccgag  5040
ggcacacccg agcagccacc cctgatcacc gaggacgaga caaggacccg gaccccagag  5100
cccatcatta tcgaggaaga ggaagaggac agcatcagcc tgctgagcga cggccccacc  5160
caccaggtgc tgcaggtgga ggccgacatc cacggcccac ccagcgtgtc cagctccagc  5220
tggagcatcc cacacgccag cgacttcgac gtggacagcc tgagcatcct ggacaccctg  5280
```

-continued

```
gagggcgcca gcgtgacctc cggcgccacc agcgccgaga ccaacagcta cttcgccaag  5340
agcatggagt tcctggccag gcccgtgcca gctcccagga ccgtgttcag gaacccaccc  5400
cacccagctc ccaggaccag gaccccaagc ctggctccca gcagggcctg cagcaggacc  5460
agcctggtga gcaccccacc cggcgtgaac agggtgatca ccagggagga actggaggcc  5520
ctgacaccca gcaggacccc cagcaggtcc gtgagcagga ctagtctggt gtccaaccca  5580
cccggcgtga acagggtgat caccagggag gaattcgagg ccttcgtggc ccagcaacag  5640
agacggttcg acgccggcgc ctacatcttc agcagcgaca ccggccaggg acacctgcag  5700
caaaagagcg tgaggcagac cgtgctgagc gaggtggtgc tggagaggac cgagctggaa  5760
atcagctacg cccccaggct ggaccaggag aaggaggaac tgctcaggaa gaaactgcag  5820
ctgaacccca ccccagccaa caggagcagg taccagagca ggaaggtgga gaacatgaag  5880
gccatcaccg ccaggcggat cctgcagggc ctgggacact acctgaaggc cgagggcaag  5940
gtggagtgct acaggaccct gcaccccgtg ccactgtaca gctccagcgt gaacagggcc  6000
ttctccagcc ccaaggtggc cgtggaggcc tgcaacgcta tgctgaagga gaacttcccc  6060
accgtggcca gctactgcat catccccgag tacgacgcct acctggacat ggtggacggc  6120
gccagctgct gcctggacac cgccagcttc tgccccgcca agctgaggag cttccccaag  6180
aaacacagct acctggagcc caccatcagg agcgccgtgc ccagcgccat ccagaacacc  6240
ctgcagaacg tgctggccgc tgccaccaag aggaactgca acgtgaccca gatgagggag  6300
ctgcccgtgc tggacagcgc tgccttcaac gtggagtgct tcaagaaata cgcctgcaac  6360
aacgagtact gggagacctt caaggagaac cccatcaggc tgaccgaaga gaacgtggtg  6420
aactacatca ccaagctgaa gggccccaag gccgctgccc tgttcgctaa gacccacaac  6480
ctgaacatgc tgcaggacat cccaatggac aggttcgtga tggacctgaa gagggacgtg  6540
aaggtgacac ccggcaccaa gcacaccgag gagaggccca aggtgcaggt gatccaggcc  6600
gctgacccac tggccaccgc ctacctgtgc ggcatccaca gggagctggt gaggcggctg  6660
aacgccgtgc tgctgcccaa catccacacc ctgttcgaca tgagcgccga ggacttcgac  6720
gccatcatcg ccgagcactt ccagcccggc gactgcgtgc tggagaccga catcgccagc  6780
ttcgacaaga gcgaggatga cgctatggcc ctgaccgctc tgatgatcct ggaggacctg  6840
ggcgtggacg ccgagctgct caccctgatc gaggctgcct tcggcgagat cagctccatc  6900
cacctgccca ccaagaccaa gttcaagttc ggcgctatga tgaaaagcgg aatgttcctg  6960
accctgttcg tgaacaccgt gatcaacatt gtgatcgcca gcagggtgct gcgggagagg  7020
ctgaccggca gcccctgcgc tgccttcatc ggcgacgaca acatcgtgaa gggcgtgaaa  7080
agcgacaagc tgatggccga caggtgcgcc acctggctga acatggaggt gaagatcatc  7140
gacgccgtgg tgggcgagaa ggccccctac ttctgcggcg gattcatcct gtgcgacagc  7200
gtgaccggca ccgcctgcag ggtggccgac cccctgaaga ggctgttcaa gctgggcaag  7260
ccactggccg ctgacgatga gcacgacgat gacaggcgga gggccctgca cgaggaaagc  7320
accaggtgga acagggtggg catcctgagc gagctgtgca aggccgtgga gagcaggtac  7380
gagaccgtgg gcaccagcat catcgtgatg gctatgacca cactggccag ctccgtcaag  7440
agcttctcct acctgagggg ggccccctata actctctacg gctaa                7485
```

SEQ ID NO: 55 moltype = AA length = 2494
FEATURE Location/Qualifiers
REGION 1..2494
note = Synthetic polypeptide
source 1..2494
mol_type = protein
organism = synthetic construct
SEQUENCE: 55

```
MPEKVHVDIE EDSPFLRALQ RSFPQFEVEA KQVTDNDHAN ARAFSHLASK LIETEVDPSD  60
TILDIGSAPA RRMYSKHKYH CICPMRCAED PDRLYKYATK LKKNCKEITD KELDKKMKEL  120
AAVMSDPDLE TETMCLHDDE SCRYEGQVAV YQDVYAVDGP TSLYHQANKG VRVAYWIGFD  180
TTPFMFKNLA GAYPSYSTNW ADETVLTARN IGLCSSDVME RSRRGMSILR KKYLKPSNNV  240
LFSVGSTIYH EKRDLLRSWH LPSVFHLRGK QNYTCRCETI VSCDGYVVKR IAISPGLYGK  300
PSGYAATMHR EGFLCCKVTD TLNGERVSFP VCTYVPATLC DQMTGILATD VSADDAQKLL  360
VGLNQRIVVN GRTQRNTNTM KNYLLPVVAQ AFARWAKEYK EDQEDERPLG LRDRQLVMGC  420
CWAFRRHKIT SIYKRPDTQT IIKVNSDFHS FVLPRIGSNT LEIGLRTRIR KMLEEHKEPS  480
PLITAEDVQE AKCAADEAKE VREAEELRAA LPPLAADVEE PTLEADVDLM LQEAGAGSVE  540
TPRGLIKVTS YDGEDKIGSY AVLSPQAVLK SEKLSCIHPL AEQVIVITHS GRKGRYAVEP  600
YHGKVVVPEG HAIPVQDFQA LSESATIVYN EREFVNRYLH HIATHGGALN TDEEYYKTVK  660
PSEHDGEYLY DIDRKQCVKK ELVTGLGLTG ELVDPPFHEF AYESLRTRPA APYQVPTIGV  720
YGVPGSGKSG IIKSAVTKKD LVVSAKKENC AEIIRDVKKM KGLDVNARTV DSVLLNGCKH  780
PVETLYIDEA FACHAGTLRA LIAIIRPKKA VLCGDPKQCG FFNMMCLKVH FNHEICTQVF  840
HKSISRRCTK SVTSVVSTLF YDKKMRTTNP KETKIVIDTT GSTKPKQDDL ILTCFRGWVK  900
QLQIDYKGNE IMTAAASQGL TRKGVYAVRY KVNENPLYAP TSEHVNVLLT RTEDRIVWKT  960
LAGDPWIKTL TAKYPGNFTA TIEEWQAEHD AIMRHILERP DPTDVFQNKA NVCWAKALVP  1020
VLKTAGIDMT TEQWNTVDYF ETDKAHSAEI VLNQLCVRFF GLDLDSGLFS APTVPLSIRN  1080
NHWDNSPSPN MYGLNKEVVR QLSRRYPQLP RAVATGRVYD MNTGTLRNYD PRINLVPVNR  1140
RLPHALVLHH NEHPQSDFSS FVSKLKGRTV LVVGEKLSVP GKMVDWLSDR PEATFRARLD  1200
LGIPGDVPKY DIIFVNVRTP YKYHHYQQCE DHAIKLSMLT KKACLHLNPG GTCVSIGYGY  1260
ADRASESIIG AIARLFKFSR VCKPKSSLEE TEVLFVFIGY DRKARTHNPY KLSSTLTNIY  1320
TGSRLHEAGC APSYHVVRGD IATATEGVII NAANSKGQPG GGVCGALYKK FPESFDLQPI  1380
EVGKARLVKG AAKHIIHAVG PNFNKVSEVE GDKQLAEAYE SIAKIVNDNN YKSVAIPLLS  1440
TGIFSGNKDR LTQSLNHLLT ALDTTDADVA IYCRDKKWEM TLKEAVARRE AVEEICISDD  1500
SSVTEPDAEL VRVHPKSSLA GRKGYSTSDG KTFSYLEGTK FHQAAKDIAE INAMWPVATE  1560
ANEQVCMYIL GESMSSIRSK CPVEESEAST PPSTLPCLCI HAMTPERVQR LKASRPEQIT  1620
VCSSFPLPKY RITGVQKIQC SQPILFSPKV PAYIHPRKYL VETPPVDETP EPSAENQSTE  1680
GTPEQPPLIT EDETRTRTPE PIIIEEEEED SISLLSDGPT HQVLQVEADI HGPPSVSSSS  1740
WSIPHASDFD VDSLSILDTL EGASVTSGAT SAETNSYFAK SMEFLARPVP APRTVFRNPP  1800
HPAPRTRTPS LAPSRACSRT SLVSTPPGVN RVITREELEA LTPSRTPSRS VSRTSLVSNP  1860
PGVNRVITRE EFEAFVAQQQ RRFDAGAYIF SSDTGQGHLQ QKSVRQTVLS EVVLERTELE  1920
ISYAPRLDQE KEELLRKKLQ LNPTPANRSR YQSRKVENMK AITARRILQG LGHYLKAEGK  1980
```

-continued

```
VECYRTLHPV PLYSSSVNRA FSSPKVAVEA CNAMLKENFP TVASYCIIPE YDAYLDMVDG  2040
ASCCLDTASF CPAKLRSFPK KHSYLEPTIR SAVPSAIQNT LQNVLAAATK RNCNVTQMRE  2100
LPVLDSAAFN VECFKKYACN NEYWETFKEN PIRLTEENVV NYITKLKGPK AAALFAKTHN  2160
LNMLQDIPMD RFVMDLKRDV KVTPGTKHTE ERPKVQVIQA ADPLATAYLC GIHRELVRRL  2220
NAVLLPNIHT LFDMSAEDFD AIIAEHFQPG DCVLETDIAS FDKSEDDAMA LTALMILEDL  2280
GVDAELLTLI EAAFGEISSI HLPTKTKFKF GAMMKSGMFL TLFVNTVINI VIASRVLRER  2340
LTGSPCAAFI GDDNIVKGVK SDKLMADRCA TWLNMEVKII DAVVGEKAPY FCGGFILCDS  2400
VTGTACRVAD PLKRLFKLGK PLAADDEHDD DRRRALHEES TRWNRVGILS ELCKAVESRY  2460
ETVGTSIIVM AMTTLASSVK SFSYLRGAPI TLYG                             2494

SEQ ID NO: 56          moltype = RNA  length = 9739
FEATURE                Location/Qualifiers
misc_feature           1..9739
                       note = Synthetic polynucleotide
source                 1..9739
                       mol_type = other RNA
                       organism = synthetic construct
SEQUENCE: 56
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccacccact ggccgagcag gtgatcgtga  1800
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
agggcaacga gatcatgacc gccgctgcca gccagggcct gaccaggaag ggcgtgtacg  2820
ccgtgaggta caaggtgaac gagaacccac tgtacgctcc caccagcgag cacgtgaacg  2880
tgctgctgac caggaccgag gacaggatcg tgtggaagac cctggccggc gacccctgga  2940
tcaagaccct gaccgccaag taccccggca acttcaccgc caccatcgaa gagtggcagg  3000
ccgagcacga cgccatcatg aggcacatcc tggagaggcc cgaccccacc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcaccctga  3420
ggaactacga ccccaggatc aacctggtgc ccgtgaacag gcggctgccc cacgccctgg  3480
tgctgcacca caacgagcac cccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc cccggcgacg  3660
```

-continued

```
tgcccaagta cgacatcatc ttcgtgaacg tcaggacccc atacaagtac caccattacc  3720
agcagtgcga ggaccacgcc atcaagctga gcatgctgac caagaaggcc tgcctgcacc  3780
tgaaccccgg aggcacctgc gtgagcatcg gctacggcta cgccgacagg gccagcgaga  3840
gcatcattgg cgccatcgcc aggctgttca agttcagcag ggtgtgcaaa cccaagagca  3900
gcctggagga aaccgaggtg ctgttcgtgt tcatcggcta cgaccggaag gccaggaccc  3960
acaaccccta caagctgagc agcaccctga caaacatcta caccggcagc aggctgcacg  4020
aggccggctg cgcccccagc taccacgtgg tcaggggcga tatcgccacc gccaccgagg  4080
gcgtgatcat caacgctgcc aacagcaagg gccagcccgg aggcggagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg ccccaacttc aacaaggtga  4260
gcgaggtgga aggcgacaag cagctggccg aagcctacga gagcatcgcc aagatcgtga  4320
acgacaataa ctacaagagc gtggccatcc cactgctcag caccggcatc ttcagcggca  4380
acaaggacag gctgacccag agcctgaacc acctgctcac cgccctggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgagggtg caccccaaga gctccctggc cggcaggaag ggctacagca  4620
ccagcgacgg caagaccttc agctacctgg agggcaccaa gttccaccag gccgctaagg  4680
acatcgccga gatcaacgct atgtggcccg tggccaccga ggccaacgag caggtgtgca  4740
tgtacatcct gggcgagagc atgtccagca tcaggagcaa gtgccccgtg gaggaaagcg  4800
aggccagcac accacccagc accctgccct gcctgtgcat ccacgctatg acacccgaga  4860
gggtgcagcg gctgaaggcc agcaggcccg agcagatcac cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagacc ccacccgtgg  5040
acgagacacc cgagccaagc gccgagaacc agagcaccga gggcacaccc gagcagccac  5100
ccctgatcac cgaggacgag acaaggaccc ggaccccaga gcccatcatt atcgaggaag  5160
aggaagagga cagcatcagc ctgctgagcg acggccccac ccaccaggtg ctgcaggtgg  5220
aggccgacat ccacggccca cccagcgtgt ccagctccag ctggagcatc ccacacgcca  5280
gcgacttcga cgtggacagc ctgagcatcc tggacaccct ggagggcgcc agcgtgacct  5340
ccggcgccac cagcgccgag accaacagct acttcgccaa gagcatggag ttcctggcca  5400
ggcccgtgcc agctcccagg accgtgttca ggaacccacc ccacccagct cccaggacca  5460
ggaccccaag cctggctccc agcagggcct gcagcaggac cagcctggtg agcaccccac  5520
ccggcgtgaa cagggtgatc accagggagg aactggaggc cctgacaccc agcaggaccc  5580
ccagcaggtc cgtgagcagg actagtctgg tgtccaaccc acccggcgtg aacagggtga  5640
tcaccaggga ggaattcgag gccttcgtgg cccagcaaca gagacggttc gacgccggcg  5700
cctacatctt cagcagcgac accggccagg gacacctgca gcaaaagagc gtgaggcaga  5760
ccgtgctgag cgaggtggtg ctggagagga ccgagctgga aatcagctac gcccccaggc  5820
tggaccagga gaaggaggaa ctgctcagga agaaactgca gctgaacccc accccagcca  5880
acaggagcag gtaccagagc aggaaggtgg agaacatgaa ggccatcacc gccaggcgga  5940
tcctgcaggg cctgggacac tacctgaagg ccgagggcaa ggtggagtgc tacaggaccc  6000
tgcaccccgt gccactgtac agctccagcg tgaacagggc cttctccagc cccaaggtgg  6060
ccgtggaggc ctgcaacgct atgctgaagg agaacttccc caccgtggcc agctactgca  6120
tcatccccga gtacgacgcc tacctggaca tggtggacgg cgccagctgc tgcctggaca  6180
ccgccagctt ctgccccgcc aagctgagga gcttccccaa gaaacacagc tacctggagc  6240
ccaccatcag gagcgccgtg cccagcgcca tccagaacac cctgcagaac gtgctggccg  6300
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggccccaa ggccgctgcc ctgttcgcta agacccacaa cctgaacatg ctgcaggaca  6540
tcccaatgga caggttcgtg atggacctga agagggacgt gaaggtgaca cccggcacca  6600
agcacaccga ggagaggccc aaggtgcagg tgatccaggc cgctgaccca ctggccaccg  6660
cctacctgtg cggcatccac agggagctgg tgaggcggct gaacgccgtg ctgctgccca  6720
acatccacac cctgttcgac atgagcgccg aggacttcga cgccatcatc gccgagcact  6780
tccagcccgg cgactgcgtg ctggagaccg acatcgccag cttcgacaag agcgaggatg  6840
acgctatggc cctgaccgct ctgatgatcc tggaggacct gggcgtggac gccgagctgc  6900
tcaccctgat cgaggctgcc ttcggcgaga tcagctccat ccacctgccc accaagacca  6960
agttcaagtt cggcgctatg atgaaaagcg gaatgttcct gaccctgttc gtgaacaccg  7020
tgatcaacat tgtgatcgcc agcagggtgc tgcgggagag gctgaccggc agcccctgcg  7080
ctgccttcat cggcgacgac aacatcgtga agggcgtgaa aagcgacaag ctgatggccg  7140
acaggtgcgc cacctggctg aacatggagg tgaagatcat cgacgccgtg gtgggcgaga  7200
aggcccccta cttctgcggc ggattcatcc tgtgcgacag cgtgaccggc accgcctgca  7260
gggtggccga ccccctgaag aggctgttca agctgggcaa gccactggcc gctgacgatg  7320
agcacgacga tgacaggcgg agggccctgc acgaggaaag caccaggtgg aacagggtgg  7380
gcatcctgag cgagctgtgc aaggccgtgg agagcaggta cgagaccgtg ggcaccagca  7440
tcatcgtgat ggctatgacc acactggcca gctccgtcaa gagcttctcc tacctgaggg  7500
gggcccctat aactctctac ggctaacctg aatggactac gacatagtct agtccgccaa  7560
ggccgccacc atgaaggcta tcctggtggt gctgctctac acctttgcca cagccaatgc  7620
tgacaccctg tgtattggct accatgccaa caacagcaca gacacagtgg acacagtgtt  7680
ggagaagaat gtgacagtga cccactctgt gaacctgttg gaggacaaac acaatggcaa  7740
actgtgtaaa ctgaggggag tggctccact gcacctgggc aagtgtaaca ttgctggctg  7800
gattctgggc aaccctgagt gtgagtccct gagcacagcc tcctcctggt cctacattgt  7860
ggagacacca tcctctgaca atggcacttg ttaccctgga gacttcattg actatgagga  7920
actgagggaa caactttcct ctgtgtcctc ctttgagagg tttgagattt ttccaaagac  7980
ctcctcctgg ccaaaccatg acagcaacaa gggagtgaca gcagcctgtc cacatgctgg  8040
agccaagtcc ttctacaaga acctgatttg gctggtgaag aagggcaact cctacccaaa  8100
actgagcaag tcctacatca atgacaaggg caaggaggtg ctggtgctgt ggggcatcca  8160
ccacccaagc acctctgctg accaacagtc cctctaccag aatgctgacg cctatgtgtt  8220
tgtgggctcc agcagataca gcaagaagtt caagcctgag attgccatca gaccaaaggt  8280
gagggatcag gagggcagga tgaactacta ctggaccctg gtggaacctg gagacaagat  8340
tacctttgag gctacaggca acctggtggt gccaagatat gcctttgcta tggagaggaa  8400
```

-continued

```
tgctggctct ggcatcatca tctctgacac acctgtccat gactgtaaca ccacttgtca  8460
gacaccaaag ggagccatca acacctccct gccattccag aacatccacc caatcaccat  8520
tggcaagtgt ccaaaatatg tcaagagcac caaactgaga ctggctacag gactgaggaa  8580
catcccaagc atccagagca ggggactgtt tggagccatt gctggcttca ttgagggagg  8640
ctggacaggg atggtggatg gctggtatgg ctaccaccac cagaatgaac agggctctgg  8700
ctatgctgct gacctgaaaa gcacccagaa tgccattgat gagattacca acaaggtgaa  8760
ctctgtgatt gagaagatga acacccagtt cacagcagtg ggcaaggagt tcaaccactt  8820
ggagaagagg attgagaacc tgaacaagaa ggtggatgat ggcttcctgg acatctggac  8880
ctacaatgct gaactgctgg tgctgttgga gaatgagagg accctggact accatgacag  8940
caatgtgaag aacctctatg agaaggtgag gagccaactt aaaaacaatg ccaaggagat  9000
tggcaatggc tgttttgagt tctaccacaa gtgtgacaac acttgtatgg agtctgtgaa  9060
gaatggcacc tatgactacc caaaatactc tgaggaggct aaactgaaca gggaggagat  9120
tgatggagtg aaattggaga gcaccaggat ttaccagatc ctggccatct acagcaccgt  9180
ggccagcagc ctggtgctgg tggtgagcct gggcgccatc agcttctgga tgtgcagcaa  9240
cggcagcttg cagtgcagga tctgcatcta aactcgagta tgttacgtgc aaaggtgatt  9300
gtcacccccc gaaagaccat attgtgacac accctcagta tcacgcccaa acatttacag  9360
ccgcggtgtc aaaaaccgcg tggacgtggt taacatccct gctgggagga tcagccgtaa  9420
ttattataat tggcttggtg ctggctacta ttgtggccat gtacgtgctg accaaccaga  9480
aacataattg aatacagcag caattggcaa gctgcttaca tagaactcgc ggcgattggc  9540
atgccgcctt aaaattttta ttttattttt tcttttcttt tccgaatcgg attttgtttt  9600
taatatttca aaaaaaaaaa aaaaaaaaaa aaaatctaga aaaaaaaaaa aaaaaaaaaa  9660
aaaaaaaaaa aaaaaaaaaa aaaaaaaaaa aaaaaaaaaa aaaaaaaaaa aaaaaaaaaa  9720
aaaaaaaaaa aaaaaaaaa                                                9739

SEQ ID NO: 57          moltype = RNA  length = 448
FEATURE                Location/Qualifiers
misc_feature           1..448
                       note = Synthetic polynucleotide
source                 1..448
                       mol_type = other RNA
                       organism = synthetic construct
SEQUENCE: 57
gataggcggc gcatgagaga agcccagacc aattacctac ccaaatagga gaaagttcac  60
gttgacatcg aggaagacag cccattcctc agagctttgc agcggagctt cccgcagttt  120
gaggtagaag ccaagcaggt cactgataat gaccatgcta atgccagagc gttttcgcat  180
ctggcttcaa aactgatcga aacggaggtg gacccatccg acacgatcct tgacattgga  240
atagtcagca tagtacattt catctgacta atactacaac accaccacca tgaatagagg  300
attctttaac atgctcggcc gccgcccctt cccggccccc actgccatgt ggaggccgcg  360
gagaaggagg caggcggccc cgggaagcgg agctactaac ttcagcctgc tgaagcaggc  420
tggagacgtg gaggagaacc ctggacct                                    448

SEQ ID NO: 58          moltype =   length =
SEQUENCE: 58
000

SEQ ID NO: 59          moltype =   length =
SEQUENCE: 59
000

SEQ ID NO: 60          moltype =   length =
SEQUENCE: 60
000

SEQ ID NO: 61          moltype =   length =
SEQUENCE: 61
000

SEQ ID NO: 62          moltype =   length =
SEQUENCE: 62
000

SEQ ID NO: 63          moltype =   length =
SEQUENCE: 63
000

SEQ ID NO: 64          moltype =   length =
SEQUENCE: 64
000

SEQ ID NO: 65          moltype =   length =
SEQUENCE: 65
000

SEQ ID NO: 66          moltype =   length =
SEQUENCE: 66
000

SEQ ID NO: 67          moltype = DNA  length = 30
FEATURE                Location/Qualifiers
```

```
misc_feature          1..30
                      note = Synthetic polynucleotide
source                1..30
                      mol_type = other DNA
                      organism = synthetic construct
SEQUENCE: 67
atggactacg acatagtcta gtccgccaag                                  30

SEQ ID NO: 68         moltype = DNA  length = 16
FEATURE               Location/Qualifiers
misc_feature          1..16
                      note = Synthetic polynucleotide
source                1..16
                      mol_type = other DNA
                      organism = synthetic construct
SEQUENCE: 68
atggactacg acatag                                                 16

SEQ ID NO: 69         moltype = DNA  length = 15
FEATURE               Location/Qualifiers
misc_feature          1..15
                      note = Synthetic polynucleotide
source                1..15
                      mol_type = other DNA
                      organism = synthetic construct
SEQUENCE: 69
atggactacg acata                                                  15

SEQ ID NO: 70         moltype =   length =
SEQUENCE: 70
000

SEQ ID NO: 71         moltype =   length =
SEQUENCE: 71
000

SEQ ID NO: 72         moltype = DNA  length = 7482
FEATURE               Location/Qualifiers
misc_feature          1..7482
                      note = Synthetic polynucleotide
source                1..7482
                      mol_type = other DNA
                      organism = synthetic construct
SEQUENCE: 72
atggagaaag ttcacgttga catcgaggaa gacagcccat tcctcagagc tttgcagcgg  60
agcttcccgc agtttgaggt agaagccaag caggtcactg ataatgacca tgctaatgcc  120
agagcgtttt cgcatctggc ttcaaaactg atcgaaacgg aggtggaccc atccgacacg  180
atccttgaca ttggaagtgc gcccgcccgc agaatgtatt ctaagcacaa gtatcattgt  240
atctgtccga tgagatgtgc ggaagatccg gacagattgt ataagtatgc aactaagctg  300
aagaaaaact gtaaggaaat aactgataag gaattggaca agaaaatgaa ggagctggcc  360
gccgtcatga gcgaccctga cctggaaact gagactatgt gcctccacga cgacgagtcg  420
tgtcgctacg aagggcaagt cgctgtttac caggatgtat acgccgtcga cggccccacc  480
agcctgtacc accaggccaa caagggcgtg agggtggcct actggatcgg cttcgacacc  540
acacccttca tgttcaagaa cctggccggc gcctacccca gctacagcac caactgggcc  600
gacgagaccg tgctgaccgc caggaacatc ggcctgtgca gcagcgacgt gatggagagg  660
agccggagag gcatgagcat cctgaggaag aaatacctga agcccagcaa caacgtgctg  720
ttcagcgtgg gcagcaccat ctaccacgag aagagggacc tgctcaggag ctggcacctg  780
cccagcgtgt tccacctgag gggcaagcag aactacacct gcaggtgcga gaccatcgtg  840
agctgcgacg gctacgtggt gaagaggatc gccatcagcc ccggcctgta cggcaagccc  900
agcggctacg ccgctacaat gcacagggag ggcttcctgt gctgcaaggt gaccgacacc  960
ctgaacggcg agagggtgag cttccccgtg tgcacctacg tgcccgccac cctgtgcgac  1020
cagatgaccg gcatcctggc caccgacgtg agcgccgacg acgcccagaa gctgctcgtg  1080
ggcctgaacc agaggatcgt ggtcaacggc aggacccaga ggaacaccaa cacaatgaag  1140
aactacctgc tgcccgtggt ggcccaggct ttcgccaggt gggccaagga gtacaaggag  1200
gaccaggaag acgagaggcc cctgggcctg agggacaggc agctggtgat gggctgctgc  1260
tgggccttca ggcggcacaa gatcaccagc atctacaaga ggcccgacac ccagaccatc  1320
atcaaggtga acagcgactt ccacagcttc gtgctgccca ggatcggcag caacaccctg  1380
gagatcggcc tgaggacccg gatcaggaag atgctggagg aacacaagga gcccagccca  1440
ctgatcaccg ccgaggacgt gcaggaggcc aagtgcgctg ccgacgaggc caaggaggtg  1500
agggaggccg aggaactgag ggccgccctg ccacccctgg ctgccgacgt ggaggaaccc  1560
accctggaag ccgacgtgga cctgatgctg caggaggccg gcgccggaag cgtggagaca  1620
cccaggggcc tgatcaaggt gaccagctac gacggcgagg acaagatcgg cagctacgcc  1680
gtgctgagcc cacaggccgt gctgaagtcc gagaagctga gctgcatcca cccactggcc  1740
gagcaggtga tcgtgatcac ccacagcggc aggaagggca ggtacgccgt ggagccctac  1800
cacggcaagg tggtcgtgcc cgagggccac gccatccccg tgcaggactt ccaggccctg  1860
agcgagagcg ccaccatcgt gtacaacgag agggagttcg tgaacaggta cctgcaccat  1920
atcgccaccc acggcggagc cctgaacacc gacgaggaat actacaagac cgtgaagccc  1980
agcgagcacg acggcgagta cctgtacgac atcgacagga agcagtgcgt gaagaaagag  2040
ctggtgaccg gcctgggact gaccggcgag ctggtggacc caccccttcca cgagttcgcc  2100
```

-continued

```
tacgagagcc tgaggaccag acccgccgct ccctaccagg tgcccaccat cggcgtgtac  2160
ggcgtgcccg gcagcggaaa gagcggcatc atcaagagcg ccgtgaccaa gaaagacctg  2220
gtggtcagcg ccaagaaaga gaactgcgcc gagatcatca gggacgtgaa gaagatgaaa  2280
ggcctggacg tgaacgcgcg caccgtggac agcgtgctgc tgaacggctg caagcacccc  2340
gtggagaccc tgtacatcga cgaggccttc gcttgccacg ccggcaccct gagggccctg  2400
atcgccatca tcaggcccaa gaaagccgtg ctgtgcggcg accccaagca gtgcggcttc  2460
ttcaacatga tgtgcctgaa ggtgcacttc aaccacgaga tctgcaccca ggtgttccac  2520
aagagcatca gcaggcggtg caccaagagc gtgaccagcg tcgtgagcac cctgttctac  2580
gacaagaaaa tgaggaccac caaccccaag gagaccaaaa tcgtgatcga caccacaggc  2640
agcaccaagc ccaagcagga cgacctgatc ctgacctgct tcaggggctg ggtgaagcag  2700
ctgcagatcg actacaaggg caacgagatc atgaccgccg ctgccagcca gggcctgacc  2760
aggaagggcg tgtacgccgt gaggtacaag gtgaacgaga acccactgta cgctccccacc  2820
agcgagcacg tgaacgtgct gctgaccagg accgaggaca ggatcgtgtg gaagaccctg  2880
gccggcgacc cctggatcaa gaccctgacc gccaagtacc ccggcaactt caccgccacc  2940
atcgaagagt ggcaggccga gcacgacgcc atcatgaggc acatcctgga gaggcccgac  3000
cccaccgacg tgttccagaa caaggccaac gtgtgctggg ccaaggccct ggtgcccgtg  3060
ctgaagaccg ccggcatcga catgaccaca gagcagtgga acaccgtgga ctacttcgag  3120
accgacaagg cccacagcgc cgagatcgtg ctgaaccagc tgtgcgtgag gttcttcggc  3180
ctggacctgg acagcggcct gttcagcgcc cccaccgtgc cactgagcat caggaacaac  3240
cactgggaca acagccccag cccaaacatg tacggcctga acaaggaggt ggtcaggcag  3300
ctgagcaggc ggtacccaca gctgcccagg gccgtggcca ccggcagggt gtacgacatg  3360
aacaccggca ccctgaggaa ctacgacccc aggatcaacc tggtgcccgt gaacaggcgg  3420
ctgccccacg ccctggtgct gcaccacaac gagcacccac agagcgactt cagctccttc  3480
gtgagcaagc tgaaaggcag gaccgtgctg gtcgtgggcg agaagctgag cgtgcccggc  3540
aagatggtgg actggctgag cgacaggccc gaggccacct tccgggccag gctggacctc  3600
ggcatccccg gcgacgtgcc caagtacgac atcatcttcg tgaacgtcag gaccccatac  3660
aagtaccacc attaccagca gtgcgaggac cacgccatca agctgagcat gctgaccaag  3720
aaggcctgcc tgcacctgaa ccccggaggc acctgcgtga gcatcggcta cggctacgcc  3780
gacagggcca gcgagagcat cattggcgcc atcgccaggc tgttcaagtt cagcagggtg  3840
tgcaaaccca agagcagcct ggaggaaacc gaggtgctgt tcgtgttcat cggctacgac  3900
cggaaggcca ggacccacaa cccctacaag ctgagcagca ccctgacaaa catctacacc  3960
ggcagcaggc tgcacgaggc cggctgcgcc cccagctacc acgtggtcag gggcgatatc  4020
gccaccgcca ccgagggcgt gatcatcaac gctgccaaca gcaagggcca gcccggaggc  4080
ggagtgtgcg gcgccctgta caagaagttc cccgagagct tcgacctgca gcccatcgag  4140
gtgggcaagg ccaggctggt gaagggcgcc gctaagcaca tcatccacgc cgtgggcccc  4200
aacttcaaca aggtgagcga ggtggaaggc gacaagcagc tggccgaagc ctacgagagc  4260
atcgccaaga tcgtgaacga caataactac aagagcgtgg ccatcccact gctcagcacc  4320
ggcatcttca gcggcaacaa ggacaggctg acccagagcc tgaaccacct gctcaccgcc  4380
ctggacacca ccgatgccga cgtggccatc tactgcaggg acaagaagtg ggagatgacc  4440
ctgaaggagg ccgtggccag gcgggaggcc gtggaagaga tctgcatcag cgacgactcc  4500
agcgtgaccg agcccgacgc cgagctggtg agggtgcacc ccaagagctc cctggccggc  4560
aggaagggct acagcaccag cgacggcaag accttcagct acctggaggg caccaagttc  4620
caccaggccg ctaaggacat cgccgagatc aacgctatgt ggcccgtggc caccgaggcc  4680
aacgagcagg tgtgcatgta catcctgggc gagagcatgt ccagcatcag gagcaagtgc  4740
cccgtggagg aaagcgaggc cagcacacca cccagcaccc tgccctgcct gtgcatccac  4800
gctatgacac ccgagagggt gcagcggctg aaggccagca ggcccgagca gatcaccgtg  4860
tgcagctcct tcccactgcc caagtacagg atcaccggcg tgcagaagat ccagtgcagc  4920
cagcccatcc tgttcagccc aaaggtgccc gcctacatcc accccaggaa gtacctggtg  4980
gagaccccac ccgtggacga gacacccgag ccaagcgccg agaaccagag caccgagggc  5040
acacccgagc agccacccct gatcaccgag gacgagacaa ggacccggac cccagagccc  5100
atcattatcg aggaagagga agaggacagc atcagcctgc tgagcgacgg ccccacccac  5160
caggtgctgc aggtggaggc cgacatccac ggcccaccca gcgtgtccag ctccagctgg  5220
agcatcccac acgccagcga cttcgacgtg gacagcctga gcatcctgga caccctggag  5280
ggcgccagcg tgacctccgg cgccaccagc gccgagacca acagctactt cgccaagagc  5340
atggagttcc tggccaggcc cgtgccagct cccaggaccg tgttcaggaa cccaccccac  5400
ccagctccca ggaccaggac cccaagcctg gctcccagca gggcctgcag caggaccagc  5460
ctggtgagca ccccacccgg cgtgaacagg gtgatcacca gggaggaact ggaggccctg  5520
acacccagca ggacccccag caggtccgtg agcaggacta gtctggtgtc caacccaccc  5580
ggcgtgaaca gggtgatcac cagggaggaa ttcgaggcct tcgtggccca gcaacagaga  5640
cggttcgacg ccggcgccta catcttcagc agcgacaccg gccagggaca cctgcagcaa  5700
aagagcgtga ggcagaccgt gctgagcgag gtggtgctgg agaggaccga gctggaaatc  5760
agctacgccc ccaggctgga ccaggagaag gaggaactgc tcaggaagaa actgcagctg  5820
aaccccaccc cagccaacag gagcaggtac cagagcagga aggtggagaa catgaaggcc  5880
atcaccgcca ggcggatcct gcagggcctg ggacactacc tgaaggccga gggcaaggtg  5940
gagtgctaca ggaccctgca ccccgtgcca ctgtacagct ccagcgtgaa cagggccttc  6000
tccagcccca aggtggccgt ggaggcctgc aacgctatgc tgaaggagaa cttccccacc  6060
gtggccagct actgcatcat ccccgagtac gacgcctacc tggacatggt ggacggcgcc  6120
agctgctgcc tggacaccgc cagcttctgc cccgccaagc tgaggagctt ccccaagaaa  6180
cacagctacc tggagcccac catcaggagc gccgtgccca gcgccatcca gaacaccctg  6240
cagaacgtgc tggccgctgc caccaagagg aactgcaacg tgacccagat gagggagctg  6300
cccgtgctgg acagcgctgc cttcaacgtg gagtgcttca agaaatacgc ctgcaacaac  6360
gagtactggg agaccttcaa ggagaacccc atcaggctga ccgaagagaa cgtggtgaac  6420
tacatcacca agctgaaggg ccccaaggcc gctgccctgt tcgctaagac ccacaacctg  6480
aacatgctgc aggacatccc aatggacagg ttcgtgatgg acctgaagag ggacgtgaag  6540
gtgacacccg gcaccaagca caccgaggag aggcccaagg tgcaggtgat ccaggccgct  6600
gacccactgg ccaccgccta cctgtgcggc atccacaggg agctggtgag gcggctgaac  6660
gccgtgctgc tgcccaacat ccacaccctg ttcgacatga gcgccgagga cttcgacgcc  6720
atcatcgccg agcacttcca gcccggcgac tgcgtgctgg agaccgacat cgccagcttc  6780
gacaagagcg aggatgacgc tatggccctg accgctctga tgatcctgga ggacctgggc  6840
```

```
gtggacgccg agctgctcac cctgatcgag gctgccttcg gcgagatcag ctccatccac  6900
ctgcccacca agaccaagtt caagttcggc gctatgatga aaagcggaat gttcctgacc  6960
ctgttcgtga acaccgtgat caacattgtg atcgccagca gggtgctgcg ggagaggctg  7020
accggcagcc cctgcgctgc cttcatcggc gacgacaaca tcgtgaaggg cgtgaaaagc  7080
gacaagctga tggccgacag gtgcgccacc tggctgaaca tggaggtgaa gatcatcgac  7140
gccgtggtgg gcgagaaggc cccctacttc tgcggcggat tcatcctgtg cgacagcgtg  7200
accggcaccg cctgcagggt ggccgacccc ctgaagaggc tgttcaagct gggcaagcca  7260
ctggccgctg acgatgagca cgacgatgac aggcggaggg ccctgcacga ggaaagcacc  7320
aggtggaaca gggtgggcat cctgagcgag ctgtgcaagg ccgtggagag caggtacgag  7380
accgtgggca ccagcatcat cgtgatggct atgaccacac tggccagctc cgtcaagagc  7440
ttctcctacc tgaggggggc ccctataact ctctacggct aa                        7482
```

SEQ ID NO: 73 moltype = DNA length = 44
FEATURE Location/Qualifiers
misc_feature 1..44
note = Synthetic polynucleotide
source 1..44
mol_type = other DNA
organism = synthetic construct
SEQUENCE: 73

```
atgggcggcg catgagagaa gcccagacca attacctacc caaa                     44
```

SEQ ID NO: 74 moltype = DNA length = 45
FEATURE Location/Qualifiers
misc_feature 1..45
note = Synthetic polynucleotide
source 1..45
mol_type = other DNA
organism = synthetic construct
SEQUENCE: 74

```
gatgggcggc gcatgagaga agcccagacc aattacctac ccaaa                    45
```

SEQ ID NO: 75 moltype = DNA length = 45
FEATURE Location/Qualifiers
misc_feature 1..45
note = Synthetic polynucleotide
source 1..45
mol_type = other DNA
organism = synthetic construct
SEQUENCE: 75

```
gataggcggc gcatgagaga agcccagacc aattacctac ccaaa                    45
```

SEQ ID NO: 76 moltype = DNA length = 468
FEATURE Location/Qualifiers
misc_feature 1..468
note = Synthetic polynucleotide
source 1..468
mol_type = other DNA
organism = synthetic construct
SEQUENCE: 76

```
actcgagtat gttacgtgca aaggtgattg tcacccccg aaagaccata ttgtgacaca  60
ccctcagtat cacgcccaaa catttacagc cgcggtgtca aaaaccgcgt ggacgtggtt  120
aacatccctg ctgggaggat cagccgtaat tattataatt ggcttggtgc tggctactat  180
tgtggccatg tacgtgctga ccaaccagaa acataattga atacagcagc aattggcaag  240
ctgcttacat agaactcgcg gcgattggca tgccgcctta aaatttttat tttatttttt  300
cttttctttt ccgaatcgga ttttgttttt aatatttcaa aaaaaaaaaa aaaaaaaaaa  360
aaatctagaa aaaaaaaaaa aaaaaaaaaa aaaaaaaaaa aaaaaaaaaa aaaaaaaaaa  420
aaaaaaaaaa aaaaaaaaaa aaaaaaaaaa aaaaaaaaaa aaaaaaaa              468
```

SEQ ID NO: 77 moltype = DNA length = 44
FEATURE Location/Qualifiers
misc_feature 1..44
note = Synthetic polynucleotide
source 1..44
mol_type = other DNA
organism = synthetic construct
SEQUENCE: 77

```
cctgaatgga ctacgacata gtctagtccg ccaaggccgc cacc                     44
```

SEQ ID NO: 78 moltype = DNA length = 8038
FEATURE Location/Qualifiers
misc_feature 1..8038
note = Synthetic polynucleotide
source 1..8038
mol_type = other DNA
organism = synthetic construct
SEQUENCE: 78

```
atgggcggcg catgagagaa gcccagacca attacctacc caaaatggag aaagttcacg  60
ttgacatcga ggaagacagc ccattcctca gagctttgca gcggagcttc ccgcagtttg  120
```

-continued

```
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccacccact ggccgagcag gtgatcgtga  1800
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
agggcaacga gatcatgacc gccgctgcca gccagggcct gaccaggaag ggcgtgtacg  2820
ccgtgaggta caaggtgaac gagaacccac tgtacgctcc caccagcgag cacgtgaacg  2880
tgctgctgac caggaccgag gacaggatcg tgtggaagac cctggccggc gacccctgga  2940
tcaagaccct gaccgccaag taccccggca acttcaccgc caccatcgaa gagtggcagg  3000
ccgagcacga cgccatcatg aggcacatcc tggagaggcc cgaccccacc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcaccctga  3420
ggaactacga ccccaggatc aacctggtgc ccgtgaacag gcggctgccc cacgccctgg  3480
tgctgcacca caacgagcac cccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc cccggcgacg  3660
tgcccaagta cgacatcatc ttcgtgaacg tcaggacccc atacaagtac caccattacc  3720
agcagtgcga ggaccacgcc atcaagctga gcatgctgac caagaaggcc tgcctgcacc  3780
tgaaccccgg aggcacctgc gtgagcatcg gctacggcta cgccgacagg gccagcgaga  3840
gcatcattgg cgccatcgcc aggctgttca agttcagcag ggtgtgcaaa cccaagagca  3900
gcctggagga aaccgaggtg ctgttcgtgt tcatcggcta cgaccggaag gccaggaccc  3960
acaaccccta caagctgagc agcaccctga caaacatcta caccggcagc aggctgcacg  4020
aggccggctg cgcccccagc taccacgtgg tcaggggcga tatcgccacc gccaccgagg  4080
gcgtgatcat caacgctgcc aacagcaagg gccagcccgg aggcggagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg ccccaacttc aacaaggtga  4260
gcgaggtgga aggcgacaag cagctggccg aagcctacga gagcatcgcc aagatcgtga  4320
acgacaataa ctacaagagc gtggccatcc cactgctcag caccggcatc ttcagcggca  4380
acaaggacag gctgacccag agcctgaacc acctgctcac cgccctggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgagggtg cacccccaaga gctccctggc cggcaggaag ggctacagca  4620
ccagcgacgg caagaccttc agctacctgg agggcaccaa gttccaccag gccgctaagg  4680
acatcgccga gatcaacgct atgtggcccg tggccaccga ggccaacgag caggtgtgca  4740
tgtacatcct gggcgagagc atgtccagca tcaggagcaa gtgccccgtg gaggaaagcg  4800
aggccagcac accacccagc accctgccct gcctgtgcat ccacgctatg acacccgaga  4860
```

-continued

```
gggtgcagcg gctgaaggcc agcaggcccg agcagatcac cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagacc ccacccgtgg  5040
acgagacacc cgagccaagc gccgagaacc agagcaccga gggcacaccc gagcagccac  5100
ccctgatcac cgaggacgag acaaggaccc ggaccccaga gcccatcatt atcgaggaag  5160
aggaagagga cagcatcagc ctgctgagcg acggccccac ccaccaggtg ctgcaggtgg  5220
aggccgacat ccacggccca cccagcgtgt ccagctccag ctggagcatc ccacacgcca  5280
gcgacttcga cgtggacagc ctgagcatcc tggacaccct ggagggcgcc agcgtgacct  5340
ccggcgccac cagcgccgag accaacagct acttcgccaa gagcatggag ttcctggcca  5400
ggcccgtgcc agctcccagg accgtgttca ggaacccacc ccacccagct cccaggacca  5460
ggaccccaag cctggctccc agcagggcct gcagcaggac cagcctggtg agcaccccac  5520
ccggcgtgaa cagggtgatc accagggagg aactggaggc cctgacaccc agcaggaccc  5580
ccagcaggtc cgtgagcagg actagtctgg tgtccaaccc acccggcgtg aacagggtga  5640
tcaccaggga ggaattcgag gccttcgtgg cccagcaaca gagacggttc gacgccggcg  5700
cctacatctt cagcagcgac accggccagg gacacctgca gcaaaagagc gtgaggcaga  5760
ccgtgctgag cgaggtggtg ctggagagga ccgagctgga aatcagctac gcccccaggc  5820
tggaccagga gaaggaggaa ctgctcagga agaaactgca gctgaacccc accccagcca  5880
acaggagcag gtaccagagc aggaaggtgg agaacatgaa ggccatcacc gccaggcgga  5940
tcctgcaggg cctgggacac tacctgaagg ccgagggcaa ggtggagtgc tacaggaccc  6000
tgcaccccgt gccactgtac agctccagcg tgaacagggc cttctccagc cccaaggtgg  6060
ccgtggaggc ctgcaacgct atgctgaagg agaacttccc caccgtggcc agctactgca  6120
tcatccccga gtacgacgcc tacctggaca tggtggacgg cgccagctgc tgcctggaca  6180
ccgccagctt ctgccccgcc aagctgagga gcttccccaa gaaacacagc tacctggagc  6240
ccaccatcag gagcgccgtg cccagcgcca tccagaacac cctgcagaac gtgctggccg  6300
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggccccaa ggccgctgcc ctgttcgcta agacccacaa cctgaacatg ctgcaggaca  6540
tcccaatgga caggttcgtg atggacctga agagggacgt gaaggtgaca cccggcacca  6600
agcacaccga ggagaggccc aaggtgcagg tgatccaggc cgctgaccca ctggccaccg  6660
cctacctgtg cggcatccac agggagctgg tgaggcggct gaacgccgtg ctgctgccca  6720
acatccacac cctgttcgac atgagcgccg aggacttcga cgccatcatc gccgagcact  6780
tccagcccgg cgactgcgtg ctggagaccg acatcgccag cttcgacaag agcgaggatg  6840
acgctatggc cctgaccgct ctgatgatcc tggaggacct gggcgtggac gccgagctgc  6900
tcaccctgat cgaggctgcc ttcggcgaga tcagctccat ccacctgccc accaagacca  6960
agttcaagtt cggcgctatg atgaaaagcg gaatgttcct gaccctgttc gtgaacaccg  7020
tgatcaacat tgtgatcgcc agcagggtgc tgcgggagag gctgaccggc agccccctgcg  7080
ctgccttcat cggcgacgac aacatcgtga agggcgtgaa aagcgacaag ctgatggccg  7140
acaggtgcgc cacctggctg aacatggagg tgaagatcat cgacgccgtg gtgggcgaga  7200
aggcccccta cttctgcggc ggattcatcc tgtgcgacag cgtgaccggc accgcctgca  7260
gggtggccga ccccctgaag aggctgttca agctgggcaa gccactggcc gctgacgatg  7320
agcacgacga tgacaggcgg agggccctgc acgaggaaag caccaggtgg aacagggtgg  7380
gcatcctgag cgagctgtgc aaggccgtgg agagcaggta cgagaccgtg ggcaccagca  7440
tcatcgtgat ggctatgacc acactggcca gctccgtcaa gagcttctcc tacctgaggg  7500
gggcccctat aactctctac ggctaacctg aatggactac gacatagtct agtccgccaa  7560
ggccgccacc actcgagtat gttacgtgca aaggtgattg tcacccccg aaagaccata  7620
ttgtgacaca ccctcagtat cacgcccaaa catttacagc cgcggtgtca aaaaccgcgt  7680
ggacgtggtt aacatccctg ctgggaggat cagccgtaat tattataatt ggcttggtgc  7740
tggctactat tgtggccatg tacgtgctga ccaaccagaa acataattga atacagcagc  7800
aattggcaag ctgcttacat agaactcgcg gcgattggca tgccgcctta aaatttttat  7860
tttatttttt cttttctttt ccgaatcgga ttttgttttt aatatttcaa aaaaaaaaaa  7920
aaaaaaaaaa aaatctagaa aaaaaaaaaa aaaaaaaaaa aaaaaaaaaa aaaaaaaaaa  7980
aaaaaaaaaa aaaaaaaaaa aaaaaaaaaa aaaaaaaaaa aaaaaaaaaa aaaaaaa     8038

SEQ ID NO: 79          moltype = AA  length = 2493
FEATURE                Location/Qualifiers
REGION                 1..2493
                       note = Synthetic polypeptide
source                 1..2493
                       mol_type = protein
                       organism = synthetic construct
SEQUENCE: 79
MEKVHVDIEE DSPFLRALQR SFPQFEVEAK QVTDNDHANA RAFSHLASKL IETEVDPSDT  60
ILDIGSAPAR RMYSKHKYHC ICPMRCAEDP DRLYKYATKL KKNCKEITDK ELDKKMKELA  120
AVMSDPDLET ETMCLHDDES CRYEGQVAVY QDVYAVDGPT SLYHQANKGV RVAYWIGFDT  180
TPFMFKNLAG AYPSYSTNWA DETVLTARNI GLCSSDVMER SRRGMSILRK KYLKPSNNVL  240
FSVGSTIYHE KRDLLRSWHL PSVFHLRGKQ NYTCRCETIV SCDGYVVKRI AISPGLYGKP  300
SGYAATMHRE GFLCCKVTDT LNGERVSFPV CTYVPATLCD QMTGILATDV SADDAQKLLV  360
GLNQRIVVNG RTQRNTNTMK NYLLPVVAQA FARWAKEYKE DQEDERPLGL RDRQLVMGCC  420
WAFRRHKITS IYKRPDTQTI IKVNSDFHSF VLPRIGSNTL EIGLRTRIRK MLEEHKEPSP  480
LITAEDVQEA KCAADEAKEV REAEELRAAL PPLAADVEEP TLEADVDLML QEAGAGSVET  540
PRGLIKVTSY DGEDKIGSYA VLSPQAVLKS EKLSCIHPLA EQVIVITHSG RKGRYAVEPY  600
HGKVVVPEGH AIPVQDFQAL SESATIVYNE REFVNRYLHH IATHGGALNT DEEYYKTVKP  660
SEHDGEYLYD IDRKQCVKKE LVTGLGLTGE LVDPPFHEFA YESLRTRPAA PYQVPTIGVY  720
GVPGSGKSGI IKSAVTKKDL VVSAKKENCA EIIRDVKKMK GLDVNARTVD SVLLNGCKHP  780
VETLYIDEAF ACHAGTLRAL IAIIRPKKAV LCGDPKQCGF FNMMCLKVHF NHEICTQVFH  840
KSISRRCTKS VTSVVSTLFY DKKMRTTNPK ETKIVIDTTG STKPKQDDLI LTCFRGWVKQ  900
LQIDYKGNEI MTAAASQGLT RKGVYAVRYK VNENPLYAPT SEHVNVLLTR TEDRIVWKTL  960
AGDPWIKTLT AKYPGNFTAT IEEWQAEHDA IMRHILERPD PTDVFQNKAN VCWAKALVPV  1020
```

```
LKTAGIDMTT EQWNTVDYFE TDKAHSAEIV LNQLCVRFFG LDLDSGLFSA PTVPLSIRNN  1080
HWDNSPSPNM YGLNKEVVRQ LSRRYPQLPR AVATGRVYDM NTGTLRNYDP RINLVPVNRR  1140
LPHALVLHHN EHPQSDFSSF VSKLKGRTVL VVGEKLSVPG KMVDWLSDRP EATFRARLDL  1200
GIPGDVPKYD IIFVNVRTPY KYHHYQQCED HAIKLSMLTK KACLHLNPGG TCVSIGYGYA  1260
DRASESIIGA IARLFKFSRV CKPKSSLEET EVLFVFIGYD RKARTHNPYK LSSTLTNIYT  1320
GSRLHEAGCA PSYHVVRGDI ATATEGVIIN AANSKGQPGG GVCGALYKKF PESFDLQPIE  1380
VGKARLVKGA AKHIIHAVGP NFNKVSEVEG DKQLAEAYES IAKIVNDNNY KSVAIPLLST  1440
GIFSGNKDRL TQSLNHLLTA LDTTDADVAI YCRDKKWEMT LKEAVARREA VEEICISDDS  1500
SVTEPDAELV RVHPKSSLAG RKGYSTSDGK TFSYLEGTKF HQAAKDIAEI NAMWPVATEA  1560
NEQVCMYILG ESMSSIRSKC PVEESEASTP PSTLPCLCIH AMTPERVQRL KASRPEQITV  1620
CSSFPLPKYR ITGVQKIQCS QPILFSPKVP AYIHPRKYLV ETPPVDETPE PSAENQSTEG  1680
TPEQPPLITE DETRTRTPEP IIIEEEEDS ISLLSDGPTH QVLQVEADIH GPPSVSSSSW  1740
SIPHASDFDV DSLSILDTLE GASVTSGATS AETNSYFAKS MEFLARPVPA PRTVFRNPPH  1800
PAPRTRTPSL APSRACSRTS LVSTPPGVNR VITREELEAL TPSRTPSRSV SRTSLVSNPP  1860
GVNRVITREE FEAFVAQQQR RFDAGAYIFS SDTGQGHLQQ KSVRQTVLSE VVLERTELEI  1920
SYAPRLDQEK EELLRKKLQL NPTPANRSRY QSRKVENMKA ITARRILQGL GHYLKAEGKV  1980
ECYRTLHPVP LYSSSVNRAF SSPKVAVEAC NAMLKENFPT VASYCIIPEY DAYLDMVDGA  2040
SCCLDTASFC PAKLRSFPKK HSYLEPTIRS AVPSAIQNTL QNVLAAATKR NCNVTQMREL  2100
PVLDSAAFNV ECFKKYACNN EYWETFKENP IRLTEENVVN YITKLKGPKA AALFAKTHNL  2160
NMLQDIPMDR FVMDLKRDVK VTPGTKHTEE RPKVQVIQAA DPLATAYLCG IHRELVRRLN  2220
AVLLPNIHTL FDMSAEDFDA IIAEHFQPGD CVLETDIASF DKSEDDAMAL TALMILEDLG  2280
VDAELLTLIE AAFGEISSIH LPTKTKFKFG AMMKSGMFLT LFVNTVINIV IASRVLRERL  2340
TGSPCAAFIG DDNIVKGVKS DKLMADRCAT WLNMEVKIID AVVGEKAPYF CGGFILCDSV  2400
TGTACRVADP LKRLFKLGKP LAADDEHDDD RRRALHEEST RWNRVGILSE LCKAVESRYE  2460
TVGTSIIVMA MTTLASSVKS FSYLRGAPIT LYG                              2493

SEQ ID NO: 80          moltype = AA  length = 2494
FEATURE                Location/Qualifiers
REGION                 1..2494
                       note = Synthetic polypeptide
source                 1..2494
                       mol_type = protein
                       organism = synthetic construct
SEQUENCE: 80
MPEKVHVDIE EDSPFLRALQ RSFPQFEVEA KQVTDNDHAN ARAFSHLASK LIETEVDPSD  60
TILDIGSAPA RRMYSKHKYH CICPMRCAED PDRLYKYATK LKKNCKEITD KELDKKMKEL  120
AAVMSDPDLE TETMCLHDDE SCRYEGQVAV YQDVYAVDGP TSLYHQANKG VRVAYWIGFD  180
TTPFMFKNLA GAYPSYSTNW ADETVLTARN IGLCSSDVME RSRRGMSILR KKYLKPSNNV  240
LFSVGSTIYH EKRDLLRSWH LPSVFHLRGK QNYTCRCETI VSCDGYVVKR IAISPGLYGK  300
PSGYAATMHR EGFLCCKVTD TLNGERVSFP VCTYVPATLC DQMTGILATD VSADDAQKLL  360
VGLNQRIVVN GRTQRNTNTM KNYLLPVVAQ AFARWAKEYK EDQEDERPLG LRDRQLVMGC  420
CWAFRRHKIT SIYKRPDTQT IIKVNSDFHS FVLPRIGSNT LEIGLRTRIR KMLEEHKEPS  480
PLITAEDVQE AKCAADEAKE VREAEELRAA LPPLAADVEE PTLEADVDLM LQEAGAGSVE  540
TPRGLIKVTS YDGEDKIGSY AVLSPQAVLK SEKLSCIHPL AEQVIVITHS GRKGRYAVEP  600
YHGKVVVPEG HAIPVQDFQA LSESATIVYN EREFVNRYLH HIATHGGALN TDEEYYKTVK  660
PSEHDGEYLY DIDRKQCVKK ELVTGLGLTG ELVDPPFHEF AYESLRTRPA APYQVPTIGV  720
YGVPGSGKSG IIKSAVTKKD LVVSAKKENC AEIIRDVKKM KGLDVNARTV DSVLLNGCKH  780
PVETLYIDEA FACHAGTLRA LIAIIRPKKA VLCGDPKQCG FFNMMCLKVH FNHEICTQVF  840
HKSISRRCTK SVTSVVSTLF YDKKMRTTNP KETKIVIDTT GSTKPKQDDL ILTCFRGWVK  900
QLQIDYKGNE IMTAAASQGL TRKGVYAVRY KVNENPLYAP TSEHVNVLLT RTEDRIVWKT  960
LAGDPWIKTL TAKYPGNFTA TIEEWQAEHD AIMRHILERP DPTDVFQNKA NVCWAKALVP  1020
VLKTAGIDMT TEQWNTVDYF ETDKAHSAEI VLNQLCVRFF GLDLDSGLFS APTVPLSIRN  1080
NHWDNSPSPN MYGLNKEVVR QLSRRYPQLP RAVATGRVYD MNTGTLRNYD PRINLVPVNR  1140
RLPHALVLHH NEHPQSDFSS FVSKLKGRTV LVVGEKLSVP GKMVDWLSDR PEATFRARLD  1200
LGIPGDVPKY DIIFVNVRTP YKYHHYQQCE DHAIKLSMLT KKACLHLNPG GTCVSIGYGY  1260
ADRASESIIG AIARLFKFSR VCKPKSSLEE TEVLFVFIGY DRKARTHNPY KLSSTLTNIY  1320
TGSRLHEAGC APSYHVVRGD IATATEGVII NAANSKGQPG GGVCGALYKK FPESFDLQPI  1380
EVGKARLVKG AAKHIIHAVG PNFNKVSEVE GDKQLAEAYE SIAKIVNDNN YKSVAIPLLS  1440
TGIFSGNKDR LTQSLNHLLT ALDTTDADVA IYCRDKKWEM TLKEAVARRE AVEEICISDD  1500
SSVTEPDAEL VRVHPKSSLA GRKGYSTSDG KTFSYLEGTK FHQAAKDIAE INAMWPVATE  1560
ANEQVCMYIL GESMSSIRSK CPVEESEAST PPSTLPCLCI HAMTPERVQR LKASRPEQIT  1620
VCSSFPLPKY RITGVQKIQC SQPILFSPKV PAYIHPRKYL VETPPVDETP EPSAENQSTE  1680
GTPEQPPLIT EDETRTRTPE PIIIEEEED SISLLSDGPT HQVLQVEADI HGPPSVSSSS  1740
WSIPHASDFD VDSLSILDTL EGASVTSGAT SAETNSYFAK SMEFLARPVP APRTVFRNPP  1800
HPAPRTRTPS LAPSRACSRT SLVSTPPGVN RVITREELEA LTPSRTPSRS VSRTSLVSNP  1860
PGVNRVITRE EFEAFVAQQQ RRFDAGAYIF SSDTGQGHLQ QKSVRQTVLS EVVLERTELE  1920
ISYAPRLDQE KEELLRKKLQ LNPTPANRSR YQSRKVENMK AITARRILQG LGHYLKAEGK  1980
VECYRTLHPV PLYSSSVNRA FSSPKVAVEA CNAMLKENFP TVASYCIIPE YDAYLDMVDG  2040
ASCCLDTASF CPAKLRSFPK KHSYLEPTIR SAVPSAIQNT LQNVLAAATK RNCNVTQMRE  2100
LPVLDSAAFN VECFKKYACN NEYWETFKEN PIRLTEENVV NYITKLKGPK AAALFAKTHN  2160
LNMLQDIPMD RFVMDLKRDV KVTPGTKHTE ERPKVQVIQA ADPLATAYLC GIHRELVRRL  2220
NAVLLPNIHT LFDMSAEDFD AIIAEHFQPG DCVLETDIAS FDKSEDDAMA LTALMILEDL  2280
GVDAELLTLI EAAFGEISSI HLPTKTKFKF GAMMKSGMFL TLFVNTVINI VIASRVLRER  2340
LTGSPCAAFI GDDNIVKGVK SDKLMADRCA TWLNMEVKII DAVVGEKAPY FCGGFILCDS  2400
VTGTACRVAD PLKRLFKLGK PLAADDEHDD DRRRALHEES TRWNRVGILS ELCKAVESRY  2460
ETVGTSIIVM AMTTLASSVK SFSYLRGAPI TLYG                             2494

SEQ ID NO: 81          moltype = AA  length = 2492
FEATURE                Location/Qualifiers
```

```
REGION                     1..2492
                           note = Synthetic polypeptide
source                     1..2492
                           mol_type = protein
                           organism = synthetic construct
SEQUENCE: 81
MEKVHVDIEE DSPFLRALQR SFPQFEVEAK QVTDNDHANA RAFSHLASKL IETEVDPSDT    60
ILDIGSAPAR RMYSKHKYHC ICPMRCAEDP DRLYKYATKL KKNCKEITDK ELDKKMKELA   120
AVMSDPDLET ETMCLHDDES CRYEGQVAVY QDVYAVDGPT SLYHQANKGV RVAYWIGFDT   180
TPFMFKNLAG AYPSYSTNWA DETVLTARNI GLCSSDVMER SRRGMSILRK KYLKPSNNVL   240
FSVGSTIYHE KRDLLRSWHL PSVFHLRGKQ NYTCRCETIV SCDGYVVKRI AISPGLYGKP   300
SGYAATMHRE GFLCCKVTDT LNGERVSFPV CTYVPATLCD QMTGILATDV SADDAQKLLV   360
GLNQRIVVNG RTQRNTNTMK NYLLPVVAQA FARWAKEYKE DQEDERPLGL RDRQLVMGCC   420
WAFRRHKITS IYKRPDTQTI IKVNSDFHSF VLPRIGSNTL EIGLRTRIRK MLEEHKEPSP   480
LITAEDIQEA KCAADEAKEV REAEELRAAL PPLAADFEEP TLEADVDLML QEAGAGSVET   540
PRGLIKVTSY AGEDKIGSYA VLSPQAVLKS EKLSCIHPLA EQVIVITHSG RKGRYAVEPY   600
HGKVVVPEGH AIPVQDFQAL SESATIVYNE REFVNRYLHH IATHGGALNT DEEYYKTVKP   660
SEHDGEYLYD IDRKQCVKKE LVTGLGLTGE LVDPPFHEFA YESLRTRPAA PYQVPTIGVY   720
GVPGSGKSGI IKSAVTKKDL VVSAKKENCA EIIRDVKKMK GLDVNARTVD SVLLNGCKHP   780
VETLYIDEAF ACHAGTLRAL IAIIRPKKAV LCGDPKQCGF FNMMCLKVHF NHEICTQVFH   840
KSISRRCTKS VTSVVSTLFY DKRMRTTNPK ETKIVIDTTG STKPKQDDLI LTCFRGWVKQ   900
LQIDYKGNEI MTAAASQGLT RKGVYAVRYK VNENPLYAPT SEHVNVLLTR TEDRIVWKTL   960
AGDPWIKILT AKYPGNFTAT IEEWQAEHDA IMRHILERPD PTDVFQNKAN VCWAKALVPV  1020
LKTAGIDMTT EQWNTVDYFE TDKAHSAEIV LNQLCVRFFG LDLDSGLFSA PTVPLSIRNN  1080
HWDNSPSPNM YGLNKEVVRQ LSRRYPQLPR AVATGRVYDM NTGTLRNYDP RINLVPVNRR  1140
LPHALVLHHN EHPQSDFSSF VSKLKGRTVL VVGEKLSVPG NKVDWLSDQP EATFRARLDL  1200
GIPGDVPKYD IVFINVRTPY KYHHYQQCED HAIKLSMLTK KACLHLNPGG TCVSIGYGYA  1260
DRASESIIGA IARQFKFSRV CKPKSSHEET EVLFVFIGYD RKARTHNPYK LSSTLTNIYT  1320
GSRLHEAGCA PSYHVVRGDI ATATEGVIIN AANSKGQPGG GVCGALYKKF PESFDLQPIE  1380
VGKARLVKGA AKHIIHAVGP NFNKVSEVEG DKQLAEAYES IAKIVNDNNY KSVAIPLLST  1440
GIFSGNKDRL TQSLNHLLTA LDTTDADVAI YCRDKKWEMT LKEAVARREA VEEICISDDS  1500
SVTEPDAELV RVHPKSSLAG RKGYSTSDGK TFSYLEGTKF HQAAKDIAEI NAMWPVATEA  1560
NEQVCMYILG ESMSSIRSKC PVEESEASTP PSTLPCLCIH AMTPERVQRL KASRPEQITV  1620
CSSFPLPKYR ITGVQKIQCS QPILFSPKVP AYIHPRKYLV ETPPVEETPE SPAENQSTEG  1680
TPEQPALVNV DATRTRMPEP IIIEEEEEDS ISLLSDGPTH QVLQVEADIH GSPSVSSSSW  1740
SIPHASDFDV DSLSILDTLD GASVTSGAVS AETNSYFARS MEFRARPVPA PRTVFRNPPH  1800
PAPRTRTPPL AHSRASSRTS LVSTPPGVNR VITREELEAL TPSRAPSRSA SRTSLVSNPP  1860
GVNRVITREE FEAFVAQQQR FDAGAYIFSS DTGQGHLQQK SVRQTVLSEV VLERTELEIS  1920
YAPRLDQEKE ELLRKKLQLN PTPANRSRYQ SRRVENMKAI TARRILQGLG HYLKAEGKVE  1980
CYRTLHPVPL YSSSVNRAFS SPKVAVEACN AMLKENFPTV ASYCIIPEYD AYLDMVDGAS  2040
CCLDTASFCP AKLRSFPKKH SYLEPTIRSA VPSAIQNTLQ NVLAAATKRN CNVTQMRELP  2100
VLDSAAFNVE CFKKYACNNE YWETFKENPI RLTEENVVNY ITKLKGPKAA ALFAKTHNLN  2160
MLQDIPMDRF VMDLKRDVKV TPGTKHTEER PKVQVIQAAD PLATADLCGI HRELVRRLNA  2220
VLLPNIHTLF DMSAEDFDAI IAEHFQPGDC VLETDIASFD KSEDDAMALT ALMILEDLGV  2280
DAELLTLIEA AFGEISSIHL PTKTKFKFGA MMKSGMFLTL FVNTVINIVI ASRVLRERLT  2340
GSPCAAFIGD DNIVKGVKSD KLMADRCATW LNMEVKIIDA VVGEKAPYFC GGFILCDSVT  2400
GTACRVADPL KRLFKLGKPL AVDDEHDDDR RRALHEESTR WNRVGILPEL CKAVESRYET  2460
VGTSIIVMAM TTLASSVKSF SYLRGAPITL YG                               2492

SEQ ID NO: 82              moltype = DNA  length = 146
FEATURE                    Location/Qualifiers
misc_feature               1..146
                           note = Synthetic polynucleotide
source                     1..146
                           mol_type = other DNA
                           organism = synthetic construct
SEQUENCE: 82
aggaaactta agtcaacaca acatatacaa aacaaacgaa tctcaagcaa tcaagcattc    60
tacttctatt gcagcaattt aaatcatttc ttttaaagca aaagcaattt tctgaaaatt   120
ttcaccattt acgaacgata gccacc                                       146

SEQ ID NO: 83              moltype = DNA  length = 270
FEATURE                    Location/Qualifiers
misc_feature               1..270
                           note = Synthetic polynucleotide
source                     1..270
                           mol_type = other DNA
                           organism = synthetic construct
SEQUENCE: 83
actcgagcta gtgactgact aggatctggt taccactaaa ccagcctcaa gaacacccga    60
atggagtctc taagctacat aataccaact tacacttaca aaatgttgtc ccccaaaatg   120
tagccattcg tatctgctcc taataaaaag aaagtttctt cacattctag aaaaaaaaaa   180
aaaaaaaaaa aaaaaaaaaa aaaaaaaaaa aaaaaaaaaa aaaaaaaaaa aaaaaaaaaa   240
aaaaaaaaaa aaaaaaaaaa aaaaaaaaaa                                   270

SEQ ID NO: 84              moltype = RNA  length = 1653
FEATURE                    Location/Qualifiers
misc_feature               1..1653
                           note = Synthetic polynucleotide
```

```
source                 1..1653
                       mol_type = other RNA
                       organism = synthetic construct
SEQUENCE: 84
atggaagatg ccaaaaacat taagaagggc ccagcgccat tctacccact cgaagacggg  60
accgccggcg agcagctgca caaagccatg aagcgctacg ccctggtgcc cggcaccatc  120
gcctttaccg acgcacatat cgaggtggac attacctacg ccgagtactt cgagatgagc  180
gttcggctgg cagaagctat gaagcgctat gggctgaata caaaccatcg gatcgtggtg  240
tgcagcgaga atagcttgca gttcttcatg cccgtgttgg gtgccctgtt catcggtgtg  300
gctgtggccc cagctaacga catctacaac gagcgcgagc tgctgaacag catgggcatc  360
agccagccca ccgtcgtatt cgtgagcaag aaagggctgc aaaagatcct caacgtgcaa  420
aagaagctac cgatcataca aaagatcatc atcatggata gcaagaccga ctaccagggc  480
ttccaaagca tgtacacctt cgtgacttcc catttgccac ccggcttcaa cgagtacgac  540
ttcgtgcccg agagcttcga ccgggacaaa accatcgccc tgatcatgaa cagtagtggc  600
agtaccggat tgcccaaggg cgtagcccta ccgcaccgca ccgcttgtgt ccgattcagt  660
catgcccgcg accccatctt cggcaaccag atcatccccg acaccgctat cctcagcgtg  720
gtgccatttc accacggctt cggcatgttc accacgctgg gctacttgat ctgcggcttt  780
cgggtcgtgc tcatgtaccg cttcgaggag gagctattct tgcgcagctt gcaagactat  840
aagattcaat ctgccctgct ggtgcccaca ctatttagct tcttcgctaa gagcactctc  900
atcgacaagt acgacctaag caacttgcac gagatcgcca gcggcggggc gccgctcagc  960
aaggaggtag gtgaggccgt ggccaaacgc ttccacctac caggcatccg acagggctac  1020
ggcctgacag aaacaaccag cgccattctg atcacccccg aaggggacga caagcctggc  1080
gcagtaggca aggtggtgcc cttcttcgag gctaaggtgg tggacttgga caccggtaag  1140
acactgggtg tgaaccagcg cggcgagctg tgcgtccgtg gccccatgat catgagcggc  1200
tacgttaaca accccgaggc tacaaacgct ctcatcgaca aggacggctg gctgcacagc  1260
ggcgacatcg cctactggga cgaggacgag cacttcttca tcgtggaccg gctgaagtcc  1320
ctgatcaaat acaagggcta ccaggtagcc ccagccgaac tggagagcat cctgctgcaa  1380
caccccaaca tcttcgacgc cggggtcgcc ggcctgcccg acgacgatgc cggcgagctg  1440
cccgccgcag tcgtcgtgct ggaacacggt aaaaccatga ccgagaagga gatcgtggac  1500
tatgtggcca gccaggttac aaccgccaag aagctgcgcg gtggtgttgt gttcgtggac  1560
gaggtgccta aaggactgac cggcaagttg gacgcccgca agatccgcga gattctcatt  1620
aaggccaaga agggcggcaa gatcgccgtg taa                               1653

SEQ ID NO: 85          moltype = RNA  length = 1653
FEATURE                Location/Qualifiers
misc_feature           1..1653
                       note = Synthetic polynucleotide
source                 1..1653
                       mol_type = other RNA
                       organism = synthetic construct
SEQUENCE: 85
atggaagatg ccaaaaacat taagaagggc ccagcgccat tctacccact cgaagacggg  60
accgccggcg agcagctgca caaagccatg aagcgctacg ccctggtgcc cggcaccatc  120
gcctttaccg acgcacatat cgaggtggac attacctacg ccgagtactt cgagatgagc  180
gttcggctgg cagaagctat gaagcgctat gggctgaata caaaccatcg gatcgtggtg  240
tgcagcgaga atagcttgca gttcttcatg cccgtgttgg gtgccctgtt catcggtgtg  300
gctgtggccc cagctaacga catctacaac gagcgcgagc tgctgaacag catgggcatc  360
agccagccca ccgtcgtatt cgtgagcaag aaagggctgc aaaagatcct caacgtgcaa  420
aagaagctac cgatcataca aaagatcatc atcatggata gcaagaccga ctaccagggc  480
ttccaaagca tgtacacctt cgtgacttcc catttgccac ccggcttcaa cgagtacgac  540
ttcgtgcccg agagcttcga ccgggacaaa accatcgccc tgatcatgaa cagtagtggc  600
agtaccggat tgcccaaggg cgtagcccta ccgcaccgca ccgcttgtgt ccgattcagt  660
catgcccgcg accccatctt cggcaaccag atcatccccg acaccgctat cctcagcgtg  720
gtgccatttc accacggctt cggcatgttc accacgctgg gctacttgat ctgcggcttt  780
cgggtcgtgc tcatgtaccg cttcgaggag gagctattct tgcgcagctt gcaagactat  840
aagattcaat ctgccctgct ggtgcccaca ctatttagct tcttcgctaa gagcactctc  900
atcgacaagt acgacctaag caacttgcac gagatcgcca gcggcggggc gccgctcagc  960
aaggaggtag gtgaggccgt ggccaaacgc ttccacctac caggcatccg acagggctac  1020
ggcctgacag aaacaaccag cgccattctg atcacccccg aaggggacga caagcctggc  1080
gcagtaggca aggtggtgcc cttcttcgag gctaaggtgg tggacttgga caccggtaag  1140
acactgggtg tgaaccagcg cggcgagctg tgcgtccgtg gccccatgat catgagcggc  1200
tacgttaaca accccgaggc tacaaacgct ctcatcgaca aggacggctg gctgcacagc  1260
ggcgacatcg cctactggga cgaggacgag cacttcttca tcgtggaccg gctgaagtcc  1320
ctgatcaaat acaagggcta ccaggtagcc ccagccgaac tggagagcat cctgctgcaa  1380
caccccaaca tcttcgacgc cggggtcgcc ggcctgcccg acgacgatgc cggcgagctg  1440
cccgccgcag tcgtcgtgct ggaacacggt aaaaccatga ccgagaagga gatcgtggac  1500
tatgtggcca gccaggttac aaccgccaag aagctgcgcg gtggtgttgt gttcgtggac  1560
gaggtgccta aaggactgac cggcaagttg gacgcccgca agatccgcga gattctcatt  1620
aaggccaaga agggcggcaa gatcgccgtg taa                               1653

SEQ ID NO: 86          moltype = RNA  length = 1653
FEATURE                Location/Qualifiers
misc_feature           1..1653
                       note = Synthetic polynucleotide
source                 1..1653
                       mol_type = other RNA
                       organism = synthetic construct
SEQUENCE: 86
atggaagatg ccaaaaacat taagaagggc ccagcgccat tctacccact cgaagacggg  60
```

```
accgccggcg agcagctgca caaagccatg aagcgctacg ccctggtgcc cggcaccatc  120
gcctttaccg acgcacatat cgaggtggac attacctacg ccgagtactt cgagatgagc  180
gttcggctgg cagaagctat gaagcgctat gggctgaata caaaccatcg gatcgtggtg  240
tgcagcgaga atagcttgca gttcttcatg cccgtgttgg gtgccctgtt catcggtgtg  300
gctgtggccc cagctaacga catctacaac gagcgcgagc tgctgaacag catgggcatc  360
agccagccca ccgtcgtatt cgtgagcaag aaagggctgc aaaagatcct caacgtgcaa  420
aagaagctac cgatcataca aaagatcatc atcatggata gcaagaccga ctaccagggc  480
ttccaaagca tgtacacctt cgtgacttcc catttgccac ccggcttcaa cgagtacgac  540
ttcgtgcccg agagcttcga ccgggacaaa accatcgccc tgatcatgaa cagtagtggc  600
agtaccggat tgcccaaggg cgtagcccta ccgcaccgca ccgcttgtgt ccgattcagt  660
catgcccgcg accccatctt cggcaaccag atcatccccg acaccgctat cctcagcgtg  720
gtgccatttc accacggctt cggcatgttc accacgctgg gctacttgat ctgcggcttt  780
cgggtcgtgc tcatgtaccg cttcgaggag gagctattct tgcgcagctt gcaagactat  840
aagattcaat ctgccctgct ggtgcccaca ctatttagct tcttcgctaa gagcactctc  900
atcgacaagt acgacctaag caacttgcac gagatcgcca gcggcggggc gccgctcagc  960
aaggaggtag gtgaggccgt ggccaaacgc ttccacctac caggcatccg acagggctac  1020
ggcctgacag aaacaaccag cgccattctg atcacccccg aaggggacga caagcctggc  1080
gcagtaggca aggtggtgcc cttcttcgag gctaaggtgg tggacttgga caccggtaag  1140
acactgggtg tgaaccagcg cggcgagctg tgcgtccgtg gccccatgat catgagcggc  1200
tacgttaaca accccgaggc tacaaacgct ctcatcgaca aggacggctg gctgcacagc  1260
ggcgacatcg cctactggga cgaggacgag cacttcttca tcgtggaccg gctgaagtcc  1320
ctgatcaaat acaagggcta ccaggtagcc ccagccgaac tggagagcat cctgctgcaa  1380
caccccaaca tcttcgacgc cggggtcgcc ggcctgcccg acgacgatgc cggcgagctg  1440
cccgccgcag tcgtcgtgct ggaacacggt aaaaccatga ccgagaagga gatcgtggac  1500
tatgtggcca gccaggttac aaccgccaag aagctgcgcg gtggtgttgt gttcgtggac  1560
gaggtgccta aaggactgac cggcaagttg gacgcccgca agatccgcga gattctcatt  1620
aaggccaaga agggcggcaa gatcgccgtg taa                               1653
```

```
SEQ ID NO: 87          moltype = RNA  length = 57
FEATURE                Location/Qualifiers
misc_feature           1..57
                       note = Synthetic polynucleotide
source                 1..57
                       mol_type = other RNA
                       organism = synthetic construct
SEQUENCE: 87
atgaagttgg tggttgtggg ggccgggggt gttggcaaaa gcgcccttac aatttga     57
```

```
SEQ ID NO: 88          moltype = RNA  length = 66
FEATURE                Location/Qualifiers
misc_feature           1..66
                       note = Synthetic polynucleotide
source                 1..66
                       mol_type = other RNA
                       organism = synthetic construct
SEQUENCE: 88
atggatccta gacgctacgc cccaatgatc cgaccagcaa aactcgatgt acttccgagg  60
aactga                                                             66
```

```
SEQ ID NO: 89          moltype = RNA  length = 837
FEATURE                Location/Qualifiers
misc_feature           1..837
                       note = Synthetic polynucleotide
source                 1..837
                       mol_type = other RNA
                       organism = synthetic construct
SEQUENCE: 89
atgagagtga cagcccctag aaccttactg cttctgcttt ggggagctgt tgctctgaca  60
gagacatggg ctggatctct gagcgaggtg accggccagg gcctgtgcat cggcgccgtg  120
cccaagaccc accaggtgct gtgcaacacc acccagaaga ccagcgacgg cagctactac  180
ctggccgctc ccaccggcac cacctgggcc tgcagcaccg gcctgacccc ttgcatcagc  240
accaccatcc tgaacctgac caccgactac tgcgtgctgg tggagctgtg gcccagggtg  300
acctaccaca gccccagcta cgcctaccac cagttcgaga ggagggccaa gtacaagagg  360
gagcccgtga gcctgaccct ggccctgctg ctgggcggcc tgacaatggg cggcatcgcc  420
gccggcgtgg gcaccggcac caccgccctg gtggccaccc agcagttcca gcagctgcag  480
gccgccatgc acgacgacct gaaggaggtg gagaagtcca tcaccaacct ggagaagtcc  540
ctgaccagcc tgagcgaggt ggtgctgcag aacaggaggg gcctggacct gctgttcctg  600
aaggagggcg gcctgtgcgc cgccctgaag gaggagtgct gcctgtacgc cgaccacacc  660
ggcctggtga tcgtgggcat tgtcgctggc ctggccgtcc tcgccgtggt ggtgattgga  720
gctgtggtcg cagctgttat gtgcagaaga aagtcatccg gcggaaaggg aggctcctac  780
tctcaggctg cttctgctac agtgcctaga gctcttatgt gtttatctca gctgtaa     837
```

```
SEQ ID NO: 90          moltype = RNA  length = 378
FEATURE                Location/Qualifiers
misc_feature           1..378
                       note = Synthetic polynucleotide
source                 1..378
                       mol_type = other RNA
                       organism = synthetic construct
```

```
SEQUENCE: 90
atgagagtga cagcccctag aaccttactg cttctgcttt ggggagctgt tgctctgaca  60
gagacatggg ctggatctta ccacagcccc agctacgcct accaccagtt cgagaggggg  120
ggaggaggct ccgggggagg aggctccctg aagatcagcc aggccgtgca cgccgcccac  180
gccgagatca acgaggccgg ccgggaggtg atcgtgggca ttgtcgctgg cctggccgtc  240
ctcgccgtgg tggtgattgg agctgtggtc gcagctgtta tgtgcagaag aaagtcatcc  300
ggcggaaagg gaggctccta ctctcaggct gcttctgcta cagtgcctag agctcttatg  360
tgtttatctc agctgtaa                                              378

SEQ ID NO: 91          moltype = RNA  length = 876
FEATURE                Location/Qualifiers
misc_feature           1..876
                       note = Synthetic polynucleotide
source                 1..876
                       mol_type = other RNA
                       organism = synthetic construct
SEQUENCE: 91
atgagagtga cagcccctag aaccttactg cttctgcttt ggggagctgt tgctctgaca  60
gagacatggg ctggatctct gagcgaggtg accggccagg gcctgtgcat cggcgccgtg  120
cccaagaccc accaggtgct gtgcaacacc acccagaaga ccagcgacgg cagctactac  180
ctggccgctc ccaccggcac cacctgggcc tgcagcaccg gcctgacccc ttgcatcagc  240
accaccatcc tgaacctgac caccgactac tgcgtgctgg tggagctgtg gcccagggtg  300
acctaccaca gccccagcta cgcctaccac cagttcgaga ggagggccaa gtacaagagg  360
gagcccgtga gcctgaccct ggccctgctg ctgggcggcc tgacaatggg cggcatcgcc  420
gccggcgtgg gcaccggcac caccgccctg gtggccaccc agcagttcca gcagctgcag  480
gccgccatgc acgacgacct gaaggaggtg gagaagtcca tcaccaacct ggagaagtcc  540
ctgaccagcc tgagcgaggt ggtgctgcag aacaggaggg gcctggacct gctgttcctg  600
aaggagggcg gcctgtgcgc cgccctgaag gaggagtgct gcctgtacgc cgaccacacc  660
ggcctggtga tcgtgggcat tgtcgctggc ctggccgtcc tcgccgtggt ggtgattgga  720
gctgtggtcg cagctgttat gtgcagaaga aagtcatccg gcggaaaggg aggctcctac  780
tctcaggctg cttctgctac agtgcctaga gctcttatgt gtttatctca gctgggcggc  840
ggaggcagcg actacaagga cgacgatgac aagtaa                            876

SEQ ID NO: 92          moltype = RNA  length = 417
FEATURE                Location/Qualifiers
misc_feature           1..417
                       note = Synthetic polynucleotide
source                 1..417
                       mol_type = other RNA
                       organism = synthetic construct
SEQUENCE: 92
atgagagtga cagcccctag aaccttactg cttctgcttt ggggagctgt tgctctgaca  60
gagacatggg ctggatctta ccacagcccc agctacgcct accaccagtt cgagaggggg  120
ggaggaggct ccgggggagg aggctccctg aagatcagcc aggccgtgca cgccgcccac  180
gccgagatca acgaggccgg ccgggaggtg atcgtgggca ttgtcgctgg cctggccgtc  240
ctcgccgtgg tggtgattgg agctgtggtc gcagctgtta tgtgcagaag aaagtcatcc  300
ggcggaaagg gaggctccta ctctcaggct gcttctgcta cagtgcctag agctcttatg  360
tgtttatctc agctgggcgg cggaggcagc gactacaagg acgacgatga caagtaa    417

SEQ ID NO: 93          moltype = AA  length = 550
FEATURE                Location/Qualifiers
REGION                 1..550
                       note = Synthetic polypeptide
source                 1..550
                       mol_type = protein
                       organism = synthetic construct
SEQUENCE: 93
MEDAKNIKKG PAPFYPLEDG TAGEQLHKAM KRYALVPGTI AFTDAHIEVD ITYAEYFEMS  60
VRLAEAMKRY GLNTNHRIVV CSENSLQFFM PVLGALFIGV AVAPANDIYN ERELLNSMGI  120
SQPTVVFVSK KGLQKILNVQ KKLPIIQKII IMDSKTDYQG FQSMYTFVTS HLPPGFNEYD  180
FVPESFDRDK TIALIMNSSG STGLPKGVAL PHRTACVRFS HARDPIFGNQ IIPDTAILSV  240
VPFHHGFGMF TTLGYLICGF RVVLMYRFEE ELFLRSLQDY KIQSALLVPT LFSFFAKSTL  300
IDKYDLSNLH EIASGGAPLS KEVGEAVAKR FHLPGIRQGY GLTETTSAIL ITPEGDDKPG  360
AVGKVVPFFE AKVVDLDTGK TLGVNQRGEL CVRGPMIMSG YVNNPEATNA LIDKDGWLHS  420
GDIAYWDEDE HFFIVDRLKS LIKYKGYQVA PAELESILLQ HPNIFDAGVA GLPDDDAGEL  480
PAAVVVLEHG KTMTEKEIVD YVASQVTTAK KLRGGVVFVD EVPKGLTGKL DARKIREILI  540
KAKKGGKIAV                                                        550

SEQ ID NO: 94          moltype = AA  length = 18
FEATURE                Location/Qualifiers
REGION                 1..18
                       note = Synthetic polypeptide
source                 1..18
                       mol_type = protein
                       organism = synthetic construct
SEQUENCE: 94
MKLVVVGAGG VGKSALTI                                                18

SEQ ID NO: 95          moltype = AA  length = 21
```

```
FEATURE                Location/Qualifiers
REGION                 1..21
                       note = Synthetic polypeptide
source                 1..21
                       mol_type = protein
                       organism = synthetic construct
SEQUENCE: 95
MDPRRYAPMI RPAKLDVLPR N                                      21

SEQ ID NO: 96          moltype = AA  length = 278
FEATURE                Location/Qualifiers
REGION                 1..278
                       note = Synthetic polypeptide
source                 1..278
                       mol_type = protein
                       organism = synthetic construct
SEQUENCE: 96
MRVTAPRTLL LLLWGAVALT ETWAGSLSEV TGQGLCIGAV PKTHQVLCNT TQKTSDGSYY  60
LAAPTGTTWA CSTGLTPCIS TTILNLTTDY CVLVELWPRV TYHSPSYAYH QFERRAKYKR  120
EPVSLTLALL LGGLTMGGIA AGVGTGTTAL VATQQFQQLQ AAMHDDLKEV EKSITNLEKS  180
LTSLSEVVLQ NRRGLDLLFL KEGGLCAALK EECCLYADHT GLVIVGIVAG LAVLAVVVIG  240
AVVAAVMCRR KSSGGKGGSY SQAASATVPR ALMCLSQL                    278

SEQ ID NO: 97          moltype = AA  length = 125
FEATURE                Location/Qualifiers
REGION                 1..125
                       note = Synthetic polypeptide
source                 1..125
                       mol_type = protein
                       organism = synthetic construct
SEQUENCE: 97
MRVTAPRTLL LLLWGAVALT ETWAGSYHSP SYAYHQFERG GGGSGGGGSL KISQAVHAAH  60
AEINEAGREV IVGIVAGLAV LAVVVIGAVV AAVMCRRKSS GGKGGSYSQA ASATVPRALM  120
CLSQL                                                        125

SEQ ID NO: 98          moltype = AA  length = 291
FEATURE                Location/Qualifiers
REGION                 1..291
                       note = Synthetic polypeptide
source                 1..291
                       mol_type = protein
                       organism = synthetic construct
SEQUENCE: 98
MRVTAPRTLL LLLWGAVALT ETWAGSLSEV TGQGLCIGAV PKTHQVLCNT TQKTSDGSYY  60
LAAPTGTTWA CSTGLTPCIS TTILNLTTDY CVLVELWPRV TYHSPSYAYH QFERRAKYKR  120
EPVSLTLALL LGGLTMGGIA AGVGTGTTAL VATQQFQQLQ AAMHDDLKEV EKSITNLEKS  180
LTSLSEVVLQ NRRGLDLLFL KEGGLCAALK EECCLYADHT GLVIVGIVAG LAVLAVVVIG  240
AVVAAVMCRR KSSGGKGGSY SQAASATVPR ALMCLSQLGG GGSDYKDDDD K         291

SEQ ID NO: 99          moltype = AA  length = 138
FEATURE                Location/Qualifiers
REGION                 1..138
                       note = Synthetic polypeptide
source                 1..138
                       mol_type = protein
                       organism = synthetic construct
SEQUENCE: 99
MRVTAPRTLL LLLWGAVALT ETWAGSYHSP SYAYHQFERG GGGSGGGGSL KISQAVHAAH  60
AEINEAGREV IVGIVAGLAV LAVVVIGAVV AAVMCRRKSS GGKGGSYSQA ASATVPRALM  120
CLSQLGGGGS DYKDDDDK                                          138

SEQ ID NO: 100         moltype = RNA  length = 9690
FEATURE                Location/Qualifiers
misc_feature           1..9690
                       note = Synthetic polynucleotide
source                 1..9690
                       mol_type = other RNA
                       organism = synthetic construct
SEQUENCE: 100
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
```

-continued

```
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccacccact ggccgagcag gtgatcgtga  1800
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
agggcaacga gatcatgacc gccgctgcca gccagggcct gaccaggaag ggcgtgtacg  2820
ccgtgaggta caaggtgaac gagaacccac tgtacgctcc caccagcgag cacgtgaacg  2880
tgctgctgac caggaccgag gacaggatcg tgtggaagac cctggccggc gacccctgga  2940
tcaagaccct gaccgccaag taccccggca acttcaccgc caccatcgaa gagtggcagg  3000
ccgagcacga cgccatcatg aggcacatcc tggagaggcc cgaccccacc gacgtgttcc  3060
agaacaaggc caacgtgtgc tggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcaccctga  3420
ggaactacga ccccaggatc aacctggtgc ccgtgaacag gcggctgccc cacgccctgg  3480
tgctgcacca caacgagcac cccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc cccggcgacg  3660
tgcccaagta cgacatcatc ttcgtgaacg tcaggacccc atacaagtac caccattacc  3720
agcagtgcga ggaccacgcc atcaagctga gcatgctgac caagaaggcc tgcctgcacc  3780
tgaaccccgg aggcacctgc gtgagcatcg gctacggcta cgccgacagg gccagcgaga  3840
gcatcattgg cgccatcgcc aggctgttca agttcagcag ggtgtgcaaa cccaagagca  3900
gcctggagga aaccgaggtg ctgttcgtgt tcatcggcta cgaccggaag gccaggaccc  3960
acaaccccta caagctgagc agcaccctga caaacatcta caccggcagc aggctgcacg  4020
aggccggctg cgcccccagc taccacgtgg tcaggggcga tatcgccacc gccaccgagg  4080
gcgtgatcat caacgctgcc aacagcaagg gccagcccgg aggcggagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg ccccaacttc aacaaggtga  4260
gcgaggtgga aggcgacaag cagctggccg aagcctacga gagcatcgcc aagatcgtga  4320
acgacaataa ctacaagagc gtggccatcc cactgctcag caccggcatc ttcagcggca  4380
acaaggacag gctgacccag agcctgaacc acctgctcac cgccctggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgagggtg caccccaaga gctccctggc cggcaggaag ggctacagca  4620
ccagcgacgg caagaccttc agctacctgg agggcaccaa gttccaccag gccgctaagg  4680
acatcgccga gatcaacgct atgtggcccg tggccaccga ggccaacgag caggtgtgca  4740
tgtacatcct gggcgagagc atgtccagca tcaggagcaa gtgccccgtg gaggaaagcg  4800
aggccagcac accacccagc accctgccct gcctgtgcat ccacgctatg acacccgaga  4860
gggtgcagcg gctgaaggcc agcaggcccg agcagatcac cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagacc ccacccgtgg  5040
acgagacacc cgagccaagc gccgagaacc agagcaccga gggcacaccc gagcagccac  5100
ccctgatcac cgaggacgag acaaggaccc ggaccccaga gcccatcatt atcgaggaag  5160
aggaagagga cagcatcagc ctgctgagcg acggccccac ccaccaggtg ctgcaggtgg  5220
aggccgacat ccacggccca cccagcgtgt ccagctccag ctggagcatc ccacacgcca  5280
gcgacttcga cgtggacagc ctgagcatcc tggacaccct ggagggcgcc agcgtgacct  5340
```

-continued

```
ccggcgccac cagcgccgag accaacagct acttcgccaa gagcatggag ttcctggcca  5400
ggcccgtgcc agctcccagg accgtgttca ggaacccacc ccacccagct cccaggacca  5460
ggaccccaag cctggctccc agcagggcct gcagcaggac cagcctggtg agcaccccac  5520
ccggcgtgaa cagggtgatc accagggagg aactggaggc cctgacaccc agcaggaccc  5580
ccagcaggtc cgtgagcagg actagtctgg tgtccaaccc acccggcgtg aacagggtga  5640
tcaccaggga ggaattcgag gccttcgtgg cccagcaaca gagacggttc gacgccggcg  5700
cctacatctt cagcagcgac accggccagg gacacctgca gcaaaagagc gtgaggcaga  5760
ccgtgctgag cgaggtggtg ctggagagga ccgagctgga aatcagctac gcccccaggc  5820
tggaccagga gaaggaggaa ctgctcagga agaaactgca gctgaacccc accccagcca  5880
acaggagcag gtaccagagc aggaaggtgg agaacatgaa ggccatcacc gccaggcgga  5940
tcctgcaggg cctgggacac tacctgaagg ccgagggcaa ggtggagtgc tacaggaccc  6000
tgcaccccgt gccactgtac agctccagcg tgaacagggc cttctccagc cccaaggtgg  6060
ccgtggaggc ctgcaacgct atgctgaagg agaacttccc caccgtggcc agctactgca  6120
tcatccccga gtacgacgcc tacctggaca tggtggacgg cgccagctgc tgcctggaca  6180
ccgccagctt ctgccccgcc aagctgagga gcttccccaa gaaacacagc tacctggagc  6240
ccaccatcag gagcgccgtg cccagcgcca tccagaacac cctgcagaac gtgctggccg  6300
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggccccaa ggccgctgcc ctgttcgcta agacccacaa cctgaacatg ctgcaggaca  6540
tcccaatgga caggttcgtg atggacctga agagggacgt gaaggtgaca cccggcacca  6600
agcacaccga ggagaggccc aaggtgcagg tgatccaggc cgctgaccca ctggccaccg  6660
cctacctgtg cggcatccac agggagctgg tgaggcggct gaacgccgtg ctgctgccca  6720
acatccacac cctgttcgac atgagcgccg aggacttcga cgccatcatc gccgagcact  6780
tccagcccgg cgactgcgtg ctggagaccg acatcgccag cttcgacaag agcgaggatg  6840
acgctatggc cctgaccgct ctgatgatcc tggaggacct gggcgtggac gccgagctgc  6900
tcaccctgat cgaggctgcc ttcggcgaga tcagctccat ccacctgccc accaagacca  6960
agttcaagtt cggcgctatg atgaaaagcg gaatgttcct gaccctgttc gtgaacaccg  7020
tgatcaacat tgtgatcgcc agcagggtgc tgcgggagag gctgaccggc agcccctgcg  7080
ctgccttcat cggcgacgac aacatcgtga agggcgtgaa aagcgacaag ctgatggccg  7140
acaggtgcgc cacctggctg aacatggagg tgaagatcat cgacgccgtg gtgggcgaga  7200
aggcccccta cttctgcggc ggattcatcc tgtgcgacag cgtgaccggc accgcctgca  7260
gggtggccga ccccctgaag aggctgttca agctgggcaa gccactggcc gctgacgatg  7320
agcacgacga tgacaggcgg agggccctgc acgaggaaag caccaggtgg aacagggtgg  7380
gcatcctgag cgagctgtgc aaggccgtgg agagcaggta cgagaccgtg ggcaccagca  7440
tcatcgtgat ggctatgacc acactggcca gctccgtcaa gagcttctcc tacctgaggg  7500
gggcccctat aactctctac ggctaacctg aatggactac gacatagtct agtccgccaa  7560
ggccgccacc atggaagatg ccaaaaacat taagaagggc ccagcgccat tctacccact  7620
cgaagacggg accgccggcg agcagctgca caaagccatg aagcgctacg ccctggtgcc  7680
cggcaccatc gcctttaccg acgcacatat cgaggtggac attacctacg ccgagtactt  7740
cgagatgagc gttcggctgg cagaagctat gaagcgctat gggctgaata caaaccatcg  7800
gatcgtggtg tgcagcgaga atagcttgca gttcttcatg cccgtgttgg gtgccctgtt  7860
catcggtgtg gctgtggccc cagctaacga catctacaac gagcgcgagc tgctgaacag  7920
catgggcatc agccagccca ccgtcgtatt cgtgagcaag aaagggctgc aaaagatcct  7980
caacgtgcaa aagaagctac cgatcataca aaagatcatc atcatggata gcaagaccga  8040
ctaccagggc ttccaaagca tgtacacctt cgtgacttcc catttgccac ccggcttcaa  8100
cgagtacgac ttcgtgcccg agagcttcga ccgggacaaa accatcgccc tgatcatgaa  8160
cagtagtggc agtaccggat tgcccaaggg cgtagcccta ccgcaccgca ccgcttgtgt  8220
ccgattcagt catgcccgcg accccatctt cggcaaccag atcatccccg acaccgctat  8280
cctcagcgtg gtgccatttc accacggctt cggcatgttc accacgctgg gctacttgat  8340
ctgcggcttt cgggtcgtgc tcatgtaccg cttcgaggag gagctattct tgcgcagctt  8400
gcaagactat aagattcaat ctgccctgct ggtgcccaca ctatttagct tcttcgctaa  8460
gagcactctc atcgacaagt acgacctaag caacttgcac gagatcgcca gcggcggggc  8520
gccgctcagc aaggaggtag gtgaggccgt ggccaaacgc ttccacctac caggcatccg  8580
acagggctac ggcctgacag aaacaaccag cgccattctg atcacccccg aaggggacga  8640
caagcctggc gcagtaggca aggtggtgcc cttcttcgag gctaaggtgg tggacttgga  8700
caccggtaag acactgggtg tgaaccagcg cggcgagctg tgcgtccgtg gccccatgat  8760
catgagcggc tacgttaaca accccgaggc tacaaacgct ctcatcgaca aggacggctg  8820
gctgcacagc ggcgacatcg cctactggga cgaggacgag cacttcttca tcgtggaccg  8880
gctgaagtcc ctgatcaaat acaagggcta ccaggtagcc ccagccgaac tggagagcat  8940
cctgctgcaa caccccaaca tcttcgacgc cggggtcgcc ggcctgcccg acgacgatgc  9000
cggcgagctg cccgccgcag tcgtcgtgct ggaacacggt aaaaccatga ccgagaagga  9060
gatcgtggac tatgtggcca gccaggttac aaccgccaag aagctgcgcg gtggtgttgt  9120
gttcgtggac gaggtgccta aaggactgac cggcaagttg gacgcccgca agatccgcga  9180
gattctcatt aaggccaaga agggcggcaa gatcgccgtg taactcgagt atgttacgtg  9240
caaaggtgat tgtcaccccc cgaaagacca tattgtgaca caccctcagt atcacgccca  9300
aacatttaca gccgcggtgt caaaaaccgc gtggacgtgg ttaacatccc tgctgggagg  9360
atcagccgta attattataa ttggcttggt gctggctact attgtggcca tgtacgtgct  9420
gaccaaccag aaacataatt gaatacagca gcaattggca agctgcttac atagaactcg  9480
cggcgattgg catgccgcct taaaattttt attttatttt ttcttttctt ttccgaatcg  9540
gattttgttt ttaatatttc aaaaaaaaaa aaaaaaaaaa aaaaatctag aaaaaaaaaa  9600
aaaaaaaaaa aaaaaaaaaa aaaaaaaaaa aaaaaaaaaa aaaaaaaaaa aaaaaaaaaa  9660
aaaaaaaaaa aaaaaaaaaa aaaaaaaaaa                                  9690
```

```
SEQ ID NO: 101         moltype = RNA  length = 9773
FEATURE                Location/Qualifiers
misc_feature           1..9773
                       note = Synthetic polynucleotide
source                 1..9773
```

-continued

```
                         mol_type = other RNA
                         organism = synthetic construct
SEQUENCE: 101
attgacggcg tagtacacac tattgaatca aacagccgac caattgcact accatcacaa  60
tggagaagcc agtagtaaac gtagacgtag acccccagag tccgtttgtc gtgcaactgc  120
aaaaaagctt cccgcaattt gaggtagtag cacagcaggt cactccaaat gaccatgcta  180
atgccagagc attttcgcat ctggccagta aactaatcga gctggaggtt cctaccacag  240
cgacgatctt ggacataggc agcgcaccgg ctcgtagaat gttttccgag caccagtatc  300
attgtgtctg ccccatgcgt agtccagaag acccggaccg catgatgaaa tatgccagta  360
aactggcgga aaaagcgtgc aagattacaa acaagaactt gcatgagaag attaaggatc  420
tccggaccgt acttgatacg ccggatgctg aaacaccatc gctctgcttt cacaacgatg  480
ttacctgcaa catgcgtgcc gaatattccg tcatgcagga cgtgtatatc aacgctcccg  540
gaactatcta tcatcaggct atgaaaggcg tgcggaccct gtactggatt ggcttcgaca  600
ccacccagtt catgttctcg gctatggcag gttcgtaccc tgcgtacaac accaactggg  660
ccgacgagaa agtccttgaa gcgcgtaaca tcggactttg cagcacaaag ctgagtgaag  720
gtaggacagg aaaattgtcg ataatgagga agaaggagtt gaagcccggg tcgcgggttt  780
atttctccgt aggatcgaca ctttatccag aacacagagc cagcttgcag agctggcatc  840
ttccatcggt gttccacttg aatggaaagc agtcgtacac ttgccgctgt gatacagtgg  900
tgagttgcga aggctacgta gtgaagaaaa tcaccatcag tcccgggatc acgggagaaa  960
ccgtgggata cgcggttaca cacaatagcg agggcttctt gctatgcaaa gttactgaca  1020
cagtaaaagg agaacgggta tcgttccctg tgtgcacgta catcccggcc accatatgcg  1080
atcagatgac tggtataatg gccacggata tatcacctga cgatgcacaa aaacttctgg  1140
ttgggctcaa ccagcgaatt gtcattaacg gtaggactaa caggaacacc aacaccatgc  1200
aaaattacct tctgccgatc atagcacaag ggttcagcaa atgggctaag gagcgcaagg  1260
atgatcttga taacgagaaa atgctgggta ctagagaacg caagcttacg tatggctgct  1320
tgtgggcgtt tcgcactaag aaagtacatt cgttttatcg cccacctgga acgcagacct  1380
gcgtaaaagt cccagcctct tttagcgctt ttcccatgtc gtccgtatgg acgacctctt  1440
tgcccatgtc gctgaggcag aaattgaaac tggcattgca accaaagaag gaggaaaaac  1500
tgctgcaggt ctcggaggaa ttagtcatgg aggccaaggc tgcttttgag gatgctcagg  1560
aggaagccag agcggagaag ctccgagaag cacttccacc attagtggca gacaaaggca  1620
tcgaggcagc cgcagaagtt gtctgcgaag tggaggggct ccaggcggac atcggagcag  1680
cattagttga aaccccgcgc ggtcacgtaa ggataatacc tcaagcaaat gaccgtatga  1740
tcggacagta tatcgttgtc tcgccaaact ctgtgctgaa gaatgccaaa ctcgcaccag  1800
cgcacccgct agcagatcag gttaagatca taacacactc cggaagatca ggaaggtacg  1860
cggtcgaacc atacgacgct aaagtactga tgccagcagg aggtgccgta ccatggccag  1920
aattcctagc actgagtgag agcgccacgt tagtgtacaa cgaaagagag tttgtgaacc  1980
gcaaactata ccacattgcc atgcatggcc ccgccaagaa tacagaagag gagcagtaca  2040
aggttacaaa ggcagagctt gcagaaacag agtacgtgtt tgacgtggac aagaagcgtt  2100
gcgttaagaa ggaagaagcc tcaggtctgg tcctctcggg agaactgacc aaccctccct  2160
atcatgagct agctctggag ggactgaaga cccgacctgc ggtcccgtac aaggtcgaaa  2220
caataggagt gataggcaca ccggggtcgg gcaagtcagc tattatcaag tcaactgtca  2280
cggcacgaga tcttgttacc agcggaaaga aagaaaattg tcgcgaaatt gaggccgacg  2340
tgctaagact gaggggtatg cagattacgt cgaagacagt agattcggtt atgctcaacg  2400
gatgccacaa agccgtagaa gtgctgtacg ttgacgaagc gttcgcgtgc cacgcaggag  2460
cactacttgc cttgattgct atcgtcaggc cccgcaagaa ggtagtacta tgcggagacc  2520
ccatgcaatg cggattcttc aacatgatgc aactaaaggt acatttcaat caccctgaaa  2580
aagacatatg caccaagaca ttctacaagt atatctcccg gcgttgcaca cagccagtta  2640
cagctattgt atcgacactg cattacgatg gaaagatgaa aaccacgaac ccgtgcaaga  2700
agaacattga aatcgatatt acaggggcca caaagccgaa gccaggggat atcatcctga  2760
catgtttccg cgggtgggtt aagcaattgc aaatcgacta tcccggacat gaagtaatga  2820
cagccgcggc ctcacaaggg ctaaccagaa aaggagtgta tgccgtccgg caaaaagtca  2880
atgaaaaccc actgtacgcg atcacatcag agcatgtgaa cgtgttgctc acccgcactg  2940
aggacaggct agtgtggaaa accttgcagg gcgacccatg gattaagcag ctcactaaca  3000
tacctaaagg aaactttcag gctactatag aggactggga agctgaacac aagggaataa  3060
ttgctgcaat aaacagcccc actccccgtg ccaatccgtt cagctgcaag accaacgttt  3120
gctgggcgaa agcattggaa ccgatactag ccacggccgg tatcgtactt accggttgcc  3180
agtggagcga actgttccca cagtttgcgg atgacaaacc acattcggcc atttacgcct  3240
tagacgtaat ttgcattaag tttttcggca tggacttgac aagcggactg ttttctaaac  3300
agagcatccc actaacgtac catcccgccg attcagcgag gccggtagct cattgggaca  3360
acagcccagg aacccgcaag tatgggtacg atcacgccat tgccgccgaa ctctcccgta  3420
gatttccggt gttccagcta gctgggaagg gcacacaact tgatttgcag acggggagaa  3480
ccagagttat ctctgcacag cataacctgg tcccggtgaa ccgcaatctt cctcacgcct  3540
tagtccccga gtacaaggag aagcaacccg gcccggtcga aaaattcttg aaccagttca  3600
aacaccactc agtacttgtg gtatcagagg aaaaaattga agctccccgt aagagaatcg  3660
aatggatcgc cccgattggc atagccggtg cagataagaa ctacaacctg gctttcgggt  3720
ttccgccgca ggcacggtac gacctggtgt tcatcaacat tggaactaaa tacagaaacc  3780
accactttca gcagtgcgaa gaccatgcgg cgaccttaaa aaccctttcg cgttcggccc  3840
tgaattgcct taacccagga ggcaccctcg tggtgaagtc ctatggctac gccgaccgca  3900
acagtgagga cgtagtcacc gctcttgcca gaaagtttgt cagggtgtct gcagcgagac  3960
cagattgtgt ctcaagcaat acagaaatgt acctgatttt ccgacaacta gacaacagcc  4020
gtacacggca attcaccccg caccatctga attgcgtgat ttcgtccgtg tatgagggta  4080
caagagatgg agttggagcc gcgccgtcat accgcaccaa aagggagaat attgctgact  4140
gtcaagagga agcagttgtc aacgcagcca atccgctggg tagaccaggc gaaggagtct  4200
gccgtgccat ctataaacgt tggccgacca gttttaccga ttcagccacg gagacaggca  4260
ccgcaagaat gactgtgtgc ctaggaaaga aagtgatcca cgcggtcggc cctgatttcc  4320
ggaagcaccc agaagcagaa gccttgaaat tgctacaaaa cgcctaccat gcagtggcag  4380
acttagtaaa tgaacataac atcaagtctg tcgccattcc actgctatct acaggcattt  4440
acgcagccgg aaaagaccgc cttgaagtat cacttaactg cttgacaacc gcgctagaca  4500
gaactgacgc ggacgtaacc atctattgcc tggataagaa gtggaaggaa agaatcgacg  4560
```

-continued

```
cggcactcca acttaaggag tctgtaacag agctgaagga tgaagatatg gagatcgacg  4620
atgagttagt atggatccat ccagacagtt gcttgaaggg aagaaaggga ttcagtacta  4680
caaaaggaaa attgtattcg tacttcgaag gcaccaaatt ccatcaagca gcaaaagaca  4740
tggcggagat aaaggtcctg ttccctaatg accaggaaag taatgaacaa ctgtgtgcct  4800
acatattggg tgagaccatg gaagcaatcc gcgaaaagtg cccggtcgac cataacccgt  4860
cgtctagccc gcccaaaacg ttgccgtgcc tttgcatgta tgccatgacg ccagaaaggg  4920
tccacagact tagaagcaat aacgtcaaag aagttacagt atgctcctcc accccccttc  4980
ctaagcacaa aattaagaat gttcagaagg ttcagtgcac gaaagtagtc ctgtttaatc  5040
cgcacactcc cgcattcgtt cccgcccgta agtacataga agtgccagaa cagcctaccg  5100
ctcctcctgc acaggccgag gaggcccccg aagttgtagc gacaccgtca ccatctacag  5160
ctgataacac ctcgcttgat gtcacagaca tctcactgga tatggatgac agtagcgaag  5220
gctcactttt ttcgagcttt agcggatcgg acaactctat tactagtatg gacagttggt  5280
cgtcaggacc tagttcacta gagatagtag accgaaggca ggtggtggtg gctgacgttc  5340
atgccgtcca agagcctgcc cctattccac cgccaaggct aaagaagatg gcccgcctgg  5400
cagcggcaag aaaagagccc actccaccgg caagcaatag ctctgagtcc ctccacctct  5460
cttttggtgg ggtatccatg tccctcggat caattttcga cggagagacg gcccgccagg  5520
cagcggtaca accccctggca acaggcccca cggatgtgcc tatgtctttc ggatcgtttt  5580
ccgacggaga gattgatgag ctgagccgca gagtaactga gtccgaaccc gtcctgtttg  5640
gatcatttga accgggcgaa gtgaactcaa ttatatcgtc ccgatcagcc gtatcttttc  5700
ctctacgcaa gcagagacgt agacgcagga gcaggaggac tgaatactga ctaaccgggg  5760
taggtgggta catattttcg acggacacag gccctgggca cttgcaaaag aagtccgttc  5820
tgcagaacca gcttacagaa ccgaccttgg agcgcaatgt cctggaaaga attcatgccc  5880
cggtgctcga cacgtcgaaa gaggaacaac tcaaactcag gtaccagatg atgcccaccg  5940
aagccaacaa aagtaggtac cagtctcgta aagtagaaaa tcagaaagcc ataaccactg  6000
agcgactact gtcaggacta cgactgtata actctgccac agatcagcca gaatgctata  6060
agatcaccta tccgaaacca ttgtactcca gtagcgtacc ggcgaactac tccgatccac  6120
agttcgctgt agctgtctgt aacaactatc tgcatgagaa ctatccgaca gtagcatctt  6180
atcagattac tgacgagtac gatgcttact tggatatggt agacgggaca gtcgcctgcc  6240
tggacactgc aaccttctgc cccgctaagc ttagaagtta cccgaaaaaa catgagtata  6300
gagccccgaa tatccgcagt gcggttccat cagcgatgca gaacacgcta caaaatgtgc  6360
tcattgccgc aactaaaaga aattgcaacg tcacgcagat gcgtgaactg ccaacactgg  6420
actcagcgac attcaatgtc gaatgctttc gaaaatatgc atgtaatgac gagtattggg  6480
aggagttcgc tcggaagcca attaggatta ccactgagtt tgtcaccgca tatgtagcta  6540
gactgaaagg ccctaaggcc gccgcactat ttgcaaagac gtataatttg gtcccattgc  6600
aagaagtgcc tatggataga ttcgtcatgg acatgaaaag agacgtgaaa gttacaccag  6660
gcacgaaaca cacagaagaa agaccgaaag tacaagtgat acaagccgca gaacccctgg  6720
cgactgctta cttatgcggg attcaccggg aattagtgcg taggcttacg gccgtcttgc  6780
ttccaaacat tcacacgctt tttgacatgt cggcggagga ttttgatgca atcatagcag  6840
aacacttcaa gcaaggcgac ccggtactgg agacggatat cgcatcattc gacaaaagcc  6900
aagacgacgc tatggcgtta accggtctga tgatcttgga ggacctgggt gtggatcaac  6960
cactactcga cttgatcgag tgcgcctttg gagaaatatc atccacccat ctacctacgg  7020
gtactcgttt taaattcggg gcgatgatga aatccggaat gttcctcaca ctttttgtca  7080
acacagtttt gaatgtcgtt atcgccagca gagtactaga ggagcggctt aaaacgtcca  7140
gatgtgcagc gttcattggc gacgacaaca tcatacatgg agtagtatct gacaaagaaa  7200
tggctgagag gtgcgccacc tggctcaaca tggaggttaa gatcatcgac gcagtcatcg  7260
gtgagagacc accttacttc tgcggcggat ttatcttgca agattcggtt acttccacag  7320
cgtgccgcgt ggcggatccc ctgaaaaggc tgtttaagtt gggtaaaccg ctcccagccg  7380
acgacgagca agacgaagac agaagacgcg ctctgctaga tgaaacaaag gcgtggttta  7440
gagtaggtat aacaggcact ttagcagtgg ccgtgacgac ccggtatgag gtagacaata  7500
ttacacctgt cctactggca ttgagaactt ttgcccagag caaaagagca ttccaagcca  7560
tcagagggga aataaagcat ctctacggtg gtcctaaata gtcagcatag tacatttcat  7620
ctgactaata ctacaacacc accaccatgg aagatgccaa aaacattaag aagggcccag  7680
cgccattcta cccactcgaa gacgggaccg ccggcgagca gctgcacaaa gccatgaagc  7740
gctacgccct ggtgcccggc accatcgcct ttaccgacgc acatatcgag gtggacatta  7800
cctacgccga gtacttcgag atgagcgttc ggctggcaga agctatgaag cgctatgggc  7860
tgaatacaaa ccatcggatc gtggtgtgca gcgagaatag cttgcagttc ttcatgcccg  7920
tgttgggtgc cctgttcatc ggtgtggctg tggccccagc taacgacatc tacaacgagc  7980
gcgagctgct gaacagcatg ggcatcagcc agcccaccgt cgtattcgtg agcaagaaag  8040
ggctgcaaaa gatcctcaac gtgcaaaaga agctaccgat catacaaaag atcatcatca  8100
tggatagcaa gaccgactac cagggcttcc aaagcatgta caccttcgtg acttcccatt  8160
tgccacccgg cttcaacgag tacgacttcg tgcccgagag cttcgaccgg gacaaaacca  8220
tcgccctgat catgaacagt agtggcagta ccggattgcc caagggcgta gccctaccgc  8280
accgcaccgc ttgtgtccga ttcagtcatg cccgcgaccc catcttcggc aaccagatca  8340
tccccgacac cgctatcctc agcgtggtgc catttcacca cggcttcggc atgttcacca  8400
cgctgggcta cttgatctgc ggctttcggg tcgtgctcat gtaccgcttc gaggaggagc  8460
tattcttgcg cagcttgcaa gactataaga ttcaatctgc cctgctggtg cccacactat  8520
ttagcttctt cgctaagagc actctcatcg acaagtacga cctaagcaac ttgcacgaga  8580
tcgccagcgg cggggcgccg ctcagcaagg aggtaggtga ggccgtggcc aaacgcttcc  8640
acctaccagg catccgacag ggctacggcc tgacagaaac aaccagcgcc attctgatca  8700
cccccgaagg ggacgacaag cctggcgcag taggcaaggt ggtgcccttc ttcgaggcta  8760
aggtggtgga cttggacacc ggtaagacac tgggtgtgaa ccagcgcggc gagctgtgcg  8820
tccgtggccc catgatcatg agcggctacg ttaacaaccc cgaggctaca aacgctctca  8880
tcgacaagga cggctggctg cacagcggcg acatcgccta ctgggacgag gacgagcact  8940
tcttcatcgt ggaccggctg aagtccctga tcaaatacaa gggctaccag gtagccccag  9000
ccgaactgga gagcatcctg ctgcaacacc ccaacatctt cgacgccggg gtcgccggcc  9060
tgcccgacga cgatgccggc gagctgcccg ccgcagtcgt cgtgctggaa cacggtaaaa  9120
ccatgaccga gaaggagatc gtggactatg tggccagcca ggttacaacc gccaagaagc  9180
tgcgcggtgg tgttgtgttc gtggacgagg tgcctaaagg actgaccggc aagttggacg  9240
cccgcaagat ccgcgagatt ctcattaagg ccaagaaggg cggcaagatc gccgtgtaaa  9300
```

```
cgcgtgctag accatggatc ctagacgcta cgccccaatg atccgaccag caaaactcga  9360
tgtacttccg aggaactgat gtgcataatg catcaggctg gtacattaga tccccgctta  9420
ccgcgggcaa tatagcaaca ctaaaaactc gatgtacttc cgaggaagcg cagtgcataa  9480
tgctgcgcag tgttgccaca taaccactat attaaccatt tatctagcgg acgccaaaaa  9540
ctcaatgtat ttctgaggaa gcgtggtgca taatgccacg cagcgtctgc ataactttta  9600
ttatttcttt tattaatcaa caaaattttg tttttaacat ttcaaaaaaa aaaaaaaaaa  9660
aaaaaaaatc tagaaaaaaa aaaaaaaaaa aaaaaaaaaa aaaaaaaaaa aaaaaaaaaa  9720
aaaaaaaaaa aaaaaaaaaa aaaaaaaaaa aaaaaaaaaa aaaaaaaaaa aaa         9773

SEQ ID NO: 102         moltype = RNA  length = 2086
FEATURE                Location/Qualifiers
misc_feature           1..2086
                       note = Synthetic polynucleotide
source                 1..2086
                       mol_type = other RNA
                       organism = synthetic construct
SEQUENCE: 102
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccatggaag atgccaaaaa cattaagaag ggcccagcgc  180
cattctaccc actcgaagac gggaccgccg gcgagcagct gcacaaagcc atgaagcgct  240
acgccctggt gcccggcacc atcgccttta ccgacgcaca tatcgaggtg gacattacct  300
acgccgagta cttcgagatg agcgttcggc tggcagaagc tatgaagcgc tatgggctga  360
atacaaacca tcggatcgtg gtgtgcagcg agaatagctt gcagttcttc atgcccgtgt  420
tgggtgccct gttcatcggt gtggctgtgg ccccagctaa cgacatctac aacgagcgcg  480
agctgctgaa cagcatgggc atcagccagc ccaccgtcgt attcgtgagc aagaaagggc  540
tgcaaaagat cctcaacgtg caaaagaagc taccgatcat acaaaagatc atcatcatgg  600
atagcaagac cgactaccag ggcttccaaa gcatgtacac cttcgtgact tcccatttgc  660
cacccggctt caacgagtac gacttcgtgc ccgagagctt cgaccgggac aaaaccatcg  720
ccctgatcat gaacagtagt ggcagtaccg gattgcccaa gggcgtagcc ctaccgcacc  780
gcaccgcttg tgtccgattc agtcatgccc gcgaccccat cttcggcaac cagatcatcc  840
ccgacaccgc tatcctcagc gtggtgccat ttcaccacgg cttcggcatg ttcaccacgc  900
tgggctactt gatctgcggc tttcgggtcg tgctcatgta ccgcttcgag gaggagctat  960
tcttgcgcag cttgcaagac tataagattc aatctgccct gctggtgccc acactattta  1020
gcttcttcgc taagagcact ctcatcgaca agtacgacct aagcaacttg cacgagatcg  1080
ccagcggcgg ggcgccgctc agcaaggagg taggtgaggc cgtggccaaa cgcttccacc  1140
taccaggcat ccgacagggc tacggcctga cagaaacaac cagcgccatt ctgatcaccc  1200
ccgaagggga cgacaagcct ggcgcagtag gcaaggtggt gcccttcttc gaggctaagg  1260
tggtggactt ggacaccggt aagacactgg gtgtgaacca gcgcggcgag ctgtgcgtcc  1320
gtggccccat gatcatgagc ggctacgtta acaaccccga ggctacaaac gctctcatcg  1380
acaaggacgg ctggctgcac agcggcgaca tcgcctactg ggacgaggac gagcacttct  1440
tcatcgtgga ccggctgaag tccctgatca aatacaaggg ctaccaggta gccccagccg  1500
aactggagag catcctgctg caacacccca acatcttcga cgccggggtc gccggcctgc  1560
ccgacgacga tgccggcgag ctgcccgccg cagtcgtcgt gctggaacac ggtaaaacca  1620
tgaccgagaa ggagatcgtg gactatgtgg ccagccaggt tacaaccgcc aagaagctgc  1680
gcggtggtgt tgtgttcgtg gacgaggtgc ctaaaggact gaccggcaag ttggacgccc  1740
gcaagatccg cgagattctc attaaggcca agaagggcgg caagatcgcc gtgtaactcg  1800
agctagtgac tgactaggat ctggttacca ctaaaccagc ctcaagaaca cccgaatgga  1860
gtctctaagc tacataatac caacttacac ttacaaaatg ttgtccccca aaatgtagcc  1920
attcgtatct gctcctaata aaaagaaagt ttcttcacat tctagaaaaa aaaaaaaaaa  1980
aaaaaaaaaa aaaaaaaaaa aaaaaaaaaa aaaaaaaaaa aaaaaaaaaa aaaaaaaaaa  2040
aaaaaaaaaa aaaaaaaaaa aaaaaaaaaa aaaaaaaaaa aaaaaa                 2086

SEQ ID NO: 103         moltype = RNA  length = 8095
FEATURE                Location/Qualifiers
misc_feature           1..8095
                       note = Synthetic polynucleotide
source                 1..8095
                       mol_type = other RNA
                       organism = synthetic construct
SEQUENCE: 103
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
```

-continued

```
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccacccact ggccgagcag gtgatcgtga  1800
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
agggcaacga gatcatgacc gccgctgcca gccagggcct gaccaggaag ggcgtgtacg  2820
ccgtgaggta caaggtgaac gagaacccac tgtacgctcc caccagcgag cacgtgaacg  2880
tgctgctgac caggaccgag gacaggatcg tgtggaagac cctggccggc gacccctgga  2940
tcaagaccct gaccgccaag taccccggca acttcaccgc caccatcgaa gagtggcagg  3000
ccgagcacga cgccatcatg aggcacatcc tggagaggcc cgaccccacc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcaccctga  3420
ggaactacga ccccaggatc aacctggtgc ccgtgaacag gcggctgccc cacgccctgg  3480
tgctgcacca caacgagcac ccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc cccggcgacg  3660
tgcccaagta cgacatcatc ttcgtgaacg tcaggacccc atacaagtac caccattacc  3720
agcagtgcga ggaccacgcc atcaagctga gcatgctgac caagaaggcc tgcctgcacc  3780
tgaaccccgg aggcacctgc gtgagcatcg gctacggcta cgccgacagg gccagcgaga  3840
gcatcattgg cgccatcgcc aggctgttca agttcagcag ggtgtgcaaa cccaagagca  3900
gcctggagga aaccgaggtg ctgttcgtgt tcatcggcta cgaccggaag gccaggaccc  3960
acaaccccta caagctgagc agcaccctga caaacatcta caccggcagc aggctgcacg  4020
aggccggctg cgcccccagc taccacgtgg tcaggggcga tatcgccacc gccaccgagg  4080
gcgtgatcat caacgctgcc aacagcaagg gccagcccgg aggcggagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg ccccaacttc aacaaggtga  4260
gcgaggtgga aggcgacaag cagctggccg aagcctacga gagcatcgcc aagatcgtga  4320
acgacaataa ctacaagagc gtggccatcc cactgctcag caccggcatc ttcagcggca  4380
acaaggacag gctgacccag agcctgaacc acctgctcac cgccctggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgagggtg caccccaaga gctccctggc cggcaggaag ggctacagca  4620
ccagcgacgg caagaccttc agctacctgg agggcaccaa gttccaccag gccgctaagg  4680
acatcgccga gatcaacgct atgtggcccg tggccaccga ggccaacgag caggtgtgca  4740
tgtacatcct gggcgagagc atgtccagca tcaggagcaa gtgccccgtg gaggaaagcg  4800
aggccagcac accacccagc accctgccct gcctgtgcat ccacgctatg acacccgaga  4860
gggtgcagcg gctgaaggcc agcaggcccg agcagatcac cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagacc ccacccgtgg  5040
acgagacacc cgagccaagc gccgagaacc agagcaccga gggcacaccc gagcagccac  5100
ccctgatcac cgaggacgag acaaggaccc ggaccccaga gcccatcatt atcgaggaag  5160
aggaagagga cagcatcagc ctgctgagcg acggccccac ccaccaggtg ctgcaggtgg  5220
aggccgacat ccacggccca cccagcgtgt ccagctccag ctggagcatc ccacacgcca  5280
gcgacttcga cgtggacagc ctgagcatcc tggacaccct ggagggcgcc agcgtgacct  5340
ccggcgccac cagcgccgag accaacagct acttcgccaa gagcatggag ttcctggcca  5400
ggcccgtgcc agctcccagg accgtgttca ggaacccacc ccacccagct cccaggacca  5460
ggaccccaag cctggctccc agcagggcct gcagcaggac cagcctggtg agcaccccac  5520
ccggcgtgaa cagggtgatc accagggagg aactggaggc cctgacaccc agcaggaccc  5580
ccagcaggtc cgtgagcagg actagtctgg tgtccaaccc acccggcgtg aacagggtga  5640
tcaccaggga ggaattcgag gccttcgtgg cccagcaaca gagacggttc gacgccggcg  5700
cctacatctt cagcagcgac accggccagg gacacctgca gcaaaagagc gtgaggcaga  5760
ccgtgctgag cgaggtggtg ctggagagga ccgagctgga aatcagctac gcccccaggc  5820
```

```
tggaccagga gaaggaggaa ctgctcagga agaaactgca gctgaacccc accccagcca  5880
acaggagcag gtaccagagc aggaaggtgg agaacatgaa ggccatcacc gccaggcgga  5940
tcctgcaggg cctgggacac tacctgaagg ccgagggcaa ggtggagtgc tacaggaccc  6000
tgcaccccgt gccactgtac agctccagcg tgaacagggc cttctccagc cccaaggtgg  6060
ccgtggaggc ctgcaacgct atgctgaagg agaacttccc caccgtggcc agctactgca  6120
tcatccccga gtacgacgcc tacctggaca tggtggacgg cgccagctgc tgcctggaca  6180
ccgccagctt ctgccccgcc aagctgagga gcttccccaa gaaacacagc tacctggagc  6240
ccaccatcag gagcgccgtg cccagcgcca tccagaacac cctgcagaac gtgctggccg  6300
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggccccaa ggccgctgcc ctgttcgcta agacccacaa cctgaacatg ctgcaggaca  6540
tcccaatgga caggttcgtg atggacctga agagggacgt gaaggtgaca cccggcacca  6600
agcacaccga ggagaggccc aaggtgcagg tgatccaggc cgctgaccca ctggccaccg  6660
cctacctgtg cggcatccac agggagctgg tgaggcggct gaacgccgtg ctgctgccca  6720
acatccacac cctgttcgac atgagcgccg aggacttcga cgccatcatc gccgagcact  6780
tccagcccgg cgactgcgtg ctggagaccg acatcgccag cttcgacaag agcgaggatg  6840
acgctatggc cctgaccgct ctgatgatcc tggaggacct gggcgtggac gccgagctgc  6900
tcaccctgat cgaggctgcc ttcggcgaga tcagctccat ccacctgccc accaagacca  6960
agttcaagtt cggcgctatg atgaaaagcg gaatgttcct gaccctgttc gtgaacaccg  7020
tgatcaacat tgtgatcgcc agcagggtgc tgcgggagag gctgaccggc agcccctgcg  7080
ctgccttcat cggcgacgac aacatcgtga agggcgtgaa aagcgacaag ctgatggccg  7140
acaggtgcgc cacctggctg aacatggagg tgaagatcat cgacgccgtg gtgggcgaga  7200
aggcccccta cttctgcggc ggattcatcc tgtgcgacag cgtgaccggc accgcctgca  7260
gggtggccga cccccctgaag aggctgttca agctgggcaa gccactggcc gctgacgatg  7320
agcacgacga tgacaggcgg agggccctgc acgaggaaag caccaggtgg aacagggtgg  7380
gcatcctgag cgagctgtgc aaggccgtgg agagcaggta cgagaccgtg ggcaccagca  7440
tcatcgtgat ggctatgacc acactggcca gctccgtcaa gagcttctcc tacctgaggg  7500
gggcccctat aactctctac ggctaacctg aatggactac gacatagtct agtccgccaa  7560
ggccgccacc catgaagttg gtggttgtgg gggccggggg tgttggcaaa agcgccctta  7620
caatttgact cgagtatgtt acgtgcaaag gtgattgtca ccccccgaaa gaccatattg  7680
tgacacaccc tcagtatcac gcccaaacat ttacagccgc ggtgtcaaaa accgcgtgga  7740
cgtggttaac atccctgctg ggaggatcag ccgtaattat tataattggc ttggtgctgg  7800
ctactattgt ggccatgtac gtgctgacca accagaaaca taattgaata cagcagcaat  7860
tggcaagctg cttacataga actcgcggcg attggcatgc cgccttaaaa tttttatttt  7920
atttttcttt ttcttttccg aatcggattt tgtttttaat atttcaaaaa aaaaaaaaaa  7980
aaaaaaaaaa tctagaaaaa aaaaaaaaaa aaaaaaaaaa aaaaaaaaaa aaaaaaaaaa  8040
aaaaaaaaaa aaaaaaaaaa aaaaaaaaaa aaaaaaaaaa aaaaaaaaaa aaaaa       8095

SEQ ID NO: 104         moltype = RNA  length = 8120
FEATURE                Location/Qualifiers
misc_feature           1..8120
                       note = Synthetic polynucleotide
source                 1..8120
                       mol_type = other RNA
                       organism = synthetic construct
SEQUENCE: 104
attgacggcg tagtacacac tattgaatca aacagccgac caattgcact accatcacaa  60
tggagaagcc agtagtaaac gtagacgtag acccccagag tccgtttgtc gtgcaactgc  120
aaaaaagctt cccgcaattt gaggtagtag cacagcaggt cactccaaat gaccatgcta  180
atgccagagc attttcgcat ctggccagta aactaatcga gctggaggtt cctaccacag  240
cgacgatctt ggacataggc agcgcaccgg ctcgtagaat gttttccgag caccagtatc  300
attgtgtctg ccccatgcgt agtccagaag acccggaccg catgatgaaa tatgccagta  360
aactggcgga aaaagcgtgc aagattacaa acaagaactt gcatgagaag attaaggatc  420
tccggaccgt acttgatacg ccggatgctg aaacaccatc gctctgcttt cacaacgatg  480
ttacctgcaa catgcgtgcc gaatattccg tcatgcagga cgtgtatatc aacgctcccg  540
gaactatcta tcatcaggct atgaaaggcg tgcggaccct gtactggatt ggcttcgaca  600
ccacccagtt catgttctcg gctatggcag gttcgtaccc tgcgtacaac accaactggg  660
ccgacgagaa agtccttgaa gcgcgtaaca tcggactttg cagcacaaag ctgagtgaag  720
gtaggacagg aaaattgtcg ataatgagga agaaggagtt gaagcccggg tcgcgggttt  780
atttctccgt aggatcgaca ctttatccag aacacagagc cagcttgcag agctggcatc  840
ttccatcggt gttccacttg aatggaaagc agtcgtacac ttgccgctgt gatacagtgg  900
tgagttgcga aggctacgta gtgaagaaaa tcaccatcag tcccgggatc acgggagaaa  960
ccgtgggata cgcggttaca cacaatagcg agggcttctt gctatgcaaa gttactgaca  1020
cagtaaaagg agaacgggta tcgttccctg tgtgcacgta catcccggcc accatatgcg  1080
atcagatgac tggtataatg gccacggata tatcacctga cgatgcacaa aaacttctgg  1140
ttgggctcaa ccagcgaatt gtcattaacg gtaggactaa caggaacacc aacaccatgc  1200
aaaattacct tctgccgatc atagcacaag ggttcagcaa atgggctaag gagcgcaagg  1260
atgatcttga taacgagaaa atgctgggta ctagagaacg caagcttacg tatggctgct  1320
tgtgggcgtt tcgcactaag aaagtacatt cgttttatcg cccacctgga acgcagacct  1380
gcgtaaaagt cccagcctct tttagcgctt ttcccatgtc gtccgtatgg acgacctctt  1440
tgcccatgtc gctgaggcag aaattgaaac tggcattgca accaaagaag gaggaaaaac  1500
tgctgcaggt ctcggaggaa ttagtcatgg aggccaaggc tgcttttgag gatgctcagg  1560
aggaagccag agcggagaag ctccgagaag cacttccacc attagtggca gacaaaggca  1620
tcgaggcagc cgcagaagtt gtctgcgaag tggaggggct ccaggcggac atcggagcag  1680
cattagttga aaccccgcgc ggtcacgtaa ggataatacc tcaagcaaat gaccgtatga  1740
tcggacagta tatcgttgtc tcgccaaact ctgtgctgaa gaatgccaaa ctcgcaccag  1800
cgcacccgct agcagatcag gttaagatca taacacactc cggaagatca ggaaggtacg  1860
cggtcgaacc atacgacgct aaagtactga tgccagcagg aggtgccgta ccatggccag  1920
```

-continued

```
aattcctagc actgagtgag agcgccacgt tagtgtacaa cgaaagagag tttgtgaacc  1980
gcaaactata ccacattgcc atgcatggcc ccgccaagaa tacagaagag gagcagtaca  2040
aggttacaaa ggcagagctt gcagaaacag agtacgtgtt tgacgtggac aagaagcgtt  2100
gcgttaagaa ggaagaagcc tcaggtctgg tcctctcggg agaactgacc aaccctccct  2160
atcatgagct agctctggag ggactgaaga cccgacctgc ggtcccgtac aaggtcgaaa  2220
caataggagt gataggcaca ccggggtcgg gcaagtcagc tattatcaag tcaactgtca  2280
cggcacgaga tcttgttacc agcggaaaga aagaaaattg tcgcgaaatt gaggccgacg  2340
tgctaagact gaggggtatg cagattacgt cgaagacagt agattcggtt atgctcaacg  2400
gatgccacaa agccgtagaa gtgctgtacg ttgacgaagc gttcgcgtgc cacgcaggag  2460
cactacttgc cttgattgct atcgtcaggc cccgcaagaa ggtagtacta tgcggagacc  2520
ccatgcaatg cggattcttc aacatgatgc aactaaaggt acatttcaat caccctgaaa  2580
aagacatatg caccaagaca ttctacaagt atatctcccg gcgttgcaca cagccagtta  2640
cagctattgt atcgacactg cattacgatg gaaagatgaa aaccacgaac ccgtgcaaga  2700
agaacattga aatcgatatt acaggggcca caaagccgaa gccaggggat atcatcctga  2760
catgtttccg cgggtgggtt aagcaattgc aaatcgacta tcccggacat gaagtaatga  2820
cagccgcggc ctcacaaggg ctaaccagaa aaggagtgta tgccgtccgg caaaaagtca  2880
atgaaaaccc actgtacgcg atcacatcag agcatgtgaa cgtgttgctc acccgcactg  2940
aggacaggct agtgtggaaa accttgcagg gcgacccatg gattaagcag ctcactaaca  3000
tacctaaagg aaactttcag gctactatag aggactggga agctgaacac aagggaataa  3060
ttgctgcaat aaacagcccc actccccgtg ccaatccgtt cagctgcaag accaacgttt  3120
gctgggcgaa agcattggaa ccgatactag ccacggccgg tatcgtactt accggttgcc  3180
agtggagcga actgttccca cagtttgcgg atgacaaacc acattcggcc atttacgcct  3240
tagacgtaat ttgcattaag tttttcggca tggacttgac aagcggactg ttttctaaac  3300
agagcatccc actaacgtac catcccgccg attcagcgag gccggtagct cattgggaca  3360
acagcccagg aacccgcaag tatgggtacg atcacgccat tgccgccgaa ctctcccgta  3420
gatttccggt gttccagcta gctgggaagg gcacacaact tgatttgcag acggggagaa  3480
ccagagttat ctctgcacag cataacctgg tcccggtgaa ccgcaatctt cctcacgcct  3540
tagtccccga gtacaaggag aagcaacccg gcccggtcga aaaattcttg aaccagttca  3600
aacaccactc agtacttgtg gtatcagagg aaaaaattga agctccccgt aagagaatcg  3660
aatggatcgc cccgattggc atagccggtg cagataagaa ctacaacctg gctttcgggt  3720
ttccgccgca ggcacggtac gacctggtgt tcatcaacat tggaactaaa tacagaaacc  3780
accactttca gcagtgcgaa gaccatgcgg cgaccttaaa aaccctttcg cgttcggccc  3840
tgaattgcct taacccagga ggcaccctcg tggtgaagtc ctatggctac gccgaccgca  3900
acagtgagga cgtagtcacc gctcttgcca gaaagtttgt cagggtgtct gcagcgagac  3960
cagattgtgt ctcaagcaat acagaaatgt acctgatttt ccgacaacta gacaacagcc  4020
gtacacggca attcaccccg caccatctga attgcgtgat ttcgtccgtg tatgagggta  4080
caagagatgg agttggagcc gcgccgtcat accgcaccaa aagggagaat attgctgact  4140
gtcaagagga agcagttgtc aacgcagcca atccgctggg tagaccaggc gaaggagtct  4200
gccgtgccat ctataaacgt tggccgacca gttttaccga ttcagccacg gagacaggca  4260
ccgcaagaat gactgtgtgc ctaggaaaga aagtgatcca cgcggtcggc cctgatttcc  4320
ggaagcaccc agaagcagaa gccttgaaat tgctacaaaa cgcctaccat gcagtggcag  4380
acttagtaaa tgaacataac atcaagtctg tcgccattcc actgctatct acaggcattt  4440
acgcagccgg aaaagaccgc cttgaagtat cacttaactg cttgacaacc gcgctagaca  4500
gaactgacgc ggacgtaacc atctattgcc tggataagaa gtggaaggaa agaatcgacg  4560
cggcactcca acttaaggag tctgtaacag agctgaagga tgaagatatg gagatcgacg  4620
atgagttagt atggatccat ccagacagtt gcttgaaggg aagaaaggga ttcagtacta  4680
caaaaggaaa attgtattcg tacttcgaag gcaccaaatt ccatcaagca gcaaaagaca  4740
tggcggagat aaaggtcctg ttccctaatg accaggaaag taatgaacaa ctgtgtgcct  4800
acatattggg tgagaccatg gaagcaatcc gcgaaaagtg cccggtcgac cataacccgt  4860
cgtctagccc gcccaaaacg ttgccgtgcc tttgcatgta tgccatgacg ccagaaaggg  4920
tccacagact tagaagcaat aacgtcaaag aagttacagt atgctcctcc acccccttc   4980
ctaagcacaa aattaagaat gttcagaagg ttcagtgcac gaaagtagtc ctgtttaatc  5040
cgcacactcc cgcattcgtt cccgcccgta agtacataga agtgccagaa cagcctaccg  5100
ctcctcctgc acaggccgag gaggcccccg aagttgtagc gacaccgtca ccatctacag  5160
ctgataacac ctcgcttgat gtcacagaca tctcactgga tatggatgac agtagcgaag  5220
gctcactttt ttcgagcttt agcggatcgg acaactctat tactagtatg gacagttggt  5280
cgtcaggacc tagttcacta gagatagtag accgaaggca ggtggtggtg gctgacgttc  5340
atgccgtcca agagcctgcc cctattccac cgccaaggct aaagaagatg gcccgcctgg  5400
cagcggcaag aaaagagccc actccaccgg caagcaatag ctctgagtcc ctccacctct  5460
cttttggtgg ggtatccatg tccctcggat caattttcga cggagagacg gcccgccagg  5520
cagcggtaca accccctggca acaggcccca cggatgtgcc tatgtctttc ggatcgtttt  5580
ccgacggaga gattgatgag ctgagccgca gagtaactga gtccgaaccc gtcctgtttg  5640
gatcatttga accgggcgaa gtgaactcaa ttatatcgtc ccgatcagcc gtatcttttc  5700
ctctacgcaa gcagagacgt agacgcagga gcaggaggac tgaatactga ctaaccgggg  5760
taggtgggta catattttcg acggacacag gccctgggca cttgcaaaag aagtccgttc  5820
tgcagaacca gcttacagaa ccgaccttgg agcgcaatgt cctggaaaga attcatgccc  5880
cggtgctcga cacgtcgaaa gaggaacaac tcaaactcag gtaccagatg atgcccaccg  5940
aagccaacaa aagtaggtac cagtctcgta aagtagaaaa tcagaaagcc ataaccactg  6000
agcgactact gtcaggacta cgactgtata actctgccac agatcagcca gaatgctata  6060
agatcaccta tccgaaacca ttgtactcca gtagcgtacc ggcgaactac tccgatccac  6120
agttcgctgt agctgtctgt aacaactatc tgcatgagaa ctatccgaca gtagcatctt  6180
atcagattac tgacgagtac gatgcttact tggatatggt agacgggaca gtcgcctgcc  6240
tggacactgc aaccttctgc cccgctaagc ttagaagtta cccgaaaaaa catgagtata  6300
gagccccgaa tatccgcagt gcggttccat cagcgatgca gaacacgcta caaaatgtgc  6360
tcattgccgc aactaaaaga aattgcaacg tcacgcagat gcgtgaactg ccaacactgg  6420
actcagcgac attcaatgtc gaatgctttc gaaaatatgc atgtaatgac gagtattggg  6480
aggagttcgc tcggaagcca attaggatta ccactgagtt tgtcaccgca tatgtagcta  6540
gactgaaagg ccctaaggcc gccgcactat ttgcaaagac gtataatttg gtcccattgc  6600
aagaagtgcc tatggataga ttcgtcatgg acatgaaaag agacgtgaaa gttacaccag  6660
```

```
gcacgaaaca cacagaagaa agaccgaaag tacaagtgat acaagccgca gaacccctgg  6720
cgactgctta cttatgcggg attcaccggg aattagtgcg taggcttacg gccgtcttgc  6780
ttccaaacat tcacacgctt tttgacatgt cggcggagga ttttgatgca atcatagcag  6840
aacacttcaa gcaaggcgac ccggtactgg agacggatat cgcatcattc gacaaaagcc  6900
aagacgacgc tatggcgtta accggtctga tgatcttgga ggacctgggt gtggatcaac  6960
cactactcga cttgatcgag tgcgcctttg gagaaatatc atccacccat ctacctacgg  7020
gtactcgttt taaattcggg gcgatgatga aatccggaat gttcctcaca ctttttgtca  7080
acacagtttt gaatgtcgtt atcgccagca gagtactaga ggagcggctt aaaacgtcca  7140
gatgtgcagc gttcattggc gacgacaaca tcatacatgg agtagtatct gacaaagaaa  7200
tggctgagag gtgcgccacc tggctcaaca tggaggttaa gatcatcgac gcagtcatcg  7260
gtgagagacc accttacttc tgcggcggat ttatcttgca agattcggtt acttccacag  7320
cgtgccgcgt ggcggatccc ctgaaaaggc tgtttaagtt gggtaaaccg ctcccagccg  7380
acgacgagca agacgaagac agaagacgcg ctctgctaga tgaaacaaag gcgtggttta  7440
gagtaggtat aacaggcact ttagcagtgg ccgtgacgac ccggtatgag gtagacaata  7500
ttacacctgt cctactggca ttgagaactt ttgcccagag caaaagagca ttccaagcca  7560
tcagagggga aataaagcat ctctacggtg gtcctaaata gtcagcatag tacatttcat  7620
ctgactaata ctacaacacc accaccacgc gtgctagacc atggatccta gacgctacgc  7680
cccaatgatc cgaccagcaa aactcgatgt acttccgagg aactgatgtg cataatgcat  7740
caggctggta cattagatcc ccgcttaccg cgggcaatat agcaacacta aaaactcgat  7800
gtacttccga ggaagcgcag tgcataatgc tgcgcagtgt tgccacataa ccactatatt  7860
aaccatttat ctagcggacg ccaaaaactc aatgtatttc tgaggaagcg tggtgcataa  7920
tgccacgcag cgtctgcata acttttatta tttcttttat taatcaacaa aattttgttt  7980
ttaacatttc aaaaaaaaaa aaaaaaaaaa aaaaatctag aaaaaaaaaa aaaaaaaaaa  8040
aaaaaaaaaa aaaaaaaaaa aaaaaaaaaa aaaaaaaaaa aaaaaaaaaa aaaaaaaaaa  8100
aaaaaaaaaa aaaaaaaaaa                                              8120

SEQ ID NO: 105          moltype = RNA  length = 8875
FEATURE                 Location/Qualifiers
misc_feature            1..8875
                        note = Synthetic polynucleotide
source                  1..8875
                        mol_type = other RNA
                        organism = synthetic construct
SEQUENCE: 105
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga agccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccacccact ggccgagcag gtgatcgtga  1800
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
```

-continued

```
aggacgacct gatcctgacc tgcttcaggg gctgggtgaa gcagctgcag atcgactaca  2760
agggcaacga gatcatgacc gccgctgcca gccagggcct gaccaggaag ggcgtgtacg  2820
ccgtgaggta caaggtgaac gagaacccac tgtacgctcc caccagcgag cacgtgaacg  2880
tgctgctgac caggaccgag gacaggatcg tgtggaagac cctggccggc gacccctgga  2940
tcaagaccct gaccgccaag taccccggca acttcaccgc caccatcgaa gagtggcagg  3000
ccgagcacga cgccatcatg aggcacatcc tggagaggcc cgaccccacc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcaccctga  3420
ggaactacga ccccaggatc aacctggtgc ccgtgaacag gcggctgccc cacgccctgg  3480
tgctgcacca caacgagcac ccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc cccggcgacg  3660
tgcccaagta cgacatcatc ttcgtgaacg tcaggacccc atacaagtac caccattacc  3720
agcagtgcga ggaccacgcc atcaagctga gcatgctgac caagaaggcc tgcctgcacc  3780
tgaaccccgg aggcacctgc gtgagcatcg gctacggcta cgccgacagg gccagcgaga  3840
gcatcattgg cgccatcgcc aggctgttca agttcagcag ggtgtgcaaa cccaagagca  3900
gcctggagga aaccgaggtg ctgttcgtgt tcatcggcta cgaccggaag gccaggaccc  3960
acaaccccta caagctgagc agcaccctga caaacatcta caccggcagc aggctgcacg  4020
aggccggctg cgcccccagc taccacgtgg tcaggggcga tatcgccacc gccaccgagg  4080
gcgtgatcat caacgctgcc aacagcaagg gccagcccgg aggcggagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg ccccaacttc aacaaggtga  4260
gcgaggtgga aggcgacaag cagctggccg aagcctacga gagcatcgcc aagatcgtga  4320
acgacaataa ctacaagagc gtggccatcc cactgctcag caccggcatc ttcagcggca  4380
acaaggacag gctgacccag agcctgaacc acctgctcac cgccctggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgagggtg caccccaaga gctccctggc cggcaggaag ggctacagca  4620
ccagcgacgg caagaccttc agctacctgg agggcaccaa gttccaccag gccgctaagg  4680
acatcgccga gatcaacgct atgtggcccg tggccaccga ggccaacgag caggtgtgca  4740
tgtacatcct gggcgagagc atgtccagca tcaggagcaa gtgccccgtg gaggaaagcg  4800
aggccagcac accacccagc accctgccct gcctgtgcat ccacgctatg acacccgaga  4860
gggtgcagcg gctgaaggcc agcaggcccg agcagatcac cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagacc ccacccgtgg  5040
acgagacacc cgagccaagc gccgagaacc agagcaccga gggcacaccc gagcagccac  5100
ccctgatcac cgaggacgag acaaggaccc ggaccccaga gcccatcatt atcgaggaag  5160
aggaagagga cagcatcagc ctgctgagcg acggccccac ccaccaggtg ctgcaggtgg  5220
aggccgacat ccacggccca cccagcgtgt ccagctccag ctggagcatc ccacacgcca  5280
gcgacttcga cgtggacagc ctgagcatcc tggacaccct ggagggcgcc agcgtgacct  5340
ccggcgccac cagcgccgag accaacagct acttcgccaa gagcatggag ttcctggcca  5400
ggcccgtgcc agctcccagg accgtgttca ggaacccacc ccacccagct cccaggacca  5460
ggaccccaag cctggctccc agcagggcct gcagcaggac cagcctggtg agcaccccac  5520
ccggcgtgaa cagggtgatc accagggagg aactggaggc cctgacaccc agcaggaccc  5580
ccagcaggtc cgtgagcagg actagtctgg tgtccaaccc acccggcgtg aacagggtga  5640
tcaccaggga ggaattcgag gccttcgtgg cccagcaaca gagacggttc gacgccggcg  5700
cctacatctt cagcagcgac accggccagg gacacctgca gcaaaagagc gtgaggcaga  5760
ccgtgctgag cgaggtggtg ctggagagga ccgagctgga aatcagctac gcccccaggc  5820
tggaccagga gaaggaggaa ctgctcagga agaaactgca gctgaacccc accccagcca  5880
acaggagcag gtaccagagc aggaaggtgg agaacatgaa ggccatcacc gccaggcgga  5940
tcctgcaggg cctgggacac tacctgaagg ccgagggcaa ggtggagtgc tacaggaccc  6000
tgcaccccgt gccactgtac agctccagcg tgaacagggc cttctccagc cccaaggtgg  6060
ccgtggaggc ctgcaacgct atgctgaagg agaacttccc caccgtggcc agctactgca  6120
tcatccccga gtacgacgcc tacctggaca tggtggacgg cgccagctgc tgcctggaca  6180
ccgccagctt ctgccccgcc aagctgagga gcttccccaa gaaacacagc tacctggagc  6240
ccaccatcag gagcgccgtg cccagcgcca tccagaacac cctgcagaac gtgctggccg  6300
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggccccaa ggccgctgcc ctgttcgcta agacccacaa cctgaacatg ctgcaggaca  6540
tcccaatgga caggttcgtg atggacctga agagggacgt gaaggtgaca cccggcacca  6600
agcacaccga ggagaggccc aaggtgcagg tgatccaggc cgctgaccca ctggccaccg  6660
cctacctgtg cggcatccac agggagctgg tgaggcggct gaacgccgtg ctgctgccca  6720
acatccacac cctgttcgac atgagcgccg aggacttcga cgccatcatc gccgagcact  6780
tccagcccgg cgactgcgtg ctggagaccg acatcgccag cttcgacaag agcgaggatg  6840
acgctatggc cctgaccgct ctgatgatcc tggaggacct gggcgtggac gccgagctgc  6900
tcaccctgat cgaggctgcc ttcggcgaga tcagctccat ccacctgccc accaagacca  6960
agttcaagtt cggcgctatg atgaaaagcg gaatgttcct gaccctgttc gtgaacaccg  7020
tgatcaacat tgtgatcgcc agcagggtgc tgcgggagag gctgaccggc agcccctgcg  7080
ctgccttcat cggcgacgac aacatcgtga agggcgtgaa aagcgacaag ctgatggccg  7140
acaggtgcgc cacctggctg aacatggagg tgaagatcat cgacgccgtg gtgggcgaga  7200
aggcccccta cttctgcggc ggattcatcc tgtgcgacag cgtgaccggc accgcctgca  7260
gggtggccga cccccctgaag aggctgttca agctgggcaa gccactggcc gctgacgatg  7320
agcacgacga tgacaggcgg agggccctgc acgaggaaag caccaggtgg aacagggtgg  7380
gcatcctgag cgagctgtgc aaggccgtgg agagcaggta cgagaccgtg ggcaccagca  7440
```

-continued

```
tcatcgtgat ggctatgacc acactggcca gctccgtcaa gagcttctcc tacctgaggg  7500
gggcccctat aactctctac ggctaacctg aatggactac gacatagtct agtccgccaa  7560
ggccgccacc atgagagtga cagcccctag aaccttactg cttctgcttt ggggagctgt  7620
tgctctgaca gagacatggg ctggatctct gagcgaggtg accggccagg gcctgtgcat  7680
cggcgccgtg cccaagaccc accaggtgct gtgcaacacc acccagaaga ccagcgacgg  7740
cagctactac ctggccgctc ccaccggcac cacctgggcc tgcagcaccg gcctgacccc  7800
ttgcatcagc accaccatcc tgaacctgac caccgactac tgcgtgctgg tggagctgtg  7860
gcccagggtg acctaccaca gccccagcta cgcctaccac cagttcgaga ggagggccaa  7920
gtacaagagg gagcccgtga gcctgaccct ggccctgctg ctgggcggcc tgacaatggg  7980
cggcatcgcc gccggcgtgg gcaccggcac caccgccctg gtggccaccc agcagttcca  8040
gcagctgcag gccgccatgc acgacgacct gaaggaggtg gagaagtcca tcaccaacct  8100
ggagaagtcc ctgaccagcc tgagcgaggt ggtgctgcag aacaggaggg gcctggacct  8160
gctgttcctg aaggagggcg gcctgtgcgc cgccctgaag gaggagtgct gcctgtacgc  8220
cgaccacacc ggcctggtga tcgtgggcat tgtcgctggc ctggccgtcc tcgccgtggt  8280
ggtgattgga gctgtggtcg cagctgttat gtgcagaaga aagtcatccg gcggaaaggg  8340
aggctcctac tctcaggctg cttctgctac agtgcctaga gctcttatgt gtttatctca  8400
gctgtaaact cgagtatgtt acgtgcaaag gtgattgtca ccccccgaaa gaccatattg  8460
tgacacaccc tcagtatcac gcccaaacat ttacagccgc ggtgtcaaaa accgcgtgga  8520
cgtggttaac atccctgctg ggaggatcag ccgtaattat tataattggc ttggtgctgg  8580
ctactattgt ggccatgtac gtgctgacca accagaaaca taattgaata cagcagcaat  8640
tggcaagctg cttacataga actcgcggcg attggcatgc cgccttaaaa tttttatttt  8700
atttttcttt ttcttttccg aatcggattt tgtttttaat atttcaaaaa aaaaaaaaaa  8760
aaaaaaaaaa tctagaaaaa aaaaaaaaaa aaaaaaaaaa aaaaaaaaaa aaaaaaaaaa  8820
aaaaaaaaaa aaaaaaaaaa aaaaaaaaaa aaaaaaaaaa aaaaaaaaaa aaaaa       8875

SEQ ID NO: 106          moltype = RNA  length = 8416
FEATURE                 Location/Qualifiers
misc_feature            1..8416
                        note = Synthetic polynucleotide
source                  1..8416
                        mol_type = other RNA
                        organism = synthetic construct
SEQUENCE: 106
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccaccccact ggccgagcag gtgatcgtga  1800
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
```

-continued

```
agggcaacga gatcatgacc gccgctgcca gccagggcct gaccaggaag ggcgtgtacg  2820
ccgtgaggta caaggtgaac gagaacccac tgtacgctcc caccagcgag cacgtgaacg  2880
tgctgctgac caggaccgag gacaggatcg tgtggaagac cctggccggc gaccccctgga  2940
tcaagaccct gaccgccaag taccccggca acttcaccgc caccatcgaa gagtggcagg  3000
ccgagcacga cgccatcatg aggcacatcc tggagaggcc cgaccccacc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcaccctga  3420
ggaactacga ccccaggatc aacctggtgc ccgtgaacag gcggctgccc cacgccctgg  3480
tgctgcacca caacgagcac cccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc cccggcgacg  3660
tgcccaagta cgacatcatc ttcgtgaacg tcaggacccc atacaagtac caccattacc  3720
agcagtgcga ggaccacgcc atcaagctga gcatgctgac caagaaggcc tgcctgcacc  3780
tgaacccccgg aggcacctgc gtgagcatcg gctacggcta cgccgacagg gccagcgaga  3840
gcatcattgg cgccatcgcc aggctgttca agttcagcag ggtgtgcaaa cccaagagca  3900
gcctggagga aaccgaggtg ctgttcgtgt tcatcggcta cgaccggaag gccaggaccc  3960
acaaccccta caagctgagc agcaccctga caaacatcta caccggcagc aggctgcacg  4020
aggccggctg cgcccccagc taccacgtgg tcaggggcga tatcgccacc gccaccgagg  4080
gcgtgatcat caacgctgcc aacagcaagg gccagcccgg aggcggagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg ccccaacttc aacaaggtga  4260
gcgaggtgga aggcgacaag cagctggccg aagcctacga gagcatcgcc aagatcgtga  4320
acgacaataa ctacaagagc gtggccatcc cactgctcag caccggcatc ttcagcggca  4380
acaaggacag gctgacccag agcctgaacc acctgctcac cgccctggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgagggtg caccccaaga gctccctggc cggcaggaag ggctacagca  4620
ccagcgacgg caagaccttc agctacctgg agggcaccaa gttccaccag gccgctaagg  4680
acatcgccga gatcaacgct atgtggcccg tggccaccga ggccaacgag caggtgtgca  4740
tgtacatcct gggcgagagc atgtccagca tcaggagcaa gtgccccgtg gaggaaagcg  4800
aggccagcac accacccagc accctgccct gcctgtgcat ccacgctatg acacccgaga  4860
gggtgcagcg gctgaaggcc agcaggcccg agcagatcac cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagacc ccacccgtgg  5040
acgagacacc cgagccaagc gccgagaacc agagcaccga gggcacaccc gagcagccac  5100
ccctgatcac cgaggacgag acaaggaccc ggaccccaga gcccatcatt atcgaggaag  5160
aggaagagga cagcatcagc ctgctgagcg acggccccac ccaccaggtg ctgcaggtgg  5220
aggccgacat ccacggccca cccagcgtgt ccagctccag ctggagcatc ccacacgcca  5280
gcgacttcga cgtggacagc ctgagcatcc tggacaccct ggagggcgcc agcgtgacct  5340
ccggcgccac cagcgccgag accaacagct acttcgccaa gagcatggag ttcctggcca  5400
ggcccgtgcc agctcccagg accgtgttca ggaacccacc ccacccagct cccaggacca  5460
ggaccccaag cctggctccc agcagggcct gcagcaggac cagcctggtg agcaccccac  5520
ccggcgtgaa cagggtgatc accagggagg aactggaggc cctgacaccc agcaggaccc  5580
ccagcaggtc cgtgagcagg actagtctgg tgtccaaccc acccggcgtg aacagggtga  5640
tcaccaggga ggaattcgag gccttcgtgg cccagcaaca gagacggttc gacgccggcg  5700
cctacatctt cagcagcgac accggccagg gacacctgca gcaaaagagc gtgaggcaga  5760
ccgtgctgag cgaggtggtg ctggagagga ccgagctgga aatcagctac gcccccaggc  5820
tggaccagga gaaggaggaa ctgctcagga agaaactgca gctgaacccc accccagcca  5880
acaggagcag gtaccagagc aggaaggtgg agaacatgaa ggccatcacc gccaggcgga  5940
tcctgcaggg cctgggacac tacctgaagg ccgagggcaa ggtggagtgc tacaggaccc  6000
tgcaccccgt gccactgtac agctccagcg tgaacagggc cttctccagc cccaaggtgg  6060
ccgtggaggc ctgcaacgct atgctgaagg agaacttccc caccgtggcc agctactgca  6120
tcatccccga gtacgacgcc tacctggaca tggtggacgg cgccagctgc tgcctggaca  6180
ccgccagctt ctgccccgcc aagctgagga gcttccccaa gaaacacagc tacctggagc  6240
ccaccatcag gagcgccgtg cccagcgcca tccagaacac cctgcagaac gtgctggccg  6300
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggccccaa ggccgctgcc ctgttcgcta agacccacaa cctgaacatg ctgcaggaca  6540
tcccaatgga caggttcgtg atggacctga agagggacgt gaaggtgaca cccggcacca  6600
agcacaccga ggagaggccc aaggtgcagg tgatccaggc cgctgaccca ctggccaccg  6660
cctacctgtg cggcatccac agggagctgg tgaggcggct gaacgccgtg ctgctgccca  6720
acatccacac cctgttcgac atgagcgccg aggacttcga cgccatcatc gccgagcact  6780
tccagcccgg cgactgcgtg ctggagaccg acatcgccag cttcgacaag agcgaggatg  6840
acgctatggc cctgaccgct ctgatgatcc tggaggacct gggcgtggac gccgagctgc  6900
tcaccctgat cgaggctgcc ttcggcgaga tcagctccat ccacctgccc accaagacca  6960
agttcaagtt cggcgctatg atgaaaagcg gaatgttcct gaccctgttc gtgaacaccg  7020
tgatcaacat tgtgatcgcc agcagggtgc tgcgggagag gctgaccggc agcccctgcg  7080
ctgccttcat cggcgacgac aacatcgtga agggcgtgaa aagcgacaag ctgatggccg  7140
acaggtgcgc cacctggctg aacatggagg tgaagatcat cgacgccgtg gtgggcgaga  7200
aggcccccta cttctgcggc ggattcatcc tgtgcgacag cgtgaccggc accgcctgca  7260
gggtggccga cccccctgaag aggctgttca agctgggcaa gccactggcc gctgacgatg  7320
agcacgacga tgacaggcgg agggccctgc acgaggaaag caccaggtgg aacagggtgg  7380
gcatcctgag cgagctgtgc aaggccgtgg agagcaggta cgagaccgtg ggcaccagca  7440
tcatcgtgat ggctatgacc acactggcca gctccgtcaa gagcttctcc tacctgaggg  7500
```

```
gggcccctat aactctctac ggctaacctg aatggactac gacatagtct agtccgccaa  7560
ggccgccacc atgagagtga cagcccctag aaccttactg cttctgcttt ggggagctgt  7620
tgctctgaca gagacatggg ctggatctta ccacagcccc agctacgcct accaccagtt  7680
cgagaggggg ggaggaggct ccgggggagg aggctccctg aagatcagcc aggccgtgca  7740
cgccgcccac gccgagatca acgaggccgg ccgggaggtg atcgtgggca ttgtcgctgg  7800
cctggccgtc ctcgccgtgg tggtgattgg agctgtggtc gcagctgtta tgtgcagaag  7860
aaagtcatcc ggcggaaagg gaggctccta ctctcaggct gcttctgcta cagtgcctag  7920
agctcttatg tgtttatctc agctgtaaac tcgagtatgt tacgtgcaaa ggtgattgtc  7980
accccccgaa agaccatatt gtgacacacc ctcagtatca cgcccaaaca tttacagccg  8040
cggtgtcaaa aaccgcgtgg acgtggttaa catccctgct gggaggatca gccgtaatta  8100
ttataattgg cttggtgctg gctactattg tggccatgta cgtgctgacc aaccagaaac  8160
ataattgaat acagcagcaa ttggcaagct gcttacatag aactcgcggc gattggcatg  8220
ccgccttaaa atttttattt tatttttttct tttcttttcc gaatcggatt ttgtttttaa  8280
tatttcaaaa aaaaaaaaaa aaaaaaaaaa atctagaaaa aaaaaaaaaa aaaaaaaaaa  8340
aaaaaaaaaa aaaaaaaaaa aaaaaaaaaa aaaaaaaaaa aaaaaaaaaa aaaaaaaaaa  8400
aaaaaaaaaa aaaaaa                                                  8416

SEQ ID NO: 107          moltype = RNA  length = 8914
FEATURE                 Location/Qualifiers
misc_feature            1..8914
                        note = Synthetic polynucleotide
source                  1..8914
                        mol_type = other RNA
                        organism = synthetic construct
SEQUENCE: 107
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccacccact ggccgagcag gtgatcgtga  1800
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
agggcaacga gatcatgacc gccgctgcca gccagggcct gaccaggaag ggcgtgtacg  2820
ccgtgaggta caaggtgaac gagaacccac tgtacgctcc caccagcgag cacgtgaacg  2880
tgctgctgac caggaccgag gacaggatcg tgtggaagac cctggccggc gacccctgga  2940
tcaagaccct gaccgccaag taccccggca acttcaccgc caccatcgaa gagtggcagg  3000
ccgagcacga cgccatcatg aggcacatcc tggagaggcc cgaccccacc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
```

-continued

```
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcaccctga  3420
ggaactacga ccccaggatc aacctggtgc ccgtgaacag gcggctgccc cacgccctgg  3480
tgctgcacca caacgagcac cccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc cccggcgacg  3660
tgcccaagta cgacatcatc ttcgtgaacg tcaggacccc atacaagtac caccattacc  3720
agcagtgcga ggaccacgcc atcaagctga gcatgctgac caagaaggcc tgcctgcacc  3780
tgaaccccgg aggcacctgc gtgagcatcg gctacggcta cgccgacagg gccagcgaga  3840
gcatcattgg cgccatcgcc aggctgttca agttcagcag ggtgtgcaaa cccaagagca  3900
gcctggagga aaccgaggtg ctgttcgtgt tcatcggcta cgaccggaag gccaggaccc  3960
acaaccccta caagctgagc agcaccctga caaacatcta caccggcagc aggctgcacg  4020
aggccggctg cgcccccagc taccacgtgg tcaggggcga tatcgccacc gccaccgagg  4080
gcgtgatcat caacgctgcc aacagcaagg gccagcccgg aggcggagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg ccccaacttc aacaaggtga  4260
gcgaggtgga aggcgacaag cagctggccg aagcctacga gagcatcgcc aagatcgtga  4320
acgacaataa ctacaagagc gtggccatcc cactgctcag caccggcatc ttcagcggca  4380
acaaggacag gctgacccag agcctgaacc acctgctcac cgccctggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgagggtg caccccaaga gctccctggc cggcaggaag ggctacagca  4620
ccagcgacgg caagaccttc agctacctgg agggcaccaa gttccaccag gccgctaagg  4680
acatcgccga gatcaacgct atgtggcccg tggccaccga ggccaacgag caggtgtgca  4740
tgtacatcct gggcgagagc atgtccagca tcaggagcaa gtgccccgtg gaggaaagcg  4800
aggccagcac accacccagc accctgccct gcctgtgcat ccacgctatg acacccgaga  4860
gggtgcagcg gctgaaggcc agcaggcccg agcagatcac cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagacc ccacccgtgg  5040
acgagacacc cgagccaagc gccgagaacc agagcaccga gggcacaccc gagcagccac  5100
ccctgatcac cgaggacgag acaaggaccc ggaccccaga gcccatcatt atcgaggaag  5160
aggaagagga cagcatcagc ctgctgagcg acggccccac ccaccaggtg ctgcaggtgg  5220
aggccgacat ccacggccca cccagcgtgt ccagctccag ctggagcatc ccacacgcca  5280
gcgacttcga cgtggacagc ctgagcatcc tggacaccct ggagggcgcc agcgtgacct  5340
ccggcgccac cagcgccgag accaacagct acttcgccaa gagcatggag ttcctggcca  5400
ggcccgtgcc agctcccagg accgtgttca ggaacccacc ccacccagct cccaggacca  5460
ggaccccaag cctggctccc agcagggcct gcagcaggac cagcctggtg agcaccccac  5520
ccggcgtgaa cagggtgatc accagggagg aactggaggc cctgacaccc agcaggaccc  5580
ccagcaggtc cgtgagcagg actagtctgg tgtccaaccc acccggcgtg aacagggtga  5640
tcaccaggga ggaattcgag gccttcgtgg cccagcaaca gagacggttc gacgccggcg  5700
cctacatctt cagcagcgac accggccagg gacacctgca gcaaaagagc gtgaggcaga  5760
ccgtgctgag cgaggtggtg ctggagagga ccgagctgga aatcagctac gcccccaggc  5820
tggaccagga gaaggaggaa ctgctcagga agaaactgca gctgaacccc accccagcca  5880
acaggagcag gtaccagagc aggaaggtgg agaacatgaa ggccatcacc gccaggcgga  5940
tcctgcaggg cctgggacac tacctgaagg ccgagggcaa ggtggagtgc tacaggaccc  6000
tgcaccccgt gccactgtac agctccagcg tgaacagggc cttctccagc cccaaggtgg  6060
ccgtggaggc ctgcaacgct atgctgaagg agaacttccc caccgtggcc agctactgca  6120
tcatccccga gtacgacgcc tacctggaca tggtggacgg cgccagctgc tgcctggaca  6180
ccgccagctt ctgccccgcc aagctgagga gcttccccaa gaaacacagc tacctggagc  6240
ccaccatcag gagcgccgtg cccagcgcca tccagaacac cctgcagaac gtgctggccg  6300
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggccccaa ggccgctgcc ctgttcgcta agacccacaa cctgaacatg ctgcaggaca  6540
tcccaatgga caggttcgtg atggacctga agagggacgt gaaggtgaca cccggcacca  6600
agcacaccga ggagaggccc aaggtgcagg tgatccaggc cgctgaccca ctggccaccg  6660
cctacctgtg cggcatccac agggagctgg tgaggcggct gaacgccgtg ctgctgccca  6720
acatccacac cctgttcgac atgagcgccg aggacttcga cgccatcatc gccgagcact  6780
tccagcccgg cgactgcgtg ctggagaccg acatcgccag cttcgacaag agcgaggatg  6840
acgctatggc cctgaccgct ctgatgatcc tggaggacct gggcgtggac gccgagctgc  6900
tcaccctgat cgaggctgcc ttcggcgaga tcagctccat ccacctgccc accaagacca  6960
agttcaagtt cggcgctatg atgaaaagcg gaatgttcct gaccctgttc gtgaacaccg  7020
tgatcaacat tgtgatcgcc agcagggtgc tgcgggagag gctgaccggc agccccctgcg  7080
ctgccttcat cggcgacgac aacatcgtga agggcgtgaa aagcgacaag ctgatggccg  7140
acaggtgcgc cacctggctg aacatggagg tgaagatcat cgacgccgtg gtgggcgaga  7200
aggcccccta cttctgcggc ggattcatcc tgtgcgacag cgtgaccggc accgcctgca  7260
gggtggccga cccccctgaag aggctgttca agctgggcaa gccactggcc gctgacgatg  7320
agcacgacga tgacaggcgg agggccctgc acgaggaaag caccaggtgg aacagggtgg  7380
gcatcctgag cgagctgtgc aaggccgtgg agagcaggta cgagaccgtg ggcaccagca  7440
tcatcgtgat ggctatgacc acactggcca gctccgtcaa gagcttctcc tacctgaggg  7500
gggcccctat aactctctac ggctaacctg aatggactac gacatagtct agtccgccaa  7560
ggccgccacc atgagagtga cagcccctag aaccttactg cttctgcttt ggggagctgt  7620
tgctctgaca gagacatggg ctggatctct gagcgaggtg accggccagg gcctgtgcat  7680
cggcgccgtg cccaagaccc accaggtgct gtgcaacacc acccagaaga ccagcgacgg  7740
cagctactac ctggccgctc ccaccggcac cacctgggcc tgcagcaccg gcctgacccc  7800
ttgcatcagc accaccatcc tgaacctgac caccgactac tgcgtgctgg tggagctgtg  7860
gcccagggtg acctaccaca gccccagcta cgcctaccac cagttcgaga ggagggccaa  7920
gtacaagagg gagcccgtga gcctgaccct ggccctgctg ctgggcggcc tgacaatggg  7980
```

```
cggcatcgcc gccggcgtgg gcaccggcac caccgccctg gtggccaccc agcagttcca  8040
gcagctgcag gccgccatgc acgacgacct gaaggaggtg gagaagtcca tcaccaacct  8100
ggagaagtcc ctgaccagcc tgagcgaggt ggtgctgcag aacaggaggg gcctggacct  8160
gctgttcctg aaggagggcg gcctgtgcgc cgccctgaag gaggagtgct gcctgtacgc  8220
cgaccacacc ggcctggtga tcgtgggcat tgtcgctggc ctggccgtcc tcgccgtggt  8280
ggtgattgga gctgtggtcg cagctgttat gtgcagaaga aagtcatccg gcggaaaggg  8340
aggctcctac tctcaggctg cttctgctac agtgcctaga gctcttatgt gtttatctca  8400
gctgggcggc ggaggcagcg actacaagga cgacgatgac aagtaaactc gagtatgtta  8460
cgtgcaaagg tgattgtcac cccccgaaag accatattgt gacacaccct cagtatcacg  8520
cccaaacatt tacagccgcg gtgtcaaaaa ccgcgtggac gtggttaaca tccctgctgg  8580
gaggatcagc cgtaattatt ataattggct tggtgctggc tactattgtg gccatgtacg  8640
tgctgaccaa ccagaaacat aattgaatac agcagcaatt ggcaagctgc ttacatagaa  8700
ctcgcggcga ttggcatgcc gccttaaaat ttttatttta ttttttcttt tcttttccga  8760
atcggatttt gtttttaata tttcaaaaaa aaaaaaaaaa aaaaaaaaat ctagaaaaaa  8820
aaaaaaaaaa aaaaaaaaaa aaaaaaaaaa aaaaaaaaaa aaaaaaaaaa aaaaaaaaaa  8880
aaaaaaaaaa aaaaaaaaaa aaaaaaaaaa aaaa                              8914

SEQ ID NO: 108          moltype = RNA  length = 8455
FEATURE                 Location/Qualifiers
misc_feature            1..8455
                        note = Synthetic polynucleotide
source                  1..8455
                        mol_type = other RNA
                        organism = synthetic construct
SEQUENCE: 108
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccacccact ggccgagcag gtgatcgtga  1800
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
agggcaacga gatcatgacc gccgctgcca gccagggcct gaccaggaag ggcgtgtacg  2820
ccgtgaggta caaggtgaac gagaacccac tgtacgctcc caccagcgag cacgtgaacg  2880
tgctgctgac caggaccgag gacaggatcg tgtggaagac cctggccggc gacccctgga  2940
tcaagaccct gaccgccaag taccccggca acttcaccgc caccatcgaa gagtggcagg  3000
ccgagcacga cgccatcatg aggcacatcc tggagaggcc cgacccccacc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
```

-continued

```
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcaccctga  3420
ggaactacga ccccaggatc aacctggtgc ccgtgaacag gcggctgccc cacgccctgg  3480
tgctgcacca caacgagcac cccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc cccggcgacg  3660
tgcccaagta cgacatcatc ttcgtgaacg tcaggacccc atacaagtac caccattacc  3720
agcagtgcga ggaccacgcc atcaagctga gcatgctgac caagaaggcc tgcctgcacc  3780
tgaaccccgg aggcacctgc gtgagcatcg gctacggcta cgccgacagg gccagcgaga  3840
gcatcattgg cgccatcgcc aggctgttca agttcagcag ggtgtgcaaa cccaagagca  3900
gcctggagga aaccgaggtg ctgttcgtgt tcatcggcta cgaccggaag gccaggaccc  3960
acaaccccta caagctgagc agcaccctga caaacatcta caccggcagc aggctgcacg  4020
aggccggctg cgcccccagc taccacgtgg tcaggggcga tatcgccacc gccaccgagg  4080
gcgtgatcat caacgctgcc aacagcaagg gccagcccgg aggcggagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg ccccaacttc aacaaggtga  4260
gcgaggtgga aggcgacaag cagctggccg aagcctacga gagcatcgcc aagatcgtga  4320
acgacaataa ctacaagagc gtggccatcc cactgctcag caccggcatc ttcagcggca  4380
acaaggacag gctgacccag agcctgaacc acctgctcac cgccctggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgagggtg caccccaaga gctccctggc cggcaggaag ggctacagca  4620
ccagcgacgg caagaccttc agctacctgg agggcaccaa gttccaccag gccgctaagg  4680
acatcgccga gatcaacgct atgtggcccg tggccaccga ggccaacgag caggtgtgca  4740
tgtacatcct gggcgagagc atgtccagca tcaggagcaa gtgccccgtg gaggaaagcg  4800
aggccagcac accacccagc accctgccct gcctgtgcat ccacgctatg acacccgaga  4860
gggtgcagcg gctgaaggcc agcaggcccg agcagatcac cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagacc ccacccgtgg  5040
acgagacacc cgagccaagc gccgagaacc agagcaccga gggcacaccc gagcagccac  5100
ccctgatcac cgaggacgag acaaggaccc ggaccccaga gcccatcatt atcgaggaag  5160
aggaagagga cagcatcagc ctgctgagcg acggccccac ccaccaggtg ctgcaggtgg  5220
aggccgacat ccacggccca cccagcgtgt ccagctccag ctggagcatc ccacacgcca  5280
gcgacttcga cgtggacagc ctgagcatcc tggacaccct ggagggcgcc agcgtgacct  5340
ccggcgccac cagcgccgag accaacagct acttcgccaa gagcatggag ttcctggcca  5400
ggcccgtgcc agctcccagg accgtgttca ggaacccacc ccacccagct cccaggacca  5460
ggaccccaag cctggctccc agcagggcct gcagcaggac cagcctggtg agcaccccac  5520
ccggcgtgaa cagggtgatc accagggagg aactggaggc cctgacaccc agcaggaccc  5580
ccagcaggtc cgtgagcagg actagtctgg tgtccaaccc acccggcgtg aacagggtga  5640
tcaccaggga ggaattcgag gccttcgtgg cccagcaaca gagacggttc gacgccggcg  5700
cctacatctt cagcagcgac accggccagg gacacctgca gcaaaagagc gtgaggcaga  5760
ccgtgctgag cgaggtggtg ctggagagga ccgagctgga aatcagctac gcccccaggc  5820
tggaccagga gaaggaggaa ctgctcagga agaaactgca gctgaacccc accccagcca  5880
acaggagcag gtaccagagc aggaaggtgg agaacatgaa ggccatcacc gccaggcgga  5940
tcctgcaggg cctgggacac tacctgaagg ccgagggcaa ggtggagtgc tacaggaccc  6000
tgcaccccgt gccactgtac agctccagcg tgaacagggc cttctccagc cccaaggtgg  6060
ccgtggaggc ctgcaacgct atgctgaagg agaacttccc caccgtggcc agctactgca  6120
tcatccccga gtacgacgcc tacctggaca tggtggacgg cgccagctgc tgcctggaca  6180
ccgccagctt ctgccccgcc aagctgagga gcttccccaa gaaacacagc tacctggagc  6240
ccaccatcag gagcgccgtg cccagcgcca tccagaacac cctgcagaac gtgctggccg  6300
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggccccaa ggccgctgcc ctgttcgcta agacccacaa cctgaacatg ctgcaggaca  6540
tcccaatgga caggttcgtg atggacctga agagggacgt gaaggtgaca cccggcacca  6600
agcacaccga ggagaggccc aaggtgcagg tgatccaggc cgctgaccca ctggccaccg  6660
cctacctgtg cggcatccac agggagctgg tgaggcggct gaacgccgtg ctgctgccca  6720
acatccacac cctgttcgac atgagcgccg aggacttcga cgccatcatc gccgagcact  6780
tccagcccgg cgactgcgtg ctggagaccg acatcgccag cttcgacaag agcgaggatg  6840
acgctatggc cctgaccgct ctgatgatcc tggaggacct gggcgtggac gccgagctgc  6900
tcaccctgat cgaggctgcc ttcggcgaga tcagctccat ccacctgccc accaagacca  6960
agttcaagtt cggcgctatg atgaaaagcg gaatgttcct gaccctgttc gtgaacaccg  7020
tgatcaacat tgtgatcgcc agcagggtgc tgcgggagag gctgaccggc agcccctgcg  7080
ctgccttcat cggcgacgac aacatcgtga agggcgtgaa aagcgacaag ctgatggccg  7140
acaggtgcgc cacctggctg aacatggagg tgaagatcat cgacgccgtg gtgggcgaga  7200
aggcccccta cttctgcggc ggattcatcc tgtgcgacag cgtgaccggc accgcctgca  7260
gggtggccga ccccctgaag aggctgttca agctgggcaa gccactggcc gctgacgatg  7320
agcacgacga tgacaggcgg agggccctgc acgaggaaag caccaggtgg aacagggtgg  7380
gcatcctgag cgagctgtgc aaggccgtgg agagcaggta cgagaccgtg ggcaccagca  7440
tcatcgtgat ggctatgacc acactggcca gctccgtcaa gagcttctcc tacctgaggg  7500
gggcccctat aactctctac ggctaacctg aatggactac gacatagtct agtccgccaa  7560
ggccgccacc atgagagtga cagcccctag aaccttactg cttctgcttt ggggagctgt  7620
tgctctgaca gagacatggg ctggatctta ccacagcccc agctacgcct accaccagtt  7680
cgagaggggg ggaggaggct ccgggggagg aggctccctg aagatcagcc aggccgtgca  7740
cgccgcccac gccgagatca acgaggccgg ccgggaggtg atcgtgggca ttgtcgctgg  7800
cctggccgtc ctcgccgtgg tggtgattgg agctgtggtc gcagctgtta tgtgcagaag  7860
aaagtcatcc ggcggaaagg gaggctccta ctctcaggct gcttctgcta cagtgcctag  7920
agctcttatg tgtttatctc agctgggcgg cggaggcagc gactacaagg acgacgatga  7980
```

-continued

```
caagtaaact cgagtatgtt acgtgcaaag gtgattgtca ccccccgaaa gaccatattg  8040
tgacacaccc tcagtatcac gcccaaacat ttacagccgc ggtgtcaaaa accgcgtgga  8100
cgtggttaac atccctgctg ggaggatcag ccgtaattat tataattggc ttggtgctgg  8160
ctactattgt ggccatgtac gtgctgacca accagaaaca taattgaata cagcagcaat  8220
tggcaagctg cttacataga actcgcggcg attggcatgc cgccttaaaa tttttatttt  8280
atttttcttt ttcttttccg aatcggattt tgtttttaat atttcaaaaa aaaaaaaaaa  8340
aaaaaaaaaa tctagaaaaa aaaaaaaaaa aaaaaaaaaa aaaaaaaaaa aaaaaaaaaa  8400
aaaaaaaaaa aaaaaaaaaa aaaaaaaaaa aaaaaaaaaa aaaaaaaaaa aaaaa       8455

SEQ ID NO: 109          moltype = AA  length = 2512
FEATURE                 Location/Qualifiers
REGION                  1..2512
                        note = Synthetic polypeptide
source                  1..2512
                        mol_type = protein
                        organism = synthetic construct
SEQUENCE: 109
MEKPVVNVDV DPQSPFVVQL QKSFPQFEVV AQQVTPNDHA NARAFSHLAS KLIELEVPTT  60
ATILDIGSAP ARRMFSEHQY HCVCPMRSPE DPDRMMKYAS KLAEKACKIT NKNLHEKIKD  120
LRTVLDTPDA ETPSLCFHND VTCNMRAEYS VMQDVYINAP GTIYHQAMKG VRTLYWIGFD  180
TTQFMFSAMA GSYPAYNTNW ADEKVLEARN IGLCSTKLSE GRTGKLSIMR KKELKPGSRV  240
YFSVGSTLYP EHRASLQSWH LPSVFHLNGK QSYTCRCDTV VSCEGYVVKK ITISPGITGE  300
TVGYAVTHNS EGFLLCKVTD TVKGERVSFP VCTYIPATIC DQMTGIMATD ISPDDAQKLL  360
VGLNQRIVIN GRTNRNTNTM QNYLLPIIAQ GFSKWAKERK DDLDNEKMLG TRERKLTYGC  420
LWAFRTKKVH SFYRPPGTQT CVKVPASFSA FPMSSVWTTS LPMSLRQKLK LALQPKKEEK  480
LLQVSEELVM EAKAAFEDAQ EEARAEKLRE ALPPLVADKG IEAAAEVVCE VEGLQADIGA  540
ALVETPRGHV RIIPQANDRM IGQYIVVSPN SVLKNAKLAP AHPLADQVKI ITHSGRSGRY  600
AVEPYDAKVL MPAGGAVPWP EFLALSESAT LVYNEREFVN RKLYHIAMHG PAKNTEEEQY  660
KVTKAELAET EYVFDVDKKR CVKKEEASGL VLSGELTNPP YHELALEGLK TRPAVPYKVE  720
TIGVIGTPGS GKSAIIKSTV TARDLVTSGK KENCREIEAD VLRLRGMQIT SKTVDSVMLN  780
GCHKAVEVLY VDEAFACHAG ALLALIAIVR PRKKVVLCGD PMQCGFFNMM QLKVHFNHPE  840
KDICTKTFYK YISRRCTQPV TAIVSTLHYD GKMKTTNPCK KNIEIDITGA TKPKPGDIIL  900
TCFRGWVKQL QIDYPGHEVM TAAASQGLTR KGVYAVRQKV NENPLYAITS EHVNVLLTRT  960
EDRLVWKTLQ GDPWIKQLTN IPKGNFQATI EDWEAEHKGI IAAINSPTPR ANPFSCKTNV  1020
CWAKALEPIL ATAGIVLTGC QWSELFPQFA DDKPHSAIYA LDVICIKFFG MDLTSGLFSK  1080
QSIPLTYHPA DSARPVAHWD NSPGTRKYGY DHAIAAELSR RFPVFQLAGK GTQLDLQTGR  1140
TRVISAQHNL VPVNRNLPHA LVPEYKEKQP GPVEKFLNQF KHHSVLVVSE EKIEAPRKRI  1200
EWIAPIGIAG ADKNYNLAFG FPPQARYDLV FINIGTKYRN HHFQQCEDHA ATLKTLSRSA  1260
LNCLNPGGTL VVKSYGYADR NSEDVVTALA RKFVRVSAAR PDCVSSNTEM YLIFRQLDNS  1320
RTRQFTPHHL NCVISSVYEG TRDGVGAAPS YRTKRENIAD CQEEAVVNAA NPLGRPGEGV  1380
CRAIYKRWPT SFTDSATETG TARMTVCLGK KVIHAVGPDF RKHPEAEALK LLQNAYHAVA  1440
DLVNEHNIKS VAIPLLSTGI YAAGKDRLEV SLNCLTTALD RTDADVTIYC LDKKWKERID  1500
AALQLKESVT ELKDEDMEID DELVWIHPDS CLKGRKGFST TKGKLYSYFE GTKFHQAAKD  1560
MAEIKVLFPN DQESNEQLCA YILGETMEAI REKCPVDHNP SSSPPKTLPC LCMYAMTPER  1620
VHRLRSNNVK EVTVCSSTPL PKHKIKNVQK VQCTKVVLFN PHTPAFVPAR KYIEVPEQPT  1680
APPAQAEEAP EVVATPSPST ADNTSLDVTD ISLDMDDSSE GSLFSSFSGS DNSITSMDSW  1740
SSGPSSLEIV DRRQVVVADV HAVQEPAPIP PPRLKKMARL AAARKEPTPP ASNSSESLHL  1800
SFGGVSMSLG SIFDGETARQ AAVQPLATGP TDVPMSFGSF SDGEIDELSR RVTESEPVLF  1860
GSFEPGEVNS IISSRSAVSF PLRKQRRRRR SRRTEYLTGV GGYIFSTDTG PGHLQKKSVL  1920
QNQLTEPTLE RNVLERIHAP VLDTSKEEQL KLRYQMMPTE ANKSRYQSRK VENQKAITTE  1980
RLLSGLRLYN SATDQPECYK ITYPKPLYSS SVPANYSDPQ FAVAVCNNYL HENYPTVASY  2040
QITDEYDAYL DMVDGTVACL DTATFCPAKL RSYPKKHEYR APNIRSAVPS AMQNTLQNVL  2100
IAATKRNCNV TQMRELPTLD SATFNVECFR KYACNDEYWE EFARKPIRIT TEFVTAYVAR  2160
LKGPKAAALF AKTYNLVPLQ EVPMDRFVMD MKRDVKVTPG TKHTEERPKV QVIQAAEPLA  2220
TAYLCGIHRE LVRRLTAVLL PNIHTLFDMS AEDFDAIIAE HFKQGDPVLE TDIASFDKSQ  2280
DDAMALTGLM ILEDLGVDQP LLDLIECAFG EISSTHLPTG TRFKFGAMMK SGMFLTLFVN  2340
TVLNVVIASR VLEERLKTSR CAAFIGDDNI IHGVVSDKEM AERCATWLNM EVKIIDAVIG  2400
ERPPYFCGGF ILQDSVTSTA CRVADPLKRL FKLGKPLPAD DEQDEDRRRA LLDETKAWFR  2460
VGITGTLAVA VTTRYEVDNI TPVLLALRTF AQSKRAFQAI RGEIKHLYGG PK          2512

SEQ ID NO: 110          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 110
SPSYVYHQF                                                          9

SEQ ID NO: 111          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 111
SPSYAYHQF                                                          9
```

```
SEQ ID NO: 112          moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 112
TPHPARIGL                                                          9

SEQ ID NO: 113          moltype = RNA  length = 1701
FEATURE                 Location/Qualifiers
misc_feature            1..1701
                        note = Synthetic polynucleotide
source                  1..1701
                        mol_type = other RNA
                        organism = synthetic construct
SEQUENCE: 113
atgaaggcta tcctggtggt gctgctctac acctttgcca cagccaatgc tgacaccctg  60
tgtattggct accatgccaa caacagcaca gacacagtgg acacagtgtt ggagaagaat  120
gtgacagtga cccactctgt gaacctgttg gaggacaaac acaatggcaa actgtgtaaa  180
ctgaggggag tggctccact gcacctgggc aagtgtaaca ttgctggctg gattctgggc  240
aaccctgagt gtgagtccct gagcacagcc tcctcctggt cctacattgt ggagacacca  300
tcctctgaca atggcacttg ttaccctgga gacttcattg actatgagga actgagggaa  360
caactttcct ctgtgtcctc ctttgagagg tttgagattt ttccaaagac ctcctcctgg  420
ccaaaccatg acagcaacaa gggagtgaca gcagcctgtc cacatgctgg agccaagtcc  480
ttctacaaga acctgatttg gctggtgaag aagggcaact cctacccaaa actgagcaag  540
tcctacatca atgacaaggg caaggaggtg ctggtgctgt ggggcatcca ccacccaagc  600
acctctgctg accaacagtc cctctaccag aatgctgacg cctatgtgtt tgtgggctcc  660
agcagataca gcaagaagtt caagcctgag attgccatca gaccaaaggt gagggatcag  720
gagggcagga tgaactacta ctggaccctg gtggaacctg gagacaagat tacctttgag  780
gctacaggca acctggtggt gccaagatat gcctttgcta tggagaggaa tgctggctct  840
ggcatcatca tctctgacac acctgtccat gactgtaaca ccacttgtca gacaccaaag  900
ggagccatca acacctccct gccattccag aacatccacc caatcaccat tggcaagtgt  960
ccaaaatatg tcaagagcac caaactgaga ctggctacag gactgaggaa catcccaagc  1020
atccagagca ggggactgtt tggagccatt gctggcttca ttgagggagg ctggacaggg  1080
atggtggatg gctggtatgg ctaccaccac cagaatgaac agggctctgg ctatgctgct  1140
gacctgaaaa gcacccagaa tgccattgat gagattacca acaaggtgaa ctctgtgatt  1200
gagaagatga acacccagtt cacagcagtg ggcaaggagt tcaaccactt ggagaagagg  1260
attgagaacc tgaacaagaa ggtggatgat ggcttcctgg acatctggac ctacaatgct  1320
gaactgctgg tgctgttgga gaatgagagg accctggact accatgacag caatgtgaag  1380
aacctctatg agaaggtgag gagccaactt aaaaacaatg ccaaggagat tggcaatggc  1440
tgttttgagt tctaccacaa gtgtgacaac acttgtatgg agtctgtgaa gaatggcacc  1500
tatgactacc caaaatactc tgaggaggct aaactgaaca gggaggagat tgatggagtg  1560
aaattggaga gcaccaggat ttaccagatc ctggccatct acagcaccgt ggccagcagc  1620
ctggtgctgg tggtgagcct gggcgccatc agcttctgga tgtgcagcaa cggcagcttg  1680
cagtgcagga tctgcatcta a                                            1701

SEQ ID NO: 114          moltype = AA  length = 566
FEATURE                 Location/Qualifiers
REGION                  1..566
                        note = Synthetic polypeptide
source                  1..566
                        mol_type = protein
                        organism = synthetic construct
SEQUENCE: 114
MKAILVVLLY TFATANADTL CIGYHANNST DTVDTVLEKN VTVTHSVNLL EDKHNGKLCK  60
LRGVAPLHLG KCNIAGWILG NPECESLSTA SSWSYIVETP SSDNGTCYPG DFIDYEELRE  120
QLSSVSSFER FEIFPKTSSW PNHDSNKGVT AACPHAGAKS FYKNLIWLVK KGNSYPKLSK  180
SYINDKGKEV LVLWGIHHPS TSADQQSLYQ NADAYVFVGS SRYSKKFKPE IAIRPKVRDQ  240
EGRMNYYWTL VEPGDKITFE ATGNLVVPRY AFAMERNAGS GIIISDTPVH DCNTTCQTPK  300
GAINTSLPFQ NIHPITIGKC PKYVKSTKLR LATGLRNIPS IQSRGLFGAI AGFIEGGWTG  360
MVDGWYGYHH QNEQGSGYAA DLKSTQNAID EITNKVNSVI EKMNTQFTAV GKEFNHLEKR  420
IENLNKKVDD GFLDIWTYNA ELLVLLENER TLDYHDSNVK NLYEKVRSQL KNNAKEIGNG  480
CFEFYHKCDN TCMESVKNGT YDYPKYSEEA KLNREEIDGV KLESTRIYQI LAIYSTVASS  540
LVLVVSLGAI SFWMCSNGSL QCRICI                                       566

SEQ ID NO: 115          moltype = RNA  length = 9911
FEATURE                 Location/Qualifiers
misc_feature            1..9911
                        note = Synthetic polynucleotide
source                  1..9911
                        mol_type = other RNA
                        organism = synthetic construct
SEQUENCE: 115
gataggcggc gcatgagaga agcccagacc aattacctac ccaaatagga gaaagttcac  60
gttgacatcg aggaagacag cccattcctc agagctttgc agcggagctt cccgcagttt  120
gaggtagaag ccaagcaggt cactgataat gaccatgcta atgccagagc gttttcgcat  180
```

-continued

```
ctggcttcaa aactgatcga aacggaggtg gacccatccg acacgatcct tgacattgga  240
atagtcagca tagtacattt catctgacta atactacaac accaccacca tgaatagagg  300
attctttaac atgctcggcc gccgcccctt cccggccccc actgccatgt ggaggccgcg  360
gagaaggagg caggcggccc cgggaagcgg agctactaac ttcagcctgc tgaagcaggc  420
tggagacgtg gaggagaacc ctggacctga gaaagttcac gttgacatcg aggaagacag  480
cccattcctc agagctttgc agcggagctt cccgcagttt gaggtagaag ccaagcaggt  540
cactgataat gaccatgcta atgccagagc gttttcgcat ctggcttcaa aactgatcga  600
aacggaggtg gacccatccg acacgatcct tgacattgga agtgcgcccg cccgcagaat  660
gtattctaag cacaagtatc attgtatctg tccgatgaga tgtgcggaag atccggacag  720
attgtataag tatgcaacta agctgaagaa aaactgtaag gaaataactg ataaggaatt  780
ggacaagaaa atgaaggagc tcgccgccgt catgagcgac cctgacctgg aaactgagac  840
tatgtgcctc cacgacgacg agtcgtgtcg ctacgaaggg caagtcgctg tttaccagga  900
tgtatacgcg gttgacggac cgacaagtct ctatcaccaa gccaataagg gagttagagt  960
cgcctactgg ataggctttg acaccacccc ttttatgttt aagaacttgg ctggagcata  1020
tccatcatac tctaccaact gggccgacga aaccgtgtta acggctcgta acataggcct  1080
atgcagctct gacgttatgg agcggtcacg tagagggatg tccattctta gaaagaagta  1140
tttgaaacca tccaacaatg ttctattctc tgttggctcg accatctacc acgagaagag  1200
ggacttactg aggagctggc acctgccgtc tgtatttcac ttacgtggca agcaaaatta  1260
cacatgtcgg tgtgagacta tagttagttg cgacgggtac gtcgttaaaa gaatagctat  1320
cagtccaggc ctgtatggga agccttcagg ctatgctgct acgatgcacc gcgagggatt  1380
cttgtgctgc aaagtgacag acacattgaa cggggagagg gtctcttttc ccgtgtgcac  1440
gtatgtgcca gctacattgt gtgaccaaat gactggcata ctggcaacag atgtcagtgc  1500
ggacgacgcg caaaaactgc tggttgggct caaccagcgt atagtcgtca acggtcgcac  1560
ccagagaaac accaatacca tgaaaaatta ccttttgccc gtagtggccc aggcatttgc  1620
taggtgggca aaggaatata aggaagatca agaagatgaa aggccactag gactacgaga  1680
tagacagtta gtcatggggt gttgttgggc ttttagaagg cacaagataa catctattta  1740
taagcgcccg gatacccaaa ccatcatcaa agtgaacagc gatttccact cattcgtgct  1800
gcccaggata ggcagtaaca cattggagat cgggctgaga acaagaatca ggaaaatgtt  1860
agaggagcac aaggagccgt cacctctcat taccgccgag gacgtacaag aagctaagtg  1920
cgcagccgat gaggctaagg aggtgcgtga agccgaggag ttgcgcgcag ctctaccacc  1980
tttggcagct gatgttgagg agcccactct ggaagccgat gtcgacttga tgttacaaga  2040
ggctggggcc ggctcagtgg agacacctcg tggcttgata aaggttacca gctacgatgg  2100
cgaggacaag atcggctctt acgctgtgct ttctccgcag gctgtactca agagtgaaaa  2160
attatcttgc atccaccctc tcgctgaaca agtcatagtg ataacacact ctggccgaaa  2220
agggcgttat gccgtggaac cataccatgg taaagtagtg gtgccagagg gacatgcaat  2280
acccgtccag gactttcaag ctctgagtga aagtgccacc attgtgtaca acgaacgtga  2340
gttcgtaaac aggtacctgc accatattgc cacacatgga ggagcgctga acactgatga  2400
agaatattac aaaactgtca agcccagcga gcacgacggc gaatacctgt acgacatcga  2460
caggaaacag tgcgtcaaga aagaactagt cactgggcta gggctcacag gcgagctggt  2520
ggatcctccc ttccatgaat tcgcctacga gagtctgaga acacgaccag ccgctcctta  2580
ccaagtacca accatagggg tgtatggcgt gccaggatca ggcaagtctg gcatcattaa  2640
aagcgcagtc accaaaaaag atctagtggt gagcgccaag aaagaaaact gtgcagaaat  2700
tataagggac gtcaagaaaa tgaaagggct ggacgtcaat gccagaactg tggactcagt  2760
gctcttgaat ggatgcaaac accccgtaga gaccctgtat attgacgaag cttttgcttg  2820
tcatgcaggt actctcagag cgctcatagc cattataaga cctaaaaagg cagtgctctg  2880
cggggatccc aaacagtgcg gtttttttaa catgatgtgc ctgaaagtgc attttaacca  2940
cgagatttgc acacaagtct tccacaaaag catctctcgc cgttgcacta aatctgtgac  3000
ttcggtcgtc tcaaccttgt tttacgacaa aaaaatgaga acgacgaatc cgaaagagac  3060
taagattgtg attgacacta ccggcagtac caaacctaag caggacgatc tcattctcac  3120
ttgtttcaga gggtgggtga agcagttgca aatagattac aaaggcaacg aaataatgac  3180
ggcagctgcc tctcaagggc tgacccgtaa aggtgtgtat gccgttcggt acaaggtgaa  3240
tgaaaatcct ctgtacgcac ccacctctga acatgtgaac gtcctactga cccgcacgga  3300
ggaccgcatc gtgtggaaaa cactagccgg cgacccatgg ataaaaacac tgactgccaa  3360
gtaccctggg aatttcactg ccacgataga ggagtggcaa gcagagcatg atgccatcat  3420
gaggcacatc ttggagagac cggaccctac cgacgtcttc cagaataagg caaacgtgtg  3480
ttgggccaag gctttagtgc cggtgctgaa gaccgctggc atagacatga ccactgaaca  3540
atggaacact gtggattatt ttgaaacgga caaagctcac tcagcagaga tagtattgaa  3600
ccaactatgc gtgaggttct ttggactcga tctggactcc ggtctatttt ctgcacccac  3660
tgttccgtta tccattagga ataatcactg ggataactcc ccgtcgccta acatgtacgg  3720
gctgaataaa gaagtggtcc gtcagctctc tcgcaggtac ccacaactgc ctcgggcagt  3780
tgccactgga agagtctatg acatgaacac tggtacactg cgcaattatg atccgcgcat  3840
aaacctagta cctgtaaaca gaagactgcc tcatgcttta gtcctccacc ataatgaaca  3900
cccacagagt gacttttctt cattcgtcag caaattgaag ggcagaactg tcctggtggt  3960
cggggaaaag ttgtccgtcc caggcaaaat ggttgactgg ttgtcagacc ggcctgaggc  4020
taccttcaga gctcggctgg atttaggcat cccaggtgat gtgcccaaat atgacataat  4080
atttgttaat gtgaggaccc catataaata ccatcactat cagcagtgtg aagaccatgc  4140
cattaagctt agcatgttga ccaagaaagc ttgtctgcat ctgaatcccg gcggaacctg  4200
tgtcagcata ggttatggtt acgctgacag ggccagcgaa agcatcattg gtgctatagc  4260
gcggcagttc aagttttccc gggtatgcaa accgaaatcc tcacttgaag agacggaagt  4320
tctgtttgta ttcattgggt acgatcgcaa ggcccgtacg cacaatcctt acaagctttc  4380
atcaaccttg accaacattt atacaggttc cagactccac gaagccggat gtgcaccctc  4440
atatcatgtg gtgcgagggg atattgccac ggccaccgaa ggagtgatta taaatgctgc  4500
taacagcaaa ggacaacctg gcggaggggt gtgcggagcg ctgtataaga aattcccgga  4560
aagcttcgat ttacagccga tcgaagtagg aaaagcgcga ctggtcaaag gtgcagctaa  4620
acatatcatt catgccgtag gaccaaactt caacaaagtt tcggaggttg aaggtgacaa  4680
acagttggca gaggcttatg agtccatcgc taagattgtc aacgataaca attacaagtc  4740
agtagcgatt ccactgttgt ccaccggcat cttttccggg aacaaagatc gactaaccca  4800
atcattgaac catttgctga cagctttaga caccactgat gcagatgtag ccatatactg  4860
cagggacaag aaatgggaaa tgactctcaa ggaagcagtg gctaggagag aagcagtgga  4920
```

-continued

```
ggagatatgc atatccgacg actcttcagt gacagaacct gatgcagagc tggtgagggt  4980
gcatccgaag agttctttgg ctggaaggaa gggctacagc acaagcgatg gcaaaacttt  5040
ctcatatttg gaagggacca agtttcacca ggcggccaag gatatagcag aaattaatgc  5100
catgtggccc gttgcaacgg aggccaatga gcaggtatgc atgtatatcc tcggagaaag  5160
catgagcagt attaggtcga aatgccccgt cgaagagtcg gaagcctcca caccacctag  5220
cacgctgcct tgcttgtgca tccatgccat gactccagaa agagtacagc gcctaaaagc  5280
ctcacgtcca gaacaaatta ctgtgtgctc atcctttcca ttgccgaagt atagaatcac  5340
tggtgtgcag aagatccaat gctcccagcc tatattgttc tcaccgaaag tgcctgcgta  5400
tattcatcca aggaagtatc tcgtggaaac accaccggta gacgagactc cggagccatc  5460
ggcagagaac caatccacag aggggacacc tgaacaacca ccacttataa ccgaggatga  5520
gaccaggact agaacgcctg agccgatcat catcgaagag gaagaagagg atagcataag  5580
tttgctgtca gatggcccga cccaccaggt gctgcaagtc gaggcagaca ttcacgggcc  5640
gccctctgta tctagctcat cctggtccat tcctcatgca tccgactttg atgtggacag  5700
tttatccata cttgacaccc tggagggagc tagcgtgacc agcggggcaa cgtcagccga  5760
gactaactct tacttcgcaa agagtatgga gtttctggcg cgaccggtgc ctgcgcctcg  5820
aacagtattc aggaaccctc cacatcccgc tccgcgcaca agaacaccgt cacttgcacc  5880
cagcagggcc tgctcgagaa ccagcctagt ttccaccccg ccaggcgtga atagggtgat  5940
cactagagag gagctcgagg cgcttacccc gtcacgcact cctagcaggt cggtctcgag  6000
aaccagcctg gtctccaacc cgccaggcgt aaatagggtg attacaagag aggagtttga  6060
ggcgttcgta gcacaacaac aatgacggtt tgatgcgggt gcatacatct tttcctccga  6120
caccggtcaa gggcatttac aacaaaaatc agtaaggcaa acggtgctat ccgaagtggt  6180
gttggagagg accgaattgg agatttcgta tgccccgcgc ctcgaccaag aaaaagaaga  6240
attactacgc aagaaattac agttaaatcc cacacctgct aacagaagca gataccagtc  6300
caggaaggtg gagaacatga aagccataac agctagacgt attctgcaag gcctagggca  6360
ttatttgaag gcagaaggaa aagtggagtg ctaccgaacc ctgcatcctg ttcctttgta  6420
ttcatctagt gtgaaccgtg ccttttcaag ccccaaggtc gcagtggaag cctgtaacgc  6480
catgttgaaa gagaactttc cgactgtggc ttcttactgt attattccag agtacgatgc  6540
ctatttggac atggttgacg gagcttcatg ctgcttagac actgccagtt tttgccctgc  6600
aaagctgcgc agctttccaa agaaacactc ctatttggaa cccacaatac gatcggcagt  6660
gccttcagcg atccagaaca cgctccagaa cgtcctggca gctgccacaa aaagaaattg  6720
caatgtcacg caaatgagag aattgcccgt attggattcg gcggccttta atgtggaatg  6780
cttcaagaaa tatgcgtgta ataatgaata ttgggaaacg tttaaagaaa accccatcag  6840
gcttactgaa gaaaacgtgg taaattacat taccaaatta aaaggaccaa aagctgctgc  6900
tctttttgcg aagacacata atttgaatat gttgcaggac ataccaatgg acaggtttgt  6960
aatggactta aagagagacg tgaaagtgac tccaggaaca aaacatactg aagaacggcc  7020
caaggtacag gtgatccagg ctgccgatcc gctagcaaca gcgtatctgt gcggaatcca  7080
ccgagagctg gttaggagat taaatgcggt cctgcttccg aacattcata cactgtttga  7140
tatgtcggct gaagactttg acgctattat agccgagcac ttccagcctg ggattgtgt   7200
tctggaaact gacatcgcgt cgtttgataa aagtgaggac gacgccatgg ctctgaccgc  7260
gttaatgatt ctggaagact taggtgtgga cgcagagctg ttgacgctga ttgaggcggc  7320
tttcggcgaa atttcatcaa tacatttgct cactaaaact aaatttaaat tcggagccat  7380
gatgaaatct ggaatgttcc tcacactgtt tgtgaacaca gtcattaaca ttgtaatcgc  7440
aagcagagtg ttgagagaac ggctaaccgg atcaccatgt gcagcattca ttggagatga  7500
caatatcgtg aaaggagtca aatcggacaa attaatggca gacaggtgcg ccacctggtt  7560
gaatatggaa gtcaagatta tagatgctgt ggtgggcgag aaagcgcctt atttctgtgg  7620
agggtttatt ttgtgtgact ccgtgaccgg cacagcgtgc cgtgtggcag accccctaaa  7680
aaggctgttt aagcttggca aacctctggc agcagacgat gaacatgatg atgacaggag  7740
aagggcattg catgaagagt caacacgctg gaaccgagtg ggtattcttt cagagctgtg  7800
caaggcagta gaatcaaggt atgaaaccgt aggaacttcc atcatagtta tggccatgac  7860
tactctagct agcagtgtta aatcattcag ctacctgaga ggggccccta taactctcta  7920
cggctaacct gaatggacta cgacatagtc tagtccgcca agatatcgca ccatggaaga  7980
tgccaaaaac attaagaagg gcccagcgcc attctaccca ctcgaagacg ggaccgccgg  8040
cgagcagctg cacaaagcca tgaagcgcta cgccctggtg cccggcacca tcgcctttac  8100
cgacgcacat atcgaggtgg acattaccta cgccgagtac ttcgagatga gcgttcggct  8160
ggcagaagct atgaagcgct atgggctgaa tacaaaccat cggatcgtgg tgtgcagcga  8220
gaatagcttg cagttcttca tgcccgtgtt gggtgccctg ttcatcggtg tggctgtggc  8280
cccagctaac gacatctaca acgagcgcga gctgctgaac agcatgggca tcagccagcc  8340
caccgtcgta ttcgtgagca agaaagggct gcaaaagatc ctcaacgtgc aaaagaagct  8400
accgatcata caaaagatca tcatcatgga tagcaagacc gactaccagg gcttccaaag  8460
catgtacacc ttcgtgactt cccatttgcc acccggcttc aacgagtacg acttcgtgcc  8520
cgagagcttc gaccgggaca aaaccatcgc cctgatcatg aacagtagtg gcagtaccgg  8580
attgcccaag ggcgtagccc taccgcaccg caccgcttgt gtccgattca gtcatgcccg  8640
cgaccccatc ttcggcaacc agatcatccc cgacaccgct atcctcagcg tggtgccatt  8700
tcaccacggc ttcggcatgt tcaccacgct gggctacttg atctgcggct ttcgggtcgt  8760
gctcatgtac cgcttcgagg aggagctatt cttgcgcagc ttgcaagact ataagattca  8820
atctgccctg ctggtgccca cactatttag cttcttcgct aagagcactc tcatcgacaa  8880
gtacgaccta agcaacttgc acgagatcgc cagcggcggg gcgccgctca gcaaggaggt  8940
aggtgaggcc gtggccaaac gcttccacct accaggcatc cgacagggct acggcctgac  9000
agaaacaacc agcgccattc tgatcacccc cgaaggggac gacaagcctg gcgcagtagg  9060
caaggtggtg cccttcttcg aggctaaggt ggtggacttg gacaccggta agacactggg  9120
tgtgaaccag cgcggcgagc tgtgcgtccg tggccccatg atcatgagcg gctacgttaa  9180
caaccccgag gctacaaacg ctctcatcga caaggacggc tggctgcaca gcggcgacat  9240
cgcctactgg gacgaggacg agcacttctt catcgtggac cggctgaagt ccctgatcaa  9300
atacaagggc taccaggtag ccccagccga actggagagc atcctgctgc aacaccccaa  9360
catcttcgac gccggggtcg ccggcctgcc cgacgacgat gccggcgagc tgcccgccgc  9420
agtcgtcgtg ctggaacacg gtaaaaccat gaccgagaag gagatcgtgg actatgtggc  9480
cagccaggtt acaaccgcca agaagctgcg cggtggtgtt gtgttcgtgg acgaggtgcc  9540
taaaggactg accggcaagt tggacgcccg caagatccgc gagattctca ttaaggccaa  9600
gaagggcggc aagatcgccg tgtaaggcgc gccgtttaaa cggccggcct taattaagta  9660
```

```
acgatacagc agcaattggc aagctgctta catagaactc gcggcgattg gcatgccgcc  9720
ttaaaatttt tattttattt tttcttttct tttccgaatc ggattttgtt tttaatattt  9780
caaaaaaaaa aaaaaaaaaa aaaaaatcta gaaaaaaaaa aaaaaaaaaa aaaaaaaaaa  9840
aaaaaaaaaa aaaaaaaaaa aaaaaaaaaa aaaaaaaaaa aaaaaaaaaa aaaaaaaaaa  9900
aaaaaaaaaa a                                                       9911

SEQ ID NO: 116         moltype = RNA  length = 2117
FEATURE                Location/Qualifiers
misc_feature           1..2117
                       note = Synthetic polynucleotide
source                 1..2117
                       mol_type = other RNA
                       organism = synthetic construct
SEQUENCE: 116
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccaccatga aggctatcct ggtggtgctg ctctacacct  180
ttgccacagc caatgctgac accctgtgta ttggctacca tgccaacaac agcacagaca  240
cagtggacac agtgttggag aagaatgtga cagtgaccca ctctgtgaac ctgttggagg  300
acaaacacaa tggcaaactg tgtaaactga ggggagtggc tccactgcac ctgggcaagt  360
gtaacattgc tggctggatt ctgggcaacc ctgagtgtga gtccctgagc acagcctcct  420
cctggtccta cattgtggag acaccatcct ctgacaatgg cacttgttac cctggagact  480
tcattgacta tgaggaactg agggaacaac tttcctctgt gtcctccttt gagaggtttg  540
agatttttcc aaagacctcc tcctggccaa accatgacag caacaaggga gtgacagcag  600
cctgtccaca tgctggagcc aagtccttct acaagaacct gatttggctg gtgaagaagg  660
gcaactccta cccaaaactg agcaagtcct acatcaatga caagggcaag gaggtgctgg  720
tgctgtgggg catccaccac ccaagcacct ctgctgacca acagtccctc taccagaatg  780
ctgacgccta tgtgtttgtg ggctccagca gatacagcaa gaagttcaag cctgagattg  840
ccatcagacc aaaggtgagg gatcaggagg gcaggatgaa ctactactgg accctggtgg  900
aacctggaga caagattacc tttgaggcta caggcaacct ggtggtgcca agatatgcct  960
ttgctatgga gaggaatgct ggctctggca tcatcatctc tgacacacct gtccatgact  1020
gtaacaccac ttgtcagaca ccaaagggag ccatcaacac ctccctgcca ttccagaaca  1080
tccacccaat caccattggc aagtgtccaa aatatgtcaa gagcaccaaa ctgagactgg  1140
ctacaggact gaggaacatc ccaagcatcc agagcagggg actgtttgga gccattgctg  1200
gcttcattga gggaggctgg acagggatgg tggatggctg gtatggctac caccaccaga  1260
atgaacaggg ctctggctat gctgctgacc tgaaaagcac ccagaatgcc attgatgaga  1320
ttaccaacaa ggtgaactct gtgattgaga agatgaacac ccagttcaca gcagtgggca  1380
aggagttcaa ccacttggag aagaggattg agaacctgaa caagaaggtg gatgatggct  1440
tcctggacat ctggacctac aatgctgaac tgctggtgct gttggagaat gagaggaccc  1500
tggactacca tgacagcaat gtgaagaacc tctatgagaa ggtgaggagc caacttaaaa  1560
acaatgccaa ggagattggc aatggctgtt ttgagttcta ccacaagtgt gacaacactt  1620
gtatggagtc tgtgaagaat ggcacctatg actacccaaa atactctgag gaggctaaac  1680
tgaacaggga ggagattgat ggagtgaaat tggagagcac caggatttac cagatcctgg  1740
ccatctacag caccgtggcc agcagcctgg tgctggtggt gagcctgggc gccatcagct  1800
tctggatgtg cagcaacggc agcttgcagt gcaggatctg catctaaact cgagctagtg  1860
actgactagg atctggttac cactaaacca gcctcaagaa cacccgaatg gagtctctaa  1920
gctacataat accaacttac acttacaaaa tgttgtcccc caaaatgtag ccattcgtat  1980
ctgctcctaa taaaaagaaa gtttcttcac attctagaaa aaaaaaaaaa aaaaaaaaaa  2040
aaaaaaaaaa aaaaaaaaaa aaaaaaaaaa aaaaaaaaaa aaaaaaaaaa aaaaaaaaaa  2100
aaaaaaaaaa aaaaaaa                                                 2117

SEQ ID NO: 117         moltype = DNA  length = 3822
FEATURE                Location/Qualifiers
misc_feature           1..3822
                       note = Synthetic polynucleotide
source                 1..3822
                       mol_type = other DNA
                       organism = synthetic construct
SEQUENCE: 117
atgtttgttt ttcttgtttt attgccacta gtctctagtc agtgtgttaa tcttacaacc  60
agaactcaat taccccctgc atacactaat tctttcacac gtggtgttta ttaccctgac  120
aaagttttca gatcctcagt tttacattca actcaggact tgttcttacc tttcttttcc  180
aatgttactt ggttccatgc tatacatgtc tctgggacca atggtactaa gaggtttgat  240
aaccctgtcc taccatttaa tgatggtgtt tattttgctt ccactgagaa gtctaacata  300
ataagaggct ggatttttgg tactacttta gattcgaaga cccagtccct acttattgtt  360
aataacgcta ctaatgttgt tattaaagtc tgtgaatttc aattttgtaa tgatccattt  420
ttgggtgttt attaccacaa aaacaacaaa agttggatgg aaagtgagtt cagagtttat  480
tctagtgcga ataattgcac ttttgaatat gtctctcagc cttttcttat ggaccttgaa  540
ggaaaacagg gtaatttcaa aaatcttagg gaatttgtgt ttaagaatat tgatggttat  600
tttaaaatat attctaagca cacgcctatt aatttagtgc gtgatctccc tcagggtttt  660
tcggctttag aaccattggt agatttgcca ataggtatta acatcactag gtttcaaact  720
ttacttgctt tacatagaag ttatttgact cctggtgatt cttcttcagg ttggacagct  780
ggtgctgcag cttattatgt gggttatctt caacctagga cttttctatt aaaatataat  840
gaaaatggaa ccattacaga tgctgtagac tgtgcacttg accctctctc agaaacaaag  900
tgtacgttga aatccttcac tgtagaaaaa ggaatctatc aaacttctaa ctttagagtc  960
caaccaacag aatctattgt tagatttcct aatattacaa acttgtgccc ttttggtgaa  1020
gtttttaacg ccaccagatt tgcatctgtt tatgcttgga acaggaagag aatcagcaac  1080
tgtgttgctg attattctgt cctatataat tccgcatcat tttccacttt taagtgttat  1140
ggagtgtctc ctactaaatt aaatgatctc tgctttacta atgtctatgc agattcattt  1200
```

-continued

```
gtaattagag gtgatgaagt cagacaaatc gctccagggc aaactggaaa gattgctgat  1260
tataattata aattaccaga tgattttaca ggctgcgtta tagcttggaa ttctaacaat  1320
cttgattcta aggttggtgg taattataat tacctgtata gattgtttag gaagtctaat  1380
ctcaaacctt ttgagagaga tatttcaact gaaatctatc aggccggtag cacaccttgt  1440
aatggtgttg aaggttttaa ttgttacttt cctttacaat catatggttt ccaacccact  1500
aatggtgttg gttaccaacc atacagagta gtagtacttt cttttgaact tctacatgca  1560
ccagcaactg tttgtggacc taaaaagtct actaatttgg ttaaaaacaa atgtgtcaat  1620
ttcaacttca atggtttaac aggcacaggt gttcttactg agtctaacaa aaagtttctg  1680
cctttccaac aatttggcag agacattgct gacactactg atgctgtccg tgatccacag  1740
acacttgaga ttcttgacat tacaccatgt tcttttggtg gtgtcagtgt tataacacca  1800
ggaacaaata cttctaacca ggttgctgtt ctttatcagg atgttaactg cacagaagtc  1860
cctgttgcta ttcatgcaga tcaacttact cctacttggc gtgtttattc tacaggttct  1920
aatgtttttc aaacacgtgc aggctgttta atagggggctg aacatgtcaa caactcatat  1980
gagtgtgaca tacccattgg tgcaggtata tgcgctagtt atcagactca gactaattct  2040
cctcggcggg cacgtagtgt agctagtcaa tccatcattg cctacactat gtcacttggt  2100
gcagaaaatt cagttgctta ctctaataac tctattgcca tacccacaaa ttttactatt  2160
agtgttacca cagaaattct accagtgtct atgaccaaga catcagtaga ttgtacaatg  2220
tacatttgtg gtgattcaac tgaatgcagc aatcttttgt tgcaatatgg cagtttttgt  2280
acacaattaa accgtgcttt aactggaata gctgttgaac aagacaaaaa cacccaagaa  2340
gtttttgcac aagtcaaaca aatttacaaa acaccaccaa ttaaagattt tggtggtttt  2400
aatttttcac aaatattacc agatccatca aaaccaagca agaggtcatt tattgaagat  2460
ctacttttca acaaagtgac acttgcagat gctggcttca tcaaacaata tggtgattgc  2520
cttggtgata ttgctgctag agacctcatt tgtgcacaaa agtttaacgg ccttactgtt  2580
ttgccacctt tgctcacaga tgaaatgatt gctcaataca cttctgcact gttagcgggt  2640
acaatcactt ctggttggac ctttggtgca ggtgctgcat tacaaatacc atttgctatg  2700
caaatggctt ataggtttaa tggtattgga gttacacaga atgttctcta tgagaaccaa  2760
aaattgattg ccaaccaatt taatagtgct attggcaaaa ttcaagactc actttcttcc  2820
acagcaagtg cacttggaaa acttcaagat gtggtcaacc aaaatgcaca agctttaaac  2880
acgcttgtta aacaacttag ctccaatttt ggtgcaattt caagtgtttt aaatgatatc  2940
ctttcacgtc ttgacaaagt tgaggctgaa gtgcaaattg ataggttgat cacaggcaga  3000
cttcaaagtt tgcagacata tgtgactcaa caattaatta gagctgcaga aatcagagct  3060
tctgctaatc ttgctgctac taaaatgtca gagtgtgtac ttggacaatc aaaaagagtt  3120
gatttttgtg gaaagggcta tcatcttatg tccttccctc agtcagcacc tcatggtgta  3180
gtcttcttgc atgtgactta tgtccctgca caagaaaaga acttcacaac tgctcctgcc  3240
atttgtcatg atggaaaagc acactttcct cgtgaaggtg tctttgtttc aaatggcaca  3300
cactggtttg taacacaaag gaatttttat gaaccacaaa tcattactac agacaacaca  3360
tttgtgtctg gtaactgtga tgttgtaata ggaattgtca acaacacagt ttatgatcct  3420
ttgcaacctg aattagactc attcaaggag gagttagata aatattttaa gaatcataca  3480
tcaccagatg ttgatttagg tgacatctct ggcattaatg cttcagttgt aaacattcaa  3540
aaagaaattg accgcctcaa tgaggttgcc aagaatttaa atgaatctct catcgatctc  3600
caagaacttg gaaagtatga gcagtatata aaatggccat ggtacatttg gctaggtttt  3660
atagctggct tgattgccat agtaatggtg acaattatgc tttgctgtat gaccagttgc  3720
tgtagttgtc tcaagggctg ttgttcttgt ggatcctgct gcaaatttga tgaagacgac  3780
tctgagccag tgctcaaagg agtcaaatta cattacacat aa                     3822
```

```
SEQ ID NO: 118          moltype = AA  length = 1273
FEATURE                 Location/Qualifiers
REGION                  1..1273
                        note = Synthetic polypeptide
source                  1..1273
                        mol_type = protein
                        organism = synthetic construct
SEQUENCE: 118
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273
```

```
SEQ ID NO: 119          moltype = DNA  length = 3822
FEATURE                 Location/Qualifiers
misc_feature            1..3822
```

-continued

```
                        note = Synthetic polynucleotide
source                  1..3822
                        mol_type = other DNA
                        organism = synthetic construct
SEQUENCE: 119
atgttcgtct tcctggtcct gctgcctctg gtctcctcac agtgcgtcaa tctgacaact  60
cggactcagc tgccacctgc ttatactaat agcttcacca gaggcgtgta ctatcctgac  120
aaggtgttta gaagctccgt gctgcactct acacaggatc tgtttctgcc attctttagc  180
aacgtgacct ggttccacgc catccacgtg agcggcacca atggcacaaa gcggttcgac  240
aatcccgtgc tgccttttaa cgatggcgtg tacttcgcct ctaccgagaa gagcaacatc  300
atcagaggct ggatctttgg caccacactg gactccaaga cacagtctct gctgatcgtg  360
aacaatgcca ccaacgtggt catcaaggtg tgcgagttcc agttttgtaa tgatcccttc  420
ctgggcgtgt actatcacaa gaacaataag agctggatgg agtccgagtt tagagtgtat  480
tctagcgcca acaactgcac atttgagtac gtgagccagc ctttcctgat ggacctggag  540
ggcaagcagg gcaatttcaa gaacctgagg gagttcgtgt ttaagaatat cgacggctac  600
ttcaaaatct actctaagca cacccccatc aacctggtgc gcgacctgcc tcagggcttc  660
agcgccctgg agcccctggt ggatctgcct atcggcatca acatcacccg gtttcagaca  720
ctgctggccc tgcacagaag ctacctgaca cccggcgact cctctagcgg atggaccgcc  780
ggcgctgccg cctactatgt gggctacctc cagccccgga ccttcctgct gaagtacaac  840
gagaatggca ccatcacaga cgcagtggat tgcgccctgg acccccctgag cgagacaaag  900
tgtacactga agtcctttac cgtggagaag ggcatctatc agacatccaa tttcagggtg  960
cagccaaccg agtctatcgt gcgctttcct aatatcacaa acctgtgccc atttggcgag  1020
gtgttcaacg caacccgctt cgccagcgtg tacgcctgga ataggaagcg gatcagcaac  1080
tgcgtggccg actatagcgt gctgtacaac tccgcctctt tcagcacctt taagtgctat  1140
ggcgtgtccc ccacaaagct gaatgacctg tgctttacca acgtctacgc cgattctttc  1200
gtgatcaggg gcgacgaggt gcgccagatc gcccccggcc agacaggcaa gatcgcagac  1260
tacaattata agctgccaga cgatttcacc ggctgcgtga tcgcctggaa cagcaacaat  1320
ctggattcca aagtgggcgg caactacaat tatctgtacc ggctgtttag aaagagcaat  1380
ctgaagccct tcgagaggga catctctaca gaaatctacc aggccggcag caccccttgc  1440
aatggcgtgg agggctttaa ctgttatttc ccactccagt cctacggctt ccagcccaca  1500
aacggcgtgg gctatcagcc ttaccgcgtg gtggtgctga gctttgagct gctgcacgcc  1560
ccagcaacag tgtgcggccc caagaagtcc accaatctgg tgaagaacaa gtgcgtgaac  1620
ttcaacttca acggcctgac cggcacaggc gtgctgaccg agtccaacaa gaagttcctg  1680
ccatttcagc agttcggcag ggacatcgca gataccacag acgccgtgcg cgacccacag  1740
accctggaga tcctggacat cacaccctgc tctttcggcg gcgtgagcgt gatcacaccc  1800
ggcaccaata caagcaacca ggtggccgtg ctgtatcagg acgtgaattg taccgaggtg  1860
cccgtggcta tccacgccga tcagctgacc ccaacatggc gggtgtacag caccggctcc  1920
aacgtcttcc agacaagagc cggatgcctg atcggagcag agcacgtgaa caattcctat  1980
gagtgcgaca tcccaatcgg cgccggcatc tgtgcctctt accagaccca gacaaactct  2040
cccagaagag cccggagcgt ggcctcccag tctatcatcg cctataccat gtccctgggc  2100
gccgagaaca gcgtggccta ctctaacaat agcatcgcca tcccaaccaa cttcacaatc  2160
tctgtgacca cagagatcct gcccgtgtcc atgaccaaga catctgtgga ctgcacaatg  2220
tatatctgtg gcgattctac cgagtgcagc aacctgctgc tccagtacgg cagcttttgt  2280
acccagctga atagagccct gacaggcatc gccgtggagc aggataagaa cacacaggag  2340
gtgttcgccc aggtgaagca aatctacaag acccccccta tcaaggactt tggcggcttc  2400
aatttttccc agatcctgcc tgatccatcc aagccttcta agcggagctt tatcgaggac  2460
ctgctgttca acaaggtgac cctggccgat gccggcttca tcaagcagta tggcgattgc  2520
ctgggcgaca tcgcagccag ggacctgatc tgcgcccaga agtttaatgg cctgaccgtg  2580
ctgccacccc tgctgacaga tgagatgatc gcacagtaca caagcgccct gctggccggc  2640
accatcacat ccggatggac cttcggcgca ggagccgccc tccagatccc ctttgccatg  2700
cagatggcct ataggttcaa cggcatcggc gtgacccaga atgtgctgta cgagaaccag  2760
aagctgatcg ccaatcagtt taactccgcc atcggcaaga tccaggacag cctgtcctct  2820
acagccagcg ccctgggcaa gctccaggat gtggtgaatc agaacgccca ggccctgaat  2880
accctggtga agcagctgag cagcaacttc ggcgccatct ctagcgtgct gaatgacatc  2940
ctgagccggc tggacaaggt ggaggcagag gtgcagatcg accggctgat caccggccgg  3000
ctccagagcc tccagaccta tgtgacacag cagctgatca gggccgccga gatcagggcc  3060
agcgccaatc tggcagcaac caagatgtcc gagtgcgtgc tgggccagtc taagagagtg  3120
gacttttgtg gcaagggcta tcacctgatg tccttccctc agtctgcccc acacggcgtg  3180
gtgtttctgc acgtgaccta cgtgcccgcc caggagaaga acttcaccac agcccctgcc  3240
atctgccacg atggcaaggc ccactttcca agggagggcg tgttcgtgtc caacggcacc  3300
cactggtttg tgacacagcg caatttctac gagccccaga tcatcaccac agacaacacc  3360
ttcgtgagcg gcaactgtga cgtggtcatc ggcatcgtga acaataccgt gtatgatcca  3420
ctccagcccg agctggacag ctttaaggag gagctggata agtatttcaa gaatcacacc  3480
tcccctgacg tggatctggg cgacatcagc ggcatcaatg cctccgtggt gaacatccag  3540
aaggagatcg accgcctgaa cgaggtggct aagaatctga acgagagcct gatcgacctc  3600
caggagctgg gcaagtatga gcagtacatc aagtggccct ggtacatctg gctgggcttc  3660
atcgccggcc tgatcgccat cgtgatggtg accatcatgc tgtgctgtat gacatcctgc  3720
tgttcttgcc tgaagggctg ctgtagctgt ggctcctgct gtaagtttga cgaggatgac  3780
tctgaacctg tgctgaaggg cgtgaagctg cattacacct aa                    3822

SEQ ID NO: 120          moltype = AA  length = 1273
FEATURE                 Location/Qualifiers
REGION                  1..1273
                        note = Synthetic polypeptide
source                  1..1273
                        mol_type = protein
                        organism = synthetic construct
SEQUENCE: 120
MFVFLVLLPL VSSQCVNLTT RTQLPPAYTN SFTRGVYYPD KVFRSSVLHS TQDLFLPFFS  60
```

-continued

```
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273

SEQ ID NO: 121          moltype = DNA  length = 3822
FEATURE                 Location/Qualifiers
misc_feature            1..3822
                        note = Synthetic polynucleotide
source                  1..3822
                        mol_type = other DNA
                        organism = synthetic construct
SEQUENCE: 121
atgtttgttt ttcttgtttt attgccacta gtctctagtc agtgtgttaa tcttacaacc  60
agaactcaat taccccctgc atacactaat tctttcacac gtggtgttta ttaccctgac  120
aaagttttca gatcctcagt tttacattca actcaggact tgttcttacc tttcttttcc  180
aatgttactt ggttccatgc tatacatgtc tctgggacca atggtactaa gaggtttgat  240
aaccctgtcc taccatttaa tgatggtgtt tattttgctt ccactgagaa gtctaacata  300
ataagaggct ggatttttgg tactacttta gattcgaaga cccagtccct acttattgtt  360
aataacgcta ctaatgttgt tattaaagtc tgtgaatttc aattttgtaa tgatccattt  420
ttgggtgttt attaccacaa aaacaacaaa agttggatgg aaagtgagtt cagagtttat  480
tctagtgcga ataattgcac ttttgaatat gtctctcagc ctttcttat ggaccttgaa  540
ggaaaacagg gtaatttcaa aaatcttagg gaatttgtgt ttaagaatat tgatggttat  600
tttaaaatat attctaagca cacgcctatt aatttagtgc gtgatctccc tcagggtttt  660
tcggctttag aaccattggt agatttgcca ataggtatta acatcactag gtttcaaact  720
ttacttgctt tacatagaag ttatttgact cctggtgatt cttcttcagg ttggacagct  780
ggtgctgcag cttattatgt gggttatctt caacctagga cttttctatt aaaatataat  840
gaaaatggaa ccattacaga tgctgtagac tgtgcacttg accctctctc agaaacaaag  900
tgtacgttga aatccttcac tgtagaaaaa ggaatctatc aaacttctaa ctttagagtc  960
caaccaacag aatctattgt tagatttcct aatattacaa acttgtgccc ttttggtgaa  1020
gtttttaacg ccaccagatt tgcatctgtt tatgcttgga acaggaagag aatcagcaac  1080
tgtgttgctg attattctgt cctatataat tccgcatcat tttccacttt taagtgttat  1140
ggagtgtctc ctactaaatt aaatgatctc tgctttacta atgtctatgc agattcattt  1200
gtaattagag gtgatgaagt cagacaaatc gctccagggc aaactggaaa gattgctgat  1260
tataattata aattaccaga tgattttaca ggctgcgtta tagcttggaa ttctaacaat  1320
cttgattcta aggttggtgg taattataat tacctgtata gattgtttag gaagtctaat  1380
ctcaaacctt ttgagagaga tatttcaact gaaatctatc aggccggtag cacaccttgt  1440
aatggtgttg aaggttttaa ttgttacttt cctttacaat catatggttt ccaacccact  1500
aatggtgttg gttaccaacc atacagagta gtagtacttt cttttgaact tctacatgca  1560
ccagcaactg tttgtggacc taaaaagtct actaatttgg ttaaaaacaa atgtgtcaat  1620
ttcaacttca atggtttaac aggcacaggt gttcttactg agtctaacaa aaagtttctg  1680
cctttccaac aatttggcag agacattgct gacactactg atgctgtccg tgatccacag  1740
acacttgaga ttcttgacat tacaccatgt tcttttggtg gtgtcagtgt tataacacca  1800
ggaacaaata cttctaacca ggttgctgtt ctttatcagg atgttaactg cacagaagtc  1860
cctgttgcta ttcatgcaga tcaacttact cctacttggc gtgtttattc tacaggttct  1920
aatgtttttc aaacacgtgc aggctgttta ataggggctg aacatgtcaa caactcatat  1980
gagtgtgaca tacccattgg tgcaggtata tgcgctagtt atcagactca gactaattct  2040
cctcggcggg cacgtagtgt agctagtcaa tccatcattg cctacactat gtcacttggt  2100
gcagaaaatt cagttgctta ctctaataac tctattgcca tacccacaaa ttttactatt  2160
agtgttacca cagaaattct accagtgtct atgaccaaga catcagtaga ttgtacaatg  2220
tacatttgtg gtgattcaac tgaatgcagc aatcttttgt tgcaatatgg cagtttttgt  2280
acacaattaa accgtgcttt aactggaata gctgttgaac aagacaaaaa cacccaagaa  2340
gtttttgcac aagtcaaaca aatttacaaa acaccaccaa ttaaagattt tggtggtttt  2400
aatttttcac aaatattacc agatccatca aaaccaagca agaggtcatt tattgaagat  2460
ctacttttca acaaagtgac acttgcagat gctggcttca tcaaacaata tggtgattgc  2520
cttggtgata ttgctgctag agacctcatt tgtgcacaaa agtttaacgg ccttactgtt  2580
ttgccacctt tgctcacaga tgaaatgatt gctcaataca cttctgcact gttagcgggt  2640
acaatcactt ctggttggac ctttggtgca ggtgctgcat tacaaatacc atttgctatg  2700
caaatggctt ataggtttaa tggtattgga gttacacaga atgttctcta tgagaaccaa  2760
aaattgattg ccaaccaatt taatagtgct attggcaaaa ttcaagactc actttcttcc  2820
acagcaagtg cacttggaaa acttcaagat gtggtcaacc aaaatgcaca agctttaaac  2880
acgcttgtta aacaacttag ctccaatttt ggtgcaattt caagtgtttt aaatgatatc  2940
```

```
ctttcacgtc ttgacaaagt tgaggctgaa gtgcaaattg ataggttgat cacaggcaga  3000
cttcaaagtt tgcagacata tgtgactcaa caattaatta gagctgcaga aatcagagct  3060
tctgctaatc ttgctgctac taaaatgtca gagtgtgtac ttggacaatc aaaaagagtt  3120
gatttttgtg gaaagggcta tcatcttatg tccttccctc agtcagcacc tcatggtgta  3180
gtcttcttgc atgtgactta tgtccctgca caagaaaaga acttcacaac tgctcctgcc  3240
atttgtcatg atggaaaagc acactttcct cgtgaaggtg tctttgtttc aaatggcaca  3300
cactggtttg taacacaaag gaatttttat gaaccacaaa tcattactac agacaacaca  3360
tttgtgtctg gtaactgtga tgttgtaata ggaattgtca acaacacagt ttatgatcct  3420
ttgcaacctg aattagactc attcaaggag gagttagata aatattttaa gaatcataca  3480
tcaccagatg ttgatttagg tgacatctct ggcattaatg cttcagttgt aaacattcaa  3540
aaagaaattg accgcctcaa tgaggttgcc aagaatttaa atgaatctct catcgatctc  3600
caagaacttg gaaagtatga gcagtatata aaatggccat ggtacatttg gctaggtttt  3660
atagctggct tgattgccat agtaatggtg acaattatgc tttgctgtat gaccagttgc  3720
tgtagttgtc tcaagggctg ttgttcttgt ggatcctgct gcaaatttga tgaagacgac  3780
tctgagccag tgctcaaagg agtcaaatta cattacacat aa                    3822

SEQ ID NO: 122          moltype = DNA  length = 3822
FEATURE                 Location/Qualifiers
misc_feature            1..3822
                        note = Synthetic polynucleotide
source                  1..3822
                        mol_type = other DNA
                        organism = synthetic construct
SEQUENCE: 122
atgttcgtct tcctggtcct gctgcctctg gtctcctcac agtgcgtcaa tctgacaact  60
cggactcagc tgccacctgc ttatactaat agcttcacca gaggcgtgta ctatcctgac  120
aaggtgttta gaagctccgt gctgcactct acacaggatc tgtttctgcc attctttagc  180
aacgtgacct ggttccacgc catccacgtg agcggcacca atggcacaaa gcggttcgac  240
aatcccgtgc tgccttttaa cgatggcgtg tacttcgcct ctaccgagaa gtccaacatc  300
atcagaggct ggatctttgg caccacactg gactccaaga cacagtctct gctgatcgtg  360
aacaatgcca ccaacgtggt catcaaggtg tgcgagttcc agttttgtaa tgatcccttc  420
ctgggcgtgt actatcacaa gaacaataag agctggatgg agtccgagtt tagagtgtat  480
tctagcgcca acaactgcac atttgagtac gtgagccagc ctttcctgat ggacctggag  540
ggcaagcagg gcaatttcaa gaacctgagg gagttcgtgt ttaagaatat cgacggctac  600
ttcaaaatct actctaagca cacccccatc aacctggtgc gcgacctgcc tcagggcttc  660
agcgccctgg agcccctggt ggatctgcct atcggcatca acatcacccg gtttcagaca  720
ctgctggccc tgcacagaag ctacctgaca cccggcgact cctctagcgg atggaccgcc  780
ggcgctgccg cctactatgt gggctacctc cagccccgga ccttcctgct gaagtacaac  840
gagaatggca ccatcacaga cgcagtggat tgcgccctgg acccccctgag cgagacaaag  900
tgtacactga agtcctttac cgtggagaag ggcatctatc agacatccaa tttcagggtg  960
cagccaaccg agtctatcgt gcgctttcct aatatcacaa acctgtgccc atttggcgag  1020
gtgttcaacg caacccgctt cgccagcgtg tacgcctgga ataggaagcg gatcagcaac  1080
tgcgtggccg actatagcgt gctgtacaac tccgcctctt tcagcacctt taagtgctat  1140
ggcgtgtccc ccacaaagct gaatgacctg tgctttacca acgtctacgc cgattctttc  1200
gtgatcaggg gcgacgaggt gcgccagatc gcccccggcc agacaggcaa gatcgcagac  1260
tacaattata agctgccaga cgatttcacc ggctgcgtga tcgcctggaa cagcaacaat  1320
ctggattcca aagtgggcgg caactacaat tatctgtacc ggctgtttag aaagagcaat  1380
ctgaagccct tcgagaggga catctctaca gaaatctacc aggccggcag caccccttgc  1440
aatggcgtgg agggctttaa ctgttatttc ccactccagt cctacggctt ccagcccaca  1500
aacggcgtgg gctatcagcc ttaccgcgtg gtggtgctga gctttgagct gctgcacgcc  1560
ccagcaacag tgtgcggccc caagaagtcc accaatctgg tgaagaacaa gtgcgtgaac  1620
ttcaacttca acggcctgac cggcacaggc gtgctgaccg agtccaacaa gaagttcctg  1680
ccatttcagc agttcggcag ggacatcgca gataccacag acgccgtgcg cgacccacag  1740
accctggaga tcctggacat cacaccctgc tctttcggcg gcgtgagcgt gatcacaccc  1800
ggcaccaata caagcaacca ggtggccgtg ctgtatcagg acgtgaattg taccgaggtg  1860
cccgtggcta tccacgccga tcagctgacc ccaacatggc gggtgtacag caccggctcc  1920
aacgtcttcc agacaagagc cggatgcctg atcggagcag agcacgtgaa caattcctat  1980
gagtgcgaca tcccaatcgg cgccggcatc tgtgcctctt accagaccca gacaaactct  2040
cccagacggg cccggagcgt ggcctcccag tctatcatcg cctataccat gtccctgggc  2100
gccgagaaca gcgtggccta ctctaacaat agcatcgcca tcccaaccaa cttcacaatc  2160
tctgtgacca cagagatcct gcccgtgtcc atgaccaaga catctgtgga ctgcacaatg  2220
tatatctgtg gcgattctac cgagtgcagc aacctgctgc tccagtacgg cagcttttgt  2280
acccagctga atagagccct gacaggcatc gccgtggagc aggataagaa cacacaggag  2340
gtgttcgccc aggtgaagca aatctacaag acccccccta tcaaggactt tggcggcttc  2400
aatttttccc agatcctgcc tgatccatcc aagccttcta agcggagctt tatcgaggac  2460
ctgctgttca acaaggtgac cctggccgat gccggcttca tcaagcagta tggcgattgc  2520
ctgggcgaca tcgcagccag ggacctgatc tgcgcccaga agtttaatgg cctgaccgtg  2580
ctgccacccc tgctgacaga tgagatgatc gcacagtaca caagcgccct gctggccggc  2640
accatcacat ccggatggac cttcggcgca ggagccgccc tccagatccc ctttgccatg  2700
cagatggcct ataggttcaa cggcatcggc gtgacccaga atgtgctgta cgagaaccag  2760
aagctgatcg ccaatcagtt taactccgcc atcggcaaga tccaggacag cctgtcctct  2820
acagccagcg ccctgggcaa gctccaggat gtggtgaatc agaacgccca ggccctgaat  2880
accctggtga agcagctgag cagcaacttc ggcgccatct ctagcgtgct gaatgacatc  2940
ctgagccggc tggacaaggt ggaggcagag gtgcagatcg accggctgat caccggccgg  3000
ctccagagcc tccagaccta tgtgacacag cagctgatca gggccgccga gatcagggcc  3060
agcgccaatc tggcagcaac caagatgtcc gagtgcgtgc tgggccagtc taagagagtg  3120
gacttttgtg gcaagggcta tcacctgatg tccttccctc agtctgcccc acacggcgtg  3180
gtgtttctgc acgtgaccta cgtgcccgcc caggagaaga acttcaccac agcccctgcc  3240
atctgccacg atggcaaggc ccactttcca agggagggcg tgttcgtgtc caacggcacc  3300
```

```
cactggtttg tgacacagcg caatttctac gagccccaga tcatcaccac agacaacacc  3360
ttcgtgagcg gcaactgtga cgtggtcatc ggcatcgtga acaataccgt gtatgatcca  3420
ctccagcccg agctggacag ctttaaggag gagctggata agtatttcaa gaatcacacc  3480
tcccctgacg tggatctggg cgacatcagc ggcatcaatg cctccgtggt gaacatccag  3540
aaggagatcg accgcctgaa cgaggtggct aagaatctga acgagagcct gatcgacctc  3600
caggagctgg gcaagtatga gcagtacatc aagtggccct ggtacatctg gctgggcttc  3660
atcgccggcc tgatcgccat cgtgatggtg accatcatgc tgtgctgtat gacatcctgc  3720
tgttcttgcc tgaagggctg ctgtagctgt ggctcctgct gtaagtttga cgaggatgac  3780
tctgaacctg tgctgaaggg cgtgaagctg cattacacct aa                    3822

SEQ ID NO: 123          moltype = AA  length = 1273
FEATURE                 Location/Qualifiers
REGION                  1..1273
                        note = Synthetic polypeptide
source                  1..1273
                        mol_type = protein
                        organism = synthetic construct
SEQUENCE: 123
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273

SEQ ID NO: 124          moltype = DNA  length = 11860
FEATURE                 Location/Qualifiers
misc_feature            1..11860
                        note = Synthetic polynucleotide
source                  1..11860
                        mol_type = other DNA
                        organism = synthetic construct
SEQUENCE: 124
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccacccact ggccgagcag gtgatcgtga  1800
```

-continued

```
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
agggcaacga gatcatgacc gccgctgcca gccagggcct gaccaggaag ggcgtgtacg  2820
ccgtgaggta caaggtgaac gagaacccac tgtacgctcc caccagcgag cacgtgaacg  2880
tgctgctgac caggaccgag gacaggatcg tgtggaagac cctggccggc gacccctgga  2940
tcaagaccct gaccgccaag taccccggca acttcaccgc caccatcgaa gagtggcagg  3000
ccgagcacga cgccatcatg aggcacatcc tggagaggcc cgaccccacc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcaccctga  3420
ggaactacga ccccaggatc aacctggtgc ccgtgaacag gcggctgccc cacgccctgg  3480
tgctgcacca caacgagcac cccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc cccggcgacg  3660
tgcccaagta cgacatcatc ttcgtgaacg tcaggaccccc atacaagtac caccattacc  3720
agcagtgcga ggaccacgcc atcaagctga gcatgctgac caagaaggcc tgcctgcacc  3780
tgaaccccgg aggcacctgc gtgagcatcg gctacggcta cgccgacagg gccagcgaga  3840
gcatcattgg cgccatcgcc aggctgttca agttcagcag ggtgtgcaaa cccaagagca  3900
gcctggagga aaccgaggtg ctgttcgtgt tcatcggcta cgaccggaag gccaggaccc  3960
acaaccccta caagctgagc agcaccctga caaacatcta caccggcagc aggctgcacg  4020
aggccggctg cgcccccagc taccacgtgg tcaggggcga tatcgccacc gccaccgagg  4080
gcgtgatcat caacgctgcc aacagcaagg gccagcccgg aggcggagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg ccccaacttc aacaaggtga  4260
gcgaggtgga aggcgacaag cagctggccg aagcctacga gagcatcgcc aagatcgtga  4320
acgacaataa ctacaagagc gtggccatcc cactgctcag caccggcatc ttcagcggca  4380
acaaggacag gctgacccag agcctgaacc acctgctcac cgccctggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgagggtg caccccaaga gctccctggc cggcaggaag ggctacagca  4620
ccagcgacgg caagaccttc agctacctgg agggcaccaa gttccaccag gccgctaagg  4680
acatcgccga gatcaacgct atgtggcccg tggccaccga ggccaacgag caggtgtgca  4740
tgtacatcct gggcgagagc atgtccagca tcaggagcaa gtgccccgtg gaggaaagcg  4800
aggccagcac accacccagc accctgccct gcctgtgcat ccacgctatg acacccgaga  4860
gggtgcagcg gctgaaggcc agcaggcccg agcagatcac cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagacc ccacccgtgg  5040
acgagacacc cgagccaagc gccgagaacc agagcaccga gggcacaccc gagcagccac  5100
ccctgatcac cgaggacgag acaaggaccc ggaccccaga gcccatcatt atcgaggaag  5160
aggaagagga cagcatcagc ctgctgagcg acggccccac ccaccaggtg ctgcaggtgg  5220
aggccgacat ccacggccca cccagcgtgt ccagctccag ctggagcatc ccacacgcca  5280
gcgacttcga cgtggacagc ctgagcatcc tggacaccct ggagggcgcc agcgtgacct  5340
ccggcgccac cagcgccgag accaacagct acttcgccaa gagcatggag ttcctggcca  5400
ggcccgtgcc agctcccagg accgtgttca ggaacccacc ccacccagct cccaggacca  5460
ggaccccaag cctggctccc agcagggcct gcagcaggac cagcctggtg agcaccccac  5520
ccggcgtgaa cagggtgatc accagggagg aactggaggc cctgacaccc agcaggaccc  5580
ccagcaggtc cgtgagcagg actagtctgg tgtccaaccc acccggcgtg aacagggtga  5640
tcaccaggga ggaattcgag gccttcgtgg cccagcaaca gagacggttc gacgccggcg  5700
cctacatctt cagcagcgac accggccagg gacacctgca gcaaaagagc gtgaggcaga  5760
ccgtgctgag cgaggtggtg ctggagagga ccgagctgga aatcagctac gcccccaggc  5820
tggaccagga gaaggaggaa ctgctcagga agaaactgca gctgaacccc accccagcca  5880
acaggagcag gtaccagagc aggaaggtgg agaacatgaa ggccatcacc gccaggcgga  5940
tcctgcaggg cctgggacac tacctgaagg ccgagggcaa ggtggagtgc tacaggaccc  6000
tgcaccccgt gccactgtac agctccagcg tgaacagggc cttctccagc cccaaggtgg  6060
ccgtggaggc ctgcaacgct atgctgaagg agaacttccc caccgtggcc agctactgca  6120
tcatccccga gtacgacgcc tacctggaca tggtggacgg cgccagctgc tgcctggaca  6180
ccgccagctt ctgccccgcc aagctgagga gcttccccaa gaaacacagc tacctggagc  6240
ccaccatcag gagcgccgtg cccagcgcca tccagaacac cctgcagaac gtgctggccg  6300
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggccccaa ggccgctgcc ctgttcgcta agacccacaa cctgaacatg ctgcaggaca  6540
```

-continued

```
tcccaatgga caggttcgtg atggacctga agagggacgt gaaggtgaca cccggcacca  6600
agcacaccga ggagaggccc aaggtgcagg tgatccaggc cgctgaccca ctggccaccg  6660
cctacctgtg cggcatccac agggagctgg tgaggcggct gaacgccgtg ctgctgccca  6720
acatccacac cctgttcgac atgagcgccg aggacttcga cgccatcatc gccgagcact  6780
tccagcccgg cgactgcgtg ctggagaccg acatcgccag cttcgacaag agcgaggatg  6840
acgctatggc cctgaccgct ctgatgatcc tggaggacct gggcgtggac gccgagctgc  6900
tcaccctgat cgaggctgcc ttcggcgaga tcagctccat ccacctgccc accaagacca  6960
agttcaagtt cggcgctatg atgaaaagcg gaatgttcct gaccctgttc gtgaacaccg  7020
tgatcaacat tgtgatcgcc agcagggtgc tgcgggagag gctgaccggc agcccctgcg  7080
ctgccttcat cggcgacgac aacatcgtga agggcgtgaa aagcgacaag ctgatggccg  7140
acaggtgcgc cacctggctg aacatggagg tgaagatcat cgacgccgtg gtgggcgaga  7200
aggcccccta cttctgcggc ggattcatcc tgtgcgacag cgtgaccggc accgcctgca  7260
gggtggccga ccccctgaag aggctgttca agctgggcaa gccactggcc gctgacgatg  7320
agcacgacga tgacaggcgg agggccctgc acgaggaaag caccaggtgg aacagggtgg  7380
gcatcctgag cgagctgtgc aaggccgtgg agagcaggta cgagaccgtg ggcaccagca  7440
tcatcgtgat ggctatgacc acactggcca gctccgtcaa gagcttctcc tacctgaggg  7500
gggcccctat aactctctac ggctaacctg aatggactac gacatagtct agtccgccaa  7560
ggccgccacc atgtttgttt ttcttgtttt attgccacta gtctctagtc agtgtgttaa  7620
tcttacaacc agaactcaat taccccctgc atacactaat tctttcacac gtggtgttta  7680
ttaccctgac aaagttttca gatcctcagt tttacattca actcaggact tgttcttacc  7740
tttcttttcc aatgttactt ggttccatgc tatacatgtc tctgggacca atggtactaa  7800
gaggtttgat aaccctgtcc taccatttaa tgatggtgtt tattttgctt ccactgagaa  7860
gtctaacata ataagaggct ggatttttgg tactacttta gattcgaaga cccagtccct  7920
acttattgtt aataacgcta ctaatgttgt tattaaagtc tgtgaatttc aattttgtaa  7980
tgatccattt ttgggtgttt attaccacaa aaacaacaaa agttggatgg aaagtgagtt  8040
cagagtttat tctagtgcga ataattgcac ttttgaatat gtctctcagc cttttcttat  8100
ggaccttgaa ggaaaacagg gtaatttcaa aaatcttagg gaatttgtgt ttaagaatat  8160
tgatggttat tttaaaatat attctaagca cacgcctatt aatttagtgc gtgatctccc  8220
tcagggtttt tcggctttag aaccattggt agatttgcca ataggtatta acatcactag  8280
gtttcaaact ttacttgctt tacatagaag ttatttgact cctggtgatt cttcttcagg  8340
ttggacagct ggtgctgcag cttattatgt gggttatctt caacctagga cttttctatt  8400
aaaatataat gaaaatggaa ccattacaga tgctgtagac tgtgcacttg accctctctc  8460
agaaacaaag tgtacgttga aatccttcac tgtagaaaaa ggaatctatc aaacttctaa  8520
ctttagagtc caaccaacag aatctattgt tagatttcct aatattacaa acttgtgccc  8580
ttttggtgaa gtttttaacg ccaccagatt tgcatctgtt tatgcttgga acaggaagag  8640
aatcagcaac tgtgttgctg attattctgt cctatataat tccgcatcat tttccacttt  8700
taagtgttat ggagtgtctc ctactaaatt aaatgatctc tgctttacta atgtctatgc  8760
agattcattt gtaattagag gtgatgaagt cagacaaatc gctccagggc aaactggaaa  8820
gattgctgat tataattata aattaccaga tgattttaca ggctgcgtta tagcttggaa  8880
ttctaacaat cttgattcta aggttggtgg taattataat tacctgtata gattgtttag  8940
gaagtctaat ctcaaacctt ttgagagaga tatttcaact gaaatctatc aggccggtag  9000
cacaccttgt aatggtgttg aaggttttaa ttgttacttt cctttacaat catatggttt  9060
ccaacccact aatggtgttg gttaccaacc atacagagta gtagtacttt cttttgaact  9120
tctacatgca ccagcaactg tttgtggacc taaaaagtct actaatttgg ttaaaaacaa  9180
atgtgtcaat ttcaacttca atggtttaac aggcacaggt gttcttactg agtctaacaa  9240
aaagtttctg cctttccaac aatttggcag agacattgct gacactactg atgctgtccg  9300
tgatccacag acacttgaga ttcttgacat tacaccatgt tcttttggtg gtgtcagtgt  9360
tataacacca ggaacaaata cttctaacca ggttgctgtt ctttatcagg atgttaactg  9420
cacagaagtc cctgttgcta ttcatgcaga tcaacttact cctacttggc gtgtttattc  9480
tacaggttct aatgttttc aaacacgtgc aggctgttta ataggggctg aacatgtcaa  9540
caactcatat gagtgtgaca tacccattgg tgcaggtata tgcgctagtt atcagactca  9600
gactaattct cctcggcggg cacgtagtgt agctagtcaa tccatcattg cctacactat  9660
gtcacttggt gcagaaaatt cagttgctta ctctaataac tctattgcca tacccacaaa  9720
ttttactatt agtgttacca cagaaattct accagtgtct atgaccaaga catcagtaga  9780
ttgtacaatg tacatttgtg gtgattcaac tgaatgcagc aatcttttgt tgcaatatgg  9840
cagtttttgt acacaattaa accgtgcttt aactggaata gctgttgaac aagacaaaaa  9900
cacccaagaa gtttttgcac aagtcaaaca aatttacaaa acaccaccaa ttaaagattt  9960
tggtggtttt aatttttcac aaatattacc agatccatca aaaccaagca agaggtcatt  10020
tattgaagat ctacttttca acaaagtgac acttgcagat gctggcttca tcaaacaata  10080
tggtgattgc cttggtgata ttgctgctag agacctcatt tgtgcacaaa agtttaacgg  10140
ccttactgtt ttgccacctt tgctcacaga tgaaatgatt gctcaataca cttctgcact  10200
gttagcgggt acaatcactt ctggttggac ctttggtgca ggtgctgcat tacaaatacc  10260
atttgctatg caaatggctt ataggtttaa tggtattgga gttacacaga atgttctcta  10320
tgagaaccaa aaattgattg ccaaccaatt taatagtgct attggcaaaa ttcaagactc  10380
actttcttcc acagcaagtg cacttggaaa acttcaagat gtggtcaacc aaaatgcaca  10440
agctttaaac acgcttgtta aacaacttag ctccaatttt ggtgcaattt caagtgtttt  10500
aaatgatatc ctttcacgtc ttgacaaagt tgaggctgaa gtgcaaattg ataggttgat  10560
cacaggcaga cttcaaagtt tgcagacata tgtgactcaa caattaatta gagctgcaga  10620
aatcagagct tctgctaatc ttgctgctac taaaatgtca gagtgtgtac ttggacaatc  10680
aaaaagagtt gatttttgtg gaaagggcta tcatcttatg tccttccctc agtcagcacc  10740
tcatggtgta gtcttcttgc atgtgactta tgtccctgca caagaaaaga acttcacaac  10800
tgctcctgcc atttgtcatg atggaaaagc acactttcct cgtgaaggtg tctttgtttc  10860
aaatggcaca cactggtttg taacacaaag gaatttttat gaaccacaaa tcattactac  10920
agacaacaca tttgtgtctg gtaactgtga tgttgtaata ggaattgtca acaacacagt  10980
ttatgatcct ttgcaacctg aattagactc attcaaggag gagttagata aatattttaa  11040
gaatcataca tcaccagatg ttgatttagg tgacatctct ggcattaatg cttcagttgt  11100
aaacattcaa aaagaaattg accgcctcaa tgaggttgcc aagaatttaa atgaatctct  11160
catcgatctc caagaacttg gaaagtatga gcagtatata aaatggccat ggtacatttg  11220
gctaggtttt atagctggct tgattgccat agtaatggtg acaattatgc tttgctgtat  11280
```

-continued

```
gaccagttgc tgtagttgtc tcaagggctg ttgttcttgt ggatcctgct gcaaatttga  11340
tgaagacgac tctgagccag tgctcaaagg agtcaaatta cattacacat aaactcgagt  11400
atgttacgtg caaaggtgat tgtcaccccc cgaaagacca tattgtgaca caccctcagt  11460
atcacgccca aacatttaca gccgcggtgt caaaaaccgc gtggacgtgg ttaacatccc  11520
tgctgggagg atcagccgta attattataa ttggcttggt gctggctact attgtggcca  11580
tgtacgtgct gaccaaccag aaacataatt gaatacagca gcaattggca agctgcttac  11640
atagaactcg cggcgattgg catgccgcct taaaattttt attttatttt ttcttttctt  11700
ttccgaatcg gattttgttt ttaatatttc aaaaaaaaaa aaaaaaaaaa aaaaatctag  11760
aaaaaaaaaa aaaaaaaaaa aaaaaaaaaa aaaaaaaaaa aaaaaaaaaa aaaaaaaaaa  11820
aaaaaaaaaa aaaaaaaaaa aaaaaaaaaa aaaaaaaaaa                        11860

SEQ ID NO: 125          moltype = DNA  length = 11860
FEATURE                 Location/Qualifiers
misc_feature            1..11860
                        note = Synthetic polynucleotide
source                  1..11860
                        mol_type = other DNA
                        organism = synthetic construct
SEQUENCE: 125
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccacccact ggccgagcag gtgatcgtga  1800
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
agggcaacga gatcatgacc gccgctgcca gccagggcct gaccaggaag ggcgtgtacg  2820
ccgtgaggta caaggtgaac gagaacccac tgtacgctcc caccagcgag cacgtgaacg  2880
tgctgctgac caggaccgag gacaggatcg tgtggaagac cctggccggc gacccctgga  2940
tcaagaccct gaccgccaag taccccggca acttcaccgc caccatcgaa gagtggcagg  3000
ccgagcacga cgccatcatg aggcacatcc tggagaggcc cgaccccacc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcaccctga  3420
ggaactacga ccccaggatc aacctggtgc ccgtgaacag gcggctgccc cacgccctgg  3480
tgctgcacca caacgagcac ccacagagcg acttcagctc cttcgtgagc aagctgaaag  3540
gcaggaccgt gctggtcgtg ggcgagaagc tgagcgtgcc cggcaagatg gtggactggc  3600
```

```
tgagcgacag gcccgaggcc accttccggg ccaggctgga cctcggcatc cccggcgacg  3660
tgcccaagta cgacatcatc ttcgtgaacg tcaggacccc atacaagtac caccattacc  3720
agcagtgcga ggaccacgcc atcaagctga gcatgctgac caagaaggcc tgcctgcacc  3780
tgaaccccgg aggcacctgc gtgagcatcg gctacggcta cgccgacagg gccagcgaga  3840
gcatcattgg cgccatcgcc aggctgttca agttcagcag ggtgtgcaaa cccaagagca  3900
gcctggagga aaccgaggtg ctgttcgtgt tcatcggcta cgaccggaag gccaggaccc  3960
acaaccccta caagctgagc agcaccctga caaacatcta caccggcagc aggctgcacg  4020
aggccggctg cgcccccagc taccacgtgg tcaggggcga tatcgccacc gccaccgagg  4080
gcgtgatcat caacgctgcc aacagcaagg gccagcccgg aggcggagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg ccccaacttc aacaaggtga  4260
gcgaggtgga aggcgacaag cagctggccg aagcctacga gagcatcgcc aagatcgtga  4320
acgacaataa ctacaagagc gtggccatcc cactgctcag caccggcatc ttcagcggca  4380
acaaggacag gctgacccag agcctgaacc acctgctcac cgccctggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgagggtg caccccaaga gctccctggc cggcaggaag ggctacagca  4620
ccagcgacgg caagaccttc agctacctgg agggcaccaa gttccaccag gccgctaagg  4680
acatcgccga gatcaacgct atgtggcccg tggccaccga ggccaacgag caggtgtgca  4740
tgtacatcct gggcgagagc atgtccagca tcaggagcaa gtgccccgtg gaggaaagcg  4800
aggccagcac accacccagc accctgccct gcctgtgcat ccacgctatg acacccgaga  4860
gggtgcagcg gctgaaggcc agcaggcccg agcagatcac cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagacc ccacccgtgg  5040
acgagacacc cgagccaagc gccgagaacc agagcaccga gggcacaccc gagcagccac  5100
ccctgatcac cgaggacgag acaaggaccc ggaccccaga gcccatcatt atcgaggaag  5160
aggaagagga cagcatcagc ctgctgagcg acggccccac ccaccaggtg ctgcaggtgg  5220
aggccgacat ccacggccca cccagcgtgt ccagctccag ctggagcatc ccacacgcca  5280
gcgacttcga cgtggacagc ctgagcatcc tggacaccct ggagggcgcc agcgtgacct  5340
ccggcgccac cagcgccgag accaacagct acttcgccaa gagcatggag ttcctggcca  5400
ggcccgtgcc agctcccagg accgtgttca ggaacccacc ccacccagct cccaggacca  5460
ggaccccaag cctggctccc agcagggcct gcagcaggac cagcctggtg agcaccccac  5520
ccggcgtgaa cagggtgatc accagggagg aactggaggc cctgacaccc agcaggaccc  5580
ccagcaggtc cgtgagcagg actagtctgg tgtccaaccc acccggcgtg aacagggtga  5640
tcaccaggga ggaattcgag gccttcgtgg cccagcaaca gagacggttc gacgccggcg  5700
cctacatctt cagcagcgac accggccagg gacacctgca gcaaaagagc gtgaggcaga  5760
ccgtgctgag cgaggtggtg ctggagagga ccgagctgga aatcagctac gcccccaggc  5820
tggaccagga gaaggaggaa ctgctcagga agaaactgca gctgaacccc accccagcca  5880
acaggagcag gtaccagagc aggaaggtgg agaacatgaa ggccatcacc gccaggcgga  5940
tcctgcaggg cctgggacac tacctgaagg ccgagggcaa ggtggagtgc tacaggaccc  6000
tgcaccccgt gccactgtac agctccagcg tgaacagggc cttctccagc cccaaggtgg  6060
ccgtggaggc ctgcaacgct atgctgaagg agaacttccc caccgtggcc agctactgca  6120
tcatccccga gtacgacgcc tacctggaca tggtggacgg cgccagctgc tgcctggaca  6180
ccgccagctt ctgccccgcc aagctgagga gcttccccaa gaaacacagc tacctggagc  6240
ccaccatcag gagcgccgtg cccagcgcca tccagaacac cctgcagaac gtgctggccg  6300
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggccccaa ggccgctgcc ctgttcgcta agacccacaa cctgaacatg ctgcaggaca  6540
tcccaatgga caggttcgtg atggacctga agagggacgt gaaggtgaca cccggcacca  6600
agcacaccga ggagaggccc aaggtgcagg tgatccaggc cgctgaccca ctggccaccg  6660
cctacctgtg cggcatccac agggagctgg tgaggcggct gaacgccgtg ctgctgccca  6720
acatccacac cctgttcgac atgagcgccg aggacttcga cgccatcatc gccgagcact  6780
tccagcccgg cgactgcgtg ctggagaccg acatcgccag cttcgacaag agcgaggatg  6840
acgctatggc cctgaccgct ctgatgatcc tggaggacct gggcgtggac gccgagctgc  6900
tcaccctgat cgaggctgcc ttcggcgaga tcagctccat ccacctgccc accaagacca  6960
agttcaagtt cggcgctatg atgaaaagcg gaatgttcct gaccctgttc gtgaacaccg  7020
tgatcaacat tgtgatcgcc agcagggtgc tgcgggagag gctgaccggc agcccctgcg  7080
ctgccttcat cggcgacgac aacatcgtga agggcgtgaa aagcgacaag ctgatggccg  7140
acaggtgcgc cacctggctg aacatggagg tgaagatcat cgacgccgtg gtgggcgaga  7200
aggcccccta cttctgcggc ggattcatcc tgtgcgacag cgtgaccggc accgcctgca  7260
gggtggccga ccccctgaag aggctgttca agctgggcaa gccactggcc gctgacgatg  7320
agcacgacga tgacaggcgg agggccctgc acgaggaaag caccaggtgg aacagggtgg  7380
gcatcctgag cgagctgtgc aaggccgtgg agagcaggta cgagaccgtg ggcaccagca  7440
tcatcgtgat ggctatgacc acactggcca gctccgtcaa gagcttctcc tacctgaggg  7500
gggcccctat aactctctac ggctaacctg aatggactac gacatagtct agtccgccaa  7560
ggccgccacc atgttcgtct tcctggtcct gctgcctctg gtctcctcac agtgcgtcaa  7620
tctgacaact cggactcagc tgccacctgc ttatactaat agcttcacca gaggcgtgta  7680
ctatcctgac aaggtgttta gaagctccgt gctgcactct acacaggatc tgtttctgcc  7740
attctttagc aacgtgacct ggttccacgc catccacgtg agcggcacca atggcacaaa  7800
gcggttcgac aatcccgtgc tgccttttaa cgatggcgtg tacttcgcct ctaccgagaa  7860
gtccaacatc atcagaggct ggatctttgg caccacactg gactccaaga cacagtctct  7920
gctgatcgtg aacaatgcca ccaacgtggt catcaaggtg tgcgagttcc agttttgtaa  7980
tgatcccttc ctgggcgtgt actatcacaa gaacaataag agctggatgg agtccgagtt  8040
tagagtgtat tctagcgcca acaactgcac atttgagtac gtgagccagc ctttcctgat  8100
ggacctggag ggcaagcagg gcaatttcaa gaacctgagg gagttcgtgt ttaagaatat  8160
cgacggctac ttcaaaatct actctaagca cacccccatc aacctggtgc gcgacctgcc  8220
tcagggcttc agcgccctgg agcccctggt ggatctgcct atcggcatca acatcacccg  8280
gtttcagaca ctgctggccc tgcacagaag ctacctgaca cccggcgact cctctagcgg  8340
```

```
atggaccgcc ggcgctgccg cctactatgt gggctacctc cagccccgga ccttcctgct  8400
gaagtacaac gagaatggca ccatcacaga cgcagtggat tgcgccctgg accccctgag  8460
cgagacaaag tgtacactga agtcctttac cgtggagaag ggcatctatc agacatccaa  8520
tttcagggtg cagccaaccg agtctatcgt gcgctttcct aatatcacaa acctgtgccc  8580
atttggcgag gtgttcaacg caacccgctt cgccagcgtg tacgcctgga ataggaagcg  8640
gatcagcaac tgcgtggccg actatagcgt gctgtacaac tccgcctctt tcagcacctt  8700
taagtgctat ggcgtgtccc ccacaaagct gaatgacctg tgctttacca acgtctacgc  8760
cgattctttc gtgatcaggg gcgacgaggt gcgccagatc gcccccggcc agacaggcaa  8820
gatcgcagac tacaattata agctgccaga cgatttcacc ggctgcgtga tcgcctggaa  8880
cagcaacaat ctggattcca aagtgggcgg caactacaat tatctgtacc ggctgtttag  8940
aaagagcaat ctgaagccct tcgagaggga catctctaca gaaatctacc aggccggcag  9000
caccccttgc aatggcgtgg agggctttaa ctgttatttc ccactccagt cctacggctt  9060
ccagcccaca aacggcgtgg gctatcagcc ttaccgcgtg gtggtgctga gctttgagct  9120
gctgcacgcc ccagcaacag tgtgcggccc caagaagtcc accaatctgg tgaagaacaa  9180
gtgcgtgaac ttcaacttca acggcctgac cggcacaggc gtgctgaccg agtccaacaa  9240
gaagttcctg ccatttcagc agttcggcag ggacatcgca gataccacag acgccgtgcg  9300
cgacccacag accctggaga tcctggacat cacaccctgc tctttcggcg gcgtgagcgt  9360
gatcacaccc ggcaccaata caagcaacca ggtggccgtg ctgtatcagg acgtgaattg  9420
taccgaggtg cccgtggcta tccacgccga tcagctgacc ccaacatggc gggtgtacag  9480
caccggctcc aacgtcttcc agacaagagc cggatgcctg atcggagcag agcacgtgaa  9540
caattcctat gagtgcgaca tcccaatcgg cgccggcatc tgtgcctctt accagaccca  9600
gacaaactct cccagacggg cccggagcgt ggcctcccag tctatcatcg cctataccat  9660
gtccctgggc gccgagaaca gcgtggccta ctctaacaat agcatcgcca tcccaaccaa  9720
cttcacaatc tctgtgacca cagagatcct gcccgtgtcc atgaccaaga catctgtgga  9780
ctgcacaatg tatatctgtg gcgattctac cgagtgcagc aacctgctgc tccagtacgg  9840
cagcttttgt acccagctga atagagccct gacaggcatc gccgtggagc aggataagaa  9900
cacacaggag gtgttcgccc aggtgaagca aatctacaag accccccccta tcaaggactt  9960
tggcggcttc aatttttccc agatcctgcc tgatccatcc aagccttcta agcggagctt  10020
tatcgaggac ctgctgttca acaaggtgac cctggccgat gccggcttca tcaagcagta  10080
tggcgattgc ctgggcgaca tcgcagccag ggacctgatc tgcgcccaga agtttaatgg  10140
cctgaccgtg ctgccacccc tgctgacaga tgagatgatc gcacagtaca caagcgccct  10200
gctggccggc accatcacat ccggatggac cttcggcgca ggagccgccc tccagatccc  10260
ctttgccatg cagatggcct ataggttcaa cggcatcggc gtgacccaga atgtgctgta  10320
cgagaaccag aagctgatcg ccaatcagtt taactccgcc atcggcaaga tccaggacag  10380
cctgtcctct acagccagcg ccctgggcaa gctccaggat gtggtgaatc agaacgccca  10440
ggccctgaat accctggtga agcagctgag cagcaacttc ggcgccatct ctagcgtgct  10500
gaatgacatc ctgagccggc tggacaaggt ggaggcagag gtgcagatcg accggctgat  10560
caccggccgg ctccagagcc tccagaccta tgtgacacag cagctgatca gggccgccga  10620
gatcagggcc agcgccaatc tggcagcaac caagatgtcc gagtgcgtgc tgggccagtc  10680
taagagagtg gacttttgtg gcaagggcta tcacctgatg tccttccctc agtctgcccc  10740
acacggcgtg gtgtttctgc acgtgaccta cgtgcccgcc caggagaaga acttcaccac  10800
agcccctgcc atctgccacg atggcaaggc ccactttcca agggagggcg tgttcgtgtc  10860
caacggcacc cactggtttg tgacacagcg caatttctac gagccccaga tcatcaccac  10920
agacaacacc ttcgtgagcg gcaactgtga cgtggtcatc ggcatcgtga acaataccgt  10980
gtatgatcca ctccagcccg agctggacag ctttaaggag gagctggata agtatttcaa  11040
gaatcacacc tcccctgacg tggatctggg cgacatcagc ggcatcaatg cctccgtggt  11100
gaacatccag aaggagatcg accgcctgaa cgaggtggct aagaatctga acgagagcct  11160
gatcgacctc caggagctgg gcaagtatga gcagtacatc aagtggccct ggtacatctg  11220
gctgggcttc atcgccggcc tgatcgccat cgtgatggtg accatcatgc tgtgctgtat  11280
gacatcctgc tgttcttgcc tgaagggctg ctgtagctgt ggctcctgct gtaagtttga  11340
cgaggatgac tctgaacctg tgctgaaggg cgtgaagctg cattacacct aaactcgagt  11400
atgttacgtg caaaggtgat tgtcaccccc cgaaagacca tattgtgaca caccctcagt  11460
atcacgccca aacatttaca gccgcggtgt caaaaaccgc gtggacgtgg ttaacatccc  11520
tgctgggagg atcagccgta attattataa ttggcttggt gctggctact attgtggcca  11580
tgtacgtgct gaccaaccag aaacataatt gaatacagca gcaattggca agctgcttac  11640
atagaactcg cggcgattgg catgccgcct taaaattttt attttatttt ttcttttctt  11700
ttccgaatcg gattttgttt ttaatatttc aaaaaaaaaa aaaaaaaaaa aaaaatctag  11760
aaaaaaaaaa aaaaaaaaaa aaaaaaaaaa aaaaaaaaaa aaaaaaaaaa aaaaaaaaaa  11820
aaaaaaaaaa aaaaaaaaaa aaaaaaaaaa aaaaaaaaaa                       11860

SEQ ID NO: 126          moltype = DNA  length = 4238
FEATURE                 Location/Qualifiers
misc_feature            1..4238
                        note = Synthetic polynucleotide
source                  1..4238
                        mol_type = other DNA
                        organism = synthetic construct
SEQUENCE: 126
aggaaactta agtcaacaca acatatacaa aacaaacgaa tctcaagcaa tcaagcattc  60
tacttctatt gcagcaattt aaatcatttc ttttaaagca aaagcaattt tctgaaaatt  120
ttcaccattt acgaacgata gccaccatgt tcgtcttcct ggtcctgctg cctctggtct  180
cctcacagtg cgtcaatctg acaactcgga ctcagctgcc acctgcttat actaatagct  240
tcaccagagg cgtgtactat cctgacaagg tgtttagaag ctccgtgctg cactctacac  300
aggatctgtt tctgccattc tttagcaacg tgacctggtt ccacgccatc cacgtgagcg  360
gcaccaatgg cacaaagcgg ttcgacaatc ccgtgctgcc ttttaacgat ggcgtgtact  420
tcgcctctac cgagaagtcc aacatcatca gaggctggat ctttggcacc acactggact  480
ccaagacaca gtctctgctg atcgtgaaca atgccaccaa cgtggtcatc aaggtgtgcg  540
agttccagtt ttgtaatgat ccccttcctgg gcgtgtacta tcacaagaac aataagagct  600
ggatggagtc cgagtttaga gtgtattcta gcgccaacaa ctgcacattt gagtacgtga  660
```

```
gccagccttt cctgatggac ctggagggca agcagggcaa tttcaagaac ctgagggagt  720
tcgtgtttaa gaatatcgac ggctacttca aaatctactc taagcacacc cccatcaacc  780
tggtgcgcga cctgcctcag ggcttcagcg ccctggagcc cctggtggat ctgcctatcg  840
gcatcaacat cacccggttt cagacactgc tggccctgca cagaagctac ctgacacccg  900
gcgactcctc tagcggatgg accgccggcg ctgccgccta ctatgtgggc tacctccagc  960
cccggacctt cctgctgaag tacaacgaga atggcaccat cacagacgca gtggattgcg  1020
ccctggaccc cctgagcgag acaaagtgta cactgaagtc ctttaccgtg gagaagggca  1080
tctatcagac atccaatttc agggtgcagc caaccgagtc tatcgtgcgc tttcctaata  1140
tcacaaacct gtgcccattt ggcgaggtgt tcaacgcaac ccgcttcgcc agcgtgtacg  1200
cctggaatag gaagcggatc agcaactgcg tggccgacta tagcgtgctg tacaactccg  1260
cctctttcag cacctttaag tgctatggcg tgtcccccac aaagctgaat gacctgtgct  1320
ttaccaacgt ctacgccgat tctttcgtga tcaggggcga cgaggtgcgc cagatcgccc  1380
ccggccagac aggcaagatc gcagactaca attataagct gccagacgat ttcaccggct  1440
gcgtgatcgc ctggaacagc aacaatctgg attccaaagt gggcggcaac tacaattatc  1500
tgtaccggct gtttagaaag agcaatctga agcccttcga gagggacatc tctacagaaa  1560
tctaccaggc cggcagcacc ccttgcaatg gcgtggaggg ctttaactgt tatttcccac  1620
tccagtccta cggcttccag cccacaaacg gcgtgggcta tcagccttac cgcgtggtgg  1680
tgctgagctt tgagctgctg cacgccccag caacagtgtg cggcccccaag aagtccacca  1740
atctggtgaa gaacaagtgc gtgaacttca acttcaacgg cctgaccggc acaggcgtgc  1800
tgaccgagtc caacaagaag ttcctgccat ttcagcagtt cggcagggac atcgcagata  1860
ccacagacgc cgtgcgcgac ccacagaccc tggagatcct ggacatcaca ccctgctctt  1920
tcggcggcgt gagcgtgatc acacccggca ccaatacaag caaccaggtg gccgtgctgt  1980
atcaggacgt gaattgtacc gaggtgcccg tggctatcca cgccgatcag ctgaccccaa  2040
catggcgggt gtacagcacc ggctccaacg tcttccagac aagagccgga tgcctgatcg  2100
gagcagagca cgtgaacaat tcctatgagt gcgacatccc aatcggcgcc ggcatctgtg  2160
cctcttacca gacccagaca aactctccca gacgggcccg gagcgtggcc tcccagtcta  2220
tcatcgccta taccatgtcc ctgggcgccg agaacagcgt ggcctactct aacaatagca  2280
tcgccatccc aaccaacttc acaatctctg tgaccacaga gatcctgccc gtgtccatga  2340
ccaagacatc tgtggactgc acaatgtata tctgtggcga ttctaccgag tgcagcaacc  2400
tgctgctcca gtacggcagc ttttgtaccc agctgaatag agccctgaca ggcatcgccg  2460
tggagcagga taagaacaca caggaggtgt tcgcccaggt gaagcaaatc tacaagaccc  2520
cccctatcaa ggactttggc ggcttcaatt tttcccagat cctgcctgat ccatccaagc  2580
cttctaagcg gagctttatc gaggacctgc tgttcaacaa ggtgaccctg gccgatgccg  2640
gcttcatcaa gcagtatggc gattgcctgg gcgacatcgc agccagggac ctgatctgcg  2700
cccagaagtt taatggcctg accgtgctgc cacccctgct gacagatgag atgatcgcac  2760
agtacacaag cgccctgctg gccggcacca tcacatccgg atggaccttc ggcgcaggag  2820
ccgccctcca gatccccttt gccatgcaga tggcctatag gttcaacggc atcggcgtga  2880
cccagaatgt gctgtacgag aaccagaagc tgatcgccaa tcagtttaac tccgccatcg  2940
gcaagatcca ggacagcctg tcctctacag ccagcgccct gggcaagctc caggatgtgg  3000
tgaatcagaa cgcccaggcc ctgaataccc tggtgaagca gctgagcagc aacttcggcg  3060
ccatctctag cgtgctgaat gacatcctga gccggctgga caaggtggag gcagaggtgc  3120
agatcgaccg gctgatcacc ggccggctcc agagcctcca gacctatgtg acacagcagc  3180
tgatcagggc cgccgagatc agggccagcg ccaatctggc agcaaccaag atgtccgagt  3240
gcgtgctggg ccagtctaag agagtggact tttgtggcaa gggctatcac ctgatgtcct  3300
tccctcagtc tgccccacac ggcgtggtgt ttctgcacgt gacctacgtg cccgcccagg  3360
agaagaactt caccacagcc cctgccatct gccacgatgg caaggcccac tttccaaggg  3420
agggcgtgtt cgtgtccaac ggcacccact ggtttgtgac acagcgcaat ttctacgagc  3480
cccagatcat caccacagac aacaccttcg tgagcggcaa ctgtgacgtg gtcatcggca  3540
tcgtgaacaa taccgtgtat gatccactcc agcccgagct ggacagcttt aaggaggagc  3600
tggataagta tttcaagaat cacacctccc ctgacgtgga tctgggcgac atcagcggca  3660
tcaatgcctc cgtggtgaac atccagaagg agatcgaccg cctgaacgag gtggctaaga  3720
atctgaacga gagcctgatc gacctccagg agctgggcaa gtatgagcag tacatcaagt  3780
ggccctggta catctggctg ggcttcatcg ccggcctgat cgccatcgtg atggtgacca  3840
tcatgctgtg ctgtatgaca tcctgctgtt cttgcctgaa gggctgctgt agctgtggct  3900
cctgctgtaa gtttgacgag gatgactctg aacctgtgct gaagggcgtg aagctgcatt  3960
acacctaaac tcgagctagt gactgactag gatctggtta ccactaaacc agcctcaaga  4020
acacccgaat ggagtctcta agctacataa taccaactta cacttacaaa atgttgtccc  4080
ccaaaatgta gccattcgta tctgctccta ataaaaagaa agtttcttca cattctagaa  4140
aaaaaaaaaa aaaaaaaaaa aaaaaaaaaa aaaaaaaaaa aaaaaaaaaa aaaaaaaaaa  4200
aaaaaaaaaa aaaaaaaaaa aaaaaaaaaa aaaaaaaa                          4238

SEQ ID NO: 127          moltype = DNA  length = 10508
FEATURE                 Location/Qualifiers
misc_feature            1..10508
                        note = Synthetic polynucleotide
source                  1..10508
                        mol_type = other DNA
                        organism = synthetic construct
SEQUENCE: 127
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
```

-continued

```
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccacccact ggccgagcag gtgatcgtga  1800
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
agggcaacga gatcatgacc gccgctgcca gccagggcct gaccaggaag ggcgtgtacg  2820
ccgtgaggta caaggtgaac gagaacccac tgtacgctcc caccagcgag cacgtgaacg  2880
tgctgctgac caggaccgag gacaggatcg tgtggaagac cctggccggc gacccctgga  2940
tcaagaccct gaccgccaag taccccggca acttcaccgc caccatcgaa gagtggcagg  3000
ccgagcacga cgccatcatg aggcacatcc tggagaggcc cgaccccacc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcaccctga  3420
ggaactacga ccccaggatc aacctggtgc ccgtgaacag gcggctgccc cacgccctgg  3480
tgctgcacca caacgagcac ccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc cccggcgacg  3660
tgcccaagta cgacatcatc ttcgtgaacg tcaggacccc atacaagtac caccattacc  3720
agcagtgcga ggaccacgcc atcaagctga gcatgctgac caagaaggcc tgcctgcacc  3780
tgaaccccgg aggcacctgc gtgagcatcg gctacggcta cgccgacagg gccagcgaga  3840
gcatcattgg cgccatcgcc aggctgttca agttcagcag ggtgtgcaaa cccaagagca  3900
gcctggagga aaccgaggtg ctgttcgtgt tcatcggcta cgaccggaag gccaggaccc  3960
acaaccccta caagctgagc agcaccctga caaacatcta caccggcagc aggctgcacg  4020
aggccggctg cgcccccagc taccacgtgg tcaggggcga tatcgccacc gccaccgagg  4080
gcgtgatcat caacgctgcc aacagcaagg gccagcccgg aggcggagtg tgcggcgccc  4140
tgtacaagaa gttccccgag agcttcgacc tgcagcccat cgaggtgggc aaggccaggc  4200
tggtgaaggg cgccgctaag cacatcatcc acgccgtggg ccccaacttc aacaaggtga  4260
gcgaggtgga aggcgacaag cagctggccg aagcctacga gagcatcgcc aagatcgtga  4320
acgacaataa ctacaagagc gtggccatcc cactgctcag caccggcatc ttcagcggca  4380
acaaggacag gctgacccag agcctgaacc acctgctcac cgccctggac accaccgatg  4440
ccgacgtggc catctactgc agggacaaga agtgggagat gaccctgaag gaggccgtgg  4500
ccaggcggga ggccgtggaa gagatctgca tcagcgacga ctccagcgtg accgagcccg  4560
acgccgagct ggtgagggtg caccccaaga gctccctggc cggcaggaag ggctacagca  4620
ccagcgacgg caagaccttc agctacctgg agggcaccaa gttccaccag gccgctaagg  4680
acatcgccga gatcaacgct atgtggccgg tggccaccga ggccaacgag caggtgtgca  4740
tgtacatcct gggcgagagc atgtccagca tcaggagcaa gtgccccgtg gaggaaagcg  4800
aggccagcac accacccagc accctgccct gcctgtgcat ccacgctatg acacccgaga  4860
gggtgcagcg gctgaaggcc agcaggcccg agcagatcac cgtgtgcagc tccttcccac  4920
tgcccaagta caggatcacc ggcgtgcaga agatccagtg cagccagccc atcctgttca  4980
gcccaaaggt gcccgcctac atccacccca ggaagtacct ggtggagacc ccacccgtgg  5040
acgagacacc cgagccaagc gccgagaacc agagcaccga gggcacaccc gagcagccac  5100
ccctgatcac cgaggacgag acaaggaccc ggaccccaga gcccatcatt atcgaggaag  5160
aggaagagga cagcatcagc ctgctgagcg acggccccac ccaccaggtg ctgcaggtgg  5220
aggccgacat ccacggccca cccagcgtgt ccagctccag ctggagcatc ccacacgcca  5280
gcgacttcga cgtggacagc ctgagcatcc tggacaccct ggagggcgcc agcgtgacct  5340
```

-continued

```
ccggcgccac cagcgccgag accaacagct acttcgccaa gagcatggag ttcctggcca  5400
ggcccgtgcc agctcccagg accgtgttca ggaacccacc ccacccagct cccaggacca  5460
ggaccccaag cctggctccc agcagggcct gcagcaggac cagcctggtg agcaccccac  5520
ccggcgtgaa cagggtgatc accagggagg aactggaggc cctgacaccc agcaggaccc  5580
ccagcaggtc cgtgagcagg actagtctgg tgtccaaccc acccggcgtg aacagggtga  5640
tcaccaggga ggaattcgag gccttcgtgg cccagcaaca gagacggttc gacgccggcg  5700
cctacatctt cagcagcgac accggccagg gacacctgca gcaaaagagc gtgaggcaga  5760
ccgtgctgag cgaggtggtg ctggagagga ccgagctgga aatcagctac gcccccaggc  5820
tggaccagga gaaggaggaa ctgctcagga agaaactgca gctgaacccc accccagcca  5880
acaggagcag gtaccagagc aggaaggtgg agaacatgaa ggccatcacc gccaggcgga  5940
tcctgcaggg cctgggacac tacctgaagg ccgagggcaa ggtggagtgc tacaggaccc  6000
tgcaccccgt gccactgtac agctccagcg tgaacagggc cttctccagc cccaaggtgg  6060
ccgtggaggc ctgcaacgct atgctgaagg agaacttccc caccgtggcc agctactgca  6120
tcatccccga gtacgacgcc tacctggaca tggtggacgg cgccagctgc tgcctggaca  6180
ccgccagctt ctgccccgcc aagctgagga gcttccccaa gaaacacagc tacctggagc  6240
ccaccatcag gagcgccgtg cccagcgcca tccagaacac cctgcagaac gtgctggccg  6300
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggccccaa ggccgctgcc ctgttcgcta agacccacaa cctgaacatg ctgcaggaca  6540
tcccaatgga caggttcgtg atggacctga agagggacgt gaaggtgaca cccggcacca  6600
agcacaccga ggagaggccc aaggtgcagg tgatccaggc cgctgaccca ctggccaccg  6660
cctacctgtg cggcatccac agggagctgg tgaggcggct gaacgccgtg ctgctgccca  6720
acatccacac cctgttcgac atgagcgccg aggacttcga cgccatcatc gccgagcact  6780
tccagcccgg cgactgcgtg ctggagaccg acatcgccag cttcgacaag agcgaggatg  6840
acgctatggc cctgaccgct ctgatgatcc tggaggacct gggcgtggac gccgagctgc  6900
tcaccctgat cgaggctgcc ttcggcgaga tcagctccat ccacctgccc accaagacca  6960
agttcaagtt cggcgctatg atgaaaagcg gaatgttcct gaccctgttc gtgaacaccg  7020
tgatcaacat tgtgatcgcc agcagggtgc tgcgggagag gctgaccggc agcccctgcg  7080
ctgccttcat cggcgacgac aacatcgtga agggcgtgaa aagcgacaag ctgatggccg  7140
acaggtgcgc cacctggctg aacatggagg tgaagatcat cgacgccgtg gtgggcgaga  7200
aggcccccta cttctgcggc ggattcatcc tgtgcgacag cgtgaccggc accgcctgca  7260
gggtggccga ccccctgaag aggctgttca agctgggcaa gccactggcc gctgacgatg  7320
agcacgacga tgacaggcgg agggccctgc acgaggaaag caccaggtgg aacagggtgg  7380
gcatcctgag cgagctgtgc aaggccgtgg agagcaggta cgagaccgtg ggcaccagca  7440
tcatcgtgat ggctatgacc acactggcca gctccgtcaa gagcttctcc tacctgaggg  7500
gggcccctat aactctctac ggctaacctg aatggactac gacatagtct agccaccatg  7560
agcaagatct acatcgacga gcggagcaac gccgagatcg tgtgcgaggc catcaagacc  7620
atcggcatcg agggcgccac cgccgcccag ctgaccaggc agctgaacat ggagaagcgg  7680
gaggtgaaca aggccctgta cgacctgcag aggagcgcta tggtgtactc cagcgacgac  7740
atccctcccc ggtggttcat gaccaccgag gccgacaagc ccgacgccga cgctatggcc  7800
gacgtgatca tcgacgacgt gagcagggag aagtccatga gggaggacca caagagcttc  7860
gacgacgtga tccccgccaa gaagatcatc gactggaagg gcgccaaccc cgtgaccgtg  7920
atcaacgagt actgccagat caccaggagg gactggagct tccggatcga gagcgtgggc  7980
cccagcaaca gccccacctt ctacgcctgc gtggacatcg acggcagggt gttcgacaag  8040
gccgacggca agagcaagcg ggacgccaag aacaacgccg ccaagctggc cgtggacaag  8100
ctgctgggct acgtgatcat ccggttctaa actcgagcta gtgactgact aggatctggt  8160
taccactaaa ccagcctcaa gaacacccga atggagtctc taagctacat aataccaact  8220
tacacttaca aaatgttgtc ccccaaaatg tagccattcg tatctgctcc taataaaaag  8280
aaagtttctt cacattctag agctccgtca agagcttctc ctacctgagg ggggccccta  8340
taactctcta cggctaacct gaatggacta cgacatagtc tagccaccat ggaagatgcc  8400
aaaaacatta agaagggccc agcgccattc tacccactcg aagacgggac cgccggcgag  8460
cagctgcaca aagccatgaa gcgctacgcc ctggtgcccg gcaccatcgc ctttaccgac  8520
gcacatatcg aggtggacat tacctacgcc gagtacttcg agatgagcgt tcggctggca  8580
gaagctatga agcgctatgg gctgaataca aaccatcgga tcgtggtgtg cagcgagaat  8640
agcttgcagt tcttcatgcc cgtgttgggt gccctgttca tcggtgtggc tgtggcccca  8700
gctaacgaca tctacaacga gcgcgagctg ctgaacagca tgggcatcag ccagcccacc  8760
gtcgtattcg tgagcaagaa agggctgcaa aagatcctca acgtgcaaaa gaagctaccg  8820
atcatacaaa agatcatcat catggatagc aagaccgact accagggctt ccaaagcatg  8880
tacaccttcg tgacttccca tttgccaccc ggcttcaacg agtacgactt cgtgcccgag  8940
agcttcgacc gggacaaaac catcgccctg atcatgaaca gtagtggcag taccggattg  9000
cccaagggcg tagccctacc gcaccgcacc gcttgtgtcc gattcagtca tgcccgcgac  9060
cccatcttcg gcaaccagat catccccgac accgctatcc tcagcgtggt gccatttcac  9120
cacggcttcg gcatgttcac cacgctgggc tacttgatct gcggctttcg ggtcgtgctc  9180
atgtaccgct tcgaggagga gctattcttg cgcagcttgc aagactataa gattcaatct  9240
gccctgctgg tgcccacact atttagcttc ttcgctaaga gcactctcat cgacaagtac  9300
gacctaagca acttgcacga gatcgccagc ggcggggcgc cgctcagcaa ggaggtaggt  9360
gaggccgtgg ccaaacgctt ccacctacca ggcatccgac agggctacgg cctgacagaa  9420
acaaccagcg ccattctgat cacccccgaa ggggacgaca agcctggcgc agtaggcaag  9480
gtggtgccct tcttcgaggc taaggtggtg gacttggaca ccggtaagac actgggtgtg  9540
aaccagcgcg gcgagctgtg cgtccgtggc cccatgatca tgagcggcta cgttaacaac  9600
cccgaggcta caaacgctct catcgacaag gacggctggc tgcacagcgg cgacatcgcc  9660
tactgggacg aggacgagca cttcttcatc gtggaccggc tgaagtccct gatcaaatac  9720
aagggctacc aggtagcccc agccgaactg gagagcatcc tgctgcaaca ccccaacatc  9780
ttcgacgccg gggtcgccgg cctgcccgac gacgatgccg gcgagctgcc cgccgcagtc  9840
gtcgtgctgg aacacggtaa aaccatgacc gagaaggaga tcgtggacta tgtggccagc  9900
caggttacaa ccgccaagaa gctgcgcggt ggtgttgtgt tcgtggacga ggtgcctaaa  9960
ggactgaccg gcaagttgga cgcccgcaag atccgcgaga ttctcattaa ggccaagaag  10020
ggcggcaaga tcgccgtgta actcgagtat gttacgtgca aaggtgattg tcaccccccg  10080
```

```
aaagaccata ttgtgacaca ccctcagtat cacgcccaaa catttacagc cgcggtgtca  10140
aaaaccgcgt ggacgtggtt aacatccctg ctgggaggat cagccgtaat tattataatt  10200
ggcttggtgc tggctactat tgtggccatg tacgtgctga ccaaccagaa acataattga  10260
atacagcagc aattggcaag ctgcttacat agaactcgcg gcgattggca tgccgcctta  10320
aaatttttat tttatttttt cttttctttt ccgaatcgga ttttgttttt aatatttcaa  10380
aaaaaaaaaa aaaaaaaaaa aaatctagaa aaaaaaaaaa aaaaaaaaaa aaaaaaaaaa  10440
aaaaaaaaaa aaaaaaaaaa aaaaaaaaaa aaaaaaaaaa aaaaaaaaaa aaaaaaaaaa  10500
aaaaaaaa                                                           10508

SEQ ID NO: 128          moltype = RNA  length = 11075
FEATURE                 Location/Qualifiers
misc_feature            1..11075
                        note = Synthetic polynucleotide
source                  1..11075
                        mol_type = other RNA
                        organism = synthetic construct
SEQUENCE: 128
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga ggccaagtgc gctgccgacg aggccaagga ggtgagggag gccgaggaac  1560
tgagggccgc cctgccaccc ctggctgccg acgtggagga acccaccctg gaagccgacg  1620
tggacctgat gctgcaggag gccggcgccg gaagcgtgga gacacccagg ggcctgatca  1680
aggtgaccag ctacgacggc gaggacaaga tcggcagcta cgccgtgctg agcccacagg  1740
ccgtgctgaa gtccgagaag ctgagctgca tccacccact ggccgagcag gtgatcgtga  1800
tcacccacag cggcaggaag ggcaggtacg ccgtggagcc ctaccacggc aaggtggtcg  1860
tgcccgaggg ccacgccatc cccgtgcagg acttccaggc cctgagcgag agcgccacca  1920
tcgtgtacaa cgagagggag ttcgtgaaca ggtacctgca ccatatcgcc acccacggcg  1980
gagccctgaa caccgacgag gaatactaca agaccgtgaa gcccagcgag cacgacggcg  2040
agtacctgta cgacatcgac aggaagcagt gcgtgaagaa agagctggtg accggcctgg  2100
gactgaccgg cgagctggtg gacccaccct tccacgagtt cgcctacgag agcctgagga  2160
ccagacccgc cgctccctac caggtgccca ccatcggcgt gtacggcgtg cccggcagcg  2220
gaaagagcgg catcatcaag agcgccgtga ccaagaaaga cctggtggtc agcgccaaga  2280
aagagaactg cgccgagatc atcagggacg tgaagaagat gaaaggcctg gacgtgaacg  2340
cgcgcaccgt ggacagcgtg ctgctgaacg gctgcaagca ccccgtggag accctgtaca  2400
tcgacgaggc cttcgcttgc cacgccggca ccctgagggc cctgatcgcc atcatcaggc  2460
ccaagaaagc cgtgctgtgc ggcgacccca agcagtgcgg cttcttcaac atgatgtgcc  2520
tgaaggtgca cttcaaccac gagatctgca cccaggtgtt ccacaagagc atcagcaggc  2580
ggtgcaccaa gagcgtgacc agcgtcgtga gcaccctgtt ctacgacaag aaaatgagga  2640
ccaccaaccc caaggagacc aaaatcgtga tcgacaccac aggcagcacc aagcccaagc  2700
aggacgacct gatcctgacc tgcttcaggg gctgggtgaa gcagctgcag atcgactaca  2760
agggcaacga gatcatgacc gccgctgcca gccagggcct gaccaggaag ggcgtgtacg  2820
ccgtgaggta caaggtgaac gagaacccac tgtacgctcc caccagcgag cacgtgaacg  2880
tgctgctgac caggaccgag gacaggatcg tgtggaagac cctggccggc gacccctgga  2940
tcaagaccct gaccgccaag taccccggca acttcaccgc caccatcgaa gagtggcagg  3000
ccgagcacga cgccatcatg aggcacatcc tggagaggcc cgacccaccc gacgtgttcc  3060
agaacaaggc caacgtgtgc tgggccaagg ccctggtgcc cgtgctgaag accgccggca  3120
tcgacatgac cacagagcag tggaacaccg tggactactt cgagaccgac aaggcccaca  3180
gcgccgagat cgtgctgaac cagctgtgcg tgaggttctt cggcctggac ctggacagcg  3240
gcctgttcag cgcccccacc gtgccactga gcatcaggaa caaccactgg gacaacagcc  3300
ccagcccaaa catgtacggc ctgaacaagg aggtggtcag gcagctgagc aggcggtacc  3360
cacagctgcc cagggccgtg gccaccggca gggtgtacga catgaacacc ggcaccctga  3420
ggaactacga ccccaggatc aacctggtgc ccgtgaacag gcggctgccc cacgccctgg  3480
tgctgcacca caacgagcac ccacagagcg acttcagctc cttcgtgagc aagctgaaag  3540
gcaggaccgt gctggtcgtg ggcgagaagc tgagcgtgcc cggcaagatg gtggactggc  3600
tgagcgacag gcccgaggcc accttccggg ccaggctgga cctcggcatc cccggcgacg  3660
tgcccaagta cgacatcatc ttcgtgaacg tcaggacccc atacaagtac caccattacc  3720
```

agcagtgcga ggaccacgcc atcaagctga gcatgctgac caagaaggcc tgcctgcacc 3780
tgaaccccgg aggcacctgc gtgagcatcg gctacggcta cgccgacagg gccagcgaga 3840
gcatcattgg cgccatcgcc aggctgttca agttcagcag ggtgtgcaaa cccaagagca 3900
gcctggagga aaccgaggtg ctgttcgtgt tcatcggcta cgaccggaag gccaggaccc 3960
acaaccccta caagctgagc agcaccctga caaacatcta caccggcagc aggctgcacg 4020
aggccggctg cgcccccagc taccacgtgg tcaggggcga tatcgccacc gccaccgagg 4080
gcgtgatcat caacgctgcc aacagcaagg gccagcccgg aggcggagtg tgcggcgccc 4140
tgtacaagaa gttccccgag agcttcgacc tgcagcccat cgaggtgggc aaggccaggc 4200
tggtgaaggg cgccgctaag cacatcatcc acgccgtggg ccccaacttc aacaaggtga 4260
gcgaggtgga aggcgacaag cagctggccg aagcctacga gagcatcgcc aagatcgtga 4320
acgacaataa ctacaagagc gtggccatcc cactgctcag caccggcatc ttcagcggca 4380
acaaggacag gctgacccag agcctgaacc acctgctcac cgccctggac accaccgatg 4440
ccgacgtggc catctactgc agggacaaga agtgggagat gaccctgaag gaggccgtgg 4500
ccaggcggga ggccgtggaa gagatctgca tcagcgacga ctccagcgtg accgagcccg 4560
acgccgagct ggtgagggtg caccccaaga gctccctggc cggcaggaag ggctacagca 4620
ccagcgacgg caagaccttc agctacctgg agggcaccaa gttccaccag gccgctaagg 4680
acatcgccga gatcaacgct atgtggcccg tggccaccga ggccaacgag caggtgtgca 4740
tgtacatcct gggcgagagc atgtccagca tcaggagcaa gtgccccgtg gaggaaagcg 4800
aggccagcac accacccagc accctgccct gcctgtgcat ccacgctatg acacccgaga 4860
gggtgcagcg gctgaaggcc agcaggcccg agcagatcac cgtgtgcagc tccttcccac 4920
tgcccaagta caggatcacc ggcgtgcaga agatccagtg cagccagccc atcctgttca 4980
gcccaaaggt gcccgcctac atccacccca ggaagtacct ggtggagacc ccacccgtgg 5040
acgagacacc cgagccaagc gccgagaacc agagcaccga gggcacaccc gagcagccac 5100
ccctgatcac cgaggacgag acaaggaccc ggaccccaga gcccatcatt atcgaggaag 5160
aggaagagga cagcatcagc ctgctgagcg acggccccac ccaccaggtg ctgcaggtgg 5220
aggccgacat ccacggccca cccagcgtgt ccagctccag ctggagcatc ccacacgcca 5280
gcgacttcga cgtggacagc ctgagcatcc tggacaccct ggagggcgcc agcgtgacct 5340
ccggcgccac cagcgccgag accaacagct acttcgccaa gagcatggag ttcctggcca 5400
ggcccgtgcc agctcccagg accgtgttca ggaacccacc ccacccagct cccaggacca 5460
ggaccccaag cctggctccc agcagggcct gcagcaggac cagcctggtg agcacccccac 5520
ccggcgtgaa cagggtgatc accagggagg aactggaggc cctgacaccc agcaggaccc 5580
ccagcaggtc cgtgagcagg actagtctgg tgtccaaccc acccggcgtg aacagggtga 5640
tcaccaggga ggaattcgag gccttcgtgg cccagcaaca gagacggttc gacgccggcg 5700
cctacatctt cagcagcgac accggccagg gacacctgca gcaaaagagc gtgaggcaga 5760
ccgtgctgag cgaggtggtg ctggagagga ccgagctgga aatcagctac gcccccaggc 5820
tggaccagga gaaggaggaa ctgctcagga agaaactgca gctgaacccc accccagcca 5880
acaggagcag gtaccagagc aggaaggtgg agaacatgaa ggccatcacc gccaggcgga 5940
tcctgcaggg cctgggacac tacctgaagg ccgagggcaa ggtggagtgc tacaggaccc 6000
tgcaccccgt gccactgtac agctccagcg tgaacagggc cttctccagc cccaaggtgg 6060
ccgtggaggc ctgcaacgct atgctgaagg agaacttccc caccgtggcc agctactgca 6120
tcatccccga gtacgacgcc tacctggaca tggtggacgg cgccagctgc tgcctggaca 6180
ccgccagctt ctgccccgcc aagctgagga gcttccccaa gaaacacagc tacctggagc 6240
ccaccatcag gagcgccgtg cccagcgcca tccagaacac cctgcagaac gtgctggccg 6300
ctgccaccaa gaggaactgc aacgtgaccc agatgaggga gctgcccgtg ctggacagcg 6360
ctgccttcaa cgtggagtgc ttcaagaaat acgcctgcaa caacgagtac tgggagacct 6420
tcaaggagaa ccccatcagg ctgaccgaag agaacgtggt gaactacatc accaagctga 6480
agggccccaa ggccgctgcc ctgttcgcta agacccacaa cctgaacatg ctgcaggaca 6540
tcccaatgga caggttcgtg atggacctga agagggacgt gaaggtgaca cccggcacca 6600
agcacaccga ggagaggccc aaggtgcagg tgatccaggc cgctgaccca ctggccaccg 6660
cctacctgtg cggcatccac agggagctgg tgaggcggct gaacgccgtg ctgctgccca 6720
acatccacac cctgttcgac atgagcgccg aggacttcga cgccatcatc gccgagcact 6780
tccagcccgg cgactgcgtg ctggagaccg acatcgccag cttcgacaag agcgaggatg 6840
acgctatggc cctgaccgct ctgatgatcc tggaggacct gggcgtggac gccgagctgc 6900
tcaccctgat cgaggctgcc ttcggcgaga tcagctccat ccacctgccc accaagacca 6960
agttcaagtt cggcgctatg atgaaaagcg gaatgttcct gaccctgttc gtgaacaccg 7020
tgatcaacat tgtgatcgcc agcagggtgc tgcgggagag gctgaccggc agcccctgcg 7080
ctgccttcat cggcgacgac aacatcgtga agggcgtgaa aagcgacaag ctgatggccg 7140
acaggtgcgc cacctggctg aacatggagg tgaagatcat cgacgccgtg gtgggcgaga 7200
aggcccccta cttctgcggc ggattcatcc tgtgcgacag cgtgaccggc accgcctgca 7260
gggtggccga cccccctgaag aggctgttca agctgggcaa gccactggcc gctgacgatg 7320
agcacgacga tgacaggcgg agggccctgc acgaggaaag caccaggtgg aacagggtgg 7380
gcatcctgag cgagctgtgc aaggccgtgg agagcaggta cgagaccgtg ggcaccagca 7440
tcatcgtgat ggctatgacc acactggcca gctccgtcaa gagcttctcc tacctgaggg 7500
gggcccctat aactctctac ggctaacctg aatggactac gacatagtct agtccgccaa 7560
ggccgccacc atggaagatg ccaaaaacat taagaagggc ccagcgccat tctacccact 7620
cgaagacggg accgccggcg agcagctgca caaagccatg aagcgctacg ccctggtgcc 7680
cggcaccatc gcctttaccg acgcacatat cgaggtggac attacctacg ccgagtactt 7740
cgagatgagc gttcggctgg cagaagctat gaagcgctat gggctgaata caaaccatcg 7800
gatcgtggtg tgcagcgaga atagcttgca gttcttcatg cccgtgttgg gtgccctgtt 7860
catcggtgtg gctgtggccc cagctaacga catctacaac gagcgcgagc tgctgaacag 7920
catgggcatc agccagccca ccgtcgtatt cgtgagcaag aaagggctgc aaaagatcct 7980
caacgtgcaa aagaagctac cgatcataca aaagatcatc atcatggata gcaagaccga 8040
ctaccagggc ttccaaagca tgtacacctt cgtgacttcc catttgccac ccggcttcaa 8100
cgagtacgac ttcgtgcccg agagcttcga ccgggacaaa accatcgccc tgatcatgaa 8160
cagtagtggc agtaccggat tgcccaaggg cgtagcccta ccgcaccgca ccgcttgtgt 8220
ccgattcagt catgcccgcg accccatctt cggcaaccag atcatccccg acaccgctat 8280
cctcagcgtg gtgccatttc accacggctt cggcatgttc accacgctgg gctacttgat 8340
ctgcggcttt cgggtcgtgc tcatgtaccg cttcgaggag gagctattct tgcgcagctt 8400
gcaagactat aagattcaat ctgccctgct ggtgcccaca ctatttagct tcttcgctaa 8460

```
gagcactctc atcgacaagt acgacctaag caacttgcac gagatcgcca gcggcggggc  8520
gccgctcagc aaggaggtag gtgaggccgt ggccaaacgc ttccacctac caggcatccg  8580
acagggctac ggcctgacag aaacaaccag cgccattctg atcacccccg aaggggacga  8640
caagcctggc gcagtaggca aggtggtgcc cttcttcgag gctaaggtgg tggacttgga  8700
caccggtaag acactgggtg tgaaccagcg cggcgagctg tgcgtccgtg gccccatgat  8760
catgagcggc tacgttaaca accccgaggc tacaaacgct ctcatcgaca aggacggctg  8820
gctgcacagc ggcgacatcg cctactggga cgaggacgag cacttcttca tcgtggaccg  8880
gctgaagtcc ctgatcaaat acaagggcta ccaggtagcc ccagccgaac tggagagcat  8940
cctgctgcaa caccccaaca tcttcgacgc cggggtcgcc ggcctgcccg acgacgatgc  9000
cggcgagctg cccgccgcag tcgtcgtgct ggaacacggt aaaaccatga ccgagaagga  9060
gatcgtggac tatgtggcca gccaggttac aaccgccaag aagctgcgcg gtggtgttgt  9120
gttcgtggac gaggtgccta aaggactgac cggcaagttg gacgcccgca agatccgcga  9180
gattctcatt aaggccaaga agggcggcaa gatcgccgtg taactcgagc cggaaacgca  9240
atagccgaaa aacaaaaaac aaaaaaaaca aaaaaaaaac caaaaaaaca aaacacatta  9300
aaacagcctg tgggttgatc ccacccacag gcccattggg cgctagcact ctggtatcac  9360
ggtacctttg tgcgcctgtt ttataccccc tcccccaact gtaacttaga agtaacacac  9420
accgatcaac agtcagcgtg gcacaccagc cacgttttga tcaagcactt ctgttacccc  9480
ggactgagta tcaatagact gctcacgcgg ttgaaggaga aagcgttcgt tatccggcca  9540
actacttcga aaaacctagt aacaccgtgg aagttgcaga gtgtttcgct cagcactacc  9600
ccagtgtaga tcaggtcgat gagtcaccgc attccccacg ggcgaccgtg gcggtggctg  9660
cgttggcggc ctgcccatgg ggaaacccat gggacgctct aatacagaca tggtgcgaag  9720
agtctattga gctagttggt agtcctccgg cccctgaatg cggctaatcc taactgcgga  9780
gcacacaccc tcaagccaga gggcagtgtg tcgtaacggg caactctgca gcggaaccga  9840
ctactttggg tgtccgtgtt tcattttatt cctatactgg ctgcttatgg tgacaattga  9900
gagatcgtta ccatatagct attggattgg ccatccggtg actaatagag ctattatata  9960
tccctttgtt gggtttatac cacttagctt gaaagaggtt aaaacattac aattcattgt  10020
taagttgaat acagcaaaat gagcaagatc tacatcgacg agcggagcaa cgccgagatc  10080
gtgtgcgagg ccatcaagac catcggcatc gagggcgcca ccgccgccca gctgaccagg  10140
cagctgaaca tggagaagcg ggaggtgaac aaggccctgt acgacctgca gaggagcgct  10200
atggtgtact ccagcgacga catccctccc cggtggttca tgaccaccga ggccgacaag  10260
cccgacgccg acgctatggc cgacgtgatc atcgacgacg tgagcaggga gaagtccatg  10320
agggaggacc acaagagctt cgacgacgtg atccccgcca agaagatcat cgactggaag  10380
ggcgccaacc ccgtgaccgt gatcaacgag tactgccaga tcaccaggag ggactggagc  10440
ttccggatcg agagcgtggg ccccagcaac agccccacct tctacgcctg cgtggacatc  10500
gacggcaggg tgttcgacaa ggccgacggc aagagcaagc gggacgccaa gaacaacgcc  10560
gccaagctgg ccgtggacaa gctgctgggc tacgtgatca tccggttcta aacgtatgtt  10620
acgtgcaaag gtgattgtca ccccccgaaa gaccatattg tgacacaccc tcagtatcac  10680
gcccaaacat ttacagccgc ggtgtcaaaa accgcgtgga cgtggttaac atccctgctg  10740
ggaggatcag ccgtaattat tataattggc ttggtgctgg ctactattgt ggccatgtac  10800
gtgctgacca accagaaaca taattgaata cagcagcaat tggcaagctg cttacataga  10860
actcgcggcg attggcatgc cgccttaaaa tttttatttt atttttcttt ttcttttccg  10920
aatcggattt tgtttttaat atttcaaaaa aaaaaaaaaa aaaaaaaaaa tctagaaaaa  10980
aaaaaaaaaa aaaaaaaaaa aaaaaaaaaa aaaaaaaaaa aaaaaaaaaa aaaaaaaaaa  11040
aaaaaaaaaa aaaaaaaaaa aaaaaaaaaa aaaaa                            11075

SEQ ID NO: 129          moltype = RNA  length = 10851
FEATURE                 Location/Qualifiers
misc_feature            1..10851
                        note = Synthetic polynucleotide
source                  1..10851
                        mol_type = other RNA
                        organism = synthetic construct
SEQUENCE: 129
atgggcggcg catgagagaa gcccagacca attacctacc caaaatggag aaagttcacg  60
ttgacatcga ggaagacagc ccattcctca gagctttgca gcggagcttc ccgcagtttg  120
aggtagaagc caagcaggtc actgataatg accatgctaa tgccagagcg ttttcgcatc  180
tggcttcaaa actgatcgaa acggaggtgg acccatccga cacgatcctt gacattggaa  240
gtgcgcccgc ccgcagaatg tattctaagc acaagtatca ttgtatctgt ccgatgagat  300
gtgcggaaga tccggacaga ttgtataagt atgcaactaa gctgaagaaa aactgtaagg  360
aaataactga taaggaattg gacaagaaaa tgaaggagct ggccgccgtc atgagcgacc  420
ctgacctgga aactgagact atgtgcctcc acgacgacga gtcgtgtcgc tacgaagggc  480
aagtcgctgt ttaccaggat gtatacgccg tcgacggccc caccagcctg taccaccagg  540
ccaacaaggg cgtgagggtg gcctactgga tcggcttcga caccacaccc ttcatgttca  600
agaacctggc cggcgcctac cccagctaca gcaccaactg ggccgacgag accgtgctga  660
ccgccaggaa catcggcctg tgcagcagcg acgtgatgga gaggagccgg agaggcatga  720
gcatcctgag gaagaaatac ctgaagccca gcaacaacgt gctgttcagc gtgggcagca  780
ccatctacca cgagaagagg gacctgctca ggagctggca cctgcccagc gtgttccacc  840
tgaggggcaa gcagaactac acctgcaggt gcgagaccat cgtgagctgc gacggctacg  900
tggtgaagag gatcgccatc agccccggcc tgtacggcaa gcccagcggc tacgccgcta  960
caatgcacag ggagggcttc ctgtgctgca aggtgaccga caccctgaac ggcgagaggg  1020
tgagcttccc cgtgtgcacc tacgtgcccg ccaccctgtg cgaccagatg accggcatcc  1080
tggccaccga cgtgagcgcc gacgacgccc agaagctgct cgtgggcctg aaccagagga  1140
tcgtggtcaa cggcaggacc cagaggaaca ccaacacaat gaagaactac ctgctgcccg  1200
tggtggccca ggctttcgcc aggtgggcca aggagtacaa ggaggaccag gaagacgaga  1260
ggcccctggg cctgagggac aggcagctgg tgatgggctg ctgctgggcc ttcaggcggc  1320
acaagatcac cagcatctac aagaggcccg acacccagac catcatcaag gtgaacagcg  1380
acttccacag cttcgtgctg cccaggatcg gcagcaacac cctggagatc ggcctgagga  1440
cccggatcag gaagatgctg gaggaacaca aggagcccag cccactgatc accgccgagg  1500
acgtgcagga ggccaagtgc gctgccgacg aggccaagga ggtgagggag gccgaggaac  1560
```

-continued tgagggccgc cctgccaccc ctggctgccg acgtggagga acccaccctg gaagccgacg 1620
tggacctgat gctgcaggag gccggcgccg gaagcgtgga gacacccagg ggcctgatca 1680
aggtgaccag ctacgacggc gaggacaaga tcggcagcta cgccgtgctg agcccacagg 1740
ccgtgctgaa gtccgagaag ctgagctgca tccacccact ggccgagcag gtgatcgtga 1800
tcacccacag cggcaggaag ggcaggtacg ccgtggagcc ctaccacggc aaggtggtcg 1860
tgcccgaggg ccacgccatc cccgtgcagg acttccaggc cctgagcgag agcgccacca 1920
tcgtgtacaa cgagagggag ttcgtgaaca ggtacctgca ccatatcgcc acccacggcg 1980
gagccctgaa caccgacgag gaatactaca agaccgtgaa gcccagcgag cacgacggcg 2040
agtacctgta cgacatcgac aggaagcagt gcgtgaagaa agagctggtg accggcctgg 2100
gactgaccgg cgagctggtg gacccaccct tccacgagtt cgcctacgag agcctgagga 2160
ccagacccgc cgctccctac caggtgccca ccatcggcgt gtacggcgtg cccggcagcg 2220
gaaagagcgg catcatcaag agcgccgtga ccaagaaaga cctggtggtc agcgccaaga 2280
aagagaactg cgccgagatc atcagggacg tgaagaagat gaaaggcctg gacgtgaacg 2340
cgcgcaccgt ggacagcgtg ctgctgaacg gctgcaagca ccccgtggag accctgtaca 2400
tcgacgaggc cttcgcttgc cacgccggca ccctgagggc cctgatcgcc atcatcaggc 2460
ccaagaaagc cgtgctgtgc ggcgacccca agcagtgcgg cttcttcaac atgatgtgcc 2520
tgaaggtgca cttcaaccac gagatctgca cccaggtgtt ccacaagagc atcagcaggc 2580
ggtgcaccaa gagcgtgacc agcgtcgtga gcaccctgtt ctacgacaag aaaatgagga 2640
ccaccaaccc caaggagacc aaaatcgtga tcgacaccac aggcagcacc aagcccaagc 2700
aggacgacct gatcctgacc tgcttcaggg gctgggtgaa gcagctgcag atcgactaca 2760
agggcaacga gatcatgacc gccgctgcca gccagggcct gaccaggaag ggcgtgtacg 2820
ccgtgaggta caaggtgaac gagaacccac tgtacgctcc caccagcgag cacgtgaacg 2880
tgctgctgac caggaccgag gacaggatcg tgtggaagac cctggccggc gacccctgga 2940
tcaagaccct gaccgccaag taccccggca acttcaccgc caccatcgaa gagtggcagg 3000
ccgagcacga cgccatcatg aggcacatcc tggagaggcc cgaccccacc gacgtgttcc 3060
agaacaaggc caacgtgtgc tgggccaagg ccctggtgcc cgtgctgaag accgccggca 3120
tcgacatgac cacagagcag tggaacaccg tggactactt cgagaccgac aaggcccaca 3180
gcgccgagat cgtgctgaac cagctgtgcg tgaggttctt cggcctggac ctggacagcg 3240
gcctgttcag cgcccccacc gtgccactga gcatcaggaa caaccactgg gacaacagcc 3300
ccagcccaaa catgtacggc ctgaacaagg aggtggtcag gcagctgagc aggcggtacc 3360
cacagctgcc cagggccgtg gccaccggca gggtgtacga catgaacacc ggcaccctga 3420
ggaactacga ccccaggatc aacctggtgc ccgtgaacag gcggctgccc cacgccctgg 3480
tgctgcacca caacgagcac ccacagagcg acttcagctc cttcgtgagc aagctgaaag 3540
gcaggaccgt gctggtcgtg ggcgagaagc tgagcgtgcc cggcaagatg gtggactggc 3600
tgagcgacag gcccgaggcc accttccggg ccaggctgga cctcggcatc cccggcgacg 3660
tgcccaagta cgacatcatc ttcgtgaacg tcaggacccc atacaagtac caccattacc 3720
agcagtgcga ggaccacgcc atcaagctga gcatgctgac caagaaggcc tgcctgcacc 3780
tgaaccccgg aggcacctgc gtgagcatcg gctacggcta cgccgacagg gccagcgaga 3840
gcatcattgg cgccatcgcc aggctgttca agttcagcag ggtgtgcaaa cccaagagca 3900
gcctggagga aaccgaggtg ctgttcgtgt tcatcggcta cgaccggaag gccaggaccc 3960
acaaccccta caagctgagc agcaccctga caaacatcta caccggcagc aggctgcacg 4020
aggccggctg cgcccccagc taccacgtgg tcaggggcga tatcgccacc gccaccgagg 4080
gcgtgatcat caacgctgcc aacagcaagg gccagcccgg aggcggagtg tgcggcgccc 4140
tgtacaagaa gttccccgag agcttcgacc tgcagcccat cgaggtgggc aaggccaggc 4200
tggtgaaggg cgccgctaag cacatcatcc acgccgtggg ccccaacttc aacaaggtga 4260
gcgaggtgga aggcgacaag cagctggccg aagcctacga gagcatcgcc aagatcgtga 4320
acgacaataa ctacaagagc gtggccatcc cactgctcag caccggcatc ttcagcggca 4380
acaaggacag gctgacccag agcctgaacc acctgctcac cgccctggac accaccgatg 4440
ccgacgtggc catctactgc agggacaaga agtgggagat gaccctgaag gaggccgtgg 4500
ccaggcggga ggccgtggaa gagatctgca tcagcgacga ctccagcgtg accgagcccg 4560
acgccgagct ggtgagggtg caccccaaga gctccctggc cggcaggaag ggctacagca 4620
ccagcgacgg caagaccttc agctacctgg agggcaccaa gttccaccag gccgctaagg 4680
acatcgccga gatcaacgct atgtggcccg tggccaccga ggccaacgag caggtgtgca 4740
tgtacatcct gggcgagagc atgtccagca tcaggagcaa gtgccccgtg gaggaaagcg 4800
aggccagcac accacccagc accctgccct gcctgtgcat ccacgctatg acacccgaga 4860
gggtgcagcg gctgaaggcc agcaggcccg agcagatcac cgtgtgcagc tccttcccac 4920
tgcccaagta caggatcacc ggcgtgcaga agatccagtg cagccagccc atcctgttca 4980
gcccaaaggt gcccgcctac atccacccca ggaagtacct ggtggagacc ccacccgtgg 5040
acgagacacc cgagccaagc gccgagaacc agagcaccga gggcacaccc gagcagccac 5100
ccctgatcac cgaggacgag acaaggaccc ggaccccaga gcccatcatt atcgaggaag 5160
aggaagagga cagcatcagc ctgctgagcg acggccccac ccaccaggtg ctgcaggtgg 5220
aggccgacat ccacggccca cccagcgtgt ccagctccag ctggagcatc ccacacgcca 5280
gcgacttcga cgtggacagc ctgagcatcc tggacaccct ggagggcgcc agcgtgacct 5340
ccggcgccac cagcgccgag accaacagct acttcgccaa gagcatggag ttcctggcca 5400
ggcccgtgcc agctcccagg accgtgttca ggaacccacc ccacccagct cccaggacca 5460
ggaccccaag cctggctccc agcagggcct gcagcaggac cagcctggtg agcaccccac 5520
ccggcgtgaa cagggtgatc accagggagg aactggaggc cctgacaccc agcaggaccc 5580
ccagcaggtc cgtgagcagg actagtctgg tgtccaaccc acccggcgtg aacagggtga 5640
tcaccaggga ggaattcgag gccttcgtgg cccagcaaca gagacggttc gacgccggcg 5700
cctacatctt cagcagcgac accggccagg gacacctgca gcaaaagagc gtgaggcaga 5760
ccgtgctgag cgaggtggtg ctggagagga ccgagctgga aatcagctac gcccccaggc 5820
tggaccagga gaaggaggaa ctgctcagga agaaactgca gctgaacccc accccagcca 5880
acaggagcag gtaccagagc aggaaggtgg agaacatgaa ggccatcacc gccaggcgga 5940
tcctgcaggg cctgggacac tacctgaagg ccgagggcaa ggtggagtgc tacaggaccc 6000
tgcaccccgt gccactgtac agctccagcg tgaacagggc cttctccagc cccaaggtgg 6060
ccgtggaggc ctgcaacgct atgctgaagg agaacttccc caccgtggcc agctactgca 6120
tcatccccga gtacgacgcc tacctggaca tggtggacgg cgccagctgc tgcctggaca 6180
ccgccagctt ctgccccgcc aagctgagga gcttccccaa gaaacacagc tacctggagc 6240
ccaccatcag gagcgccgtg cccagcgcca tccagaacac cctgcagaac gtgctggccg 6300

-continued

```
ctgccaccaa gaggaactgc aacgtgaccc agatgaggga gctgcccgtg ctggacagcg  6360
ctgccttcaa cgtggagtgc ttcaagaaat acgcctgcaa caacgagtac tgggagacct  6420
tcaaggagaa ccccatcagg ctgaccgaag agaacgtggt gaactacatc accaagctga  6480
agggccccaa ggccgctgcc ctgttcgcta agacccacaa cctgaacatg ctgcaggaca  6540
tcccaatgga caggttcgtg atggacctga agagggacgt gaaggtgaca cccggcacca  6600
agcacaccga ggagaggccc aaggtgcagg tgatccaggc cgctgaccca ctggccaccg  6660
cctacctgtg cggcatccac agggagctgg tgaggcggct gaacgccgtg ctgctgccca  6720
acatccacac cctgttcgac atgagcgccg aggacttcga cgccatcatc gccgagcact  6780
tccagcccgg cgactgcgtg ctggagaccg acatcgccag cttcgacaag agcgaggatg  6840
acgctatggc cctgaccgct ctgatgatcc tggaggacct gggcgtggac gccgagctgc  6900
tcaccctgat cgaggctgcc ttcggcgaga tcagctccat ccacctgccc accaagacca  6960
agttcaagtt cggcgctatg atgaaaagcg gaatgttcct gaccctgttc gtgaacaccg  7020
tgatcaacat tgtgatcgcc agcagggtgc tgcgggagag gctgaccggc agcccctgcg  7080
ctgccttcat cggcgacgac aacatcgtga agggcgtgaa aagcgacaag ctgatggccg  7140
acaggtgcgc cacctggctg aacatggagg tgaagatcat cgacgccgtg gtgggcgaga  7200
aggcccccta cttctgcggc ggattcatcc tgtgcgacag cgtgaccggc accgcctgca  7260
gggtggccga cccccctgaag aggctgttca agctgggcaa gccactggcc gctgacgatg  7320
agcacgacga tgacaggcgg agggccctgc acgaggaaag caccaggtgg aacagggtgg  7380
gcatcctgag cgagctgtgc aaggccgtgg agagcaggta cgagaccgtg ggcaccagca  7440
tcatcgtgat ggctatgacc acactggcca gctccgtcaa gagcttctcc tacctgaggg  7500
gggcccctat aactctctac ggctaacctg aatggactac gacatagtct agtccgccaa  7560
ggccgccacc atggaagatg ccaaaaacat taagaagggc ccagcgccat tctacccact  7620
cgaagacggg accgccggcg agcagctgca caaagccatg aagcgctacg ccctggtgcc  7680
cggcaccatc gcctttaccg acgcacatat cgaggtggac attacctacg ccgagtactt  7740
cgagatgagc gttcggctgg cagaagctat gaagcgctat gggctgaata caaaccatcg  7800
gatcgtggtg tgcagcgaga atagcttgca gttcttcatg cccgtgttgg gtgccctgtt  7860
catcggtgtg gctgtggccc cagctaacga catctacaac gagcgcgagc tgctgaacag  7920
catgggcatc agccagccca ccgtcgtatt cgtgagcaag aaagggctgc aaaagatcct  7980
caacgtgcaa aagaagctac cgatcataca aaagatcatc atcatggata gcaagaccga  8040
ctaccagggc ttccaaagca tgtacacctt cgtgacttcc catttgccac ccggcttcaa  8100
cgagtacgac ttcgtgcccg agagcttcga ccgggacaaa accatcgccc tgatcatgaa  8160
cagtagtggc agtaccggat tgcccaaggg cgtagcccta ccgcaccgca ccgcttgtgt  8220
ccgattcagt catgcccgcg accccatctt cggcaaccag atcatccccg acaccgctat  8280
cctcagcgtg gtgccatttc accacggctt cggcatgttc accacgctgg gctacttgat  8340
ctgcggcttt cgggtcgtgc tcatgtaccg cttcgaggag gagctattct tgcgcagctt  8400
gcaagactat aagattcaat ctgccctgct ggtgcccaca ctatttagct tcttcgctaa  8460
gagcactctc atcgacaagt acgacctaag caacttgcac gagatcgcca gcggcggggc  8520
gccgctcagc aaggaggtag gtgaggccgt ggccaaacgc ttccacctac caggcatccg  8580
acagggctac ggcctgacag aaacaaccag cgccattctg atcacccccg aaggggacga  8640
caagcctggc gcagtaggca aggtggtgcc cttcttcgag gctaaggtgg tggacttgga  8700
caccggtaag acactgggtg tgaaccagcg cggcgagctg tgcgtccgtg gccccatgat  8760
catgagcggc tacgttaaca accccgaggc tacaaacgct ctcatcgaca aggacggctg  8820
gctgcacagc ggcgacatcg cctactggga cgaggacgag cacttcttca tcgtggaccg  8880
gctgaagtcc ctgatcaaat acaagggcta ccaggtagcc ccagccgaac tggagagcat  8940
cctgctgcaa caccccaaca tcttcgacgc cggggtcgcc ggcctgcccg acgacgatgc  9000
cggcgagctg cccgccgcag tcgtcgtgct ggaacacggt aaaaccatga ccgagaagga  9060
gatcgtggac tatgtggcca gccaggttac aaccgccaag aagctgcgcg gtggtgttgt  9120
gttcgtggac gaggtgccta aaggactgac cggcaagttg gacgcccgca agatccgcga  9180
gattctcatt aaggccaaga agggcggcaa gatcgccgtg taactcgagc cggaaacgca  9240
atagccgaaa aacaaaaaac aaaaaaaaca aaaaaaaaac caaaaaaaca aaacacatta  9300
aaacagcctg tgggttgatc ccacccacag gcccattggg cgctagcact ctggtatcac  9360
ggtacctttg tgcgcctgtt ttatacccc tcccccaact gtaacttaga agtaacacac  9420
accgatcaac agtcagcgtg gcacaccagc cacgttttga tcaagcactt ctgttacccc  9480
ggactgagta tcaatagact gctcacgcgg ttgaaggaga aagcgttcgt tatccggcca  9540
actacttcga aaaacctagt aacaccgtgg aagttgcaga gtgtttcgct cagcactacc  9600
ccagtgtaga tcaggtcgat gagtcaccgc attccccacg ggcgaccgtg gcggtggctg  9660
cgttggcggc ctgcccatgg ggaaacccat gggacgctct aatacagaca tggtgcgaag  9720
agtctattga gctagttggt agtcctccgg cccctgaatg cggctaatcc taactgcgga  9780
gcacacaccc tcaagccaga gggcagtgtg tcgtaacggg caactctgca gcggaaccga  9840
ctactttggg tgtccgtgtt tcattttatt cctatactgg ctgcttatgg tgacaattga  9900
gagatcgtta ccatatagct attggattgg ccatccggtg actaatagag ctattatata  9960
tccctttgtt gggtttatac cacttagctt gaaagaggtt aaaacattac aattcattgt  10020
taagttgaat acagcaaaat gagcaagatc tacatcgacg agcggagcaa cgccgagatc  10080
gtgtgcgagg ccatcaagac catcggcatc gagggcgcca ccgccgccca gctgaccagg  10140
cagctgaaca tggagaagcg ggaggtgaac aaggccctgt acgacctgca gaggagcgct  10200
atggtgtact ccagcgacga catccctccc cggtggttca tgaccaccga ggccgacaag  10260
cccgacgccg acgctatggc cgacgtgatc atcgacgacg tgagcaggga gaagtccatg  10320
agggaggacc acaagagctt cgacgacgtg atccccgcca agaagatcat cgactggaag  10380
ggcgccaacc ccgtgaccgt gatcaacgag tactgccaga tcaccaggag ggactggagc  10440
ttccggatcg agagcgtggg ccccagcaac agccccacct tctacgcctg cgtggacatc  10500
gacggcaggg tgttcgacaa ggccgacggc aagagcaagc gggacgccaa gaacaacgcc  10560
gccaagctgg ccgtggacaa gctgctgggc tacgtgatca tccggttcta aacaattggc  10620
aagctgctta catagaactc gcggcgattg gcatgccgcc ttaaaatttt tattttattt  10680
tttcttttct tttccgaatc ggattttgtt tttaatattt caaaaaaaaa aaaaaaaaaa  10740
aaaaaatcta gaaaaaaaaa aaaaaaaaaa aaaaaaaaaa aaaaaaaaaa aaaaaaaaaa  10800
aaaaaaaaaa aaaaaaaaaa aaaaaaaaaa aaaaaaaaaa aaaaaaaaaa a           10851
```

CORONAVIRUS VACCINE COMPOSITIONS AND METHODS

CROSS-REFERENCES TO RELATED APPLICATIONS

This application claims the benefit of U.S. Provisional Application No. 62/987,191, filed Mar. 9, 2020 and U.S. Provisional Application No. 63/073,900, filed Sep. 2, 2020.

REFERENCE TO A SEQUENCE LISTING

The instant application contains a Sequence Listing which has been submitted electronically in ASCII format and is hereby incorporated by reference in its entirety. Said ASCII copy, created on Mar. 8, 2021 is named 049386-538001US_SequenceListing_ST25.txt and is 481,150 bytes in size.

TECHNICAL FIELD

The present disclosure relates generally to inducing immune responses against infectious agents and tumor antigens and more specifically to self-transcribing and replicating RNA for antigen expression.

BACKGROUND

Infectious diseases and cancer represent significant burdens on health worldwide. According to the World Health Organization (WHO), lower respiratory tract infection was the deadliest infectious disease worldwide in 2016, causing approximately 3 million deaths. The impact of infectious diseases is illustrated by the coronavirus disease 2019 (COVID-19) pandemic caused by severe acute respiratory syndrome-coronavirus-2 (SARS-CoV-2). SARS-CoV-2 is a novel coronavirus that was first identified in December 2019 in Wuhan, China and that has caused more than 20 million confirmed infections with more than 700,000 deaths worldwide as of August 2020. Current control measures to curb the rapid worldwide spread of SARS-CoV-2, such as national lockdowns, closure of work places and schools, and reduction of international travel are threatening to result in a global economic recession to an extent not seen since the Great Depression.

Cancer is the second leading cause of death globally, accounting for approximately 9.6 million deaths worldwide in 2018. Cancer is a large group of diseases that can affect almost any organ or tissue in the body. Cancer burden continues to grow globally, exerting physical, emotional, and financial strains on patients and health care providers.

Self-replicating ribonucleic acids (RNAs), e.g., derived from viral replicons, are useful for expression of proteins, such as heterologous proteins, for a variety of purposes, such as expression of therapeutic proteins and expression of antigens for vaccines. A desirable property of such replicons is the ability for sustained expression of the protein.

Few treatments for infections caused by viruses and eukaryotic organisms are available, and resistance to antibiotics for the treatment of bacterial infections is increasing. In addition, rapid responses, including rapid vaccine development, are required to effectively control emerging infectious diseases and pandemics. Moreover, many cancer treatments include costly and painful surgeries and chemotherapies that are often unsuccessful or only modestly prolong life despite serious side effects. Thus, there exists a need for the prevention and/or treatment of infectious diseases and cancer.

SUMMARY

In one aspect, the present disclosure provides a nucleic acid molecule comprising (i) a first polynucleotide encoding one or more viral replication proteins, wherein the first polynucleotide is codon-optimized as compared to a wild-type polynucleotide encoding the one or more viral replication proteins; and (ii) a second polynucleotide comprising a first transgene encoding a first antigenic protein or a fragment thereof, wherein the first antigenic protein is a coronavirus protein.

In some embodiments, the one or more viral replication proteins are alphavirus proteins or rubivirus proteins.

In some embodiments, the alphavirus proteins are from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), Buggy Creek Virus (BCRV), or any combination thereof.

In some embodiments, the first polynucleotide encodes a polyprotein comprising an alphavirus nsP1 protein, an alphavirus nsP2 protein, an alphavirus nsP3 protein, an alphavirus nsP4 protein, or any combination thereof.

In some embodiments, the first polynucleotide encodes a polyprotein comprising an alphavirus nsP1 protein, an alphavirus nsP2 protein, an alphavirus nsP3 protein, or any combination thereof, and an alphavirus nsP4 protein.

In some embodiments, the nucleic acid molecule further comprises a first intergenic region between a sequence encoding the polyprotein comprising an alphavirus nsP1 protein, an alphavirus nsP2 protein, an alphavirus nsP3 protein, or any combination thereof, and a sequence encoding an alphavirus nsP4 protein.

In some embodiments, the first intergenic region comprises an alphavirus sequence.

In some embodiments, the first polynucleotide comprises a sequence having at least 80% identity to a sequence of SEQ ID NO:72.

In some embodiments, the nucleic acid molecule further comprises a 5' untranslated region (UTR).

In some embodiments, the 5' UTR comprises a viral 5' UTR, a non-viral 5' UTR, or a combination of viral and non-viral 5' UTR sequences.

In some embodiments, the 5' UTR comprises an alphavirus 5' UTR.

In some embodiments, the alphavirus 5' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 5' UTR sequence.

In some embodiments, the 5' UTR comprises a sequence of SEQ ID NO:73, SEQ ID NO:74, or SEQ ID NO:75.

In some embodiments, the nucleic acid molecule further comprises a 3' untranslated region (UTR).

In some embodiments, the 3' UTR comprises a viral 3' UTR, a non-viral 3' UTR, or a combination of viral and non-viral 3' UTR sequences. In some embodiments, the 3' UTR comprises an alphavirus 3' UTR.

In some embodiments, the alphavirus 3' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 3' UTR sequence.

In some embodiments, the 3' UTR comprises a poly-A sequence.

In some embodiments, the 3' UTR comprises a sequence of SEQ ID NO:76.

In some embodiments, the antigenic protein is a SARS-CoV-2 protein.

In some embodiments, the antigenic protein is a SARS-CoV-2 spike glycoprotein.

In some embodiments, the SARS-CoV-2 spike glycoprotein is a wild-type SARS-CoV-2 spike glycoprotein having an amino acid sequence of SEQ ID NO: 123.

In some embodiments, the second polynucleotide comprises a sequence having at least 85% identity to a sequence of SEQ ID NO:121 or SEQ ID NO:122.

In some embodiments, the second polynucleotide comprises at least two transgenes.

In some embodiments, a second transgene encodes a second antigenic protein or a fragment thereof or an immunomodulatory protein.

In some embodiments, the second polynucleotide further comprises a sequence encoding a 2A peptide, an internal ribosomal entry site (IRES), or a combination thereof, located between transgenes.

In some embodiments, the immunomodulatory protein is a cytokine, a chemokine, or an interleukin.

In some embodiments, the second transgene encodes a second coronavirus protein.

In some embodiments, the first polynucleotide is located 5' of the second polynucleotide.

In some embodiments, the nucleic acid molecule further comprises a second intergenic region located between the first polynucleotide and the second polynucleotide.

In some embodiments, the second intergenic region comprises a sequence having at least 85% identity to a sequence of SEQ ID NO:77.

In some embodiments, the nucleic acid molecule is (a) a DNA molecule; or (b) an RNA molecule, wherein T is substituted with U.

In some embodiments, the DNA molecule further comprises a promoter.

In some embodiments, the promoter is located 5' of the 5'UTR.

In some embodiments, the promoter is a T7 promoter, a T3 promoter, or an SP6 promoter.

In some embodiments, the RNA molecule is a self-replicating RNA molecule.

In some embodiments, the RNA molecule further comprises a 5' cap.

In some embodiments, the 5' cap has a Cap 1 structure, a Cap 1 ($^{m6}$A) structure, a Cap 2 structure, a Cap 0 structure, or any combination thereof.

In another aspect, the disclosure provides a nucleic acid molecule comprising (a) a sequence of SEQ ID NO:124;

(b) a sequence of SEQ ID NO:124, wherein T is substituted with U;

(c) a sequence of SEQ ID NO:125; or (d) a sequence of SEQ ID NO:125, wherein T is substituted with U.

In some embodiments, the nucleic acid molecule is an RNA molecule.

In some embodiments, the nucleic acid molecule further comprises a 5' cap having a Cap 1 structure.

In yet another aspect the disclosure provides a nucleic acid molecule comprising:

(i) a first polynucleotide comprising a sequence having at least 80% identity to a sequence of SEQ ID NO:72; and (ii) a second polynucleotide comprising a first transgene encoding a first antigenic protein or a fragment thereof, wherein the first antigenic protein is a coronavirus protein.

In some embodiments, the nucleic acid molecule further comprises a 5' untranslated region (UTR).

In some embodiments, the 5' UTR comprises a viral 5' UTR, a non-viral 5' UTR, or a combination of viral and non-viral 5' UTR sequences.

In some embodiments, the 5' UTR comprises an alphavirus 5' UTR.

In some embodiments, the alphavirus 5' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 5' UTR sequence.

In some embodiments, the 5' UTR comprises a sequence of SEQ ID NO:73, SEQ ID NO:74, or SEQ ID NO:75.

In some embodiments, the nucleic acid molecule further comprises a 3' untranslated region (UTR).

In some embodiments, the 3' UTR comprises a viral 3' UTR, a non-viral 3' UTR, or a combination of viral and non-viral 3' UTR sequences.

In some embodiments, the 3' UTR comprises an alphavirus 3' UTR.

In some embodiments, the alphavirus 3' UTR comprises a Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV) 3' UTR sequence.

In some embodiments, the 3' UTR comprises a poly-A sequence.

In some embodiments, the 3' UTR comprises a sequence of SEQ ID NO:76.

In some embodiments, the antigenic protein is a SARS-CoV-2 protein.

In some embodiments, the antigenic protein is a SARS-CoV-2 spike glycoprotein.

In some embodiments, the SARS-CoV-2 spike glycoprotein is a wild-type SARS-CoV-2 spike glycoprotein having an amino acid sequence of SEQ ID NO: 123.

In some embodiments, the second polynucleotide comprises a sequence having at least 85% identity to a sequence of SEQ ID NO:121 or SEQ ID NO:122.

In some embodiments, the second polynucleotide comprises at least two transgenes.

In some embodiments, a second transgene encodes a second antigenic protein or a fragment thereof or an immunomodulatory protein.

In some embodiments, the second polynucleotide further comprises a sequence encoding a 2A peptide, an internal ribosomal entry site (IRES), or a combination thereof, located between transgenes.

In some embodiments, the immunomodulatory protein is a cytokine, a chemokine, or an interleukin.

In some embodiments, the second transgene encodes a second coronavirus protein.

In some embodiments, the first polynucleotide is located 5' of the second polynucleotide.

In some embodiments, the nucleic acid molecule further comprises a second intergenic region located between the first polynucleotide and the second polynucleotide.

In some embodiments, the second intergenic region comprises a sequence having at least 85% identity to a sequence of SEQ ID NO:77.

In some embodiments, the nucleic acid molecule is (a) a DNA molecule; or (b) an RNA molecule, wherein T is substituted with U.

In some embodiments, the DNA molecule further comprises a promoter.

In some embodiments, the promoter is located 5' of the 5'UTR.

In some embodiments, the promoter is a T7 promoter, a T3 promoter, or an SP6 promoter.

In some embodiments, the RNA molecule is a self-replicating RNA molecule.

In some embodiments, the RNA molecule further comprises a 5' cap.

In some embodiments, the 5' cap has a Cap 1 structure, a Cap 1 ($^{m6}$A) structure, a Cap 2 structure, a Cap 0 structure, or any combination thereof.

In yet another aspect, the disclosure provides a composition comprising any of the nucleic acid molecules provided herein. In some embodiments, the composition further comprises a lipid.

In some embodiments, the lipid comprises an ionizable cationic lipid.

In some embodiments, the ionizable cationic lipid has a structure of

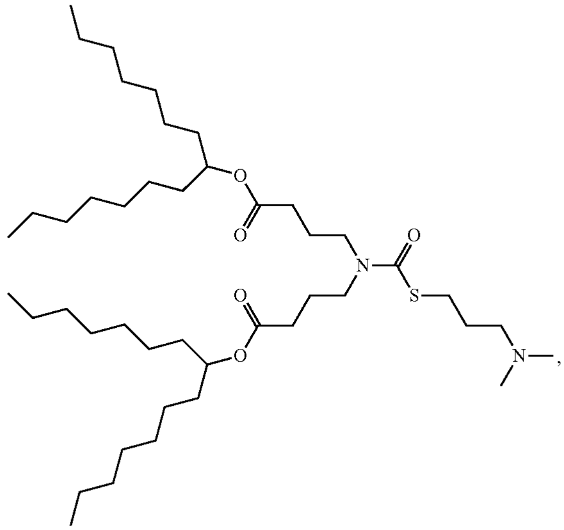

,

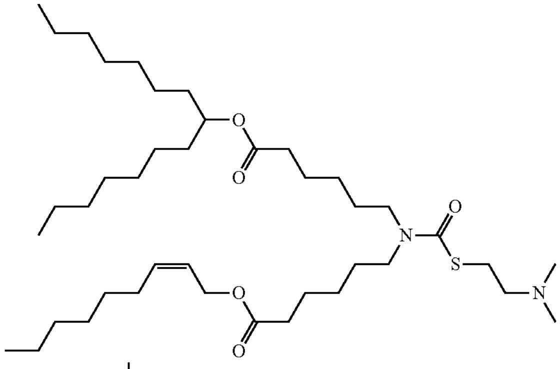

,

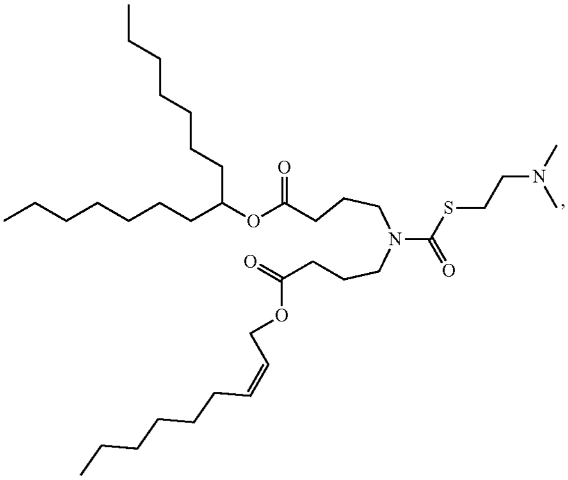

, or a pharmaceutically acceptable salt thereof.

In yet another aspect, the disclosure provides a composition comprising any of the nucleic acid molecules described herein and a lipid formulation.

In some embodiments, the lipid formulation comprises an ionizable cationic lipid.

In some embodiments, the ionizable cationic lipid has a structure of

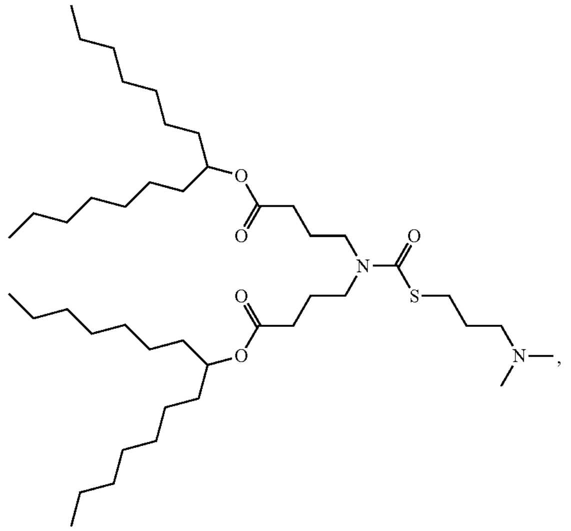

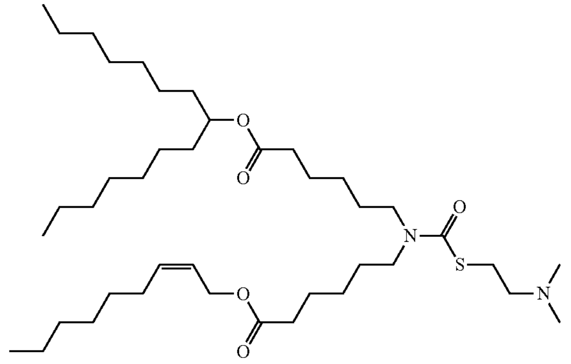

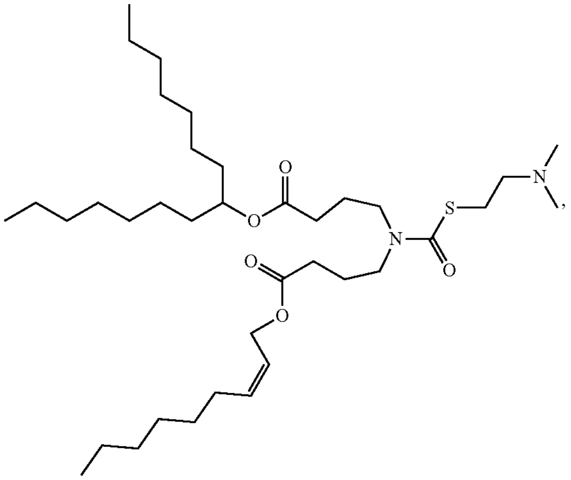

or a pharmaceutically acceptable salt thereof.

In some embodiments, the lipid formulation is selected from a lipoplex, a liposome, a lipid nanoparticle, a polymer-based carrier, an exosome, a lamellar body, a micelle, and an emulsion.

In some embodiments, the lipid formulation is a liposome selected from a cationic liposome, a nanoliposome, a proteoliposome, a unilamellar liposome, a multilamellar liposome, a ceramide-containing nanoliposome, and a multivesicular liposome.

In some embodiments, the lipid formulation is a lipid nanoparticle.

In some embodiments, the lipid nanoparticle has a size of less than about 200 nm. In some embodiments, the lipid nanoparticle has a size of less than about 150 nm. In some embodiments, the lipid nanoparticle has a size of less than about 100 nm. In some embodiments, the lipid nanoparticle has a size of about 55 nm to about 90 nm.

In some embodiments, the lipid formulation comprises one or more cationic lipids.

In some embodiments, the one or more cationic lipids is selected from 5-carboxyspermylglycinedioctadecylamide (DOGS), 2,3-dioleyloxy-N-[2(spermine-carboxamido) ethyl]-N,N-dimethyl-1-propanaminium (DOSPA), 1,2-Dioleoyl-3-Dimethylammonium-Propane (DODAP), 1,2-Dioleoyl-3-Trimethylammonium-Propane (DOTAP), 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA), N-dioleyl-N,N-dimethylammonium chloride (DODAC), N,N-distearyl-N,N-dimethylammonium bromide (DDAB), N-(1,2-dimyristyloxyprop-3-yl)-N,N-dimethyl-N-hydroxyethyl ammonium bromide (DMRIE), 3-dimethylamino-2-(cholest-5-en-3-beta-oxybutan-4-oxy)-1-(cis,cis-9,12-oc-tadecadienoxy)propane (CLinDMA), 2-[5'-(cholest-5-en-3-beta-oxy)-3'-oxapentoxy)-3-dimethy 1-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), and 2,2-dilinoleyl-4-dimethylaminoethyl-[1,3]-dioxolane or (DLin-K-XTC2-DMA).

In some embodiments, the lipid formulation comprises an ionizable cationic lipid.

In some embodiments, the ionizable cationic lipid has a structure of Formula I.

(I)

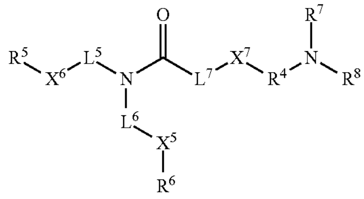

or a pharmaceutically acceptable salt or solvate thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl; $L^5$ and $L^6$ are each independently selected from the group consisting of a linear $C_1$-$C_{20}$ alkyl and $C_2$-$C_{20}$ alkenyl; $X^5$ is —C(O)O—, whereby —C(O)O—$R^6$ is formed or —OC(O)— whereby —OC(O)—$R^6$ is formed; $X^6$ is —C(O)O— whereby —C(O)O—$R^5$ is formed or —OC(O)— whereby —OC(O)—$R^5$ is formed; $X^7$ is S or O; $L^7$ is absent or lower alkyl; $R^4$ is a linear or branched $C_1$-$C_6$ alkyl; and $R^7$ and $R^8$ are each independently selected from the group consisting of a hydrogen and a linear or branched $C_1$-$C_6$ alkyl.

In some embodiments, the ionizable cationic lipid is selected from
ATX-001
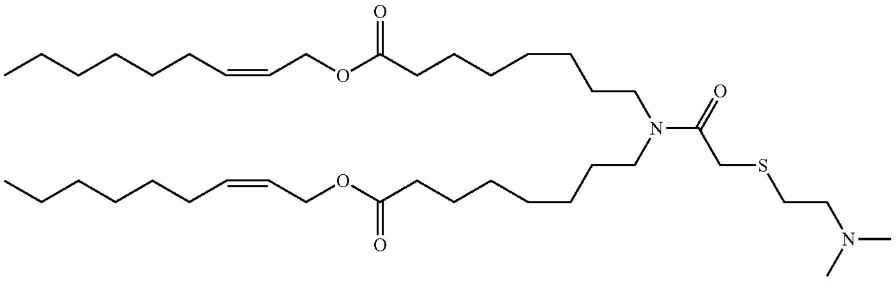
ATX-002
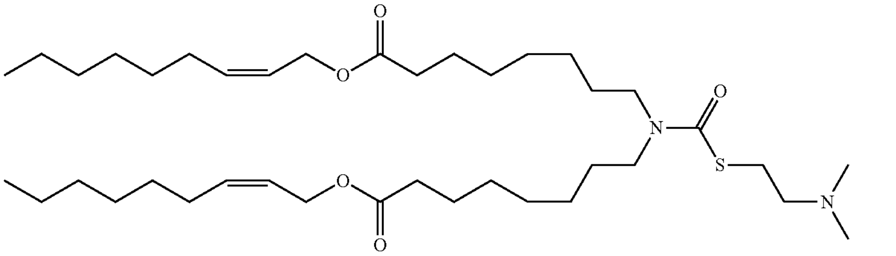
ATX-003
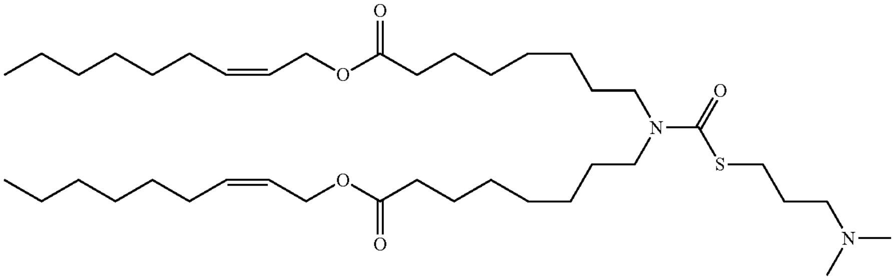
ATX-004
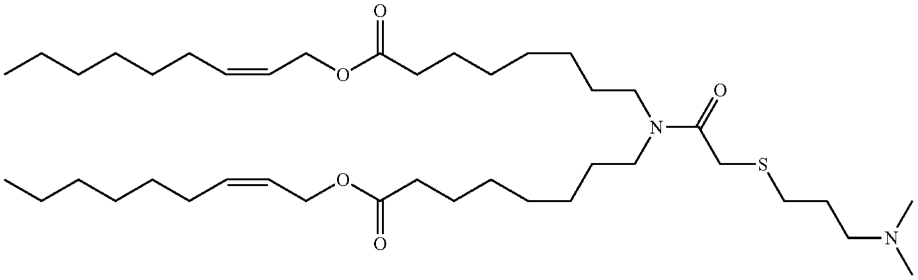
ATX-005
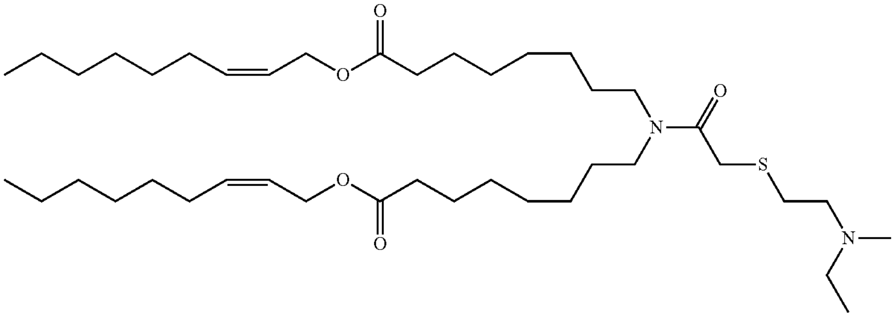

-continued
ATX-006
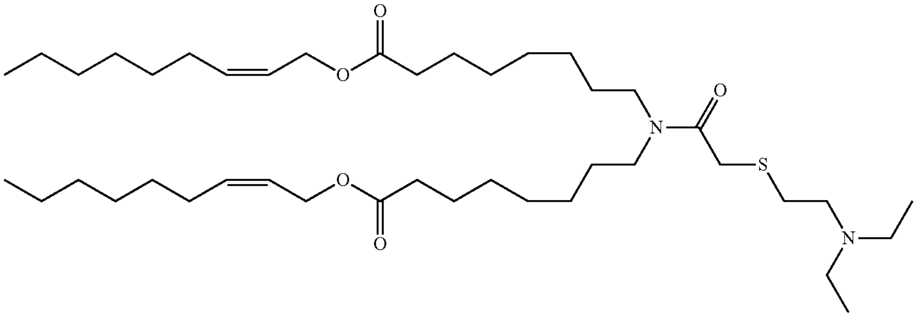
ATX-007
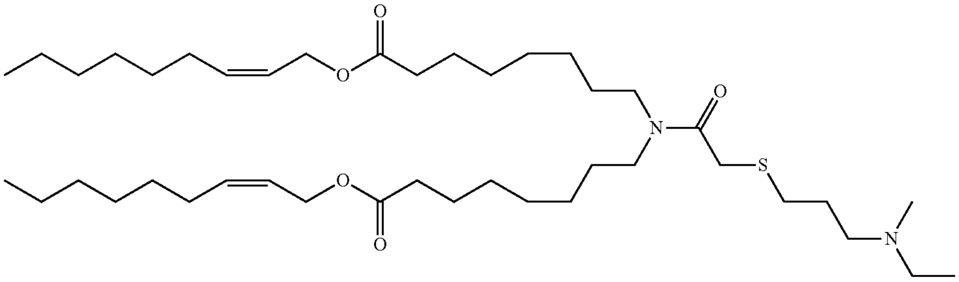
ATX-008
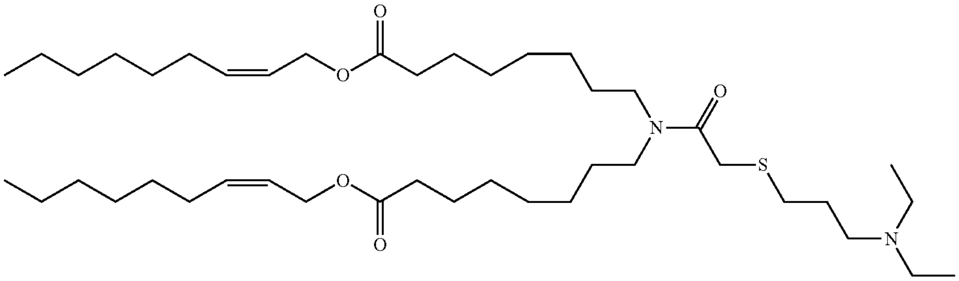
ATX-009
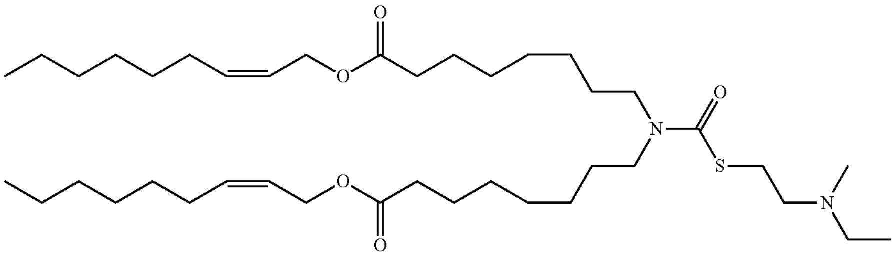
ATX-010
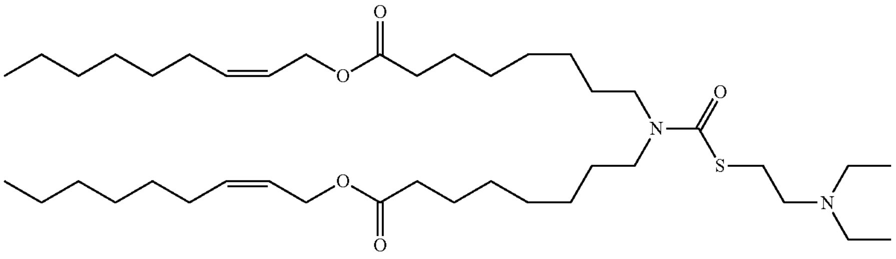

-continued
ATX-011
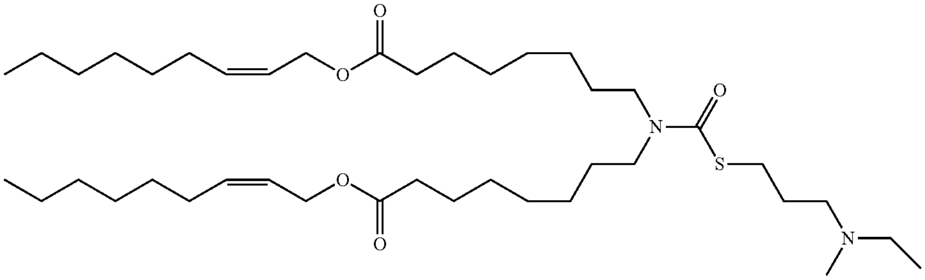
ATX-012
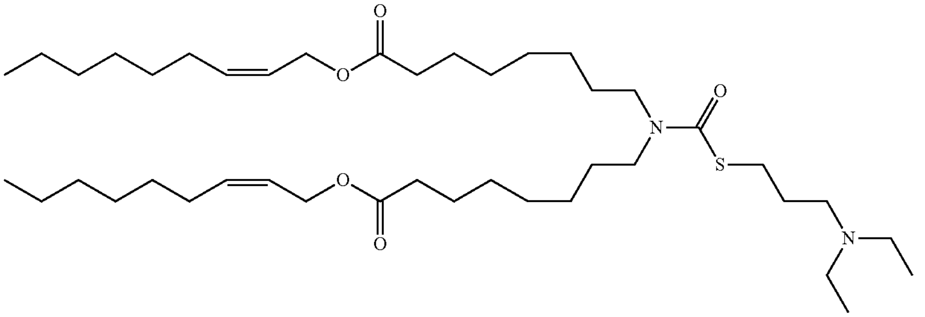
ATX-013
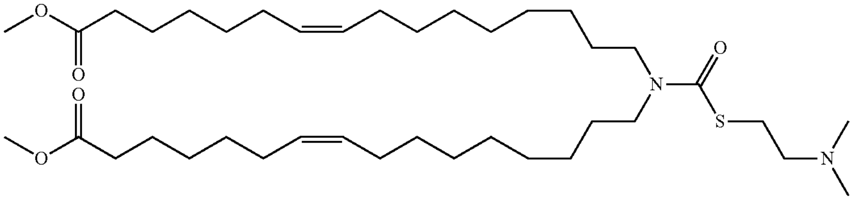
ATX-014
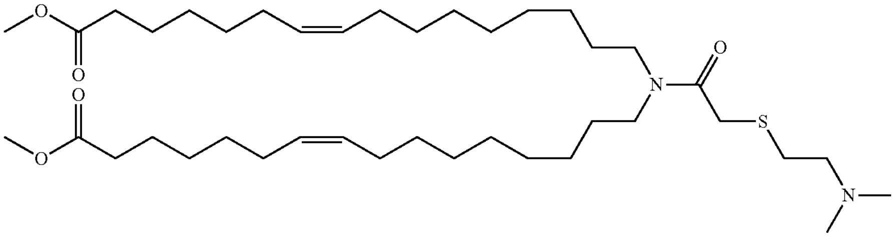
ATX-015
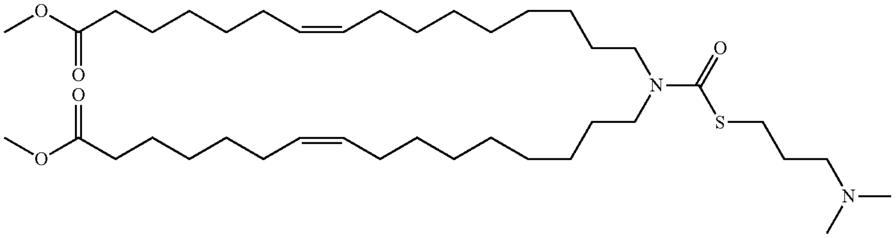
ATX-016
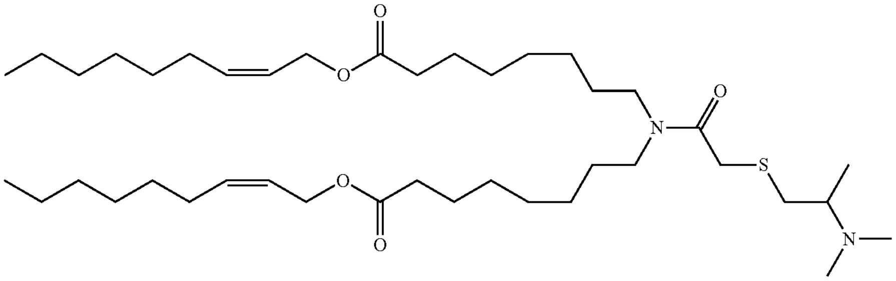

-continued
ATX-018
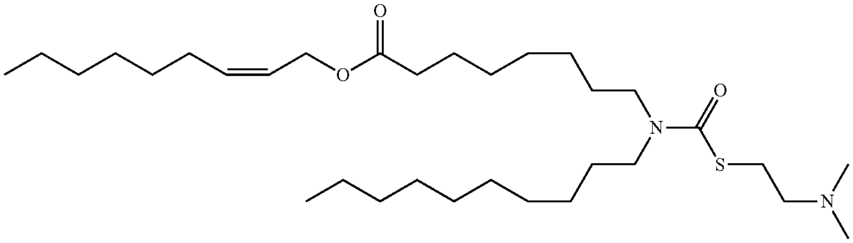
ATX-019
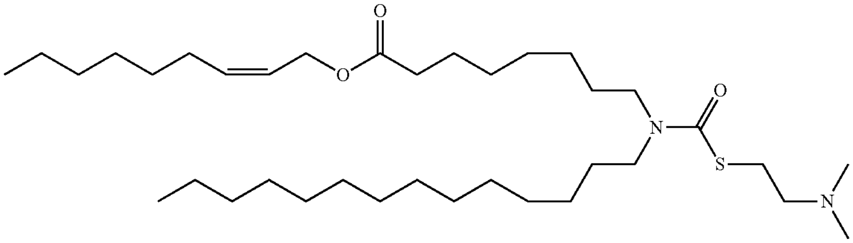
ATX-020
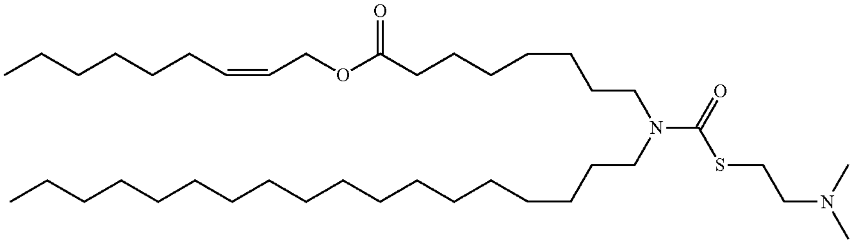
ATX-021
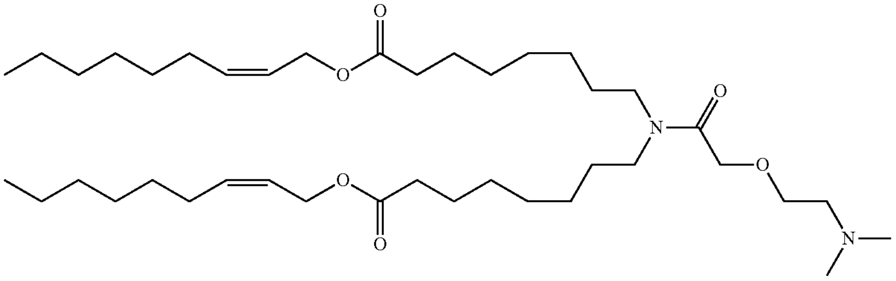
ATX-022
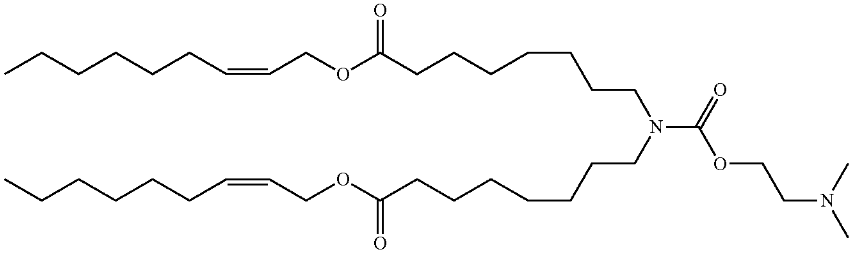
ATX-023
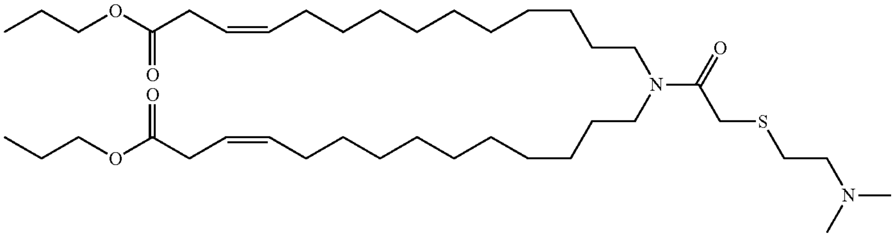

-continued
ATX-024
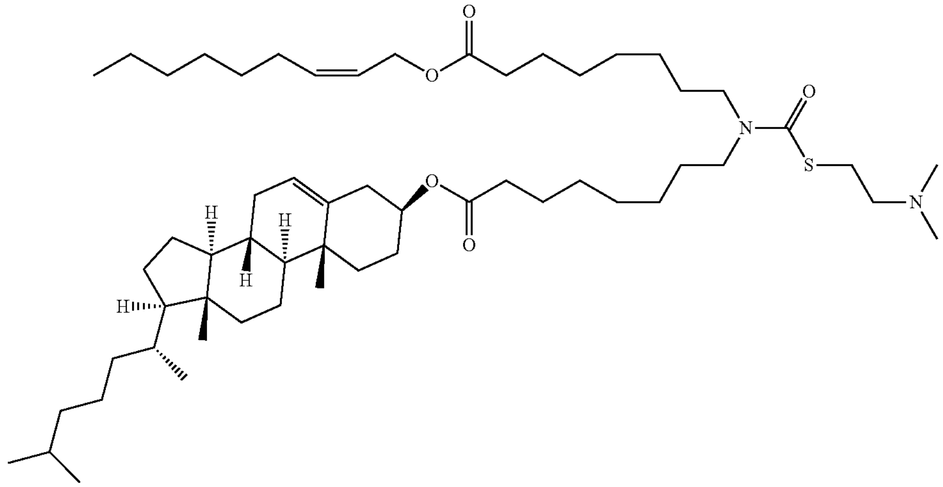
ATX-025
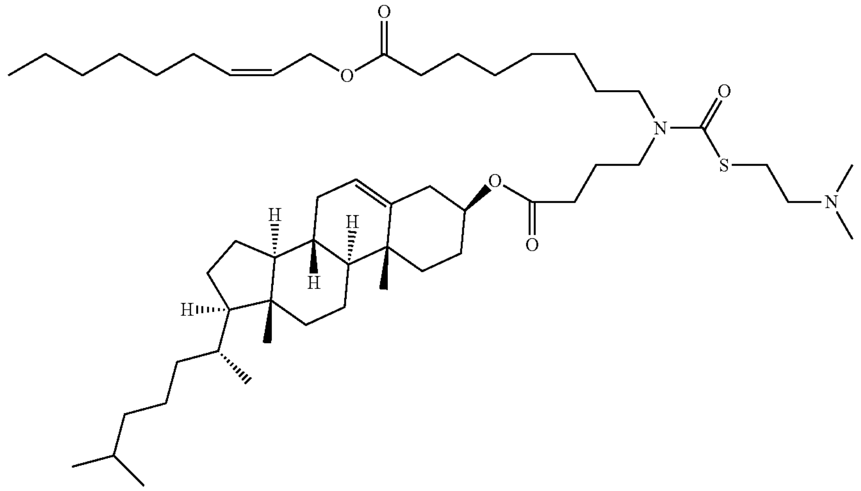
ATX-026
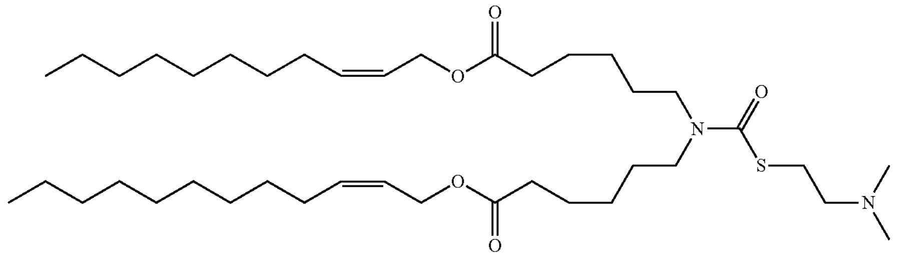
ATX-027
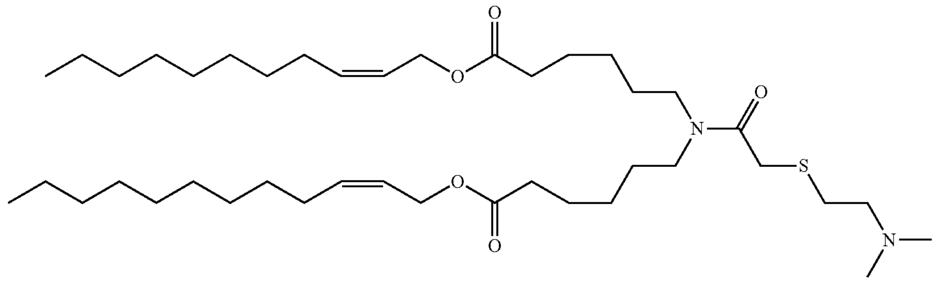

-continued
ATX-028
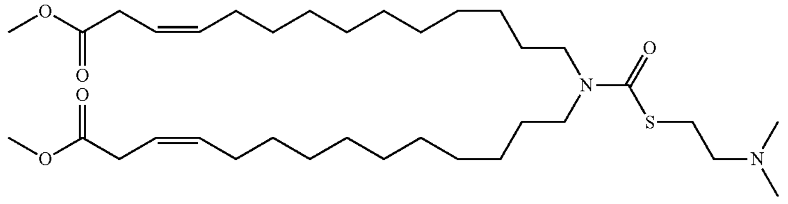
ATX-029
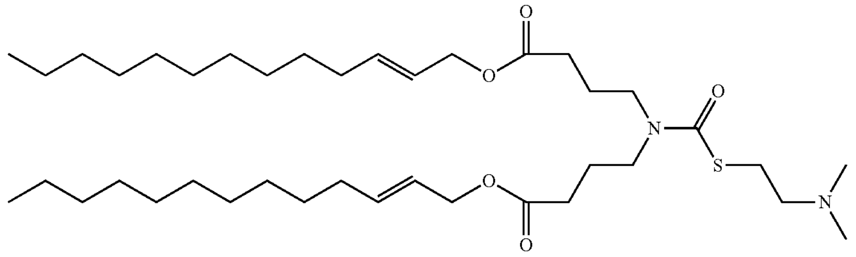
ATX-030
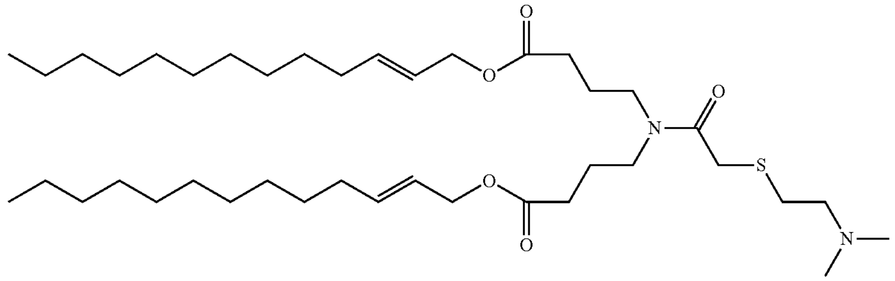
ATX-031
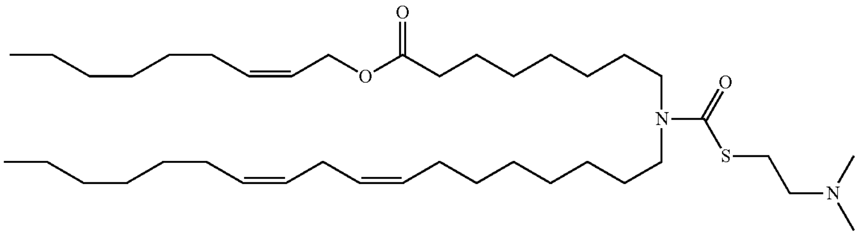
ATX-032
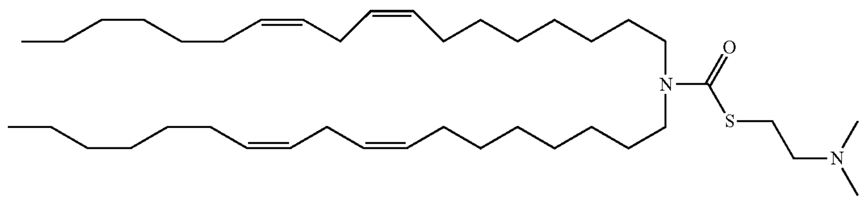

-continued
ATX-43
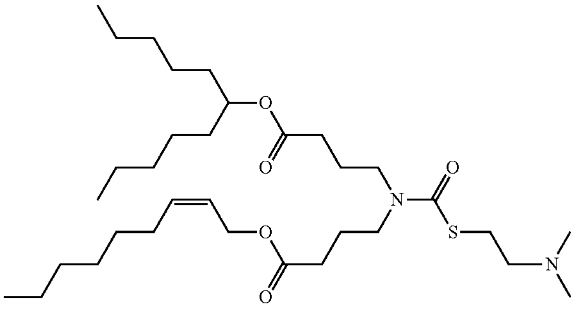
ATX-057
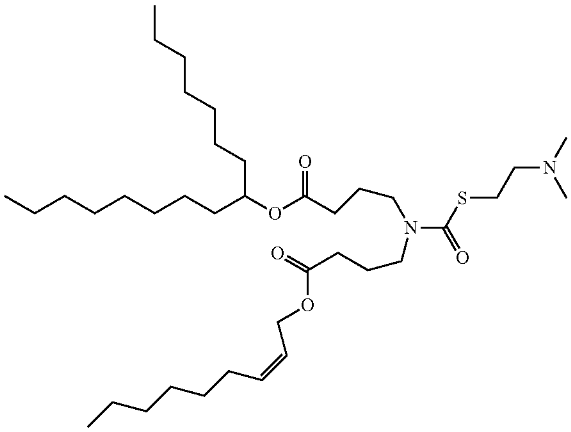
ATX-058
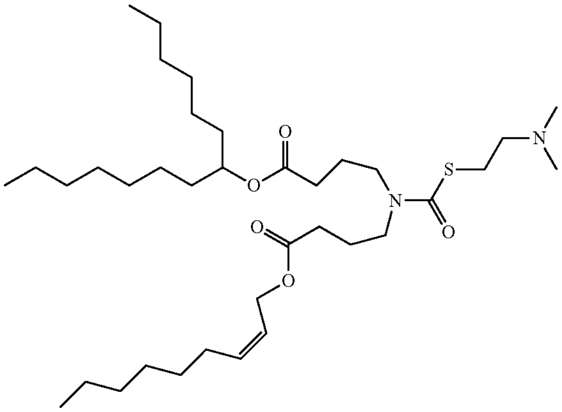
ATX-061
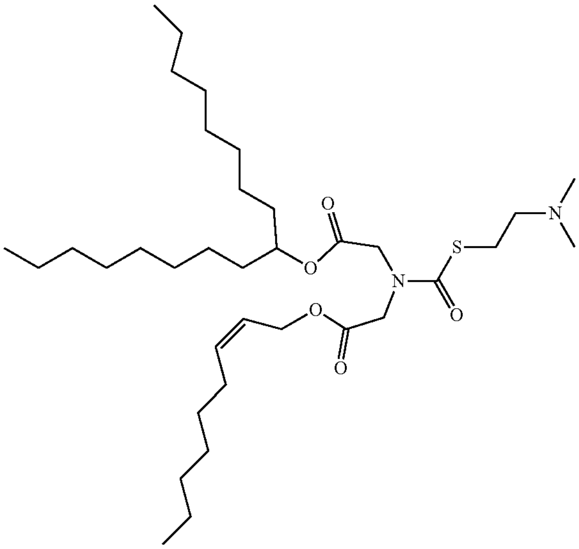
ATX-063
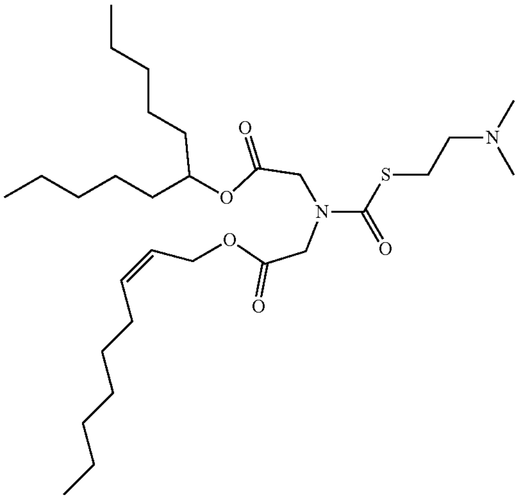
ATX-064
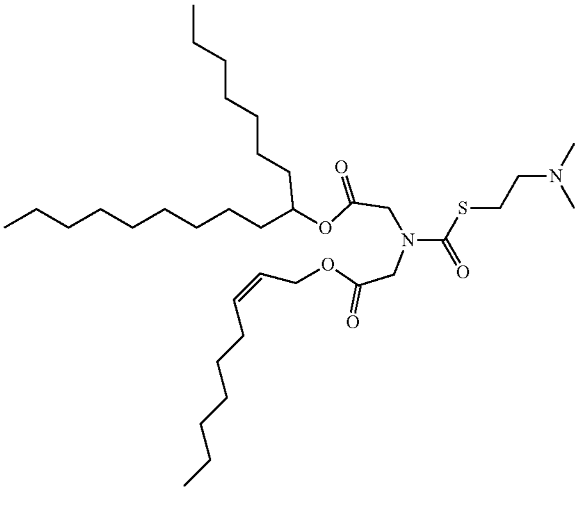

-continued
ATX-082
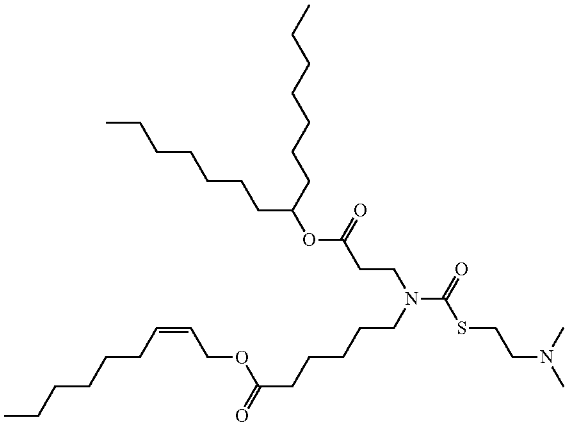
ATX-083
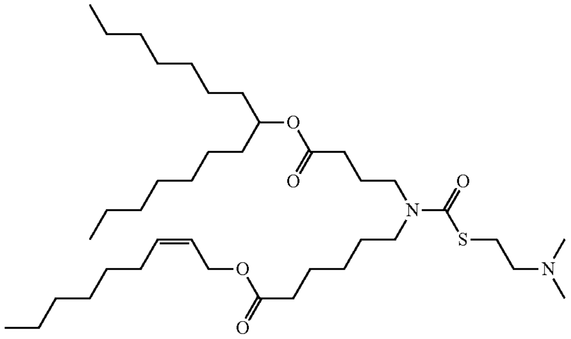
ATX-086
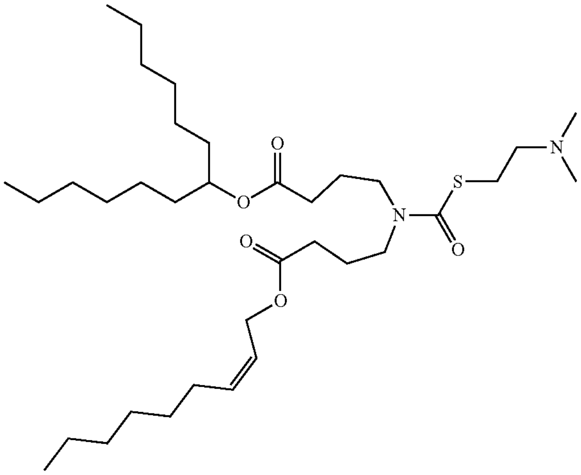
ATX-087
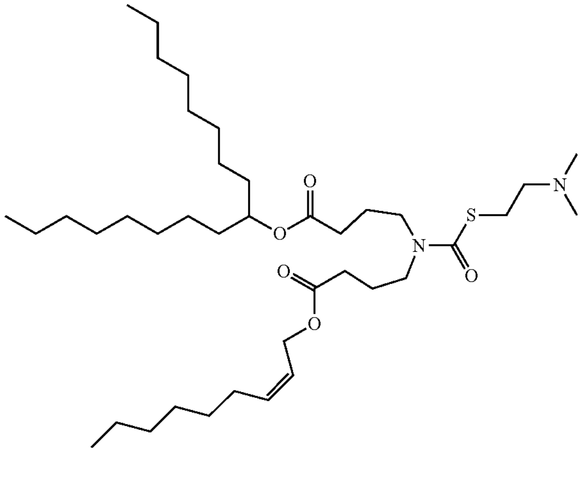
ATX-088
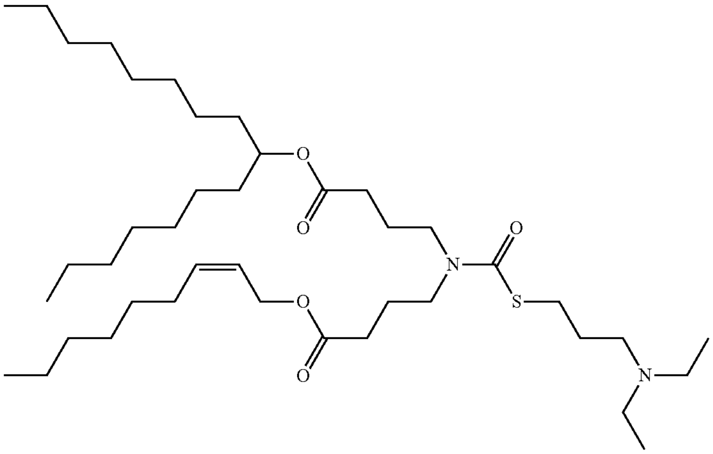

-continued
ATX-109
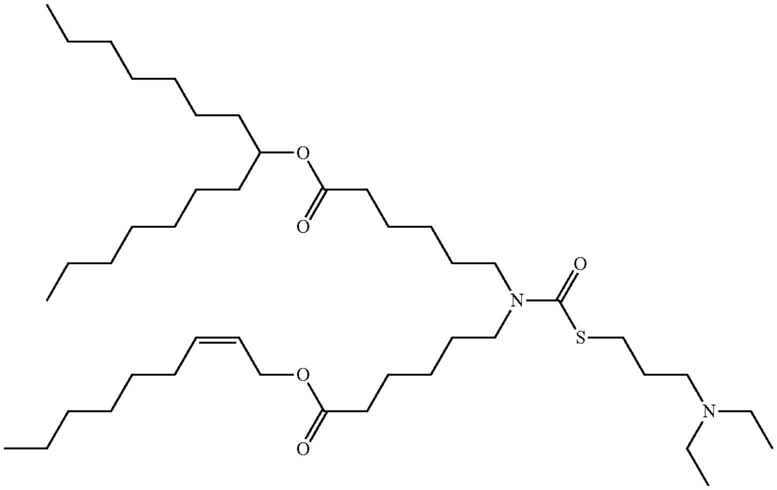
ATX-085
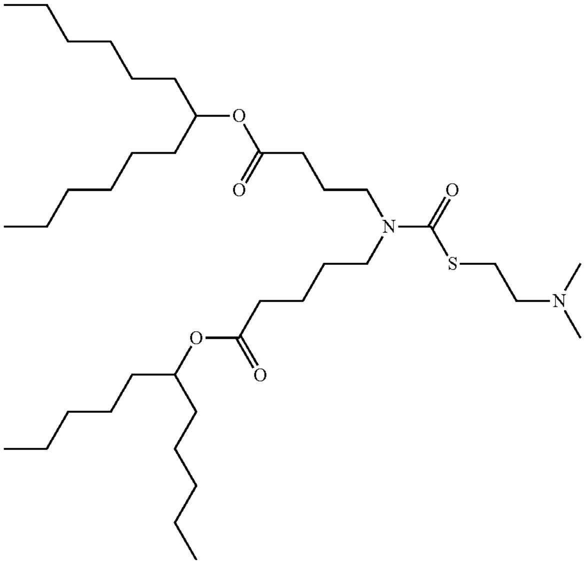
ATX-0121
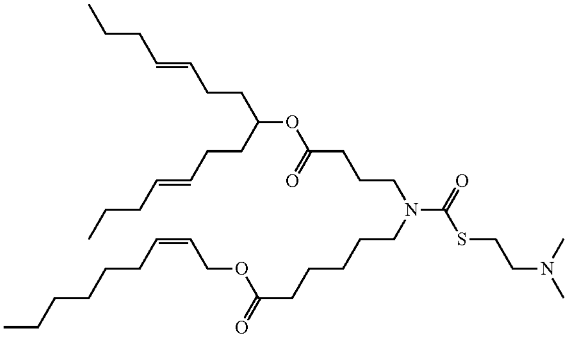
ATX-091
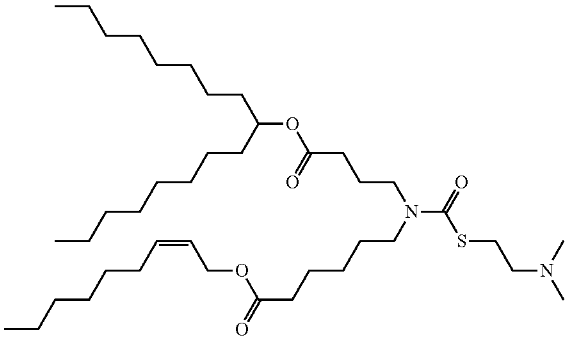
ATX-0102
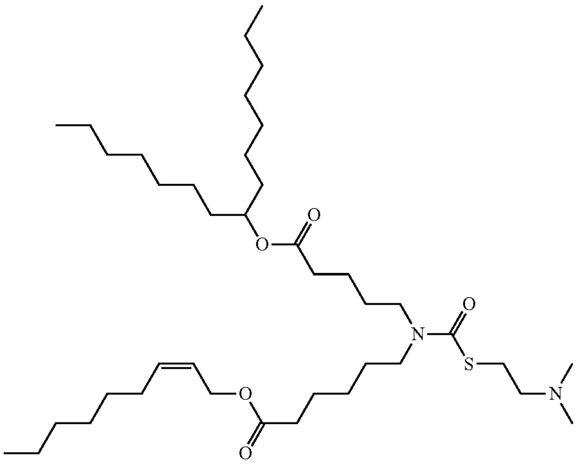

-continued
ATX-098
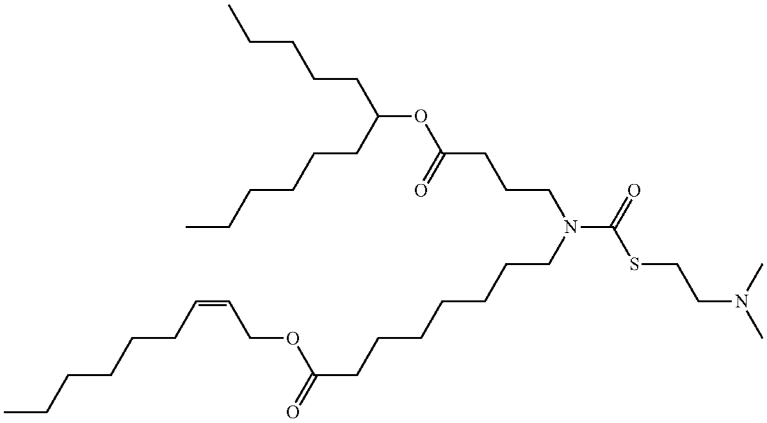
ATX-092
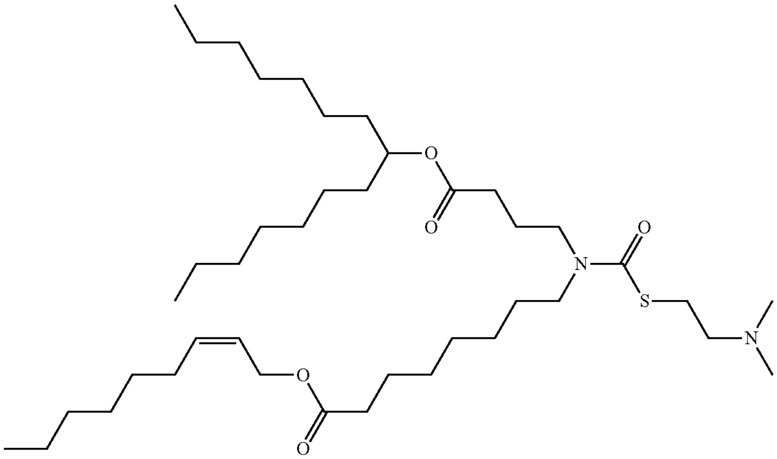
ATX-084
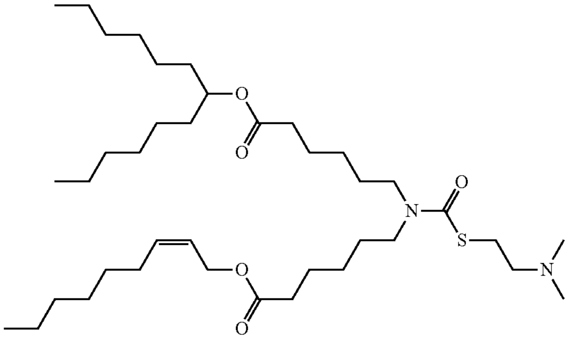
ATX-0125
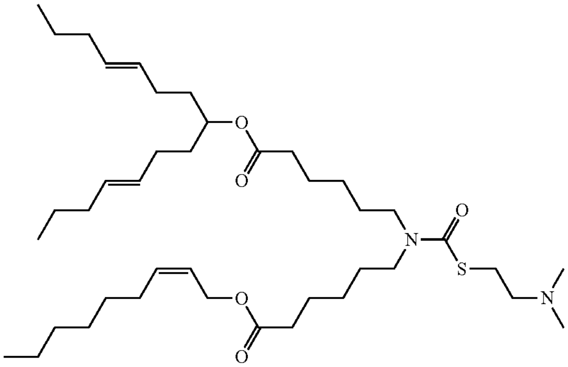

-continued
ATX-094
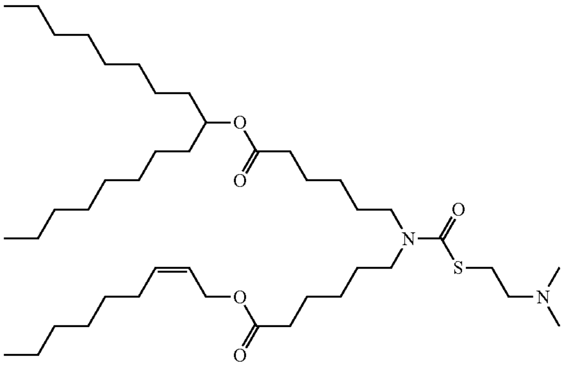
ATX-0110
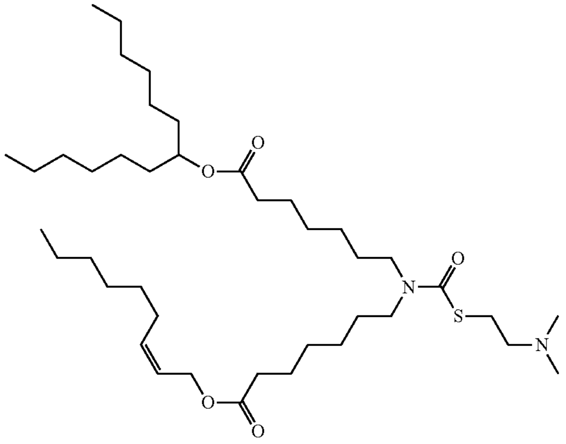
ATX-0118
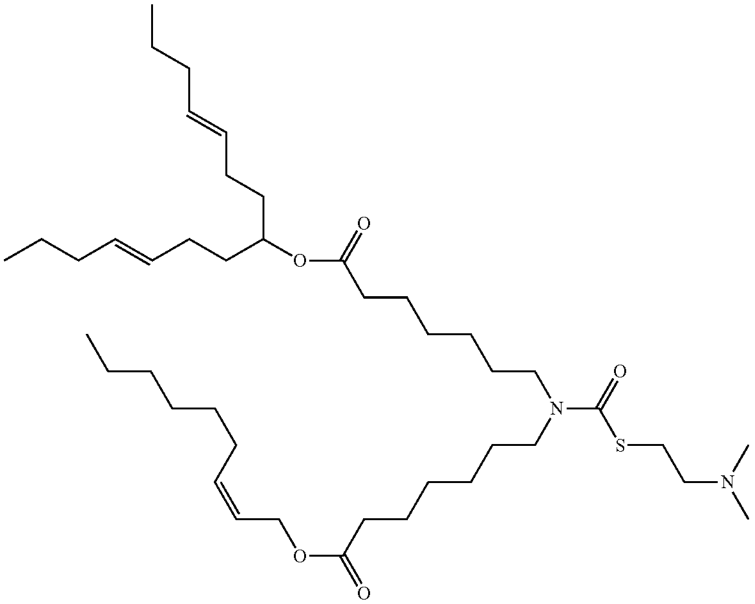
ATX-0108
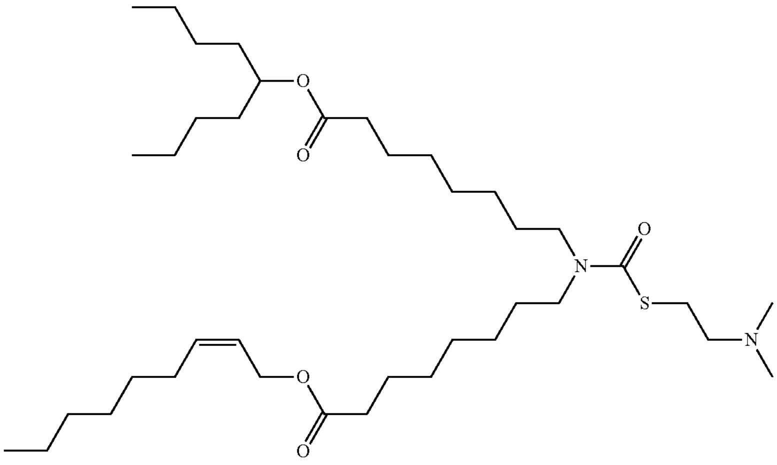

-continued
ATX-0107
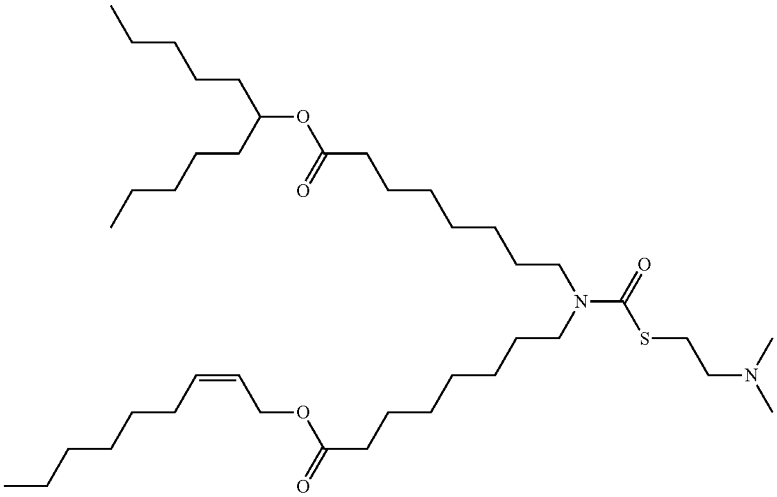
ATX-093
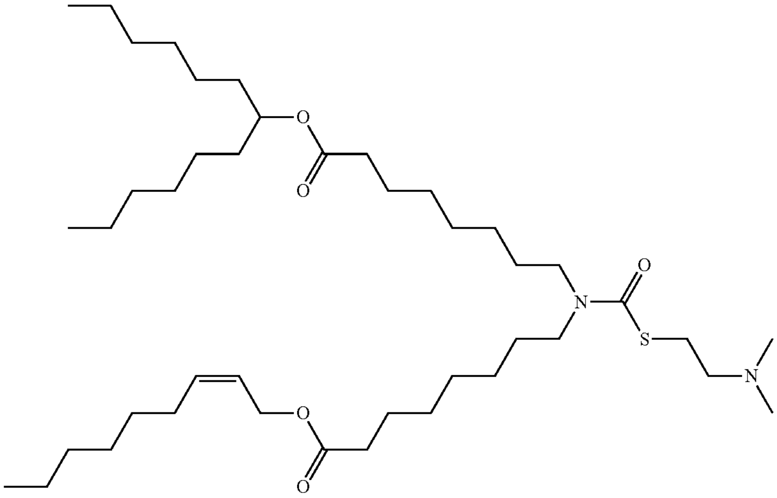
ATX-097
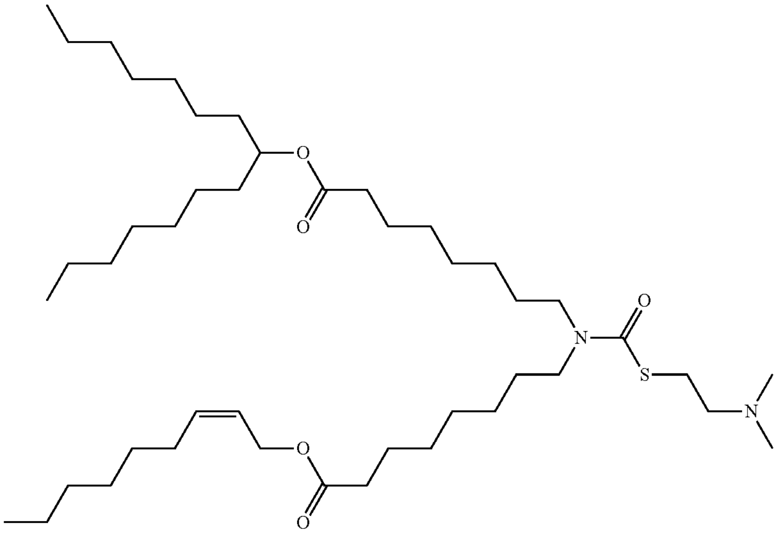

-continued
ATX-096
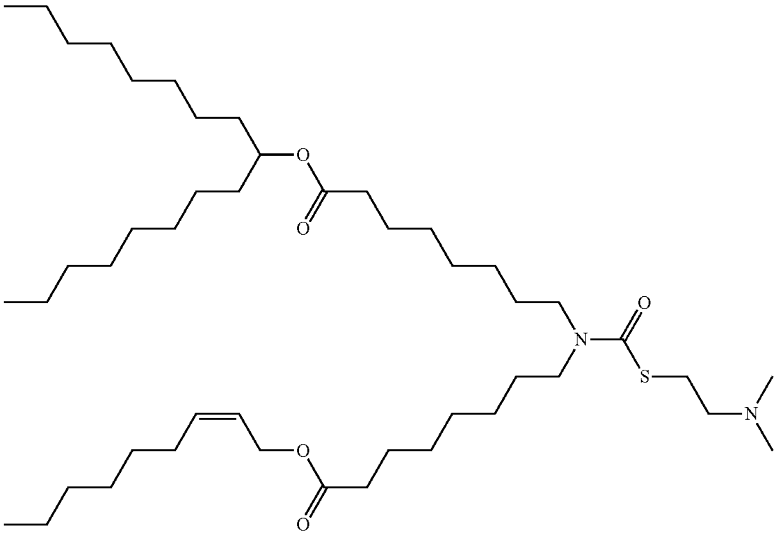
ATX-0111
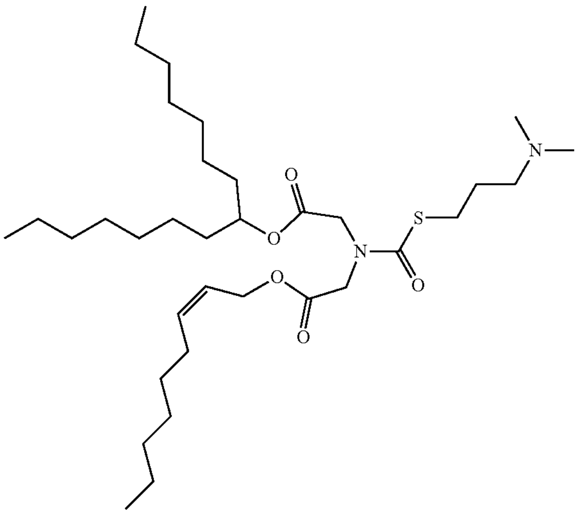
ATX-0132
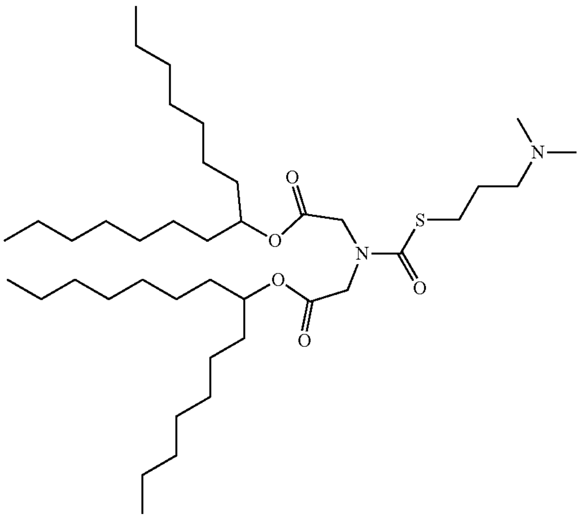
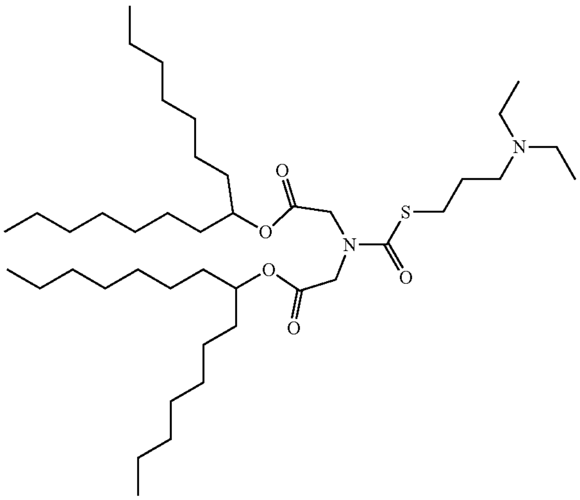
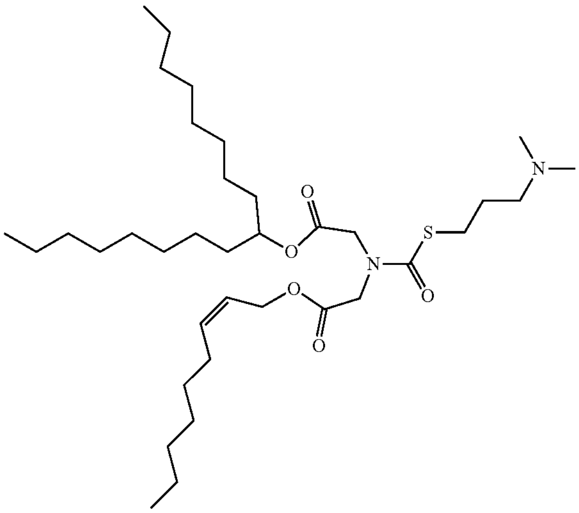

-continued
ATX-0117
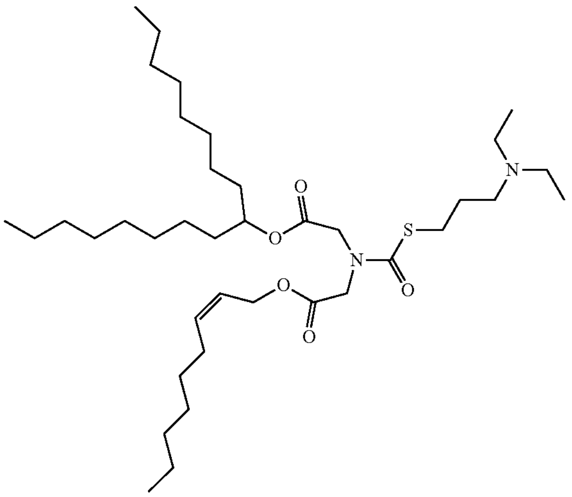
ATX-0114
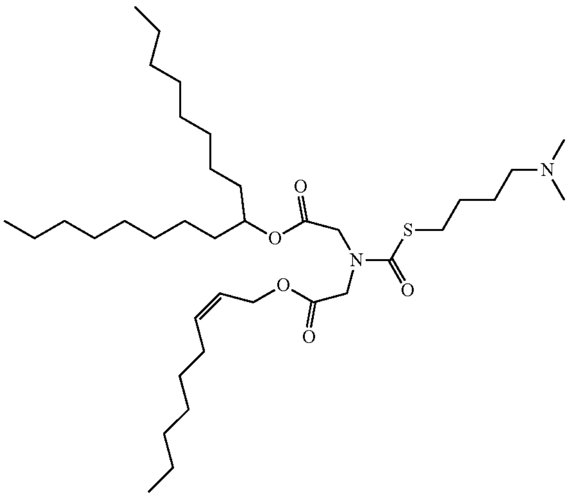
ATX-0115
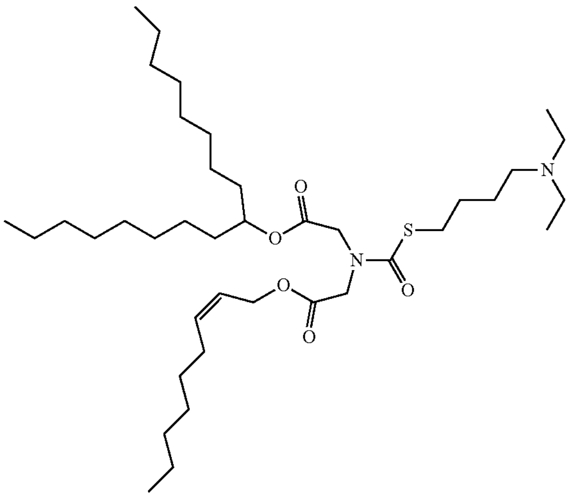
ATX-0101
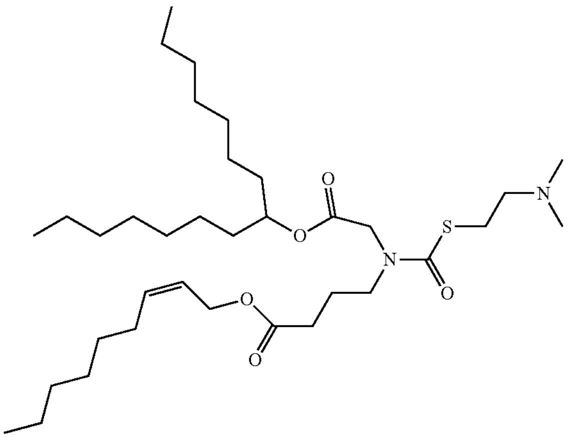
ATX-0106
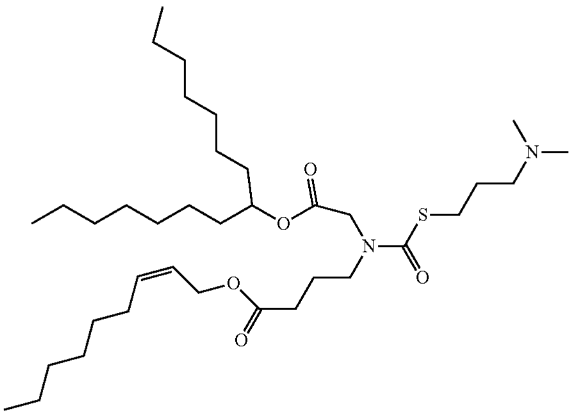
ATX-0116
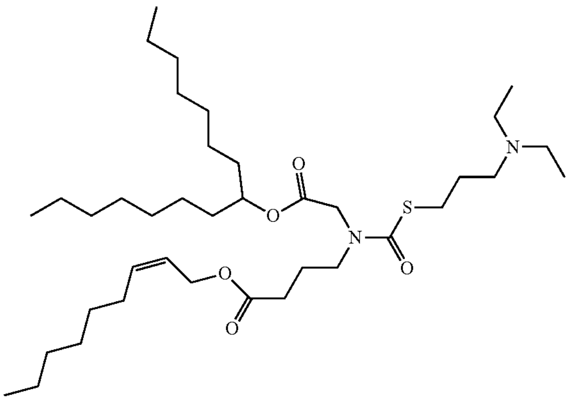

-continued
ATX-0123
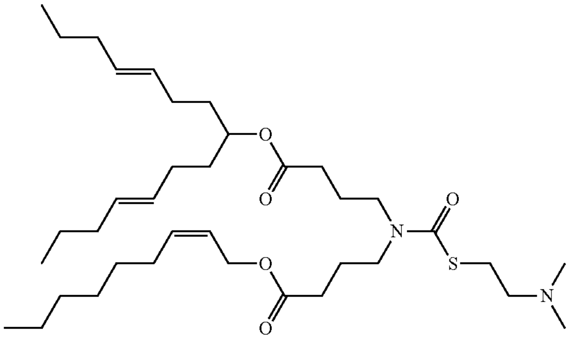
ATX-0122
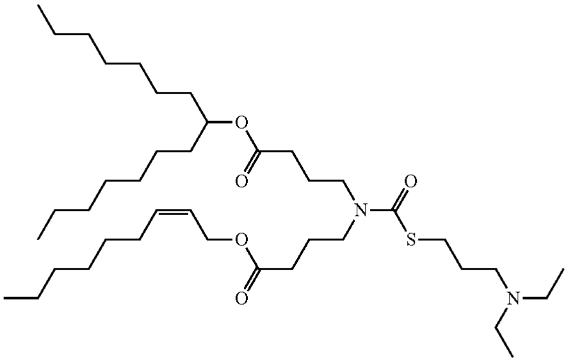
ATX-0124
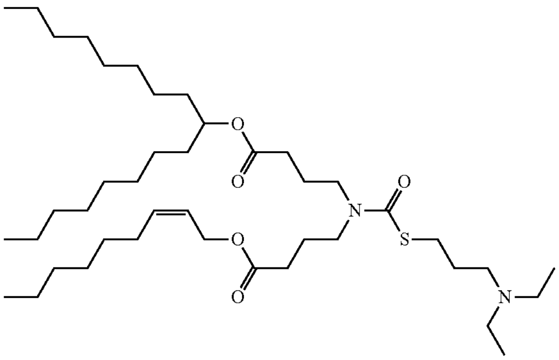
ATX-0129
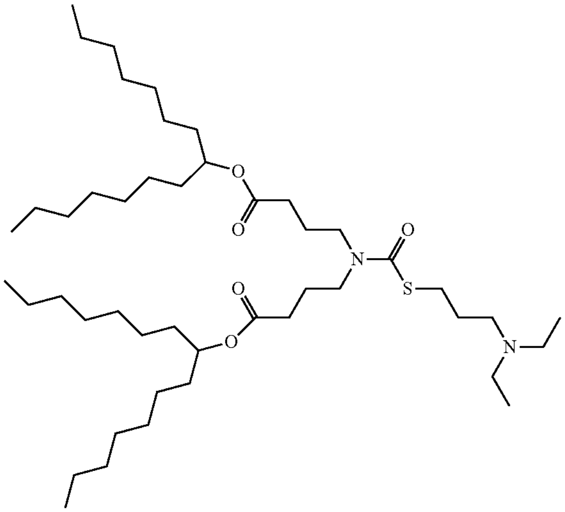
ATX-081
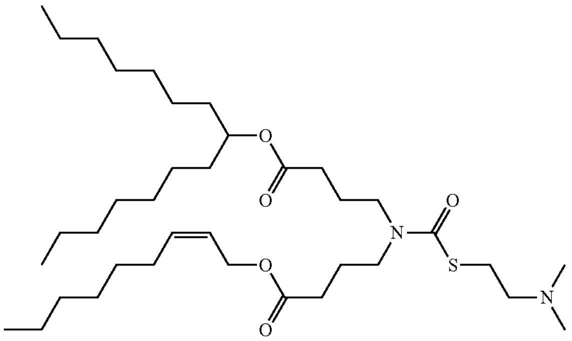
ATX-095
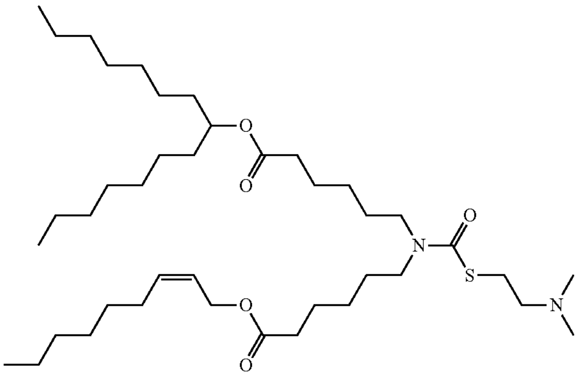
and -continued

ATX-0126

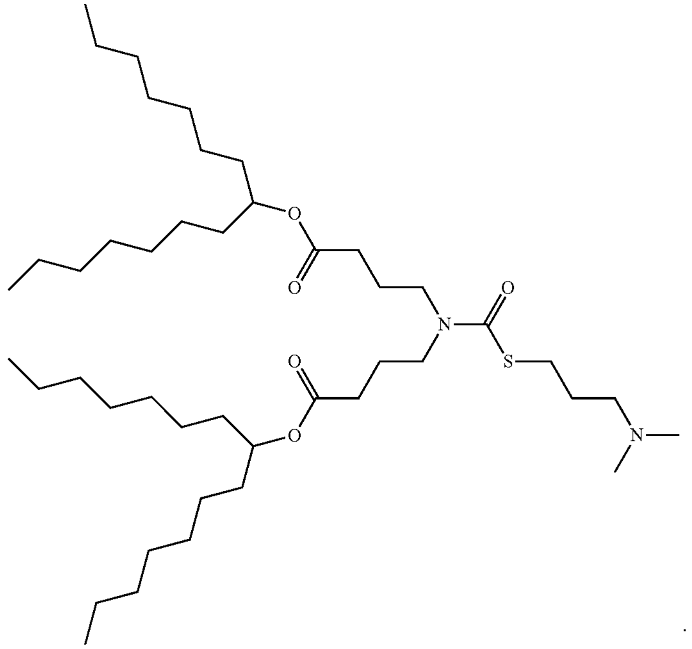

In some embodiments, the ionizable cationic lipid is ATX-126:

ATX-126

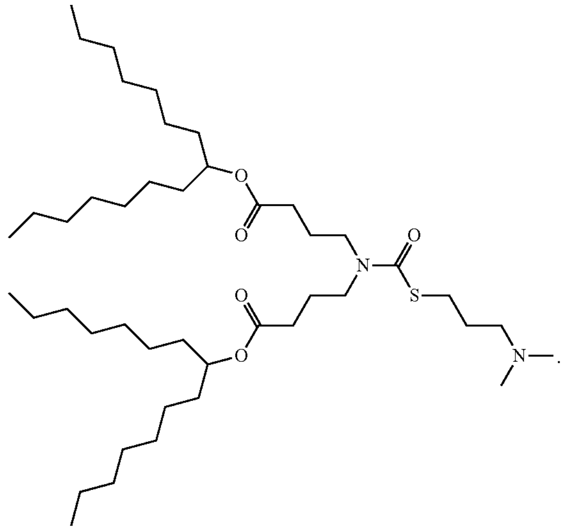

In some embodiments, the lipid formulation encapsulates the nucleic acid molecule.

In some embodiments, the lipid formulation is complexed to the nucleic acid molecule.

In some embodiments, the lipid formulation further comprises a helper lipid. In some embodiments, the helper lipid is a phospholipid. In some embodiments, the helper lipid is selected from dioleoylphosphatidyl ethanolamine (DOPE), dimyristoylphosphatidyl choline (DMPC), distearoylphosphatidyl choline (DSPC), dimyristoylphosphatidyl glycerol (DMPG), dipalmitoyl phosphatidylcholine (DPPC), and phosphatidylcholine (PC). In specific embodiments, the helper lipid is distearoylphosphatidylcholine (DSPC).

In some embodiments, the lipid formulation further comprises cholesterol.

In some embodiments, the lipid formulation further comprises a polyethylene glycol (PEG)-lipid conjugate. In some embodiments, the PEG-lipid conjugate is PEG-DMG. In some embodiments, the PEG-DMG is PEG2000-DMG.

In some embodiments, the lipid portion of the lipid formulation comprises about 40 mol % to about 60 mol % of the ionizable cationic lipid, about 4 mol % to about 16 mol % DSPC, about 30 mol % to about 47 mol % cholesterol, and about 0.5 mol % to about 3 mol % PEG2000-DMG.

In some embodiments, the lipid portion of the lipid formulation comprises about 42 mol % to about 58 mol % of the ionizable cationic lipid, about 6 mol % to about 14 mol % DSPC, about 32 mol % to about 44 mol % cholesterol, and about 1 mol % to about 2 mol % PEG2000-DMG.

In some embodiments, the lipid portion of the lipid formulation comprises about 45 mol % to about 55 mol % of the ionizable cationic lipid, about 8 mol % to about 12 mol % DSPC, about 35 mol % to about 42 mol % cholesterol, and about 1.25 mol % to about 1.75 mol % PEG2000-DMG.

In some embodiments, the composition has a total lipid:nucleic acid molecule weight ratio of about 50:1 to about 10:1. In some embodiments, the composition has a total lipid:nucleic acid molecule weight ratio of about 44:1 to about 24:1. In some embodiments, the composition has a total lipid:nucleic acid molecule weight ratio of about 40:1 to about 28:1. In some embodiments, the composition has a total lipid:nucleic acid molecule weight ratio of about 38:1 to about 30:1. In some embodiments, the composition has a total lipid:nucleic acid molecule weight ratio of about 37:1 to about 33:1. In some embodiments, the composition comprises a HEPES or TRIS buffer at a pH of about 7.0 to about 8.5.

In some embodiments, the HEPES or TRIS buffer is at a concentration of about 7 mg/mL to about 15 mg/mL.

In some embodiments, the composition further comprises about 2.0 mg/mL to about 4.0 mg/mL of NaCl.

In some embodiments, the composition further comprises one or more cryoprotectants.

In some embodiments, the one or more cryoprotectants are selected from sucrose, glycerol, or a combination of sucrose and glycerol.

In some embodiments, the composition comprises a combination of sucrose at a concentration of about 70 mg/mL to about 110 mg/mL of sucrose and glycerol at a concentration of about 50 mg/mL to about 70 mg/mL.

In some embodiments, the composition is a lyophilized composition.

In some embodiments, the lyophilized composition comprises one or more lyoprotectants.

In some embodiments, the lyophilized composition comprises a poloxamer, potassium sorbate, sucrose, or any combination thereof.

In some embodiments, the poloxamer is poloxamer 188.

In some embodiments, the lyophilized composition comprises about 0.01 to about 1.0% w/w of the nucleic acid molecule.

In some embodiments, the lyophilized composition comprises about 1.0 to about 5.0% w/w lipids.

In some embodiments, the lyophilized composition comprises about 0.5 to about 2.5% w/w of TRIS buffer.

In some embodiments, the lyophilized composition comprises about 0.75 to about 2.75% w/w of NaCl.

In some embodiments, the lyophilized composition comprises about 85 to about 95% w/w of a sugar. In some embodiments, the sugar is sucrose.

In some embodiments, the lyophilized composition comprises about 0.01 to about 1.0% w/w of a poloxamer. In some embodiments, the poloxamer is poloxamer 188.

In some embodiments, the lyophilized composition comprises about 1.0 to about 5.0% w/w of potassium sorbate.

In some embodiments, the nucleic acid molecule comprises (a) a sequence of SEQ ID NO: 124;

(b) a sequence of SEQ ID NO: 124, wherein T is substituted with U;

(c) a sequence of SEQ ID NO: 125; or (d) a sequence of SEQ ID NO: 125, wherein T is substituted with U.

In yet another aspect, the disclosure provides a lipid nanoparticle composition comprising a. a lipid formulation comprising i. about 45 mol % to about 55 mol % of an ionizable cationic lipid having the structure of ATX-126:

ATX-126

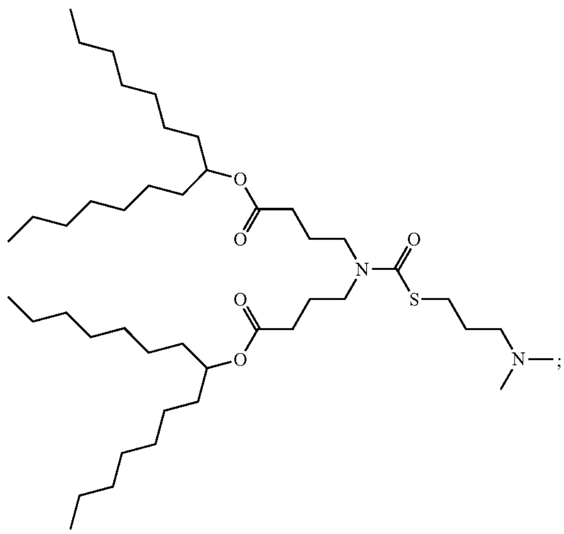

;

ii. about 8 mol % to about 12 mol % DSPC;

iii. about 35 mol % to about 42 mol % cholesterol; and iv. about 1.25 mol % to about 1.75 mol % PEG2000-DMG; and b. a nucleic acid molecule having at least 85% sequence identity to SEQ ID NO:125; wherein the lipid formulation encapsulates the nucleic acid molecule and the lipid nanoparticle has a size of about 60 to about 90 nm.

In yet another aspect, the disclosure provides a method for administering any of the compositions described herein to a subject in need thereof, wherein the composition is administered intramuscularly, subcutaneously, intradermally, transdermally, intranasally, orally, sublingually, intravenously, intraperitoneally, topically, by aerosol, or by a pulmonary route. In specific embodiments, n the composition is administered intramuscularly.

In yet another aspect, the disclosure provides a method of administering any of the compositions described herein to a subject in need thereof, wherein the composition is lyophilized and is reconstituted prior to administration.

In yet another aspect, the disclosure provides a method of ameliorating COVID-19, comprising administering any of the compositions described herein to a subject in need thereof.

In some embodiments, the composition is administered one time. In some embodiments, the composition is administered two times.

In yet another aspect, the disclosure provides a method of administering a booster dose to a vaccinated subject, comprising administering any of the compositions described herein to a subject who was previously vaccinated against coronavirus.

In some embodiments, the composition is administered at a dosage of about 0.01 μg to about 1,000 μg of nucleic acid.

In some embodiments, the composition is administered at a dosage of about 1, 2, 5, 7.5, or 10 μg of nucleic acid.

In yet another aspect, the disclosure provides a method of inducing an immune response in a subject comprising administering to the subject an effective amount of any of the nucleic acid molecules described herein.

In some embodiments, the nucleic acid molecule may be administered intramuscularly, subcutaneously, intradermally, transdermally, intranasally, orally, sublingually, intravenously, intraperitoneally, topically, by aerosol, or by a pulmonary route.

In yet another aspect, the disclosure provides a method of inducing an immune response in a subject comprising administering to the subject an effective amount of any of the compositions described herein.

In some embodiments, the composition may be administered intramuscularly, subcutaneously, intradermally, transdermally, intranasally, orally, sublingually, intravenously, intraperitoneally, topically, by aerosol, or by a pulmonary route.

In some embodiments, the nucleic acid molecules described herein may be used in inducing an immune response to the first antigenic protein or fragment thereof.

In some embodiments, the nucleic acid molecules described herein may be used in the manufacture of a medicament for inducing an immune response to the first antigenic protein or fragment thereof.

DETAILED DESCRIPTION

Figures 1A, 1B:
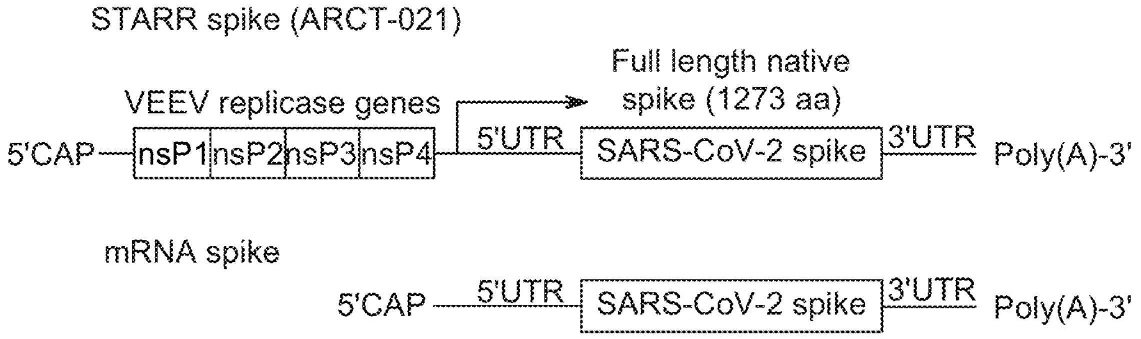
FIGS. 1A-1D show design and expression of a SARS-CoV-2 vaccine in mRNA and self-replicating RNA (STARR™) platforms. (1A) Schematic diagram of the SARS-CoV-2 self-replicating STARR™ RNA and mRNA vaccine constructs. The STARR™ construct encodes for the four non-structural proteins, ns1-ns4, from Venezuelan equine encephalitis virus (VEEV) and the SARS-CoV-2 full length spike (S) protein. The mRNA construct codes for the SARS-CoV-2 full length spike S protein. (1B) Physical characteristics and RNA trapping efficiency of the LNP in the mRNA and STARR™ (self-replicating RNA corresponding to SEQ ID NO: 125; referred to herein as "STARR™ SARS-CoV-2 RNA") vaccines. (1C) Western blot detection of SARS-CoV-2 S protein following transfection of HEK293 cells with the STARR™ RNA and mRNA constructs. (1D) In vivo comparison of protein expression following intramuscular (IM) administration of LNP containing luciferase-expressing STARR™ RNA or mRNA. Balb/c mice (n=3/group) were injected IM with 0.2 μg, 2.0 μg and 10.0 μg of STARR™ RNA or mRNA in lipid formulation. Luciferase expression was measured by in vivo bioluminescence on days 1, 3 and 7 post-IM administration. S domain 1=S1, S domain 2=S2, transmembrane domain=TM, cytoplasmic domain=CP.

The present disclosure relates to self-replicating RNAs and nucleic acids encoding the same for expression of transgenes such as antigenic proteins and tumor antigens, for example. Also provided herein are methods of administration (e.g., to a host, such as a mammalian subject) of self-replicating RNAs, whereby the self-replicating RNA is translated in vivo and the heterologous protein-coding sequence is expressed and, e.g., can elicit an immune response to the heterologous protein-coding sequence in the recipient or provide a therapeutic effect, where the heterologous protein-coding sequence is a therapeutic protein. Self-replicating RNAs provided herein are useful as vaccines that can be rapidly generated and that can be effective at low and/or single doses. The present disclosure further relates to methods of inducing an immune response using self-replicating RNAs provided herein.

In some embodiments, an immune response can be elicited against Coronavirus: immunogens that include, but are not limited to, those derived from a SARS coronavirus, avian infectious bronchitis (IBV), Mouse hepatitis virus (MHV), and Porcine transmissible gastroenteritis virus (TGEV). The coronavirus immunogen may be a spike polypeptide.

Self-replicating RNAs are described, for example, in U.S. 2018/0036398, the contents of which are incorporated by reference in their entirety.

Definitions

As used herein, the term "fragment," when referring to a protein or nucleic acid, for example, means any shorter sequence than the full-length protein or nucleic acid. Accordingly, any sequence of a nucleic acid or protein other than the full-length nucleic acid or protein sequence can be a fragment. In some aspects, a protein fragment includes an epitope. In other aspects, a protein fragment is an epitope.

As used herein, the term "nucleic acid" refers to any deoxyribonucleic acid (DNA) molecule, ribonucleic acid (RNA) molecule, or nucleic acid analogues. A DNA or RNA molecule can be double-stranded or single-stranded and can be of any size. Exemplary nucleic acids include, but are not limited to, chromosomal DNA, plasmid DNA, cDNA, cell-free DNA (cfDNA), mitochondrial DNA, chloroplast DNA, viral DNA, mRNA, tRNA, rRNA, long non-coding RNA, siRNA, micro RNA (miRNA or miR), hnRNA, and viral RNA. Exemplary nucleic analogues include peptide nucleic acid, morpholino- and locked nucleic acid, glycol nucleic acid, and threose nucleic acid. As used herein, the term "nucleic acid molecule" is meant to include fragments of nucleic acid molecules as well as any full-length or non-fragmented nucleic acid molecule, for example. As used herein, the terms "nucleic acid" and "nucleic acid molecule" can be used interchangeably, unless context clearly indicates otherwise.

As used herein, the term "protein" refers to any polymeric chain of amino acids. The terms "peptide" and "polypeptide" can be used interchangeably with the term protein, unless context clearly indicates otherwise, and can also refer to a polymeric chain of amino acids. The term "protein" encompasses native or artificial proteins, protein fragments and polypeptide analogs of a protein sequence. A protein may be monomeric or polymeric. The term "protein" encompasses fragments and variants (including fragments of variants) thereof, unless otherwise contradicted by context.

In general, "sequence identity" or "sequence homology," which can be used interchangeably, refer to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby or the amino acid sequence of a polypeptide, and comparing these sequences to a second nucleotide or amino acid sequence. As used herein, the term "percent (%) sequence identity" or "percent (%) identity," also including "homology," refers to the percentage of amino acid residues or nucleotides in a sequence that are identical with the amino acid residues or nucleotides in a reference sequence after aligning the sequences and introducing gaps, if necessary, to achieve the maximum percent sequence identity, and not considering any conservative substitutions as part of the sequence identity. Thus, two or more sequences (polynucleotide or amino acid) can be compared by determining their "percent identity," also referred to as "percent homology." The percent identity to a reference sequence (e.g., nucleic acid or amino acid sequences), which may be a sequence within a longer molecule (e.g., polynucleotide or polypeptide), may be calculated as the number of exact matches between two optimally aligned sequences divided by the length of the reference sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul et al., J. Mol. Biol. 215:403-410 (1990); Karlin and Altschul, Proc. Natl. Acad. sci. USA 90:5873-5877 (1993); and Altschul et al., Nucleic Acids Res. 25:3389-3402 (1997). Briefly, the BLAST program defines identity as the number of identical aligned symbols (i.e., nucleotides or amino acids), divided by the total number of symbols in the shorter of the two sequences. The program may be used to determine percent identity over the entire length of the sequences being compared. Default parameters are provided to optimize searches with short query sequences, for example, with the blastp program. The program also allows use of an SEG filter to mask-off segments of the query sequences as determined by the SEG program of Wootton and Federhen, Computers and Chemistry 17: 149-163 (1993). Ranges of desired degrees of sequence identity are approximately 80% to 100% and integer values in between. Percent identities between a reference sequence and a claimed sequence can be at least 80%, at least 85%, at least 90%, at least 95%, at least 98%, at least 99%, at least 99.5%, or at least 99.9%. In general, an exact match indicates 100% identity over the length of the reference sequence. Additional programs and methods for comparing sequences and/or assessing sequence identity include the Needleman-Wunsch algorithm (see, e.g., the EMBOSS Needle aligner available at ebi.ac.uk/Tools/psa/emboss needle/, optionally with default settings), the Smith-Waterman algorithm (see, e.g., the EMBOSS Water aligner available at ebi.ac.uk/Tools/psa/emboss water/, optionally with default settings), the similarity search method of Pearson and Lipman, 1988, Proc. Natl. Acad. Sci. USA 85, 2444, or computer programs which use these algorithms (GAP, BESTFIT, FASTA, BLAST P, BLAST N and TFASTA in Wisconsin Genetics Software Package, Genetics Computer Group. 575 Science Drive, Madison, Wis.). In some aspects, reference to percent sequence identity refers to sequence identity as measured using BLAST (Basic Local Alignment Search Tool). In other aspects, ClustalW is used for multiple sequence alignment. Optimal alignment may be assessed using any suitable parameters of a chosen algorithm, including default parameters.

As used herein, the term "drug" or "medicament," means a pharmaceutical formulation or composition as described herein.

As used herein, the singular forms "a," "an," and "the" include plural references unless the context clearly dictates otherwise. Thus, for example, references to "the method" includes one or more methods, and/or steps of the type described herein which will become apparent to those persons skilled in the art upon reading this disclosure and so forth.

"About" as used herein when referring to a measurable value such as an amount, a temporal duration, and the like, is meant to encompass variations of +20%, or ±10%, or ±5%, or even ±1% from the specified value, as such variations are appropriate for the disclosed methods or to perform the disclosed methods.

The term "expression" refers to the process by which a nucleic acid sequence or a polynucleotide is transcribed from a DNA template (such as into mRNA or other RNA transcript) and/or the process by which a transcribed mRNA or other RNA is subsequently translated into peptides, polypeptides, or proteins. Transcripts and encoded polypeptides may be collectively referred to as "gene product."

As used herein, the terms "self-replicating RNA," "self-transcribing and self-replicating RNA," "self-amplifying RNA (saRNA)," and "replicon" may be used interchangeably, unless context clearly indicates otherwise. Generally, the term "replicon" or "viral replicon" refers to a self-replicating subgenomic RNA derived from a viral genome that includes viral genes encoding non-structural proteins important for viral replication and that lacks viral genes encoding structural proteins. A self-replicating RNA can encode further subgenomic RNAs that are not able to self-replicate.

As used herein, "operably linked," "operable linkage," "operatively linked," or grammatical equivalents thereof refer to juxtaposition of genetic elements, e.g., a promoter, an enhancer, a polyadenylation sequence, etc., wherein the elements are in a relationship permitting them to operate in the expected manner. For instance, a regulatory element, which can comprise promoter and/or enhancer sequences, is operatively linked to a coding region if the regulatory element helps initiate transcription of the coding sequence. There may be intervening residues between the regulatory element and coding region so long as this functional relationship is maintained.

Nucleic Acid Molecules

In some embodiments, provided herein are nucleic acid molecules comprising: (i) a first polynucleotide encoding one or more viral replication proteins, wherein the first polynucleotide is codon-optimized as compared to a wild-type polynucleotide encoding the one or more viral replication proteins; and (ii) a second polynucleotide comprising a first transgene encoding a first antigenic protein or a fragment thereof, wherein the first antigenic protein is a coronavirus protein.

An RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

Also provided herein, in some embodiments, are nucleic acid molecules comprising: (i) a first polynucleotide comprising a sequence having at least 80% identity to a sequence of SEQ ID NO:72; and (ii) a second polynucleotide comprising a first transgene encoding a first antigenic protein or a fragment thereof.

Codon Optimization

In some embodiments, first polynucleotides of nucleic acid molecules provided herein encoding one or more viral replication proteins include codon-optimized sequences. As used herein, the term "codon-optimized" means a polynucleotide, nucleic acid sequence, or coding sequence has been redesigned as compared to a wild-type or reference polynucleotide, nucleic acid sequence, or coding sequence by choosing different codons without altering the amino acid sequence of the encoded protein. Accordingly, codon-optimization generally refers to replacement of codons with synonymous codons to optimize expression of a protein while keeping the amino acid sequence of the translated protein the same. Codon optimization of a sequence can increase protein expression levels (Gustafsson et al., Codon bias and heterologous protein expression. 2004, Trends Biotechnol 22: 346-53) of the encoded proteins, for example, and provide other advantages. Variables such as codon usage preference as measured by codon adaptation index (CAI), for example, the presence or frequency of U and other nucleotides, mRNA secondary structures, cis-regulatory sequences, GC content, and other variables may correlate with protein expression levels (Villalobos et al., Gene Designer: a synthetic biology tool for constructing artificial DNA segments. 2006, BMC Bioinformatics 7:285).

Any method of codon optimization can be used to codon optimize polynucleotides and nucleic acid molecules provided herein, and any variable can be altered by codon optimization. Accordingly, any combination of codon optimization methods can be used. Exemplary methods include the high codon adaptation index (CAI) method, the Low U method, and others. The CAI method chooses a most frequently used synonymous codon for an entire protein coding sequence. As an example, the most frequently used codon for each amino acid can be deduced from 74,218 protein-coding genes from a human genome. The Low U method targets U-containing codons that can be replaced with a synonymous codon with fewer U moieties, generally without changing other codons. If there is more than one choice for replacement, the more frequently used codon can be selected. Any polynucleotide, nucleic acid sequence, or codon sequence provided herein can be codon-optimized.

In some embodiments, the nucleotide sequence of any region of the RNA or DNA templates described herein may be codon optimized. Preferably, the primary cDNA template may include reducing the occurrence or frequency of appearance of certain nucleotides in the template strand. For example, the occurrence of a nucleotide in a template may be reduced to a level below 25% of said nucleotides in the template. In further examples, the occurrence of a nucleotide in a template may be reduced to a level below 20% of said nucleotides in the template. In some examples, the occurrence of a nucleotide in a template may be reduced to a level below 16% of said nucleotides in the template. Preferably, the occurrence of a nucleotide in a template may be reduced to a level below 15%, and preferably may be reduced to a level below 12% of said nucleotides in the template.

In some embodiments, the nucleotide reduced is uridine. For example, the present disclosure provides nucleic acids with altered uracil content wherein at least one codon in the wild-type sequence has been replaced with an alternative codon to generate a uracil-altered sequence. Altered uracil sequences can have at least one of the following properties:

(i) an increase or decrease in global uracil content (i.e., the percentage of uracil of the total nucleotide content in the nucleic acid of a section of the nucleic acid, e.g., the open reading frame);

(ii) an increase or decrease in local uracil content (i.e., changes in uracil content are limited to specific subsequences);

(iii) a change in uracil distribution without a change in the global uracil content;

(iv) a change in uracil clustering (e.g., number of clusters, location of clusters, or distance between clusters); or (v) combinations thereof.

In some embodiments, the percentage of uracil nucleobases in the nucleic acid sequence is reduced with respect to the percentage of uracil nucleobases in the wild-type nucleic acid sequence. For example, 30% of nucleobases may be uracil in the wild-type sequence but the nucleobases that are uracil are preferably lower than 15%, preferably lower than 12% and preferably lower than 10% of the nucleobases in the nucleic acid sequences of the disclosure. The percentage uracil content can be determined by dividing the number of uracil in a sequence by the total number of nucleotides and multiplying by 100.

In some embodiments, the percentage of uracil nucleobases in a subsequence of the nucleic acid sequence is reduced with respect to the percentage of uracil nucleobases in the corresponding subsequence of the wild-type sequence. For example, the wild-type sequence may have a 5'-end region (e.g., 30 codons) with a local uracil content of 30%, and the uracil content in that same region could be reduced to preferably 15% or lower, preferably 12% or lower and preferably 10% or lower in the nucleic acid sequences of the disclosure. These subsequences can also be part of the wild-type sequences of the heterologous 5' and 3' UTR sequences of the present disclosure.

In some embodiments, codons in the nucleic acid sequence of the disclosure reduce or modify, for example, the number, size, location, or distribution of uracil clusters that could have deleterious effects on protein translation. Although lower uracil content is desirable in certain aspects, the uracil content, and in particular the local uracil content, of some subsequences of the wild-type sequence can be greater than the wild-type sequence and still maintain beneficial features (e.g., increased expression).

In some embodiments, the uracil-modified sequence induces a lower Toll-Like Receptor (TLR) response when compared to the wild-type sequence. Several TLRs recognize and respond to nucleic acids. Double-stranded (ds) RNA, a frequent viral constituent, has been shown to activate TLR3. Single-stranded (ss)RNA activates TLR7. RNA oligonucleotides, for example RNA with phosphorothioate internucleotide linkages, are ligands of human TLR8. DNA containing unmethylated CpG motifs, characteristic of bacterial and viral DNA, activate TLR9.

As used herein, the term "TLR response" is defined as the recognition of single-stranded RNA by a TLR7 receptor, and preferably encompasses the degradation of the RNA and/or physiological responses caused by the recognition of the single-stranded RNA by the receptor. Methods to determine and quantify the binding of an RNA to a TLR7 are known in the art. Similarly, methods to determine whether an RNA has triggered a TLR7-mediated physiological response (e.g., cytokine secretion) are well known in the art. In some embodiments, a TLR response can be mediated by TLR3, TLR8, or TLR9 instead of TLR7. Suppression of TLR7-mediated response can be accomplished via nucleoside modification. RNA undergoes over a hundred different nucleoside modifications in nature. Human rRNA, for example, has ten times more pseudouracil ('P) and 25 times more 2'-O-methylated nucleosides than bacterial rRNA. Bacterial RNA contains no nucleoside modifications, whereas mammalian RNAs have modified nucleosides such as 5-methylcytidine (m5C), N6-methyladenosine (m6A), inosine and many 2'-O-methylated nucleosides in addition to N7-methylguanosine (m7G).

In some embodiments, the uracil content of polynucleotides disclosed herein is less than about 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total nucleobases in the sequence in the reference sequence. In some embodiments, the uracil content of polynucleotides disclosed herein is between about 5% and about 25%. In some embodiments, the uracil content of polynucleotides disclosed herein is between about 15% and about 25%.

In some embodiments, first polynucleotides of nucleic acid molecules provided herein comprise a sequence having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:72. In some embodiments, first polynucleotides of nucleic acid molecules provided herein comprise a sequence of SEQ ID NO:72.

In some aspects, first polynucleotides and second polynucleotides of nucleic acid molecules provided herein are included in the same (i.e., a single) or in separate nucleic acid molecules. Generally, first polynucleotides and second polynucleotides of nucleic acid molecules provided herein are included in a single nucleic acid molecule. In one aspect, the first polynucleotide is located 5' of the second polynucleotide. In one aspect, first polynucleotides and second polynucleotides of nucleic acid molecules provided herein are included in separate nucleic acid molecules. In yet another aspect, first polynucleotides and second polynucleotides are included in two separate nucleic acid molecules.

In some aspects, first polynucleotides and second polynucleotides are included in the same (i.e., a single) nucleic acid molecule. First polynucleotides and second polynucleotides of nucleic acid molecules provided herein can be contiguous, i.e., adjacent to each other without nucleotides in between. In one aspect, an intergenic region is located between the first polynucleotide and the second polynucleotide. In another aspect, the intergenic region located between the first polynucleotide and the second polynucleotide is a second intergenic region, with a first intergenic region included in the first polynucleotide as described below. As used herein, the terms "intergenic region" and intergenic sequence" can be used interchangeably, unless context clearly indicates otherwise.

An intergenic region located between the first polynucleotide and the second polynucleotide can be of any length and can have any nucleotide sequence. As an example, the intergenic region between the first polynucleotide and the second polynucleotide can include about one nucleotide, about two nucleotides, about three nucleotides, about four nucleotides, about five nucleotides, about six nucleotides, about seven nucleotides, about eight nucleotides, about nine nucleotides, about ten nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, about 50 nucleotides, about 60 nucleotides, about 70 nucleotides, about 80 nucleotides, about 90 nucleotides, about 100 nucleotides, about 125 nucleotides, about 150 nucleotides, about 175 nucleotides, about 200 nucleotides, about 250 nucleotides, about 300 nucleotides, about 350 nucleotides, about 400 nucleotides, about 450 nucleotides, about 500 nucleotides, about 600 nucleotides, about 700 nucleotides, about 800 nucleotides, about 1,000 nucleotides, about 1,500 nucleotides, about 2,000 nucleotides, about 2,500 nucleotides, about 3,000 nucleotides, about 3,500 nucleotides, about 4,000 nucleotides, about 4,500 nucleotides, about 5,000 nucleotides, about 6,000 nucleotides, about 7,000 nucleotides, about 8,000 nucleotides, about 9,000 nucleotides, about 10,000 nucleotides, and any number or range in between. In one aspect, the intergenic region between first and second polynucleotides includes about 10-100 nucleotides, about 10-200 nucleotides, about 10-300 nucleotides, about 10-400 nucleotides, or about 10-500 nucleotides. In another aspect, the intergenic region between first and second polynucleotides includes about 1-10 nucleotides, about 1-20 nucleotides, about 1-30 nucleotides, about 1-40 nucleotides, or about 1-50 nucleotides. In yet another aspect, the region includes about 44 nucleotides. In one aspect, the intergenic region between first and second polynucleotides of nucleic acid molecules provided herein is a second intergenic region.

In one aspect, the intergenic region between first and second polynucleotides includes a viral sequence. The intergenic region between first and second polynucleotides can include a sequence from any virus, such as alphaviruses and rubiviruses, for example. In one aspect, the intergenic region between the first polynucleotide and the second polynucleotide comprises an alphavirus sequence, such as a sequence from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), Buggy Creek Virus (BCRV), or any combination thereof. In another aspect, the intergenic region between first and second polynucleotides comprises a sequence from Venezuelan Equine Encephalitis Virus (VEEV). In yet another aspect, the intergenic region between first and second polynucleotides comprises a sequence having at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to SEQ ID NO:77. In a further aspect, the intergenic region between first and second polynucleotides comprises a sequence of SEQ ID NO:77. In yet a further aspect, the intergenic region between first and second polynucleotides is a second intergenic region comprising a sequence having at least 85% identity to SEQ ID NO:77.

Natural and Modified Nucleotides

A self-replicating RNA of the disclosure can comprise one or more chemically modified nucleotides. Examples of nucleic acid monomers include non-natural, modified, and chemically-modified nucleotides, including any such nucleotides known in the art. Nucleotides can be artificially modified at either the base portion or the sugar portion. In nature, most polynucleotides comprise nucleotides that are "unmodified" or "natural" nucleotides, which include the purine bases adenine (A) and guanine (G), and the pyrimidine bases thymine (T), cytosine (C) and uracil (U). These bases are typically fixed to a ribose or deoxy ribose at the 1' position. The use of RNA polynucleotides comprising chemically modified nucleotides have been shown to improve RNA expression, expression rates, half-life and/or expressed protein concentrations. RNA polynucleotides comprising chemically modified nucleotides have also been useful in optimizing protein localization thereby avoiding deleterious bio-responses such as immune responses and/or degradation pathways.

Examples of modified or chemically-modified nucleotides include 5-hydroxycytidines, 5-alkylcytidines, 5-hydroxyalkylcytidines, 5-carboxycytidines, 5-formylcytidines, 5-alkoxycytidines, 5-alkynylcytidines, 5-halocytidines, 2-thiocytidines, N4-alkylcytidines, N4-aminocytidines, N4-acetylcytidines, and N4,N4-dialkylcytidines.

Examples of modified or chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; N4-methylcytidine, N4-aminocytidine, N4-acetylcytidine, and N4,N4-dimethylcytidine.

Examples of modified or chemically-modified nucleotides include 5-hydroxyuridines, 5-alkyluridines, 5-hydroxyalkyluridines, 5-carboxyuridines, 5-carboxyalkylesteruridines, 5-formyluridines, 5-alkoxyuridines, 5-alkynyluridines, 5-halouridines, 2-thiouridines, and 6-alkyluridines.

Examples of modified or chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine (also referred to herein as "5MeOU"), 5-propynyluridine, 5-bromouridine, 5-fluorouridine, 5-iodouridine, 2-thiouridine, and 6-methyluridine.

Examples of modified or chemically-modified nucleotides include 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'O-methyluridine, and 3,2'-O-dimethyluridine.

Examples of modified or chemically-modified nucleotides include N6-methyladenosine, 2-aminoadenosine, 3-methyladenosine, 8-azaadenosine, 7-deazaadenosine, 8-oxoadenosine, 8-bromoadenosine, 2-methylthio-N6-methyladenosine, N6-isopentenyladenosine, 2-methylthio-N6-isopentenyladenosine, N6-(cis-hydroxyisopentenyl) adenosine, 2-methylthio-N6-(cis-hydroxyisopentenyl) adenosine, N6-glycinylcarbamoyladenosine, N6-threonylcarbamoyl-adenosine, N6-methyl-N6-threonylcarbamoyl-adenosine, 2-methylthio-N6-threonylcarbamoyladenosine, N6,N6-dimethyladenosine, N6-hydroxynorvalylcarbamoyladenosine, 2-methylthio-N6-hydroxynorvalylcarbamoyl-adenosine, N6-acetyladenosine, 7-methyl-adenine, 2-methylthio-adenine, 2-methoxy-adenine, alpha-thio-adenosine, 2'-O-methyl-adenosine, N6,2'-O-dimethyl-adenosine, N6,N6,2'-O-trimethyl-adenosine, 1,2'-O-dimethyl-adenosine, 2'-O-ribosyladenosine, 2-amino-N6-methyl-purine, 1-thio-adenosine, 2'-F-ara-adenosine, 2'-F-adenosine, 2'-OH-ara-adenosine, and N6-(19-amino-pentaoxanonadecyl)-adenosine.

Examples of modified or chemically-modified nucleotides include N1-alkylguanosines, N2-alkylguanosines, thienoguanosines, 7-deazaguanosines, 8-oxoguanosines, 8-bromoguanosines, 06-alkylguanosines, xanthosines, inosines, and N1-alkylinosines.

Examples of modified or chemically-modified nucleotides include N1-methylguanosine, N2-methylguanosine, thienoguanosine, 7-deazaguanosine, 8-oxoguanosine, 8-bromoguanosine, O6-methylguanosine, xanthosine, inosine, and N1-methylinosine.

Examples of modified or chemically-modified nucleotides include pseudouridines. Examples of pseudouridines include N1-alkylpseudouridines, N1-cycloalkylpseudouridines, N1-hydroxypseudouridines, N1-hydroxyalkylpseudouridines, N1-phenylpseudouridines, N1-phenylalkylpseudouridines, N1-aminoalkylpseudouridines, N3-alkylpseudouridines, N6-alkylpseudouridines, N6-alkoxypseudouridines, N6-hydroxypseudouridines, N6-hydroxyalkylpseudouridines, N6-morpholinopseudouridines, N6-phenylpseudouridines, and N6-halopseudouridines. Examples of pseudouridines include N1-alkyl-N6-alkylpseudouridines, N1-alkyl-N6-alkoxypseudouridines, N1-alkyl-N6-hydroxypseudouridines, N1-alkyl-N6-hydroxyalkylpseudouridines, N1-alkyl-N6-morpholinopseudouridines, N1-alkyl-N6-phenylpseudouridines, and N1-alkyl-N6-halopseudouridines. In these examples, the alkyl, cycloalkyl, and phenyl substituents may be unsubstituted, or further substituted with alkyl, halo, haloalkyl, amino, or nitro substituents.

Examples of pseudouridines include N1-methylpseudouridine (also referred to herein as "N1MPU"), N1-ethylpseudouridine, N1-propylpseudouridine, N1-cyclopropylpseudouridine, N1-phenylpseudouridine, N1-aminomethylpseudouridine, N3-methylpseudouridine, N1-hydroxypseudouridine, and N1-hydroxymethylpseudouridine.

Examples of nucleic acid monomers include modified and chemically-modified nucleotides, including any such nucleotides known in the art.

Examples of modified and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of modified and chemically-modified nucleotide monomers include 3'-end stabilized nucleotides, 3'-glyceryl nucleotides, 3'-inverted abasic nucleotides, and 3'-inverted thymidine.

Examples of modified and chemically-modified nucleotide monomers include locked nucleic acid nucleotides (LNA), 2'-0,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides. In an exemplary embodiment, the modified monomer is a locked nucleic acid nucleotide (LNA).

Examples of modified and chemically-modified nucleotide monomers include 2',4'-constrained 2'-O-methoxyethyl (cMOE) and 2'-O-Ethyl (cEt) modified DNAs.

Examples of modified and chemically-modified nucleotide monomers include 2'-amino nucleotides, 2'-O-amino nucleotides, 2'-C-allyl nucleotides, and 2'-O-allyl nucleotides.

Examples of modified and chemically-modified nucleotide monomers include N6-methyladenosine nucleotides.

Examples of modified and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of modified and chemically-modified nucleotide monomers include 2'-O-aminopropyl substituted nucleotides.

Examples of modified and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Example of base modifications described above can be combined with additional modifications of nucleoside or nucleotide structure, including sugar modifications and linkage modifications. Certain modified or chemically-modified nucleotide monomers may be found in nature.

Preferred nucleotide modifications include N1-methylpseudouridine and 5-methoxyuridine.

Viral Replication Proteins and Polynucleotides Encoding Them

Provided herein, in some embodiments, are nucleic acid molecules comprising a first polynucleotide encoding one or more viral replication proteins. As used herein, the term "replication protein" or "viral replication protein" refers to any protein or any protein subunit of a protein complex that functions in replication of a viral genome. Generally, viral replication proteins are non-structural proteins. Viral replication proteins encoded by nucleic acid molecules provided herein can function in the replication of any viral genome. The viral genome can be a single-stranded positive-sense RNA genome, a single-stranded negative-sense RNA genome, a double-stranded RNA genome, a single-stranded positive-sense DNA genome, a single-stranded negative-sense DNA genome, or a double-stranded DNA genome. Viral genomes can include a single nucleic acid molecule or more than one nucleic acid molecule. Nucleic acid molecules provided herein can encode one or more viral replication proteins from any virus or virus family, including animal viruses and plant viruses, for example. Viral replication proteins encoded by first polynucleotides included in nucleic acid molecules provided herein can be expressed from self-replicating RNA.

First polynucleotide sequences of nucleic acid molecules provided herein can encode one or more togavirus replication proteins. In some aspects, the one or more viral replication proteins encoded by first polynucleotides of nucleic acid molecules provided herein are alphavirus proteins. In some embodiments, the one or more viral replication proteins encoded by first polynucleotides of nucleic acid molecules provided herein are rubivirus proteins. First polynucleotide sequences of nucleic acid molecules provided herein can encode any alphavirus replication protein and any rubivirus replication protein. Exemplary replication proteins from alphaviruses include proteins from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), Buggy Creek Virus (BCRV), and any combination thereof. Exemplary rubivirus replication proteins include proteins from rubella virus.

Viral replication proteins encoded by first polynucleotides of nucleic acid molecules provided herein can be expressed as one or more polyproteins or as separate or single proteins. Generally, polyproteins are precursor proteins that are cleaved to generate individual or separate proteins. Accordingly, proteins derived from a precursor polyprotein can be expressed from a single open reading frame (ORF). As used herein, the term "ORF" refers to a nucleotide sequence that begins with a start codon, generally ATG, and that ends with a stop codon, such as TAA, TAG, or TGA, for example. It will be appreciated that T is present in DNA, while U is present in RNA. Accordingly, a start codon of ATG in DNA corresponds to AUG in RNA, and the stop codons TAA, TAG, and TGA in DNA correspond to UAA, UAG, and UGA in RNA. It will further be appreciated that for any sequence provided in the present disclosure, T is present in DNA, while U is present in RNA. Accordingly, for any sequence provided herein, T present in DNA is substituted with U for an RNA molecule, and U present in RNA is substituted with T for a DNA molecule.

The protease cleaving a polyprotein can be a viral protease or a cellular protease. In some aspects, the first polynucleotide of nucleic acid molecules provided herein encodes a polyprotein comprising an alphavirus nsP1 protein, an alphavirus nsP2 protein, an alphavirus nsP3 protein, an alphavirus nsP4 protein, or any combination thereof. In other aspects, the first polynucleotide of nucleic acid molecules provided herein encodes a polyprotein comprising an alphavirus nsP1 protein, an alphavirus nsP2 protein, an alphavirus nsP3 protein, or any combination thereof, and an alphavirus nsP4 protein. In some aspects, the polyprotein is a VEEV polyprotein. In other aspects, the alphavirus nsP1, nsP2, nsP3, and nsP4 proteins are VEEV proteins.

In one aspect, first polynucleotides of nucleic acid molecules provided herein lack a stop codon between sequences encoding an nsP3 protein and an nsP4 protein. Accordingly, in some aspects, first polynucleotides of nucleic acid molecules provided herein encode a P1234 polyprotein comprising nsP1, nsP2, nsP3, and nsP4. First polynucleotides of nucleic acid molecules provided herein can also include a stop codon between sequences encoding an nsP3 and an nsP4 protein. Accordingly, in some aspects, first polynucleotides of nucleic acid molecules provided herein encode a P123 polyprotein comprising nsP1, nsP2, and nsP3 and a P1234 polyprotein comprising nsP1, nsP2, nsP3, and nsP4 as a result of stop codon readthrough, for example. In other aspects, first polynucleotides of nucleic acid molecules provided herein encode a polyprotein having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:79. In some embodiments, first polynucleotides of nucleic acid molecules provided herein encode a polyprotein having a sequence of SEQ ID NO:79. Further exemplary polyproteins comprise a sequence of SEQ ID NO:80 or SEQ ID NO:81. In one aspect, nsP2 and nsP3 proteins include mutations. Exemplary mutations include G1309R and S1583G mutations of VEEV proteins. In another aspect, the nsP1, nsP2, and nsP4 proteins are VEEV proteins, and the nsP3 protein is a chikungunya virus (CHIKV) nsP3 protein.

In some aspects, first polynucleotides of nucleic acid molecules provided herein can include a first intergenic region. In some aspects, the first intergenic region is located between a sequence encoding a polyprotein comprising an alphavirus nsP1 protein, an alphavirus nsP2 protein, an alphavirus nsP3 protein, or any combination thereof, and a sequence encoding an alphavirus nsP4 protein. A first intergenic region can comprise any sequence, such as any viral or non-viral sequence. In one aspect, the first intergenic region comprises a viral sequence. In another aspect, the first intergenic region comprises an alphavirus sequence. In yet another aspect, the alphavirus is VEEV. In one aspect, nsP2 and nsP3 proteins include mutations. Exemplary mutations include G1309R and S1583G mutations of VEEV proteins. In another aspect, the nsP1, nsP2, and nsP4 proteins are VEEV proteins, and the nsP3 protein is a chikungunya virus (CHIKV) nsP3 protein.

In some embodiments, the first polynucleotide may comprise a sequence having at least 80% identity to a sequence of SEQ ID NO:72.

In some embodiments, the nucleic acid molecule described herein may further comprise a second polynucleotide comprising a first transgene encoding a first antigenic protein or fragment thereof, wherein the first antigenic protein is a coronavirus protein. In specific embodiments, the antigenic protein may be a SARS-CoV-2 protein. In specific embodiments, the antigenic protein is a SARS-CoV-2 spike glycoprotein. In specific embodiments, the SARS-CoV-2 spike glycoprotein is a wild-type SARS-CoV-2 spike glycoprotein having an amino acid sequence of SEQ ID NO:123.

In some embodiments, the second polynucleotide comprises a sequence having at least 85% identity to a sequence of SEQ ID NO:121 or SEQ ID NO:122.

5' Untranslated Region (5' UTR)

Nucleic acid molecules provided herein can further comprise untranslated regions (UTRs). Untranslated regions, including 5' UTRs and 3' UTRs, for example, can affect RNA stability and/or efficiency of RNA translation, such as translation of cellular and viral mRNAs, for example. 5' UTRs and 3' UTRs can also affect stability and translation of viral genomic RNAs and self-replicating RNAs, including virally derived self-replicating RNAs or replicons. Exemplary viral genomic RNAs whose stability and/or efficiency of translation can be affected by 5' UTRs and 3' UTRs include the genome nucleic acid of positive-sense RNA viruses. Both genome nucleic acid of positive-sense RNA viruses and self-replicating RNAs, including virally derived self-replicating RNAs or replicons, can be translated upon infection or introduction into a cell.

In some aspects, nucleic acid molecules provided herein further include a 5' untranslated region (5' UTR). Any 5' UTR sequence can be included in nucleic acid molecules provided herein. In some embodiments, nucleic acid molecules provided herein include a viral 5' UTR. In one aspect, nucleic acid molecules provided herein include a non-viral 5' UTR. Any non-viral 5' UTR can be included in nucleic acid molecules provided herein, such as 5' UTRs of transcripts expressed in any cell or organ, including muscle, skin, subcutaneous tissue, liver, spleen, lymph nodes, antigen-presenting cells, and others. In another aspect, nucleic acid molecules provided herein include a 5' UTR comprising viral and non-viral sequences. Accordingly, a 5' UTR included in nucleic acid molecules provided herein can comprise a combination of viral and non-viral 5' UTR sequences. In some aspects, the 5' UTR included in nucleic acid molecules provided herein is located upstream of or 5' of the first polynucleotide that encodes one or more viral replication proteins. In other aspects, the 5' UTR is located 5' of or upstream of the first polynucleotide of nucleic acid molecules provided herein that encodes one or more viral replication proteins, and the first polynucleotide is located 5' of or upstream of the second polynucleotide of nucleic acid molecules provided herein.

In one aspect, the 5' UTR of nucleic acid molecules provided herein comprises an alphavirus 5' UTR. A 5' UTR from any alphavirus can be included in nucleic acid molecules provided herein, including 5' UTR sequences from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV). In another aspect, the 5' UTR comprises a sequence having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:73, SEQ ID NO:74, or SEQ ID NO:75. In yet another aspect, the 5' UTR comprises a sequence of SEQ ID NO:73, SEQ ID NO: 74, or SEQ ID NO:75.

In some embodiments, the 5' UTR comprises a sequence selected from the 5' UTRs of human IL-6, alanine aminotransferase 1, human apolipoprotein E, human fibrinogen alpha chain, human transthyretin, human haptoglobin, human alpha-1-antichymotrypsin, human antithrombin, human alpha-1-antitrypsin, human albumin, human beta globin, human complement C3, human complement C5, SynK (thylakoid potassium channel protein derived from the cyanobacteria, *Synechocystis* sp.), mouse beta globin, mouse albumin, and a tobacco etch virus, or fragments of any of the foregoing. Preferably, the 5' UTR is derived from a tobacco etch virus (TEV). Preferably, an mRNA described herein comprises a 5' UTR sequence that is derived from a gene expressed by *Arabidopsis thaliana*. Preferably, the 5' UTR sequence of a gene expressed by *Arabidopsis thaliana* is AT1G58420. Examples of 5 UTRs and 3' UTRs are described in PCT/US2018/035419, the contents of which are herein incorporated by reference. Preferred 5' UTR sequences comprise SEQ ID NOs: 5-10 and 25-45: as shown in Table 1.

TABLE 1

5′ UTR Sequences

| Name | Sequence | Seq ID No.: |
| --- | --- | --- |
| EV | UCAACACAACAUAUACAAAACAAACGAAUCUCAAGCAAUC AAGCAUUCUACUUCUAUUGCAGCAAUUUAAAUCAUUUCU UUUAAAGCAAAAGCAAUUUUCUGAAAAUUUUCACCAUUU ACGAACGAUAG | SEQ ID NO: 5 |
| AT1G58420 | AUUAUUACAUCAAAACAAAAAGCCGCCA | SEQ ID NO: 6 |
| ARC5-2 | CUUAAGGGGGCGCUGCCUACGGAGGUGGCAGCCAUCUCCU UCUCGGCAUCAAGCUUACCAUGGUGCCCCAGGCCCUGCUC UUGGUCCCGCUGCUGGUGUUCCCCCUCUGCUUCGGCAAGU UCCCCAUCUACACCAUCCCCGACAAGCUGGGGCCGUGGAG CCCCAUCGACAUCCACCACCUGUCCUGCCCCAACAACCUCG UGGUCGAGGACGAGGGCUGCACCAACCUGAGCGGGUUCUC CUAC | SEQ ID NO: 7 |

TABLE 1-continued

| 5′ UTR Sequences | | |
|---|---|---|
| Name | Sequence | Seq ID No.: |
| HCV | UGAGUGUCGU ACAGCCUCCA GGCCCCCCCC UCCCGGGAGA GCCAUAGUGG UCUGCGGAACCGGUGAGUAC ACCGGAAUUG CCGGGAAGAC UGGGUCCUUU CUUGGAUAAA CCCACUCUAUGCCCGGCCAU UUGGGCGUGC CCCCGCAAGA CUGCUAGCCG AGUAGUGUUG GGUUGCG | SEQ ID NO : 8 |
| HUMAN ALBUMIN | AAUUAUUGGUUAAAGAAGUAUAUUAGUGCUAAUUUCCCU CCGUUUGUCCUAGCUUUUCUCUUCUGUCAACCCCACACGC CUUUGGCACA | SEQ ID NO: 9 |
| EMCV | CUCCCUCCCC CCCCCCUAAC GUUACUGGCC GAAGCCGCUU GGAAUAAGGC CGGUGUGCGU UUGUCUAUAU GUUAUUUUCC ACCAUAUUGC CGUCUUUUGG CAAUGUGAGG GCCCGGAAAC CUGGCCCUGU CUUCUUGACG AGCAUUCCUA GGGGUCUUUC CCCUCUCGCC AAAGGAAUGC AAGGUCUGUU GAAUGUCGUG AAGGAAGCAG UUCCUCUGGA AGCUUCUUGA AGACAAACAA CGUCUGUAGC GACCCUUUGC AGGCAGCGGA ACCCCCCACC UGGCGACAGG UGCCUCUGCG GCCAAAAGCC ACGUGUAUAA GAUACACCUG CAAAGGCGGC ACAACCCCAG UGCCACGUUG UGAGUUGGAU AGUUGUGGAA AGAGUCAAAU GGCUCUCCUC AAGCGUAUUC AACAAGGGGC UGAAGGAUGC CCAGAAGGUA CCCCAUUGUA UGGGAUCUGA UCUGGGGCCU CGGUGCACAU GCUUUACGUG UGUUUAGUCG AGGUUAAAAA ACGUCUAGGC CCCCCGAACC ACGGGGACGU GGUUUUCCUU UGAAAAACAC GAUGAUAAU | SEQ ID NO: 10 |
| AT1G67090 | CACAAAGAGUAAAGAAGAACA | SEQ ID NO: 25 |
| AT1G35720 | AACACUAAAAGUAGAAGAAAA | SEQ ID NO: 26 |
| AT5G45900 | CUCAGAAAGAUAAGAUCAGCC | SEQ ID NO: 27 |
| AT5G61250 | AACCAAUCGAAAGAAACCAAA | SEQ ID NO: 28 |
| AT5G46430 | CUCUAAUCACCAGGAGUAAAA | SEQ ID NO: 29 |
| AT5G47110 | GAGAGAGAUCUUAACAAAAAA | SEQ ID NO: 30 |
| AT1G03110 | UGUGUAACAACAACAACAACA | SEQ ID NO: 31 |
| AT3G12380 | CCGCAGUAGGAAGAGAAAGCC | SEQ ID NO: 32 |
| AT5G45910 | AAAAAAAAAAGAAAUCAUAAA | SEQ ID NO: 33 |
| AT1G07260 | GAGAGAAGAAAGAAGAAGACG | SEQ ID NO: 34 |
| AT3G55500 | CAAUUAAAAAUACUUACCAAA | SEQ ID NO: 35 |
| AT3G46230 | GCAAACAGAGUAAGCGAAACG | SEQ ID NO: 36 |
| AT2G36170 | GCGAAGAAGACGAACGCAAAG | SEQ ID NO: 37 |
| AT1G10660 | UUAGGACUGUAUUGACUGGCC | SEQ ID NO: 38 |
| AT4G14340 | AUCAUCGGAAUUCGGAAAAAG | SEQ ID NO: 39 |
| AT1G49310 | AAAACAAAAGUUAAAGCAGAC | SEQ ID NO: 40 |
| AT4G14360 | UUUAUCUCAAAUAAGAAGGCA | SEQ ID NO: 41 |
| AT1G28520 | GGUGGGGAGGUGAGAUUUCUU | SEQ ID NO: 42 |
| AT1G20160 | UGAUUAGGAAACUACAAAGCC | SEQ ID NO: 43 |
| AT5G37370 | CAUUUUUCAAUUUCAUAAAAC | SEQ ID NO: 44 |
| AT4G11320 | UUACUUUUAAGCCCAACAAAA | SEQ ID NO: 45 |
| AT5G40850 | GGCGUGUGUGUGUGUUGUUGA | SEQ ID NO: 46 |

TABLE 1-continued

| 5′ UTR Sequences | | |
|---|---|---|
| Name | Sequence | Seq ID No.: |
| AT1G06150 | GUGGUGAAGGGGAAGGUUUAG | SEQ ID NO: 47 |
| AT2G26080 | UUGUUUUUUUUUUGGUUUGGUU | SEQ ID NO: 48 |

3' Untranslated Region (3' UTR)

In some aspects, nucleic acid molecules provided herein further include a 3' untranslated region (3' UTR). Any 3' UTR sequence can be included in nucleic acid molecules provided herein. In one aspect, nucleic acid molecules provided herein include a viral 3' UTR. In another aspect, nucleic acid molecules provided herein include a non-viral 3' UTR. Any non-viral 3' UTR can be included in nucleic acid molecules provided herein, such as 3' UTRs of transcripts expressed in any cell or organ, including muscle, skin, subcutaneous tissue, liver, spleen, lymph nodes, antigen-presenting cells, and others. In some aspects, nucleic acid molecules provided herein include a 3' UTR comprising viral and non-viral sequences. Accordingly, a 3' UTR included in nucleic acid molecules provided herein can comprise a combination of viral and non-viral 3' UTR sequences. In one aspect, the 3' UTR is located 3' of or downstream of the second polynucleotide of nucleic acid molecules provided herein that comprises a first transgene encoding a first antigenic protein or a fragment thereof. In another aspect, the 3' UTR is located 3' of or downstream of the second polynucleotide of nucleic acid molecules provided herein that comprises a first transgene encoding a first antigenic protein or a fragment thereof, and the second polynucleotide is located 3' of or downstream of the first polynucleotide of nucleic acid molecules provided herein.

In one aspect, the 3' UTR of nucleic acid molecules provided herein comprises an alphavirus 3' UTR. A 3' UTR from any alphavirus can be included in nucleic acid molecules provided herein, including 3' UTR sequences from Venezuelan Equine Encephalitis Virus (VEEV), Eastern Equine Encephalitis Virus (EEEV), Everglades Virus (EVEV), Mucambo Virus (MUCV), Semliki Forest Virus (SFV), Pixuna Virus (PIXV), Middleburg Virus (MIDV), Chikungunya Virus (CHIKV), O'Nyong-Nyong Virus (ONNV), Ross River Virus (RRV), Barmah Forest Virus (BFV), Getah Virus (GETV), Sagiyama Virus (SAGV), Bebaru Virus (BEBV), Mayaro Virus (MAYV), Una Virus (UNAV), Sindbis Virus (SINV), Aura Virus (AURAV), Whataroa Virus (WHAV), Babanki Virus (BABV), Kyzylagach Virus (KYZV), Western Equine Encephalitis Virus (WEEV), Highland J Virus (HJV), Fort Morgan Virus (FMV), Ndumu Virus (NDUV), Salmonid Alphavirus (SAV), or Buggy Creek Virus (BCRV). In another aspect, the 3' UTR comprises a sequence having at least 80%, at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:76. In yet another aspect, the 3' UTR comprises a poly-A sequence. In a further aspect, the 3' UTR comprises a sequence of SEQ ID NO:76.

In some embodiments, the 3' UTR comprises a sequence selected from the 3' UTRs of alanine aminotransferase 1, human apolipoprotein E, human fibrinogen alpha chain, human haptoglobin, human antithrombin, human alpha globin, human beta globin, human complement C3, human growth factor, human hepcidin, MALAT-1, mouse beta globin, mouse albumin, and Xenopus beta globin, or fragments of any of the foregoing. In some embodiments, the 3' UTR is derived from Xenopus beta globin. Exemplary 3' UTR sequences include SEQ ID NOs: 16-22 as shown in Table 2.

TABLE 2

| 3′ UTR sequences. | | |
|---|---|---|
| Name | Sequence | Seq ID No.: |
| XBG | CUAGUGACUGACUAGGAUCUGGUUACCACUAAACCAG<br>CCUCAAGAACACCCGAAUGGAGUCUCUAAGCUACAUA<br>AUACCAACUUACACUUACAAAAUGUUGUCCCCCAAAA<br>UGUAGCCAUUCGUAUCUGCUCCUAAUAAAAAGAAAGU<br>UUCUUCACAU | SEQ ID NO: 16 |
| HUMAN HAPTOGLOBIN | UGCAAGGCUGGCCGGAAGCCCUUGCCUGAAAGCAAGA<br>UUUCAGCCUGGAAGAGGGCAAAGUGGACGGGAGUGG<br>ACAGGAGUGGAUGCGAUAAGAUGUGGUUUGAAGCUG<br>AUGGGUGCCAGCCCUGCAUUGCUGAGUCAAUCAAUAA<br>AGAGCUUUCUUUUGACCCAU | SEQ ID NO: 17 |
| HUMAN APOLIPO-PROTEIN E | ACGCCGAAGCCUGCAGCCAUGCGACCCCACGCCACCCC<br>GUGCCUCCUGCCUCCGCGCAGCCUGCAGCGGGAGACC<br>CUGUCCCCGCCCCAGCCGUCCUCCUGGGGUGGACCCU<br>AGUUUAAUAAAGAUUCACCAAGUUUCACGCA | SEQ ID NO: 18 |
| HCV | UAGAGCGGCAAACCCUAGCUACACUCCAUAGCUAGUU<br>UCUUUUUUUUUUGUUUUUUUUUUUUUUUUUUUUUUU<br>UUUUUUUUUUUUUUUUUCCUUUCUUUUCCUUCUUUUU<br>UUCCUCUUUUCUUGGUGGCUCCAUCUUAGCCCUAGUC<br>ACGGCUAGCUGUGAAAGGUCCGUGAGCCGCAUGACUG<br>CAGAGAGUGCCGUAACUGGUCUCUCUGCAGAUCAUGU | SEQ ID NO: 19 |

TABLE 2-continued

| 3′ UTR sequences. | | |
|---|---|---|
| Name | Sequence | Seq ID No.: |
| MOUSE ALBUMIN | ACACAUCACAACCACAACCUUCUCAGGCUACCCUGAG AAAAAAAGACAUGAAGACUCAGGACUCAUCUUUUCUG UUGGUGUAAAAUCAACACCCUAAGGAACACAAAUUUC UUUAAACAUUUGACUUCUUGUCUCUGUGCUGCAAUUA AUAAAAAAUGGAAAGAAUCUAC | SEQ ID NO: 20 |
| HUMAN ALPHA GLOBIN | GCUGGAGCCUCGGUAGCCGUUCCUCCUGCCCGCUGGG CCUCCCAACGGGCCCUCCUCCCCUCCUUGCACCGGCCC UUCCUGGUCUUUGAAUAAAGUCUGAGUGGGCAGCA | SEQ ID NO: 21 |
| EMCV | UAGUGCAGUCAC UGGCACAACG CGUUGCCCGG UAAGCCAAUC GGGUAUACAC GGUCGUCAUACUGCAGACAG GGUUCUUCUA CUUUGCAAGA UAGUCUAGAG UAGUAAAAUA AAUAGUAUAAG | SEQ ID NO: 22 |

Triple Stop Codon

In some embodiments, the self-replicating RNA may comprise a sequence immediately downstream of a coding region (i.e., ORF) that creates a triple stop codon. A triple stop codon is a sequence of three consecutive stop codons. The triple stop codon can ensure total insulation of an expression cassette and may be incorporated to enhance the efficiency of translation. In some embodiments, a self-replicating RNA of the disclosure may comprise a triple combination of any of the sequences UAG, UGA, or UAA immediately downstream of a ORF described herein. The triple combination can be three of the same codons, three different codons, or any other permutation of the three stop codons.

Translation Enhancers and Kozak Sequences

For translation initiation, proper interactions between ribosomes and mRNAs must be established to determine the exact position of the translation initiation region. However, ribosomes also must dissociate from the translation initiation region to slide toward the downstream sequence during mRNA translation. Translation enhancers upstream from initiation sequences of mRNAs enhance the yields of protein biosynthesis. Several studies have investigated the effects of translation enhancers. In some embodiments, an mRNA described herein comprises a translation enhancer sequence. These translation enhancer sequences enhance the translation efficiency of a self-replicating RNA of the disclosure and thereby provide increased production of the protein encoded by the mRNA. The translation enhancer region may be located in the 5' or 3' UTR of an mRNA sequence. Examples of translation enhancer regions include naturally-occurring enhancer regions from the TEV 5' UTR and the Xenopus beta-globin 3' UTR. Exemplary 5' UTR enhancer sequences include but are not limited to those derived from mRNAs encoding human heat shock proteins (HSP) including HSP70-P2, HSP70-M1 HSP72-M2, HSP17.9 and HSP70-P1. Preferred translation enhancer sequences used in accordance with the embodiments of the present disclosure are represented by SEQ ID Nos: 11-15 as shown in Table 3.

TABLE 3

| 5′ UTR Enhancers | | |
|---|---|---|
| Name | Sequence | Seq ID No.: |
| HSP70-P2 | GUCAGCUUUCAAACUCUUUGUUUCUUGUUU GUUGAUUGAGAAUA | SEQ ID NO: 11 |

TABLE 3-continued

| 5′ UTR Enhancers | | |
|---|---|---|
| Name | Sequence | Seq ID No.: |
| HSP70-M1 | CUCUCGCCUGAGAAAAAAAAUCCACGAACC AAUUUCUCAGCAACCAGCAGCACG | SEQ ID NO: 12 |
| HISP72-M2 | ACCUGUGAGGGUUCGAAGGAAGUAGCAGUG UUUUUUGUUCCUAGAGGAAGAG | SEQ ID NO: 13 |
| HSP17.9 | ACACAGAAACAUUCGCAAAAACAAAAUCCC AGUAUCAAAAUUCUUCUCUUUUUUUCAUAU UUCGCAAAGAC | SEQ ID NO: 14 |
| HSP70-P1 | CAGAAAAAUUUGCUACAUUGUUUCACAAAC UUCAAAUAUUAUUCAUUUAUUU | SEQ ID NO: 15 |

In some embodiments, a self-replicating RNA of the disclosure comprises a Kozak sequence. As is understood in the art, a Kozak sequence is a short consensus sequence centered around the translational initiation site of eukaryotic mRNAs that allows for efficient initiation of translation of the mRNA. See, for example, Kozak, Marilyn (1988) Mol. and Cell Biol, 8:2737-2744; Kozak, Marilyn (1991) J. Biol. Chem, 266: 19867-19870; Kozak, Marilyn (1990) Proc Natl. Acad. Sci. USA, 87:8301-8305; and Kozak, Marilyn (1989) J. Cell Biol, 108:229-241. It ensures that a protein is correctly translated from the genetic message, mediating ribosome assembly and translation initiation. The ribosomal translation machinery recognizes the AUG initiation codon in the context of the Kozak sequence. A Kozak sequence may be inserted upstream of the coding sequence for the protein of interest, downstream of a 5' UTR or inserted upstream of the coding sequence for the protein of interest and downstream of a 5' UTR. In some embodiments, a self-replicating RNA described herein comprises a Kozak sequence having the amino acid sequence GCCACC (SEQ ID NO: 23). Preferably a self-replicating RNA described herein comprises a partial Kozak sequence "p" having the amino acid sequence GCCA (SEQ ID NO: 24).

Transgenes

Transgenes included in nucleic acid molecules provided herein can encode an antigenic protein or a fragment thereof. In some embodiments, second polynucleotides of nucleic acid molecules provided herein comprise a first transgene. A first transgene included in second polynucleotides of nucleic acid molecules provided herein can encode a first antigenic protein or a fragment thereof. A transgene included in second polynucleotides of nucleic acid molecules provided herein can comprise a sequence encoding the full amino acid sequence of an antigenic protein or a sequence encoding any suitable portion or fragment of the full amino acid sequence of an antigenic protein. In some embodiments, the antigenic protein is a coronavirus protein.

In another embodiment, the antigenic protein, when administered to a mammalian subject, raises an immune response to a pathogen, such as a coronavirus. In some more particular embodiments, the antigenic protein is expressed on the outer surface of the coronavirus; while in other more particular embodiments, the antigen may be a non-surface antigen, e.g., useful as a T-cell epitope. The immunogen may elicit an immune response against a coronavirus. The immune response may comprise an antibody response (usually including IgG) and/or a cell mediated immune response. The polypeptide immunogen will typically elicit an immune response that recognizes the corresponding coronavirus The immunogen will typically be a surface polypeptide e.g. an envelope glycoprotein, a spike glycoprotein, etc.

In some aspects, the viral protein encoded by transgenes included in nucleic acid molecules provided herein is a coronavirus protein. In some embodiments, the antigenic protein is a SARS-CoV-2 protein.

In one aspect, the antigenic protein is a SARS-CoV-2 spike glycoprotein or a fragment thereof. In another aspect, the SARS-CoV-2 spike glycoprotein is a wild-type SARS-CoV-2 spike glycoprotein. In some aspects, the wild-type SARS-CoV-2 spike glycoprotein has an amino acid sequence of SEQ ID NO:123. In yet another aspect, the second polynucleotide of nucleic acid molecules provided herein comprises a sequence having at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, identity to a sequence of SEQ ID NO:121 or SEQ ID NO:122. In another aspect, the second polynucleotide of nucleic acid molecules provided herein comprises a sequence of SEQ ID NO:121 or SEQ ID NO:122. Accordingly, in some aspects, first transgenes included in second polynucleotides of nucleic acid molecules provided herein comprise a sequence having at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, or 100% identity to a sequence of SEQ ID NO:121 or SEQ ID NO:122.

In one aspect, the second polynucleotide of nucleic acid molecules provided herein encodes a wild-type SARS-CoV-2 spike glycoprotein or a fragment thereof. In some aspects, a wild-type SARS-CoV-2 spike glycoprotein comprises a sequence of SEQ ID NO:123. In another aspect, the second polynucleotide of nucleic acid molecules provided herein encodes a SARS-CoV-2 spike protein comprising one or more mutations as compared to a wild-type SARS-CoV-2 spike glycoprotein sequence. Mutations can include substitutions, deletions, insertions, and others. Mutations can be present at any position or at any combination of positions of a SARS-CoV-2 spike glycoprotein. Any number of substitutions, insertions, deletions, or combinations thereof, can be present at any one or more positions of a SARS-CoV-2 spike glycoprotein. As an example, substitutions can include a change of a wild-type amino acid at any position or at any combination of positions to any other amino acid or combination of any other amino acids. Exemplary mutations include mutations at positions 614, 936, 320, 477, 986, 987, or any combination thereof. In one aspect, a SARS-CoV-2 spike glycoprotein or a fragment thereof encoded by transgenes of second polynucleotides included in nucleic acid molecules provided herein includes a D614G mutation, a D936Y mutation, a D936H mutation, a V320G mutation, an S477N mutation, an S477I mutation, an S477T mutation, a K986P mutation, a V987P mutation, or any combination thereof. Additional mutations and variants can be found in the National Bioinformatics Center 2019 Novel Coronavirus Information Database (2019nCoVR), National Genomics Data Center, China National Center for Bioinformation/Beijing Institute of Genomics, Chinese Academy of Science at bigd.big.ac.cn/ncov/variation/annotation. In another aspect, the second polynucleotide includes a transgene encoding a SARS-CoV-2 glycoprotein having at least 85%, at least 90%, at least 91%, at least 92%, at least 93%, at least 94%, at least 95%, at least 96%, at least 97%, at least 97.5%, at least 98%, at least 98.5%, at least 99%, at least 99.5%, at least 99.6%, at least 99.7%, at least 99.8%, at least 99.9%, and any number or range in between, or 100% identity to a sequence of SEQ ID NO:123.

In some aspects, the second polynucleotide of nucleic acid molecules provided herein comprises at least two transgenes, such as a second coronavirus protein. Any number of transgenes can be included in second polynucleotides of nucleic acid molecules provided herein, such as one, two, three, four, five, six, seven, eight, nine, ten, or more transgenes. In one aspect, the second polynucleotide of nucleic acid molecules provided herein includes a second transgene encoding a second antigenic protein or a fragment thereof or an immunomodulatory protein. In one aspect, the second polynucleotide further comprises an internal ribosomal entry site (IRES), a sequence encoding a 2A peptide, or a combination thereof, located between transgenes. As used herein, the term "2A peptide" refers to a small (generally 18-22 amino acids) sequence that allows for efficient, stoichiometric production of discrete protein products within a single reading frame through a ribosomal skipping event within the 2A peptide sequence. As used herein, the term "internal ribosomal entry site" or "IRES" refers to a nucleotide sequence that allows for the initiation of protein translation of a messenger RNA (mRNA) sequence in the absence of an AUG start codon or without using an AUG start codon. An IRES can be found anywhere in an mRNA sequence, such as at or near the beginning, at or near the middle, or at or near the end of the mRNA sequence, for example.

Any number of transgenes included in second polynucleotides of nucleic acid molecules provided herein can be expressed via any combination of 2A peptide and IRES sequences. For example, a second transgene located 3' of a first transgene can be expressed via a 2A peptide sequence or via an IRES sequence. As another example, a second transgene located 3' of a first transgene and a third transgene located 3' of the second transgene can be expressed via 2A peptide sequences located between the first and second transgenes and the second and third transgenes, via an IRES sequence located between the first and second transgenes and the second and third transgenes, via a 2A peptide sequence located between the first and second transgenes and an IRES located between the second and third transgenes, or via an IRES sequence located between the first and second transgenes and a 2A peptide sequence located between the second and third transgenes. Similar configurations and combinations of 2A peptide and IRES sequences located between transgenes are contemplated for any number of transgenes included in second polynucleotides of nucleic acid molecules provided herein. In addition to expression via 2A peptide and IRES sequences, two or more transgenes included in nucleic acid molecules provided herein can also be expressed from separate subgenomic RNAs.

A second, third, fourth, fifth, sixth, seventh, eighth, ninth, tenth, etc., transgene included in second polynucleotides of nucleic acid molecules provided herein can encode an immunomodulatory protein or a functional fragment or functional variant thereof. Any immunomodulatory protein or a functional fragment or functional variant thereof can be encoded by a transgene included in second polynucleotides.

As used herein, the terms "functional variant" or "functional fragment" refer to a molecule, including a nucleic acid or protein, for example, that comprises a nucleotide and/or amino acid sequence that is altered by one or more nucleotides and/or amino acids compared to the nucleotide and/or amino acid sequences of the parent or reference molecule. For a protein, a functional variant is still able to function in a manner that is similar to the parent molecule. In other words, the modifications in the amino acid and/or nucleotide sequence of the parent molecule do not significantly affect or alter the functional characteristics of the molecule encoded by the nucleotide sequence or containing the amino acid sequence. The functional variant may have conservative sequence modifications including nucleotide and amino acid substitutions, additions and deletions. These modifications can be introduced by standard techniques known in the art, such as site-directed mutagenesis and random PCR-mediated mutagenesis. Functional variants can also include, but are not limited to, derivatives that are substantially similar in primary structural sequence, but which contain, e.g., in vitro or in vivo modifications, chemical and/or biochemical, that are not found in the parent molecule. Such modifications include, inter alia, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI-anchor formation, hydroxylation, iodination, methylation, myristoylation, oxidation, pegylation, proteolytic processing, phosphorylation, prenylation, racemization, selenoylation, sulfation, transfer-RNA-mediated addition of amino acids to proteins such as arginylation, ubiquitination, and the like.

In one aspect, a second transgene included in second polynucleotides of nucleic acid molecules provided herein encodes a cytokine, a chemokine, or an interleukin. Exemplary cytokines include interferons, TNF-α, TGF-β, G-CSF, and GM-CSF. Exemplary chemokines include CCL3, CCL26, and CXCL7. Exemplary interleukins include IL-I, IL-2, IL-3, IL-4, IL-5, IL-6, IL-7, IL-8, IL-10, IL-12, IL-15, IL-18, IL-21, and IL-23. Any transgene or combination of transgenes encoding any cytokine, chemokine, interleukin, or combinations thereof, can be included in second polynucleotides of nucleic acid molecules provided herein.

In some embodiments, the second transgene encodes a second coronavirus protein.

DNA and RNA Molecules

Nucleic acid molecules provided herein can be DNA molecules or RNA molecules. It will be appreciated that T present in DNA is substituted with U in RNA, and vice versa. In one aspect, nucleic acid molecules provided herein are DNA molecules. In another aspect, DNA molecules provided herein further comprise a promoter. As used herein, the term "promoter" refers to a regulatory sequence that initiates transcription. A promoter can be operably linked to first and second polynucleotides of nucleic acid molecules provided herein. Generally, promoters included in DNA molecules provided herein include promoters for in vitro transcription (IVT). Any suitable promoter for in vitro transcription can be included in DNA molecules provided herein, such as a T7 promoter, a T3 promoter, an SP6 promoter, and others. In one aspect, DNA molecules provided herein comprise a T7 promoter. In another aspect, the promoter is located 5' of the 5' UTR included in DNA molecules provided herein. In yet another aspect, the promoter is a T7 promoter located 5' of the 5' UTR included in DNA molecules provided herein. In yet another aspect, the promoter overlaps with the 5' UTR. A promoter and a 5' UTR can overlap by about one nucleotide, about two nucleotides, about three nucleotides, about four nucleotides, about five nucleotides, about six nucleotides, about seven nucleotides, about eight nucleotides, about nine nucleotides, about ten nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, about 50 nucleotides, or more nucleotides.

In some aspects, DNA molecules provided herein include a promoter for in vivo transcription. Generally, the promoter for in vivo transcription is an RNA polymerase II (RNA pol II) promoter. Any RNA pol II promoter can be included in DNA molecules provided herein, including constitutive promoters, inducible promoters, and tissue-specific promoters. Exemplary constitutive promoters include a cytomegalovirus (CMV) promoter, an EF1α promoter, an SV40 promoter, a PGK1 promoter, a Ubc promoter, a human beta actin promoter, a CAG promoter, and others. Any tissue-specific promoter can be included in DNA molecules provided herein. In one aspect, the RNA pol II promoter is a muscle-specific promoter, skin-specific promoter, subcutaneous tissue-specific promoter, liver-specific promoter, spleen-specific promoter, lymph node-specific promoter, or a promoter with any other tissue specificity. DNA molecules provided herein can also include an enhancer. Any enhancer that increases transcription can be included in DNA molecules provided herein.

In some aspects, nucleic acid molecules provided herein are RNA molecules. An RNA molecule provided herein can be generated by in vitro transcription (IVT) of DNA molecules provided herein. In one aspect, RNA molecules provided herein are self-replicating RNA molecules. In another aspect, RNA molecules provided herein further comprise a 5' cap. Any 5' cap can be included in RNA molecules provided herein, including 5' caps having a Cap 1 structure, a Cap 1 (m6A) structure, a Cap 2 structure, a Cap 0 structure, or any combination thereof. In one aspect, RNA molecules provided herein include a 5' cap having Cap 1 structure. In yet another aspect, RNA molecules provided herein are self-replicating RNA molecules comprising a 5' cap having a Cap 1 structure. In a further aspect, RNA molecules provided herein comprise a cap having a Cap 1 structure, wherein a m7G is linked via a 5'-5' triphosphate to the 5' end of the 5' UTR. In yet a further aspect, RNA molecules provided herein comprise a cap having a Cap 1 structure, wherein a m7G is linked via a 5'-5' triphosphate to the 5' end of the 5' UTR comprising a sequence of SEQ ID NO:73. Any method of capping can be used, including, but not limited to using a Vaccinia Capping enzyme (New England Biolabs, Ipswich, Mass.) and co-transcriptional capping or capping at or shortly after initiation of in vitro transcription (IVT), by for example, including a capping agent as part of an in vitro transcription (IVT) reaction. (Nuc. Acids Symp. (2009) 53:129).

Provided herein, in some embodiments, are nucleic acid molecules comprising (a) a sequence of SEQ ID NO:10; (b) a sequence of SEQ ID NO:72, SEQ ID NO:73, SEQ ID NO:76, and SEQ ID NO:77, wherein T is substituted with U; (c) a sequence of SEQ ID NO: 124; (d) a sequence of SEQ ID NO:124, wherein T is substituted with U; (e) a sequence of SEQ ID NO:125; or (f) a sequence of SEQ ID NO:125, wherein T is substituted with U. In one aspect, nucleic acid molecules provided herein are RNA molecules. In another aspect, RNA molecules provided herein further comprise a 5' cap having a Cap 1 structure. Any RNA molecules provided herein can be self-replicating RNA molecules.

Only those mRNAs that carry the Cap structure are active in Cap dependent translation; "decapitation" of mRNA results in an almost complete loss of their template activity for protein synthesis (Nature, 255:33-37, (1975); J. Biol. Chem., vol. 253:5228-5231, (1978); and Proc. Natl. Acad. Sci. USA, 72:1189-1193, (1975)).

Another element of eukaryotic mRNA is the presence of 2'-O-methyl nucleoside residues at transcript position 1 (Cap 1), and in some cases, at transcript positions 1 and 2 (Cap 2). The 2'-O-methylation of mRNA provides higher efficacy of mRNA translation in vivo (Proc. Natl. Acad. Sci. USA, 77:3952-3956 (1980)) and further improves nuclease stability of the 5'-capped mRNA. The mRNA with Cap 1 (and Cap 2) is a distinctive mark that allows cells to recognize the bona fide mRNA 5' end, and in some instances, to discriminate against transcripts emanating from infectious genetic elements (Nucleic Acid Research 43: 482-492 (2015)).

Some examples of 5' cap structures and methods for preparing mRNAs comprising the same are given in WO2015/051169A2, WO/2015/061491, US 2018/0273576, and U.S. Pat. Nos. 8,093,367, 8,304,529, and 10,487,105. In some embodiments, the 5' cap is m7GpppAmpG, which is known in the art. In some embodiments, the 5' cap is m7GpppG or m7GpppGm, which are known in the art. Structural formulas for embodiments of 5' cap structures are provided below.

In some embodiments, a self-replicating RNA of the disclosure comprises a 5' cap having the structure of Formula (Cap I).

(Cap I)

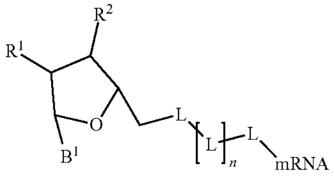

wherein $B^1$ is a natural or modified nucleobase; $R^1$ and $R^2$ are each independently selected from a halogen, OH, and $OCH_3$; each L is independently selected from the group consisting of phosphate, phophorothioate, and boranophosphate wherein each L is linked by diester bonds; n is 0 or 1. and mRNA represents an mRNA of the present disclosure linked at its 5' end. In some embodiments $B^1$ is G, $m^7G$, or A. In some embodiments, n is 0. In some embodiments n is 1. In some embodiments, $B^1$ is A or $m^6A$ and $R^1$ is $OCH_3$; wherein G is guanine, $m^7G$ is 7-methylguanine, A is adenine, and $m^6A$ is $N^6$-methyladenine.

In some embodiments, a self-replicating RNA of the disclosure comprises a 5' cap having the structure of Formula (Cap II).

(Cap II)

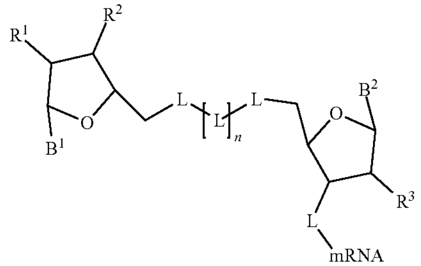

wherein $B^1$ and $B^2$ are each independently a natural or modified nucleobase; $R^1$, $R^2$, and $R^3$ are each independently selected from a halogen, OH, and $OCH_3$; each L is independently selected from the group consisting of phosphate, phophorothioate, and boranophosphate wherein each L is linked by diester bonds; mRNA represents an mRNA of the present disclosure linked at its 5' end; and n is 0 or 1. In some embodiments $B^1$ is G, $m^7G$, or A. In some embodiments, n is 0. In some embodiments, n is 1. In some embodiments, $B^1$ is A or $m^6A$ and $R^1$ is $OCH_3$; wherein G is guanine, $m^7G$ is 7-methylguanine, A is adenine, and $m^6A$ is $N^6$-methyladenine.

In some embodiments, a self-replicating RNA of the disclosure comprises a 5' cap having the structure of Formula (Cap III).

(Cap III)

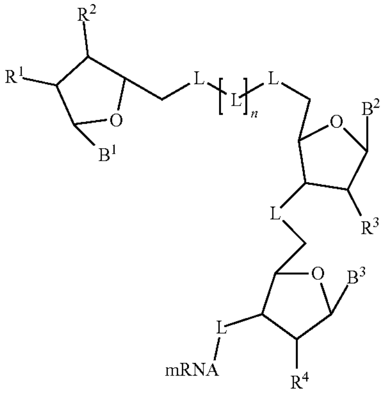

wherein B1, B2, and B3 are each independently a natural or modified nucleobase; R1, R2, R3, and R4 are each independently selected from a halogen, OH, and OCH3; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of R1, R2, R3, and R4 is OH. In some embodiments B1 is G, m7G, or A. In some embodiments, B1 is A or m6A and R1 is OCH3; wherein G is guanine, m7G is 7-methylguanine, A is adenine, and m6A is N6-methyladenine. In some embodiments, n is 1.

In some embodiments, a self-replicating RNA of the disclosure comprises a m7GpppG 5' cap analog having the structure of Formula (Cap IV).

(Cap IV)

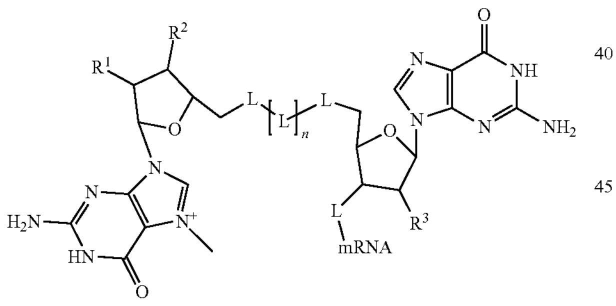

wherein, $R^1$, $R^2$, and $R^3$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; n is 0 or 1. In some embodiments, at least one of $R^1$, $R^2$, and $R^3$ is OH. In some embodiments, the 5' cap is $m^7GpppG$ wherein $R^1$, $R^2$, and $R^3$ are each OH, n is 1, and each L is a phosphate. In some embodiments, n is 1. In some embodiments, the 5' cap is m7GpppGm, wherein $R^1$ and $R^2$ are each OH, $R^3$ is $OCH_3$, each L is a phosphate, mRNA is the mRNA encoding an enzyme having OTC activity linked at its 5' end, and n is 1.

In some embodiments, a self-replicating RNA of the disclosure comprises a m7Gpppm7G 5' cap analog having the structure of Formula (Cap V).

(Cap V)

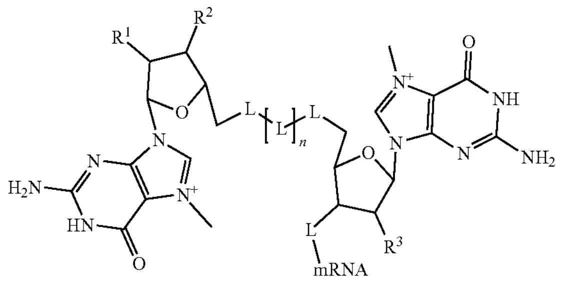

wherein, $R^1$, $R^2$, and $R^3$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^3$ is OH. In some embodiments, n is 1.

In some embodiments, a self-replicating RNA of the disclosure comprises a m7Gpppm7GpN, 5' cap analog, wherein N is a natural or modified nucleotide, the 5' cap analog having the structure of Formula (Cap VI).

(Cap VI)

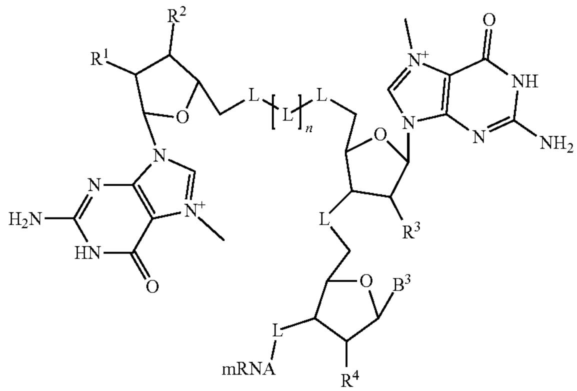

wherein $B^3$ is a natural or modified nucleobase; $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 3. In some embodiments, at least one of $R^1$, $R^2$, $R^3$, and $R^4$ is OH. In some embodiments $B^1$ is G, $m^7G$, or A. In some embodiments, $B^1$ is A or $m^6A$ and $R^1$ is $OCH_3$; wherein G is guanine, $m^7G$ is 7-methylguanine, A is adenine, and $m^6A$ is $N^6$-methyladenine. In some embodiments, n is 1.

In some embodiments, a self-replicating RNA of the disclosure comprises a m7Gpppm7GpG 5' cap analog having the structure of Formula (Cap VII).

(Cap VII)

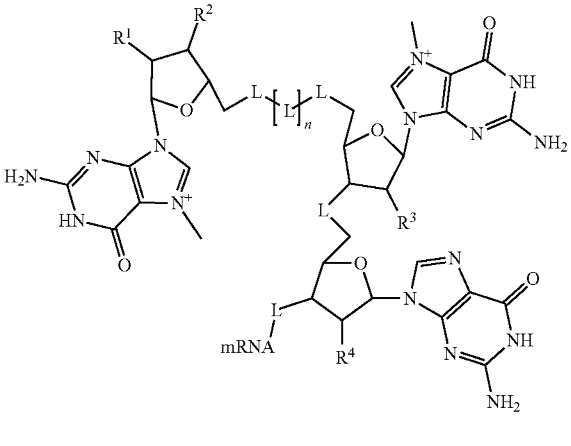

wherein, $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments, n is 1.

In some embodiments, a self-replicating RNA of the disclosure comprises a m7Gpppm7Gpm7G 5' cap analog having the structure of Formula (Cap VIII).

(Cap VIII)

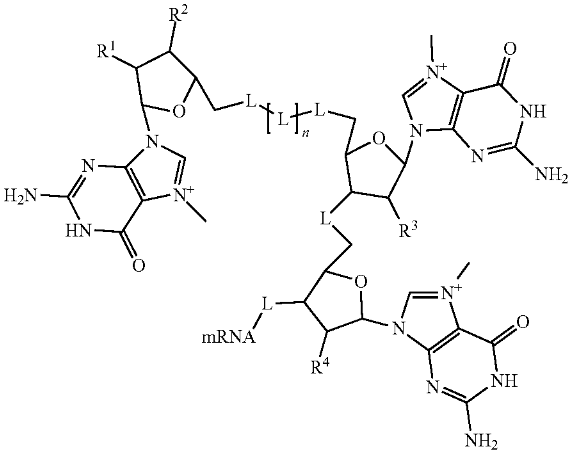

wherein, $R^1$, $R^2$, $R^3$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; n is 0 or 1. In some embodiments, at least one of $R^1$, $R^2$, $R^3$, and $R^4$ is OH. In some embodiments, n is 1.

In some embodiments, a self-replicating RNA of the disclosure comprises a m7GpppA 5' cap analog having the structure of Formula (Cap IX).

(Cap IX)

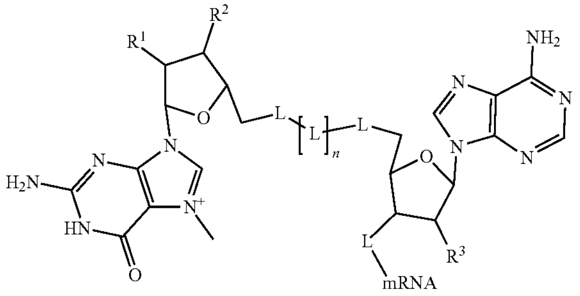

wherein, $R^1$, $R^2$, and $R^3$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^3$ is OH. In some embodiments, n is 1.

In some embodiments, a self-replicating RNA of the disclosure comprises a m7GpppApN 5' cap analog, wherein N is a natural or modified nucleotide, and the 5' cap has the structure of Formula (Cap X).

(Cap X)

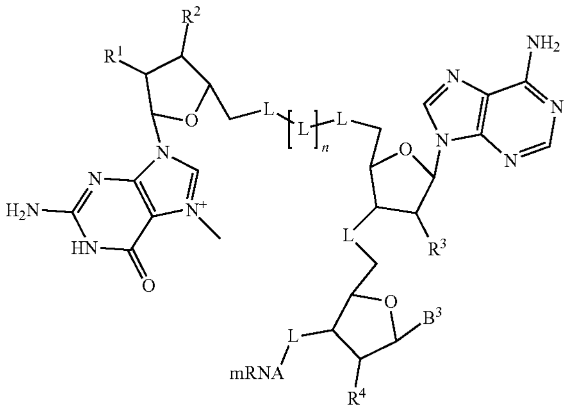

wherein $B^3$ is a natural or modified nucleobase; $R^1$, $R^2$, $R^3$, and $R^4$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments $B^3$ is G, $m^7G$, A or $m^6A$; wherein G is guanine, $m^7G$ is 7-methylguanine, A is adenine, and $m^6A$ is $N^6$-methyladenine. In some embodiments, n is 1.

In some embodiments, a self-replicating RNA of the disclosure comprises a m7GpppAmpG 5' cap analog having the structure of Formula (Cap XI).

(Cap XI)

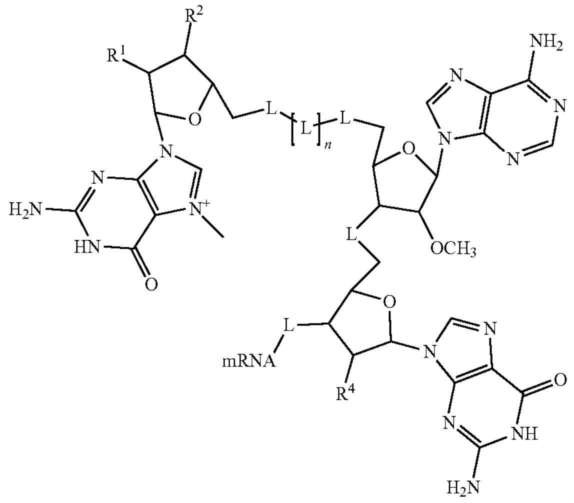

wherein, $R^1$, $R^2$, and $R^4$ are each independently selected from a halogen, OH, and $OCH_3$; each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^4$ is OH. In some embodiments, the compound of Formula Cap XI is $m^7$GpppAmpG, wherein $R^1$, $R^2$, and $R^4$ are each OH, n is 1, and each L is a phosphate linkage. In some embodiments, n is 1.

In some embodiments, a self-replicating RNA of the disclosure comprises a m7GpppApm7G 5' cap analog having the structure of Formula (Cap XII).

(Cap XII)

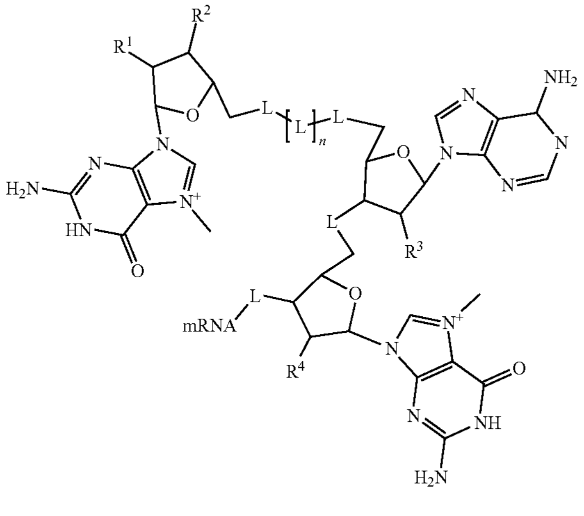

wherein, $R^1$, $R^2$, $R^3$, and $R^4$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, $R^3$, and $R^4$ is OH. In some embodiments, n is 1.

In some embodiments, a self-replicating RNA of the disclosure comprises a m7GpppApm7G 5' cap analog having the structure of Formula (Cap XIII).

(Cap XIII)

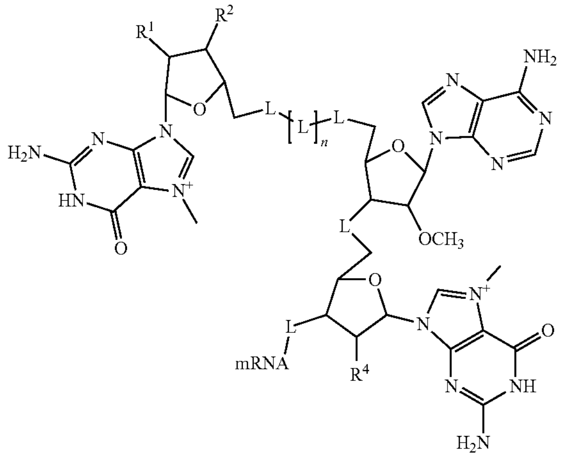

wherein, $R^1$, $R^2$, and $R^4$ are each independently selected from a halogen, OH, and $OCH_3$, each L is independently selected from the group consisting of phosphate, phosphorothioate, and boranophosphate wherein each L is linked by diester bonds; mRNA represents an mRNA of the present disclosure linked at its 5' end; and n is 0 or 1. In some embodiments, at least one of $R^1$, $R^2$, and $R^4$ is OH. In some embodiments, n is 1.

Poly-Adenine (Poly-A) Tail

Polyadenylation is the addition of a poly(A) tail, a chain of adenine nucleotides usually about 100-120 monomers in length, to a mRNA. In eukaryotes, polyadenylation is part of the process that produces mature mRNA for translation and begins as the transcription of a gene terminates. The 3'-most segment of a newly made pre-mRNA is first cleaved off by a set of proteins; these proteins then synthesize the poly(A) tail at the 3' end. The poly(A) tail is important for the nuclear export, translation, and stability of mRNA. The tail is shortened over time, and, when it is short enough, the mRNA is enzymatically degraded. However, in a few cell types, mRNAs with short poly(A) tails are stored for later activation by re-polyadenylation in the cytosol.

Preferably, a self-replicating RNA of the disclosure comprises a 3' tail region, which can serve to protect the RNA from exonuclease degradation. The tail region may be a 3'poly(A) and/or 3'poly(C) region. Preferably, the tail region is a 3' poly(A) tail. As used herein a "3' poly(A) tail" is a polymer of sequential adenine nucleotides that can range in size from, for example: 10 to 250 sequential adenine nucleotides; 60-125 sequential adenine nucleotides, 90-125 sequential adenine nucleotides, 95-125 sequential adenine nucleotides, 95-121 sequential adenine nucleotides, 100 to 121 sequential adenine nucleotides, 110-121 sequential adenine nucleotides; 112-121 sequential adenine nucleotides; 114-121 adenine sequential nucleotides; or 115 to 121 sequential adenine nucleotides. Preferably, a 3' poly(A) tail as described herein comprise 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 sequential adenine nucleotides. 3' Poly(A) tails can be added using a variety of methods known in the art, e.g., using poly(A) polymerase to add tails to synthetic or in vitro transcribed RNA. Other methods include the use of a transcription vector to encode poly(A) tails or the use of a ligase (e.g., via splint ligation using a T4 RNA ligase and/or T4 DNA ligase), wherein poly(A) may be ligated to the 3' end of a sense RNA. In some embodiments, a combination of any of the above methods is utilized.

Design and Synthesis of Self-Replicating RNA

The constructs for exemplary self-replicating RNA sequences of the present disclosure are provided in Tables 4-5.

TABLE 4

Comparison of STARR ™ self-replicating RNA of the disclosure with comparative self-replicating RNA as described

| Construct | Position | Sequence Type | Sequence |
|---|---|---|---|
| STARR ™ (SEQ ID NO: 49) | 5′ UTR | nucleotide | ATGGGCGGCGCATGAGAGAAGCCCAGACCAATTACCT<br>ACCCAAA |
| STARR ™ (SEQ ID NO: 50) | non-structural gene ORF | nucleotide | ATGGAGAAAGTTCACGTTGACATCGAGGAAGACAGCC<br>CATTCCTCAGAGCTTTGCAGCGGAGCTTCCCGCAGTTT<br>GAGGTAGAAGCCAAGCAGGTCACTGATAATGACCATG<br>CTAATGCCAGAGCGTTTTCGCATCTGGCTTCAAAACTG<br>ATCGAAACGGAGGTGGACCCATCCGACACGATCCTTG<br>ACATTGGAAGTGCGCCCGCCCGCAGAATGTATTCTAA<br>GCACAAGTATCOATTGTATCTGTCCGATGAGATGTGCGG<br>AAGATCCGGACAGATTGTATAAGTATGCAACTAAGCT<br>GAAGAAAAACTGTAAGGAAATAACTGATAAGGAATTG<br>GACAAGAAAATGAAGGAGCTGGCCGCCGTCATGAGCG<br>ACCCTGACCTGGAAACTGAGACTATGTGCCTCCACGA<br>CGACGAGTCGTGTCGCTACGAAGGGCAAGTCGCTGTT<br>TACCAGGATGTATACGCCGTCGACGGCCCCACCAGCC<br>TGTACCACCAGGCCAACAAGGGCGTGAGGGTGGCCTA<br>CTGGATCGGCTTCGACACCACACCCTTCATGTTCAAGA<br>ACCTGGCCGGCGCCTACCCCAGCTACAGCACCAACTG<br>GGCCGACGAGACCGTGCTGACCGCCAGGAACATCGGC<br>CTGTGCAGCAGCGACGTGATGGAGAGGAGCCGGAGAG<br>GCATGAGCATCCTGAGGAAGAAATACCTGAAGCCCAG<br>CAACAACGTGCTGTTCAGCGTGGGCAGCACCATCTAC<br>CACGAGAAGAGGGACCTGCTCAGGAGCTGGCACCTGC<br>CCAGCGTGTTCCACCTGAGGGGCAAGCAGAACTACAC<br>CTGCAGGTGCGAGACCATCGTGAGCTGCGACGGCTAC<br>GTGGTGAAGAGGATCGCCATCAGCCCCGGCCTGTACG<br>GCAAGCCCAGCGGCTACGCCGCTACAATGCACAGGGA<br>GGGCTTCCTGTGCTGCAAGGTGACCGACACCCTGAAC<br>GGCGAGAGGGTGAGCTTCCCCGTGTGCACCTACGTGC<br>CCGCCACCCTGTGCGACCAGATGACCGGCATCCTGGC<br>CACCGACGTGAGCGCCGACGACGCCCAGAAGCTGCTC<br>GTGGGCCTGAACCAGAGGATCGTGGTCAACGGCAGGA<br>CCCAGAGGAACACCAACACAATGAAGAACTACCTGCT<br>GCCCGTGGTGGCCCAGGCTTTCGCCAGGTGGGCCAAG<br>GAGTACAAGGAGGACCAGGAAGACGAGAGGCCCCTG<br>GGCCTGAGGGACAGGCAGCTGGTGATGGGCTGCTGCT<br>GGGCCTTCAGGCGGCACAAGATCACCAGCATCTACAA<br>GAGGCCCGACACCCAGACCATCATCAAGGTGAACAGC<br>GACTTCCACAGCTTCGTGCTGCCCAGGATCGGCAGCA<br>ACACCCTGGAGATCGGCCTGAGGACCCGGATCAGGAA<br>GATGCTGGAGGAACACAAGGAGCCCAGCCCACTGATC<br>ACCGCCGAGGACGTGCAGGAGGCCAAGTGCGCTGCCG<br>ACGAGGCCAAGGAGGTGAGGGAGGCCGAGGAACTGA<br>GGGCCGCCCTGCCACCCCTGGCTGCCGACGTGGAGGA<br>ACCCACCCTGGAAGCCGACGTGGACCTGATGCTGCAG<br>GAGGCCGGCGCCGGAAGCGTGGAGACACCCAGGGGC<br>CTGATCAAGGTGACCAGCTACGACGGCGAGGACAAGA<br>TCGGCAGCTACGCCGTGCTGAGCCCACAGGCCGTGCT<br>GAAGTCCGAGAAGCTGAGCTGCATCCACCCACTGGCC<br>GAGCAGGTGATCGTGATCACCCACAGCGGCAGGAAGG<br>GCAGGTACGCCGTGGAGCCCTACCACGGCAAGGTGGT<br>CGTGCCCGAGGGCCACGCCATCCCCGTGCAGGACTTC<br>CAGGCCCTGAGCGAGAGCGCCACCATCGTGTACAACG<br>AGAGGGAGTTCGTGAACAGGTACCTGCACCATATCGC<br>CACCCACGGCGGAGCCCTGAACACCGACGAGGAATAC<br>TACAAGACCGTGAAGCCCAGCGAGCACGACGGCGAGT<br>ACCTGTACGACATCGACAGGAAGCAGTGCGTGAAGAA<br>AGAGCTGGTGACCGGCCTGGGACTGACCGGCGAGCTG<br>GTGGACCCACCCTTCCACGAGTTCGCCTACGAGAGCCT<br>GAGGACCAGACCCGCCGCTCCCTACCAGGTGCCCACC<br>ATCGGCGTGTACGGCGTGCCCGGCAGCGGAAAGAGCG |

TABLE 4-continued

Comparison of STARR ™ self-replicating RNA of the disclosure with comparative self-replicating RNA as described

| Construct | Position | Sequence Type | Sequence |
|---|---|---|---|
| | | | GCATCATCAAGAGCGCCGTGACCAAGAAAGACCTGGT |
| | | | GGTCAGCGCCAAGAAAGAGAACTGCGCCGAGATCATC |
| | | | AGGGACGTGAAGAAGATGAAAGGCCTGGACGTGAAC |
| | | | GCGCGCACCGTGGACAGCGTGCTGCTGAACGGCTGCA |
| | | | AGCACCCCGTGGAGACCCTGTACATCGACGAGGCCTT |
| | | | CGCTTGCCACGCCGGCACCCTGAGGGCCCTGATCGCC |
| | | | ATCATCAGGCCCAAGAAAGCCGTGCTGTGCGGCGACC |
| | | | CCAAGCAGTGCGGCTTCTTCAACATGATGTGCCTGAAG |
| | | | GTGCACTTCAACCACGAGATCTGCACCCAGGTGTTCCA |
| | | | CAAGAGCATCAGCAGGCGGTGCACCAAGAGCGTGACC |
| | | | AGCGTCGTGAGCACCCTGTTCTACGACAAGAAAATGA |
| | | | GGACCACCAACCCCAAGGAGACCAAAATCGTGATCGA |
| | | | CACCACAGGCAGCACCAAGCCCAAGCAGGACGACCTG |
| | | | ATCCTGACCTGCTTCAGGGGCTGGGTGAAGCAGCTGC |
| | | | AGATCGACTACAAGGGCAACGAGATCATGACCGCCGC |
| | | | TGCCAGCCAGGGCCTGACCAGGAAGGGCGTGTACGCC |
| | | | GTGAGGTACAAGGTGAACGAGAACCCACTGTACGCTC |
| | | | CCACCAGCGAGCACGTGAACGTGCTGCTGACCAGGAC |
| | | | CGAGGACAGGATCGTGTGGAAGACCCTGGCCGGCGAC |
| | | | CCCTGGATCAAGACCCTGACCGCCAAGTACCCCGGCA |
| | | | ACTTCACCGCCACCATCGAAGAGTGGCAGGCCGAGCA |
| | | | CGACGCCATCATGAGGCACATCCTGGAGAGGCCCGAC |
| | | | CCCACCGACGTGTTCCAGAACAAGGCCAACGTGTGCT |
| | | | GGGCCAAGGCCCTGGTGCCCGTGCTGAAGACCGCCGG |
| | | | CATCGACATGACCACAGAGCAGTGGAACACCGTGGAC |
| | | | TACTTCGAGACCGACAAGGCCCACAGCGCCGAGATCG |
| | | | TGCTGAACCAGCTGTGCGTGAGGTTCTTCGGCCTGGAC |
| | | | CTGGACAGCGGCCTGTTCAGCGCCCCCACCGTGCCACT |
| | | | GAGCATCAGGAACAACCACTGGGACAACAGCCCCAGC |
| | | | CCAAACATGTACGGCCTGAACAAGGAGGTGGTCAGGC |
| | | | AGCTGAGCAGGCGGTACCCACAGCTGCCCAGGGCCGT |
| | | | GGCCACCGGCAGGGTGTACGACATGAACACCGGCACC |
| | | | CTGAGGAACTACGACCCCAGGATCAACCTGGTGCCCG |
| | | | TGAACAGGCGGCTGCCCCACGCCCTGGTGCTGCACCA |
| | | | CAACGAGCACCCACAGAGCGACTTCAGCTCCTTCGTG |
| | | | AGCAAGCTGAAAGGCAGGACCGTGCTGGTCGTGGGCG |
| | | | AGAAGCTGAGCGTGCCCGGCAAGATGGTGGACTGGCT |
| | | | GAGCGACAGGCCCGAGGCCACCTTCCGGGCCAGGCTG |
| | | | GACCTCGGCATCCCCGGCGACGTGCCCAAGTACGACA |
| | | | TCATCTTCGTGAACGTCAGGACCCCATACAAGTACCAC |
| | | | CATTACCAGCAGTGCGAGGACCACGCCATCAAGCTGA |
| | | | GCATGCTGACCAAGAAGGCCTGCCTGCACCTGAACCC |
| | | | CGGAGGCACCTGCGTGAGCATCGGCTACGGCTACGCC |
| | | | GACAGGGCCAGCGAGAGCATCATTGGCGCCATCGCCA |
| | | | GGCTGTTCAAGTTCAGCAGGGTGTGCAAACCCAAGAG |
| | | | CAGCCTGGAGGAAACCGAGGTGCTGTTCGTGTTCATC |
| | | | GGCTACGACCGGAAGGCCAGGACCCACAACCCCTACA |
| | | | AGCTGAGCAGCACCCTGACAAACATCTACACCGGCAG |
| | | | CAGGCTGCACGAGGCCGGCTGCGCCCCCAGCTACCAC |
| | | | GTGGTCAGGGGCGATATCGCCACCGCCACCGAGGGCG |
| | | | TGATCATCAACGCTGCCAACAGCAAGGGCCAGCCCGG |
| | | | AGGCGGAGTGTGCGGCGCCCTGTACAAGAAGTTCCCC |
| | | | GAGAGCTTCGACCTGCAGCCCATCGAGGTGGGCAAGG |
| | | | CCAGGCTGGTGAAGGGCGCCGCTAAGCACATCATCCA |
| | | | CGCCGTGGGCCCCAACTTCAACAAGGTGAGCGAGGTG |
| | | | GAAGGCGACAAGCAGCTGGCCGAAGCCTACGAGAGC |
| | | | ATCGCCAAGATCGTGAACGACAATAACTACAAGAGCG |
| | | | TGGCCATCCCACTGCTCAGCACCGGCATCTTCAGCGGC |
| | | | AACAAGGACAGGCTGACCCAGAGCCTGAACCACCTGC |
| | | | TCACCGCCCTGGACACCACCGATGCCGACGTGGCCAT |
| | | | CTACTGCAGGGACAAGAAGTGGGAGATGACCCTGAAG |
| | | | GAGGCCGTGGCCAGGCGGGAGGCCGTGGAAGAGATCT |
| | | | GCATCAGCGACGACTCCAGCGTGACCGAGCCCGACGC |
| | | | CGAGCTGGTGAGGGTGCACCCCAAGAGCTCCCTGGCC |
| | | | GGCAGGAAGGGCTACAGCACCAGCGACGGCAAGACCT |
| | | | TCAGCTACCTGGAGGGCACCAAGTTCCACCAGGCCGC |
| | | | TAAGGACATCGCCGAGATCAACGCTATGTGGCCCGTG |
| | | | GCCACCGAGGCCAACGAGCAGGTGTGCATGTACATCC |
| | | | TGGGCGAGAGCATGTCCAGCATCAGGAGCAAGTGCCC |
| | | | CGTGGAGGAAAGCGAGGCCAGCACACCACCCAGCACC |
| | | | CTGCCCTGCCTGTGCATCCACGCTATGACACCCGAGAG |
| | | | GGTGCAGCGGCTGAAGGCCAGCAGGCCCGAGCAGATC |
| | | | ACCGTGTGCAGCTCCTTCCCACTGCCCAAGTACAGGAT |

TABLE 4-continued

Comparison of STARR ™ self-replicating RNA of the disclosure with comparative self-replicating RNA as described

| Construct | Position | Sequence Type | Sequence |
|---|---|---|---|
| | | | CACCGGCGTGCAGAAGATCCAGTGCAGCCAGCCCATC<br>CTGTTCAGCCCAAAGGTGCCCGCCTACATCCACCCCAG<br>GAAGTACCTGGTGGAGACCCCACCCGTGGACGAGACA<br>CCCGAGCCAAGCGCCGAGAACCAGAGCACCGAGGGC<br>ACACCCGAGCAGCCACCCCTGATCACCGAGGACGAGA<br>CAAGGACCCGGACCCCAGAGCCCATCATTATCGAGGA<br>AGAGGAAGAGGACAGCATCAGCCTGCTGAGCGACGGC<br>CCCACCCACCAGGTGCTGCAGGTGGAGGCCGACATCC<br>ACGGCCCACCCAGCGTGTCCAGCTCCAGCTGGAGCAT<br>CCCACACGCCAGCGACTTCGACGTGGACAGCCTGAGC<br>ATCCTGGACACCCTGGAGGGCGCCAGCGTGACCTCCG<br>GCGCCACCAGCGCCGAGACCAACAGCTACTTCGCCAA<br>GAGCATGGAGTTCCTGGCCAGGCCCGTGCCAGCTCCC<br>AGGACCGTGTTCAGGAACCCACCCCACCCAGCTCCCA<br>GGACCAGGACCCCAAGCCTGGCTCCCAGCAGGGCCTG<br>CAGCAGGACCAGCCTGGTGAGCACCCCACCCGGCGTG<br>AACAGGGTGATCACCAGGGAGGAACTGGAGGCCCTGA<br>CACCCAGCAGGACCCCCAGCAGGTCCGTGAGCAGGAC<br>TAGTCTGGTGTCCAACCCACCCGGCGTGAACAGGGTG<br>ATCACCAGGGAGGAATTCGAGGCCTTCGTGGCCCAGC<br>AACAGAGACGGTTCGACGCCGGCGCCTACATCTTCAG<br>CAGCGACACCGGCCAGGGACACCTGCAGCAAAAGAGC<br>GTGAGGCAGACCGTGCTGAGCGAGGTGGTGCTGGAGA<br>GGACCGAGCTGGAAATCAGCTACGCCCCCAGGCTGGA<br>CCAGGAGAAGGAGGAACTGCTCAGGAAGAAACTGCA<br>GCTGAACCCCACCCCAGCCAACAGGAGCAGGTACCAG<br>AGCAGGAAGGTGGAGAACATGAAGGCCATCACCGCCA<br>GGCGGATCCTGCAGGGCCTGGGACACTACCTGAAGGC<br>CGAGGGCAAGGTGGAGTGCTACAGGACCCTGCACCCC<br>GTGCCACTGTACAGCTCCAGCGTGAACAGGGCCTTCTC<br>CAGCCCCAAGGTGGCCGTGGAGGCCTGCAACGCTATG<br>CTGAAGGAGAACTTCCCCACCGTGGCCAGCTACTGCA<br>TCATCCCCGAGTACGACGCCTACCTGGACATGGTGGA<br>CGGCGCCAGCTGCTGCCTGGACACCGCCAGCTTCTGCC<br>CCGCCAAGCTGAGGAGCTTCCCCAAGAAACACAGCTA<br>CCTGGAGCCCACCATCAGGAGCGCCGTGCCCAGCGCC<br>ATCCAGAACACCCTGCAGAACGTGCTGGCCGCTGCCA<br>CCAAGAGGAACTGCAACGTGACCCAGATGAGGGAGCT<br>GCCCGTGCTGGACAGCGCTGCCTTCAACGTGGAGTGCT<br>TCAAGAAATACGCCTGCAACAACGAGTACTGGGAGAC<br>CTTCAAGGAGAACCCCATCAGGCTGACCGAAGAGAAC<br>GTGGTGAACTACATCACCAAGCTGAAGGGCCCCAAGG<br>CCGCTGCCCTGTTCGCTAAGACCCACAACCTGAACATG<br>CTGCAGGACATCCCAATGGACAGGTTCGTGATGGACC<br>TGAAGAGGGACGTGAAGGTGACACCCGGCACCAAGCA<br>CACCGAGGAGAGGCCCAAGGTGCAGGTGATCCAGGCC<br>GCTGACCCACTGGCCACCGCCTACCTGTGCGGCATCCA<br>CAGGGAGCTGGTGAGGCGGCTGAACGCCGTGCTGCTG<br>CCCAACATCCACACCCTGTTCGACATGAGCGCCGAGG<br>ACTTCGACGCCATCATCGCCGAGCACTTCCAGCCCGGC<br>GACTGCGTGCTGGAGACCGACATCGCCAGCTTCGACA<br>AGAGCGAGGATGACGCTATGGCCCTGACCGCTCTGAT<br>GATCCTGGAGGACCTGGGCGTGGACGCCGAGCTGCTC<br>ACCCTGATCGAGGCTGCCTTCGGCGAGATCAGCTCCAT<br>CCACCTGCCCACCAAGACCAAGTTCAAGTTCGGCGCT<br>ATGATGAAAAGCGGAATGTTCCTGACCCTGTTCGTGA<br>ACACCGTGATCAACATTGTGATCGCCAGCAGGGTGCT<br>GCGGGAGAGGCTGACCGGCAGCCCCTGCGCTGCCTTC<br>ATCGGCGACGACAACATCGTGAAGGGCGTGAAAAGCG<br>ACAAGCTGATGGCCGACAGGTGCGCCACCTGGCTGAA<br>CATGGAGGTGAAGATCATCGACGCCGTGGTGGGCGAG<br>AAGGCCCCCTACTTCTGCGGCGGATTCATCCTGTGCGA<br>CAGCGTGACCGGCACCGCCTGCAGGGTGGCCGACCCC<br>CTGAAGAGGCTGTTCAAGCTGGGCAAGCCACTGGCCG<br>CTGACGATGAGCACGACGATGACAGGCGGAGGGCCCT<br>GCACGAGGAAAGCACCAGGTGGAACAGGGTGGGCAT<br>CCTGAGCGAGCTGTGCAAGGCCGTGGAGAGCAGGTAC<br>GAGACCGTGGGCACCAGCATCATCGTGATGGCTATGA<br>CCACACTGGCCAGCTCCGTCAAGAGCTTCTCCTACCTG<br>AGGGGGGCCCCTATAACTCTCTACGGCTAA |

TABLE 4-continued

Comparison of STARR ™ self-replicating RNA of the disclosure with comparative self-replicating RNA as described

| Construct | Position | Sequence Type | Sequence |
|---|---|---|---|
| STARR ™ (SEQ ID NO: 51) | non-structural gene ORF | amino acid | MEKVHVDIEEDSPFLRALQRSFPQFEVEAKQVTDNDHAN ARAFSHLASKLIETEVDPSDTILDIGSAPARRMYSKHKYH CICPMRCAEDPDRLYKYATKLKKNCKEITDKELDKKMK ELAAVMSDPDLETETMCLHDDESCRYEGQVAVYQDVY AVDGPTSLYHQANKGVRVAYWIGFDTTPFMFKNLAGAY PSYSTNWADETVLTARNIGLCSSDVMERSRRGMSILRKK YLKPSNNVLFSVGSTIYHEKRDLLRSWHLPSVFHLRGKQ NYTCRCETIVSCDGYVVKRIAISPGLYGKPSGYAATMHR EGFLCCKVTDTLNGERVSFPVCTYVPATLCDQMTGILAT DVSADDAQKLLVGLNQRIVVNGRTQRNTNTMKNYLLPV VAQAFARWAKEYKEDQEDERPLGLRDRQLVMGCCWAF RRHKITSIYKRPDTQTIIKVNSDFHSFVLPRIGSNTLEIGLR TRIRKMLEEHKEPSPLITAEDVQEAKCAADEAKEVREAE ELRAALPPLAADVEEPTLEADVDLMLQEAGAGSVETPRG LIKVTSYDGEDKIGSYAVLSPQAVLKSEKLSCIHPLAEQVI VITHSGRKGRYAVEPYHGKVVVPEGHAIPVQDFQALSES ATIVYNEREFVNRYLHHIATHGGALNTDEEYYKTVKPSE HDGEYLYDIDRKQCVKKELVTGLGLTGELVDPPFHEFAY ESLRTRPAAPYQVPTIGVYGVPGSGKSGIIKSAVTKKDLV VSAKKENCAEIIRDVKKMKGLDVNARTVDSVLLNGCKH PVETLYIDEAFACHAGTLRALIAIIRPKKAVLCGDPKQCG FFNMMCLKVHFNHEICTQVFHKSISRRCTKSVTSVVSTLF YDKKMRTTNPKETKIVIDTTGSTKPKQDDLILTCFRGWV KQLQIDYKGNEIMTAAASQGLTRKGVYAVRYKVNENPL YAPTSEHVNVLLTRTEDRIVWKTLAGDPWIKTLTAKYPG NFTATIEEWQAEHDAIMRHILERPDPTDVFQNKANVCWA KALVPVLKTAGIDMTTEQWNTVDYFETDKAHSAEIVLN QLCVRFFGLDLDSGLFSAPTVPLSIRNNHWDNSPSPNMY GLNKEVVRQLSRRYPQLPRAVATGRVYDMNTGTLRNYD PRINLVPVNRRLPHALVLHHNEHPQSDFSSFVSKLKGRTV LVVGEKLSVPGKMVDWLSDRPEATFRARLDLGIPGDVP KYDIIFVNVRTPYKYHHYQQCEDHAIKLSMLTKKACLHL NPGGTCVSIGYGYADRASESIIGAIARLFKFSRVCKPKSSL EETEVLFVFIGYDRKARTHNPYKLSSTLTNIYTGSRLHEA GCAPSYHVVRGDIATATEGVIINAANSKGQPGGGVCGAL YKKFPESFDLQPIEVGKARLVKGAAKHIIHAVGPNFNKVS EVEGDKQLAEAYESIAKIVNDNNYKSVAIPLLSTGIFSGN KDRLTQSLNHLLTALDTTDADVAIYCRDKKWEMTLKEA VARREAVEEICISDDSSVTEPDAELVRVHPKSSLAGRKGY STSDGKTFSYLEGTKFHQAAKDIAEINAMWPVATEANEQ VCMYILGESMSSIRSKCPVEESEASTPPSTLPCLCIHAMTP ERVQRLKASRPEQITVCSSFPLPKYRITGVQKIQCSQPILFS PKVPAYIHPRKYLVETPPVDETPEPSAENQSTEGTPEQPPL ITEDETRTRTPEPIIIEEEEEDSISLLSDGPTHQVLQVEADIH GPPSVSSSSWSIPHASDFDVDSLSILDTLEGASVTSGATSA ETNSYFAKSMEFLARPVPAPRTVFRNPPHPAPRTRTPSLA PSRACSRTSLVSTPPGVNRVITREELEALTPSRTPSRSVSR TSLVSNPPGVNRVITREEFEAFVAQQQRRFDAGAYIFSSD TGQGHLQQKSVRQTVLSEVVLERTELEISYAPRLDQEKE ELLRKKLQLNPTPANRSRYQSRKVENMKAITARRILQGL GHYLKAEGKVECYRTLHPVPLYSSSVNRAFSSPKVAVEA CNAMLKENFPTVASYCIIPEYDAYLDMVDGASCCLDTAS FCPAKLRSFPKKHSYLEPTIRSAVPSAIQNTLQNVLAAAT KRNCNVTQMRELPVLDSAAFNVECFKKYACNNEYWETF KENPIRLTEENVVNYITKLKGPKAAALFAKTHNLNMLQD IPMDRFVMDLKRDVKVTPGTKHTEERPKVQVIQAADPL ATAYLCGIHRELVRRLNAVLLPNIHTLFDMSAEDFDAIIA EHFQPGDCVLETDIASFDKSEDDAMALTALMILEDLGVD AELLTLIEAAFGEISSIHLPTKTKFKFGAMMKSGMFLTLF VNTVINIVIASRVLRERLTGSPCAAFIGDDNIVKGVKSDK LMADRCATWLNMEVKIIDAVVGEKAPYFCGGFILCDSVT GTACRVADPLKRLFKLGKPLAADDEHDDDRRRALHEES TRWNRVGILSELCKAVESRYETVGTSIIVMAMTTLASSV KSFSYLRGAPITLYG* |
| STARR ™ (SEQ ID NO: 52) | intergenic region | nucleotide | CCTGAATGGACTACGACATAGTCTAGTCCGCCAAGGC CGCCACC |
| STARR ™ | transgene ORF | nucleotide | n/a (depends on gene of our interest) |

TABLE 4-continued

Comparison of STARR ™ self-replicating RNA of the disclosure with comparative self-replicating RNA as described

| Construct | Position | Sequence Type | Sequence |
|---|---|---|---|
| STARR ™ (SEQ ID NO: 53) | 3′ UTR | nucleotide | ACTCGAGTATGTTACGTGCAAAGGTGATTGTCACCCCC CGAAAGACCATATTGTGACACACCCTCAGTATCACGC CCAAACATTTACAGCCGCGGTGTCAAAAACCGCGTGG ACGTGGTTAACATCCCTGCTGGGAGGATCAGCCGTAA TTATTATAATTGGCTTGGTGCTGGCTACTATTGTGGCC ATGTACGTGCTGACCAACCAGAAACATAATTGAATAC AGCAGCAATTGGCAAGCTGCTTACATAGAACTCGCGG CGATTGGCATGCCGCCTTAAAATTTTTATTTTATTTTTT CTTTTCTTTTCCGAATCGGATTTTGTTTTTAATATTTCA AAAAAAAAAAAAAAAAAAAAAAATCTAGAAAAAA AAAAAAAAAAAAAAAAAAAAAAAAAAAAAAAAAAA AAAAAAAAAAAAAAAAAAAAAAAAAAAAAAAAAAA AAAAAAAAAAAAAAAAAAAAAAA |
| Comparitive | 5′ UTR | nucleotide | unknown |
| Original (SEQ ID NO: 54) | non-structural gene ORF | nucleotide | ATGCCCGAGAAGGTGCACGTGGACATCGAGGAGGACA GCCCCTTCCTGAGGGCCCTGCAGAGGAGCTTCCCACA GTTCGAAGTGGAGGCCAAGCAGGTGACCGACAACGAC CACGCCAACGCCAGGGCCTTCAGCCACCTGGCCAGCA AGCTGATCGAGACCGAGGTGGACCCCAGCGACACCAT CCTGGACATCGGCAGCGCCCCAGCCAGGAGAATGTAC AGCAAGCACAAGTACCACTGCATCTGCCCCATGAGGT GCGCCGAGGACCCCGACAGGCTGTACAAGTACGCCAC CAAACTGAAGAAGAACTGCAAGGAGATCACCGACAA GGAGCTGGACAAGAAAATGAAGGAGCTGGCCGCCGTG ATGAGCGACCCCGACCTGGAGACCGAGACAATGTGCC TGCACGACGACGAGAGCTGCAGGTACGAGGGCCAGGT GGCCGTCTACCAGGACGTGTACGCCGTCGACGGCCCC ACCAGCCTGTACCACCAGGCCAACAAGGGCGTGAGGG TGGCCTACTGGATCGGCTTCGACACCACACCCTTCATG TTCAAGAACCTGGCCGGCGCCTACCCCAGCTACAGCA CCAACTGGGCCGACGAGACCGTGCTGACCGCCAGGAA CATCGGCCTGTGCAGCAGCGACGTGATGGAGAGGAGC CGGAGAGGCATGAGCATCCTGAGGAAGAAATACCTGA AGCCCAGCAACAACGTGCTGTTCAGCGTGGGCAGCAC CATCTACCACGAGAAGAGGGACCTGCTCAGGAGCTGG CACCTGCCCAGCGTGTTCCACCTGAGGGGCAAGCAGA ACTACACCTGCAGGTGCGAGACCATCGTGAGCTGCGA CGGCTACGTGGTGAAGAGGATCGCCATCAGCCCCGGC CTGTACGGCAAGCCCAGCGGCTACGCCGCTACAATGC ACAGGGAGGGCTTCCTGTGCTGCAAGGTGACCGACAC CCTGAACGGCGAGAGGGTGAGCTTCCCCGTGTGCACC TACGTGCCCGCCACCCTGTGCGACCAGATGACCGGCA TCCTGGCCACCGACGTGAGCGCCGACGACGCCCAGAA GCTGCTCGTGGGCCTGAACCAGAGGATCGTGGTCAAC GGCAGGACCCAGAGGAACACCAACACAATGAAGAAC TACCTGCTGCCCGTGGTGGCCCAGGCTTTCGCCAGGTG GGCCAAGGAGTACAAGGAGGACCAGGAAGACGAGAG GCCCCTGGGCCTGAGGGACAGGCAGCTGGTGATGGGC TGCTGCTGGGCCTTCAGGCGGCACAAGATCACCAGCA TCTACAAGAGGCCCGACACCCAGACCATCATCAAGGT GAACAGCGACTTCCACAGCTTCGTGCTGCCCAGGATC GGCAGCAACACCCTGGAGATCGGCCTGAGGACCCGGA TCAGGAAGATGCTGGAGGAACACAAGGAGCCCAGCCC ACTGATCACCGCCGAGGACGTGCAGGAGGCCAAGTGC GCTGCCGACGAGGCCAAGGAGGTGAGGGAGGCCGAG GAACTGAGGGCCGCCCTGCCACCCCTGGCTGCCGACG TGGAGGAACCCACCCTGGAAGCCGACGTGGACCTGAT GCTGCAGGAGGCCGGCGCCGGAAGCGTGGAGACACCC AGGGGCCTGATCAAGGTGACCAGCTACGACGGCGAGG ACAAGATCGGCAGCTACGCCGTGCTGAGCCCACAGGC CGTGCTGAAGTCCGAGAAGCTGAGCTGCATCCACCCA CTGGCCGAGCAGGTGATCGTGATCACCCACAGCGGCA GGAAGGGCAGGTACGCCGTGGAGCCCTACCACGGCAA GGTGGTCGTGCCCGAGGGCCACGCCATCCCCGTGCAG GACTTCCAGGCCCTGAGCGAGAGCGCCACCATCGTGT ACAACGAGAGGGAGTTCGTGAACAGGTACCTGCACCA TATCGCCACCCACGGCGGAGCCCTGAACACCGACGAG GAATACTACAAGACCGTGAAGCCCAGCGAGCACGACG GCGAGTACCTGTACGACATCGACAGGAAGCAGTGCGT GAAGAAAGAGCTGGTGACCGGCCTGGGACTGACCGGC GAGCTGGTGGACCCACCCTTCCACGAGTTCGCCTACGA |

TABLE 4-continued

Comparison of STARR ™ self-replicating RNA of the disclosure with comparative self-replicating RNA as described

| Construct | Position | Sequence Type | Sequence |
|---|---|---|---|
| | | | GAGCCTGAGGACCAGACCCGCCGCTCCCTACCAGGTG |
| | | | CCCACCATCGGCGTGTACGGCGTGCCCGGCAGCGGAA |
| | | | AGAGCGGCATCATCAAGAGCGCCGTGACCAAGAAAGA |
| | | | CCTGGTGGTCAGCGCCAAGAAAGAGAACTGCGCCGAG |
| | | | ATCATCAGGGACGTGAAGAAGATGAAAGGCCTGGACG |
| | | | TGAACGCGCGCACCGTGGACAGCGTGCTGCTGAACGG |
| | | | CTGCAAGCACCCCGTGGAGACCCTGTACATCGACGAG |
| | | | GCCTTCGCTTGCCACGCCGGCACCCTGAGGGCCCTGAT |
| | | | CGCCATCATCAGGCCCAAGAAAGCCGTGCTGTGCGGC |
| | | | GACCCCAAGCAGTGCGGCTTCTTCAACATGATGTGCCT |
| | | | GAAGGTGCACTTCAACCACGAGATCTGCACCCAGGTG |
| | | | TTCCACAAGAGCATCAGCAGGCGGTGCACCAAGAGCG |
| | | | TGACCAGCGTCGTGAGCACCCTGTTCTACGACAAGAA |
| | | | AATGAGGACCACCAACCCCAAGGAGACCAAAATCGTG |
| | | | ATCGACACCACAGGCAGCACCAAGCCCAAGCAGGACG |
| | | | ACCTGATCCTGACCTGCTTCAGGGGCTGGGTGAAGCA |
| | | | GCTGCAGATCGACTACAAGGGCAACGAGATCATGACC |
| | | | GCCGCTGCCAGCCAGGGCCTGACCAGGAAGGGCGTGT |
| | | | ACGCCGTGAGGTACAAGGTGAACGAGAACCCACTGTA |
| | | | CGCTCCCACCAGCGAGCACGTGAACGTGCTGCTGACC |
| | | | AGGACCGAGGACAGGATCGTGTGGAAGACCCTGGCCG |
| | | | GCGACCCCTGGATCAAGACCCTGACCGCCAAGTACCC |
| | | | CGGCAACTTCACCGCCACCATCGAAGAGTGGCAGGCC |
| | | | GAGCACGACGCCATCATGAGGCACATCCTGGAGAGGC |
| | | | CCGACCCCACCGACGTGTTCCAGAACAAGGCCAACGT |
| | | | GTGCTGGGCCAAGGCCCTGGTGCCCGTGCTGAAGACC |
| | | | GCCGGCATCGACATGACCACAGAGCAGTGGAACACCG |
| | | | TGGACTACTTCGAGACCGACAAGGCCCACAGCGCCGA |
| | | | GATCGTGCTGAACCAGCTGTGCGTGAGGTTCTTCGGCC |
| | | | TGGACCTGGACAGCGGCCTGTTCAGCGCCCCCACCGT |
| | | | GCCACTGAGCATCAGGAACAACCACTGGGACAACAGC |
| | | | CCCAGCCCAAACATGTACGGCCTGAACAAGGAGGTGG |
| | | | TCAGGCAGCTGAGCAGGCGGTACCCACAGCTGCCCAG |
| | | | GGCCGTGGCCACCGGCAGGGTGTACGACATGAACACC |
| | | | GGCACCCTGAGGAACTACGACCCCAGGATCAACCTGG |
| | | | TGCCCGTGAACAGGCGGCTGCCCCACGCCCTGGTGCT |
| | | | GCACCACAACGAGCACCCACAGAGCGACTTCAGCTCC |
| | | | TTCGTGAGCAAGCTGAAAGGCAGGACCGTGCTGGTCG |
| | | | TGGGCGAGAAGCTGAGCGTGCCCGGCAAGATGGTGGA |
| | | | CTGGCTGAGCGACAGGCCCGAGGCCACCTTCCGGGCC |
| | | | AGGCTGGACCTCGGCATCCCCGGCGACGTGCCCAAGT |
| | | | ACGACATCATCTTCGTGAACGTCAGGACCCCATACAA |
| | | | GTACCACCATTACCAGCAGTGCGAGGACCACGCCATC |
| | | | AAGCTGAGCATGCTGACCAAGAAGGCCTGCCTGCACC |
| | | | TGAACCCCGGAGGCACCTGCGTGAGCATCGGCTACGG |
| | | | CTACGCCGACAGGGCCAGCGAGAGCATCATTGGCGCC |
| | | | ATCGCCAGGCTGTTCAAGTTCAGCAGGGTGTGCAAAC |
| | | | CCAAGAGCAGCCTGGAGGAAACCGAGGTGCTGTTCGT |
| | | | GTTCATCGGCTACGACCGGAAGGCCAGGACCCACAAC |
| | | | CCCTACAAGCTGAGCAGCACCCTGACAAACATCTACA |
| | | | CCGGCAGCAGGCTGCACGAGGCCGGCTGCGCCCCCAG |
| | | | CTACCACGTGGTCAGGGGCGATATCGCCACCGCCACC |
| | | | GAGGGCGTGATCATCAACGCTGCCAACAGCAAGGGCC |
| | | | AGCCCGGAGGCGGAGTGTGCGGCGCCCTGTACAAGAA |
| | | | GTTCCCCGAGAGCTTCGACCTGCAGCCCATCGAGGTG |
| | | | GGCAAGGCCAGGCTGGTGAAGGGCGCCGCTAAGCACA |
| | | | TCATCCACGCCGTGGGCCCCAACTTCAACAAGGTGAG |
| | | | CGAGGTGGAAGGCGACAAGCAGCTGGCCGAAGCCTAC |
| | | | GAGAGCATCGCCAAGATCGTGAACGACAATAACTACA |
| | | | AGAGCGTGGCCATCCCACTGCTCAGCACCGGCATCTTC |
| | | | AGCGGCAACAAGGACAGGCTGACCCAGAGCCTGAACC |
| | | | ACCTGCTCACCGCCCTGGACACCACCGATGCCGACGT |
| | | | GGCCATCTACTGCAGGGACAAGAAGTGGGAGATGACC |
| | | | CTGAAGGAGGCCGTGGCCAGGCGGGAGGCCGTGGAA |
| | | | GAGATCTGCATCAGCGACGACTCCAGCGTGACCGAGC |
| | | | CCGACGCCGAGCTGGTGAGGGTGCACCCCAAGAGCTC |
| | | | CCTGGCCGGCAGGAAGGGCTACAGCACCAGCGACGGC |
| | | | AAGACCTTCAGCTACCTGGAGGGCACCAAGTTCCACC |
| | | | AGGCCGCTAAGGACATCGCCGAGATCAACGCTATGTG |
| | | | GCCCGTGGCCACCGAGGCCAACGAGCAGGTGTGCATG |
| | | | TACATCCTGGGCGAGAGCATGTCCAGCATCAGGAGCA |
| | | | AGTGCCCCGTGGAGGAAAGCGAGGCCAGCACACCACC |
| | | | CAGCACCCTGCCCTGCCTGTGCATCCACGCTATGACAC |

TABLE 4-continued

Comparison of STARR ™ self-replicating RNA of the disclosure with comparative self-replicating RNA as described

| Construct | Position | Sequence Type | Sequence |
|---|---|---|---|
| | | | CCGAGAGGGTGCAGCGGCTGAAGGCCAGCAGGCCCGA<br>GCAGATCACCGTGTGCAGCTCCTTCCCACTGCCCAAGT<br>ACAGGATCACCGGCGTGCAGAAGATCCAGTGCAGCCA<br>GCCCATCCTGTTCAGCCCAAAGGTGCCCGCCTACATCC<br>ACCCCAGGAAGTACCTGGTGGAGACCCCACCCGTGGA<br>CGAGACACCCGAGCCAAGCGCCGAGAACCAGAGCACC<br>GAGGGCACACCCGAGCAGCCACCCCTGATCACCGAGG<br>ACGAGACAAGGACCCGGACCCCAGAGCCCATCATTAT<br>CGAGGAAGAGGAAGAGGACAGCATCAGCCTGCTGAG<br>CGACGGCCCCACCCACCAGGTGCTGCAGGTGGAGGCC<br>GACATCCACGGCCCACCCAGCGTGTCCAGCTCCAGCT<br>GGAGCATCCCACACGCCAGCGACTTCGACGTGGACAG<br>CCTGAGCATCCTGGACACCCTGGAGGGCGCCAGCGTG<br>ACCTCCGGCGCCACCAGCGCCGAGACCAACAGCTACT<br>TCGCCAAGAGCATGGAGTTCCTGGCCAGGCCCGTGCC<br>AGCTCCCAGGACCGTGTTCAGGAACCCACCCCACCCA<br>GCTCCCAGGACCAGGACCCCAAGCCTGGCTCCCAGCA<br>GGGCCTGCAGCAGGACCAGCCTGGTGAGCACCCCACC<br>CGGCGTGAACAGGGTGATCACCAGGGAGGAACTGGAG<br>GCCCTGACACCCAGCAGGACCCCCAGCAGGTCCGTGA<br>GCAGGACTAGTCTGGTGTCCAACCCACCCGGCGTGAA<br>CAGGGTGATCACCAGGGAGGAATTCGAGGCCTTCGTG<br>GCCCAGCAACAGAGACGGTTCGACGCCGGCGCCTACA<br>TCTTCAGCAGCGACACCGGCCAGGGACACCTGCAGCA<br>AAAGAGCGTGAGGCAGACCGTGCTGAGCGAGGTGGTG<br>CTGGAGAGGACCGAGCTGGAAATCAGCTACGCCCCCA<br>GGCTGGACCAGGAGAAGGAGGAACTGCTCAGGAAGA<br>AACTGCAGCTGAACCCCACCCCAGCCAACAGGAGCAG<br>GTACCAGAGCAGGAAGGTGGAGAACATGAAGGCCATC<br>ACCGCCAGGCGGATCCTGCAGGGCCTGGGACACTACC<br>TGAAGGCCGAGGGCAAGGTGGAGTGCTACAGGACCCT<br>GCACCCCGTGCCACTGTACAGCTCCAGCGTGAACAGG<br>GCCTTCTCCAGCCCCAAGGTGGCCGTGGAGGCCTGCA<br>ACGCTATGCTGAAGGAGAACTTCCCCACCGTGGCCAG<br>CTACTGCATCATCCCCGAGTACGACGCCTACCTGGACA<br>TGGTGGACGGCGCCAGCTGCTGCCTGGACACCGCCAG<br>CTTCTGCCCCGCCAAGCTGAGGAGCTTCCCCAAGAAA<br>CACAGCTACCTGGAGCCCACCATCAGGAGCGCCGTGC<br>CCAGCGCCATCCAGAACACCCTGCAGAACGTGCTGGC<br>CGCTGCCACCAAGAGGAACTGCAACGTGACCCAGATG<br>AGGGAGCTGCCCGTGCTGGACAGCGCTGCCTTCAACG<br>TGGAGTGCTTCAAGAAATACGCCTGCAACAACGAGTA<br>CTGGGAGACCTTCAAGGAGAACCCCATCAGGCTGACC<br>GAAGAGAACGTGGTGAACTACATCACCAAGCTGAAGG<br>GCCCCAAGGCCGCTGCCCTGTTCGCTAAGACCCACAA<br>CCTGAACATGCTGCAGGACATCCCAATGGACAGGTTC<br>GTGATGGACCTGAAGAGGGACGTGAAGGTGACACCCG<br>GCACCAAGCACACCGAGGAGAGGCCCAAGGTGCAGGT<br>GATCCAGGCCGCTGACCCACTGGCCACCGCCTACCTGT<br>GCGGCATCCACAGGGAGCTGGTGAGGCGGCTGAACGC<br>CGTGCTGCTGCCCAACATCCACACCCTGTTCGACATGA<br>GCGCCGAGGACTTCGACGCCATCATCGCCGAGCACTT<br>CCAGCCCGGCGACTGCGTGCTGGAGACCGACATCGCC<br>AGCTTCGACAAGAGCGAGGATGACGCTATGGCCCTGA<br>CCGCTCTGATGATCCTGGAGGACCTGGGCGTGGACGC<br>CGAGCTGCTCACCCTGATCGAGGCTGCCTTCGGCGAG<br>ATCAGCTCCATCCACCTGCCCACCAAGACCAAGTTCAA<br>GTTCGGCGCTATGATGAAAAGCGGAATGTTCCTGACC<br>CTGTTCGTGAACACCGTGATCAACATTGTGATCGCCAG<br>CAGGGTGCTGCGGGAGAGGCTGACCGGCAGCCCCTGC<br>GCTGCCTTCATCGGCGACGACAACATCGTGAAGGGCG<br>TGAAAAGCGACAAGCTGATGGCCGACAGGTGCGCCAC<br>CTGGCTGAACATGGAGGTGAAGATCATCGACGCCGTG<br>GTGGGCGAGAAGGCCCCCTACTTCTGCGGCGGATTCA<br>TCCTGTGCGACAGCGTGACCGGCACCGCCTGCAGGGT<br>GGCCGACCCCCTGAAGAGGCTGTTCAAGCTGGGCAAG<br>CCACTGGCCGCTGACGATGAGCACGACGATGACAGGC<br>GGAGGGCCCTGCACGAGGAAAGCACCAGGTGGAACA<br>GGGTGGGCATCCTGAGCGAGCTGTGCAAGGCCGTGGA<br>GAGCAGGTACGAGACCGTGGGCACCAGCATCATCGTG<br>ATGGCTATGACCACACTGGCCAGCTCCGTCAAGAGCTT<br>CTCCTACCTGAGGGGGGCCCCTATAACTCTCTACGGCT<br>AA |

TABLE 4-continued

Comparison of STARR ™ self-replicating RNA of the disclosure with comparative self-replicating RNA as described

| Construct | Position | Sequence Type | Sequence |
|---|---|---|---|
| Comparitive (SEQ ID NO: 55) | non-structural gene ORF | amino acid | MPEKVHVDIEEDSPFLRALQRSFPQFEVEAKQVTDNDHA<br>NARAFSHLASKLIETEVDPSDTILDIGSAPARRMYSKHKY<br>HCICPMRCAEDPDRLYKYATKLKKNCKEITDKELDKKM<br>KELAAVMSDPDLETETMCLHDDESCRYEGQVAVYQDV<br>YAVDGPTSLYHQANKGVRVAYWIGFDTTPFMFKNLAGA<br>YPSYSTNWADETVLTARNIGLCSSDVMERSRRGMSILRK<br>KYLKPSNNVLFSVGSTIYHEKRDLLRSWHLPSVFHLRGK<br>QNYTCRCETIVSCDGYVVKRIAISPGLYGKPSGYAATMH<br>REGFLCCKVTDTLNGERVSFPVCTYVPATLCDQMTGILA<br>TDVSADDAQKLLVGLNQRIVVNGRTQRNTNTMKNYLLP<br>VVAQAFARWAKEYKEDQEDERPLGLRDRQLVMGCCWA<br>FRRHKITSIYKRPDTQTIIKVNSDFHSFVLPRIGSNTLEIGL<br>RTRIRKMLEEHKEPSPLITAEDVQEAKCAADEAKEVREA<br>EELRAALPPLAADVEEPTLEADVDLMLQEAGAGSVETPR<br>GLIKVTSYDGEDKIGSYAVLSPQAVLKSEKLSCIHPLAEQ<br>VIVITHSGRKGRYAVEPYHGKVVVPEGHAIPVQDFQALS<br>ESATIVYNEREFVNRYLHHIATHGGALNTDEEYYKTVKP<br>SEHDGEYLYDIDRKQCVKKELVTGLGLTGELVDPPFHEF<br>AYESLRTRPAAPYQVPTIGVYGVPGSGKSGIIKSAVTKKD<br>LVVSAKKENCAEIIRDVKKMKGLDVNARTVDSVLLNGC<br>KHPVETLYIDEAFACHAGTLRALIAIIRPKKAVLCGDPKQ<br>CGFFNMMCLKVHFNHEICTQVFHKSISRRCTKSVTSVVS<br>TLFYDKKMRTTNPKETKIVIDTTGSTKPKQDDLILTCFRG<br>WVKQLQIDYKGNEIMTAAASQGLTRKGVYAVRYKVNE<br>NPLYAPTSEHVNVLLTRTEDRIVWKTLAGDPWIKTLTAK<br>YPGNFTATIEEWQAEHDAIMRHILERPDPTDVFQNKANV<br>CWAKALVPVLKTAGIDMTTEQWNTVDYFETDKAHSAEI<br>VLNQLCVRFFGLDLDSGLFSAPTVPLSIRNNHWDNSPSPN<br>MYGLNKEVVRQLSRRYPQLPRAVATGRVYDMNTGTLR<br>NYDPRINLVPVNRRLPHALVLHHNEHPQSDFSSFVSKLK<br>GRTVLVVGEKLSVPGKMVDWLSDRPEATFRARLDLGIP<br>GDVPKYDIIFVNVRTPYKYHHYQQCEDHAIKLSMLTKKA<br>CLHLNPGGTCVSIGYGYADRASESIIGAIARLFKFSRVCKP<br>KSSLEETEVLFVFIGYDRKARTHNPYKLSSTLTNIYTGSRL<br>HEAGCAPSYHVVRGDIATATEGVIINAANSKGQPGGGVC<br>GALYKKFPESFDLQPIEVGKARLVKGAAKHIIHAVGPNF<br>NKVSEVEGDKQLAEAYESIAKIVNDNNYKSVAIPLLSTGI<br>FSGNKDRLTQSLNHLLTALDTTDADVAIYCRDKKWEMT<br>LKEAVARREAVEEICISDDSSVTEPDAELVRVHPKSSLAG<br>RKGYSTSDGKTFSYLEGTKFHQAAKDIAEINAMWPVATE<br>ANEQVCMYILGESMSSIRSKCPVEESEASTPPSTLPCLCIH<br>AMTPERVQRLKASRPEQITVCSSFPLPKYRITGVQKIQCS<br>QPILFSPKVPAYIHPRKYLVETPPVDETPEPSAENQSTEGT<br>PEQPPLITEDETRTRTPEPINIEEEEEDSISLLSDGPTHQVLQ<br>VEADIHGPPSVSSSSWSIPHASDFDVDSLSILDTLEGASVT<br>SGATSAETNSYFAKSMEFLARPVPAPRTVFRNPPHPAPRT<br>RTPSLAPSRACSRTSLVSTPPGVNRVITREELEALTPSRTP<br>SRSVSRTSLVSNPPGVNRVITREEFEAFVAQQQRRFDAGA<br>YIFSSDTGQGHLQQKSVRQTVLSEVVLERTELEISYAPRL<br>DQEKEELLRKKLQLNPTPANRSRYQSRKVENMKAITARR<br>ILQGLGHYLKAEGKVECYRTLHPVPLYSSSVNRAFSSPK<br>VAVEACNAMLKENFPTVASYCIIPEYDAYLDMVDGASC<br>CLDTASFCPAKLRSFPKKHSYLEPTIRSAVPSAIQNTLQNV<br>LAAATKRNCNVTQMRELPVLDSAAFNVECFKKYACNNE<br>YWETFKENPIRLTEENVVNYITKLKGPKAAALFAKTHNL<br>NMLQDIPMDRFVMDLKRDVKVTPGTKHTEERPKVQVIQ<br>AADPLATAYLCGIHRELVRRLNAVLLPNIHTLFDMSAED<br>FDAIIAEHFQPGDCVLETDIASFDKSEDDAMALTALMILE<br>DLGVDAELLTLIEAAFGEISSIHLPTKTKFKFGAMMKSGM<br>FLTLFVNTVINIVIASRVLRERLTGSPCAAFIGDDNIVKGV<br>KSDKLMADRCATWLNMEVKIIDAVVGEKAPYFCGGFIL<br>CDSVTGTACRVADPLKRLFKLGKPLAADDEHDDDRRRA<br>LHEESTRWNRVGILSELCKAVESRYETVGTSIIVMAMTTL<br>ASSVKSFSYLRGAPITLYG* |
| Comparitive | intergenic region | nucleotide | unknown |
| Comparitive | 3′ UTR | nucleotide | unknown |

TABLE 5

ORF of Peptide of Interest for Self-Replicating RNAs of the Disclosure

| ORF Identity | Sequence Type | Sequence |
| --- | --- | --- |
| 2019-nCoV Spike gene (SEQ ID NO: 117) | nucleotide | ATGTTTGTTTTTCTTGTTTTATTGCCACTAGTCTCTAGTCAGTGTGT<br>TAATCTTACAACCAGAACTCAATTACCCCCTGCATACACTAATTC<br>TTTCACACGTGGTGTTTATTACCCTGACAAAGTTTTCAGATCCTCA<br>GTTTTACATTCAACTCAGGACTTGTTCTTACCTTTCTTTTCCAATGT<br>TACTTGGTTCCATGCTATACATGTCTCTGGGACCAATGGTACTAA<br>GAGGTTTGATAACCCTGTCCTACCATTTAATGATGGTGTTTATTTT<br>GCTTCCACTGAGAAGTCTAACATAATAAGAGGCTGGATTTTTGGT<br>ACTACTTTAGATTCGAAGACCCAGTCCCTACTTATTGTTAATAAC<br>GCTACTAATGTTGTTATTAAAGTCTGTGAATTTCAATTTTGTAATG<br>ATCCATTTTTGGGTGTTTATTACCACAAAAACAACAAAAGTTGGA<br>TGGAAAGTGAGTTCAGAGTTTATTCTAGTGCGAATAATTGCACTT<br>TTGAATATGTCTCTCAGCCTTTTCTTATGGACCTTGAAGGAAAAC<br>AGGGTAATTTCAAAAATCTTAGGGAATTTGTGTTTAAGAATATTG<br>ATGGTTATTTTAAAATATATTCTAAGCACACGCCTATTAATTTAGT<br>GCGTGATCTCCCTCAGGGTTTTTCGGCTTTAGAACCATTGGTAGAT<br>TTGCCAATAGGTATTAACATCACTAGGTTTCAAACTTTACTTGCTT<br>TACATAGAAGTTATTTGACTCCTGGTGATTCTTCTTCAGGTTGGAC<br>AGCTGGTGCTGCAGCTTATTATGTGGGTTATCTTCAACCTAGGAC<br>TTTTCTATTAAAATATAATGAAAATGGAACCATTACAGATGCTGT<br>AGACTGTGCACTTGACCCTCTCTCAGAAACAAAGTGTACGTTGAA<br>ATCCTTCACTGTAGAAAAAGGAATCTATCAAACTTCTAACTTTAG<br>AGTCCAACCAACAGAATCTATTGTTAGATTTCCTAATATTACAAA<br>CTTGTGCCCTTTTGGTGAAGTTTTTAACGCCACCAGATTTGCATCT<br>GTTTATGCTTGGAACAGGAAGAGAATCAGCAACTGTGTTGCTGAT<br>TATTCTGTCCTATATAATTCCGCATCATTTTCCACTTTTAAGTGTT<br>ATGGAGTGTCTCCTACTAAATTAAATGATCTCTGCTTTACTAATGT<br>CTATGCAGATTCATTTGTAATTAGAGGTGATGAAGTCAGACAAAT<br>CGCTCCAGGGCAAACTGGAAAGATTGCTGATTATAATTATAAATT<br>ACCAGATGATTTTACAGGCTGCGTTATAGCTTGGAATTCTAACAA<br>TCTTGATTCTAAGGTTGGTGGTAATTATAATTACCTGTATAGATTG<br>TTTAGGAAGTCTAATCTCAAACCTTTTGAGAGAGATATTTCAACT<br>GAAATCTATCAGGCCGGTAGCACACCTTGTAATGGTGTTGAAGGT<br>TTTAATTGTTACTTTCCTTTACAATCATATGGTTTCCAACCCACTA<br>ATGGTGTTGGTTACCAACCATACAGAGTAGTAGTACTTTCTTTTG<br>AACTTCTACATGCACCAGCAACTGTTTGTGGACCTAAAAAGTCTA<br>CTAATTTGGTTAAAAACAAATGTGTCAATTTCAACTTCAATGGTTT<br>AACAGGCACAGGTGTTCTTACTGAGTCTAACAAAAAGTTTCTGCC<br>TTTCCAACAATTTGGCAGAGACATTGCTGACACTACTGATGCTGT<br>CCGTGATCCACAGACACTTGAGATTCTTGACATTACACCATGTTC<br>TTTTGGTGGTGTCAGTGTTATAACACCAGGAACAAATACTTCTAA<br>CCAGGTTGCTGTTCTTTATCAGGATGTTAACTGCACAGAAGTCCC<br>TGTTGCTATTCATGCAGATCAACTTACTCCTACTTGGCGTGTTTAT<br>TCTACAGGTTCTAATGTTTTTCAAACACGTGCAGGCTGTTTAATAG<br>GGGCTGAACATGTCAACAACTCATATGAGTGTGACATACCCATTG<br>GTGCAGGTATATGCGCTAGTTATCAGACTCAGACTAATTCTCCTC<br>GGCGGGCACGTAGTGTAGCTAGTCAATCCATCATTGCCTACACTA<br>TGTCACTTGGTGCAGAAAATTCAGTTGCTTACTCTAATAACTCTAT<br>TGCCATACCCACAAATTTTACTATTAGTGTTACCACAGAAATTCT<br>ACCAGTGTCTATGACCAAGACATCAGTAGATTGTACAATGTACAT<br>TTGTGGTGATTCAACTGAATGCAGCAATCTTTTGTTGCAATATGG<br>CAGTTTTTGTACACAATTAAACCGTGCTTTAACTGGAATAGCTGTT<br>GAACAAGACAAAAACACCCAAGAAGTTTTTGCACAAGTCAAACA<br>AATTTACAAAACACCACCAATTAAAGATTTTGGTGGTTTTAATTTT<br>TCACAAATATTACCAGATCCATCAAAACCAAGCAAGAGGTCATTT<br>ATTGAAGATCTACTTTTCAACAAAGTGACACTTGCAGATGCTGGC<br>TTCATCAAACAATATGGTGATTGCCTTGGTGATATTGCTGCTAGA<br>GACCTCATTTGTGCACAAAAGTTTAACGGCCTTACTGTTTTGCCAC<br>CTTTGCTCACAGATGAAATGATTGCTCAATACACTTCTGCACTGTT<br>AGCGGGTACAATCACTTCTGGTTGGACCTTTGGTGCAGGTGCTGC<br>ATTACAAATACCATTTGCTATGCAAATGGCTTATAGGTTTAATGG<br>TATTGGAGTTACACAGAATGTTCTCTATGAGAACCAAAAATTGAT<br>TGCCAACCAATTTAATAGTGCTATTGGCAAAATTCAAGACTCACT<br>TTCTTCCACAGCAAGTGCACTTGGAAAACTTCAAGATGTGGTCAA<br>CCAAAATGCACAAGCTTTAAACACGCTTGTTAAACAACTTAGCTC<br>CAATTTTGGTGCAATTTCAAGTGTTTTAAATGATATCCTTTCACGT<br>CTTGACAAAGTTGAGGCTGAAGTGCAAATTGATAGGTTGATCACA<br>GGCAGACTTCAAAGTTTGCAGACATATGTGACTCAACAATTAATT<br>AGAGCTGCAGAAATCAGAGCTTCTGCTAATCTTGCTGCTACTAAA<br>ATGTCAGAGTGTGTACTTGGACAATCAAAAAGAGTTGATTTTTGT<br>GGAAAGGGCTATCATCTTATGTCCTTCCCTCAGTCAGCACCTCAT<br>GGTGTAGTCTTCTTGCATGTGACTTATGTCCCTGCACAAGAAAAG<br>AACTTCACAACTGCTCCTGCCATTTGTCATGATGGAAAAGCACAC<br>TTTCCTCGTGAAGGTGTCTTTGTTTCAAATGGCACACACTGGTTTG<br>TAACACAAAGGAATTITTATGAACCACAAATCATTACTACAGACA |

TABLE 5-continued

ORF of Peptide of Interest for Self-Replicating RNAs of the Disclosure

| ORF Identity | Sequence Type | Sequence |
|---|---|---|
| | | ACACATTTGTGTCTGGTAACTGTGATGTTGTAATAGGAATTGTCA<br>ACAACACAGTTTATGATCCTTTGCAACCTGAATTAGACTCATTCA<br>AGGAGGAGTTAGATAAATATTTTAAGAATCATACATCACCAGATG<br>TTGATTTAGGTGACATCTCTGGCATTAATGCTTCAGTTGTAAACAT<br>TCAAAAAGAAATTGACCGCCTCAATGAGGTTGCCAAGAATTTAA<br>ATGAATCTCTCATCGATCTCCAAGAACTTGGAAAGTATGAGCAGT<br>ATATAAAATGGCCATGGTACATTTGGCTAGGTTTTATAGCTGGCT<br>TGATTGCCATAGTAATGGTGACAATTATGCTTTGCTGTATGACCA<br>GTTGCTGTAGTTGTCTCAAGGGCTGTTGTTCTTGTGGATCCTGCTG<br>CAAATTTGATGAAGACGACTCTGAGCCAGTGCTCAAAGGAGTCA<br>AATTACATTACACATAA |
| 2019-nCoV Spike gene (SEQ ID NO: 118) | amino acid | MFVFLVLLPLVSSQCVNLTTRTQLPPAYTNSFTRGVYYPDKVFRSSV<br>LHSTQDLFLPFFSNVTWFHAIHVSGTNGTKRFDNPVLPFNDGVYFAS<br>TEKSNIIRGWIFGTTLDSKTQSLLIVNNATNVVIKVCEFQFCNDPFLG<br>VYYHKNNKSWMESEFRVYSSANNCTFEYVSQPFLMDLEGKQGNFK<br>NLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENG<br>TITDAVDCALDPLSETKCTLKSFTVEKGIYQTSNFRVQPTESIVRFPNI<br>TNLCPFGEVFNATRFASVYAWNRKRISNCVADYSVLYNSASFSTFKC<br>YGVSPTKLNDLCFTNVYADSFVIRGDEVRQIAPGQTGKIADYNYKLP<br>DDFTGCVIAWNSNNLDSKVGGNYNYLYRLFRKSNLKPFERDISTEIY<br>QAGSTPCNGVEGFNCYFPLQSYGFQPTNGVGYQPYRVVVLSFELLH<br>APATVCGPKKSTNLVKNKCVNFNFNGLTGTGVLTESNKKFLPFQQF<br>GRDIADTTDAVRDPQTLEILDITPCSFGGVSVITPGTNTSNQVAVLYQ<br>DVNCTEVPVAIHADQLTPTWRVYSTGSNVFQTRAGCLIGAEHVNNS<br>YECDIPIGAGICASYQTQTNSPRRARSVASQSIIAYTMSLGAENSVAY<br>SNNSIAIPTNFTISVTTEILPVSMTKTSVDCTMYICGDSTECSNLLLQY<br>GSFCTQLNRALTGIAVEQDKNTQEVFAQVKQIYKTPPIKDFGGFNFS<br>QILPDPSKPSKRSFIEDLLFNKVTLADAGFIKQYGDCLGDIAARDLICA<br>QKFNGLTVLPPLLTDEMIAQYTSALLAGTITSGWTFGAGAALQIPFA<br>MQMAYRFNGIGVTQNVLYENQKLIANQFNSAIGKIQDSLSSTASALG<br>KLQDVVNQNAQALNTLVKQLSSNFGAISSVLNDILSRLDKVEAEVQI<br>DRLITGRLQSLQTYVTQQLIRAAEIRASANLAATKMSECVLGQSKRV<br>DFCGKGYHLMSFPQSAPHGVVFLHVTYVPAQEKNFTTAPAICHDGK<br>AHFPREGVFVSNGTHWFVTQRNFYEPQUITTDNTFVSGNCDVVIGIVN<br>NTVYDPLQPELDSFKEELDKYFKNHTSPDVDLGDISGINASVVNIQKE<br>IDRLNEVAKNLNESLIDLQELGKYEQYIKWPWYIWLGFIAGLIAIVM<br>VTIMLCCMTSCCSCLKGCCSCGSCCKFDEDDSEPVLKGVKLHYT* |
| 2019-nCoV Spike gene (SEQ ID NO: 119) | nucleotide | ATGTTCGTCTTCCTGGTCCTGCTGCCTCTGGTCTCCTCACAGTGCG<br>TCAATCTGACAACTCGGACTCAGCTGCCACCTGCTTATACTAATA<br>GCTTCACCAGAGGCGTGTACTATCCTGACAAGGTGTTTAGAAGCT<br>CCGTGCTGCACTCTACACAGGATCTGTTTCTGCCATTCTTTAGCAA<br>CGTGACCTGGTTCCACGCCATCCACGTGAGCGGCACCAATGGCAC<br>AAAGCGGTTCGACAATCCCGTGCTGCCTTTTAACGATGGCGTGTA<br>CTTCGCCTCTACCGAGAAGAGCAACATCATCAGAGGCTGGATCTT<br>TGGCACCACACTGGACTCCAAGACACAGTCTCTGCTGATCGTGAA<br>CAATGCCACCAACGTGGTCATCAAGGTGTGCGAGTTCCAGTTTTG<br>TAATGATCCCTTCCTGGGCGTGTACTATCACAAGAACAATAAGAG<br>CTGGATGGAGTCCGAGTTTAGAGTGTATTCTAGCGCCAACAACTG<br>CACATTTGAGTACGTGAGCCAGCCTTTCCTGATGGACCTGGAGGG<br>CAAGCAGGGCAATTTCAAGAACCTGAGGGAGTTCGTGTTTAAGA<br>ATATCGACGGCTACTTCAAAATCTACTCTAAGCACACCCCCATCA<br>ACCTGGTGCGCGACCTGCCTCAGGGCTTCAGCGCCCTGGAGCCCC<br>TGGTGGATCTGCCTATCGGCATCAACATCACCCGGTTTCAGACAC<br>TGCTGGCCCTGCACAGAAGCTACCTGACACCCGGCGACTCCTCTA<br>GCGGATGGACCGCCGGCGCTGCCGCCTACTATGTGGGCTACCTCC<br>AGCCCCGGACCTTCCTGCTGAAGTACAACGAGAATGGCACCATCA<br>CAGACGCAGTGGATTGCGCCCTGGACCCCCTGAGCGAGACAAAG<br>TGTACACTGAAGTCCTTTACCGTGGAGAAGGGCATCTATCAGACA<br>TCCAATTTCAGGGTGCAGCCAACCGAGTCTATCGTGCGCTTTCCT<br>AATATCACAAACCTGTGCCCATTTGGCGAGGTGTTCAACGCAACC<br>CGCTTCGCCAGCGTGTACGCCTGGAATAGGAAGCGGATCAGCAA<br>CTGCGTGGCCGACTATAGCGTGCTGTACAACTCCGCCTCTTTCAG<br>CACCTTTAAGTGCTATGGCGTGTCCCCCACAAAGCTGAATGACCT<br>GTGCTTTACCAACGTCTACGCCGATTCTTTCGTGATCAGGGGCGA<br>CGAGGTGCGCCAGATCGCCCCCGGCCAGACAGGCAAGATCGCAG<br>ACTACAATTATAAGCTGCCAGACGATTTCACCGGCTGCGTGATCG<br>CCTGGAACAGCAACAATCTGGATTCCAAAGTGGGCGGCAACTAC<br>AATTATCTGTACCGGCTGTTTAGAAAGAGCAATCTGAAGCCCTTC<br>GAGAGGGACATCTCTACAGAAATCTACCAGGCCGGCAGCACCCC<br>TTGCAATGGCGTGGAGGGCTTTAACTGTTATTTCCCACTCCAGTCC<br>TACGGCTTCCAGCCCACAAACGGCGTGGGCTATCAGCCTTACCGC |

TABLE 5-continued

| ORF of Peptide of Interest for Self-Replicating RNAs of the Disclosure | | |
|---|---|---|
| ORF Identity | Sequence Type | Sequence |
| | | GTGGTGGTGCTGAGCTTTGAGCTGCTGCACGCCCCAGCAACAGTG<br>TGCGGCCCCAAGAAGTCCACCAATCTGGTGAAGAACAAGTGCGT<br>GAACTTCAACTTCAACGGCCTGACCGGCACAGGCGTGCTGACCGA<br>GTCCAACAAGAAGTTCCTGCCATTTCAGCAGTTCGGCAGGGACAT<br>CGCAGATACCACAGACGCCGTGCGCGACCCACAGACCCTGGAGA<br>TCCTGGACATCACACCCTGCTCTTTCGGCGGCGTGAGCGTGATCA<br>CACCCGGCACCAATACAAGCAACCAGGTGGCCGTGCTGTATCAG<br>GACGTGAATTGTACCGAGGTGCCCGTGGCTATCCACGCCGATCAG<br>CTGACCCCAACATGGCGGGTGTACAGCACCGGCTCCAACGTCTTC<br>CAGACAAGAGCCGGATGCCTGATCGGAGCAGAGCACGTGAACAA<br>TTCCTATGAGTGCGACATCCCAATCGGCGCCGGCATCTGTGCCTC<br>TTACCAGACCCAGACAAACTCTCCCAGAAGAGCCCGGAGCGTGG<br>CCTCCCAGTCTATCATCGCCTATACCATGTCCCTGGGCGCCGAGA<br>ACAGCGTGGCCTACTCTAACAATAGCATCGCCATCCCAACCAACT<br>TCACAATCTCTGTGACCACAGAGATCCTGCCCGTGTCCATGACCA<br>AGACATCTGTGGACTGCACAATGTATATCTGTGGCGATTCTACCG<br>AGTGCAGCAACCTGCTGCTCCAGTACGGCAGCTTTTGTACCCAGC<br>TGAATAGAGCCCTGACAGGCATCGCCGTGGAGCAGGATAAGAAC<br>ACACAGGAGGTGTTCGCCCAGGTGAAGCAAATCTACAAGACCCC<br>CCCTATCAAGGACTTTGGCGGCTTCAATTTTTCCCAGATCCTGCCT<br>GATCCATCCAAGCCTTCTAAGCGGAGCTTTATCGAGGACCTGCTG<br>TTCAACAAGGTGACCCTGGCCGATGCCGGCTTCATCAAGCAGTAT<br>GGCGATTGCCTGGGCGACATCGCAGCCAGGGACCTGATCTGCGCC<br>CAGAAGTTTAATGGCCTGACCGTGCTGCCACCCCTGCTGACAGAT<br>GAGATGATCGCACAGTACACAAGCGCCCTGCTGGCCGGCACCAT<br>CACATCCGGATGGACCTTCGGCGCAGGAGCCGCCCTCCAGATCCC<br>CTTTGCCATGCAGATGGCCTATAGGTTCAACGGCATCGGCGTGAC<br>CCAGAATGTGCTGTACGAGAACCAGAAGCTGATCGCCAATCAGTT<br>TAACTCCGCCATCGGCAAGATCCAGGACAGCCTGTCCTCTACAGC<br>CAGCGCCCTGGGCAAGCTCCAGGATGTGGTGAATCAGAACGCCC<br>AGGCCCTGAATACCCTGGTGAAGCAGCTGAGCAGCAACTTCGGC<br>GCCATCTCTAGCGTGCTGAATGACATCCTGAGCCGGCTGGACAAG<br>GTGGAGGCAGAGGTGCAGATCGACCGGCTGATCACCGGCCGGCT<br>CCAGAGCCTCCAGACCTATGTGACACAGCAGCTGATCAGGGCCG<br>CCGAGATCAGGGCCAGCGCCAATCTGGCAGCAACCAAGATGTCC<br>GAGTGCGTGCTGGGCCAGTCTAAGAGAGTGGACTTTTGTGGCAAG<br>GGCTATCACCTGATGTCCTTCCCTCAGTCTGCCCCACACGGCGTG<br>GTGTTTCTGCACGTGACCTACGTGCCCGCCCAGGAGAAGAACTTC<br>ACCACAGCCCCTGCCATCTGCCACGATGGCAAGGCCCACTTTCCA<br>AGGGAGGGCGTGTTCGTGTCCAACGGCACCCACTGGTTTGTGACA<br>CAGCGCAATTTCTACGAGCCCCAGATCATCACCACAGACAACACC<br>TTCGTGAGCGGCAACTGTGACGTGGTCATCGGCATCGTGAACAAT<br>ACCGTGTATGATCCACTCCAGCCCGAGCTGGACAGCTTTAAGGAG<br>GAGCTGGATAAGTATTTCAAGAATCACACCTCCCCTGACGTGGAT<br>CTGGGCGACATCAGCGGCATCAATGCCTCCGTGGTGAACATCCAG<br>AAGGAGATCGACCGCCTGAACGAGGTGGCTAAGAATCTGAACGA<br>GAGCCTGATCGACCTCCAGGAGCTGGGCAAGTATGAGCAGTACA<br>TCAAGTGGCCCTGGTACATCTGGCTGGGCTTCATCGCCGGCCTGA<br>TCGCCATCGTGATGGTGACCATCATGCTGTGCTGTATGACATCCT<br>GCTGTTCTTGCCTGAAGGGCTGCTGTAGCTGTGGCTCCTGCTGTA<br>AGTTTGACGAGGATGACTCTGAACCTGTGCTGAAGGGCGTGAAG<br>CTGCATTACACCTAA |
| 2019-nCoV Spike gene (SEQ ID NO: 120) | amino acid | MFVFLVLLPLVSSQCVNLTTRTQLPPAYTNSFTRGVYYPDKVFRSSV<br>LHSTQDLFLPFFSNVTWFHAIHVSGTNGTKRFDNPVLPFNDGVYFAS<br>TEKSNIIRGWIFGTTLDSKTQSLLIVNNATNVVIKVCEFQFCNDPFLG<br>VYYHKNNKSWMESEFRVYSSANNCTFEYVSQPFLMDLEGKQGNFK<br>NLREFVFKNIDGYFKIYSKHTPINLVRDLPQGFSALEPLVDLPIGINITR<br>FQTLLALHRSYLTPGDSSSGWTAGAAAYYVGYLQPRTFLLKYNENG<br>TITDAVDCALDPLSETKCTLKSFTVEKGIYQTSNFRVQPTESIVRFPNI<br>TNLCPFGEVFNATRFASVYAWNRKRISNCVADYSVLYNSASFSTFKC<br>YGVSPTKLNDLCFTNVYADSFVIRGDEVRQIAPGQTGKIADYNYKLP<br>DDFTGCVIAWNSNNLDSKVGGNYNYLYRLFRKSNLKPFERDISTEIY<br>QAGSTPCNGVEGFNCYFPLQSYGFQPTNGVGYQPYRVVVLSFELLH<br>APATVCGPKKSTNLVKNKCVNFNFNGLTGTGVLTESNKKFLPFQQF<br>GRDIADTTDAVRDPQTLEILDITPCSFGGVSVITPGTNTSNQVAVLYQ<br>DVNCTEVPVAIHADQLTPTWRVYSTGSNVFQTRAGCLIGAEHVNNS<br>YECDIPIGAGICASYQTQTNSPRRARSVASQSIIAYTMSLGAENSVAY<br>SNNSIAIPTNFTISVTTEILPVSMTKTSVDCTMYICGDSTECSNLLLQY<br>GSFCTQLNRALTGIAVEQDKNTQEVFAQVKQIYKTPPIKDFGGFNFS<br>QILPDPSKPSKRSFIEDLLFNKVTLADAGFIKQYGDCLGDIAARDLICA<br>QKFNGLTVLPPLLTDEMIAQYTSALLAGTITSGWTFGAGAALQIPFA<br>MQMAYRFNGIGVTQNVLYENQKLIANQFNSAIGKIQDSLSSTASALG<br>KLQDVVNQNAQALNTLVKQLSSNFGAISSVLNDILSRLDKVEAEVQI |

TABLE 5-continued

ORF of Peptide of Interest for Self-Replicating RNAs of the Disclosure

| ORF Identity | Sequence Type | Sequence |
|---|---|---|
| | | DRLITGRLQSLQTYVTQQLIRAAEIRASANLAATKMSECVLGQSKRV<br>DFCGKGYHLMSFPQSAPHGVVFLHVTYVPAQEKNFTTAPAICHDGK<br>AHFPREGVFVSNGTHWFVTQRNFYEPQUITTDNTFVSGNCDVVIGIVN<br>NTVYDPLQPELDSFKEELDKYFKNHTSPDVDLGDISGINASVVNIQKE<br>IDRLNEVAKNLNESLIDLQELGKYEQYIKWPWYIWLGFIAGLIAIVM<br>VTIMLCCMTSCCSCLKGCCSCGSCCKFDEDDSEPVLKGVKLHYT* |

RNA sequences can include any combination of the RNA sequences listed in Tables 4 and 5. In some embodiments, RNA sequences of the present disclosure include any combination of the RNA sequences listed in Tables 4 and 5 in which 0% to 100%, 1% to 100%, 25% to 100%, 50% to 100% and 75% to 100% of the uracil nucleotides of the mRNA sequences are modified. In some embodiments, 1% to 100% of the uracil nucleotides are N1-methylpseudouridine or 5-methoxyuridine. In some embodiments, 100% of the uracil nucleotides are N1-methylpseudouridine. In some embodiments, 100% of the uracil nucleotides are 5-methoxyuridine.

A self-replicating RNA of the disclosure may be obtained by any suitable means. Methods for the manufacture of self-replicating RNA are known in the art and would be readily apparent to a person of ordinary skill. A self-replicating RNA of the disclosure may be prepared according to any available technique including, but not limited to chemical synthesis, in vitro transcription (IVT) or enzymatic or chemical cleavage of a longer precursor, etc.

In some embodiments, a self-replicating RNA of the disclosure is produced from a primary complementary DNA (cDNA) construct. The cDNA constructs can be produced on an RNA template by the action of a reverse transcriptase (e.g., RNA-dependent DNA-polymerase). The process of design and synthesis of the primary cDNA constructs described herein generally includes the steps of gene construction, RNA production (either with or without modifications) and purification. In the IVT method, a target polynucleotide sequence encoding a self-replicating RNA of the disclosure is first selected for incorporation into a vector which will be amplified to produce a cDNA template. Optionally, the target polynucleotide sequence and/or any flanking sequences may be codon optimized. The cDNA template is then used to produce a self-replicating RNA of the disclosure through in vitro transcription (IVT). After production, the self-replicating RNA of the disclosure may undergo purification and clean-up processes. The steps of which are provided in more detail below.

The step of gene construction may include, but is not limited to gene synthesis, vector amplification, plasmid purification, plasmid linearization and clean-up, and cDNA template synthesis and clean-up. Once a protein of interest is selected for production, a primary construct is designed. Within the primary construct, a first region of linked nucleosides encoding the polypeptide of interest may be constructed using an open reading frame (ORF) of a selected nucleic acid (DNA or RNA) transcript. The ORF may comprise the wild type ORF, an isoform, variant or a fragment thereof. As used herein, an "open reading frame" or "ORF" is meant to refer to a nucleic acid sequence (DNA or RNA) which is capable of encoding a polypeptide of interest. ORFs often begin with the start codon, ATG and end with a nonsense or termination codon or signal.

The cDNA templates may be transcribed to produce a self-replicating RNA of the disclosure using an in vitro transcription (IVT) system. The system typically comprises a transcription buffer, nucleotide triphosphates (NTPs), an RNase inhibitor and a polymerase. The NTPs may be selected from, but are not limited to, those described herein including natural and unnatural (modified) NTPs. The polymerase may be selected from, but is not limited to, T7 RNA polymerase, T3 RNA polymerase and mutant polymerases such as, but not limited to, polymerases able to incorporate modified nucleic acids.

The primary cDNA template or transcribed RNA sequence may also undergo capping and/or tailing reactions. A capping reaction may be performed by methods known in the art to add a 5' cap to the 5' end of the primary construct. Methods for capping include, but are not limited to, using a Vaccinia Capping enzyme (New England Biolabs, Ipswich, Mass.) or capping at initiation of in vitro transcription, by for example, including a capping agent as part of the IVT reaction. (Nuc. Acids Symp. (2009) 53:129). A poly(A) tailing reaction may be performed by methods known in the art, such as, but not limited to, 2' O-methyltransferase and by methods as described herein. If the primary construct generated from cDNA does not include a poly-T, it may be beneficial to perform the poly(A)-tailing reaction before the primary construct is cleaned.

Codon optimized cDNA constructs encoding the non-structural proteins and the transgene for a self-replicating RNA protein are particularly suitable for generating self-replicating RNA sequences described herein. For example, such cDNA constructs may be used as the basis to transcribe, in vitro, a polyribonucleotide encoding a protein of interest as part of a self-replicating RNA.

The present disclosure also provides expression vectors comprising a nucleotide sequence encoding a self-replicating RNA that is preferably operably linked to at least one regulatory sequence. Regulatory sequences are art-recognized and are selected to direct expression of the encoded polypeptide.

Accordingly, the term regulatory sequence includes promoters, enhancers, and other expression control elements. The design of the expression vector may depend on such factors as the choice of the host cell to be transformed and/or the type of protein desired to be expressed.

The present disclosure also provides polynucleotides (e.g. DNA, RNA, cDNA, mRNA, etc.) directed to a self-replicating RNA of the disclosure that may be operably linked to one or more regulatory nucleotide sequences in an expression construct, such as a vector or plasmid. In certain embodiments, such constructs are DNA constructs. Regulatory nucleotide sequences will generally be appropriate for a host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the embodiments of the present disclosure. The promoters may be either naturally occurring promoters, or hybrid promoters that combine elements of more than one promoter.

An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

The present disclosure also provides a host cell transfected with a self-replicating RNA or DNA described herein. The self-replicating RNA or DNA can encode any coronavirus protein of interest, for example an antigen, including the S-antigen of the COVID-19 virus. The host cell may be any prokaryotic or eukaryotic cell. For example, a polypeptide encoded by a self-replicating RNA may be expressed in bacterial cells such as *E. coli*, insect cells (e.g., using a baculovirus expression system), yeast, or mammalian cells. Other suitable host cells are known to those skilled in the art.

A host cell transfected with an expression vector comprising a self-replicating RNA of the disclosure can be cultured under appropriate conditions to allow expression of the amplification of the self-replicating RNA and translation of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art.

The expressed proteins described herein can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the polypeptide.

Compositions and Pharmaceutical Compositions

Provided herein, in some embodiments, are compositions comprising any of the nucleic acid molecules provided herein. Compositions provided herein can include a lipid. Any lipid can be included in compositions provided herein. In one aspect, the lipid is an ionizable cationic lipid. Any ionizable cationic lipid can be included in compositions comprising nucleic acid molecules provided herein.

The compositions and polynucleotides of the present disclosure may be used to immunize or vaccinate a subject against a viral infection. In some embodiments, the compositions and polynucleotides of the present disclosure may be used to vaccinate or immunize a subject against COVID-19 virus.

Also provided herein, in some embodiments, are pharmaceutical compositions comprising any of the nucleic acid molecules provided herein and a lipid formulation. Any lipid can be included in lipid formulations of pharmaceutical compositions provided herein. In one aspect, lipid formulations of pharmaceutical compositions provided herein include an ionizable cationic lipid. Exemplary ionizable cationic lipids of compositions and pharmaceutical compositions provided herein include the following:

ATX-001

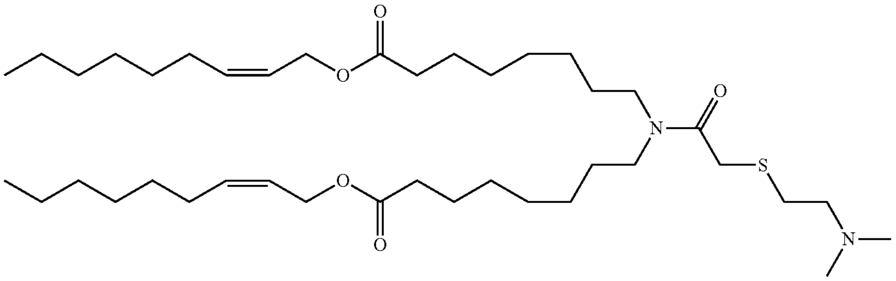

ATX-002

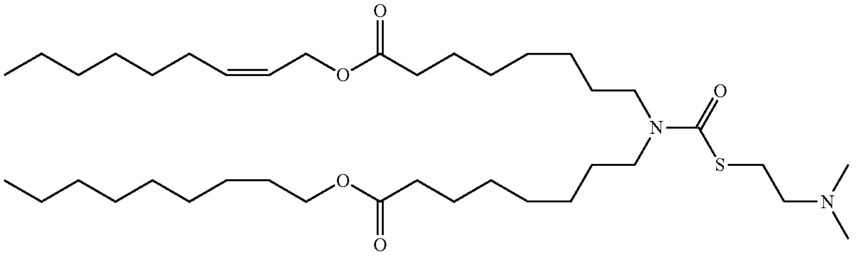

-continued
ATX-003
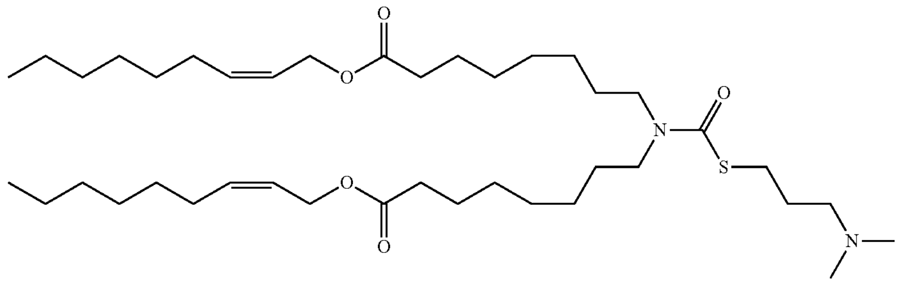
ATX-004
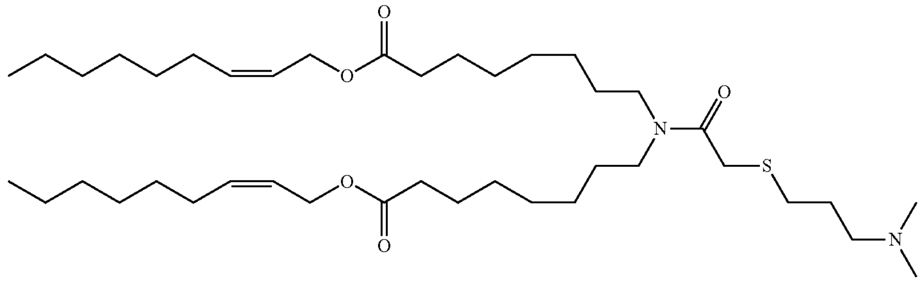
ATX-005
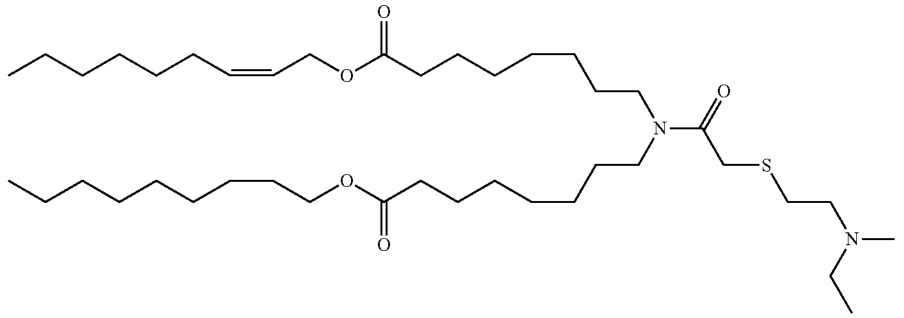
ATX-006
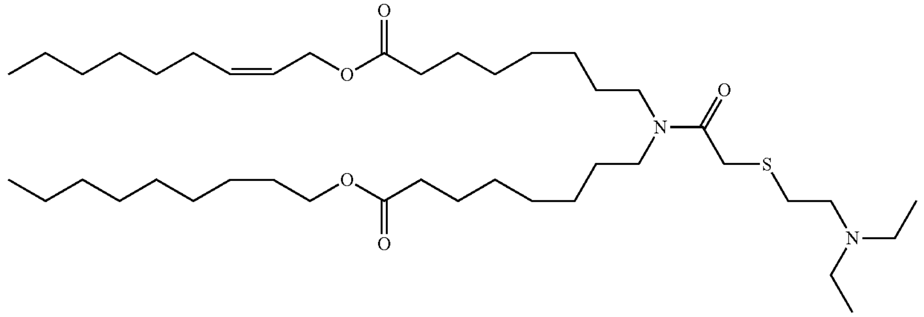
ATX-007
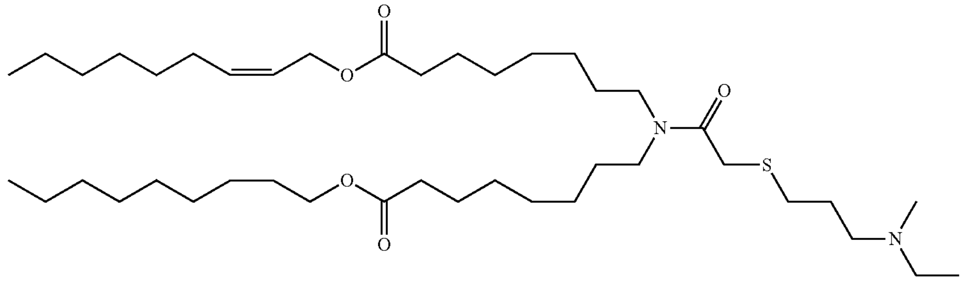

-continued
ATX-008
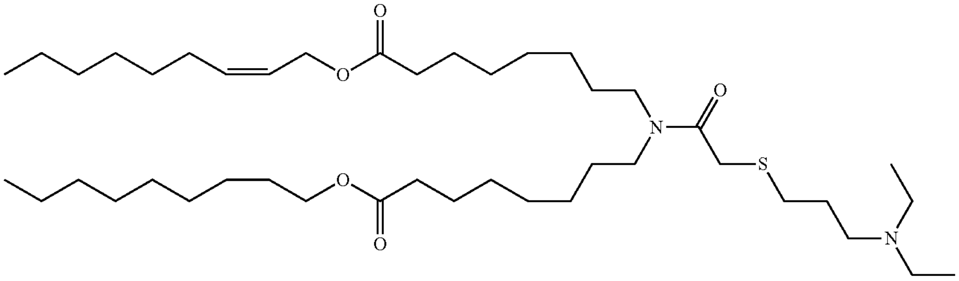
ATX-009
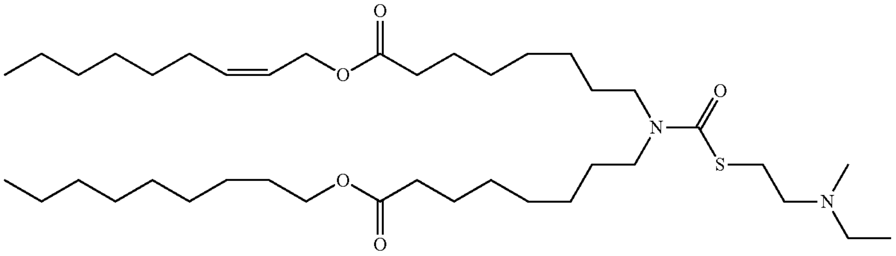
ATX-010
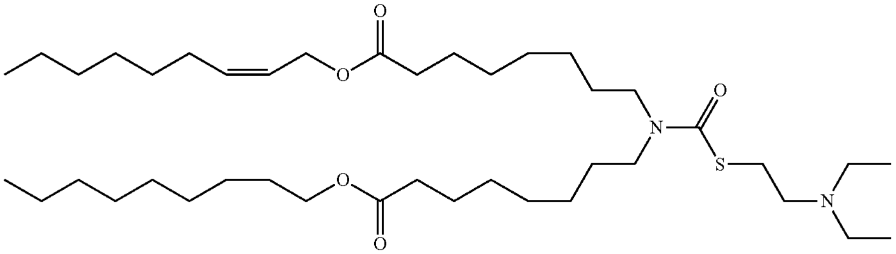
ATX-011
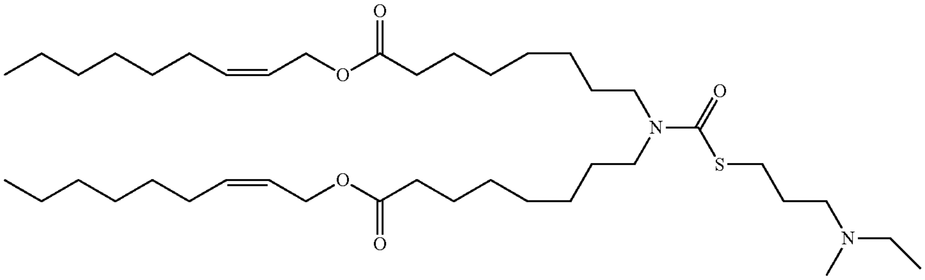
ATX-012
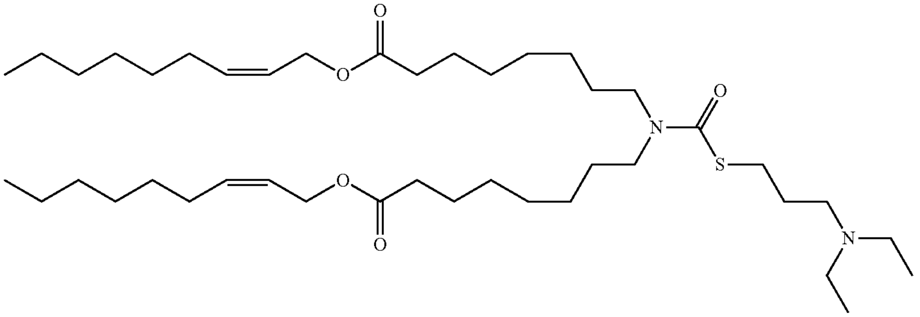
ATX-013
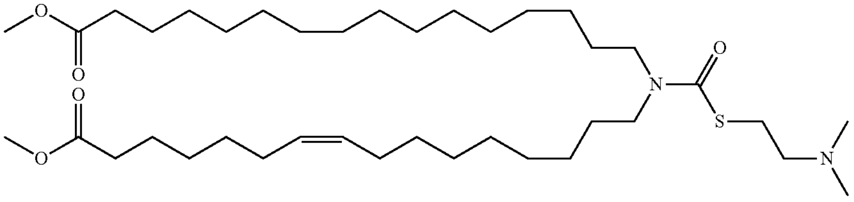

-continued
ATX-014
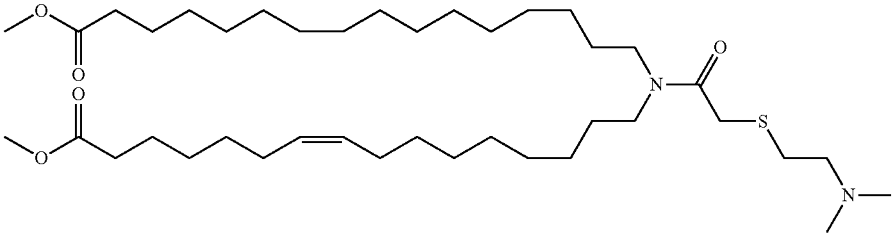
ATX-015
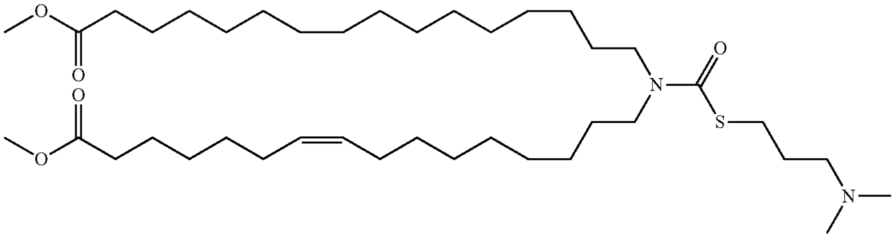
ATX-016
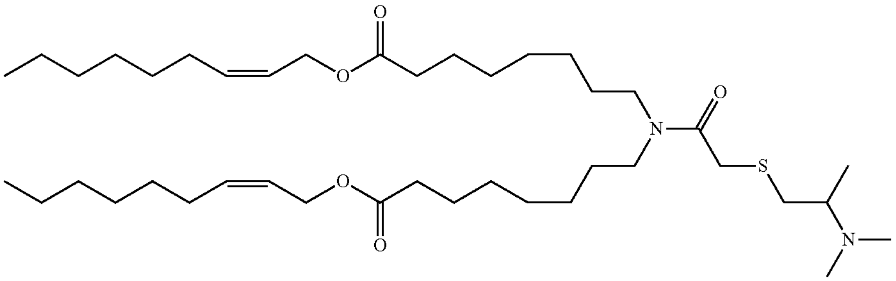
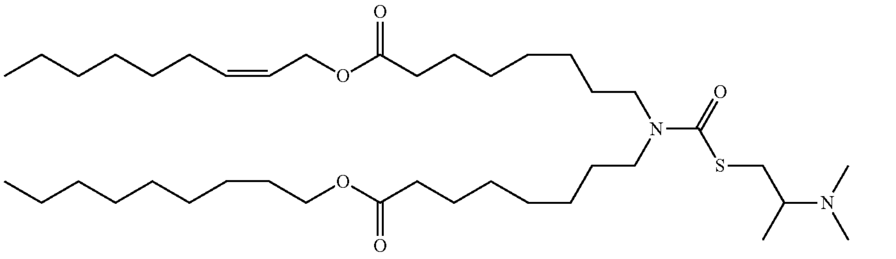
ATX-018
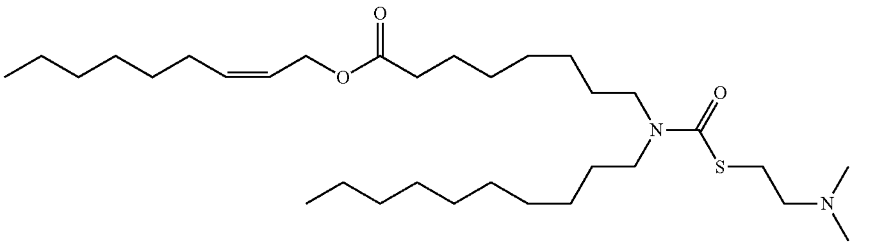
ATX-019
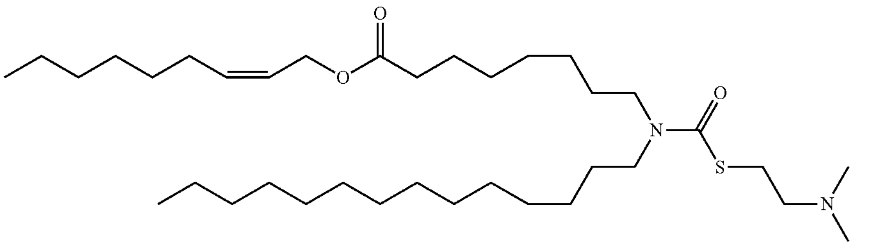

-continued
ATX-020
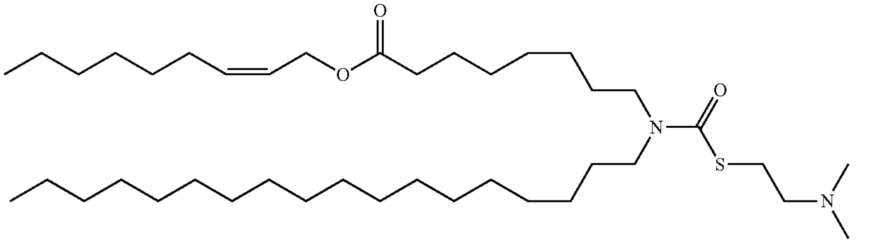
ATX-021
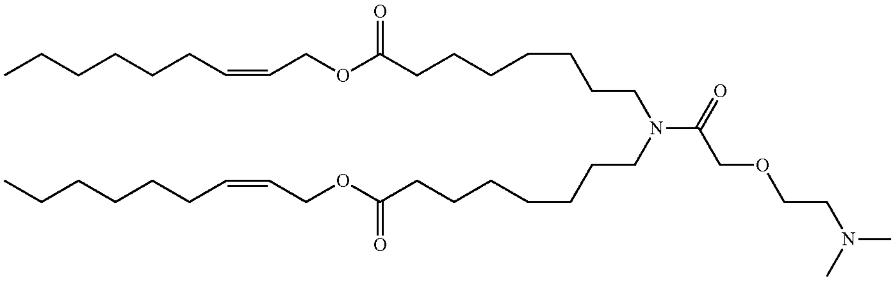
ATX-022
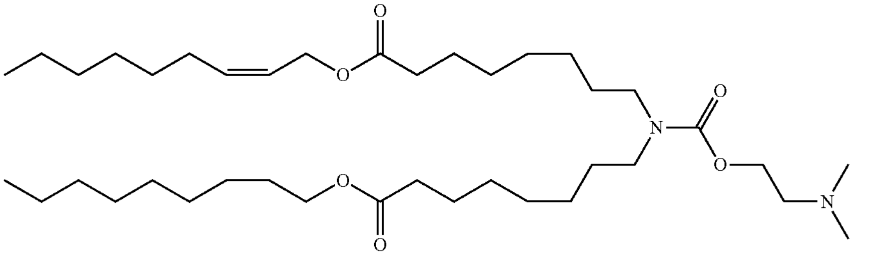
ATX-023
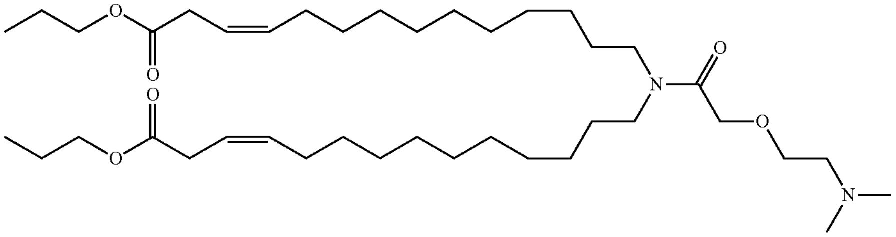
ATX-024
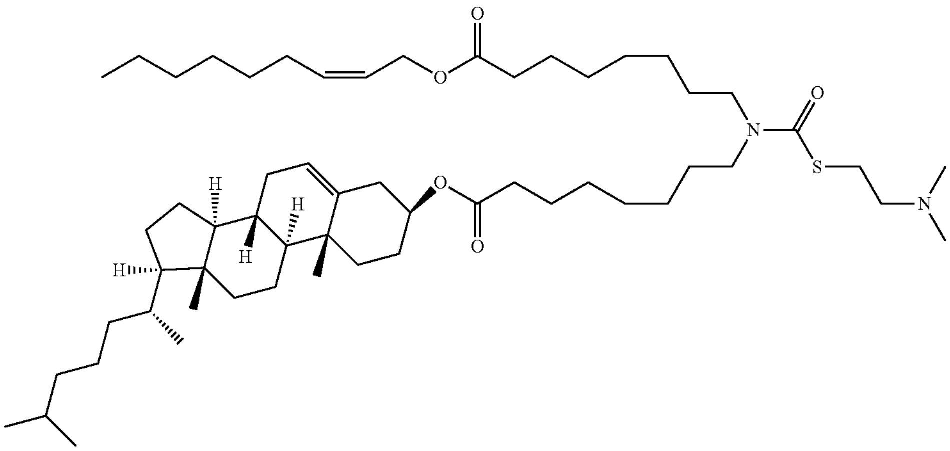

-continued
ATX-025
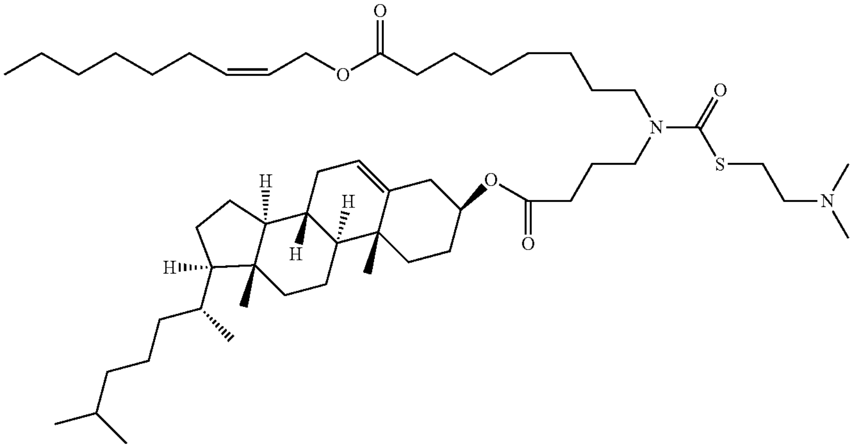
ATX-026
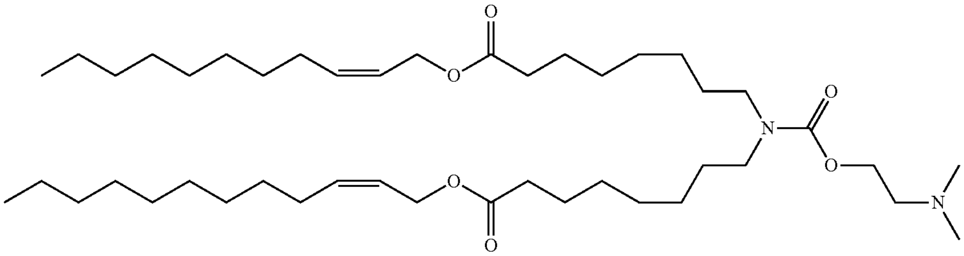
ATX-027
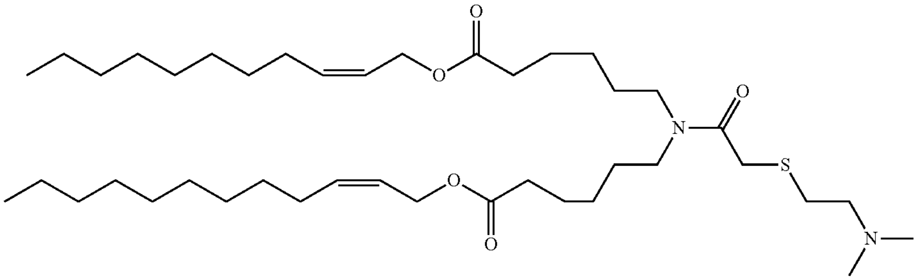
ATX-028
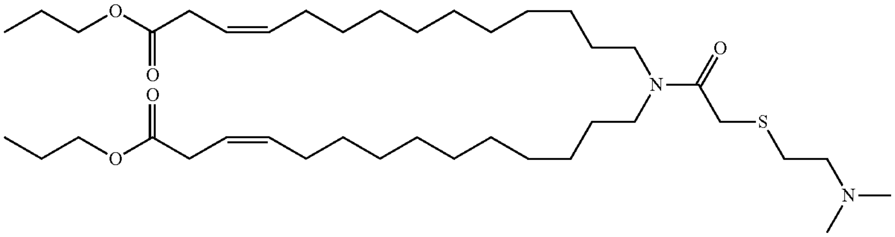
ATX-029
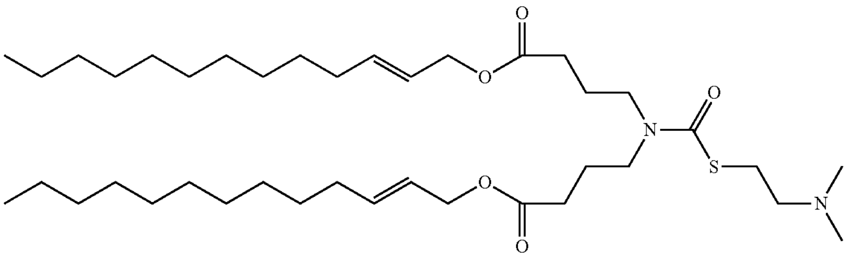

-continued
ATX-030
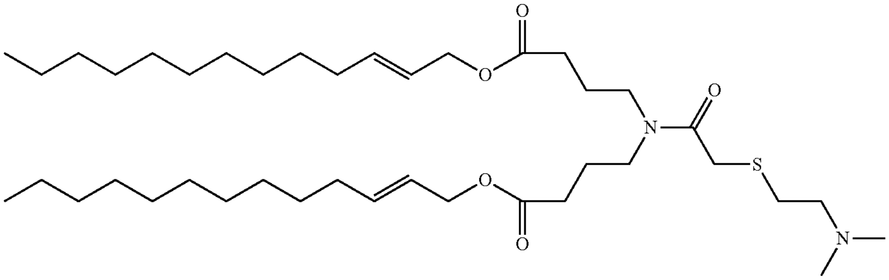
ATX-031
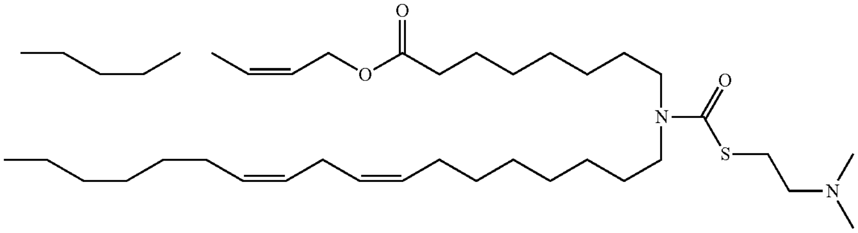
ATX-032
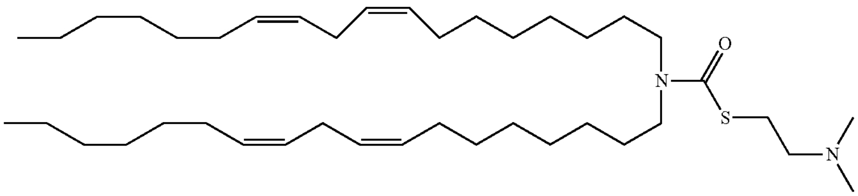
ATX-086
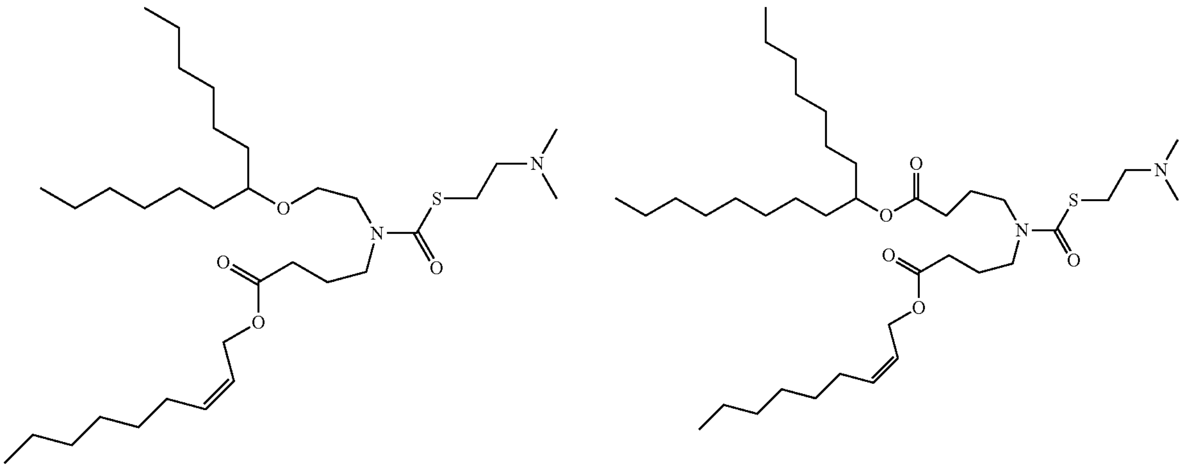

-continued
ATX-058
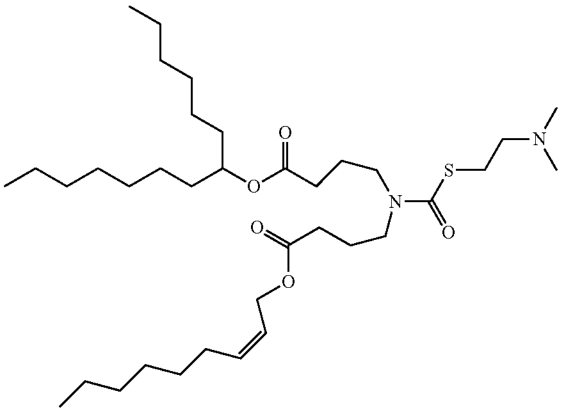
ATX-061
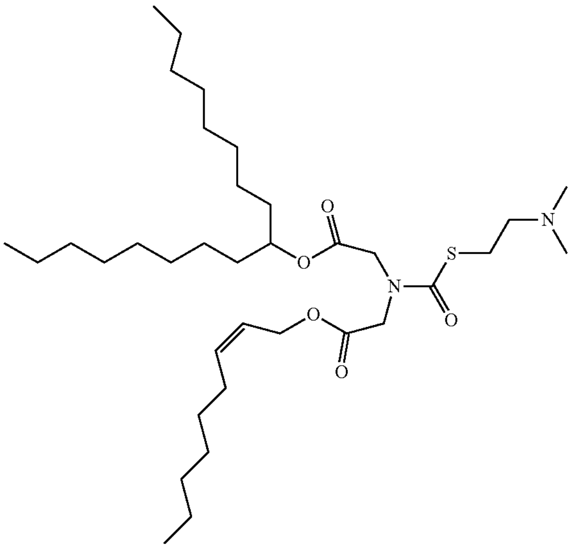
ATX-063
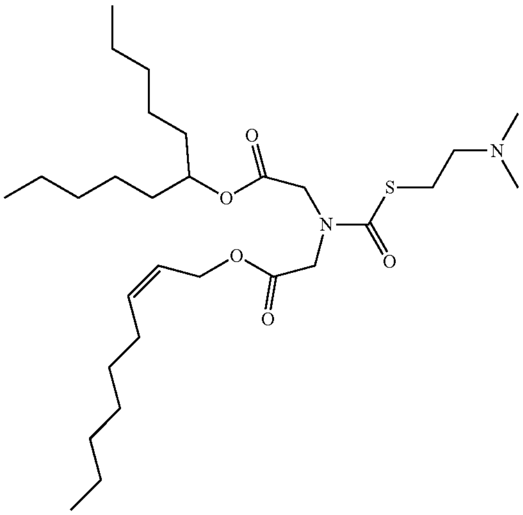
ATX-064
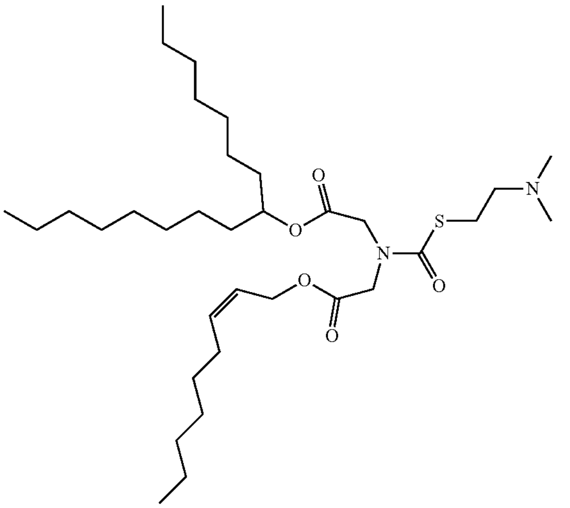
ATX-082
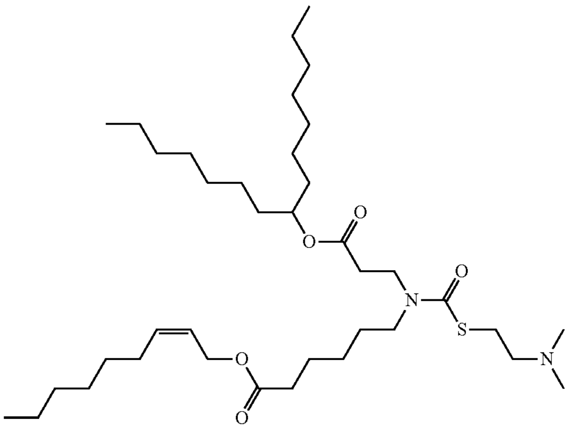
ATX-043
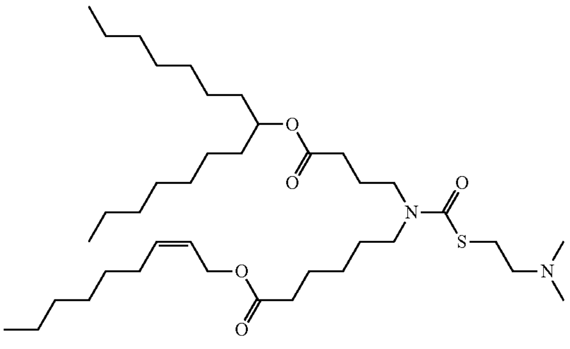

-continued
ATX-057
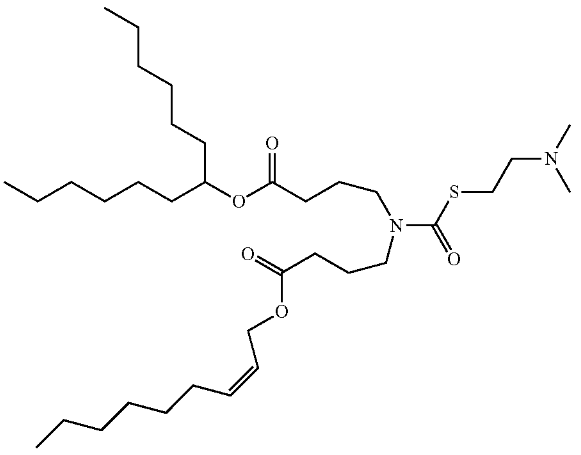
ATX-087
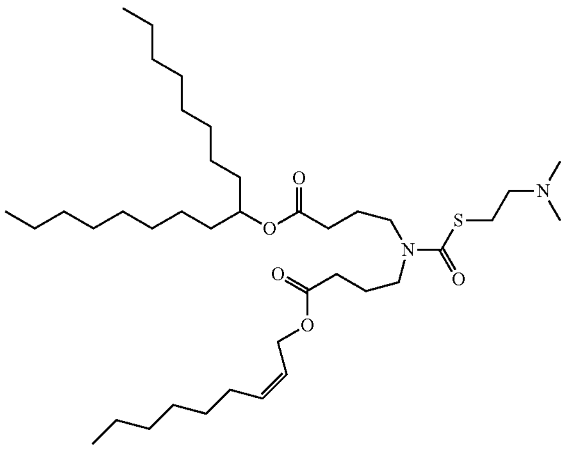
ATX-088
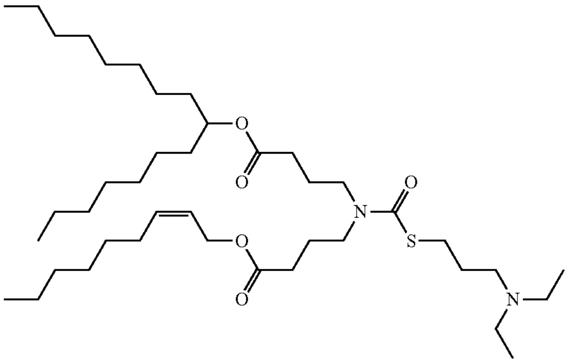
ATX-085
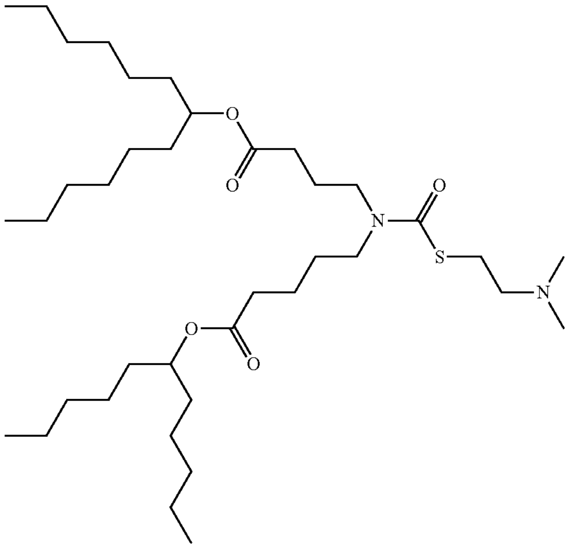
ATX-083
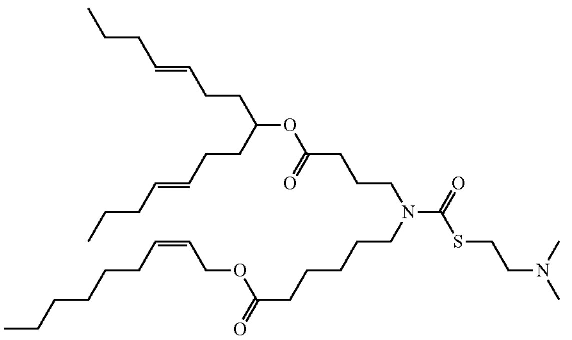
ATX-091
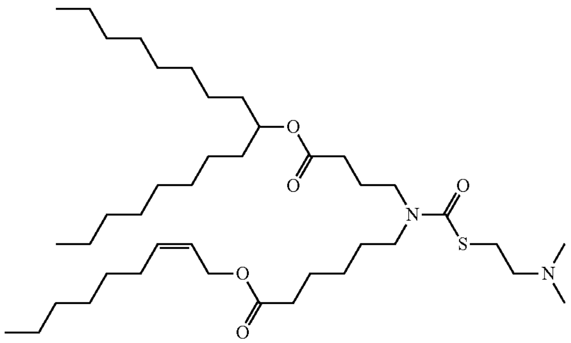

-continued
ATX-0102
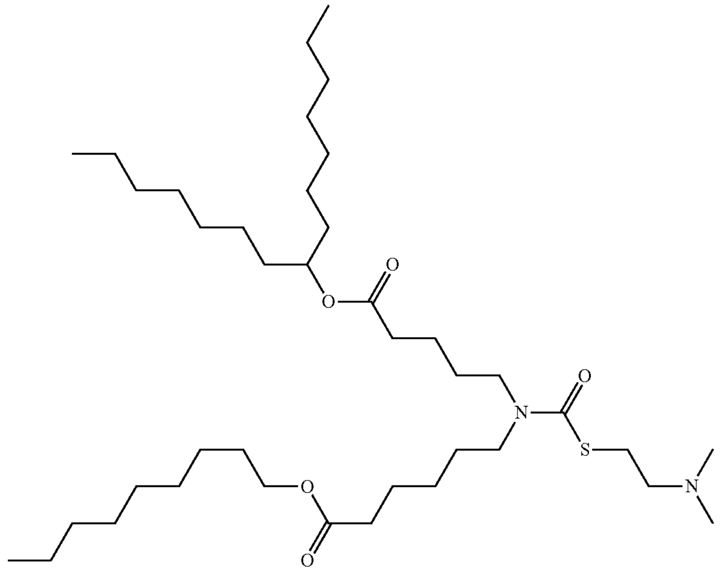
ATX-098
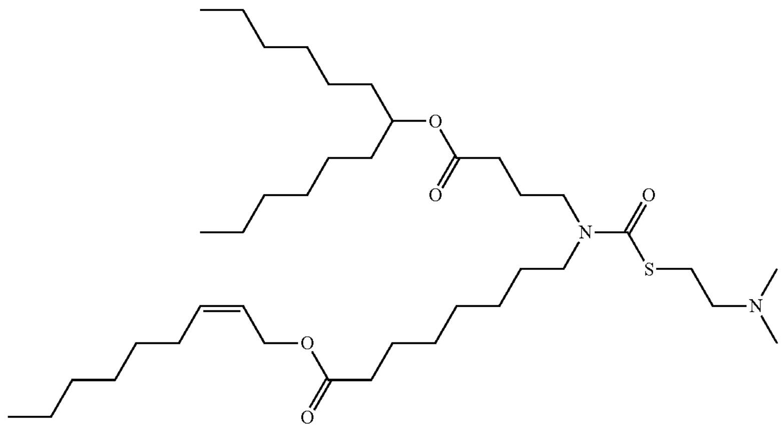
ATX-092
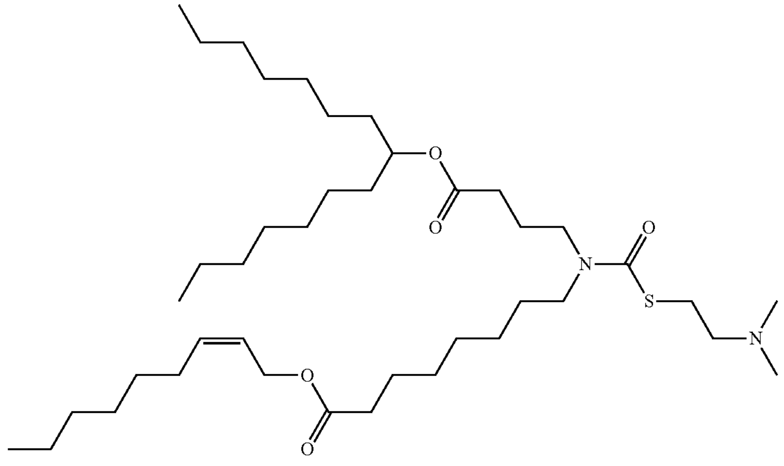

-continued
ATX-084
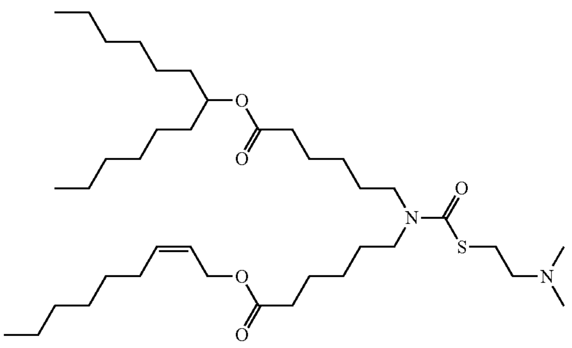
ATX-0125
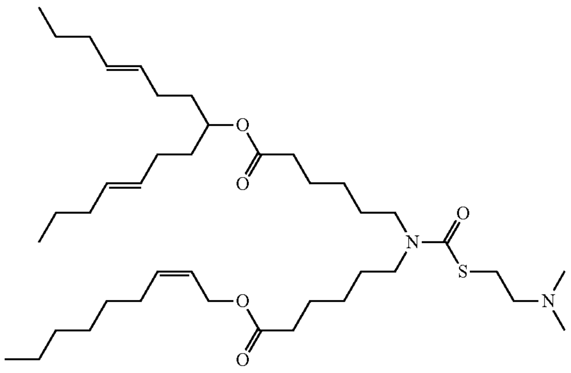
ATX-094
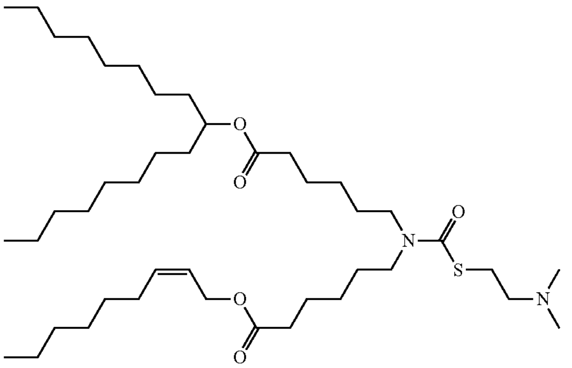
ATX-0110
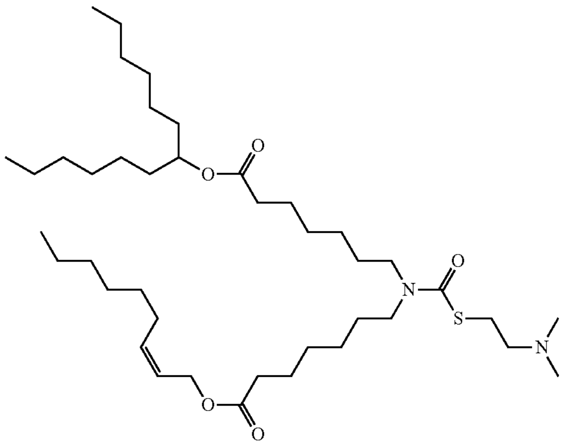
ATX-0118
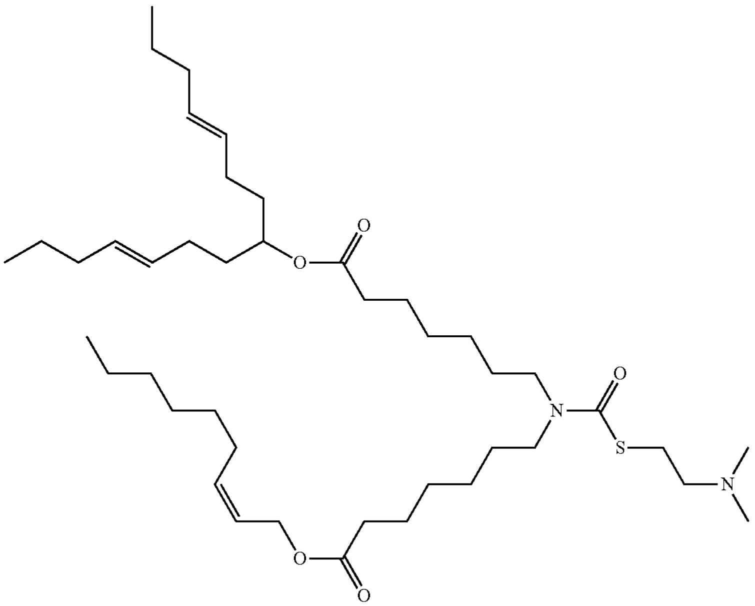

-continued
ATX-0108
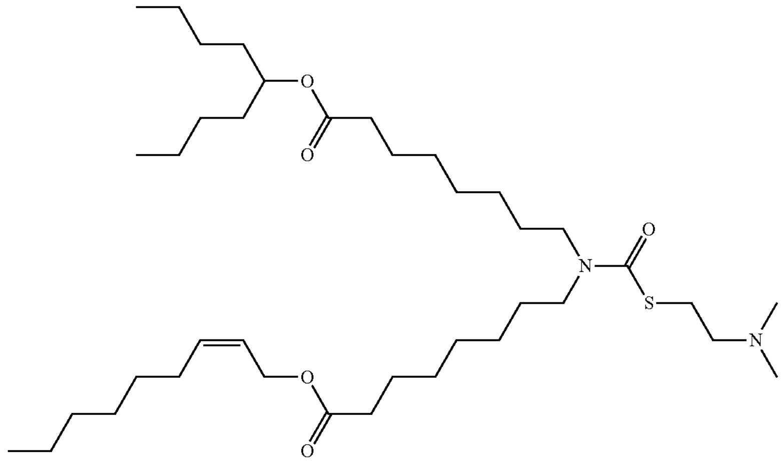
ATX-0107
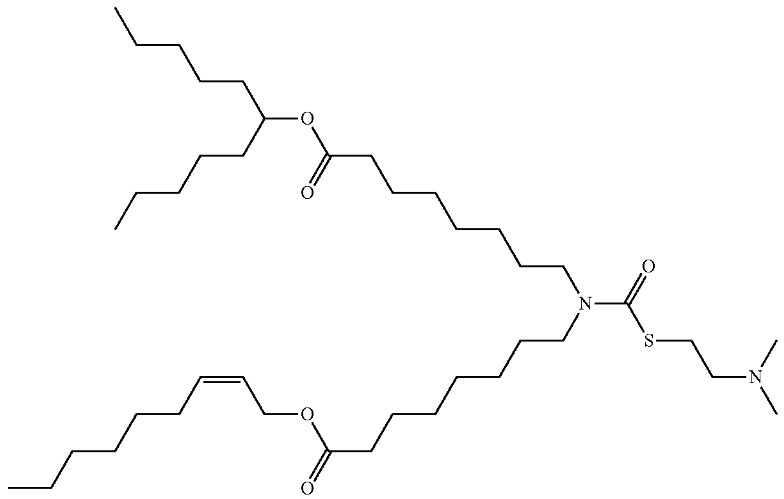
ATX-093
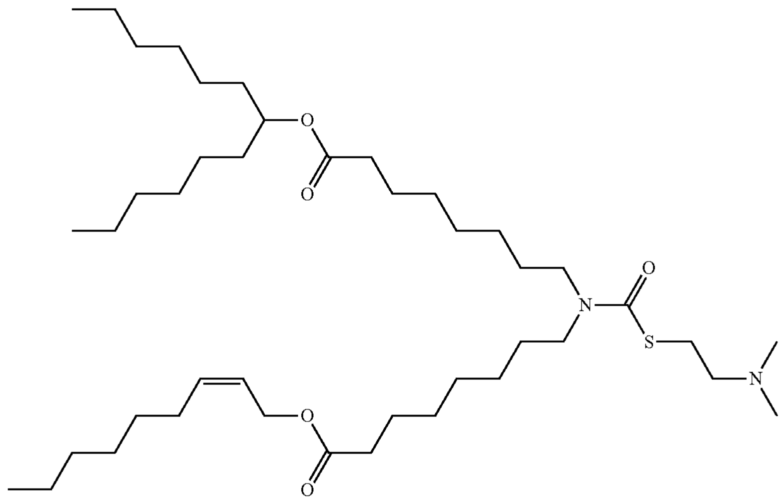

-continued
ATX-097
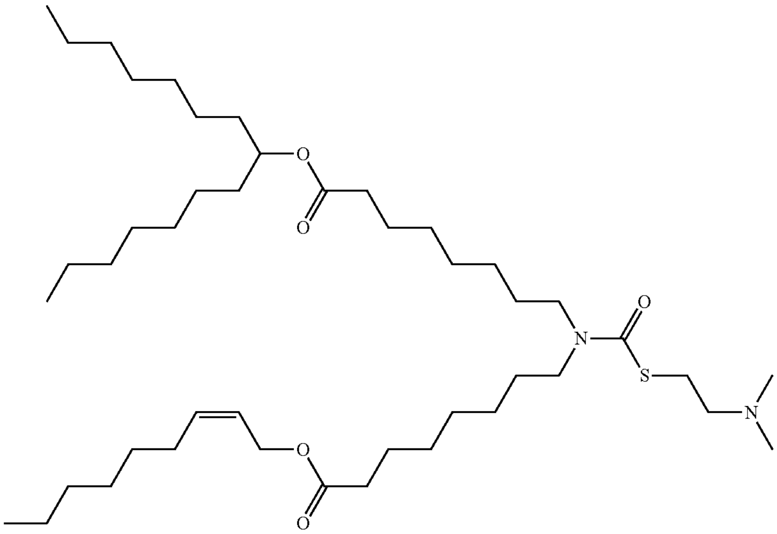
ATX-096
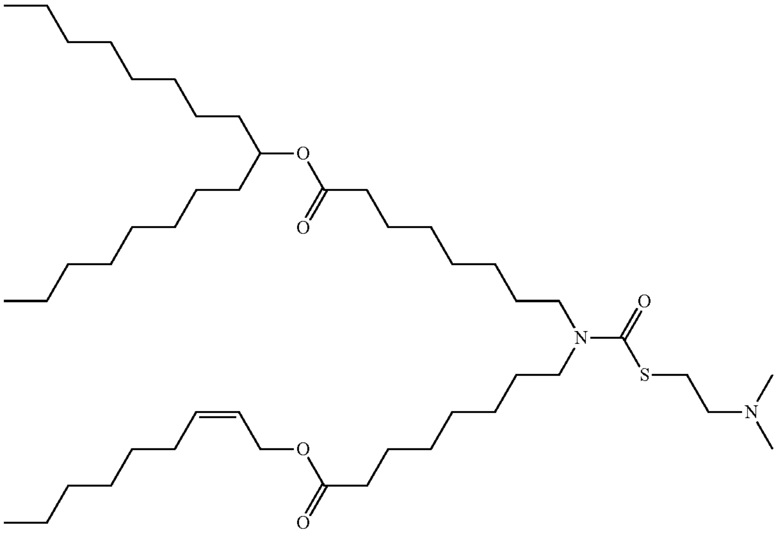
ATX-0111
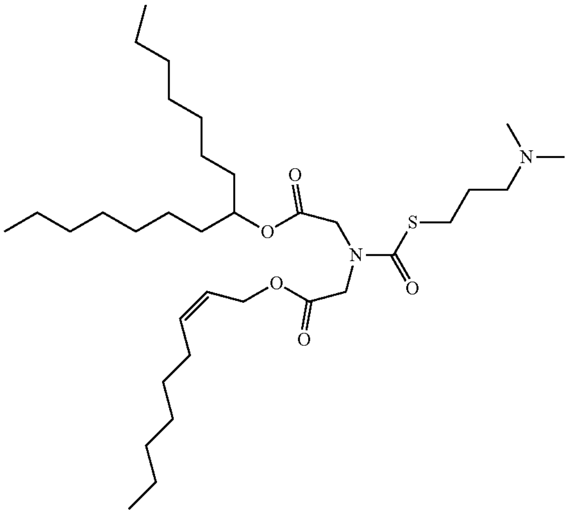
ATX-0132
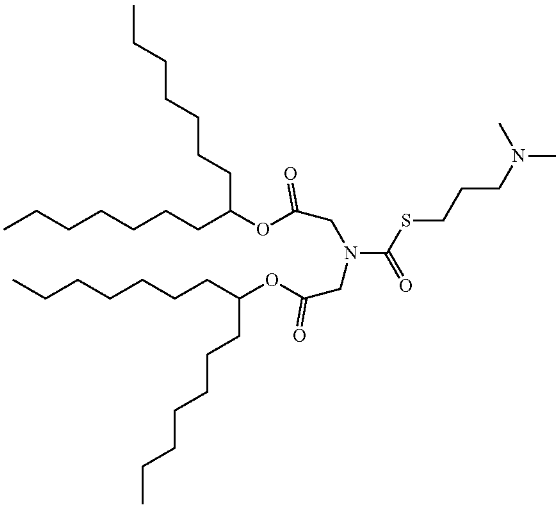

-continued
ATX-0134
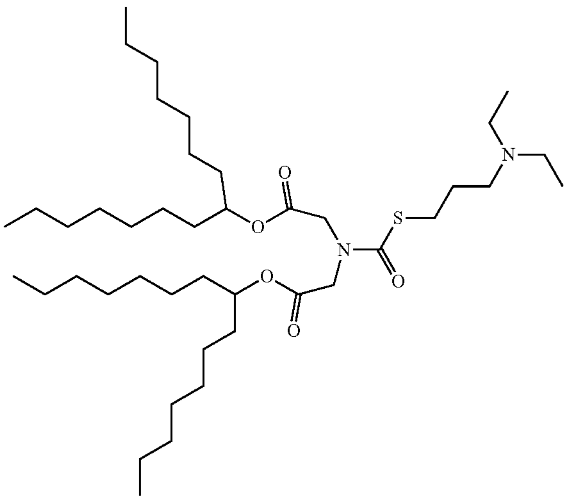
ATX-0100
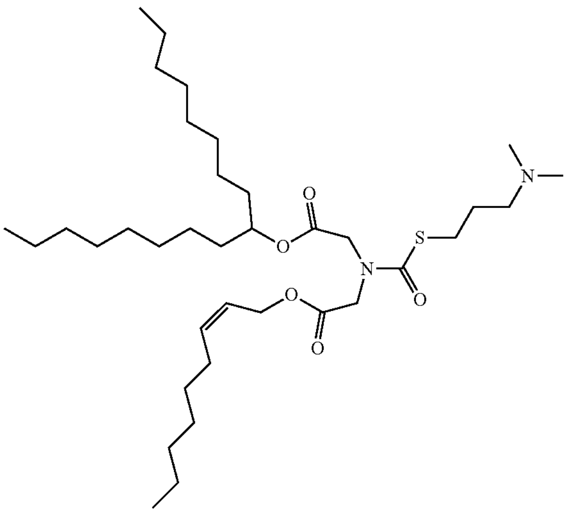
ATX-0117
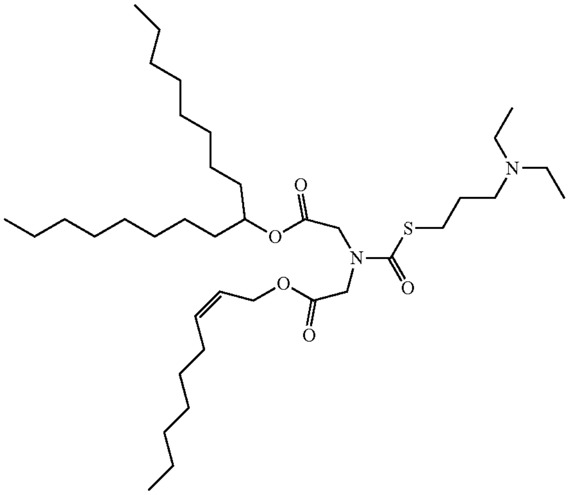
ATX-0114
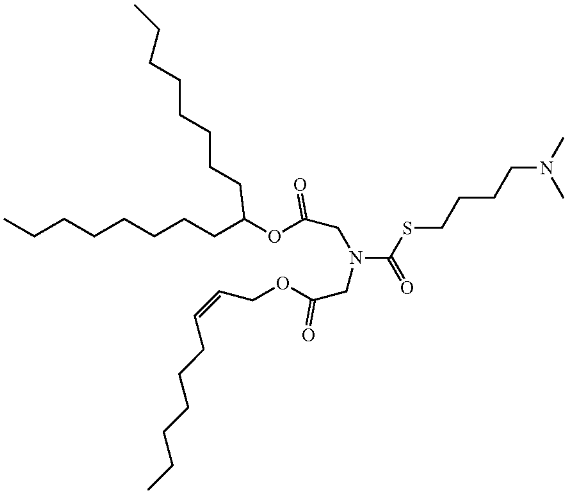
ATX-0115
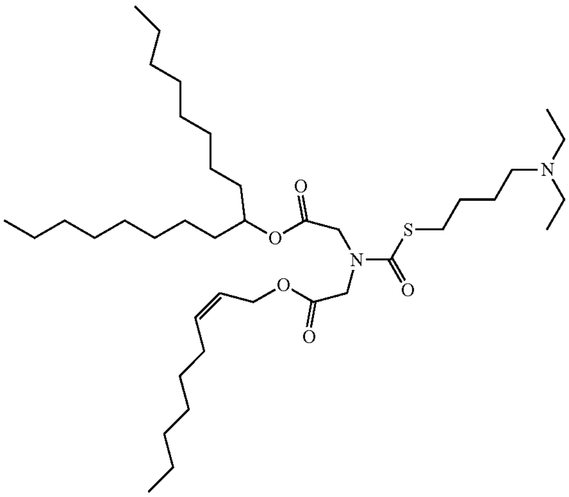
ATX-0101
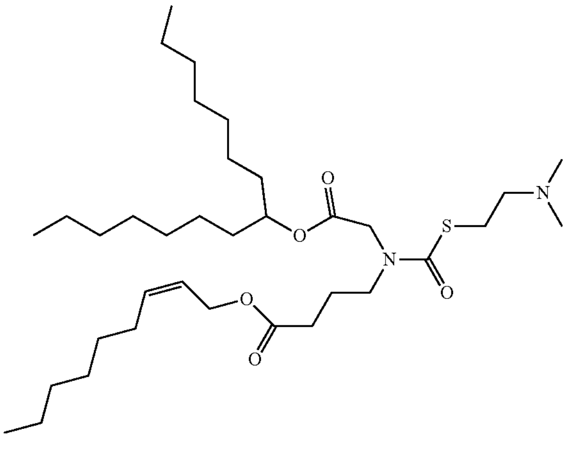

-continued
ATX-0106
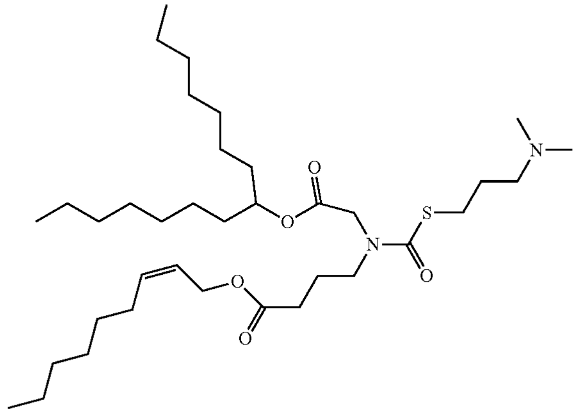
ATX-0116
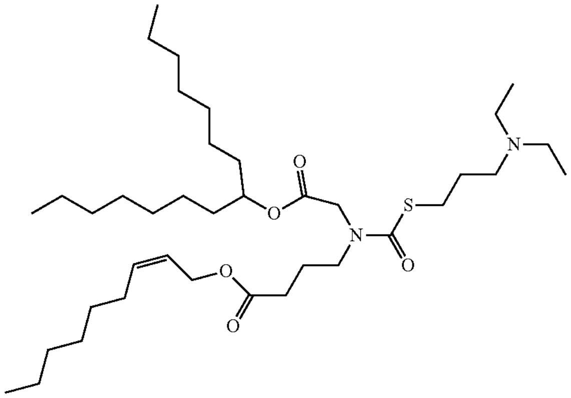
ATX-0123
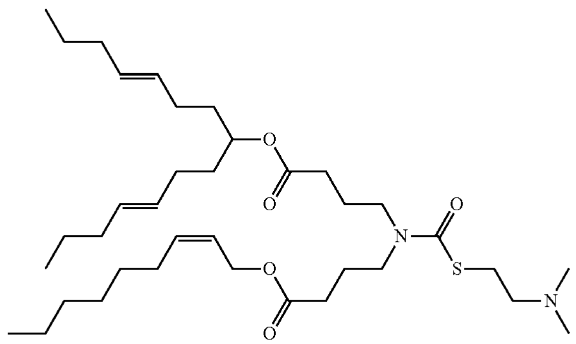
ATX-0122
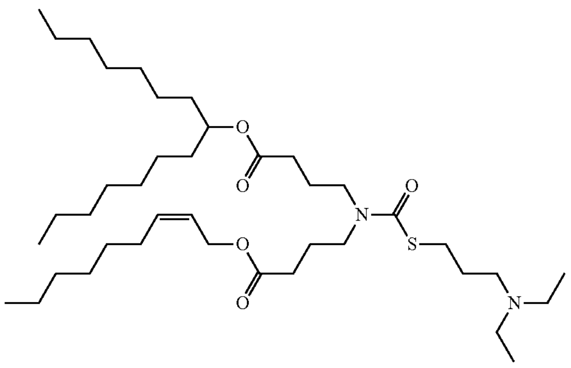
ATX-0124
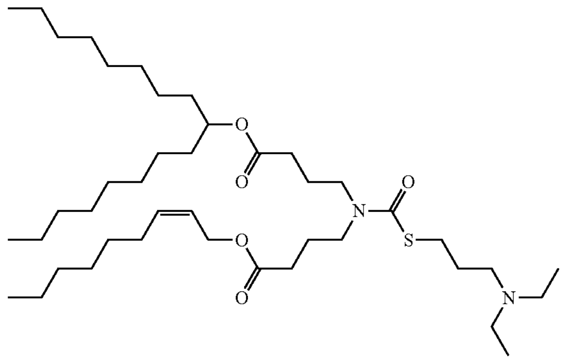
ATX-0129
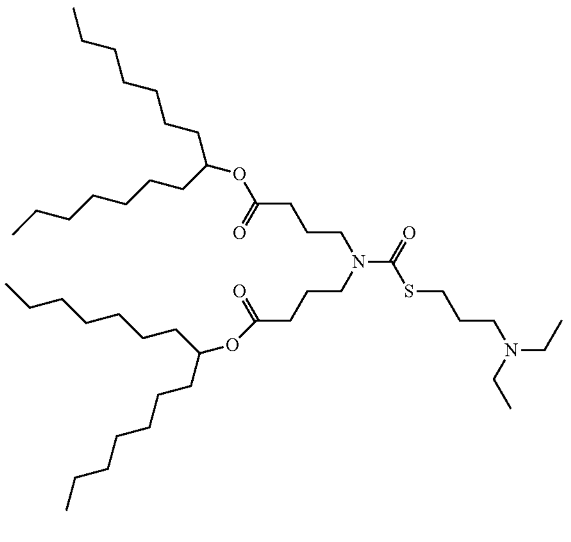

-continued
ATX-081
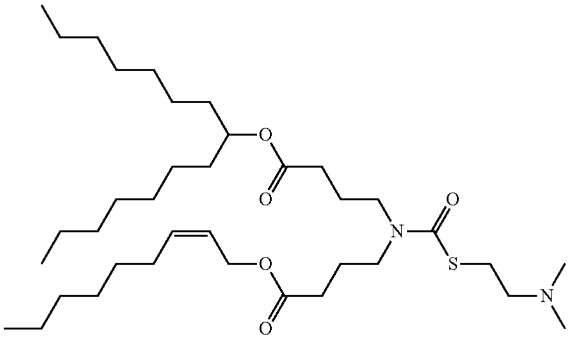
ATX-095
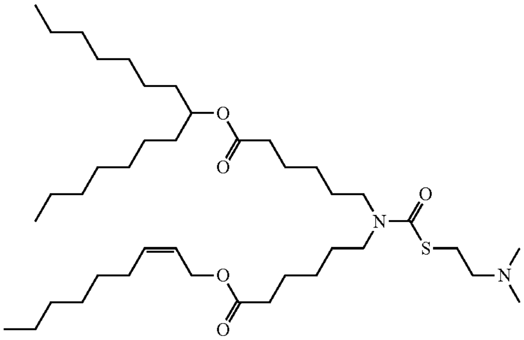
and
ATX-0126
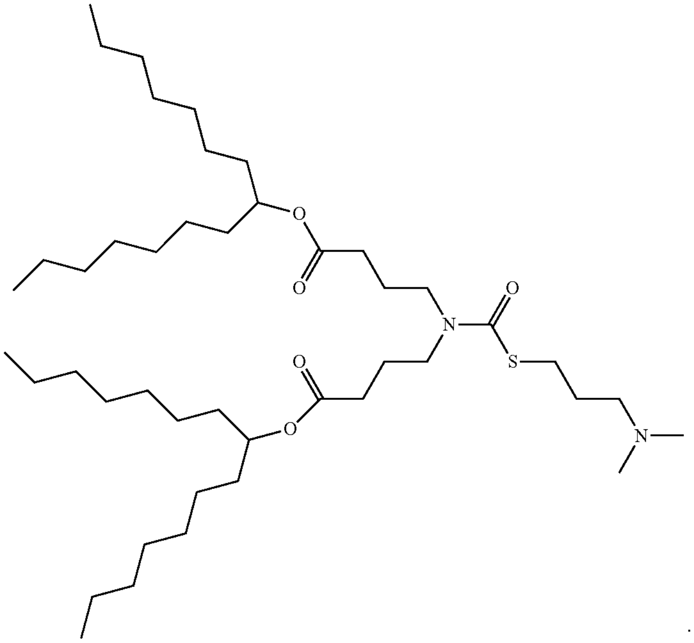
.
In one aspect, the ionizable cationic lipid of compositions provided herein has a structure of
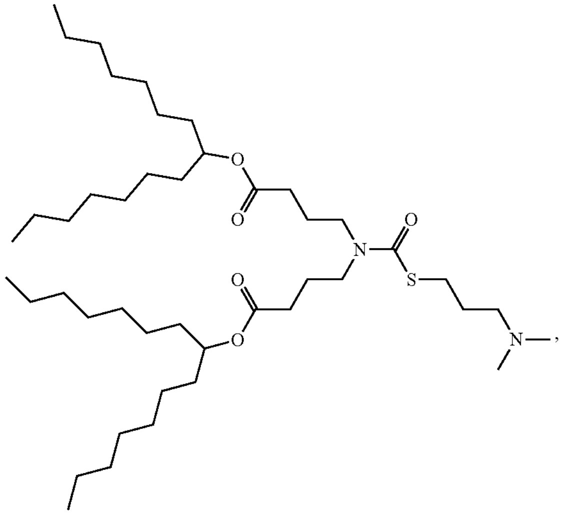
,
-continued
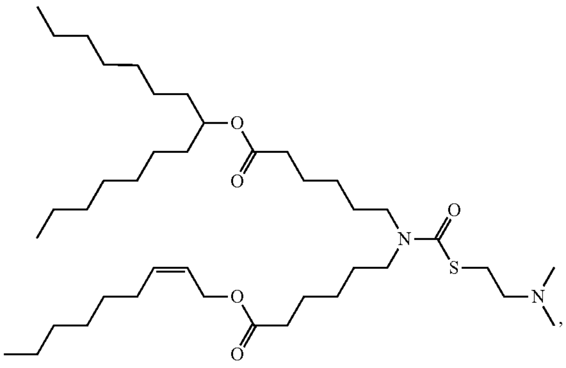
, -continued

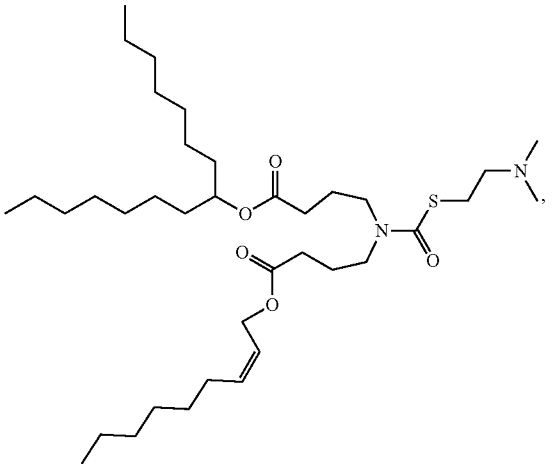

or a pharmaceutically acceptable salt thereof.

In another aspect, the ionizable cationic lipid of compositions provided herein has a structure of

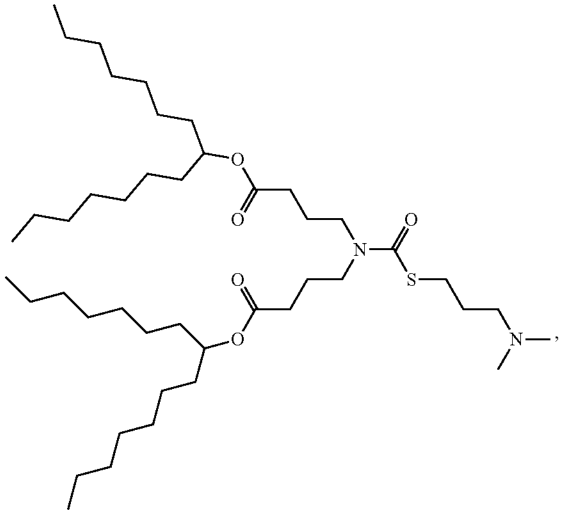 [SMILES: CCCCCCCC(CCCCCCC)OC(=O)CCCN(CCCC(=O)OC(CCCCCCC)CCCCCCC)C(=O)SCCCN(C)C]

or a pharmaceutically acceptable salt thereof.

In one aspect, the ionizable cationic lipid included in lipid formulations of pharmaceutical compositions provided herein has a structure of

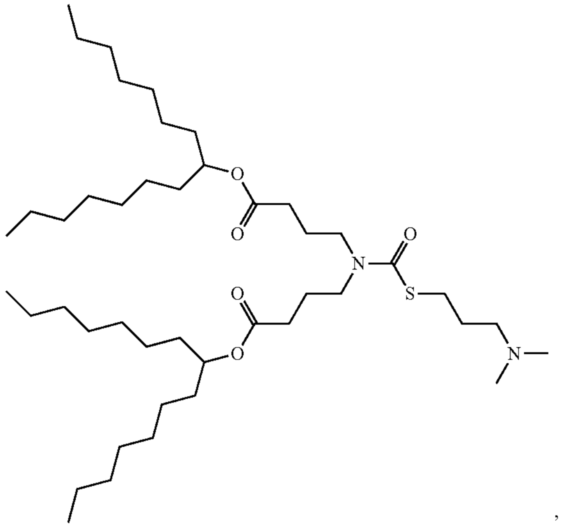

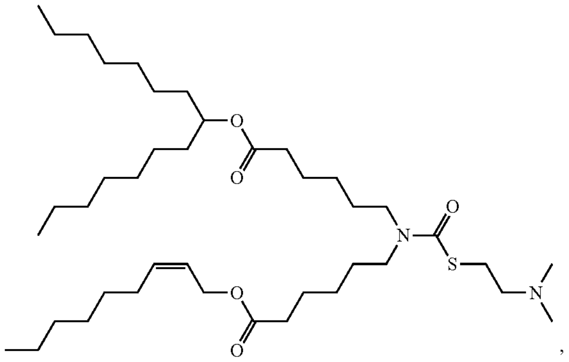

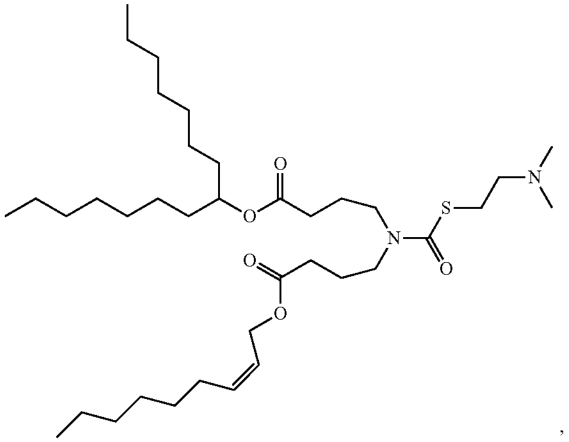

or a pharmaceutically acceptable salt thereof.

In another aspect, the ionizable cationic lipid included in lipid formulations of pharmaceutical compositions provided herein has a structure of

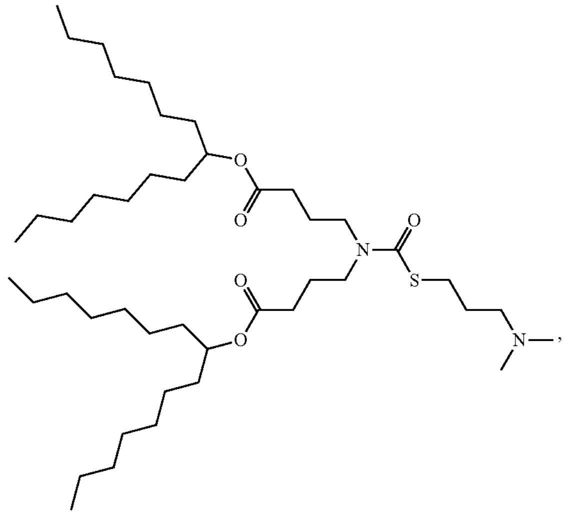 [SMILES: CCCCCCCC(CCCCCCC)OC(=O)CCCN(CCCC(=O)OC(CCCCCCC)CCCCCCC)C(=O)SCCCN(C)C]

or a pharmaceutically acceptable salt thereof.

Lipid Formulations/LNPs

Therapies based on the intracellular delivery of nucleic acids to target cells face both extracellular and intracellular barriers. Indeed, naked nucleic acid materials cannot be easily systemically administered due to their toxicity, low stability in serum, rapid renal clearance, reduced uptake by target cells, phagocyte uptake and their ability in activating the immune response, all features that preclude their clinical development. When exogenous nucleic acid material (e.g., mRNA) enters the human biological system, it is recognized by the reticuloendothelial system (RES) as foreign pathogens and cleared from blood circulation before having the chance to encounter target cells within or outside the vascular system. It has been reported that the half-life of naked nucleic acid in the blood stream is around several minutes (Kawabata K, Takakura Y, Hashida MPharm Res. 1995 June; 12(6):825-30). Chemical modification and a proper delivery method can reduce uptake by the RES and protect nucleic acids from degradation by ubiquitous nucleases, which increase stability and efficacy of nucleic acid-based therapies. In addition, RNAs or DNAs are anionic hydrophilic polymers that are not favorable for uptake by cells, which are also anionic at the surface. The success of nucleic acid-based therapies thus depends largely on the development of vehicles or vectors that can efficiently and effectively deliver genetic material to target cells and obtain sufficient levels of expression in vivo with minimal toxicity.

Moreover, upon internalization into a target cell, nucleic acid delivery vectors are challenged by intracellular barriers, including endosome entrapment, lysosomal degradation, nucleic acid unpacking from vectors, translocation across the nuclear membrane (for DNA), release at the cytoplasm (for RNA), and so on. Successful nucleic acid-based therapy thus depends upon the ability of the vector to deliver the nucleic acids to the target sites inside of the cells in order to obtain sufficient levels of a desired activity such as expression of a gene.

While several gene therapies have been able to successfully utilize a viral delivery vector (e.g., AAV), lipid-based formulations have been increasingly recognized as one of the most promising delivery systems for RNA and other nucleic acid compounds due to their biocompatibility and their ease of large-scale production. One of the most significant advances in lipid-based nucleic acid therapies happened in August 2018 when Patisiran (ALN-TTR02) was the first siRNA therapeutic approved by the Food and Drug Administration (FDA) and by the European Commission (EC). ALN-TTR02 is an siRNA formulation based upon the so-called Stable Nucleic Acid Lipid Particle (SNALP) transfecting technology. Despite the success of Patisiran, the delivery of nucleic acid therapeutics, including mRNA, via lipid formulations is still under ongoing development.

Some art-recognized lipid-formulated delivery vehicles for nucleic acid therapeutics include, according to various embodiments, polymer based carriers, such as polyethyleneimine (PEI), lipid nanoparticles and liposomes, nanoliposomes, ceramide-containing nanoliposomes, multivesicular liposomes, proteoliposomes, both natural and synthetically-derived exosomes, natural, synthetic and semi-synthetic lamellar bodies, nanoparticulates, micelles, and emulsions. These lipid formulations can vary in their structure and composition, and as can be expected in a rapidly evolving field, several different terms have been used in the art to describe a single type of delivery vehicle. At the same time, the terms for lipid formulations have varied as to their intended meaning throughout the scientific literature, and this inconsistent use has caused confusion as to the exact meaning of several terms for lipid formulations. Among the several potential lipid formulations, liposomes, cationic liposomes, and lipid nanoparticles are specifically described in detail and defined herein for the purposes of the present disclosure.

Liposomes

Conventional liposomes are vesicles that consist of at least one bilayer and an internal aqueous compartment. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). They generally present as spherical vesicles and can range in size from 20 nm to a few microns. Liposomal formulations can be prepared as a colloidal dispersion or they can be lyophilized to reduce stability risks and to improve the shelf-life for liposome-based drugs. Methods of preparing liposomal compositions are known in the art and would be within the skill of an ordinary artisan.

Liposomes that have only one bilayer are referred to as being unilamellar, and those having more than one bilayer are referred to as multilamellar. The most common types of liposomes are small unilamellar vesicles (SUV), large unilamellar vesicle (LUV), and multilamellar vesicles (MLV). In contrast to liposomes, lysosomes, micelles, and reversed micelles are composed of monolayers of lipids. Generally, a liposome is thought of as having a single interior compartment, however some formulations can be multivesicular liposomes (MVL), which consist of numerous discontinuous internal aqueous compartments separated by several non-concentric lipid bilayers.

Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9:1833-1843). In their use as drug delivery vehicles, because a liposome has an aqueous solution core surrounded by ahydrophobic membrane, hydrophilic solutes dissolved in the core cannot readily pass through the bilayer, and hydrophobic compounds will associate with the bilayer. Thus, a liposome can be loaded with hydrophobic and/or hydrophilic molecules. When a liposome is used to carry a nucleic acid such as RNA, the nucleic acid will be contained within the liposomal compartment in an aqueous phase.

Cationic Liposomes

Liposomes can be composed of cationic, anionic, and/or neutral lipids. As an important subclass of liposomes, cationic liposomes are liposomes that are made in whole or part from positively charged lipids, or more specifically a lipid that comprises both a cationic group and a lipophilic portion. In addition to the general characteristics profiled above for liposomes, the positively charged moieties of cationic lipids used in cationic liposomes provide several advantages and some unique structural features. For example, the lipophilic portion of the cationic lipid is hydrophobic and thus will direct itself away from the aqueous interior of the liposome and associate with other nonpolar and hydrophobic species. Conversely, the cationic moiety will associate with aqueous media and more importantly with polar molecules and species with which it can complex in the aqueous interior of the cationic liposome. For these reasons, cationic liposomes are increasingly being researched for use in gene therapy due to their favorability towards negatively charged nucleic acids via electrostatic interactions, resulting in complexes that offer biocompatibility, low toxicity, and the possibility of the large-scale production required for in vivo clinical applications. Cationic lipids suitable for use in cationic liposomes are listed herein below.

Lipid Nanoparticles

In contrast to liposomes and cationic liposomes, lipid nanoparticles (LNP) have a structure that includes a single monolayer or bilayer of lipids that encapsulates a compound in a solid phase. Thus, unlike liposomes, lipid nanoparticles do not have an aqueous phase or other liquid phase in its interior, but rather the lipids from the bilayer or monolayer shell are directly complexed to the internal compound thereby encapsulating it in a solid core. Lipid nanoparticles are typically spherical vesicles having a relatively uniform dispersion of shape and size. While sources vary on what size qualifies a lipid particle as being a nanoparticle, there is some overlap in agreement that a lipid nanoparticle can have a diameter in the range of from 10 nm to 1000 nm. However, more commonly they are considered to be smaller than 120 nm or even 100 nm.

For lipid nanoparticle nucleic acid delivery systems, the lipid shell is formulated to include an ionizable cationic lipid which can complex to and associate with the negatively charged backbone of the nucleic acid core. Ionizable cationic lipids with apparent pKa values below about 7 have the benefit of providing a cationic lipid for complexing with the nucleic acid's negatively charged backbone and loading into the lipid nanoparticle at pH values below the pKa of the ionizable lipid where it is positively charged. Then, at physiological pH values, the lipid nanoparticle can adopt a relatively neutral exterior allowing for a significant increase in the circulation half-lives of the particles following i.v. administration. In the context of nucleic acid delivery, lipid nanoparticles offer many advantages over other lipid-based nucleic acid delivery systems including high nucleic acid encapsulation efficiency, potent transfection, improved penetration into tissues to deliver therapeutics, and low levels of cytotoxicity and immunogenicity.

Prior to the development of lipid nanoparticle delivery systems for nucleic acids, cationic lipids were widely studied as synthetic materials for delivery of nucleic acid medicines. In these early efforts, after mixing together at physiological pH, nucleic acids were condensed by cationic lipids to form lipid-nucleic acid complexes known as lipoplexes. However, lipoplexes proved to be unstable and characterized by broad size distributions ranging from the submicron scale to a few microns. Lipoplexes, such as the Lipofectamine® reagent, have found considerable utility for in vitro transfection. However, these first-generation lipoplexes have not proven useful in vivo. The large particle size and positive charge (Imparted by the cationic lipid) result in rapid plasma clearance, hemolytic and other toxicities, as well as immune system activation. In some aspects, nucleic acid molecules provided herein and lipids or lipid formulations provided herein form a lipid nanoparticle (LNP).

In other aspects, nucleic acid molecules provided herein are incorporated into a lipid formulation (i.e., a lipid-based delivery vehicle).

In the context of the present disclosure, a lipid-based delivery vehicle typically serves to transport a desired RNA to a target cell or tissue. The lipid-based delivery vehicle can be any suitable lipid-based delivery vehicle known in the art. In some aspects, the lipid-based delivery vehicle is a liposome, a cationic liposome, or a lipid nanoparticle containing a self-replicating RNA of the disclosure. In some aspects, the lipid-based delivery vehicle comprises a nanoparticle or a bilayer of lipid molecules and a self-replicating RNA of the disclosure. In some aspects, the lipid bilayer further comprises a neutral lipid or a polymer. In some aspects, the lipid formulation comprises a liquid medium. In some aspects, the formulation further encapsulates a nucleic acid. In some aspects, the lipid formulation further comprises a nucleic acid and a neutral lipid or a polymer. In some aspects, the lipid formulation encapsulates the nucleic acid.

The description provides lipid formulations comprising one or more self-replicating RNA molecules encapsulated within the lipid formulation. In some aspects, the lipid formulation comprises liposomes. In some aspects, the lipid formulation comprises cationic liposomes. In some aspects, the lipid formulation comprises lipid nanoparticles.

In some aspects, the self-replicating RNA is fully encapsulated within the lipid portion of the lipid formulation such that the RNA in the lipid formulation is resistant in aqueous solution to nuclease degradation. In other aspects, the lipid formulations described herein are substantially non-toxic to animals such as humans and other mammals.

The lipid formulations of the disclosure also typically have a total lipid:RNA ratio (mass/mass ratio) of from about 1:1 to about 100:1, from about 1:1 to about 50:1, from about 2:1 to about 45:1, from about 3:1 to about 40:1, from about 5:1 to about 45:1, or from about 10:1 to about 40:1, or from about 15:1 to about 40:1, or from about 20:1 to about 40:1; or from about 25:1 to about 45:1; or from about 30:1 to about 45:1; or from about 32:1 to about 42:1; or from about 34:1 to about 42:1. In some aspects, the total lipid:RNA ratio (mass/mass ratio) is from about 30:1 to about 45:1. The ratio may be any value or subvalue within the recited ranges, including endpoints.

The lipid formulations of the present disclosure typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, or about 150 nm, and are substantially non-toxic. The diameter may be any value or subvalue within the recited ranges, including endpoints. In addition, nucleic acids, when present in the lipid nanoparticles of the present disclosure, generally are resistant in aqueous solution to degradation with a nuclease.

In some embodiments, the lipid nanoparticle has a size of less than about 500 nm, less than about 400 nm, less than about 300 nm, less than about 200 nm, less than about 100 nm, or less than about 50 nm. In specific embodiments, the lipid nanoparticle has a size of about 55 nm to about 90 nm.

In some aspects, the lipid formulations comprise a self-replicating RNA, a cationic lipid (e.g., one or more cationic lipids or salts thereof described herein), a phospholipid, and a conjugated lipid that inhibits aggregation of the particles (e.g., one or more PEG-lipid conjugates). The lipid formulations can also include cholesterol. In one aspect, the cationic lipid is an ionizable cationic lipid.

In the nucleic acid-lipid formulations, the RNA may be fully encapsulated within the lipid portion of the formulation, thereby protecting the nucleic acid from nuclease degradation. In some aspects, a lipid formulation comprising an RNA is fully encapsulated within the lipid portion of the lipid formulation, thereby protecting the nucleic acid from nuclease degradation. In certain aspects, the RNA in the lipid formulation is not substantially degraded after exposure of the particle to a nuclease at 37° C. for at least 20, 30, 45, or 60 minutes. In certain other aspects, the RNA in the lipid formulation is not substantially degraded after incubation of the formulation in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In some aspects, the RNA is complexed with the lipid portion of the formulation. One of the benefits of the formulations of the present disclosure is that the nucleic acid-lipid compositions are substantially non-toxic to animals such as humans and other mammals.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a lipid formulation, measuring the resulting fluorescence, and comparing it to the fluorescence observed upon addition of a small amount of nonionic detergent. Detergent-mediated disruption of the lipid layer releases the encapsulated nucleic acid, allowing it to interact with the membrane-impermeable dye. Nucleic acid encapsulation may be calculated as E=(I0−I)/I0, where/and I0 refers to the fluorescence intensities before and after the addition of detergent.

In some aspects, the present disclosure provides a nucleic acid-lipid composition comprising a plurality of nucleic acid-liposomes, nucleic acid-cationic liposomes, or nucleic acid-lipid nanoparticles. In some aspects, the nucleic acid-lipid composition comprises a plurality of RNA-liposomes. In some aspects, the nucleic acid-lipid composition comprises a plurality of RNA-cationic liposomes. In some aspects, the nucleic acid-lipid composition comprises a plurality of RNA-lipid nanoparticles.

In some aspects, the lipid formulations comprise RNA that is fully encapsulated within the lipid portion of the formulation, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% (or any fraction thereof or range therein) of the particles have the RNA encapsulated therein. The amount may be any value or subvalue within the recited ranges, including endpoints. The RNA included in any RNA-lipid composition or RNA-lipid formulation provided herein can be a self-replicating RNA.

Depending on the intended use of the lipid formulation, the proportions of the components can be varied, and the delivery efficiency of a particular formulation can be measured using assays known in the art.

In some aspects, nucleic acid molecules provided herein are lipid formulated. The lipid formulation is preferably selected from, but not limited to, liposomes, cationic liposomes, and lipid nanoparticles. In one aspect, a lipid formulation is a cationic liposome or a lipid nanoparticle (LNP) comprising:

(a) an RNA of the present disclosure,
(b) a cationic lipid,
(c) an aggregation reducing agent (such as polyethylene glycol (PEG) lipid or PEG-modified lipid),
(d) optionally a non-cationic lipid (such as a neutral lipid), and
(e) optionally, a sterol.

In another aspect, the cationic lipid is an ionizable cationic lipid. Any ionizable cationic lipid can be included in lipid formulations, including exemplary cationic lipids provided herein.

Cationic Lipids

In one aspect, the lipid nanoparticle formulation comprises (i) at least one cationic lipid; (ii) a helper lipid; (iii) a sterol (e.g., cholesterol); and (iv) a PEG-lipid. In another aspect, the cationic lipid is an ionizable cationic lipid. In yet another aspect, the lipid nanoparticle formulation comprises (i) at least one cationic lipid; (ii) a helper lipid; (iii) a sterol (e.g., cholesterol); and (iv) a PEG-lipid, in a molar ratio of about 40-70% ionizable cationic lipid:about 2-15% helper lipid:about 20-45% sterol; about 0.5-5% PEG-lipid. In a further aspect, the cationic lipid is an ionizable cationic lipid.

In one aspect, the lipid nanoparticle formulation consists of (i) at least one cationic lipid; (ii) a helper lipid; (iii) a sterol (e.g., cholesterol); and (iv) a PEG-lipid. In another aspect, the cationic lipid is an ionizable cationic lipid. In yet another aspect, the lipid nanoparticle formulation consists of (i) at least one cationic lipid; (ii) a helper lipid; (iii) a sterol (e.g., cholesterol); and (iv) a PEG-lipid, in a molar ratio of about 40-70% ionizable cationic lipid:about 2-15% helper lipid:about 20-45% sterol; about 0.5-5% PEG-lipid. In a further aspect, the cationic lipid is an ionizable cationic lipid.

In the presently disclosed lipid formulations, the cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-γ-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA·Cl), 1,2-Dilinoleoyl-3-trimethylaminopropane chloride salt (DLin-TAP·Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanediol (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl4-(dimethylamino) butanoate (MC3), 1,1'-(2-(4-(2-((2-(bis(2-hydroxydodecyl) amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6,9,28 31-tetraen-19-yl 4-(dimethylamino) butanoate (DLin-M-C3-DMA), 3-((6Z,9Z,28Z,31Z)-heptatriaconta-6,9,28,31-tetraen-19-yloxy)-N,N-dimethylpropan-1-amine (MC3 Ether), 4-((6Z,9Z,28Z,31Z)-heptatriaconta-6,9,28,31-tetraen-19-yloxy)-N,N-dimethylbutan-1-amine (MC4 Ether), or any combination thereof. Other cationic lipids include, but are not limited to, N,N-distearyl-N,N-dimethylammonium bromide (DDAB), 3P-(N—(N',N'-dimethylaminoethane)-carbamoyl)cholesterol (DC-Choi), N-(1-(2,3-dioleyloxy)propyl)-N-2-(sperminecarboxamido)ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107(5), 1864-69, 2010, the contents of which are herein incorporated by reference.

The RNA-lipid formulations of the present disclosure can comprise a helper lipid, which can be referred to as a neutral helper lipid, non-cationic lipid, non-cationic helper lipid, anionic lipid, anionic helper lipid, or a neutral lipid. It has been found that lipid formulations, particularly cationic liposomes and lipid nanoparticles have increased cellular uptake if helper lipids are present in the formulation. (Curr. Drug Metab. 2014; 15(9):882-92). For example, some studies have indicated that neutral and zwitterionic lipids such as 1,2-dioleoylsn-glycero-3-phosphatidylcholine (DOPC), Di-Oleoyl-Phosphatidyl-Ethanoalamine (DOPE) and 1,2-DiStearoyl-sn-glycero-3-PhosphoCholine (DSPC), being more fusogenic (i.e., facilitating fusion) than cationic lipids, can affect the polymorphic features of lipid-nucleic acid complexes, promoting the transition from a lamellar to a hexagonal phase, and thus inducing fusion and a disruption of the cellular membrane. (Nanomedicine (Lond). 2014 January; 9(1):105-20). In addition, the use of helper lipids can help to reduce any potential detrimental effects from using many prevalent cationic lipids such as toxicity and immunogenicity.

Non-limiting examples of non-cationic lipids suitable for lipid formulations of the present disclosure include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, palmitoyl, stearoyl, or oleoyl.

Additional examples of non-cationic lipids include sterols such as cholesterol and derivatives thereof. As a helper lipid, cholesterol increases the spacing of the charges of the lipid layer interfacing with the nucleic acid making the charge distribution match that of the nucleic acid more closely. (J. R. Soc. Interface. 2012 Mar. 7; 9(68): 548-561). Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In some aspects, the cholesterol derivative is a polar analogue such as cholesteryl-(4'-hydroxy)-butyl ether.

In some aspects, the helper lipid present in the lipid formulation comprises or consists of a mixture of one or more phospholipids and cholesterol or a derivative thereof. In other aspects, the neutral lipid present in the lipid formulation comprises or consists of one or more phospholipids, e.g., a cholesterol-free lipid formulation. In yet other aspects, the neutral lipid present in the lipid formulation comprises or consists of cholesterol or a derivative thereof, e.g., a phospholipid-free lipid formulation.

Other examples of helper lipids include nonphosphorous containing lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, and sphingomyelin.

Other suitable cationic lipids include those having alternative fatty acid groups and other dialkylamino groups, including those, in which the alkyl substituents are different (e.g., N-ethyl-N-methylamino-, and N-propyl-N-ethylamino-). These lipids are part of a subcategory of cationic lipids referred to as amino lipids. In some embodiments of the lipid formulations described herein, the cationic lipid is an amino lipid. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of $C_{14}$ to $C_{22}$ may be used. Other scaffolds can also be used to separate the amino group and the fatty acid or fatty alkyl portion of the amino lipid.

In some embodiments, the lipid formulation comprises the cationic lipid with Formula I according to the patent application PCT/EP2017/064066. In this context, the disclosure of PCT/EP2017/064066 is also incorporated herein by reference.

In some embodiments, amino or cationic lipids of the present disclosure are ionizable and have at least one protonatable or deprotonatable group, such that the lipid is positively charged at a pH at or below physiological pH (e.g., pH 7.4), and neutral at a second pH, preferably at or above physiological pH. Of course, it will be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the disclosure. In certain embodiments, the protonatable lipids have a pKa of the protonatable group in the range of about 4 to about 11. In some embodiments, the ionizable cationic lipid has a pKa of about 5 to about 7. In some embodiments, the pKa of an ionizable cationic lipid is about 6 to about 7.

In some embodiments, the lipid formulation comprises an ionizable cationic lipid of Formula I.

(I)

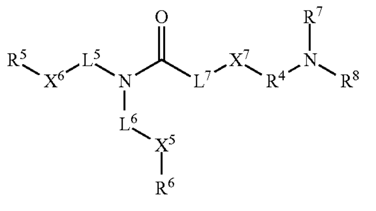

or a pharmaceutically acceptable salt or solvate thereof, wherein R5 and R6 are each independently selected from the group consisting of a linear or branched C1-C31 alkyl, C2-C31 alkenyl or C2-C31 alkynyl and cholesteryl; L5 and L6 are each independently selected from the group consisting of a linear C1-C20 alkyl and C2-C20 alkenyl; X5 is —C(O)O—, whereby —C(O)O—R6 is formed or —OC(O)— whereby —OC(O)—R6 is formed; X6 is —C(O)O— whereby —C(O)O—R5 is formed or —OC(O)— whereby —OC(O)—R5 is formed; X7 is S or O; L7 is absent or lower alkyl; R4 is a linear or branched C1-C6 alkyl; and R7 and R8 are each independently selected from the group consisting of a hydrogen and a linear or branched C1-C6 alkyl.

In some embodiments, X7 is S.

In some embodiments, X5 is —C(O)O—, whereby —C(O)O—R6 is formed and X6 is —C(O)O— whereby —C(O)O—R5 is formed.

In some embodiments, R7 and R8 are each independently selected from the group consisting of methyl, ethyl and isopropyl.

In some embodiments, L5 and L6 are each independently a C1-C10 alkyl. In some embodiments, L5 is C1-C3 alkyl, and L6 is C1-C5 alkyl. In some embodiments, L6 is C1-C2 alkyl. In some embodiments, L5 and L6 are each a linear C7 alkyl. In some embodiments, L5 and L6 are each a linear C9 alkyl.

In some embodiments, R5 and R6 are each independently an alkenyl. In some embodiments, R6 is alkenyl. In some embodiments, R6 is C2-C9 alkenyl. In some embodiments, the alkenyl comprises a single double bond. In some embodiments, R5 and R6 are each alkyl. In some embodiments, R5 is a branched alkyl. In some embodiments, R5 and R6 are each independently selected from the group consisting of a C9 alkyl, C9 alkenyl and C9 alkynyl. In some embodiments, R5 and R6 are each independently selected from the group consisting of a C11 alkyl, C11 alkenyl and C11 alkynyl. In some embodiments, R5 and R6 are each independently selected from the group consisting of a C7 alkyl, C7 alkenyl and C7 alkynyl. In some embodiments, R5 is —CH((CH2)pCH3)2 or —CH((CH2)pCH3)((CH2)p-1CH3), wherein p is 4-8. In some embodiments, p is 5 and L5 is a C1-C3 alkyl. In some embodiments, p is 6 and L5 is a C3 alkyl. In some embodiments, p is 7. In some embodiments, p is 8 and L5 is a C1-C3 alkyl. In some embodiments, R5 consists of —CH((CH2)pCH3)((CH2)p-1CH3), wherein p is 7 or 8.

In some embodiments, R4 is ethylene or propylene. In some embodiments, R4 is n-propylene or isobutylene.

In some embodiments, L7 is absent, R4 is ethylene, X7 is S and R7 and R8 are each methyl. In some embodiments, L7 is absent, R4 is n-propylene, X7 is S and R7 and R8 are each methyl. In some embodiments, L7 is absent, R4 is ethylene, X7 is S and R7 and R8 are each ethyl.

In some embodiments, X7 is S, X5 is —C(O)O—, whereby —C(O)O—R6 is formed, X6 is —C(O)O— whereby —C(O)O—R5 is formed, L5 and L6 are each independently a linear C3-C7 alkyl, L7 is absent, R5 is —CH((CH2)pCH3)2, and R6 is C7-C12 alkenyl. In some further embodiments, p is 6 and R6 is C9 alkenyl.

In some embodiments, the lipid formulation can comprise an ionizable cationic lipid selected from the group consisting of LIPID #1 to LIPID #8:

TABLE 6
| LIPID # | STRUCTURE |
| --- | --- |
| 1 | 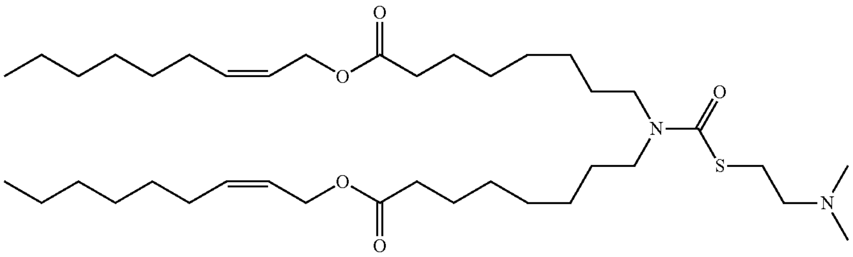 [SMILES: CCCCCC/C=C\COC(=O)CCCCCCCN(CCCCCCCC(=O)OC/C=C\CCCCCC)C(=O)SCCN(C)C] |
| 2 | 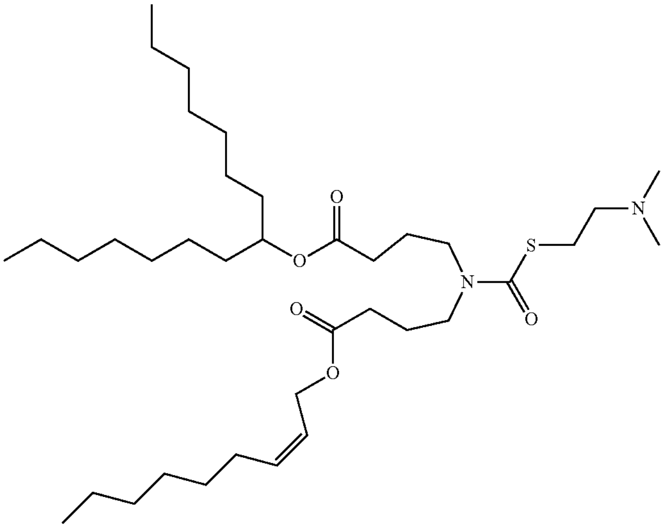 [SMILES: CCCCCC/C=C\COC(=O)CCCN(CCCC(=O)OC(CCCCCCC)CCCCCCC)C(=O)SCCN(C)C] |
| 3 | 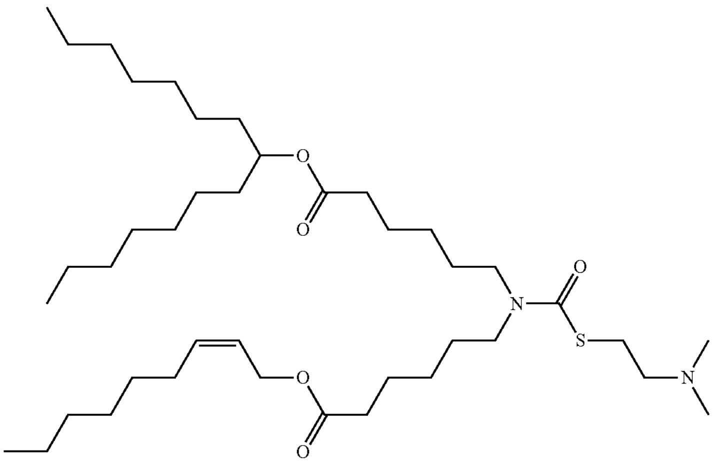 [SMILES: CCCCCC/C=C\COC(=O)CCCCCN(CCCCCC(=O)OC(CCCCCCC)CCCCCCC)C(=O)SCCN(C)C] |

TABLE 6-continued
| LIPID # | STRUCTURE |
|---|---|
| 4 | 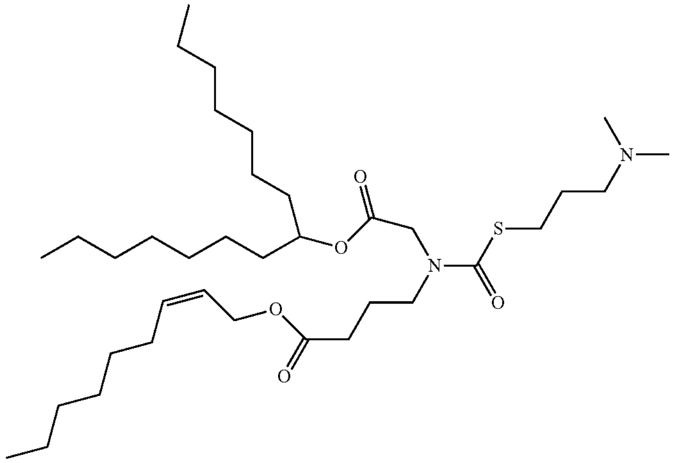 [SMILES: CCCCCC/C=C\COC(=O)CCCN(CC(=O)OC(CCCCCCC)CCCCCCC)C(=O)SCCCN(C)C] |
| 5 | 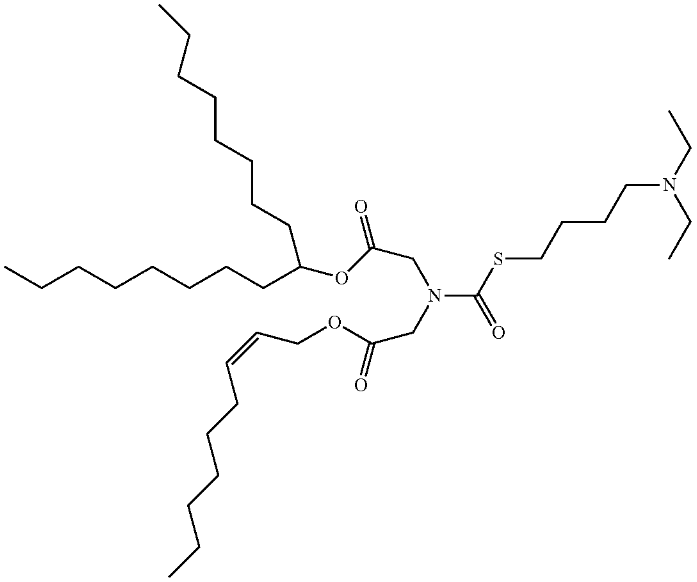 [SMILES: CCCCCC/C=C\COC(=O)CN(CC(=O)OC(CCCCCCCC)CCCCCCCC)C(=O)SCCCCN(CC)CC] |
| 6 | 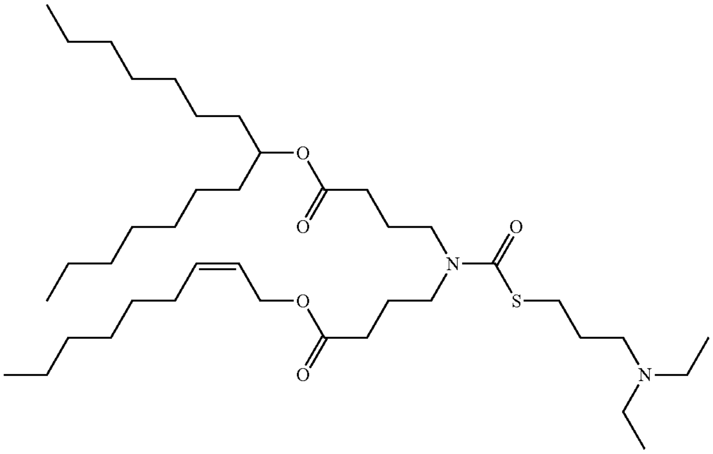 [SMILES: CCCCCC/C=C\COC(=O)CCCN(CCCC(=O)OC(CCCCCCC)CCCCCCC)C(=O)SCCCN(CC)CC] |

TABLE 6-continued
| LIPID # | STRUCTURE |
|---|---|
| 7 | 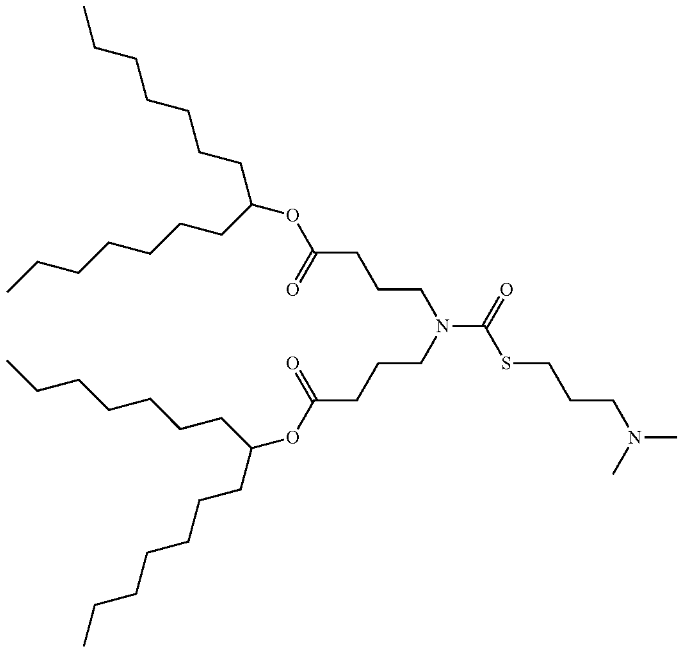 [SMILES: CCCCCCCC(CCCCCCC)OC(=O)CCCN(CCCC(=O)OC(CCCCCCC)CCCCCCC)C(=O)SCCCN(C)C] |
| 8 | 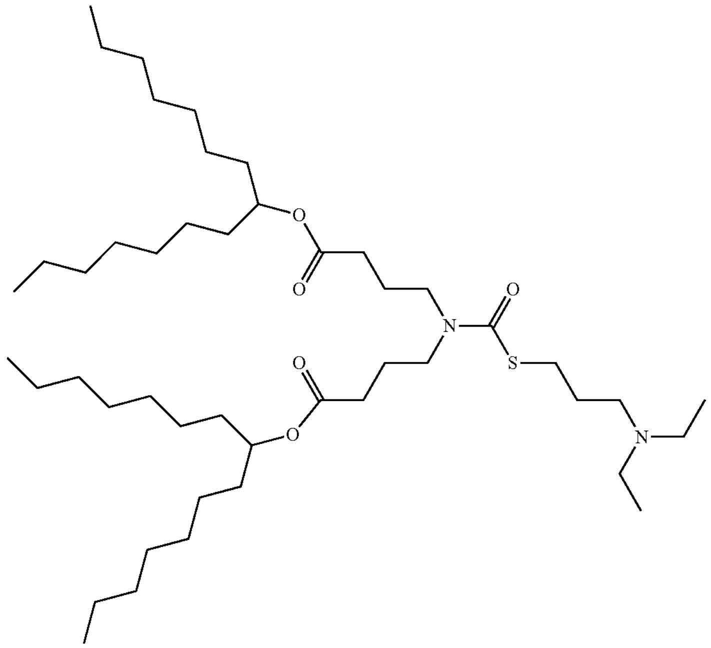 [SMILES: CCCCCCCC(CCCCCCC)OC(=O)CCCN(CCCC(=O)OC(CCCCCCC)CCCCCCC)C(=O)SCCCN(CC)CC] |

In some embodiments, the lipid formulation comprises an ionizable cationic lipid having a structure selected from

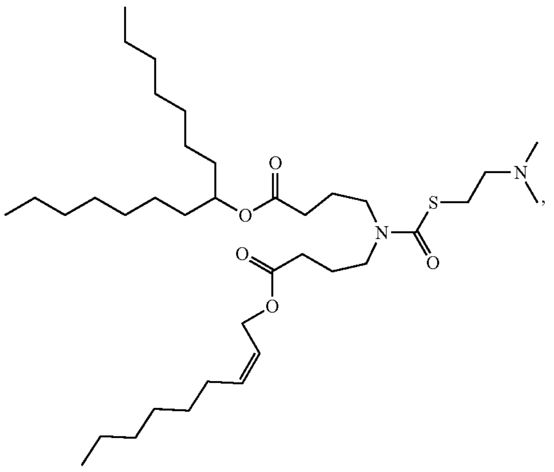

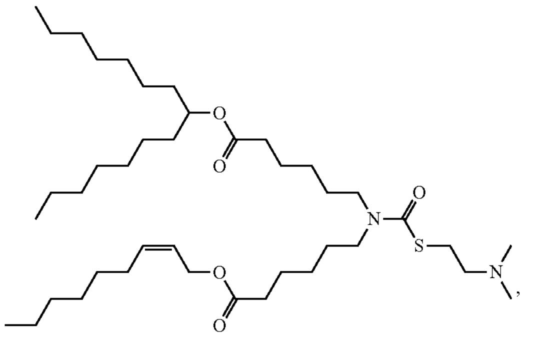

and

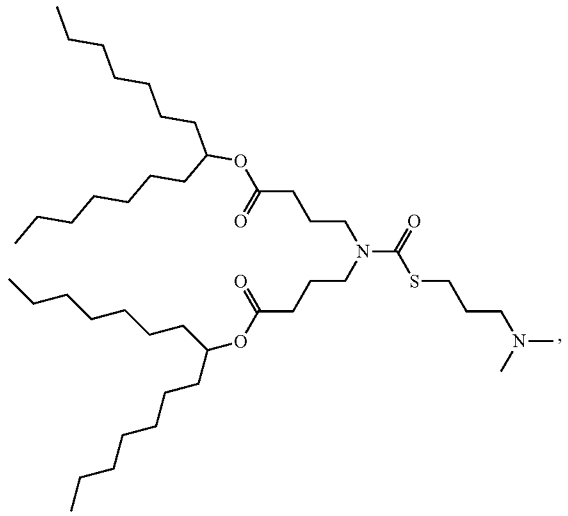

or a pharmaceutically acceptable salt thereof.

In some preferred embodiments, the lipid formulation comprises an ionizable cationic lipid having the structure

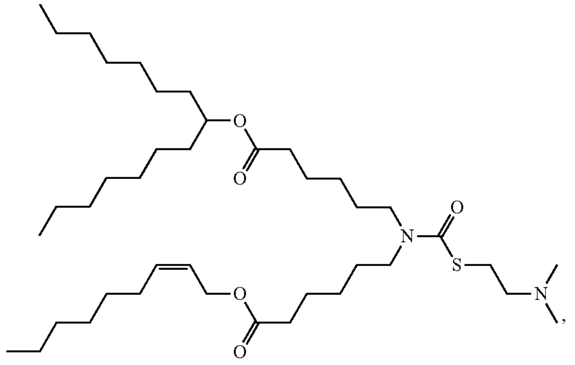 [SMILES: CCCCCC/C=C\COC(=O)CCCCCN(CCCCCC(=O)OC(CCCCCCC)CCCCCCC)C(=O)SCCN(C)C]

or a pharmaceutically acceptable salt thereof.

In embodiments, any one or more lipids recited herein may be expressly excluded.

In some aspects, the helper lipid comprises from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid formulation.

The lipid portion, or the cholesterol or cholesterol derivative in the lipid formulation may comprise up to about 40 mol %, about 45 mol %, about 50 mol %, about 55 mol %, or about 60 mol % of the total lipid present in the lipid formulation. In some aspects, the cholesterol or cholesterol derivative comprises about 15 mol % to about 45 mol %, about 20 mol % to about 40 mol %, about 25 mol % to about 35 mol %, or about 28 mol % to about 35 mol %; or about 25 mol %, about 26 mol %, about 27 mol %, about 28 mol %, about 29 mol %, about 30 mol %, about 31 mol %, about 32 mol %, about 33 mol %, about 34 mol %, about 35 mol %, about 36 mol %, or about 37 mol % of the total lipid present in the lipid formulation.

In specific embodiments, the lipid portion of the lipid formulation is about 35 mol % to about 42 mol % cholesterol.

In some aspects, the phospholipid component in the mixture may comprise from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid formulation.

In certain embodiments, the lipid portion of the lipid formulation comprises about, but is not necessarily limited to, 40 mol % to about 60 mol % of the ionizable cationic lipid, about 4 mol % to about 16 mol % DSPC, about 30 mol % to about 47 mol % cholesterol, and about 0.5 mol % to about 3 mol % PEG2000-DMG.

In certain embodiments, the lipid portion of the lipid formulation may comprise, but is not necessarily limited to, about 42 mol % to about 58 mol % of the ionizable cationic lipid, about 6 mol % to about 14 mol % DSPC, about 32 mol % to about 44 mol % cholesterol, and about 1 mol % to about 2 mol % PEG2000-DMG.

In certain embodiments, the lipid portion of the lipid formulation may comprise, but is not necessarily limited to, about 45 mol % to about 55 mol % of the ionizable cationic lipid, about 8 mol % to about 12 mol % DSPC, about 35 mol % to about 42 mol % cholesterol, and about 1.25 mol % to about 1.75 mol % PEG2000-DMG.

The percentage of helper lipid present in the lipid formulation is a target amount, and the actual amount of helper lipid present in the formulation may vary, for example, by ±5 mol %.

A lipid formulation that includes a cationic lipid compound or ionizable cationic lipid compound may be on a molar basis about 30-70% cationic lipid compound, about 25-40% cholesterol, about 2-15% helper lipid, and about 0.5-5% of a polyethylene glycol (PEG) lipid, wherein the percent is of the total lipid present in the formulation. In some aspects, the composition is about 40-65% cationic lipid compound, about 25-35% cholesterol, about 3-9% helper lipid, and about 0.5-3% of a PEG-lipid, wherein the percent is of the total lipid present in the formulation.

The formulation may be a lipid particle formulation, for example containing 8-30% nucleic acid compound, 5-30% helper lipid, and 0-20% cholesterol; 4-25% cationic lipid, 4-25% helper lipid, 2-25% cholesterol, 10-35% cholesterol-PEG, and 5% cholesterol-amine; or 2-30% cationic lipid, 2-30% helper lipid, 1-15% cholesterol, 2-35% cholesterol-PEG, and 1-20% cholesterol-amine; or up to 90% cationic lipid and 2-10% helper lipids, or even 100% cationic lipid.

Lipid Conjugates

The lipid formulations described herein may further comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof. Furthermore, lipid delivery vehicles can be used for specific targeting by attaching ligands (e.g., antibodies, peptides, and carbohydrates) to its surface or to the terminal end of the attached PEG chains (Front Pharmacol. 2015 Dec. 1; 6:286).

In some aspects, the lipid conjugate is a PEG-lipid. The inclusion of polyethylene glycol (PEG) in a lipid formulation as a coating or surface ligand, a technique referred to as PEGylation, helps to protect nanoparticles from the immune system and their escape from RES uptake (Nanomedicine (Lond). 2011 June; 6(4):715-28). PEGylation has been used to stabilize lipid formulations and their payloads through physical, chemical, and biological mechanisms. Detergent-like PEG lipids (e.g., PEG-DSPE) can enter the lipid formulation to form a hydrated layer and steric barrier on the surface. Based on the degree of PEGylation, the surface layer can be generally divided into two types, brush-like and mushroom-like layers. For PEG-DSPE-stabilized formulations, PEG will take on the mushroom conformation at a low degree of PEGylation (usually less than 5 mol %) and will shift to brush conformation as the content of PEG-DSPE is increased past a certain level (Journal of Nanomaterials. 2011; 2011:12). PEGylation leads to a significant increase in the circulation half-life of lipid formulations (Annu. Rev. Biomed. Eng. 2011 Aug. 15; 13( ):507-30; J. Control Release. 2010 Aug. 3; 145(3):178-81).

Examples of PEG-lipids include, but are not limited to, PEG coupled to dialkyloxypropyls (PEG-DAA), PEG coupled to diacylglycerol (PEG-DAG), methoxypolyethyleneglycol (PEG-DMG or PEG2000-DMG), PEG coupled to phospholipids such as phosphatidylethanolamine (PEG-PE), PEG conjugated to ceramides, PEG conjugated to cholesterol or a derivative thereof, and mixtures thereof.

PEG is a linear, water-soluble polymer of ethylene PEG repeating units with two terminal hydroxyl groups. PEGs are classified by their molecular weights and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S—NHS, HO-PEG-NH2).

The PEG moiety of the PEG-lipid conjugates described herein may comprise an average molecular weight ranging from about 550 daltons to about 10,000 daltons. In certain aspects, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons). In some aspects, the PEG moiety has an average molecular weight of about 2,000 daltons or about 750 daltons. The average molecular weight may be any value or subvalue within the recited ranges, including endpoints.

In certain aspects, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In one aspect, the linker moiety is a non-ester-containing linker moiety. Exemplary non-ester-containing linker moieties include, but are not limited to, amido (—C(O)NH—), amino (—NR—), carbonyl (—C(O)—), carbamate (—NHC(O)O—), urea (—NHC(O)NH—), disulfide (—S—S—), ether (—O—), succinyl (—(O)CCH2CH2C(O)—), succinamidyl (—NHC(O)CH2CH2C(O)NH—), ether, as well as combinations thereof (such as a linker containing both a carbamate linker moiety and an amido linker moiety). In one aspect, a carbamate linker is used to couple the PEG to the lipid.

In some aspects, an ester-containing linker moiety is used to couple the PEG to the lipid. Exemplary ester-containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available or can be isolated or synthesized using conventional techniques known to those of skill in the art. Phosphatidylethanolamines containing saturated or unsaturated fatty acids with carbon chain lengths in the range of $C_{10}$ to $C_{20}$ are preferred. Phosphatidylethanolamines with mono- or di-unsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoyl-phosphatidylethanolamine (DOPE), and distearoyl-phosphatidylethanolamine (DSPE).

In some aspects, the PEG-DAA conjugate is a PEG-didecyloxypropyl (C10) conjugate, a PEG-dilauryloxypropyl (C12) conjugate, a PEG-dimyristyloxypropyl (C14) conjugate, a PEG-dipalmityloxypropyl (C16) conjugate, or a PEG-distearyloxypropyl (C18) conjugate. In some aspects, the PEG has an average molecular weight of about 750 or about 2,000 daltons. In some aspects, the terminal hydroxyl group of the PEG is substituted with a methyl group.

In addition to the foregoing, other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl, methacrylamide, polymethacrylamide, and polydimethylacrylamide, polylactic acid, polyglycolic acid, and derivatized celluloses such as hydroxymethylcellulose or hydroxyethylcellulose.

In some aspects, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.6 mol % (or any fraction thereof or range therein) of the total lipid present in the lipid formulation. In other embodiments, the lipid conjugate (e.g., PEG-lipid) comprises about 0.5%, 0.6%, 0.7%, 0.8%, 0.9%, 1.0%, 1.2%, 1.3%, 1.4%, 1.5%, 1.6%, 1.7%, 1.8%, 1.9%, 2.0%, 2.5%, 3.0%, 3.5%, 4.0%, 4.5%, or 5%, (or any fraction thereof or range therein) of the total lipid present in the lipid formulation. The amount may be any value or subvalue within the recited ranges, including endpoints.

The percentage of lipid conjugate (e.g., PEG-lipid) present in the lipid formulations of the disclosure is a target amount, and the actual amount of lipid conjugate present in the formulation may vary, for example, by ±0.5 mol %. One of ordinary skill in the art will appreciate that the concentration of the lipid conjugate can be varied depending on the lipid conjugate employed and the rate at which the lipid formulation is to become fusogenic.

In some embodiments, the lipid formulation for any of the compositions described herein comprises a lipoplex, a liposome, a lipid nanoparticle, a polymer-based particle, an exosome, a lamellar body, a micelle, or an emulsion.

Mechanism of Action for Cellular Uptake of Lipid Formulations

In some aspects, lipid formulations for the intracellular delivery of nucleic acids, particularly liposomes, cationic liposomes, and lipid nanoparticles, are designed for cellular uptake by penetrating target cells through exploitation of the target cells' endocytic mechanisms where the contents of the lipid delivery vehicle are delivered to the cytosol of the target cell. (Nucleic Acid Therapeutics, 28(3):146-157, 2018). Prior to endocytosis, functionalized ligands such as PEG-lipid at the surface of the lipid delivery vehicle are shed from the surface, which triggers internalization into the target cell. During endocytosis, some part of the plasma membrane of the cell surrounds the vector and engulfs it into a vesicle that then pinches off from the cell membrane, enters the cytosol and ultimately enters and moves through the endolysosomal pathway. For ionizable cationic lipid-containing delivery vehicles, the increased acidity as the endosome ages results in a vehicle with a strong positive charge on the surface. Interactions between the delivery vehicle and the endosomal membrane then result in a membrane fusion event that leads to cytosolic delivery of the payload. For RNA payloads, the cell's own internal translation processes will then translate the RNA into the encoded protein. The encoded protein can further undergo postranslational processing, including transportation to a targeted organelle or location within the cell or excretion from the cell.

By controlling the composition and concentration of the lipid conjugate, one can control the rate at which the lipid conjugate exchanges out of the lipid formulation and, in turn, the rate at which the lipid formulation becomes fusogenic. In addition, other variables including, e.g., pH, temperature, or ionic strength, can be used to vary and/or control the rate at which the lipid formulation becomes fusogenic. Other methods which can be used to control the rate at which the lipid formulation becomes fusogenic will become apparent to those of skill in the art upon reading this disclosure. Also, by controlling the composition and concentration of the lipid conjugate, one can control the liposomal or lipid particle size.

Lipid Formulation Manufacture

There are many different methods for the preparation of lipid formulations comprising a nucleic acid. (Curr. Drug Metabol. 2014, 15, 882-892; Chem. Phys. Lipids 2014, 177, 8-18; Int. J. Pharm. Stud. Res. 2012, 3, 14-20). The techniques of thin film hydration, double emulsion, reverse phase evaporation, microfluidic preparation, dual assymetric centrifugation, ethanol injection, detergent dialysis, spontaneous vesicle formation by ethanol dilution, and encapsulation in preformed liposomes are briefly described herein.

Thin Film Hydration

In Thin Film Hydration (TFH) or the Bangham method, the lipids are dissolved in an organic solvent, then evaporated through the use of a rotary evaporator leading to a thin lipid layer formation. After the layer hydration by an aqueous buffer solution containing the compound to be loaded, Multilamellar Vesicles (MLVs) are formed, which can be reduced in size to produce Small or Large Unilamellar vesicles (LUV and SUV) by extrusion through membranes or by the sonication of the starting MLV.

Double Emulsion

Lipid formulations can also be prepared through the Double Emulsion technique, which involves lipids dissolution in a water/organic solvent mixture. The organic solution, containing water droplets, is mixed with an excess of aqueous medium, leading to a water-in-oil-in-water (W/O/W) double emulsion formation. After mechanical vigorous shaking, part of the water droplets collapse, giving Large Unilamellar Vesicles (LUVs).

Reverse Phase Evaporation

The Reverse Phase Evaporation (REV) method also allows one to achieve LUVs loaded with nucleic acid. In this technique a two-phase system is formed by phospholipids dissolution in organic solvents and aqueous buffer. The resulting suspension is then sonicated briefly until the mixture becomes a clear one-phase dispersion. The lipid formulation is achieved after the organic solvent evaporation under reduced pressure. This technique has been used to encapsulate different large and small hydrophilic molecules including nucleic acids.

Microfluidic Preparation

The Microfluidic method, unlike other bulk techniques, gives the possibility of controlling the lipid hydration process. The method can be classified in continuous-flow microfluidic and droplet-based microfluidic, according to the way in which the flow is manipulated. In the microfluidic hydrodynamic focusing (MHF) method, which operates in a continuous flow mode, lipids are dissolved in isopropyl alcohol which is hydrodynamically focused in a microchannel cross junction between two aqueous buffer streams. Vesicles size can be controlled by modulating the flow rates, thus controlling the lipids solution/buffer dilution process. The method can be used for producing oligonucleotide (ON) lipid formulations by using a microfluidic device consisting of three-inlet and one-outlet ports.

Dual Asymmetric Centrifugation

Dual Asymmetric Centrifugation (DAC) differs from more common centrifugation as it uses an additional rotation around its own vertical axis. An efficient homogenization is achieved due to the two overlaying movements generated: the sample is pushed outwards, as in a normal centrifuge, and then it is pushed towards the center of the vial due to the additional rotation. By mixing lipids and an NaCl-solution a viscous vesicular phospholipid gel (VPC) is achieved, which is then diluted to obtain a lipid formulation dispersion. The lipid formulation size can be regulated by optimizing DAC speed, lipid concentration and homogenization time.

Ethanol Injection

The Ethanol Injection (EI) method can be used for nucleic acid encapsulation. This method provides the rapid injection of an ethanolic solution, in which lipids are dissolved, into an aqueous medium containing nucleic acids to be encapsulated, through the use of a needle. Vesicles are spontaneously formed when the phospholipids are dispersed throughout the medium.

Detergent Dialysis

The Detergent dialysis method can be used to encapsulate nucleic acids. Briefly lipid and plasmid are solubilized in a detergent solution of appropriate ionic strength, after removing the detergent by dialysis, a stabilized lipid formulation is formed. Unencapsulated nucleic acid is then removed by ion-exchange chromatography and empty vesicles by sucrose density gradient centrifugation. The technique is highly sensitive to the cationic lipid content and to the salt concentration of the dialysis buffer, and the method is also difficult to scale.

Spontaneous Vesicle Formation by Ethanol Dilution

Stable lipid formulations can also be produced through the Spontaneous Vesicle Formation by Ethanol Dilution method in which a stepwise or dropwise ethanol dilution provides the instantaneous formation of vesicles loaded with nucleic acid by the controlled addition of lipid dissolved in ethanol to a rapidly mixing aqueous buffer containing the nucleic acid.

Encapsulation in Preformed Liposomes

The entrapment of nucleic acids can also be obtained starting with preformed liposomes through two different methods: (1) A simple mixing of cationic liposomes with nucleic acids which gives electrostatic complexes called "lipoplexes", where they can be successfully used to transfect cell cultures, but are characterized by their low encapsulation efficiency and poor performance in vivo; and (2) a liposomal destabilization, slowly adding absolute ethanol to a suspension of cationic vesicles up to a concentration of 40% v/v followed by the dropwise addition of nucleic acids achieving loaded vesicles; however, the two main steps characterizing the encapsulation process are too sensitive, and the particles have to be downsized.

Excipients

The pharmaceutical compositions disclosed herein can be formulated using one or more excipients to: (1) increase stability; (2) increase cell transfection; (3) permit a sustained or delayed release (e.g., from a depot formulation of the polynucleotide, primary construct, or RNA); (4) alter the biodistribution (e.g., target the polynucleotide, primary construct, or RNA to specific tissues or cell types); (5) increase the translation of encoded protein in vivo; and/or (6) alter the release profile of encoded protein in vivo.

The pharmaceutical compositions described herein may be prepared by any method known or hereafter developed in the art of pharmacology. In general, such preparatory methods include the step of associating the active ingredient (i.e., nucleic acid) with an excipient and/or one or more other accessory ingredients. A pharmaceutical composition in accordance with the present disclosure may be prepared, packaged, and/or sold in bulk, as a single unit dose, and/or as a plurality of single unit doses.

Pharmaceutical compositions may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired.

In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, liposomes, lipid nanoparticles, polymers, lipoplexes, core-shell nanoparticles, peptides, proteins, cells transfected with primary DNA construct, or RNA (e.g., for transplantation into a subject), hyaluronidase, nanoparticle mimics and combinations thereof.

Accordingly, the pharmaceutical compositions described herein can include one or more excipients, each in an amount that together increases the stability of the nucleic acid in the lipid formulation, increases cell transfection by the nucleic acid, increases the expression of the encoded protein, and/or alters the release profile of encoded proteins. Further, the RNA of the present disclosure may be formulated using self-assembled nucleic acid nanoparticles.

Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference in its entirety). The use of a conventional excipient medium may be contemplated within the scope of the embodiments of the present disclosure, except insofar as any conventional excipient medium may be incompatible with a substance or its derivatives, such as by producing any undesirable biological effect or otherwise interacting in a deleterious manner with any other component(s) of the pharmaceutical composition.

The pharmaceutical compositions of this disclosure may further contain as pharmaceutically acceptable carriers substances as required to approximate physiological conditions, such as pH adjusting and buffering agents, tonicity adjusting agents, and wetting agents, for example, sodium acetate, sodium lactate, sodium chloride, potassium chloride, calcium chloride, sorbitan monolaurate, triethanolamine oleate, and mixtures thereof. For solid compositions, conventional nontoxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

In certain embodiments of the disclosure, the RNA-lipid formulation may be administered in a time release formulation, for example in a composition which includes a slow release polymer. The active agent can be prepared with carriers that will protect against rapid release, for example a controlled release vehicle such as a polymer, microencapsulated delivery system, or a bioadhesive gel. Prolonged delivery of the RNA, in various compositions of the disclosure can be brought about by including in the composition agents that delay absorption, for example, aluminum monostearate hydrogels and gelatin.

Methods of Inducing Immune Responses

Provided herein, in some embodiments, are methods of inducing an immune response in a subject. Any type of immune response can be induced using the methods provided herein, including adaptive and innate immune responses. In one aspect, immune responses induced using the methods provided herein include an antibody response, a cellular immune response, or both an antibody response and a cellular immune response.

Methods of inducing an immune response provided herein include administering to a subject an effective amount of any nucleic acid molecule provided herein. In one aspect, methods of inducing an immune response include administering to a subject an effective amount of any composition comprising a nucleic acid molecule and a lipid provided herein. In another aspect, methods of inducing an immune response include administering to a subject an effective amount of any pharmaceutical composition comprising a nucleic acid molecule and a lipid formulation provided herein. In some aspects, nucleic acid molecules, compositions, and pharmaceutical composition provided here are vaccines that can elicit a protective or a therapeutic immune response, for example.

As used herein, the term "subject" refers to any individual or patient on which the methods disclosed herein are performed. The term "subject" can be used interchangeably with the term "individual" or "patient." The subject can be a human, although the subject may be an animal, as will be appreciated by those in the art. Thus, other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. As used herein, the term "effective amount" or "therapeutically effective amount" refers to that amount of a nucleic acid molecule, composition, or pharmaceutical composition described herein that is sufficient to effect the intended application, including but not limited to inducing an immune response and/or disease treatment, as defined herein. The therapeutically effective amount may vary depending upon the intended application (e.g., inducing an immune response, treatment, application in vivo), or the subject or patient and disease condition being treated, e.g., the weight and age of the subject, the species, the severity of the disease condition, the manner of administration and the like, which can readily be determined by one of ordinary skill in the art. The term also applies to a dose that will induce a particular response in a target cell. The specific dose will vary depending on the particular nucleic acid molecule, composition, or pharmaceutical composition chosen, the dosing regimen to be followed, whether it is administered in combination with other compounds, timing of administration, the tissue to which it is administered, and the physical delivery system in which it is carried.

Exemplary doses of nucleic acid molecules that can be administered include about 0.01 μg, about 0.02 μg, about 0.03 μg, about 0.04 μg, about 0.05 μg, about 0.06 μg, about 0.07 μg, about 0.08 μg, about 0.09 μg, about 0.1 μg, about 0.2 μg, about 0.3 μg, about 0.4 μg, about 0.5 μg, about 0.6 μg, about 0.7 μg, about 0.8 μg, about 0.9 μg, about 1.0 μg, about 1.5 μg, about 2.0 μg, about 2.5 μg, about 3.0 μg, about 3.5 μg, about 4.0 μg, about 4.5 μg, about 5.0 μg, about 5.5 μg, about 6.0 μg, about 6.5 μg, about 7.0 μg, about 7.5 μg, about 8.0 μg, about 8.5 μg, about 9.0 μg, about 9.5 μg, about 10 μg, about 11 μg, about 12 μg, about 13μ, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, about 100 μg, about 125 μg, about 150 μg, about 175 μg, about 200 μg, about 250 μg, about 300 μg, about 350 μg, about 400 μg, about 450 μg, about 500 μg, about 600 μg, about 700 μg, about 800 μg, about 900 μg, about 1,000 μg, or more, and any number or range in between. In one aspect, the nucleic acid molecules are RNA molecules. In another aspect, the nucleic acid molecules are DNA molecules. Nucleic acid molecules can have a unit dosage comprising about 0.01 μg to about 1,000 μg or more nucleic acid in a single dose.

In some aspects, compositions provided herein that can be administered include about 0.01 μg, about 0.02 μg, about 0.03 μg, about 0.04 μg, about 0.05 μg, about 0.06 μg, about 0.07 μg, about 0.08 μg, about 0.09 μg, about 0.1 μg, about 0.2 μg, about 0.3 μg, about 0.4 μg, about 0.5 μg, about 0.6 μg, about 0.7 μg, about 0.8 μg, about 0.9 μg, about 1.0 μg, about 1.5 μg, about 2.0 μg, about 2.5 μg, about 3.0 μg, about 3.5 μg, about 4.0 μg, about 4.5 μg, about 5.0 μg, about 5.5 μg, about 6.0 μg, about 6.5 μg, about 7.0 μg, about 7.5 μg, about 8.0 μg, about 8.5 μg, about 9.0 μg, about 9.5 μg, about 10 μg, about 11 μg, about 12 μg, about 13 μg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, about 100 μg, about 125 μg, about 150 μg, about 175 μg, about 200 μg, about 250 μg, about 300 μg, about 350 μg, about 400 μg, about 450 μg, about 500 μg, about 600 μg, about 700 μg, about 800 μg, about 900 μg, about 1,000 μg, or more, and any number or range in between, nucleic acid and lipid. In other aspects, pharmaceutical compositions provided herein that can be administered include about 0.01 μg, about 0.02 μg, about 0.03 μg, about 0.04 μg, about 0.05 μg, about 0.06 μg, about 0.07 μg, about 0.08 μg, about 0.09 μg, about 0.1 μg, about 0.2 μg, about 0.3 μg, about 0.4 μg, about 0.5 μg, about 0.6 μg, about 0.7 μg, about 0.8 μg, about 0.9 μg, about 1.0 μg, about 1.5 μg, about 2.0 μg, about 2.5 μg, about 3.0 μg, about 3.5 μg, about 4.0 μg, about 4.5 μg, about 5.0 μg, about 5.5 μg, about 6.0 μg, about 6.5 μg, about 7.0 μg, about 7.5 μg, about 8.0 μg, about 8.5 μg, about 9.0 μg, about 9.5 μg, about 10 μg, about 11 μg, about 12 μg, about 13 μg, about 14 μg, about 15 μg, about 16 μg, about 17 μg, about 18 μg, about 19 μg, about 20 μg, about 21 μg, about 22 μg, about 23 μg, about 24 μg, about 25 μg, about 26 μg, about 27 μg, about 28 μg, about 29 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, about 100 μg, about 125 μg, about 150 μg, about 175 μg, about 200 μg, about 250 μg, about 300 μg, about 350 μg, about 400 μg, about 450 μg, about 500 μg, about 600 μg, about 700 μg, about 800 μg, about 900 μg, about 1,000 μg, or more, and any number or range in between, nucleic acid and lipid formulation.

In one aspect, compositions provided herein can have a unit dosage comprising about 0.01 μg to about 1,000 μg or more nucleic acid and lipid in a single dose. In another aspect, pharmaceutical compositions provided herein can have a unit dosage comprising about 0.01 μg to about 1,000 μg or more nucleic acid and lipid formulation in a single dose. A vaccine unit dosage can correspond to the unit dosage of nucleic acid molecules, compositions, or pharmaceutical compositions provided herein and that can be administered to a subject. In one aspect, vaccine compositions of the instant disclosure have a unit dosage comprising about 0.01 μg to about 1,000 μg or more nucleic acid and lipid formulation in a single dose. In another aspect, vaccine compositions of the instant disclosure have a unit dosage comprising about 0.01 μg to about 50 μg nucleic acid and lipid formulation in a single dose. In yet another aspect, vaccine compositions of the instant disclosure have a unit dosage comprising about 0.2 μg to about 20 μg nucleic acid and lipid formulation in a single dose.

A dosage form of the composition of this disclosure can be solid, which can be reconstituted in a liquid prior to administration. The solid can be administered as a powder. The solid can be in the form of a capsule, tablet, or gel. In some embodiments, the pharmaceutical composition comprises a nucleic acid lipid formulation that has been lyophilized. In some embodiments, the lyophilized composition may comprise one or more lyoprotectants, such as, including but not necessarily limited to, glucose, trehalose, sucrose, maltose, lactose, mannitol, inositol, hydroxypropyl-β-cyclodextrin, and/or polyethylene glycol. In some embodiments, the lyophilized composition comprises a poloxamer, potassium sorbate, sucrose, or any combination thereof. In specific embodiments, the poloxamer is poloxamer 188. In some embodiments, the lyophilized compositions described herein may comprise about 0.01 to about 1.0% w/w of a poloxamer. In some embodiments, the lyophilized compositions described herein may comprise about 1.0 to about 5.0% w/w of potassium sorbate. The percentages may be any value or subvalue within the recited ranges, including endpoints.

In some embodiments, the lyophilized composition may comprise about 0.01 to about 1.0% w/w of the nucleic acid molecule. In some embodiments, the composition may comprise about 1.0 to about 5.0% w/w lipids. In some embodiments, the composition may comprise about 0.5 to about 2.5% w/w of TRIS buffer. In some embodiments, the composition may comprise about 0.75 to about 2.75% w/w of NaCl. In some embodiments, the composition may comprise about 85 to about 95% w/w of a sugar. The percentages may be any value or subvalue within the recited ranges, including endpoints.

In a preferred embodiment, the dosage form of the pharmaceutical compositions described herein can be a liquid suspension of self-replicating RNA lipid nanoparticles described herein. In some embodiments, the liquid suspension is in a buffered solution. In some embodiments, the buffered solution comprises a buffer selected from the group consisting of HEPES, MOPS, TES, and TRIS. In some embodiments, the buffer has a pH of about 7.4. In some preferred embodiments, the buffer is HEPES. In some further embodiments, the buffered solution further comprises a cryoprotectant. In some embodiments, the cryoprotectant is selected from a sugar and glycerol or a combination of a sugar and glycerol. In some embodiments, the sugar is a dimeric sugar. In some embodiments, the sugar is sucrose. In some preferred embodiments, the buffer comprises HEPES, sucrose, and glycerol at a pH of 7.4. In certain embodiments, the composition comprises a HEPES, MOPS, TES, or TRIS buffer at a pH of about 7.0 to about 8.5. In some embodiments, the HEPES, MOPS, TES, or TRIS buffer may at a concentration ranging from 7 mg/ml to about 15 mg/ml. The pH or concentration may be any value or subvalue within the recited ranges, including endpoints.

In some embodiments, the suspension is frozen during storage and thawed prior to administration. In some embodiments, the suspension is frozen at a temperature below about 70° C. In some embodiments, the suspension is diluted with sterile water during intravenous administration. In some embodiments, intravenous administration comprises diluting the suspension with about 2 volumes to about 6 volumes of sterile water. In some embodiments, the suspension comprises about 0.1 mg to about 3.0 mg self-replicating RNA/mL, about 15 mg/mL to about 25 mg/mL of an ionizable cationic lipid, about 0.5 mg/mL to about 2.5 mg/mL of a PEG-lipid, about 1.8 mg/mL to about 3.5 mg/mL of a helper lipid, about 4.5 mg/mL to about 7.5 mg/mL of a cholesterol, about 7 mg/mL to about 15 mg/mL of a buffer, about 2.0 mg/mL to about 4.0 mg/mL of NaCl, about 70 mg/mL to about 110 mg/mL of sucrose, and about 50 mg/mL to about 70 mg/mL of glycerol. In some embodiments, a lyophilized self-replicating RNA-lipid nanoparticle formulation can be resuspended in a buffer as described herein.

In some embodiments, the compositions of the disclosure are administered to a subject such that a self-replicating RNA concentration of at least about 0.05 mg/kg, at least about 0.1 mg/kg, at least about 0.5 mg/kg, at least about 1.0 mg/kg, at least about 2.0 mg/kg, at least about 3.0 mg/kg, at least about 4.0 mg/kg, at least about 5.0 mg/kg of body weight is administered in a single dose or as part of single treatment cycle. In some embodiments, the compositions of the disclosure are administered to a subject such that a total amount of at least about 0.1 mg, at least about 0.5 mg, at least about 1.0 mg, at least about 2.0 mg, at least about 3.0 mg, at least about 4.0 mg, at least about 5.0 mg, at least about 6.0 mg, at least about 7.0 mg, at least about 8.0 mg, at least about 9.0 mg, at least about 10 mg, at least about 15 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 105 mg, at least about 110 mg, at least about 115 mg, at least about 120 mg, or at least about 125 mg self-replicating RNA is administered in one or more doses up to a maximum dose of about 300 mg, about 350 mg, about 400 mg, about 450 mg, or about 500 mg self-replicating RNA.

Any route of administration can be included in methods provided herein. In some aspects, nucleic acid molecules, compositions, and pharmaceutical compositions provided herein are administered intramuscularly, subcutaneously, intradermally, transdermally, intranasally, orally, sublingually, intravenously, intraperitoneally, topically, by aerosol, or by a pulmonary route, such as by inhalation or by nebulization, for example. In some embodiments, the pharmaceutical compositions described are administered systemically. Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments, the pharmaceutical composition is administered intravenously.

Pharmaceutical compositions may be administered to any desired tissue. In some embodiments, the self-replicating RNA delivered is expressed in a tissue different from the tissue in which the lipid formulation or pharmaceutical composition was administered. In preferred embodiments, self-replicating RNA is delivered and expressed in the liver.

In other aspects, nucleic acid molecules, compositions, and pharmaceutical compositions provided herein are administered intramuscularly.

In some aspects, the subject in which an immune response is induced is a healthy subject. As used herein, the term "healthy subject" refers to a subject not having a condition or disease, including an infectious disease or cancer, for example, or not having a condition or disease against which an immune response is induced. Accordingly, in some aspects, a nucleic acid molecule, composition, or pharmaceutical composition provided herein is administered prophylactically to prevent an infectious disease or cancer, for example. In other aspects, the subject in which an immune response is induced has cancer. The subject may suffer from any cancer or have any tumor, including solid and liquid tumors. In one aspect, the cancer is kidney cancer, renal cancer, urinary bladder cancer, prostate cancer, uterine cancer, breast cancer, cervical cancer, ovarian cancer, lung cancer, liver cancer, stomach cancer, colon cancer, rectal cancer, oral cavity cancer, pharynx cancer, pancreatic cancer, thyroid cancer, melanoma, skin cancer, head and neck cancer, brain cancer, hematopoietic cancer, leukemia, lymphoma, bone cancer, or sarcoma. Accordingly, a nucleic acid molecule, composition, or pharmaceutical composition provided herein can be administered therapeutically, i.e., to treat a condition or disease, such as cancer, after the onset of the condition or disease.

As used herein, the terms "treat," "treatment," "therapy," "therapeutic," and the like refer to obtaining a desired pharmacologic and/or physiologic effect, including, but not limited to, alleviating, delaying or slowing the progression, reducing the effects or symptoms, preventing onset, inhibiting, ameliorating the onset of a diseases or disorder, obtaining a beneficial or desired result with respect to a disease, disorder, or medical condition, such as a therapeutic benefit and/or a prophylactic benefit. "Treatment," as used herein, includes any treatment of a disease in a mammal, particularly in a human, and includes: (a) preventing the disease from occurring in a subject, including a subject which is predisposed to the disease or at risk of acquiring the disease but has not yet been diagnosed as having it; (b) inhibiting the disease, i.e., arresting its development; and (c) relieving the disease, i.e., causing regression of the disease. A therapeutic benefit includes eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In some aspects, for prophylactic benefit, treatment or compositions for treatment, including pharmaceutical compositions, are administered to a subject at risk of developing a particular disease, or to a subject reporting one or more of the physiological symptoms of a disease, even though a diagnosis of this disease may not have been made. The methods of the present disclosure may be used with any mammal or other animal. In some aspects, treatment results in a decrease or cessation of symptoms. A prophylactic effect includes delaying or eliminating the appearance of a disease or condition, delaying or eliminating the onset of symptoms of a disease or condition, slowing, halting, or reversing the progression of a disease or condition, or any combination thereof.

Nucleic acid molecules, compositions, and pharmaceutical compositions provided herein can be administered once or multiple times. Accordingly, nucleic acid molecules, compositions, and pharmaceutical compositions provided herein can be administered one, two, three, four, five, six, seven, eight, nine, ten, or more times. Timing between two or more administrations can be one week, two weeks, three weeks, four weeks, five weeks, six weeks, seven weeks, eight weeks, nine weeks, weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or more weeks, and any number or range in between. In some aspects, timing between two or more administrations is one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months, 24 months, or more months, and any number or range in between. In other aspects, timing between two or more administrations can be one year, two years, three years, four years, five years, six years, seven years, eight years, nine years, ten years, or more years, and any number or range in between, Timing between the first and any subsequent administration can be the same or different. In one aspect, nucleic acid molecules, compositions, or pharmaceutical compositions provided herein are administered once.

More than one nucleic acid molecule, composition, or pharmaceutical composition can be administered in the methods provided herein. In one aspect, two or more nucleic acid molecules, compositions, or pharmaceutical compositions provided herein are administered simultaneously. In another aspect, two or more nucleic acid molecules, compositions, or pharmaceutical compositions provided herein are administered sequentially. Simultaneous and sequential administrations can include any number and any combination of nucleic acid molecules, compositions, or pharmaceutical compositions provided herein. Multiple nucleic acid molecules, compositions, or pharmaceutical compositions that are administered together or sequentially can include transgenes encoding different antigenic proteins or fragments thereof. In this manner, immune responses against different antigenic targets can be induced. Two, three, four, five, six, seven, eight, nine, ten, or more nucleic acid molecules, compositions, or pharmaceutical compositions including transgenes encoding different antigenic proteins or fragments thereof can be administered simultaneously or sequentially. Any combination of nucleic acid molecules, compositions, and pharmaceutical compositions including any combination of transgenes can be administered simultaneously or sequentially. In some aspects, administration is simultaneous. In other aspects, administration is sequential. Timing between two or more administrations can be one week, two weeks, three weeks, four weeks, five weeks, six weeks, seven weeks, eight weeks, nine weeks, weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks, 31 weeks, 32 weeks, 33 weeks, 34 weeks, 35 weeks, 36 weeks, 37 weeks, 38 weeks, 39 weeks, 40 weeks, 41 weeks, 42 weeks, 43 weeks, 44 weeks, 45 weeks, 46 weeks, 47 weeks, 48 weeks, 49 weeks, 50 weeks, 51 weeks, 52 weeks, or more weeks, and any number or range in between. In some aspects, timing between two or more administrations is one month, two months, three months, four months, five months, six months, seven months, eight months, nine months, ten months, 11 months, 12 months, 13 months, 14 months, 15 months, months, 16 months, 17 months, 18 months, 19 months, 20 months, 21 months, 22 months, 23 months, 24 months, or more months, and any number or range in between. In other aspects, timing between two or more administrations can be one year, two years, three years, four years, five years, six years, seven years, eight years, nine years, ten years, or more years, and any number or range in between, Timing between the first and any subsequent administration can be the same or different. Nucleic acid molecules, compositions, and pharmaceutical compositions provided herein can be administered with any other vaccine or treatment.

Following administration of the composition to the subject, the protein product encoded by the self-replicating RNA of the disclosure (e.g., an antigen) is detectable in the target tissues for at least about one to seven days or longer. The amount of protein product necessary to achieve a therapeutic effect will vary depending on antibody titer necessary to generate an immunity to COVID-19 in the patient. For example, the protein product may be detectable in the target tissues at a concentration (e.g., a therapeutic concentration) of at least about 0.025-1.5 μg/ml (e.g., at least about 0.050 μg/ml, at least about 0.075 μg/ml, at least about 0.1 μg/ml, at least about 0.2 μg/ml, at least about 0.3 μg/ml, at least about 0.4 μg/ml, at least about 0.5 μg/ml, at least about 0.6 μg/ml, at least about 0.7 μg/ml, at least about 0.8 μg/ml, at least about 0.9 μg/ml, at least about 1.0 μg/ml, at least about 1.1 μg/ml, at least about 1.2 μg/ml, at least about 1.3 μg/ml, at least about 1.4 μg/ml, or at least about 1.5 μg/ml), for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 days or longer following administration of the composition to the subject.

In some embodiments, the composition described herein may be administered one time. In some embodiments, the composition described herein may be administered two times.

In some embodiments, the composition may be administered in the form of a booster dose, to a subject who was previously vaccinated against coronavirus.

In some embodiments, a pharmaceutical composition of the present disclosure is administered to a subject once per month. In some embodiments, a pharmaceutical composition of the present disclosure is administered to a subject twice per month. In some embodiments, a pharmaceutical composition of the present disclosure is administered to a subject three times per month. In some embodiments, a pharmaceutical composition of the present disclosure is administered to a subject four times per month.

Alternatively, the compositions of the present disclosure may be administered in a local rather than systemic manner, for example, via injection of the pharmaceutical composition directly into a targeted tissue, preferably in a depot or sustained release formulation. Local delivery can be affected in various ways, depending on the tissue to be targeted. For example, aerosols containing compositions of the present disclosure can be inhaled (for nasal, tracheal, or bronchial delivery); compositions of the present disclosure can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing compositions of the present disclosure complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Combinations

The self-replicating RNA, formulations thereof, or encoded proteins described herein may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. Preferably, the methods of treatment of the present disclosure encompass the delivery of pharmaceutical, prophylactic, diagnostic, or imaging compositions in combination with agents that may improve their bioavailability, reduce and/or modify their metabolism, inhibit their excretion, and/or modify their distribution within the body. As a non-limiting example, a self-replicating RNA of the disclosure may be used in combination with a pharmaceutical agent for immunizing or vaccinating a subject. In general, it is expected that agents utilized in combination with the presently disclosed self-replicating RNA and formulations thereof be utilized at levels that do not exceed the levels at which they are utilized individually. In some embodiments, the levels utilized in combination will be lower than those utilized individually. In one embodiment, the combinations, each or together may be administered according to the split dosing regimens as are known in the art.

Ranges

Throughout this disclosure, various aspects can be presented in range format. It should be understood that any description in range format is merely for convenience and brevity and not meant to be limiting. Accordingly, the description of a range should be considered to have specifically disclosed all possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example 1, 2, 2.1, 2.2, 2.5, 3, 4, 4.75, 4.8, 4.85, 4.95, 5, 5.5, 5.75, 5.9, 5.00, and 6. This applies to a range of any breadth.

Example 1

This example describes a comparison of design and expression of mRNA and self-replicating RNA (STARR™) platforms.

Both mRNA and STARR™ vaccine constructs were designed to encode the full-length SARS-CoV-2 S protein (1273 aa), with the STARR™ self-replicating RNA additionally encoding for the Venezuelan equine encephalitis virus (VEEV) replicase genes (FIG. 1A; STARR™ vaccine construct corresponding to an RNA having a sequence of SEQ ID NO:125, with U in place of T, referred to herein as "STARR™ SARS-CoV-2 RNA"; mRNA corresponding to a sequence of SEQ ID NO: 126, with U in place of T and including a tobacco etch virus (TEV) 5' UTR, a Xenopus beta-globin (Xbg) 3' UTR, and a codon-optimized open reading frame encoding the SARS-CoV-2 glycoprotein). The characteristics of these different constructs was studied first. Constructs were encapsulated in the same LNP composition. Briefly, RNA constructs were encapsulated into lipid nanoparticles (LNPs) that included four lipid excipients (an ionizable cationic lipid, 1,2-distearoyl-sn-glycero-3-phosphocholine (DSPC), cholesterol, and PEG2000-DMG) dispersed in HEPES buffer (pH 8.0) containing sodium chloride and the cryoprotectants sucrose and glycerol. The ionizable cationic lipid had the following structure:

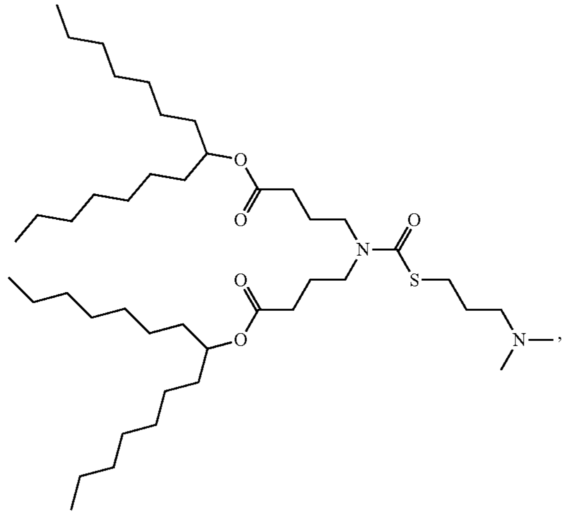 [SMILES: CCCCCCCC(CCCCCCC)OC(=O)CCCN(CCCC(=O)OC(CCCCCCC)CCCCCCC)C(=O)SCCCN(C)C]

Figure 1C:
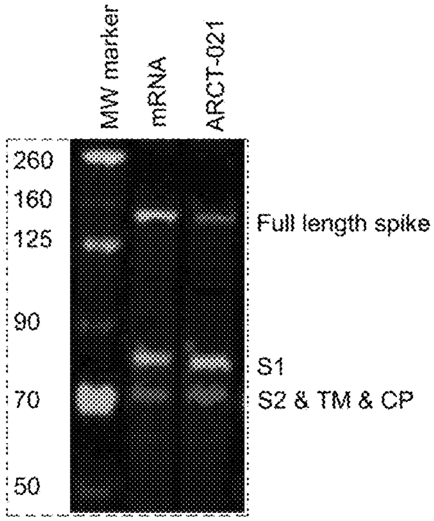
Figure 1D:
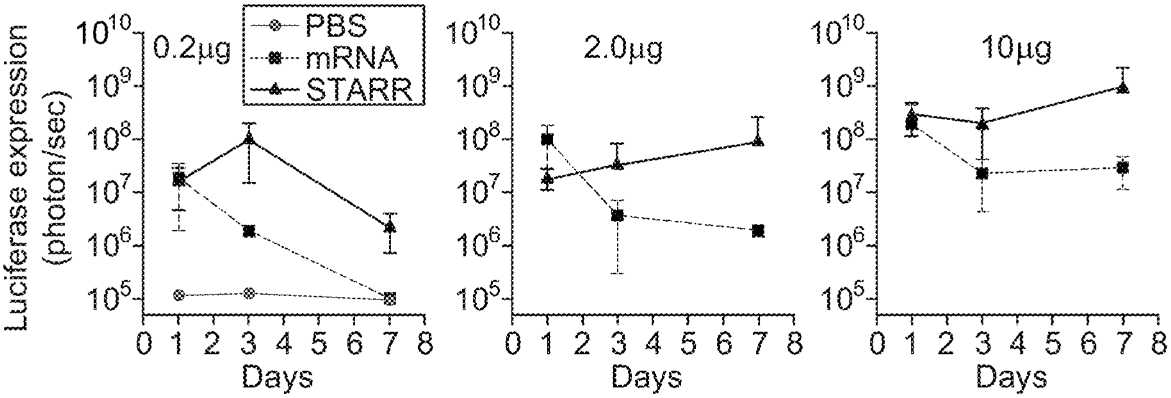

Despite differences in RNA lengths of mRNA and the STARR™ SARS-CoV-2 RNA construct, the LNP diameter, polydispersity index and RNA trapping efficiency were similar (FIG. 1B). In vitro expression of the mRNA vaccine and the STARR™ SARS-CoV-2 RNA construct were confirmed in cell lysate 24 hours post-transfection through positive western blot detection of the S protein (FIG. 1C). It was also observed that both mRNA and STARR™ vaccines expressed a mixture of full-length S protein and cleaved S protein, i.e., S was cleaved into S1 and S2 transmembrane and cytoplasmic membrane domains (FIG. 1C). In vivo protein expression of the two RNA platforms in BALB/c mice was compared by using mRNA and STARR™ constructs that expressed a luciferase reporter (FIG. 1D). Animals injected with the mRNA vaccine construct showed high in vivo luciferase expression at day 1, although the expression levels declined over time. In contrast, luciferase expression in STARR™ injected mice showed sustained or even increased signals, apart from those given the 0.2 μg dose, until day 7 post-inoculation (FIG. 1D).

These data show that dose-for-dose, antigen expression was more prolonged with the STARR™ compared to the mRNA vaccine.

Example 2

This example describes immune gene expression following the STARR™ construct and mRNA vaccination.

Figure 2A:
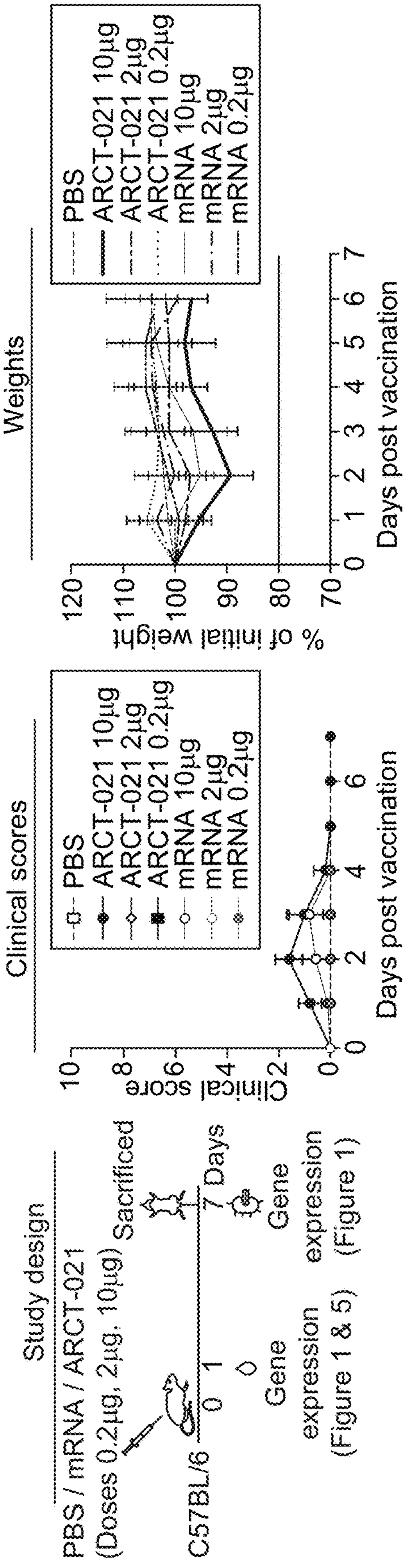
FIGS. 2A-2I show clinical scores, mouse weights and transcriptomic analysis of immune genes following vaccination with STARR™ RNA or mRNA SARS-CoV-2 vaccine candidates. (2A) C57BL/6 mice were immunized with either PBS, mRNA or STARR™ SARS-CoV-2 RNA (doses 0.2 μg, 2 μg or 10 μg), weight and clinical scores assessed every day, bled at day 1 post-immunization, sacrificed at 7 days post-vaccination and lymph nodes harvested. Gene expression of inflammatory genes and immune genes were measured in whole blood (at day 1) and lymph nodes (at day 7), respectively. (2B) Expression of IFN and inflammatory response genes in whole blood presented as heatmap of z scores. (2C) Lymph node weights at 7 days post-vaccination. Principal component analysis (PCA) of immune gene expression following vaccination with mRNA or STARR™ SARS-CoV-2 RNA at doses (2D) 0.2 μg, (2E) 2 μg and (2F) 10 μg. Volcano plots of fold change of STARR™ SARS-CoV-2 RNA versus mRNA (x-axis) and Log 10 P-value of STARR™ SARS-CoV-2 RNA versus mRNA (y-axis) for doses (2G) 0.2 μg, (2H) 2 μg and (2I) 10 μg.

C57BL/6J mice were inoculated with STARR™ SARS-CoV-2 RNA (encoding the SARS-CoV-2 glycoprotein as described above (Example 1)) and mRNA vaccines at 0.2 μg, 2 μg and 10 μg doses or PBS control. No significant mean loss in animal weight occurred over the first 4 days, except for those that received 10 μg of STARR™ SARS-CoV-2 RNA (FIG. 2A). However, apart from weight loss, there were few other clinical signs as indicated by the minimal differences in clinical scores. Both weight and clinical scores improved after day 3 post vaccination.

Figure 2B:
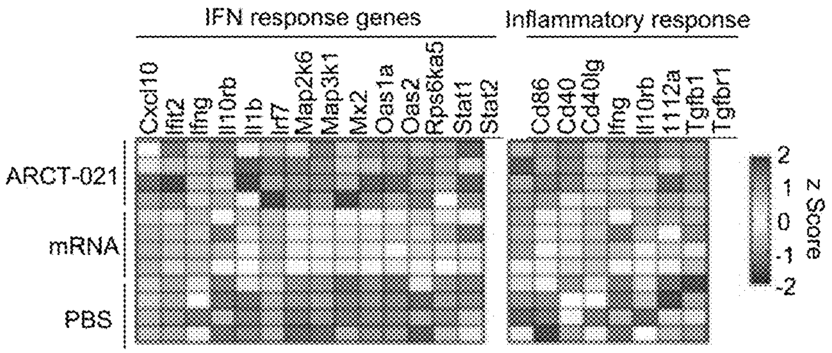
Figure 8A:
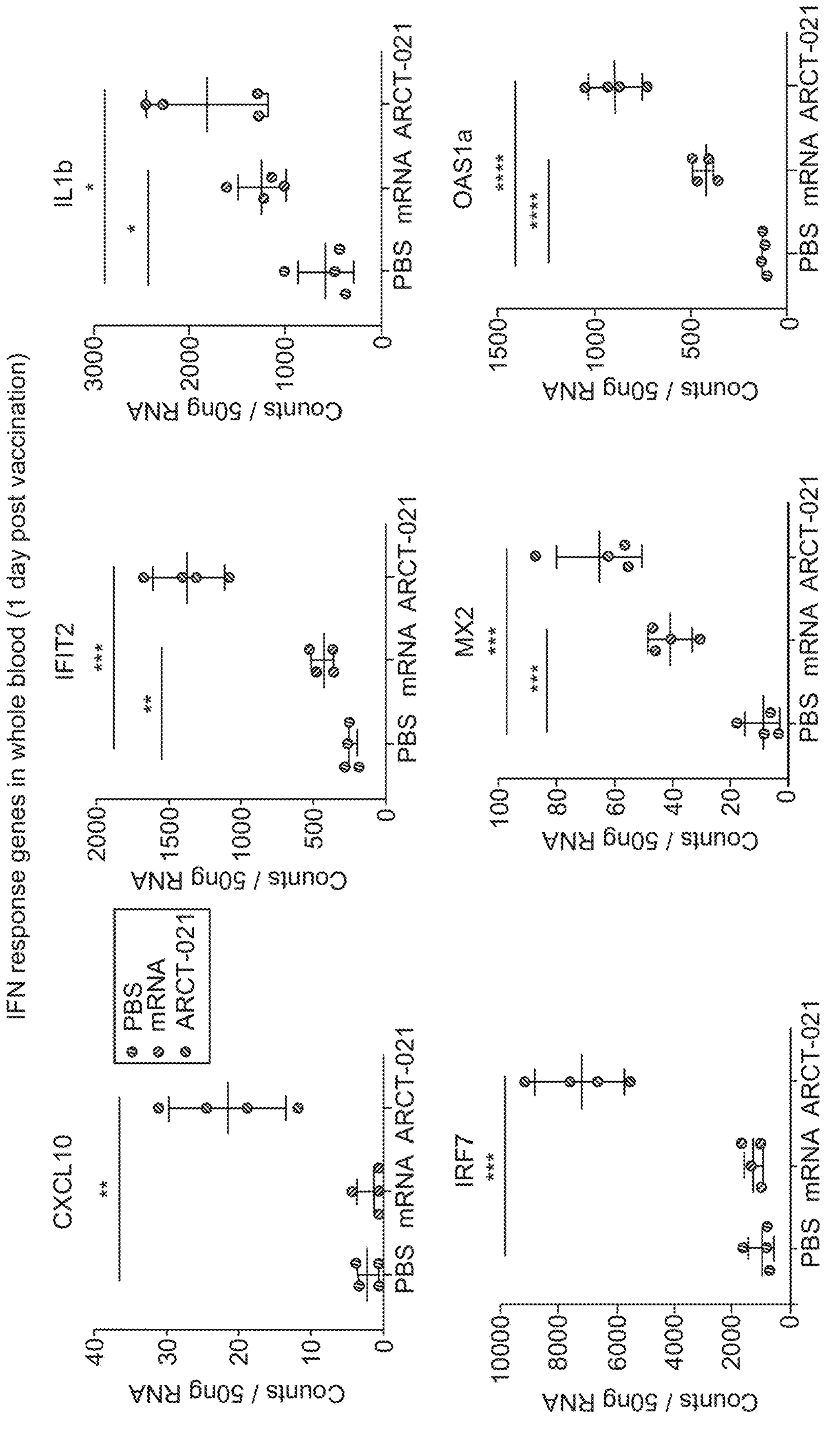
FIGS. 8A-8B show whole blood transcriptomic data at 1-day post-prime vaccination showing Nanostring counts per 50 ng RNA of selected (8A) IFN and (8B) inflammatory genes.
Figure 8B:
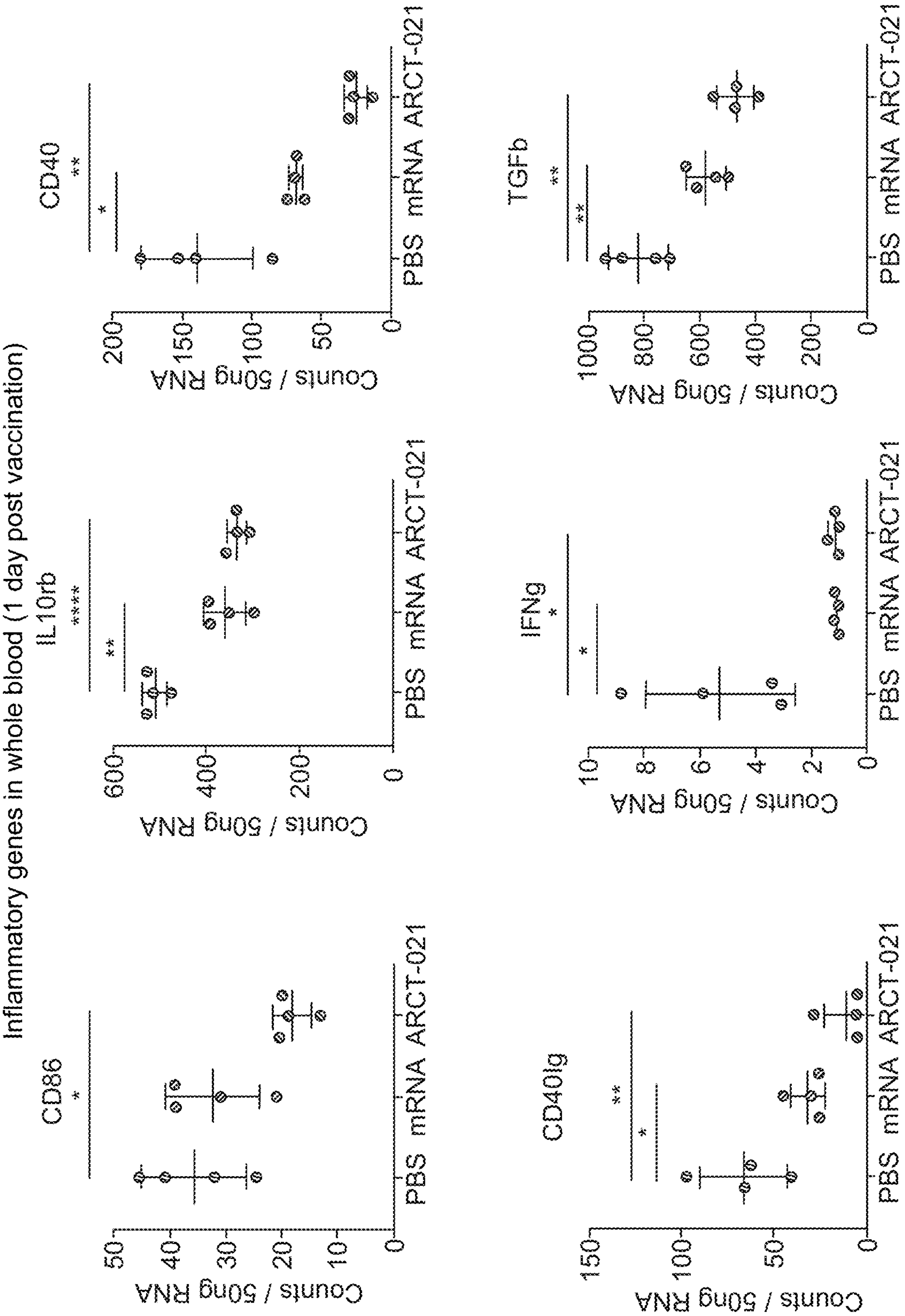

The innate immune response, such as the type-I interferon (IFN) response, has previously been shown to be associated with vaccine immunogenicity following yellow fever vaccination, for example. Furthermore, reactive oxygen species-driven pro-inflammatory responses have been shown to underpin systemic adverse events in yellow fever vaccination. Therefore, the expression of innate immune and pro-inflammatory genes in whole blood of C57BL/6 mice inoculated was measured with either PBS, mRNA vaccine, or the STARR™ SARS-CoV-2 RNA construct. Genes in the type-I IFN pathway were the most highly expressed in animals inoculated with STARR™ SARS-CoV-2 RNA compared to either mRNA vaccine or PBS (FIG. 2B and FIG. 8). By contrast, genes associated with pro-inflammatory responses were mostly reduced in abundance following vaccination STARR™ SARS-CoV-2 RNA compared with either mRNA vaccine or PBS (FIG. 2B and FIG. 8).

Figure 2C:
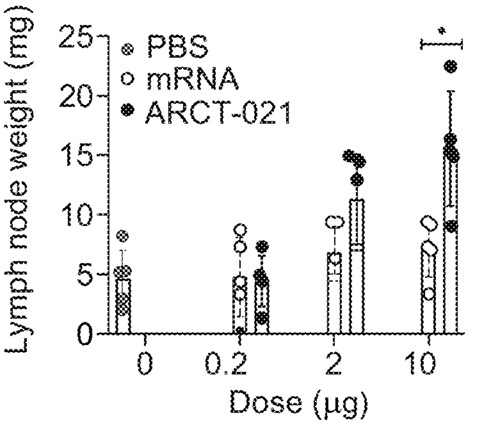

Since adaptive immune responses develop in germinal centers in the draining lymph nodes, the draining lymph nodes were dissected at day 7 post-inoculation (study schematic in FIG. 2A). The inguinal lymph nodes of mice inoculated with STARR™ SARS-CoV-2 RNA showed a dose-dependent increase in weight, unlike those from mice inoculated with either mRNA vaccine or PBS; the mean weight of lymph nodes from mice given 10 μg of STARR™ SARS-CoV-2 RNA was significantly higher than those given the equivalent mRNA vaccine (FIG. 2C). Principal component analysis (PCA) of immune gene expression showed clustering of responses to each of the 3 doses of STARR™ SARS-CoV-2 RNA away from the PBS control (STARR™ RNA): depicted as lower sphere in FIG. 2D, smallest sphere in FIG. 2E, and lower sphere in FIG. 2F; PBS control: depicted as upper sphere in FIG. 2D, lower elongated and narrow sphere in FIG. 2E, and upper sphere in FIG. 2F) indicating clear differences in immune gene expression between STARR™ SARS-CoV-2 RNA vaccinated and placebo groups. These trends were also dissimilar to those from mice given mRNA vaccine where at all tested doses, the PCA displayed substantial overlap with placebo (mRNA: shown as center sphere in FIG. 2D, large upright sphere in FIG. 2E, and as flat line with four data points along the bottom of the center square in FIG. 2F; placebo (PBS control): shown as upper sphere in FIG. 2D, lower elongated and narrow sphere in FIG. 2E, and upper sphere in FIG. 2F).

Figures 2D, 2E, 2F, 2G, 2H, 2I:
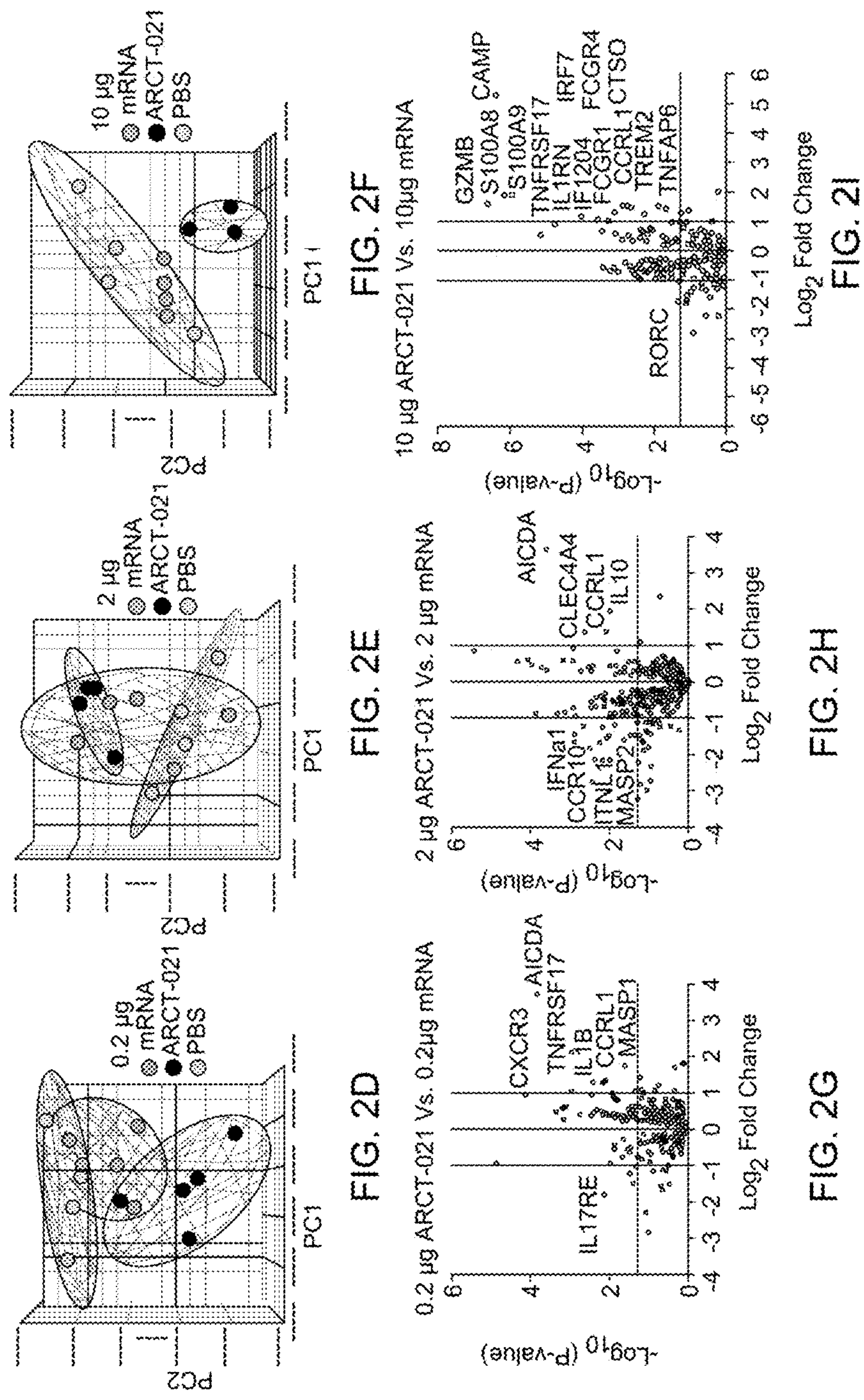

Differentially expressed genes in the lymph nodes of mice given STARR™ SARS-CoV-2 RNA compared to those inoculated with mRNA vaccine were assessed next. Volcano plot analysis identified significant upregulation of several innate, B cell, and T cells genes in STARR™ SARS-CoV-2 RNA immunized animals (FIG. 2G-2I). Some of the most highly differentially expressed genes included, for example, GZMB (important for target cell killing by cytotoxic immune cells), S100A8 and S100A9 (factors that regulate immune responses via TLR4), TNFRSF17 (also known as BCMA and regulates humoral immunity), CXCR3 (chemokine receptor involved in T cell trafficking and function) and AICDA (mediates antibody class switching and somatic hypermutation in B cells).

These findings collectively indicate that the adaptive immune responses in the draining lymph nodes of mice inoculated with STARR™ SARS-CoV-2 RNA appeared to be significantly different compared to immune responses in mice inoculated with a non-replicating mRNA vaccine.

Example 3

This example describes STARR™ SARS-CoV-2 RNA-induced T cell responses.

Figure 3A:
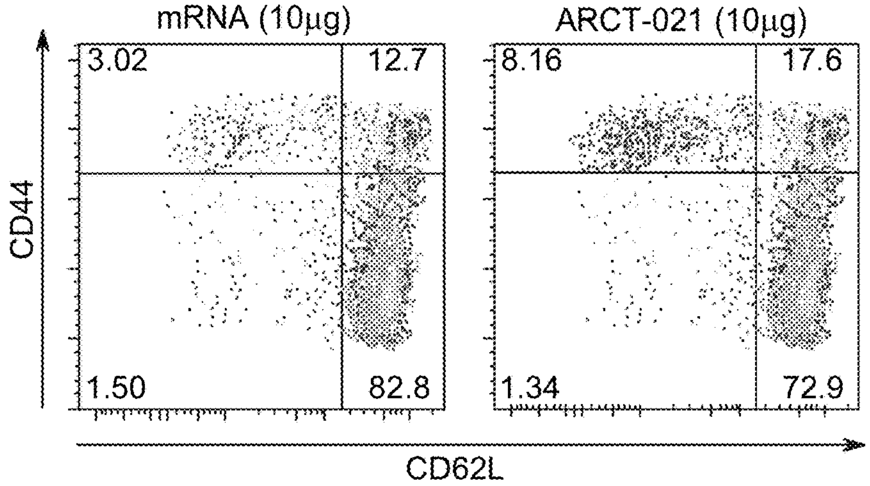
FIGS. 3A-3J show cellular immune responses following vaccination with SARS-CoV-2 STARR™ RNA and mRNA. C57BL/6 mice (n=5 per group) were immunized with 0.2 μg, 2 μg, or 10 μg of STARR™ RNA or mRNA via IM, sacrificed at day 7 post-vaccination and spleens analyzed for cellular T cell responses by flow-cytometry and ELISPOT. (3A-3B) CD8+ and C) CD4+ T effector cells were assessed in vaccinated animals using surface staining for T cell markers and flow-cytometry. (3D-3E) IFNγ+CD8+ T cells and (3F) Ratio of IFNγ+/IL4+CD4+ T cells in spleens of immunized mice were assessed following ex vivo stimulation with PMA/ionomycin (IO) and intracellular staining. (3G-3I) SARS-CoV-2 S protein-specific responses to pooled S protein peptides were assessed using IFNγ ELISPOT assays following vaccination with mRNA (3H) or STARR™ RNA (3I). A schematic of S protein domains is shown in (3J).
Figure 3B:
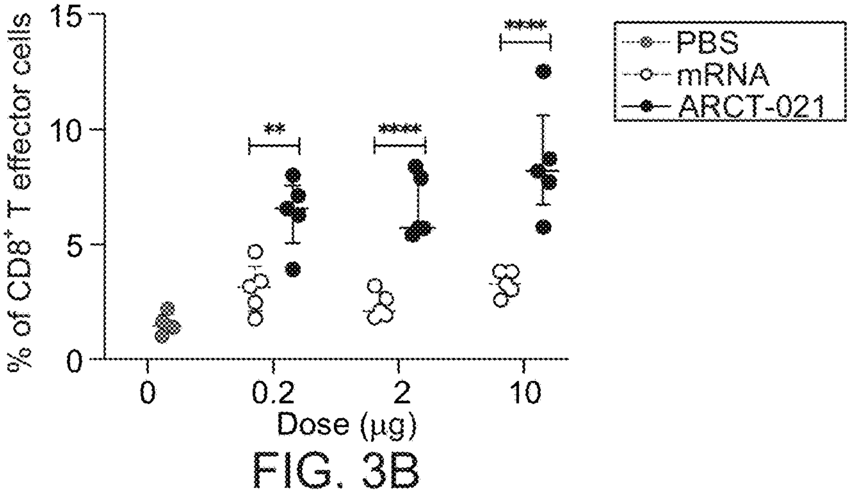
Figure 3C:
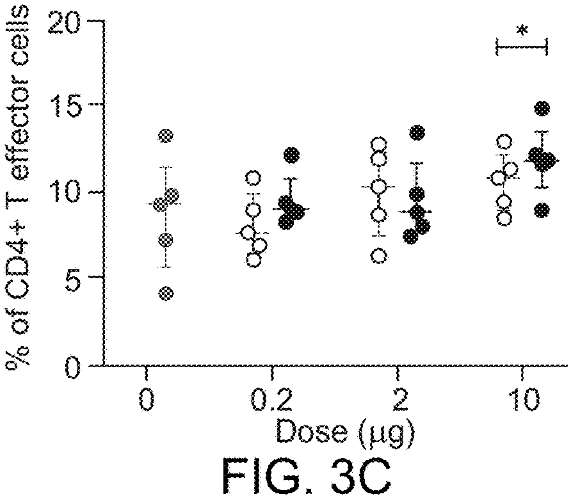
Figure 3D:
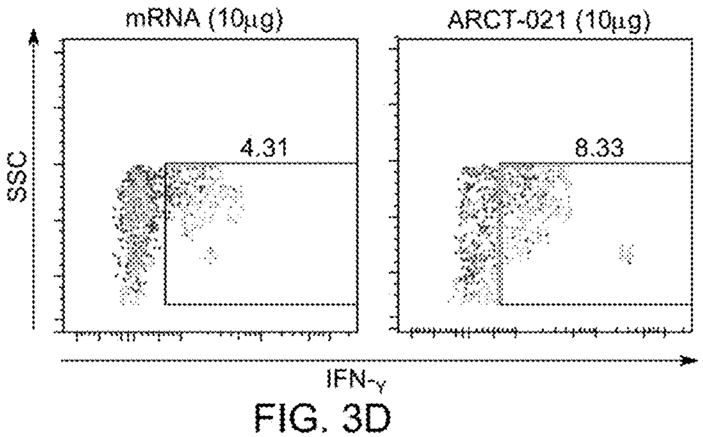
Figure 3E:
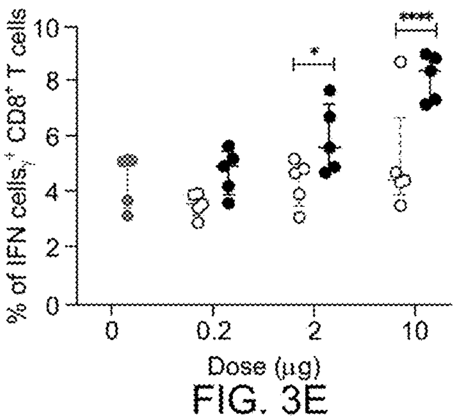
Figure 3F:
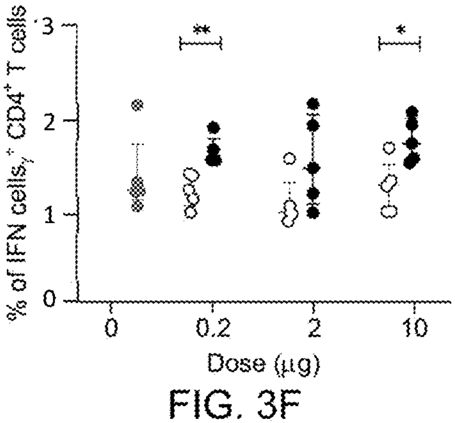

The cellular immune response following vaccination of C57BL/6 mice (n=5 per group) with mRNA or the STARR™ SARS-CoV-2 RNA construct encoding the SARS-CoV-2 glycoprotein described above (Example 1) was investigated next. At day 7 post-vaccination, spleens were harvested and assessed for CD8 and CD4 T cells by flow-cytometry. The CD8+ T cell CD44+CD62L− effector/memory subset was significantly expanded in STARR™ SARS-CoV-2 RNA vaccinated mice compared to those given either PBS or mRNA vaccine (FIG. 3A-B). There was no statistically significant difference in the proportion of CD4+ T effector cells of these animals (FIG. 3C). IFNγ+CD8+ T cells (with 2 μg and 10 μg doses) and IFNγ+CD4+ T cells (in 0.2 μg and 10 μg) were proportionately higher, as found using intracellular staining (ICS) with flow cytometry, in STARR™ SARS-CoV-2 RNA as compared to mRNA vaccinated animals (FIG. 3D-3F).

Figure 3G:
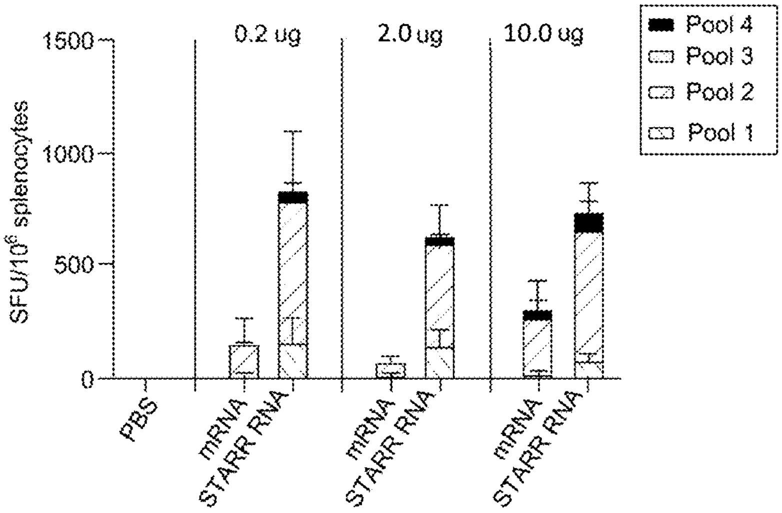
Figure 3H:
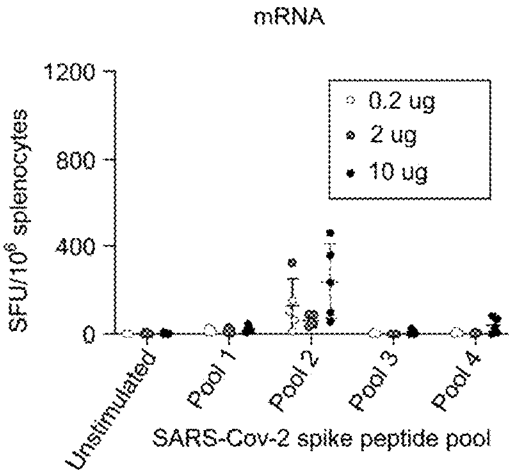
Figure 3I:
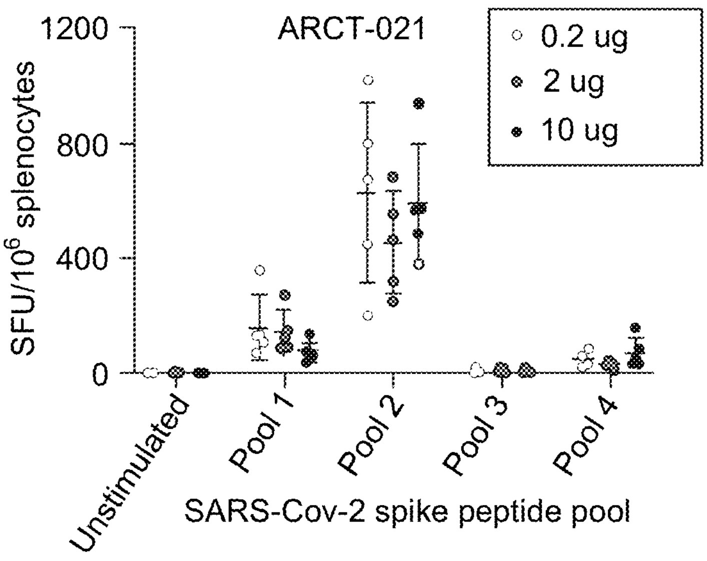
Figure 3J:
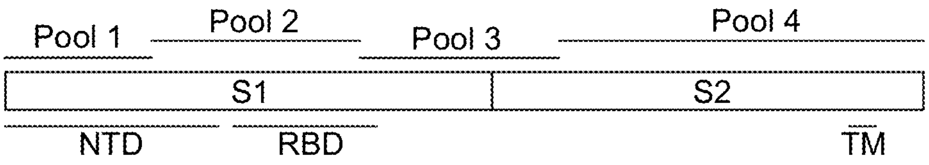

SARS-CoV-2 specific cellular responses were assessed in vaccinated animals by ELISPOT. A set of 15-mer peptides covering the SARS-CoV-2 S protein were divided into 4 pools and tested for IFNγ+ responses in splenocytes of vaccinated and non-vaccinated animals. SARS-CoV-2-specific cellular responses (displayed as IFNγ+ SFU/106 cells) were detected by ELISPOT in both STARR™ SARS-CoV-2 RNA and mRNA vaccine immunized animals compared to PBS control (FIG. 3G-3I). These responses were higher across the doses in STARR™ SARS-CoV-2 RNA compared to mRNA vaccinated groups (FIG. 3G-3I). Even the highest tested dose (10 μg) of mRNA vaccine produced IFNγ+ ELISPOT responses that were appreciably lower than those by the lowest dose (0.2 μg) of STARR™ SARS-CoV-2 RNA.

These results show that the STARR™ SARS-CoV-2 RNA construct induced strong T cell responses.

Example 4

This example illustrates humoral responses following vaccination with STARR™ SARS-CoV-2 RNA.

Figure 4A:
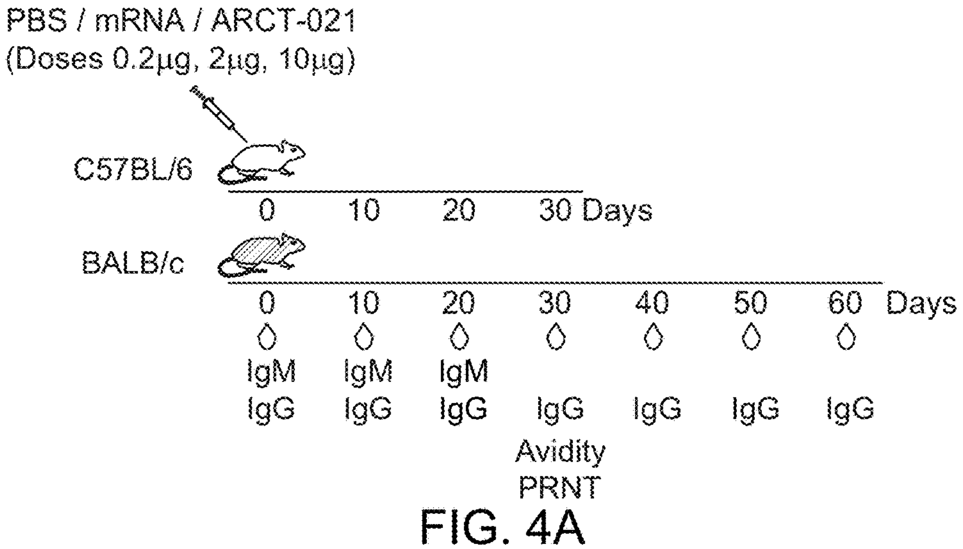
FIGS. 4A-4G show humoral responses in multiple mouse strains following immunization with mRNA and STARR™ vaccine candidates. (4A) BALB/c and C57BL/6J mice were immunized via IM with 0.2 μg, 2 μg, or 10 μg of STARR™ RNA or mRNA (n=5/group). Blood sampling was conducted at baseline, and days 10, 19, 30, 40, 50 and 60 post-vaccination for BALB/c and days 10, 20 and 30 for C57BL/6J. (4B-4C) IgM and (4D-4E) IgG against the SARS-CoV-2 S protein over time, assessed using insect cell-derived whole S protein in a Luminex immuno-assay (measured as MFI). IgG endpoint titers to mammalian-derived whole S protein, S1, S2 and receptor binding domain (RBD) proteins at day 30 post-vaccination were assessed in (4F) BALB/c and (4G) C57BL/6J.
Figure 4B:
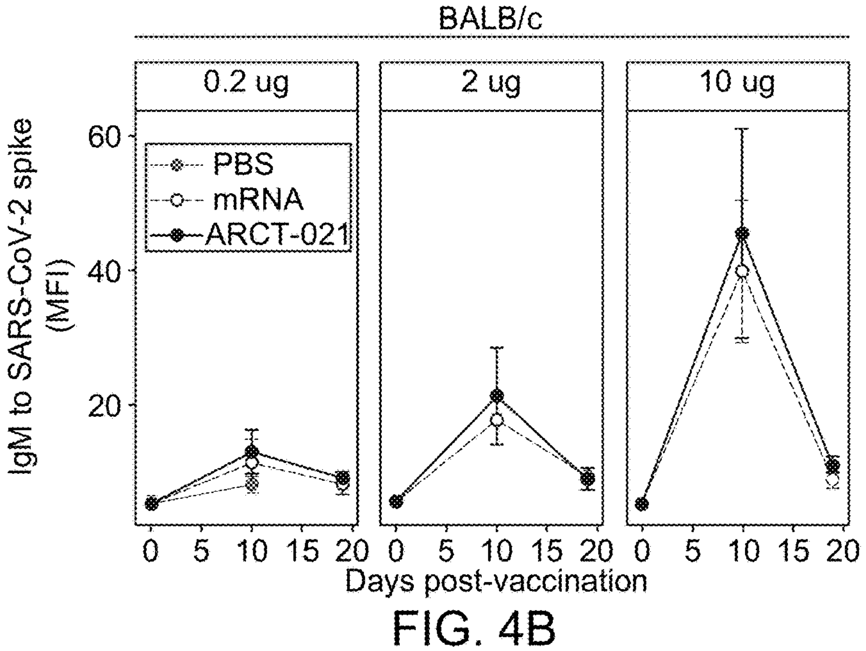
Figure 4C:
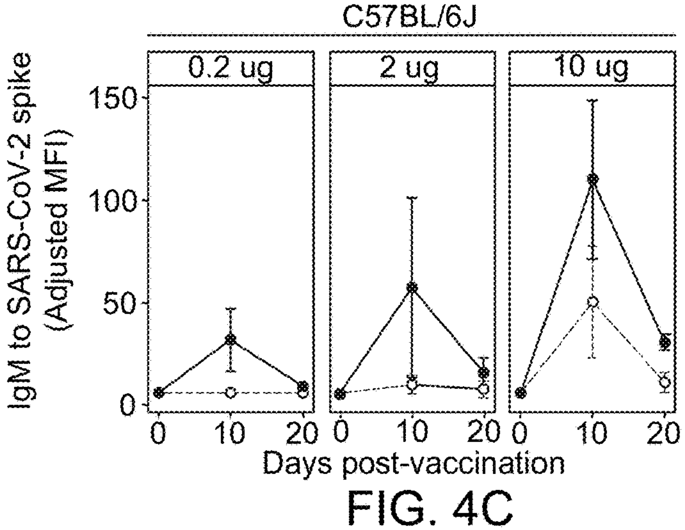
Figure 4D:
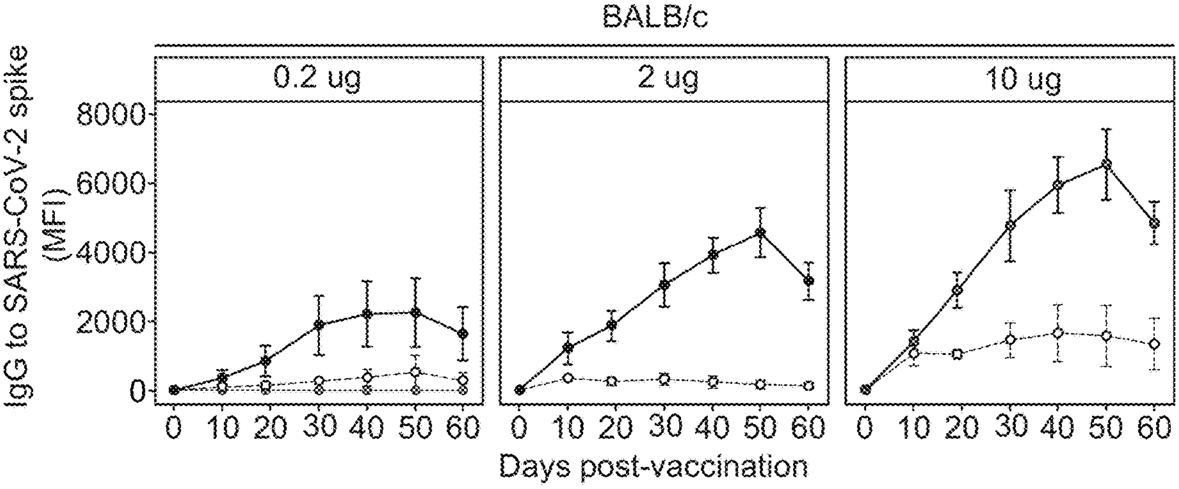
Figure 4E:
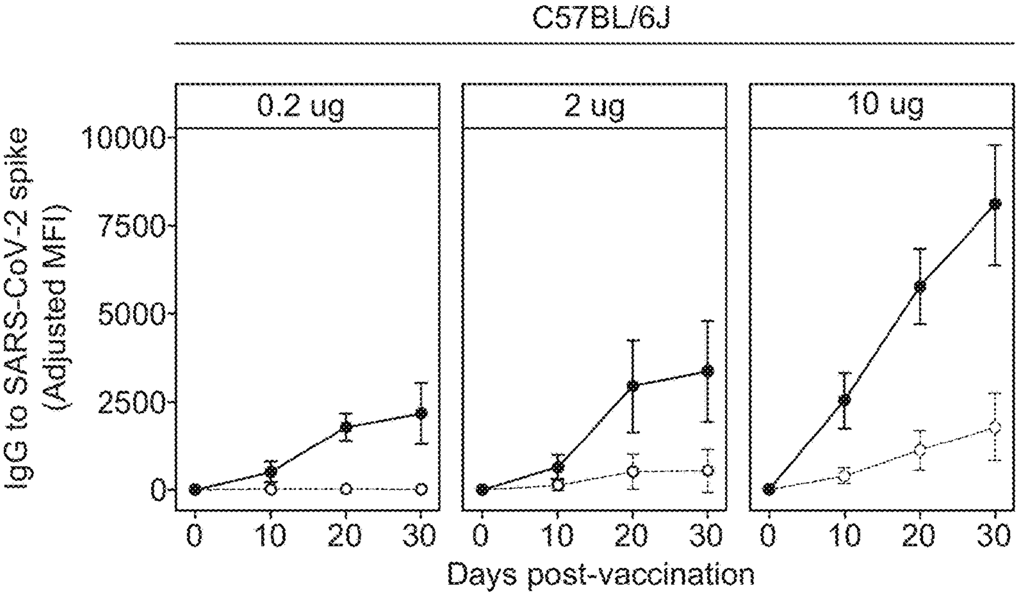

SARS-CoV-2-specific humoral responses following vaccination were characterized in two different mouse models, BALB/c and C57BL/6. Female mice (n=5 per group) were vaccinated at day 0 and bled every 10 days, up to day 60 for BALB/c and day 30 for C57BL/6 (FIG. 4A). SARS-CoV-2 S-specific IgM responses were tested at 1:2000 serum dilution using an in-house Luminex immuno-assay. All tested doses of mRNA vaccine and STARR™ SARS-CoV-2 RNA (corresponding to SEQ ID NO: 125, as described in Example 1 above) produced detectable S-specific IgM responses in both mouse models (FIG. 4B-4C). When comparing mRNA to STARR™ SARS-CoV-2 RNA vaccinated BALC/c mice, no difference in IgM responses was observed; IgM levels in C57BL/6 mice were higher in STARR™ SARS-CoV-2 RNA vaccinated C57BL/6 mice at day 10 post vaccination. In contrast, SARS-CoV-2 S-specific IgG (at 1:2000 serum dilution) levels were higher from day 20 onwards in animals inoculated with STARR™ SARS-CoV-2 RNA compared to mRNA vaccine (FIG. 4D-4E). Remarkably, the IgG levels continued to show an increasing trend in STARR™ SARS-CoV-2 RNA vaccinated mice, both BALB/c and C57BL/6, until day 50 post-vaccination with a single inoculation across all the doses. This trend contrasted with mice that received the mRNA vaccine where in BALB/c mice antibody levels plateaued after day 10 post-vaccination; increasing S-specific IgG levels were observed in mRNA-vaccinated C57BL/6 mice but these were lower than those seen in mice that received STARR™ SARS-CoV-2 RNA.

Figure 4F:
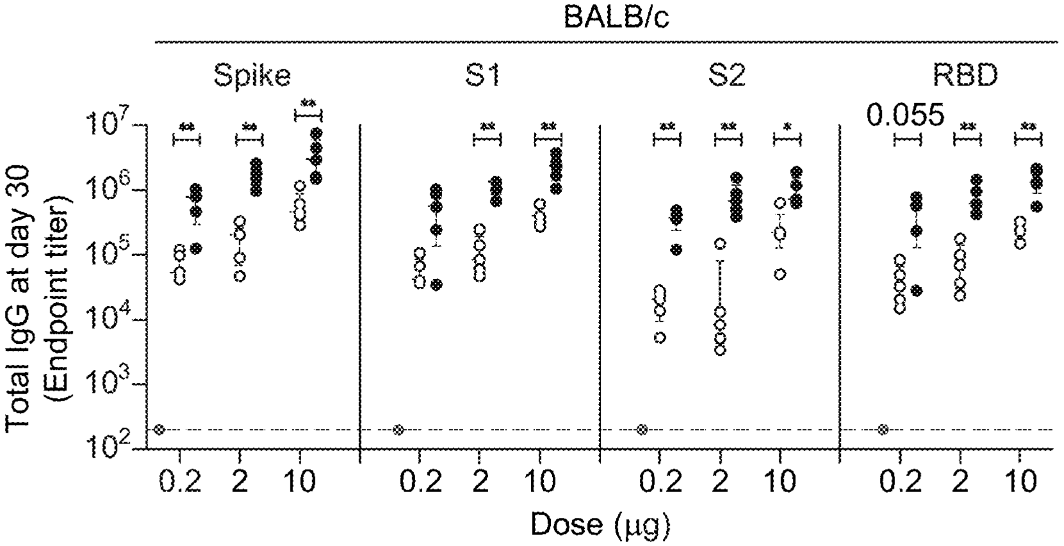
Figure 4G:
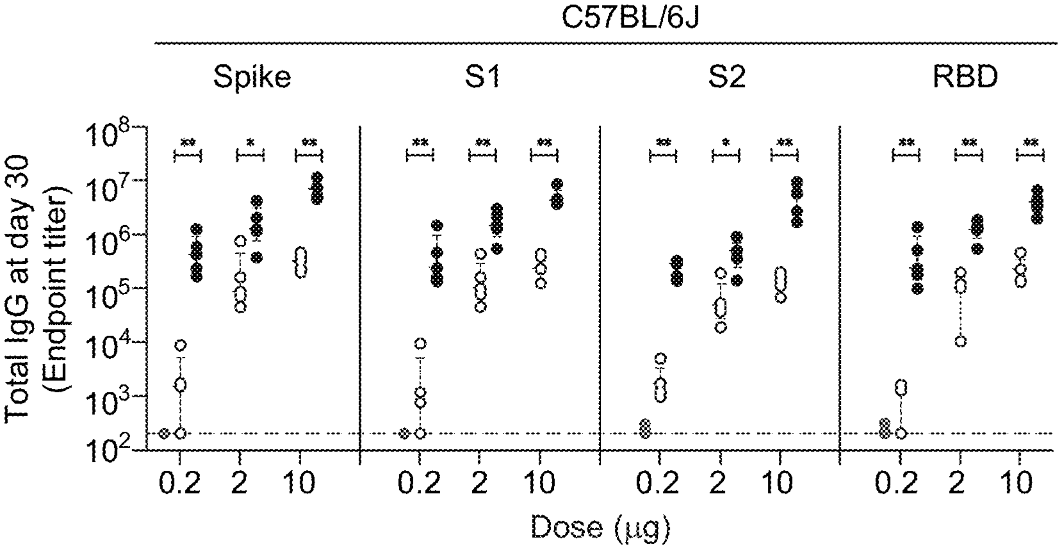

Further characterization of the SARS-CoV-2 specific IgG response in vaccinated animals was conducted at day 30 post-immunization to assess which regions of the S protein are targeted. IgG endpoint titers were estimated to full ectodomain S protein, S1, S2 and receptor binding domain (RBD) regions. For both vaccine candidates the majority of SARS-CoV-2 specific IgG recognized S1, although high IgG endpoint titers were also detected to S2 protein (FIG. 4F-4G). However, STARR™ SARS-CoV-2 RNA elicited IgG endpoint titers were significantly higher compared to those produced by mRNA vaccination (FIG. 4F-4G). Notably, IgG that bind the receptor binding domain (RBD) of S protein, which is an immunodominant site of neutralizing antibodies, were also higher in STARR™ SARS-CoV-2 RNA compared to mRNA vaccinated animals. Furthermore, at lower doses, mRNA vaccine but not STARR™ SARS-CoV-2 RNA struggled to elicit high SARS-CoV-2 specific IgG titers in the more Th1 dominant C57BL/6 mouse strain (FIG. 4G). Taken collectively, a single dose of STARR™ SARS-CoV-2 RNA induced significant differences in immune gene expression and superior cellular immune responses in draining lymph nodes compared to mRNA vaccine and consequently humoral immune responses.

These data show that STARR™ SARS-CoV-2 RNA vaccination induced elevated humoral responses as compared to mRNA vaccination.

Example 5

This example illustrates reduced risk of immune enhancement upon STARR™ SARS-CoV-2 RNA vaccination.

Figure 5A:
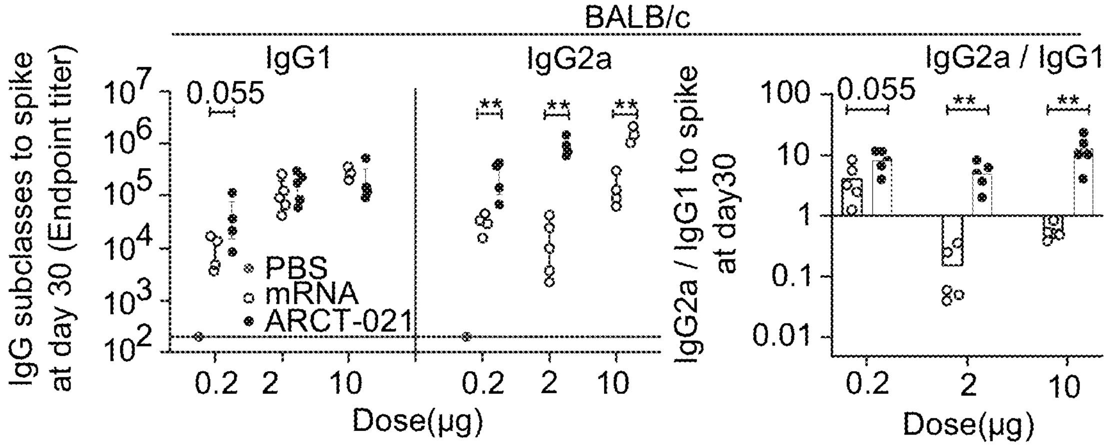
FIGS. 5A-5D show that STARR™ SARS-CoV-2 RNA elicits Th1 skewed immune responses. SARS-CoV-2 spike-specific IgG subclasses and the ratio of IgG2a/c/IgG1 at 30 days post-vaccination with STARR™ RNA and mRNA in (5A) BALB/c and (5B) C57BL/6J mice. Th2 cytokine and Th1/Th2 skew in CD4 T cells at day 7 post-vaccination in C57BL/6J mice measured by ICS as (5C) percentage of IL4+ CD4 T cells and (5D) ratio of IFNγ+/IL4+ CD4+ T cells.
Figure 5B:
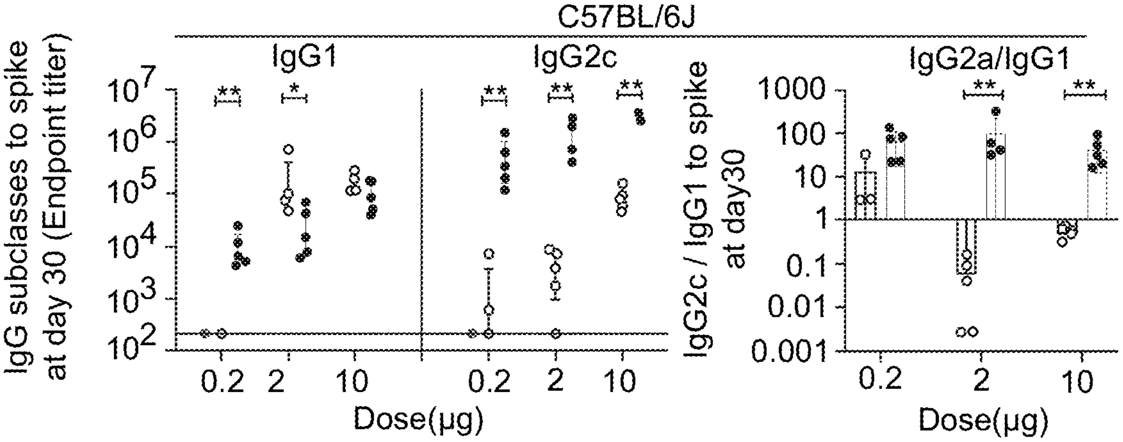

A safety consideration for coronavirus vaccine is a risk of vaccine-mediate immune enhancement of respiratory disease. Indeed, SARS-CoV and MERS-CoV vaccine development have highlighted the importance of Th1 skewed responses to avoid vaccine-induced immune enhancement. Therefore, the Th1/Th2 balance elicited by both mRNA and STARR™ SARS-CoV-2 RNA (self-replicating RNA construct as described in Example 1 above) vaccination was investigated. The IgG subclass fate of plasma cells is influenced by T helper (Th) cells. At day 30 post-vaccination, both mRNA and STARR™ SARS-CoV-2 RNA, except the 0.2 μg dose in C56BL/6J mice, induced comparable amounts of SARS-CoV-2 S-specific IgG1, a Th2-associated IgG subclass in mice (FIG. 5A-5B). In contrast, the Th1-associated IgG subclasses—IgG2a in BALB/c and IgG2c in C56BL/6J—were significantly greater in STARR™ SARS-CoV-2 RNA vaccinated animals. The ratios of S protein-specific IgG2a/IgG1 (BALBc) and IgG2c/IgG1 (C57BL/6) were greater than 1 in STARR™ SARS-CoV-2 RNA vaccinated animals (FIG. 5A-5B). Except for the 0.2 ug dose, these ratios were all significantly greater with STARR™ SARS-CoV-2 RNA compared to mRNA vaccinated animals.

Figure 5C:
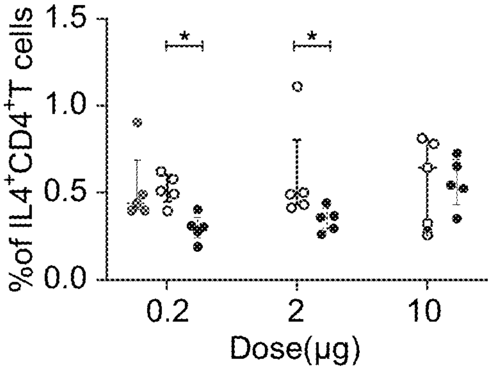
Figure 5D:
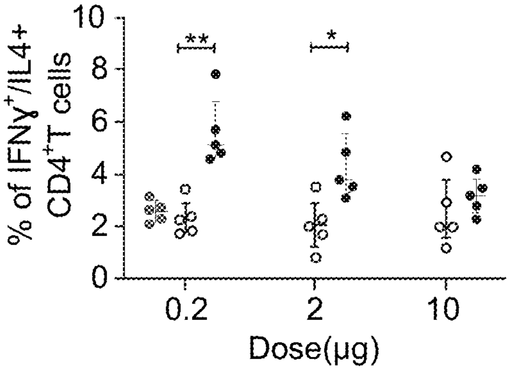

ICS was used to investigate the production of IFNγ (Th1 cytokine) and IL4 (Th2 cytokine) by CD4+ T cells in spleens of day 7 vaccinated C56BL/6J mice. As shown above (Example 3), compared to mRNA vaccination, IFNγ levels were significantly greater in STARR™ SARS-CoV-2 RNA vaccinated animals (FIG. 3F). IL4 expression in CD4 T cells was slightly higher in mRNA as compared to STARR™ SARS-CoV-2 RNA at 0.2 μg and 2 μg doses (FIG. 5C). In comparing the IFNγ and IL4 levels in individual mice, the ratios of IFNγ/IL4 in CD4+ T cells for both STARR™ SARS-CoV-2 RNA and mRNA vaccinated mice were above 1 (FIG. 5D). The ratio of IFNγ/IL4 in CD4+ T cells in mice given the 0.2 μg and 2 μg doses were significantly greater with STARR™ SARS-CoV-2 RNA than mRNA vaccination (FIG. 5F). However, without being limited by theory, the elevated ratios in these doses appeared to be due to the lowered IL4 expression at levels below background (i.e., PBS control mice), rather than reduced IFNγ and hence Th1 activity.

Taken collectively, these data show that STARR™ SARS-CoV-2 RNA produced Th1 instead of Th2 skewed adaptive immune responses.

Example 6

This example illustrates the quality of STARR™ SARS-CoV-2 RNA-induced humoral immune responses.

Figure 6A:
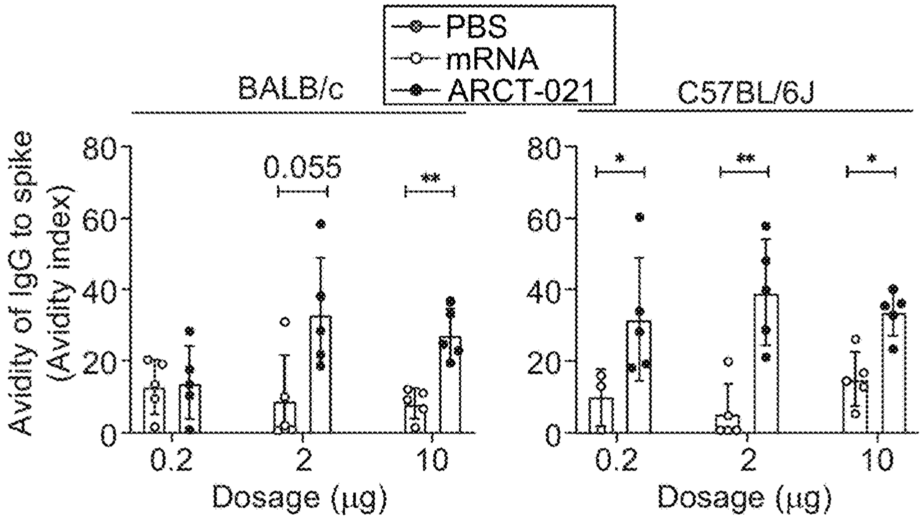
FIGS. 6A-6E show that STARR™ SARS-CoV-2 RNA elicits a higher quality humoral response than mRNA platform. (6A) Avidity of SARS-CoV-2 S protein-specific IgG at day 30 post-immunization was measured using 8M urea washes. (6B) Neutralizing antibody (PRNT50 titers) at day 30 post-vaccination against a clinically isolated live SARS-CoV-2 virus measured in both BALB/c and C57BL/6J. Dashed lines depict the serum dilution range (i.e. from 1:20 to 1:320) tested by PRNT. (6C) PRNT50 and (6D) PRNT70 of SARS-CoV-2 neutralization at day 60 post-vaccination and convalescent sera from COVID-19 patients. (6E) Correlation analysis of Spike-specific IgG endpoint titers against SARS-CoV-2 neutralization (PRNT50). PRNT—plaque reduction neutralization test.

The binding strength (avidity) and the neutralizing ability of the antibody response elicited by the self-replicating STARR™ SARS-CoV-2 RNA (construct as described in Example 1 above) and mRNA vaccine constructs was assessed next. Serum IgG avidity was measured at day 30 post-vaccination using a modified Luminex immuno-assay with 8M urea washes. STARR™ SARS-CoV-2 RNA elicited higher avidity S protein-specific IgG than mRNA in both mouse models at all tested doses (FIG. 6A). These differences were observed, with the exception of 0.2 μg in BALB/c, across all doses (FIG. 6A), indicating that STARR™ SARS-CoV-2 RNA elicited better quality antibodies than conventional mRNA.

Figure 6B:
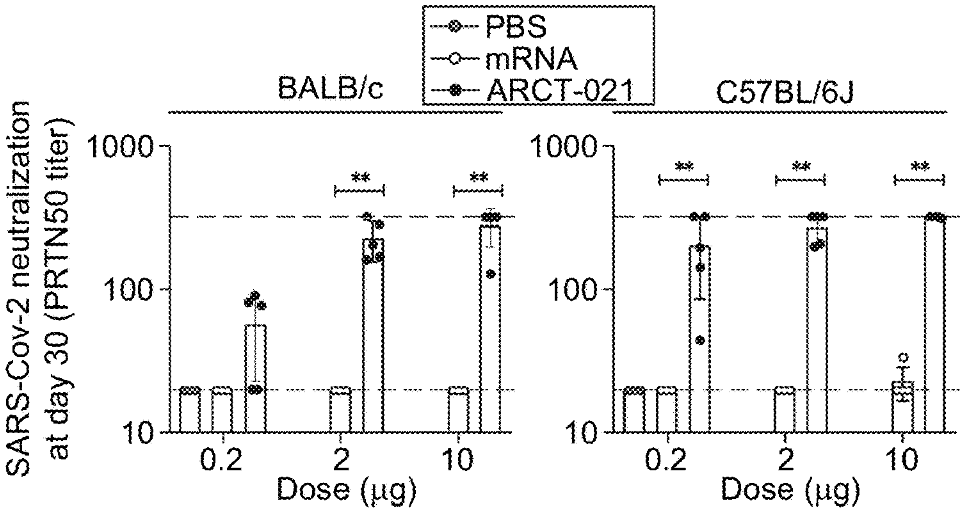
Figure 6C:
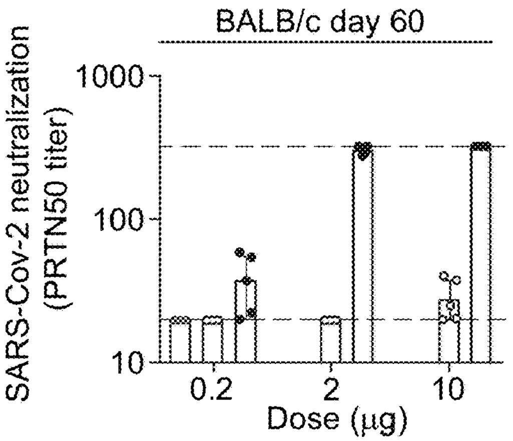
Figure 6D:
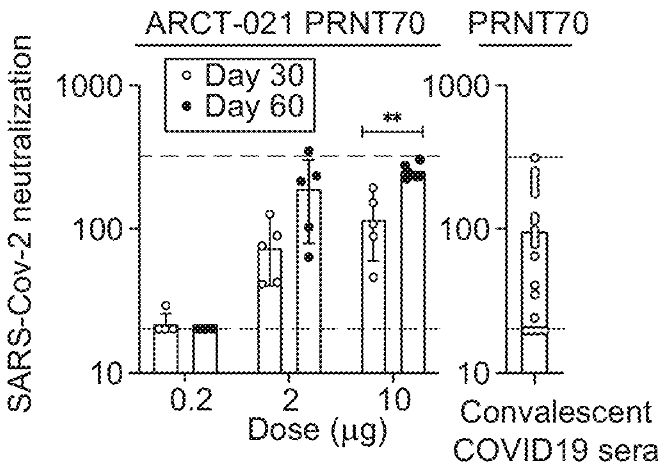

Neutralization of live SARS-CoV-2 by serum from vaccinated animals was assessed using the plaque reduction neutralization test (PRNT). At day 30 STARR™ SARS-CoV-2 RNA vaccinated BALB/c showed a clear dose dependent elevation in PRNT50 titers; 4 out of 5 (80%) of mice in the 10 μg STARR™ SARS-CoV-2 RNA group showed PRNT50 titers above the 320 upper limit (FIG. 6B). Similar dose-dependent trends in PRNT50 titers were also found in C57BL/6 mice, although in these animals, the PRNT50 titers of several animals exceeded the 320 upper limit even with a low 0.2 μg dose vaccination (FIG. 6B). In contrast, PRNT50 titers in animals inoculated with mRNA vaccine construct were, except for one C57BL/6J mouse that received 10 μg dose, all <20 (FIG. 6B). Unexpectedly and surprisingly, PRNT50 and PRNT70 titers of STARR™ SARS-CoV-2 RNA vaccinated BALBc mice continued to rise between day 30 and day 60 after a single dose of vaccination (FIG. 6C-6D). These titers were also comparable to PRNT70 titers in sera from convalescent COVID-19 patients (FIG. 6D).

Figure 6E:
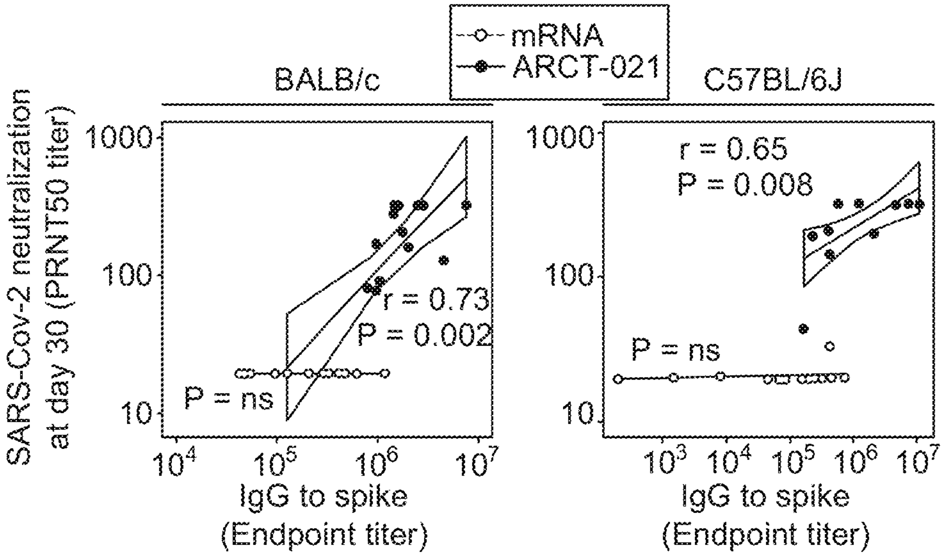
Figure 9A:
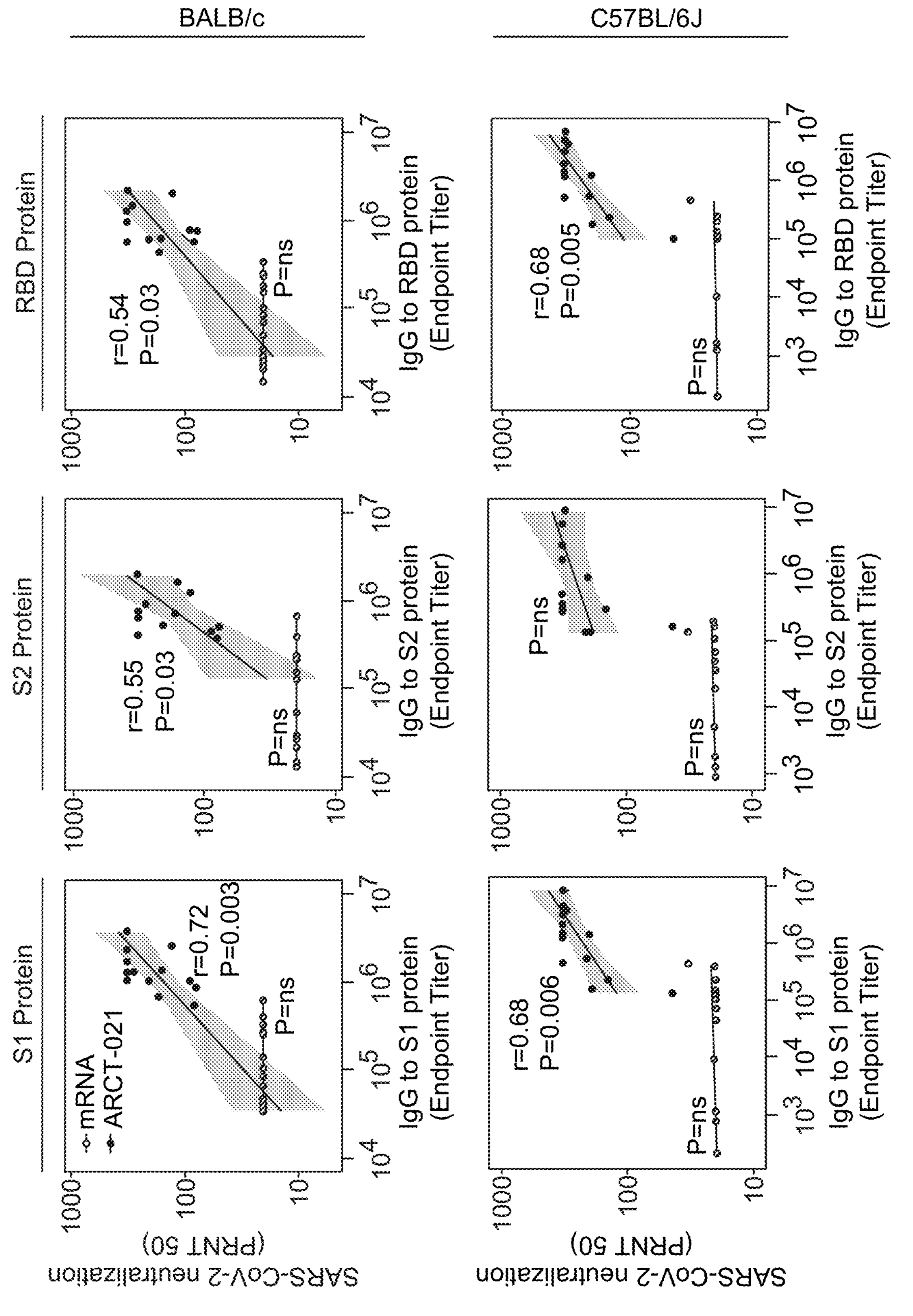
FIGS. 9A-9B show correlation analysis of live SARS-CoV-2 neutralization against binding IgG and IgG subclasses in BALB/c and C57BL/6J mouse strains. (9A) Spearman correlation analysis of SARS-CoV-2 neutralization (PRNT50) against total IgG specific to several SARS-CoV-2 antigens, including S, S1, and RBD recombinant proteins. (9B) Spearman correlation analysis of SARS-CoV-2 neutralization (PRNT50) against SARS-CoV-2 S-specific IgG subclasses (IgG1 and IgG2a or IgG2c).
Figure 9B:
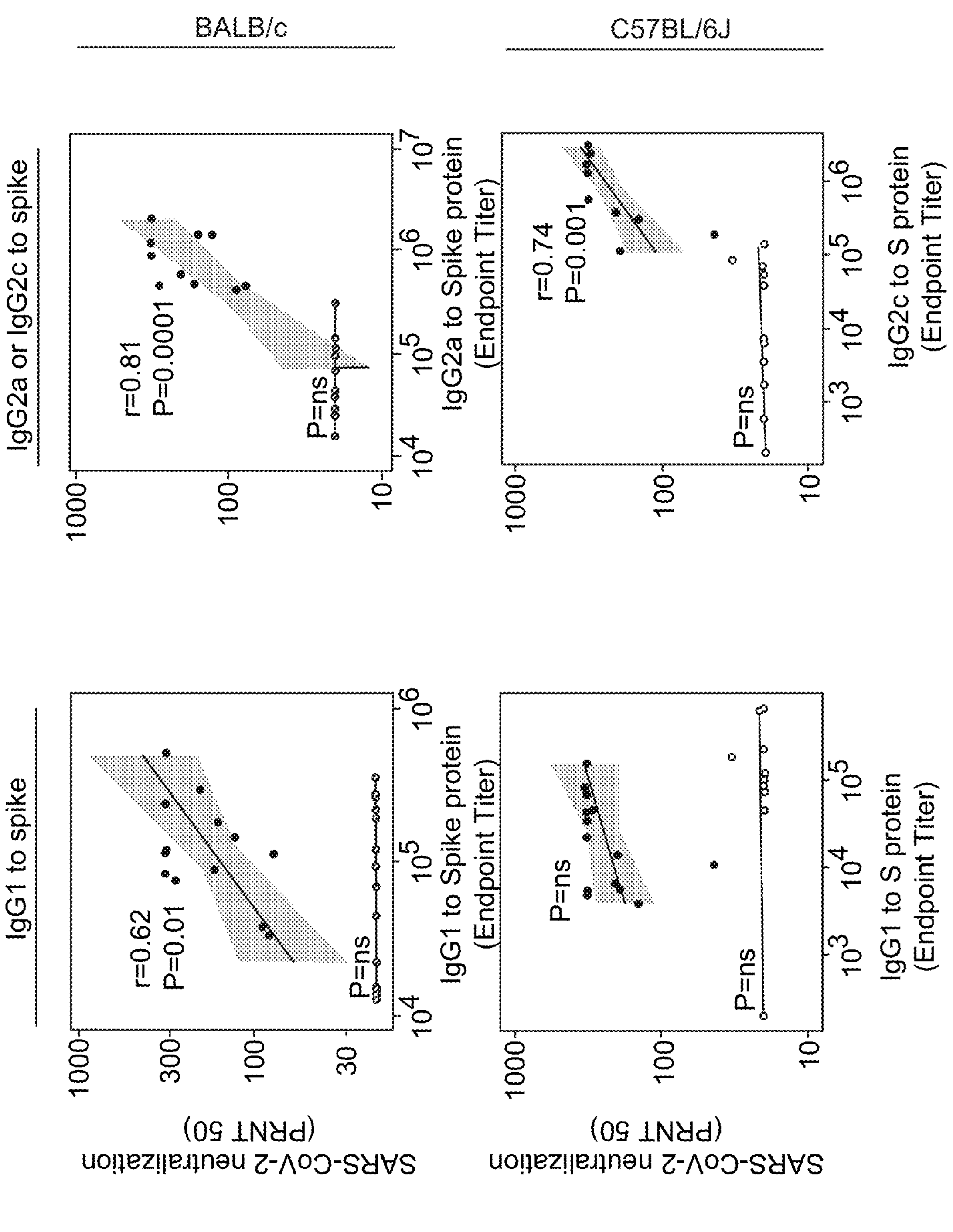

S protein IgG titers also positively correlated with PRNT50 titers in both mouse models (FIG. 6E). Similar positive correlations were also observed with IgG against S1 and RBD (FIG. 9). By contrast, no correlation was found between IgG and PRNT50 titers in mRNA vaccinated mice (FIG. 6E). Taken collectively, without being limited by theory, these antibody response analyses indicate that the higher PRNT50 titers following STARR™ SARS-CoV-2 RNA vaccination are not only attributable to the amount of IgG produced but also due to superiority of the quality of the anti-SARS-CoV-2 antibodies.

In summary, STARR™ SARS-CoV-2 RNA induced qualitatively superior humoral immune response than conventional mRNA.

Example 7

This example illustrates the effect of a second dose of STARR™ SARS-CoV-2 RNA.

Figure 7A:
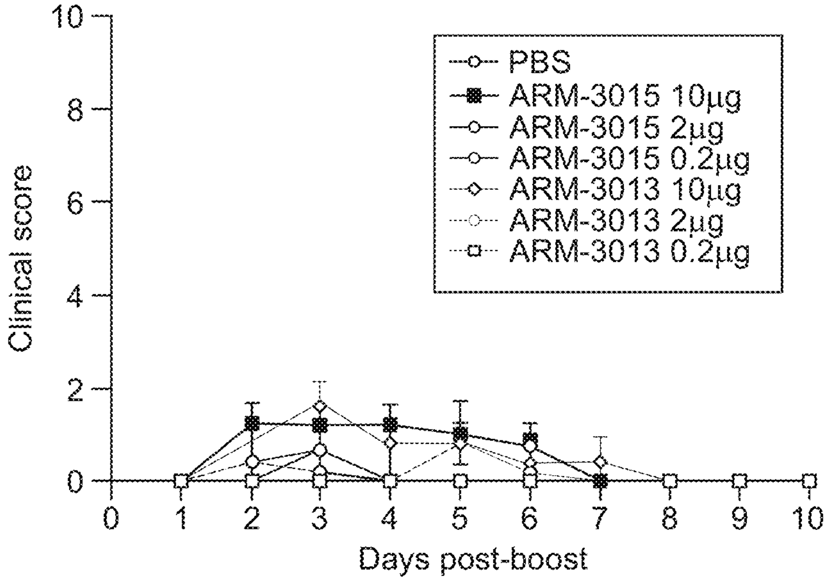
FIGS. 7A-7E show clinical scores, body weight and immune responses to STARR™ SARS-CoV-2 RNA and mRNA following boost at day 30 post-prime in C57BL/6J. (7A) Clinical scores and (7B) percentage of initial body weight following boost vaccinations. (7C) Anti-Spike IgG responses following boost by mRNA and STARR™ SARS-CoV-2 RNA. Grey dashed line marks the experimental assay saturation point. IFN γ+ CD8+ T effector cells responses (fold change over PBS) in animals either primed or prime & boosted with either (7D) mRNA or (7E) STARR™ SARS-CoV-2 RNA vaccine candidates.
Figure 7B:
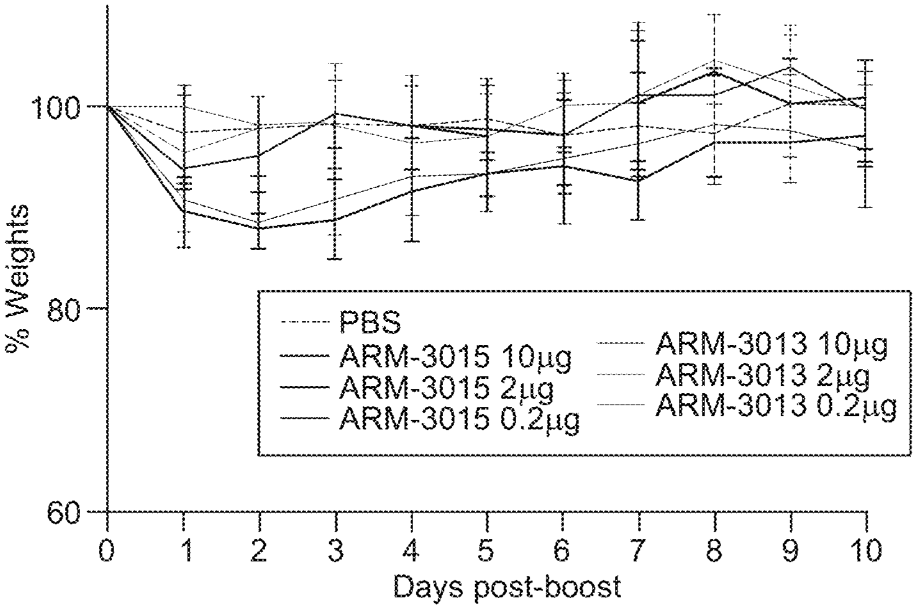
Figure 7C:
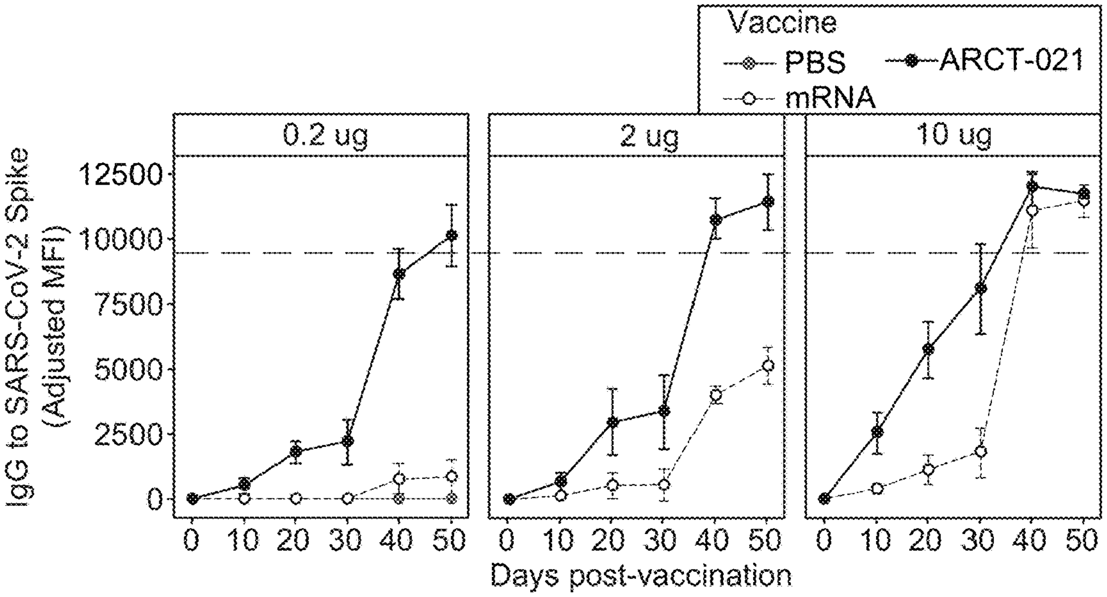

A possible added benefit of a second dose of STARR™ SARS-CoV-2 RNA (self-replicating RNA construct as described in Example 1 above) to the cellular and humoral immune responses to the S protein of SARS-CoV-2 was explored next. The clinical scores after the second dose were higher than after the first dose (FIG. 7A). Like the first dose, mice that received 2 μg and 10 μg of STARR™ SARS-CoV-2 RNA experienced weight loss (FIG. 7B). The IgG response to a second dose of STARR™ SARS-CoV-2 RNA produced an appreciable boost in S protein-specific IgG levels, but only with 0.2 μg and 2 μg of STARR™ SARS-CoV-2 RNA (FIG. 7C). Without being limited by theory, a likely reason for the lack of increase in the anti-S protein specific IgG levels for the 10 μg dose is that the amount of fluorescence is near the saturation point of the detector and sera was not further diluted to observe and increase. However, in a subsequent Balb/c mouse study, the sera from mice vaccinated with a 5 μg RNA dose administered unilaterally in a 0.05 mL injection volume produced a significant increase in neutralizing antibody titers as assayed using a 96 well microneutralization assay format. Mice were bled every 14 days and a second vaccination of 5 μg was administered on day 28. 4 mice were injected with a VEEV replicon RNA expressing luciferase as a negative control and 6 mice were vaccinated with STARR™ SARS-CoV-2 RNA. The results are shown in Table 8 below.

TABLE 7

Microneutralization Titers (MN50) in Balb/c Mice

| Mouse No. | Treatment | Microneutralization Titers (MN50) Wk 0 | Wk2 | Wk4 | Wk6 | Wk8 |
|---|---|---|---|---|---|---|
| 1 | Luciferase | <10 | <10 | <10 | <10 | <10 |
| 2 | Luciferase | <10 | <10 | <10 | <10 | <10 |
| 3 | Luciferase | <10 | <10 | <10 | <10 | <10 |
| 4 | Luciferase | <10 | <10 | <10 | <10 | <10 |
| 5 | STARR ™ SARS-CoV-2 RNA | <10 | 1,280 | 5,120 | 327,680 | 81,920 |
| 6 | STARR ™ SARS-CoV-2 RNA | <10 | 640 | 20,480 | 327,680 | 327,680 |
| 7 | STARR ™ SARS-CoV-2 RNA | <10 | 1,280 | 2,560 | 163,840 | 163,840 |
| 8 | STARR ™ SARS-CoV-2 RNA | <10 | 1,280 | 10,240 | 327,680 | 163,840 |

TABLE 7-continued

Microneutralization Titers (MN50) in Balb/c Mice

| Mouse No. | Treatment | Microneutralization Titers (MN50) Wk 0 | Wk2 | Wk4 | Wk6 | Wk8 |
|---|---|---|---|---|---|---|
| 9 | STARR ™ SARS-COV-2 RNA | <10 | 640 | 40,960 | 327,680 | 327,680 |
| 10 | STARR ™ SARS-CoV-2 RNA | <10 | 1,280 | 10,240 | 327,680 | 327,680 |
| Avg Geometric Mean | | | 1,016 | 10,240 | 29,1930 | 206,426 |

The neutralization titers increased 10 fold between day 14 and day 28 post vaccination. Following the boost on day 28, the neutralization titers increased an additional 20 fold 14 days post boost.

Figure 7D:
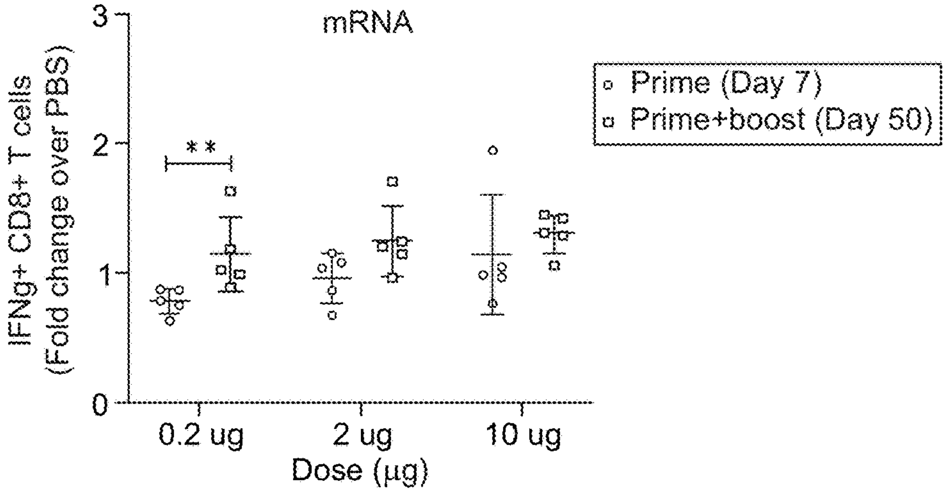
Figure 7E:
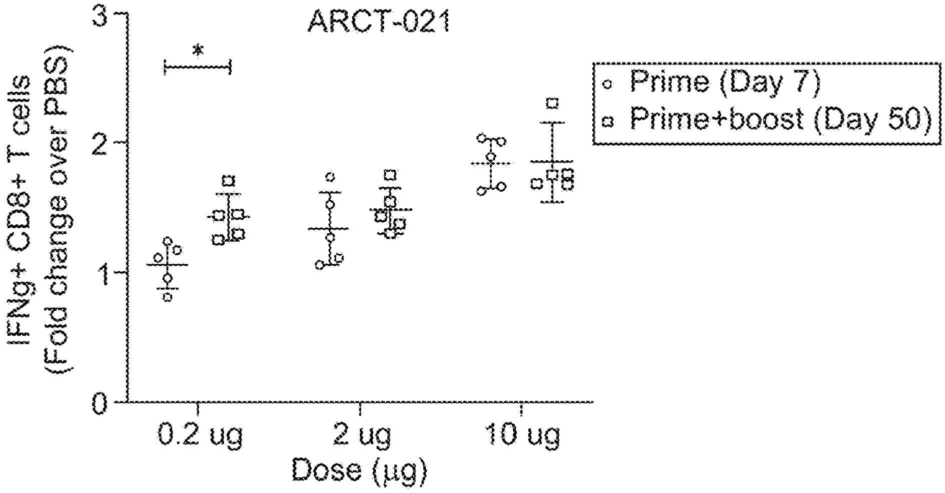

To determine if there was added benefit in IFNγ+CD8+ T cell counts from a second dose vaccination, CD8 T cell IFNγ responses in mice given only a prime were compared to responses of mice given a prime and a boost. Fold change in IFNγ+CD8+ T cells in the vaccinated over PBS control mice was calculated for mice given either a prime only or given a prime and boost. The fold change of IFNγ+CD8+ T cells was similar following the prime and prime+boost for 2 μg and 10 μg doses of STARR™ SARS-CoV-2 RNA (FIG. 7D-7E); the 0.2 μg dose showed higher fold change of IFNγ+CD8+ T cells between prime (at day 7) and prime+ boost (day 50). Vaccination with 0.2 μg of mRNA also showed increased IFNγ+CD8+ T cells relative to PBS control after two doses of vaccination. Without being limited by theory, these findings suggest that a second 10 μg dose of STARR™ SARS-CoV-2 RNA did not produce superior cellular immunity compared to single dose vaccination. Thus, there was no apparent benefit from a second 10 μg dose of STARR™ SARS-CoV-2 RNA.

Taken collectively, these data suggest that 10 gSTARR™ SARS-CoV-2 RNA offers the opportunity of a single dose vaccination to protect against COVID-19.

Example 8

This example illustrates protection from SARS-CoV-2 viral challenge in mice following vaccination with STARR™ SARS-CoV-2 self-replicating RNA.

A mouse viral challenge study was conducted with human ACE2 transgenic mice. Mice were immunized with 2 μg and 10 μg RNA doses of STARR™ SARS-CoV-2 RNA (RNA construct as described in Example 1 above) or injected with PBS. There were three different cohorts with 5 mice in each treatment group. Cohorts 1 and 3 received a lethal SARS-CoV-2 virus challenge load of 5×105 TCID50. Cohort 1 was monitored for survival and Cohort 3 was euthanized 5 days after challenge. Lungs were assayed for viral load and processed for histopathology. Cohorts 2 received a sublethal viral load of 5×104 TCID50. Cohort 2 was euthanized 5 days after virus challenge and lungs were assayed for infectious virus and processed for histopathology. All mice were inoculated intratracheally 30 days post-vaccination with a single dose of STARR™ SARS-CoV-2 RNA.

Figure 10:
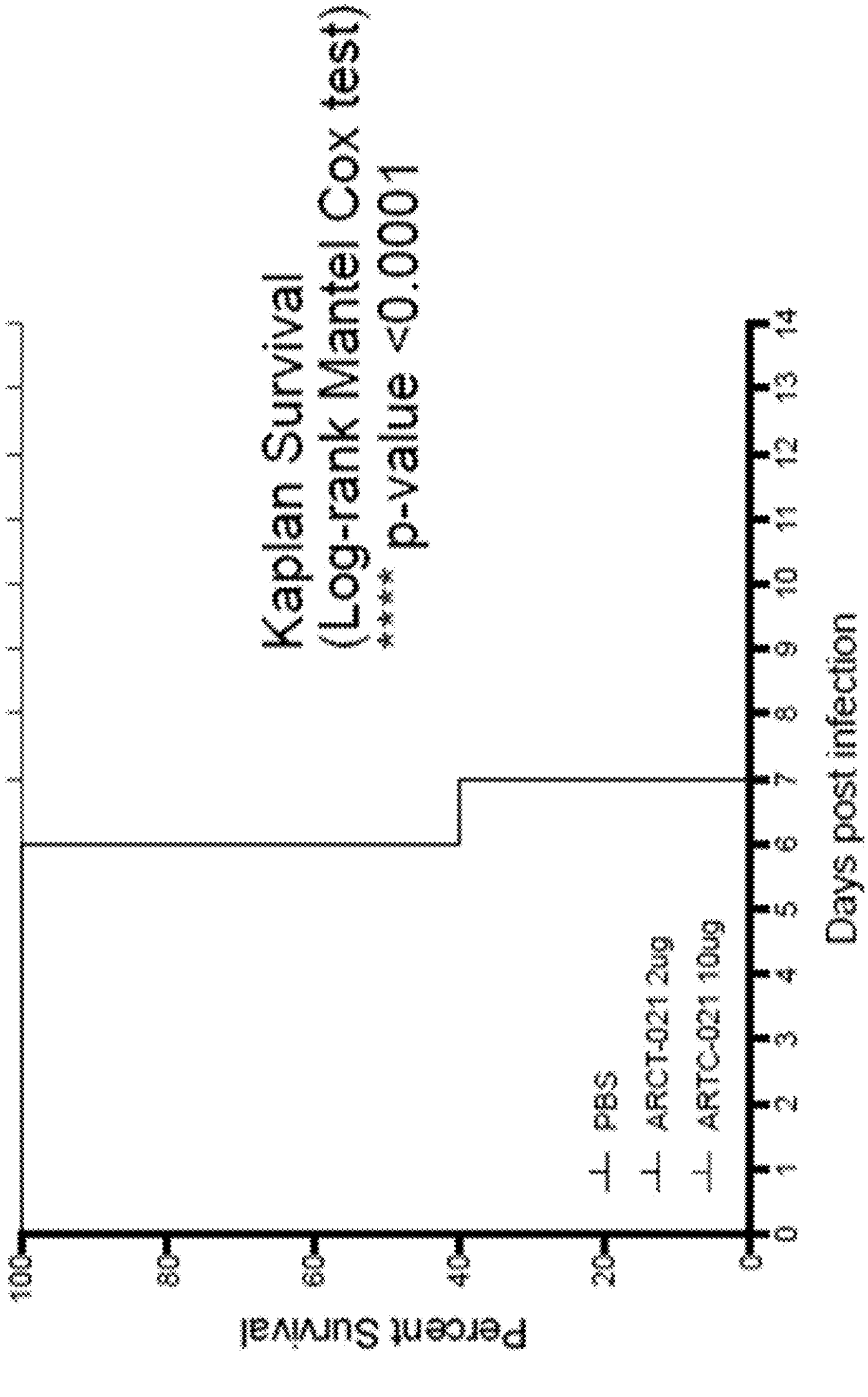
FIG. 10 shows Kaplan-Meier survival curves for unvaccinated mice (PBS) and mice vaccinated with STARR™ SARS-CoV-2 RNA following challenge with a lethal dose of SARS-CoV-2 virus. Upper line—STARR™ SARS-CoV-2 RNA (2 μg, 10 μg); dropping line—PBS.
Figure 11:
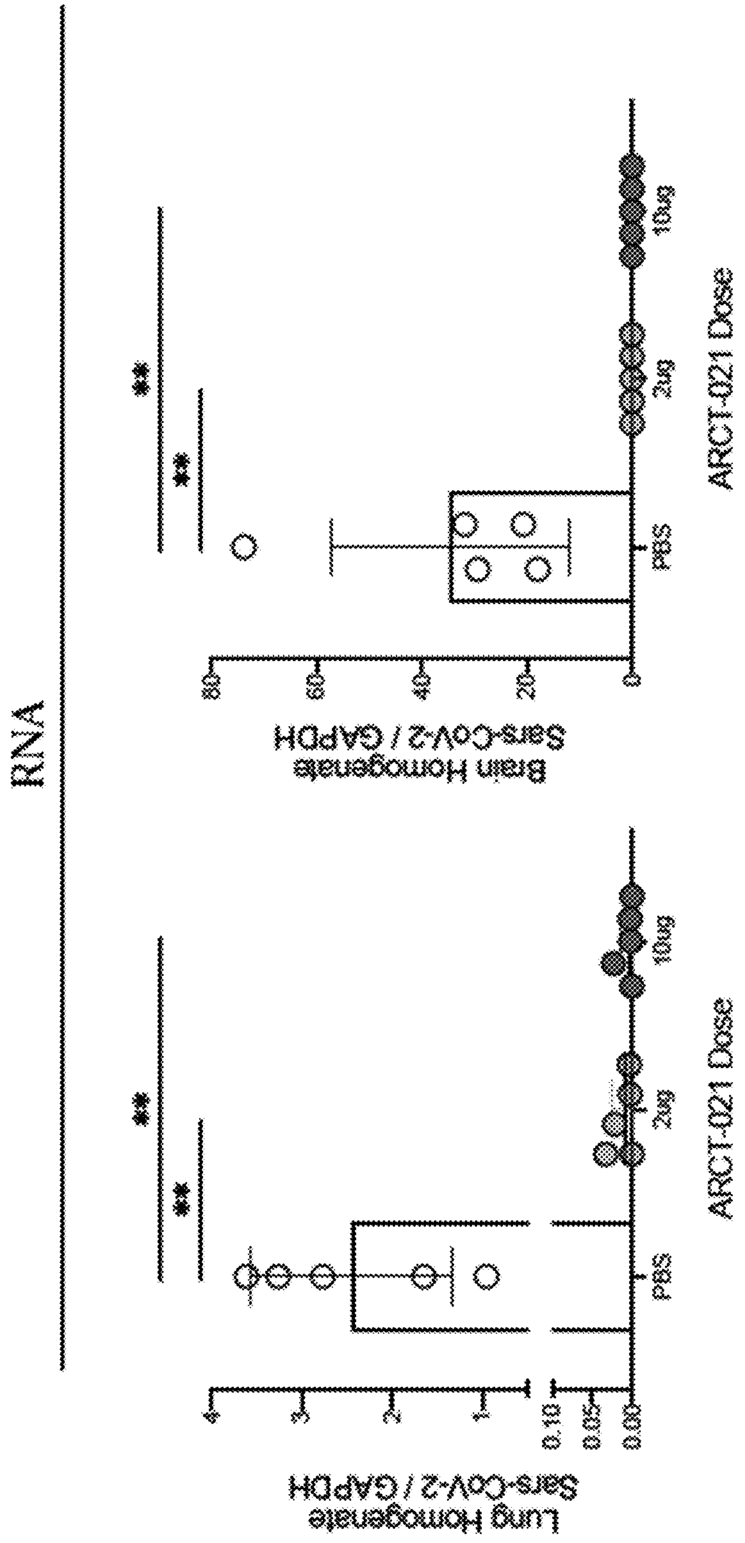
FIG. 11 shows that STARR™ SARS-CoV-2 RNA vaccination protects against lung and brain SARS-CoV-2 infection. Viral RNA levels in lungs (FIG. 11, left) and in brains (FIG. 11, right) of unvaccinated mice (PBS) and mice vaccinated with the indicated dose of STARR™ SARS-CoV-2 RNA are shown.
Figure 12:
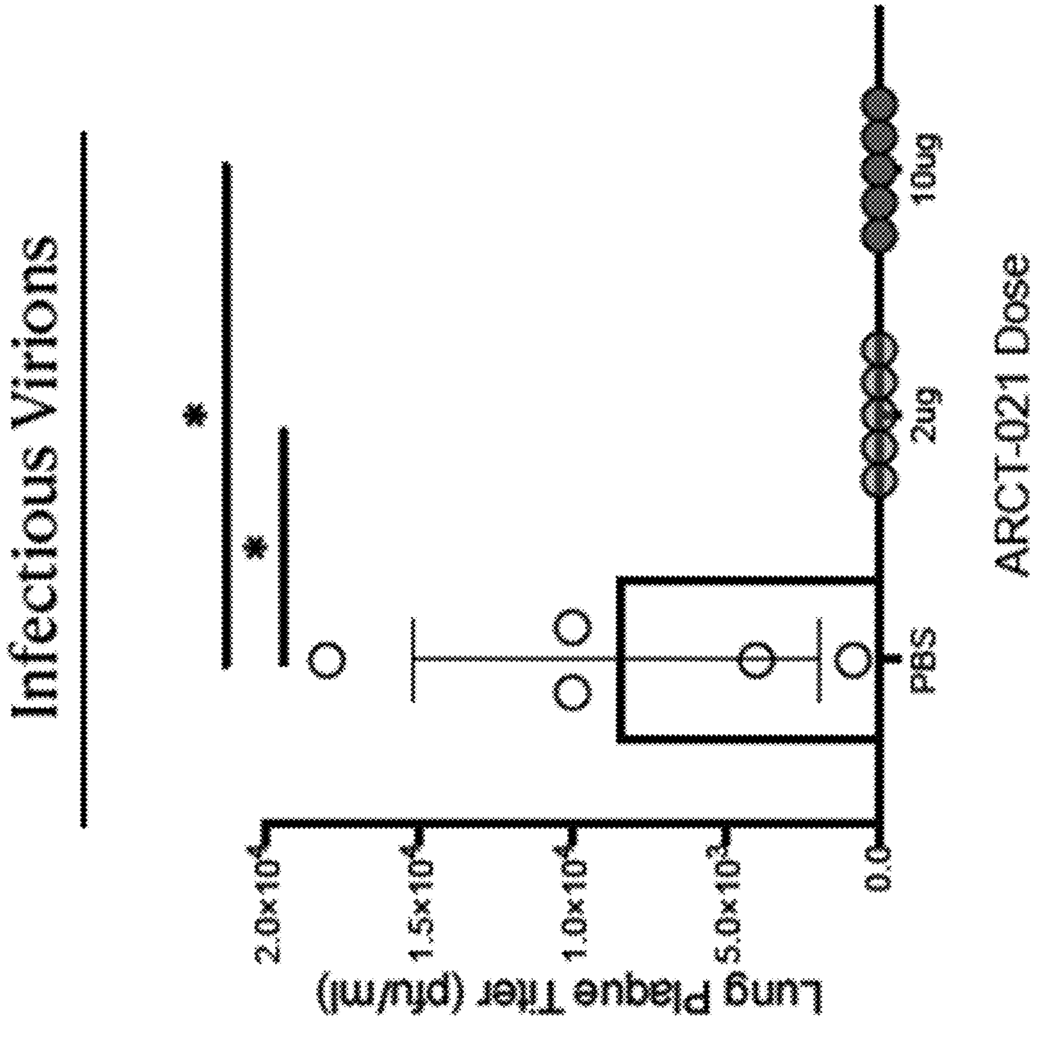
FIG. 12 shows viral titers in lungs of unvaccinated mice (PBS) and mice vaccinated with the indicated dose of STARR™ SARS-CoV-2 RNA following challenge with SARS-CoV-2.

All mice injected with PBS in cohort 1 were dead by day 7, whereas all vaccinated mice showed no signs of infection 15 days after viral challenge (FIG. 10). For Cohort 2 receiving a sublethal viral load, 10 to 3,300 copies of virus was measured by RT-PCR in the lungs with an average of 1,200 copies, whereas no copies of viral RNA were measured in mice vaccinated with ARTC-021 at 2 μg and 10 μg RNA doses (LOD was 0.1 copies; FIG. 11, left). Copies of viral RNA were also observed in the brain ranging from 20 to 80 in the PBS treatment group, whereas no viral RNA copies were measured in the brains of mice vaccinated with either 2.0 μg or 10.0 μg RNA doses (FIG. 11, right). Lastly, lungs were carefully processed and assayed for lung plaque titers. The average plaque titers for the group injected with PBS was 8×103/mL of lung homogenate, whereas no plaques were detected for mice vaccinated with either 2.0 μg or 10.0 μg or STARR™ SARS-CoV-2 RNA (FIG. 12). Lung and brain tissues from Cohort 3 are being assayed for viral copy number and infectious virus. Histopathology of lungs for cohorts 2 and 3 is in progress.

These results show that vaccination with STARR™ SARS-CoV-2 self-replicating RNA protected mice from a lethal SARS-CoV-2 infection and protected against lung and brain infection upon challenge with a sublethal dose of SARS-CoV-2.

Example 9

Figure 13:
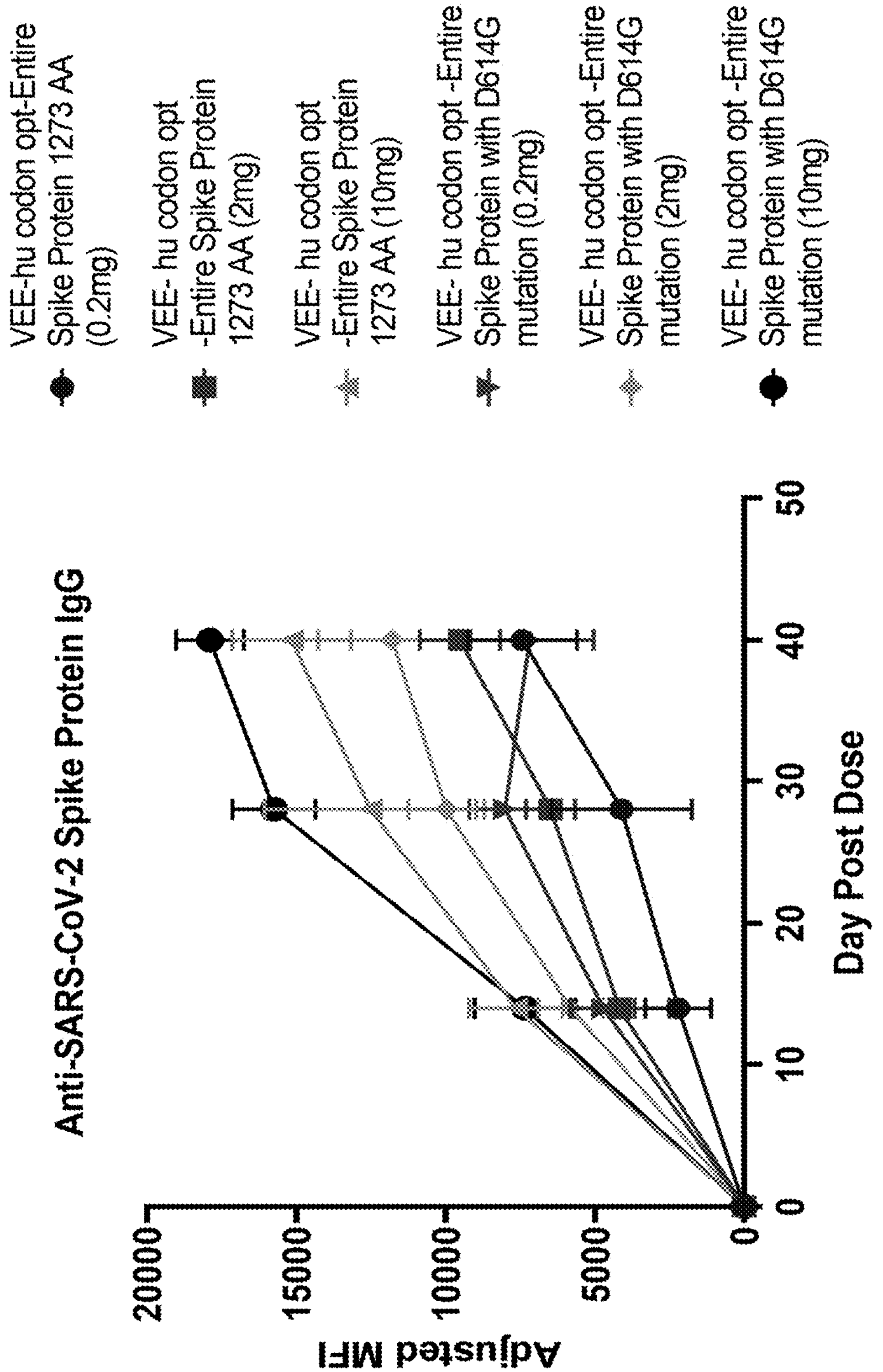
FIG. 13 shows an RNA dose-dependent immunogenicity comparison between G614 and D614 SARS CoV-2 glycoprotein expressed from self-replicating RNA.
Figure 14:
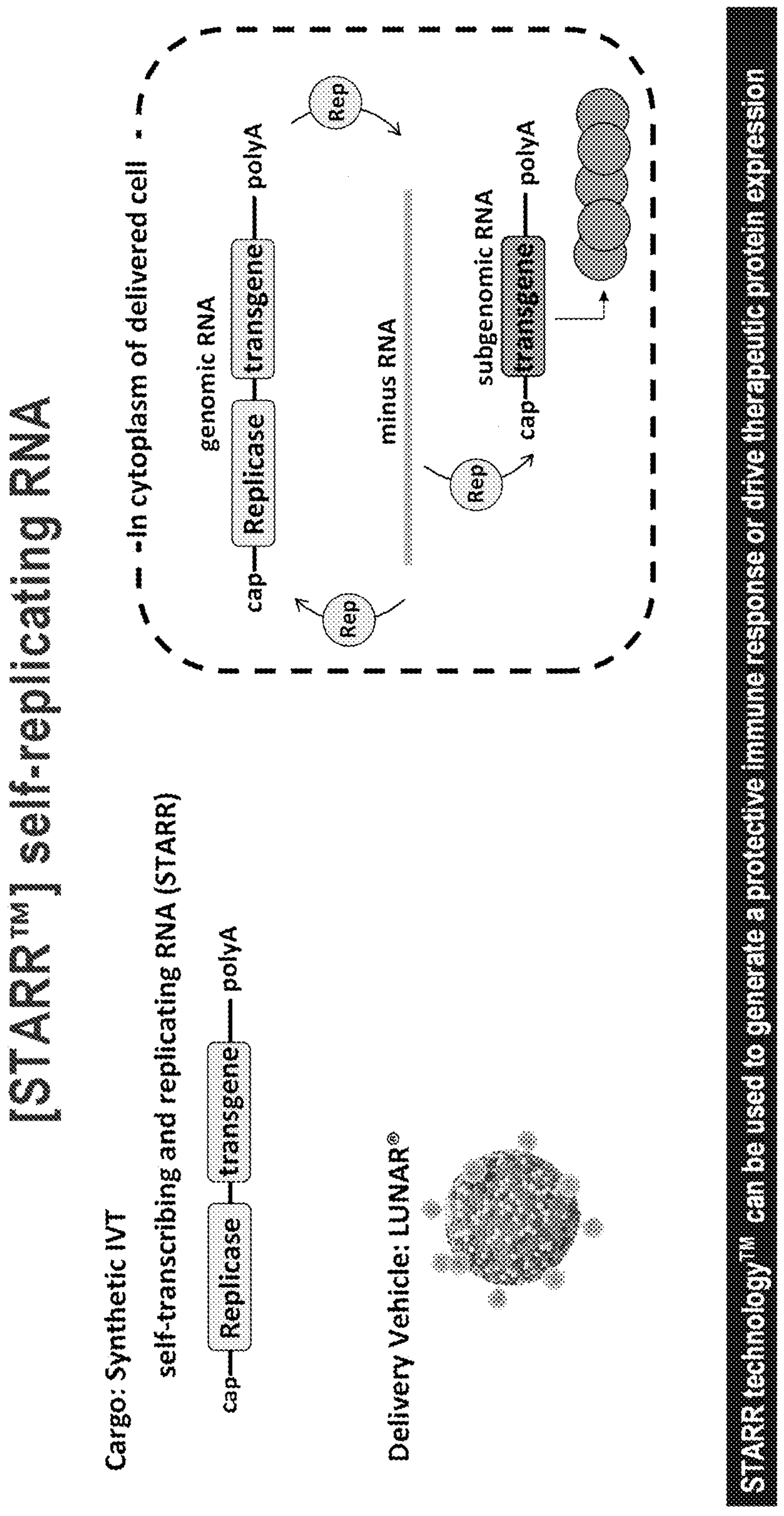
FIG. 14 shows a schematic illustrating one aspect of STARR™ technology and lipid-mediated delivery.

The COVID-19 pandemic is caused by infection with the SARS-CoV-2 virus. A major mutation detected to date in the SARS-CoV-2 viral envelope spike protein, which is responsible for virus attachment to the host and is also the main target for host antibodies, is a mutation of an aspartate (D) at position 614 found frequently in Chinese strains to a glycine (G). VEEV Replicon transcripts expressing the D614 and G614 versions of the SARS-CoV-2 spike glycoprotein were formulated with the exact same lipid formulation as studies described in Examples 1-8. Balb/c mice were vaccinated with a single RNA administration of 0.2 μg, 2.0 μg and 10.0 μg of RNA. There were 5 mice per dose. Mice were bled on days, 14, 28 and 42 post vaccination. Sera was diluted 1/2000 and incubated with Luminex beads derivatized with the SARS-CoV-2 spike glycoprotein containing the D614 amino acid sequence. A secondary mouse antibody derivatized with a fluorophore was used to assay for bound antibody to the beads and adjusted mean fluorescence intensity (MFI) was measured as a function of RNA dose, shown in FIG. 13. The results showed that MFI increased as a function of RNA dose with slightly higher MFI observed for the serum from mice immunized with the G614 spike glycoprotein. This slight elevation is attributed to a lower percentage of full length RNA with the D614 amino acid sequence. An important conclusion is that the serum from mice immunized with the G614 spike glycoprotein RNA construct was able to bind to spike glycoprotein with the D614 amino acid sequence, indicative of cross reactivity.

These results show that immunization with a G614 spike glycoprotein expressed from self-replicating RNA results in production of antibodies that are able to bind to a D614 spike glycoprotein.

Discussion of Examples 1-9

The pandemic of COVID-19 has necessitated rapid development of vaccines, as physical distancing to prevent SARS-CoV-2 transmission is not a sustainable long-term solution. Several COVID-19 vaccine candidates are now in clinical trials and more are entering first-in-human trials. However, a majority of vaccine candidates being developed require two doses for sufficient adaptive immunity. A single dose vaccine that generates both cellular and humoral immunity, without elevating the risk of vaccine-mediated immune enhancement, remains an unmet need. Without being limited by theory, deployment of a single dose vaccine would enable greater level of compliance and enable distribution of finite production of vaccines to more susceptible people globally.

Among licensed vaccines, live attenuated vaccines can offer durable protection against viral diseases. Live vaccines infect and replicate at sites of inoculation and some even in draining lymph nodes. Replication enables endogenous expression of viral antigens that enables antigen presentation to stimulate cytotoxic CD8+ T cells. Expressed antigens would also be taken up by antigen presenting cells to trigger CD4+ T cell help that drive affinity maturation in B cells. Studies on the live attenuated yellow fever vaccine have shown that a longer period of stimulation of the adaptive immune response results in superior adaptive immune responses. Without being limited by theory, simulating the processes of live vaccination could offer a chance of durable immunity against COVID-19.

In a crisis such as COVID-19, a nucleic acid vaccine platform offers opportunities for accelerated development. In studies described herein, a side-by-side comparison of the immunogenicity elicited by two SARS-CoV-2 vaccines candidates was conducted, a non-replicative mRNA construct and STARR™ SARS-CoV-2 RNA. Compared to an mRNA vaccine, STARR™ SARS-CoV-2 RNA produced higher and longer protein expression in vivo and upregulated gene expression of several innate, B cell, and T cell response genes in the blood and draining lymph nodes. These properties translated into significantly greater CD8+ T cell responses, IFNγ+ ELISPOT responses, and SARS-CoV-2 specific IgG and Th1 skewed responses. Interestingly, despite the highest tested dose of mRNA eliciting comparable S protein-specific antibodies as the lowest tested dose of STARR™ SARS-CoV-2 RNA, mRNA-elicited IgG did not show similar avidity or neutralization activity as those from STARR™ SARS-CoV-2 RNA vaccination. These findings thus highlight the immunological advantages of self-replicating RNA over mRNA platforms. In addition, mouse challenge studies with SARS-CoV-2 virus showed that vaccination with a single high dose (10 μg) or a single low dose (2 μg) of STARR™ SARS-CoV-2 self-replicating RNA protected mice from a lethal SARS-CoV-2 infection and protected from lung and brain infection upon challenge with a sublethal SARS-CoV-2 dose.

The extent to which STARR™ vaccines reproduce the features of live vaccines remain to be experimentally defined. Without being limited by theory, the superior quality of immune responses elicited by STARR™ SARS-CoV-2 RNA over the mRNA vaccine construct could be attributable to multiple factors, all of which have been found to be associated with live vaccination. For example, higher and longer expression of immunogens produce better immunity, likely through better engagement of T follicular helper cells and thereby leading to more diverse antibody targets and more neutralizing antibody responses. Replication of STARR™ SARS-CoV-2 RNA would result in the formation of a negative-strand template for production of more positive-strand mRNA and sub-genomic mRNA expressing the S transgene. Interaction between the negative- and positive-strands would form double stranded RNA (dsRNA), which would interact with TLR3 and RIG-I-like receptors to stimulate interferon responses, which has been shown to correlate with superior adaptive immune responses. Production of IFNγ can then stimulate development of cytotoxic CD8+ T cells. Importantly, the S protein does contain human CD8+ T cell epitopes. Without being limited by theory, the development of T cell memory could be important for long-term immunity, as suggested by recent findings on T cell responses to SARS-CoV-2 and other coronavirus infections.

It is unclear whether the VEEV nsP1-4 forming the replication complex contains any immunogenic properties, although mutations in the nsP proteins have been shown to affect induction of type I IFN. VEEV replicons have also been shown to adjuvant immune responses at mucosal sites, further illustrating the advantages of using the STARR™ platform to develop a COVID-19 vaccine. Without being limited by theory, there does not appear to be an immune response to replicon non-structural proteins, as indicated by an increase in antigen-specific IgG production upon a second administration of replicon to animals. In the presence of an immune response to non-structural proteins, a limited or no increase in antigen-specific IgG production may have resulted following a second administration. The RNA is encapsulated in lipid nanoparticles (LNP), which together can form potent adjuvants leading to robust immune responses. In addition, using the genetic sequence of an antigen, including a viral antigen such as the spike protein from SARS-CoV-2, for example, STARR™ vaccines can be rapidly generated and manufactured using cell-free and rapidly scalable techniques.

In conclusion, a STARR™ vaccine as exemplified by STARR™ SARS-CoV-2 RNA offers an approach to simulate several of the properties of live vaccination and offers a potential for single-dose vaccination against COVID-19.

SEQUENCES

SEQ ID NO: 72

ATGGAGAAAGTTCACGTTGACATCGAGGAAGACAGCCCATTCCTCAGAGCTTTG

CAGCGGAGCTTCCCGCAGTTTGAGGTAGAAGCCAAGCAGGTCACTGATAATGAC

CATGCTAATGCCAGAGCGTTTTCGCATCTGGCTTCAAAACTGATCGAAACGGAGG

TGGACCCATCCGACACGATCCTTGACATTGGAAGTGCGCCCGCCCGCAGAATGT

ATTCTAAGCACAAGTATCATTGTATCTGTCCGATGAGATGTGCGGAAGATCCGGA

CAGATTGTATAAGTATGCAACTAAGCTGAAGAAAAACTGTAAGGAAATAACTGA

TAAGGAATTGGACAAGAAAATGAAGGAGCTGGCCGCCGTCATGAGCGACCCTGA

CCTGGAAACTGAGACTATGTGCCTCCACGACGACGAGTCGTGTCGCTACGAAGG

GCAAGTCGCTGTTTACCAGGATGTATACGCCGTCGACGGCCCCACCAGCCTGTAC

CACCAGGCCAACAAGGGCGTGAGGGTGGCCTACTGGATCGGCTTCGACACCACA

-continued

CCCTTCATGTTCAAGAACCTGGCCGGCGCCTACCCCAGCTACAGCACCAACTGGG

CCGACGAGACCGTGCTGACCGCCAGGAACATCGGCCTGTGCAGCAGCGACGTGA

TGGAGAGGAGCCGGAGAGGCATGAGCATCCTGAGGAAGAAATACCTGAAGCCC

AGCAACAACGTGCTGTTCAGCGTGGGCAGCACCATCTACCACGAGAAGAGGGAC

CTGCTCAGGAGCTGGCACCTGCCCAGCGTGTTCCACCTGAGGGGCAAGCAGAAC

TACACCTGCAGGTGCGAGACCATCGTGAGCTGCGACGGCTACGTGGTGAAGAGG

ATCGCCATCAGCCCCGGCCTGTACGGCAAGCCCAGCGGCTACGCCGCTACAATG

CACAGGGAGGGCTTCCTGTGCTGCAAGGTGACCGACACCCTGAACGGCGAGAGG

GTGAGCTTCCCCGTGTGCACCTACGTGCCCGCCACCCTGTGCGACCAGATGACCG

GCATCCTGGCCACCGACGTGAGCGCCGACGACGCCCAGAAGCTGCTCGTGGGCC

TGAACCAGAGGATCGTGGTCAACGGCAGGACCCAGAGGAACACCAACACAATG

AAGAACTACCTGCTGCCCGTGGTGGCCCAGGCTTTCGCCAGGTGGGCCAAGGAG

TACAAGGAGGACCAGGAAGACGAGAGGCCCCTGGGCCTGAGGGACAGGCAGCT

GGTGATGGGCTGCTGCTGGGCCTTCAGGCGGCACAAGATCACCAGCATCTACAA

GAGGCCCGACACCCAGACCATCATCAAGGTGAACAGCGACTTCCACAGCTTCGT

GCTGCCCAGGATCGGCAGCAACACCCTGGAGATCGGCCTGAGGACCCGGATCAG

GAAGATGCTGGAGGAACACAAGGAGCCCAGCCCACTGATCACCGCCGAGGACGT

GCAGGAGGCCAAGTGCGCTGCCGACGAGGCCAAGGAGGTGAGGGAGGCCGAGG

AACTGAGGGCCGCCCTGCCACCCCTGGCTGCCGACGTGGAGGAACCCACCCTGG

AAGCCGACGTGGACCTGATGCTGCAGGAGGCCGGCGCCGGAAGCGTGGAGACA

CCCAGGGGCCTGATCAAGGTGACCAGCTACGACGGCGAGGACAAGATCGGCAGC

TACGCCGTGCTGAGCCCACAGGCCGTGCTGAAGTCCGAGAAGCTGAGCTGCATC

CACCCACTGGCCGAGCAGGTGATCGTGATCACCCACAGCGGCAGGAAGGGCAGG

TACGCCGTGGAGCCCTACCACGGCAAGGTGGTCGTGCCCGAGGGCCACGCCATC

CCCGTGCAGGACTTCCAGGCCCTGAGCGAGAGCGCCACCATCGTGTACAACGAG

AGGGAGTTCGTGAACAGGTACCTGCACCATATCGCCACCCACGGCGGAGCCCTG

AACACCGACGAGGAATACTACAAGACCGTGAAGCCCAGCGAGCACGACGGCGA

GTACCTGTACGACATCGACAGGAAGCAGTGCGTGAAGAAAGAGCTGGTGACCGG

CCTGGGACTGACCGGCGAGCTGGTGGACCCACCCTTCCACGAGTTCGCCTACGA

GAGCCTGAGGACCAGACCCGCCGCTCCCTACCAGGTGCCCACCATCGGCGTGTA

CGGCGTGCCCGGCAGCGGAAAGAGCGGCATCATCAAGAGCGCCGTGACCAAGA

AAGACCTGGTGGTCAGCGCCAAGAAAGAGAACTGCGCCGAGATCATCAGGGAC

GTGAAGAAGATGAAAGGCCTGGACGTGAACGCGCGCACCGTGGACAGCGTGCTG

CTGAACGGCTGCAAGCACCCCGTGGAGACCCTGTACATCGACGAGGCCTTCGCTT

GCCACGCCGGCACCCTGAGGGCCCTGATCGCCATCATCAGGCCCAAGAAAGCCG

TGCTGTGCGGCGACCCCAAGCAGTGCGGCTTCTTCAACATGATGTGCCTGAAGGT

GCACTTCAACCACGAGATCTGCACCCAGGTGTTCCACAAGAGCATCAGCAGGCG

GTGCACCAAGAGCGTGACCAGCGTCGTGAGCACCCTGTTCTACGACAAGAAAAT

GAGGACCACCAACCCCAAGGAGACCAAAATCGTGATCGACACCACAGGCAGCA

CCAAGCCCAAGCAGGACGACCTGATCCTGACCTGCTTCAGGGGCTGGGTGAAGC

AGCTGCAGATCGACTACAAGGGCAACGAGATCATGACCGCCGCTGCCAGCCAGG

-continued

GCCTGACCAGGAAGGGCGTGTACGCCGTGAGGTACAAGGTGAACGAGAACCCAC

TGTACGCTCCCACCAGCGAGCACGTGAACGTGCTGCTGACCAGGACCGAGGACA

GGATCGTGTGGAAGACCCTGGCCGGCGACCCCTGGATCAAGACCCTGACCGCCA

AGTACCCCGGCAACTTCACCGCCACCATCGAAGAGTGGCAGGCCGAGCACGACG

CCATCATGAGGCACATCCTGGAGAGGCCCGACCCCACCGACGTGTTCCAGAACA

AGGCCAACGTGTGCTGGGCCAAGGCCCTGGTGCCCGTGCTGAAGACCGCCGGCA

TCGACATGACCACAGAGCAGTGGAACACCGTGGACTACTTCGAGACCGACAAGG

CCCACAGCGCCGAGATCGTGCTGAACCAGCTGTGCGTGAGGTTCTTCGGCCTGGA

CCTGGACAGCGGCCTGTTCAGCGCCCCCACCGTGCCACTGAGCATCAGGAACAA

CCACTGGGACAACAGCCCCAGCCCAAACATGTACGGCCTGAACAAGGAGGTGGT

CAGGCAGCTGAGCAGGCGGTACCCACAGCTGCCCAGGGCCGTGGCCACCGGCAG

GGTGTACGACATGAACACCGGCACCCTGAGGAACTACGACCCCAGGATCAACCT

GGTGCCCGTGAACAGGCGGCTGCCCCACGCCCTGGTGCTGCACCACAACGAGCA

CCCACAGAGCGACTTCAGCTCCTTCGTGAGCAAGCTGAAAGGCAGGACCGTGCT

GGTCGTGGGCGAGAAGCTGAGCGTGCCCGGCAAGATGGTGGACTGGCTGAGCGA

CAGGCCCGAGGCCACCTTCCGGGCCAGGCTGGACCTCGGCATCCCCGGCGACGT

GCCCAAGTACGACATCATCTTCGTGAACGTCAGGACCCCATACAAGTACCACCAT

TACCAGCAGTGCGAGGACCACGCCATCAAGCTGAGCATGCTGACCAAGAAGGCC

TGCCTGCACCTGAACCCCGGAGGCACCTGCGTGAGCATCGGCTACGGCTACGCC

GACAGGGCCAGCGAGAGCATCATTGGCGCCATCGCCAGGCTGTTCAAGTTCAGC

AGGGTGTGCAAACCCAAGAGCAGCCTGGAGGAAACCGAGGTGCTGTTCGTGTTC

ATCGGCTACGACCGGAAGGCCAGGACCCACAACCCCTACAAGCTGAGCAGCACC

CTGACAAACATCTACACCGGCAGCAGGCTGCACGAGGCCGGCTGCGCCCCCAGC

TACCACGTGGTCAGGGGCGATATCGCCACCGCCACCGAGGGCGTGATCATCAAC

GCTGCCAACAGCAAGGGCCAGCCCGGAGGCGGAGTGTGCGGCGCCCTGTACAAG

AAGTTCCCCGAGAGCTTCGACCTGCAGCCCATCGAGGTGGGCAAGGCCAGGCTG

GTGAAGGGCGCCGCTAAGCACATCATCCACGCCGTGGGCCCCAACTTCAACAAG

GTGAGCGAGGTGGAAGGCGACAAGCAGCTGGCCGAAGCCTACGAGAGCATCGC

CAAGATCGTGAACGACAATAACTACAAGAGCGTGGCCATCCCACTGCTCAGCAC

CGGCATCTTCAGCGGCAACAAGGACAGGCTGACCCAGAGCCTGAACCACCTGCT

CACCGCCCTGGACACCACCGATGCCGACGTGGCCATCTACTGCAGGGACAAGAA

GTGGGAGATGACCCTGAAGGAGGCCGTGGCCAGGCGGGAGGCCGTGGAAGAGA

TCTGCATCAGCGACGACTCCAGCGTGACCGAGCCCGACGCCGAGCTGGTGAGGG

TGCACCCCAAGAGCTCCCTGGCCGGCAGGAAGGGCTACAGCACCAGCGACGGCA

AGACCTTCAGCTACCTGGAGGGCACCAAGTTCCACCAGGCCGCTAAGGACATCG

CCGAGATCAACGCTATGTGGCCCGTGGCCACCGAGGCCAACGAGCAGGTGTGCA

TGTACATCCTGGGCGAGAGCATGTCCAGCATCAGGAGCAAGTGCCCCGTGGAGG

AAAGCGAGGCCAGCACACCACCCAGCACCCTGCCCTGCCTGTGCATCCACGCTA

TGACACCCGAGAGGGTGCAGCGGCTGAAGGCCAGCAGGCCCGAGCAGATCACC

GTGTGCAGCTCCTTCCCACTGCCCAAGTACAGGATCACCGGCGTGCAGAAGATCC

-continued
AGTGCAGCCAGCCCATCCTGTTCAGCCCAAAGGTGCCCGCCTACATCCACCCCAG
GAAGTACCTGGTGGAGACCCCACCCGTGGACGAGACACCCGAGCCAAGCGCCGA
GAACCAGAGCACCGAGGGCACACCCGAGCAGCCACCCCTGATCACCGAGGACG
AGACAAGGACCCGGACCCCAGAGCCCATCATTATCGAGGAAGAGGAAGAGGAC
AGCATCAGCCTGCTGAGCGACGGCCCCACCCACCAGGTGCTGCAGGTGGAGGCC
GACATCCACGGCCCACCCAGCGTGTCCAGCTCCAGCTGGAGCATCCCACACGCC
AGCGACTTCGACGTGGACAGCCTGAGCATCCTGGACACCCTGGAGGGCGCCAGC
GTGACCTCCGGCGCCACCAGCGCCGAGACCAACAGCTACTTCGCCAAGAGCATG
GAGTTCCTGGCCAGGCCCGTGCCAGCTCCCAGGACCGTGTTCAGGAACCCACCCC
ACCCAGCTCCCAGGACCAGGACCCCAAGCCTGGCTCCCAGCAGGGCCTGCAGCA
GGACCAGCCTGGTGAGCACCCCACCCGGCGTGAACAGGGTGATCACCAGGGAGG
AACTGGAGGCCCTGACACCCAGCAGGACCCCCAGCAGGTCCGTGAGCAGGACTA
GTCTGGTGTCCAACCCACCCGGCGTGAACAGGGTGATCACCAGGGAGGAATTCG
AGGCCTTCGTGGCCCAGCAACAGAGACGGTTCGACGCCGGCGCCTACATCTTCA
GCAGCGACACCGGCCAGGGACACCTGCAGCAAAAGAGCGTGAGGCAGACCGTG
CTGAGCGAGGTGGTGCTGGAGAGGACCGAGCTGGAAATCAGCTACGCCCCCAGG
CTGGACCAGGAGAAGGAGGAACTGCTCAGGAAGAAACTGCAGCTGAACCCCAC
CCCAGCCAACAGGAGCAGGTACCAGAGCAGGAAGGTGGAGAACATGAAGGCCA
TCACCGCCAGGCGGATCCTGCAGGGCCTGGGACACTACCTGAAGGCCGAGGGCA
AGGTGGAGTGCTACAGGACCCTGCACCCCGTGCCACTGTACAGCTCCAGCGTGA
ACAGGGCCTTCTCCAGCCCCAAGGTGGCCGTGGAGGCCTGCAACGCTATGCTGA
AGGAGAACTTCCCCACCGTGGCCAGCTACTGCATCATCCCCGAGTACGACGCCTA
CCTGGACATGGTGGACGGCGCCAGCTGCTGCCTGGACACCGCCAGCTTCTGCCCC
GCCAAGCTGAGGAGCTTCCCCAAGAAACACAGCTACCTGGAGCCCACCATCAGG
AGCGCCGTGCCCAGCGCCATCCAGAACACCCTGCAGAACGTGCTGGCCGCTGCC
ACCAAGAGGAACTGCAACGTGACCCAGATGAGGGAGCTGCCCGTGCTGGACAGC
GCTGCCTTCAACGTGGAGTGCTTCAAGAAATACGCCTGCAACAACGAGTACTGG
GAGACCTTCAAGGAGAACCCCATCAGGCTGACCGAAGAGAACGTGGTGAACTAC
ATCACCAAGCTGAAGGGCCCCAAGGCCGCTGCCCTGTTCGCTAAGACCCACAAC
CTGAACATGCTGCAGGACATCCCAATGGACAGGTTCGTGATGGACCTGAAGAGG
GACGTGAAGGTGACACCCGGCACCAAGCACACCGAGGAGAGGCCCAAGGTGCA
GGTGATCCAGGCCGCTGACCCACTGGCCACCGCCTACCTGTGCGGCATCCACAG
GGAGCTGGTGAGGCGGCTGAACGCCGTGCTGCTGCCCAACATCCACACCCTGTTC
GACATGAGCGCCGAGGACTTCGACGCCATCATCGCCGAGCACTTCCAGCCCGGC
GACTGCGTGCTGGAGACCGACATCGCCAGCTTCGACAAGAGCGAGGATGACGCT
ATGGCCCTGACCGCTCTGATGATCCTGGAGGACCTGGGCGTGGACGCCGAGCTG
CTCACCCTGATCGAGGCTGCCTTCGGCGAGATCAGCTCCATCCACCTGCCCACCA
AGACCAAGTTCAAGTTCGGCGCTATGATGAAAAGCGGAATGTTCCTGACCCTGTT
CGTGAACACCGTGATCAACATTGTGATCGCCAGCAGGGTGCTGCGGGAGAGGCT
GACCGGCAGCCCCTGCGCTGCCTTCATCGGCGACGACAACATCGTGAAGGGCGT
GAAAAGCGACAAGCTGATGGCCGACAGGTGCGCCACCTGGCTGAACATGGAGGT -continued GAAGATCATCGACGCCGTGGTGGGCGAGAAGGCCCCCTACTTCTGCGGCGGATT
CATCCTGTGCGACAGCGTGACCGGCACCGCCTGCAGGGTGGCCGACCCCCTGAA
GAGGCTGTTCAAGCTGGGCAAGCCACTGGCCGCTGACGATGAGCACGACGATGA
CAGGCGGAGGGCCCTGCACGAGGAAAGCACCAGGTGGAACAGGGTGGGCATCC
TGAGCGAGCTGTGCAAGGCCGTGGAGAGCAGGTACGAGACCGTGGGCACCAGC
ATCATCGTGATGGCTATGACCACACTGGCCAGCTCCGTCAAGAGCTTCTCCTACC
TGAGGGGGGCCCCTATAACTCTCTACGGCTAA

SEQ ID NO: 73
ATGGGCGGCGCATGAGAGAAGCCCAGACCAATTACCTACCCAAA

SEQ ID NO: 74
GATGGGCGGCGCATGAGAGAAGCCCAGACCAATTACCTACCCAAA

SEQ ID NO: 75
GATAGGCGGCGCATGAGAGAAGCCCAGACCAATTACCTACCCAAA

SEQ ID NO: 76
ACTCGAGTATGTTACGTGCAAAGGTGATTGTCACCCCCCGAAAGACCATATTGTG
ACACACCCTCAGTATCACGCCCAAACATTTACAGCCGCGGTGTCAAAAACCGCG
TGGACGTGGTTAACATCCCTGCTGGGAGGATCAGCCGTAATTATTATAATTGGCT
TGGTGCTGGCTACTATTGTGGCCATGTACGTGCTGACCAACCAGAAACATAATTG
AATACAGCAGCAATTGGCAAGCTGCTTACATAGAACTCGCGGCGATTGGCATGC
CGCCTTAAAATTTTTATTTTATTTTTTCTTTTCTTTTCCGAATCGGATTTTGTTTTTA
ATATTTCAAAAAAAAAAAAAAAAAAAAAAAAAAATCTAGAAAAAAAAAAAAAAAA
AAAAAAAAAAAAAAA
AAAAAAAAAAAAAAAAAAAAAAAAAAAAAAAAAAA
AAAAAAAAAAAAAAAAAAAAAAAAAAAAAAA

SEQ ID NO: 121
ATGTTTGTTTTTCTTGTTTTATTGCCACTAGTCTCTAGTCAGTGTGTTAATCTTACA
ACCAGAACTCAATTACCCCCTGCATACACTAATTCTTTCACACGTGGTGTTTATTA
CCCTGACAAAGTTTTCAGATCCTCAGTTTTACATTCAACTCAGGACTTGTTCTTAC
CTTTCTTTTCCAATGTTACTTGGTTCCATGCTATACATGTCTCTGGGACCAATGGT
ACTAAGAGGTTTGATAACCCTGTCCTACCATTTAATGATGGTGTTTATTTTGCTTC
CACTGAGAAGTCTAACATAATAAGAGGCTGGATTTTTGGTACTACTTTAGATTCG
AAGACCCAGTCCCTACTTATTGTTAATAACGCTACTAATGTTGTTATTAAAGTCTG
TGAATTTCAATTTTGTAATGATCCATTTTTGGGTGTTTATTACCACAAAAACAACA
AAAGTTGGATGGAAAGTGAGTTCAGAGTTTATTCTAGTGCGAATAATTGCACTTT
TGAATATGTCTCTCAGCCTTTTCTTATGGACCTTGAAGGAAAACAGGGTAATTTC
AAAAATCTTAGGGAATTTGTGTTTAAGAATATTGATGGTTATTTTAAAATATATT
CTAAGCACACGCCTATTAATTTAGTGCGTGATCTCCCTCAGGGTTTTTCGGCTTTA
GAACCATTGGTAGATTTGCCAATAGGTATTAACATCACTAGGTTTCAAACTTTAC
TTGCTTTACATAGAAGTTATTTGACTCCTGGTGATTCTTCTTCAGGTTGGACAGCT
GGTGCTGCAGCTTATTATGTGGGTTATCTTCAACCTAGGACTTTTCTATTAAAATA
TAATGAAAATGGAACCATTACAGATGCTGTAGACTGTGCACTTGACCCTCTCTCA
GAAACAAAGTGTACGTTGAAATCCTTCACTGTAGAAAAAGGAATCTATCAAACT
TCTAACTTTAGAGTCCAACCAACAGAATCTATTGTTAGATTTCCTAATATTACAA

-continued

ACTTGTGCCCTTTTGGTGAAGTTTTTAACGCCACCAGATTTGCATCTGTTTATGCT
TGGAACAGGAAGAGAATCAGCAACTGTGTTGCTGATTATTCTGTCCTATATAATT
CCGCATCATTTTCCACTTTTAAGTGTTATGGAGTGTCTCCTACTAAATTAAATGAT
CTCTGCTTTACTAATGTCTATGCAGATTCATTTGTAATTAGAGGTGATGAAGTCA
GACAAATCGCTCCAGGGCAAACTGGAAAGATTGCTGATTATAATTATAAATTAC
CAGATGATTTTACAGGCTGCGTTATAGCTTGGAATTCTAACAATCTTGATTCTAA
GGTTGGTGGTAATTATAATTACCTGTATAGATTGTTTAGGAAGTCTAATCTCAAA
CCTTTTGAGAGAGATATTTCAACTGAAATCTATCAGGCCGGTAGCACACCTTGTA
ATGGTGTTGAAGGTTTTAATTGTTACTTTCCTTTACAATCATATGGTTTCCAACCC
ACTAATGGTGTTGGTTACCAACCATACAGAGTAGTAGTACTTTCTTTTGAACTTCT
ACATGCACCAGCAACTGTTTGTGGACCTAAAAAGTCTACTAATTTGGTTAAAAAC
AAATGTGTCAATTTCAACTTCAATGGTTTAACAGGCACAGGTGTTCTTACTGAGT
CTAACAAAAAGTTTCTGCCTTTCCAACAATTTGGCAGAGACATTGCTGACACTAC
TGATGCTGTCCGTGATCCACAGACACTTGAGATTCTTGACATTACACCATGTTCTT
TTGGTGGTGTCAGTGTTATAACACCAGGAACAAATACTTCTAACCAGGTTGCTGT
TCTTTATCAGGATGTTAACTGCACAGAAGTCCCTGTTGCTATTCATGCAGATCAA
CTTACTCCTACTTGGCGTGTTTATTCTACAGGTTCTAATGTTTTTCAAACACGTGC
AGGCTGTTTAATAGGGGCTGAACATGTCAACAACTCATATGAGTGTGACATACCC
ATTGGTGCAGGTATATGCGCTAGTTATCAGACTCAGACTAATTCTCCTCGGCGGG
CACGTAGTGTAGCTAGTCAATCCATCATTGCCTACACTATGTCACTTGGTGCAGA
AAATTCAGTTGCTTACTCTAATAACTCTATTGCCATACCCACAAATTTTACTATTA
GTGTTACCACAGAAATTCTACCAGTGTCTATGACCAAGACATCAGTAGATTGTAC
AATGTACATTTGTGGTGATTCAACTGAATGCAGCAATCTTTTGTTGCAATATGGC
AGTTTTTGTACACAATTAAACCGTGCTTTAACTGGAATAGCTGTTGAACAAGACA
AAAACACCCAAGAAGTTTTTGCACAAGTCAAACAAATTTACAAAACACCACCAA
TTAAAGATTTTGGTGGTTTTAATTTTTCACAAATATTACCAGATCCATCAAAACCA
AGCAAGAGGTCATTTATTGAAGATCTACTTTTCAACAAAGTGACACTTGCAGATG
CTGGCTTCATCAAACAATATGGTGATTGCCTTGGTGATATTGCTGCTAGAGACCT
CATTTGTGCACAAAAGTTTAACGGCCTTACTGTTTTGCCACCTTTGCTCACAGATG
AAATGATTGCTCAATACACTTCTGCACTGTTAGCGGGTACAATCACTTCTGGTTG
GACCTTTGGTGCAGGTGCTGCATTACAAATACCATTTGCTATGCAAATGGCTTAT
AGGTTTAATGGTATTGGAGTTACACAGAATGTTCTCTATGAGAACCAAAAATTGA
TTGCCAACCAATTTAATAGTGCTATTGGCAAAATTCAAGACTCACTTTCTTCCAC
AGCAAGTGCACTTGGAAAACTTCAAGATGTGGTCAACCAAAATGCACAAGCTTT
AAACACGCTTGTTAAACAACTTAGCTCCAATTTTGGTGCAATTTCAAGTGTTTTA
AATGATATCCTTTCACGTCTTGACAAAGTTGAGGCTGAAGTGCAAATTGATAGGT
TGATCACAGGCAGACTTCAAAGTTTGCAGACATATGTGACTCAACAATTAATTAG
AGCTGCAGAAATCAGAGCTTCTGCTAATCTTGCTGCTACTAAAATGTCAGAGTGT
GTACTTGGACAATCAAAAAGAGTTGATTTTTGTGGAAAGGGCTATCATCTTATGT
CCTTCCCTCAGTCAGCACCTCATGGTGTAGTCTTCTTGCATGTGACTTATGTCCCT

-continued

GCACAAGAAAAGAACTTCACAACTGCTCCTGCCATTTGTCATGATGGAAAAGCA

CACTTTCCTCGTGAAGGTGTCTTTGTTTCAAATGGCACACACTGGTTTGTAACAC

AAAGGAATTTTTATGAACCACAAATCATTACTACAGACAACACATTTGTGTCTGG

TAACTGTGATGTTGTAATAGGAATTGTCAACAACACAGTTTATGATCCTTTGCAA

CCTGAATTAGACTCATTCAAGGAGGAGTTAGATAAATATTTTAAGAATCATACAT

CACCAGATGTTGATTTAGGTGACATCTCTGGCATTAATGCTTCAGTTGTAAACAT

TCAAAAAGAAATTGACCGCCTCAATGAGGTTGCCAAGAATTTAAATGAATCTCTC

ATCGATCTCCAAGAACTTGGAAAGTATGAGCAGTATATAAAATGGCCATGGTAC

ATTTGGCTAGGTTTTATAGCTGGCTTGATTGCCATAGTAATGGTGACAATTATGCT

TTGCTGTATGACCAGTTGCTGTAGTTGTCTCAAGGGCTGTTGTTCTTGTGGATCCT

GCTGCAAATTTGATGAAGACGACTCTGAGCCAGTGCTCAAAGGAGTCAAATTAC

ATTACACATAA

SEQ ID NO: 122

ATGTTCGTCTTCCTGGTCCTGCTGCCTCTGGTCTCCTCACAGTGCGTCAATCTGAC

AACTCGGACTCAGCTGCCACCTGCTTATACTAATAGCTTCACCAGAGGCGTGTAC

TATCCTGACAAGGTGTTTAGAAGCTCCGTGCTGCACTCTACACAGGATCTGTTTC

TGCCATTCTTTAGCAACGTGACCTGGTTCCACGCCATCCACGTGAGCGGCACCAA

TGGCACAAAGCGGTTCGACAATCCCGTGCTGCCTTTTAACGATGGCGTGTACTTC

GCCTCTACCGAGAAGTCCAACATCATCAGAGGCTGGATCTTTGGCACCACACTGG

ACTCCAAGACACAGTCTCTGCTGATCGTGAACAATGCCACCAACGTGGTCATCAA

GGTGTGCGAGTTCCAGTTTTGTAATGATCCCTTCCTGGGCGTGTACTATCACAAG

AACAATAAGAGCTGGATGGAGTCCGAGTTTAGAGTGTATTCTAGCGCCAACAAC

TGCACATTTGAGTACGTGAGCCAGCCTTTCCTGATGGACCTGGAGGGCAAGCAG

GGCAATTTCAAGAACCTGAGGGAGTTCGTGTTTAAGAATATCGACGGCTACTTCA

AAATCTACTCTAAGCACACCCCCATCAACCTGGTGCGCGACCTGCCTCAGGGCTT

CAGCGCCCTGGAGCCCCTGGTGGATCTGCCTATCGGCATCAACATCACCCGGTTT

CAGACACTGCTGGCCCTGCACAGAAGCTACCTGACACCCGGCGACTCCTCTAGC

GGATGGACCGCCGGCGCTGCCGCCTACTATGTGGGCTACCTCCAGCCCCGGACCT

TCCTGCTGAAGTACAACGAGAATGGCACCATCACAGACGCAGTGGATTGCGCCC

TGGACCCCCTGAGCGAGACAAAGTGTACACTGAAGTCCTTTACCGTGGAGAAGG

GCATCTATCAGACATCCAATTTCAGGGTGCAGCCAACCGAGTCTATCGTGCGCTT

TCCTAATATCACAAACCTGTGCCCATTTGGCGAGGTGTTCAACGCAACCCGCTTC

GCCAGCGTGTACGCCTGGAATAGGAAGCGGATCAGCAACTGCGTGGCCGACTAT

AGCGTGCTGTACAACTCCGCCTCTTTCAGCACCTTTAAGTGCTATGGCGTGTCCC

CCACAAAGCTGAATGACCTGTGCTTTACCAACGTCTACGCCGATTCTTTCGTGAT

CAGGGGCGACGAGGTGCGCCAGATCGCCCCCGGCCAGACAGGCAAGATCGCAG

ACTACAATTATAAGCTGCCAGACGATTTCACCGGCTGCGTGATCGCCTGGAACAG

CAACAATCTGGATTCCAAAGTGGGCGGCAACTACAATTATCTGTACCGGCTGTTT

AGAAAGAGCAATCTGAAGCCCTTCGAGAGGGACATCTCTACAGAAATCTACCAG

GCCGGCAGCACCCCTTGCAATGGCGTGGAGGGCTTTAACTGTTATTTCCCACTCC

AGTCCTACGGCTTCCAGCCCACAAACGGCGTGGGCTATCAGCCTTACCGCGTGGT

-continued

GGTGCTGAGCTTTGAGCTGCTGCACGCCCCAGCAACAGTGTGCGGCCCCAAGAA
GTCCACCAATCTGGTGAAGAACAAGTGCGTGAACTTCAACTTCAACGGCCTGAC
CGGCACAGGCGTGCTGACCGAGTCCAACAAGAAGTTCCTGCCATTTCAGCAGTTC
GGCAGGGACATCGCAGATACCACAGACGCCGTGCGCGACCCACAGACCCTGGAG
ATCCTGGACATCACACCCTGCTCTTTCGGCGGCGTGAGCGTGATCACACCCGGCA
CCAATACAAGCAACCAGGTGGCCGTGCTGTATCAGGACGTGAATTGTACCGAGG
TGCCCGTGGCTATCCACGCCGATCAGCTGACCCCAACATGGCGGGTGTACAGCA
CCGGCTCCAACGTCTTCCAGACAAGAGCCGGATGCCTGATCGGAGCAGAGCACG
TGAACAATTCCTATGAGTGCGACATCCCAATCGGCGCCGGCATCTGTGCCTCTTA
CCAGACCCAGACAAACTCTCCCAGACGGGCCCGGAGCGTGGCCTCCCAGTCTAT
CATCGCCTATACCATGTCCCTGGGCGCCGAGAACAGCGTGGCCTACTCTAACAAT
AGCATCGCCATCCCAACCAACTTCACAATCTCTGTGACCACAGAGATCCTGCCCG
TGTCCATGACCAAGACATCTGTGGACTGCACAATGTATATCTGTGGCGATTCTAC
CGAGTGCAGCAACCTGCTGCTCCAGTACGGCAGCTTTTGTACCCAGCTGAATAGA
GCCCTGACAGGCATCGCCGTGGAGCAGGATAAGAACACACAGGAGGTGTTCGCC
CAGGTGAAGCAAATCTACAAGACCCCCCCTATCAAGGACTTTGGCGGCTTCAATT
TTTCCCAGATCCTGCCTGATCCATCCAAGCCTTCTAAGCGGAGCTTTATCGAGGA
CCTGCTGTTCAACAAGGTGACCCTGGCCGATGCCGGCTTCATCAAGCAGTATGGC
GATTGCCTGGGCGACATCGCAGCCAGGGACCTGATCTGCGCCCAGAAGTTTAAT
GGCCTGACCGTGCTGCCACCCCTGCTGACAGATGAGATGATCGCACAGTACACA
AGCGCCCTGCTGGCCGGCACCATCACATCCGGATGGACCTTCGGCGCAGGAGCC
GCCCTCCAGATCCCCTTTGCCATGCAGATGGCCTATAGGTTCAACGGCATCGGCG
TGACCCAGAATGTGCTGTACGAGAACCAGAAGCTGATCGCCAATCAGTTTAACT
CCGCCATCGGCAAGATCCAGGACAGCCTGTCCTCTACAGCCAGCGCCCTGGGCA
AGCTCCAGGATGTGGTGAATCAGAACGCCCAGGCCCTGAATACCCTGGTGAAGC
AGCTGAGCAGCAACTTCGGCGCCATCTCTAGCGTGCTGAATGACATCCTGAGCCG
GCTGGACAAGGTGGAGGCAGAGGTGCAGATCGACCGGCTGATCACCGGCCGGCT
CCAGAGCCTCCAGACCTATGTGACACAGCAGCTGATCAGGGCCGCCGAGATCAG
GGCCAGCGCCAATCTGGCAGCAACCAAGATGTCCGAGTGCGTGCTGGGCCAGTC
TAAGAGAGTGGACTTTTGTGGCAAGGGCTATCACCTGATGTCCTTCCCTCAGTCT
GCCCCACACGGCGTGGTGTTTCTGCACGTGACCTACGTGCCCGCCCAGGAGAAG
AACTTCACCACAGCCCCTGCCATCTGCCACGATGGCAAGGCCCACTTTCCAAGGG
AGGGCGTGTTCGTGTCCAACGGCACCCACTGGTTTGTGACACAGCGCAATTTCTA
CGAGCCCCAGATCATCACCACAGACAACACCTTCGTGAGCGGCAACTGTGACGT
GGTCATCGGCATCGTGAACAATACCGTGTATGATCCACTCCAGCCCGAGCTGGAC
AGCTTTAAGGAGGAGCTGGATAAGTATTTCAAGAATCACACCTCCCCTGACGTG
GATCTGGGCGACATCAGCGGCATCAATGCCTCCGTGGTGAACATCCAGAAGGAG
ATCGACCGCCTGAACGAGGTGGCTAAGAATCTGAACGAGAGCCTGATCGACCTC
CAGGAGCTGGGCAAGTATGAGCAGTACATCAAGTGGCCCTGGTACATCTGGCTG
GGCTTCATCGCCGGCCTGATCGCCATCGTGATGGTGACCATCATGCTGTGCTGTA
TGACATCCTGCTGTTCTTGCCTGAAGGGCTGCTGTAGCTGTGGCTCCTGCTGTAA

-continued

GTTTGACGAGGATGACTCTGAACCTGTGCTGAAGGGCGTGAAGCTGCATTACAC
CTAA

SEQ ID NO: 123

MFVFLVLLPLVSSQCVNLTTRTQLPPAYTNSFTRGVYYPDKVFRSSVLHSTQDLFLPF
FSNVTWFHAIHVSGTNGTKRFDNPVLPFNDGVYFASTEKSNIIRGWIFGTTLDSKTQS
LLIVNNATNVVIKVCEFQFCNDPFLGVYYHKNNKSWMESEFRVYSSANNCTFEYVS
QPFLMDLEGKQGNFKNLREFVFKNIDGYFKIYSKHTPINLVRDLPQGFSALEPLVDLP
IGINITRFQTLLALHRSYLTPGDSSSGWTAGAAAYYVGYLQPRTFLLKYNENGTITDA
VDCALDPLSETKCTLKSFTVEKGIYQTSNFRVQPTESIVRFPNITNLCPFGEVFNATRF
ASVYAWNRKRISNCVADYSVLYNSASFSTFKCYGVSPTKLNDLCFTNVYADSFVIRG
DEVRQIAPGQTGKIADYNYKLPDDFTGCVIAWNSNNLDSKVGGNYNYLYRLFRKSN
LKPFERDISTEIYQAGSTPCNGVEGENCYFPLQSYGFQPTNGVGYQPYRVVVLSFELL
HAPATVCGPKKSTNLVKNKCVNFNFNGLTGTGVLTESNKKFLPFQQFGRDIADTTD
AVRDPQTLEILDITPCSFGGVSVITPGTNTSNQVAVLYQDVNCTEVPVAIHADQLTPT
WRVYSTGSNVFQTRAGCLIGAEHVNNSYECDIPIGAGICASYQTQTNSPRRARSVAS
QSIIAYTMSLGAENSVAYSNNSIAIPTNFTISVTTEILPVSMTKTSVDCTMYICGDSTEC
SNLLLQYGSFCTQLNRALTGIAVEQDKNTQEVFAQVKQIYKTPPIKDFGGFNFSQILP
DPSKPSKRSFIEDLLFNKVTLADAGFIKQYGDCLGDIAARDLICAQKFNGLTVLPPLLT
DEMIAQYTSALLAGTITSGWTFGAGAALQIPFAMQMAYRFNGIGVTQNVLYENQKLI
ANQFNSAIGKIQDSLSSTASALGKLQDVVNQNAQALNTLVKQLSSNFGAISSVLNDIL
SRLDKVEAEVQIDRLITGRLQSLQTYVTQQLIRAAEIRASANLAATKMSECVLGQSK
RVDFCGKGYHLMSFPQSAPHGVVFLHVTYVPAQEKNFTTAPAICHDGKAHFPREGV
FVSNGTHWFVTQRNFYEPQIITTDNTFVSGNCDVVIGIVNNTVYDPLQPELDSFKEEL
DKYFKNHTSPDVDLGDISGINASVVNIQKEIDRLNEVAKNLNESLIDLQELGKYEQYI
KWPWYIWLGFIAGLIAIVMVTIMLCCMTSCCSCLKGCCSCGSCCKFDEDDSEPVLKG
VKLHYT

SEQ ID NO: 77

CCTGAATGGACTACGACATAGTCTAGTCCGCCAAGGCCGCCACC

SEQ ID NO: 78

ATGGGCGGCGCATGAGAGAAGCCCAGACCAATTACCTACCCAAAATGGAGAAA
GTTCACGTTGACATCGAGGAAGACAGCCCATTCCTCAGAGCTTTGCAGCGGAGCT
TCCCGCAGTTTGAGGTAGAAGCCAAGCAGGTCACTGATAATGACCATGCTAATG
CCAGAGCGTTTTCGCATCTGGCTTCAAAACTGATCGAAACGGAGGTGGACCCATC
CGACACGATCCTTGACATTGGAAGTGCGCCCGCCCGCAGAATGTATTCTAAGCAC
AAGTATCATTGTATCTGTCCGATGAGATGTGCGGAAGATCCGGACAGATTGTATA
AGTATGCAACTAAGCTGAAGAAAAACTGTAAGGAAATAACTGATAAGGAATTGG
ACAAGAAAATGAAGGAGCTGGCCGCCGTCATGAGCGACCCTGACCTGGAAACTG
AGACTATGTGCCTCCACGACGACGAGTCGTGTCGCTACGAAGGGCAAGTCGCTG
TTTACCAGGATGTATACGCCGTCGACGGCCCCACCAGCCTGTACCACCAGGCCAA
CAAGGGCGTGAGGGTGGCCTACTGGATCGGCTTCGACACCACACCCTTCATGTTC
AAGAACCTGGCCGGCGCCTACCCCAGCTACAGCACCAACTGGGCCGACGAGACC
GTGCTGACCGCCAGGAACATCGGCCTGTGCAGCAGCGACGTGATGGAGAGGAGC

-continued

CGGAGAGGCATGAGCATCCTGAGGAAGAAATACCTGAAGCCCAGCAACAACGT

GCTGTTCAGCGTGGGCAGCACCATCTACCACGAGAAGAGGGACCTGCTCAGGAG

CTGGCACCTGCCCAGCGTGTTCCACCTGAGGGGCAAGCAGAACTACACCTGCAG

GTGCGAGACCATCGTGAGCTGCGACGGCTACGTGGTGAAGAGGATCGCCATCAG

CCCCGGCCTGTACGGCAAGCCCAGCGGCTACGCCGCTACAATGCACAGGGAGGG

CTTCCTGTGCTGCAAGGTGACCGACACCCTGAACGGCGAGAGGGTGAGCTTCCC

CGTGTGCACCTACGTGCCCGCCACCCTGTGCGACCAGATGACCGGCATCCTGGCC

ACCGACGTGAGCGCCGACGACGCCCAGAAGCTGCTCGTGGGCCTGAACCAGAGG

ATCGTGGTCAACGGCAGGACCCAGAGGAACACCAACACAATGAAGAACTACCTG

CTGCCCGTGGTGGCCCAGGCTTTCGCCAGGTGGGCCAAGGAGTACAAGGAGGAC

CAGGAAGACGAGAGGCCCCTGGGCCTGAGGGACAGGCAGCTGGTGATGGGCTG

CTGCTGGGCCTTCAGGCGGCACAAGATCACCAGCATCTACAAGAGGCCCGACAC

CCAGACCATCATCAAGGTGAACAGCGACTTCCACAGCTTCGTGCTGCCCAGGATC

GGCAGCAACACCCTGGAGATCGGCCTGAGGACCCGGATCAGGAAGATGCTGGAG

GAACACAAGGAGCCCAGCCCACTGATCACCGCCGAGGACGTGCAGGAGGCCAA

GTGCGCTGCCGACGAGGCCAAGGAGGTGAGGGAGGCCGAGGAACTGAGGGCCG

CCCTGCCACCCCTGGCTGCCGACGTGGAGGAACCCACCCTGGAAGCCGACGTGG

ACCTGATGCTGCAGGAGGCCGGCGCCGGAAGCGTGGAGACACCCAGGGGCCTGA

TCAAGGTGACCAGCTACGACGGCGAGGACAAGATCGGCAGCTACGCCGTGCTGA

GCCCACAGGCCGTGCTGAAGTCCGAGAAGCTGAGCTGCATCCACCCACTGGCCG

AGCAGGTGATCGTGATCACCCACAGCGGCAGGAAGGGCAGGTACGCCGTGGAGC

CCTACCACGGCAAGGTGGTCGTGCCCGAGGGCCACGCCATCCCCGTGCAGGACT

TCCAGGCCCTGAGCGAGAGCGCCACCATCGTGTACAACGAGAGGGAGTTCGTGA

ACAGGTACCTGCACCATATCGCCACCCACGGCGGAGCCCTGAACACCGACGAGG

AATACTACAAGACCGTGAAGCCCAGCGAGCACGACGGCGAGTACCTGTACGACA

TCGACAGGAAGCAGTGCGTGAAGAAAGAGCTGGTGACCGGCCTGGGACTGACCG

GCGAGCTGGTGGACCCACCCTTCCACGAGTTCGCCTACGAGAGCCTGAGGACCA

GACCCGCCGCTCCCTACCAGGTGCCCACCATCGGCGTGTACGGCGTGCCCGGCA

GCGGAAAGAGCGGCATCATCAAGAGCGCCGTGACCAAGAAAGACCTGGTGGTC

AGCGCCAAGAAAGAGAACTGCGCCGAGATCATCAGGGACGTGAAGAAGATGAA

AGGCCTGGACGTGAACGCGCGCACCGTGGACAGCGTGCTGCTGAACGGCTGCAA

GCACCCCGTGGAGACCCTGTACATCGACGAGGCCTTCGCTTGCCACGCCGGCACC

CTGAGGGCCCTGATCGCCATCATCAGGCCCAAGAAAGCCGTGCTGTGCGGCGAC

CCCAAGCAGTGCGGCTTCTTCAACATGATGTGCCTGAAGGTGCACTTCAACCACG

AGATCTGCACCCAGGTGTTCCACAAGAGCATCAGCAGGCGGTGCACCAAGAGCG

TGACCAGCGTCGTGAGCACCCTGTTCTACGACAAGAAAATGAGGACCACCAACC

CCAAGGAGACCAAAATCGTGATCGACACCACAGGCAGCACCAAGCCCAAGCAG

GACGACCTGATCCTGACCTGCTTCAGGGGCTGGGTGAAGCAGCTGCAGATCGAC

TACAAGGGCAACGAGATCATGACCGCCGCTGCCAGCCAGGGCCTGACCAGGAAG

GGCGTGTACGCCGTGAGGTACAAGGTGAACGAGAACCCACTGTACGCTCCCACC

-continued

AGCGAGCACGTGAACGTGCTGCTGACCAGGACCGAGGACAGGATCGTGTGGAAG

ACCCTGGCCGGCGACCCCTGGATCAAGACCCTGACCGCCAAGTACCCCGGCAAC

TTCACCGCCACCATCGAAGAGTGGCAGGCCGAGCACGACGCCATCATGAGGCAC

ATCCTGGAGAGGCCCGACCCCACCGACGTGTTCCAGAACAAGGCCAACGTGTGC

TGGGCCAAGGCCCTGGTGCCCGTGCTGAAGACCGCCGGCATCGACATGACCACA

GAGCAGTGGAACACCGTGGACTACTTCGAGACCGACAAGGCCCACAGCGCCGAG

ATCGTGCTGAACCAGCTGTGCGTGAGGTTCTTCGGCCTGGACCTGGACAGCGGCC

TGTTCAGCGCCCCCACCGTGCCACTGAGCATCAGGAACAACCACTGGGACAACA

GCCCCAGCCCAAACATGTACGGCCTGAACAAGGAGGTGGTCAGGCAGCTGAGCA

GGCGGTACCCACAGCTGCCCAGGGCCGTGGCCACCGGCAGGGTGTACGACATGA

ACACCGGCACCCTGAGGAACTACGACCCCAGGATCAACCTGGTGCCCGTGAACA

GGCGGCTGCCCCACGCCCTGGTGCTGCACCACAACGAGCACCCACAGAGCGACT

TCAGCTCCTTCGTGAGCAAGCTGAAAGGCAGGACCGTGCTGGTCGTGGGCGAGA

AGCTGAGCGTGCCCGGCAAGATGGTGGACTGGCTGAGCGACAGGCCCGAGGCCA

CCTTCCGGGCCAGGCTGGACCTCGGCATCCCCGGCGACGTGCCCAAGTACGACA

TCATCTTCGTGAACGTCAGGACCCCATACAAGTACCACCATTACCAGCAGTGCGA

GGACCACGCCATCAAGCTGAGCATGCTGACCAAGAAGGCCTGCCTGCACCTGAA

CCCCGGAGGCACCTGCGTGAGCATCGGCTACGGCTACGCCGACAGGGCCAGCGA

GAGCATCATTGGCGCCATCGCCAGGCTGTTCAAGTTCAGCAGGGTGTGCAAACC

CAAGAGCAGCCTGGAGGAAACCGAGGTGCTGTTCGTGTTCATCGGCTACGACCG

GAAGGCCAGGACCCACAACCCCTACAAGCTGAGCAGCACCCTGACAAACATCTA

CACCGGCAGCAGGCTGCACGAGGCCGGCTGCGCCCCCAGCTACCACGTGGTCAG

GGGCGATATCGCCACCGCCACCGAGGGCGTGATCATCAACGCTGCCAACAGCAA

GGGCCAGCCCGGAGGCGGAGTGTGCGGCGCCCTGTACAAGAAGTTCCCCGAGAG

CTTCGACCTGCAGCCCATCGAGGTGGGCAAGGCCAGGCTGGTGAAGGGCGCCGC

TAAGCACATCATCCACGCCGTGGGCCCCAACTTCAACAAGGTGAGCGAGGTGGA

AGGCGACAAGCAGCTGGCCGAAGCCTACGAGAGCATCGCCAAGATCGTGAACG

ACAATAACTACAAGAGCGTGGCCATCCCACTGCTCAGCACCGGCATCTTCAGCG

GCAACAAGGACAGGCTGACCCAGAGCCTGAACCACCTGCTCACCGCCCTGGACA

CCACCGATGCCGACGTGGCCATCTACTGCAGGGACAAGAAGTGGGAGATGACCC

TGAAGGAGGCCGTGGCCAGGCGGGAGGCCGTGGAAGAGATCTGCATCAGCGAC

GACTCCAGCGTGACCGAGCCCGACGCCGAGCTGGTGAGGGTGCACCCCAAGAGC

TCCCTGGCCGGCAGGAAGGGCTACAGCACCAGCGACGGCAAGACCTTCAGCTAC

CTGGAGGGCACCAAGTTCCACCAGGCCGCTAAGGACATCGCCGAGATCAACGCT

ATGTGGCCCGTGGCCACCGAGGCCAACGAGCAGGTGTGCATGTACATCCTGGGC

GAGAGCATGTCCAGCATCAGGAGCAAGTGCCCCGTGGAGGAAAGCGAGGCCAG

CACACCACCCAGCACCCTGCCCTGCCTGTGCATCCACGCTATGACACCCGAGAGG

GTGCAGCGGCTGAAGGCCAGCAGGCCCGAGCAGATCACCGTGTGCAGCTCCTTC

CCACTGCCCAAGTACAGGATCACCGGCGTGCAGAAGATCCAGTGCAGCCAGCCC

ATCCTGTTCAGCCCAAAGGTGCCCGCCTACATCCACCCCAGGAAGTACCTGGTGG

AGACCCCACCCGTGGACGAGACACCCGAGCCAAGCGCCGAGAACCAGAGCACC

-continued

GAGGGCACACCCGAGCAGCCACCCCTGATCACCGAGGACGAGACAAGGACCCG

GACCCCAGAGCCCATCATTATCGAGGAAGAGGAAGAGGACAGCATCAGCCTGCT

GAGCGACGGCCCCACCCACCAGGTGCTGCAGGTGGAGGCCGACATCCACGGCCC

ACCCAGCGTGTCCAGCTCCAGCTGGAGCATCCCACACGCCAGCGACTTCGACGT

GGACAGCCTGAGCATCCTGGACACCCTGGAGGGCGCCAGCGTGACCTCCGGCGC

CACCAGCGCCGAGACCAACAGCTACTTCGCCAAGAGCATGGAGTTCCTGGCCAG

GCCCGTGCCAGCTCCCAGGACCGTGTTCAGGAACCCACCCCACCCAGCTCCCAG

GACCAGGACCCCAAGCCTGGCTCCCAGCAGGGCCTGCAGCAGGACCAGCCTGGT

GAGCACCCCACCCGGCGTGAACAGGGTGATCACCAGGGAGGAACTGGAGGCCCT

GACACCCAGCAGGACCCCCAGCAGGTCCGTGAGCAGGACTAGTCTGGTGTCCAA

CCCACCCGGCGTGAACAGGGTGATCACCAGGGAGGAATTCGAGGCCTTCGTGGC

CCAGCAACAGAGACGGTTCGACGCCGGCGCCTACATCTTCAGCAGCGACACCGG

CCAGGGACACCTGCAGCAAAAGAGCGTGAGGCAGACCGTGCTGAGCGAGGTGG

TGCTGGAGAGGACCGAGCTGGAAATCAGCTACGCCCCCAGGCTGGACCAGGAGA

AGGAGGAACTGCTCAGGAAGAAACTGCAGCTGAACCCCACCCCAGCCAACAGG

AGCAGGTACCAGAGCAGGAAGGTGGAGAACATGAAGGCCATCACCGCCAGGCG

GATCCTGCAGGGCCTGGGACACTACCTGAAGGCCGAGGGCAAGGTGGAGTGCTA

CAGGACCCTGCACCCCGTGCCACTGTACAGCTCCAGCGTGAACAGGGCCTTCTCC

AGCCCCAAGGTGGCCGTGGAGGCCTGCAACGCTATGCTGAAGGAGAACTTCCCC

ACCGTGGCCAGCTACTGCATCATCCCCGAGTACGACGCCTACCTGGACATGGTGG

ACGGCGCCAGCTGCTGCCTGGACACCGCCAGCTTCTGCCCCGCCAAGCTGAGGA

GCTTCCCCAAGAAACACAGCTACCTGGAGCCCACCATCAGGAGCGCCGTGCCCA

GCGCCATCCAGAACACCCTGCAGAACGTGCTGGCCGCTGCCACCAAGAGGAACT

GCAACGTGACCCAGATGAGGGAGCTGCCCGTGCTGGACAGCGCTGCCTTCAACG

TGGAGTGCTTCAAGAAATACGCCTGCAACAACGAGTACTGGGAGACCTTCAAGG

AGAACCCCATCAGGCTGACCGAAGAGAACGTGGTGAACTACATCACCAAGCTGA

AGGGCCCCAAGGCCGCTGCCCTGTTCGCTAAGACCCACAACCTGAACATGCTGC

AGGACATCCCAATGGACAGGTTCGTGATGGACCTGAAGAGGGACGTGAAGGTGA

CACCCGGCACCAAGCACACCGAGGAGAGGCCCAAGGTGCAGGTGATCCAGGCC

GCTGACCCACTGGCCACCGCCTACCTGTGCGGCATCCACAGGGAGCTGGTGAGG

CGGCTGAACGCCGTGCTGCTGCCCAACATCCACACCCTGTTCGACATGAGCGCCG

AGGACTTCGACGCCATCATCGCCGAGCACTTCCAGCCCGGCGACTGCGTGCTGG

AGACCGACATCGCCAGCTTCGACAAGAGCGAGGATGACGCTATGGCCCTGACCG

CTCTGATGATCCTGGAGGACCTGGGCGTGGACGCCGAGCTGCTCACCCTGATCGA

GGCTGCCTTCGGCGAGATCAGCTCCATCCACCTGCCCACCAAGACCAAGTTCAAG

TTCGGCGCTATGATGAAAAGCGGAATGTTCCTGACCCTGTTCGTGAACACCGTGA

TCAACATTGTGATCGCCAGCAGGGTGCTGCGGGAGAGGCTGACCGGCAGCCCCT

GCGCTGCCTTCATCGGCGACGACAACATCGTGAAGGGCGTGAAAAGCGACAAGC

TGATGGCCGACAGGTGCGCCACCTGGCTGAACATGGAGGTGAAGATCATCGACG

CCGTGGTGGGCGAGAAGGCCCCCTACTTCTGCGGCGGATTCATCCTGTGCGACAG

-continued

CGTGACCGGCACCGCCTGCAGGGTGGCCGACCCCCTGAAGAGGCTGTTCAAGCT

GGGCAAGCCACTGGCCGCTGACGATGAGCACGACGATGACAGGCGGAGGGCCCT

GCACGAGGAAAGCACCAGGTGGAACAGGGTGGGCATCCTGAGCGAGCTGTGCA

AGGCCGTGGAGAGCAGGTACGAGACCGTGGGCACCAGCATCATCGTGATGGCTA

TGACCACACTGGCCAGCTCCGTCAAGAGCTTCTCCTACCTGAGGGGGGCCCCTAT

AACTCTCTACGGCTAACCTGAATGGACTACGACATAGTCTAGTCCGCCAAGGCCG

CCACCACTCGAGTATGTTACGTGCAAAGGTGATTGTCACCCCCCGAAAGACCATA

TTGTGACACACCCTCAGTATCACGCCCAAACATTTACAGCCGCGGTGTCAAAAAC

CGCGTGGACGTGGTTAACATCCCTGCTGGGAGGATCAGCCGTAATTATTATAATT

GGCTTGGTGCTGGCTACTATTGTGGCCATGTACGTGCTGACCAACCAGAAACATA

ATTGAATACAGCAGCAATTGGCAAGCTGCTTACATAGAACTCGCGGCGATTGGC

ATGCCGCCTTAAAATTTTTATTTTATTTTTTCTTTTCTTTTCCGAATCGGATTTTGT

TTTTAATATTTCAAAAAAAAAAAAAAAAAAAAAAAAAATCTAGAAAAAAAAAAAA

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAA

SEQ ID NO: 124

ATGGGCGGCGCATGAGAGAAGCCCAGACCAATTACCTACCCAAAATGGAGAAA

GTTCACGTTGACATCGAGGAAGACAGCCCATTCCTCAGAGCTTTGCAGCGGAGCT

TCCCGCAGTTTGAGGTAGAAGCCAAGCAGGTCACTGATAATGACCATGCTAATG

CCAGAGCGTTTTCGCATCTGGCTTCAAAACTGATCGAAACGGAGGTGGACCCATC

CGACACGATCCTTGACATTGGAAGTGCGCCCGCCCGCAGAATGTATTCTAAGCAC

AAGTATCATTGTATCTGTCCGATGAGATGTGCGGAAGATCCGGACAGATTGTATA

AGTATGCAACTAAGCTGAAGAAAAACTGTAAGGAAATAACTGATAAGGAATTGG

ACAAGAAAATGAAGGAGCTGGCCGCCGTCATGAGCGACCCTGACCTGGAAACTG

AGACTATGTGCCTCCACGACGACGAGTCGTGTCGCTACGAAGGGCAAGTCGCTG

TTTACCAGGATGTATACGCCGTCGACGGCCCCACCAGCCTGTACCACCAGGCCAA

CAAGGGCGTGAGGGTGGCCTACTGGATCGGCTTCGACACCACACCCTTCATGTTC

AAGAACCTGGCCGGCGCCTACCCCAGCTACAGCACCAACTGGGCCGACGAGACC

GTGCTGACCGCCAGGAACATCGGCCTGTGCAGCAGCGACGTGATGGAGAGGAGC

CGGAGAGGCATGAGCATCCTGAGGAAGAAATACCTGAAGCCCAGCAACAACGT

GCTGTTCAGCGTGGGCAGCACCATCTACCACGAGAAGAGGGACCTGCTCAGGAG

CTGGCACCTGCCCAGCGTGTTCCACCTGAGGGGCAAGCAGAACTACACCTGCAG

GTGCGAGACCATCGTGAGCTGCGACGGCTACGTGGTGAAGAGGATCGCCATCAG

CCCCGGCCTGTACGGCAAGCCCAGCGGCTACGCCGCTACAATGCACAGGGAGGG

CTTCCTGTGCTGCAAGGTGACCGACACCCTGAACGGCGAGAGGGTGAGCTTCCC

CGTGTGCACCTACGTGCCCGCCACCCTGTGCGACCAGATGACCGGCATCCTGGCC

ACCGACGTGAGCGCCGACGACGCCCAGAAGCTGCTCGTGGGCCTGAACCAGAGG

ATCGTGGTCAACGGCAGGACCCAGAGGAACACCAACACAATGAAGAACTACCTG

CTGCCCGTGGTGGCCCAGGCTTTCGCCAGGTGGGCCAAGGAGTACAAGGAGGAC

CAGGAAGACGAGAGGCCCCTGGGCCTGAGGGACAGGCAGCTGGTGATGGGCTG

CTGCTGGGCCTTCAGGCGGCACAAGATCACCAGCATCTACAAGAGGCCCGACAC

-continued

CCAGACCATCATCAAGGTGAACAGCGACTTCCACAGCTTCGTGCTGCCCAGGATC

GGCAGCAACACCCTGGAGATCGGCCTGAGGACCCGGATCAGGAAGATGCTGGAG

GAACACAAGGAGCCCAGCCCACTGATCACCGCCGAGGACGTGCAGGAGGCCAA

GTGCGCTGCCGACGAGGCCAAGGAGGTGAGGGAGGCCGAGGAACTGAGGGCCG

CCCTGCCACCCCTGGCTGCCGACGTGGAGGAACCCACCCTGGAAGCCGACGTGG

ACCTGATGCTGCAGGAGGCCGGCGCCGGAAGCGTGGAGACACCCAGGGGCCTGA

TCAAGGTGACCAGCTACGACGGCGAGGACAAGATCGGCAGCTACGCCGTGCTGA

GCCCACAGGCCGTGCTGAAGTCCGAGAAGCTGAGCTGCATCCACCCACTGGCCG

AGCAGGTGATCGTGATCACCCACAGCGGCAGGAAGGGCAGGTACGCCGTGGAGC

CCTACCACGGCAAGGTGGTCGTGCCCGAGGGCCACGCCATCCCCGTGCAGGACT

TCCAGGCCCTGAGCGAGAGCGCCACCATCGTGTACAACGAGAGGGAGTTCGTGA

ACAGGTACCTGCACCATATCGCCACCCACGGCGGAGCCCTGAACACCGACGAGG

AATACTACAAGACCGTGAAGCCCAGCGAGCACGACGGCGAGTACCTGTACGACA

TCGACAGGAAGCAGTGCGTGAAGAAAGAGCTGGTGACCGGCCTGGGACTGACCG

GCGAGCTGGTGGACCCACCCTTCCACGAGTTCGCCTACGAGAGCCTGAGGACCA

GACCCGCCGCTCCCTACCAGGTGCCCACCATCGGCGTGTACGGCGTGCCCGGCA

GCGGAAAGAGCGGCATCATCAAGAGCGCCGTGACCAAGAAAGACCTGGTGGTC

AGCGCCAAGAAAGAGAACTGCGCCGAGATCATCAGGGACGTGAAGAAGATGAA

AGGCCTGGACGTGAACGCGCGCACCGTGGACAGCGTGCTGCTGAACGGCTGCAA

GCACCCCGTGGAGACCCTGTACATCGACGAGGCCTTCGCTTGCCACGCCGGCACC

CTGAGGGCCCTGATCGCCATCATCAGGCCCAAGAAAGCCGTGCTGTGCGGCGAC

CCCAAGCAGTGCGGCTTCTTCAACATGATGTGCCTGAAGGTGCACTTCAACCACG

AGATCTGCACCCAGGTGTTCCACAAGAGCATCAGCAGGCGGTGCACCAAGAGCG

TGACCAGCGTCGTGAGCACCCTGTTCTACGACAAGAAAATGAGGACCACCAACC

CCAAGGAGACCAAAATCGTGATCGACACCACAGGCAGCACCAAGCCCAAGCAG

GACGACCTGATCCTGACCTGCTTCAGGGGCTGGGTGAAGCAGCTGCAGATCGAC

TACAAGGGCAACGAGATCATGACCGCCGCTGCCAGCCAGGGCCTGACCAGGAAG

GGCGTGTACGCCGTGAGGTACAAGGTGAACGAGAACCCACTGTACGCTCCCACC

AGCGAGCACGTGAACGTGCTGCTGACCAGGACCGAGGACAGGATCGTGTGGAAG

ACCCTGGCCGGCGACCCCTGGATCAAGACCCTGACCGCCAAGTACCCCGGCAAC

TTCACCGCCACCATCGAAGAGTGGCAGGCCGAGCACGACGCCATCATGAGGCAC

ATCCTGGAGAGGCCCGACCCCACCGACGTGTTCCAGAACAAGGCCAACGTGTGC

TGGGCCAAGGCCCTGGTGCCCGTGCTGAAGACCGCCGGCATCGACATGACCACA

GAGCAGTGGAACACCGTGGACTACTTCGAGACCGACAAGGCCCACAGCGCCGAG

ATCGTGCTGAACCAGCTGTGCGTGAGGTTCTTCGGCCTGGACCTGGACAGCGGCC

TGTTCAGCGCCCCCACCGTGCCACTGAGCATCAGGAACAACCACTGGGACAACA

GCCCCAGCCCAAACATGTACGGCCTGAACAAGGAGGTGGTCAGGCAGCTGAGCA

GGCGGTACCCACAGCTGCCCAGGGCCGTGGCCACCGGCAGGGTGTACGACATGA

ACACCGGCACCCTGAGGAACTACGACCCCAGGATCAACCTGGTGCCCGTGAACA

GGCGGCTGCCCCACGCCCTGGTGCTGCACCACAACGAGCACCCACAGAGCGACT

TCAGCTCCTTCGTGAGCAAGCTGAAAGGCAGGACCGTGCTGGTCGTGGGCGAGA

-continued

AGCTGAGCGTGCCCGGCAAGATGGTGGACTGGCTGAGCGACAGGCCCGAGGCCA

CCTTCCGGGCCAGGCTGGACCTCGGCATCCCCGGCGACGTGCCCAAGTACGACA

TCATCTTCGTGAACGTCAGGACCCCATACAAGTACCACCATTACCAGCAGTGCGA

GGACCACGCCATCAAGCTGAGCATGCTGACCAAGAAGGCCTGCCTGCACCTGAA

CCCCGGAGGCACCTGCGTGAGCATCGGCTACGGCTACGCCGACAGGGCCAGCGA

GAGCATCATTGGCGCCATCGCCAGGCTGTTCAAGTTCAGCAGGGTGTGCAAACC

CAAGAGCAGCCTGGAGGAAACCGAGGTGCTGTTCGTGTTCATCGGCTACGACCG

GAAGGCCAGGACCCACAACCCCTACAAGCTGAGCAGCACCCTGACAAACATCTA

CACCGGCAGCAGGCTGCACGAGGCCGGCTGCGCCCCCAGCTACCACGTGGTCAG

GGGCGATATCGCCACCGCCACCGAGGGCGTGATCATCAACGCTGCCAACAGCAA

GGGCCAGCCCGGAGGCGGAGTGTGCGGCGCCCTGTACAAGAAGTTCCCCGAGAG

CTTCGACCTGCAGCCCATCGAGGTGGGCAAGGCCAGGCTGGTGAAGGGCGCCGC

TAAGCACATCATCCACGCCGTGGGCCCCAACTTCAACAAGGTGAGCGAGGTGGA

AGGCGACAAGCAGCTGGCCGAAGCCTACGAGAGCATCGCCAAGATCGTGAACG

ACAATAACTACAAGAGCGTGGCCATCCCACTGCTCAGCACCGGCATCTTCAGCG

GCAACAAGGACAGGCTGACCCAGAGCCTGAACCACCTGCTCACCGCCCTGGACA

CCACCGATGCCGACGTGGCCATCTACTGCAGGGACAAGAAGTGGGAGATGACCC

TGAAGGAGGCCGTGGCCAGGCGGGAGGCCGTGGAAGAGATCTGCATCAGCGAC

GACTCCAGCGTGACCGAGCCCGACGCCGAGCTGGTGAGGGTGCACCCCAAGAGC

TCCCTGGCCGGCAGGAAGGGCTACAGCACCAGCGACGGCAAGACCTTCAGCTAC

CTGGAGGGCACCAAGTTCCACCAGGCCGCTAAGGACATCGCCGAGATCAACGCT

ATGTGGCCCGTGGCCACCGAGGCCAACGAGCAGGTGTGCATGTACATCCTGGGC

GAGAGCATGTCCAGCATCAGGAGCAAGTGCCCCGTGGAGGAAAGCGAGGCCAG

CACACCACCCAGCACCCTGCCCTGCCTGTGCATCCACGCTATGACACCCGAGAGG

GTGCAGCGGCTGAAGGCCAGCAGGCCCGAGCAGATCACCGTGTGCAGCTCCTTC

CCACTGCCCAAGTACAGGATCACCGGCGTGCAGAAGATCCAGTGCAGCCAGCCC

ATCCTGTTCAGCCCAAAGGTGCCCGCCTACATCCACCCCAGGAAGTACCTGGTGG

AGACCCCACCCGTGGACGAGACACCCGAGCCAAGCGCCGAGAACCAGAGCACC

GAGGGCACACCCGAGCAGCCACCCCTGATCACCGAGGACGAGACAAGGACCCG

GACCCCAGAGCCCATCATTATCGAGGAAGAGGAAGAGGACAGCATCAGCCTGCT

GAGCGACGGCCCCACCCACCAGGTGCTGCAGGTGGAGGCCGACATCCACGGCCC

ACCCAGCGTGTCCAGCTCCAGCTGGAGCATCCCACACGCCAGCGACTTCGACGT

GGACAGCCTGAGCATCCTGGACACCCTGGAGGGCGCCAGCGTGACCTCCGGCGC

CACCAGCGCCGAGACCAACAGCTACTTCGCCAAGAGCATGGAGTTCCTGGCCAG

GCCCGTGCCAGCTCCCAGGACCGTGTTCAGGAACCCACCCCACCCAGCTCCCAG

GACCAGGACCCCAAGCCTGGCTCCCAGCAGGGCCTGCAGCAGGACCAGCCTGGT

GAGCACCCCACCCGGCGTGAACAGGGTGATCACCAGGGAGGAACTGGAGGCCCT

GACACCCAGCAGGACCCCCAGCAGGTCCGTGAGCAGGACTAGTCTGGTGTCCAA

CCCACCCGGCGTGAACAGGGTGATCACCAGGGAGGAATTCGAGGCCTTCGTGGC

CCAGCAACAGAGACGGTTCGACGCCGGCGCCTACATCTTCAGCAGCGACACCGG

-continued

CCAGGGACACCTGCAGCAAAAGAGCGTGAGGCAGACCGTGCTGAGCGAGGTGG

TGCTGGAGAGGACCGAGCTGGAAATCAGCTACGCCCCCAGGCTGGACCAGGAGA

AGGAGGAACTGCTCAGGAAGAAACTGCAGCTGAACCCCACCCCAGCCAACAGG

AGCAGGTACCAGAGCAGGAAGGTGGAGAACATGAAGGCCATCACCGCCAGGCG

GATCCTGCAGGGCCTGGGACACTACCTGAAGGCCGAGGGCAAGGTGGAGTGCTA

CAGGACCCTGCACCCCGTGCCACTGTACAGCTCCAGCGTGAACAGGGCCTTCTCC

AGCCCCAAGGTGGCCGTGGAGGCCTGCAACGCTATGCTGAAGGAGAACTTCCCC

ACCGTGGCCAGCTACTGCATCATCCCCGAGTACGACGCCTACCTGGACATGGTGG

ACGGCGCCAGCTGCTGCCTGGACACCGCCAGCTTCTGCCCCGCCAAGCTGAGGA

GCTTCCCCAAGAAACACAGCTACCTGGAGCCCACCATCAGGAGCGCCGTGCCCA

GCGCCATCCAGAACACCCTGCAGAACGTGCTGGCCGCTGCCACCAAGAGGAACT

GCAACGTGACCCAGATGAGGGAGCTGCCCGTGCTGGACAGCGCTGCCTTCAACG

TGGAGTGCTTCAAGAAATACGCCTGCAACAACGAGTACTGGGAGACCTTCAAGG

AGAACCCCATCAGGCTGACCGAAGAGAACGTGGTGAACTACATCACCAAGCTGA

AGGGCCCCAAGGCCGCTGCCCTGTTCGCTAAGACCCACAACCTGAACATGCTGC

AGGACATCCCAATGGACAGGTTCGTGATGGACCTGAAGAGGGACGTGAAGGTGA

CACCCGGCACCAAGCACACCGAGGAGAGGCCCAAGGTGCAGGTGATCCAGGCC

GCTGACCCACTGGCCACCGCCTACCTGTGCGGCATCCACAGGGAGCTGGTGAGG

CGGCTGAACGCCGTGCTGCTGCCCAACATCCACACCCTGTTCGACATGAGCGCCG

AGGACTTCGACGCCATCATCGCCGAGCACTTCCAGCCCGGCGACTGCGTGCTGG

AGACCGACATCGCCAGCTTCGACAAGAGCGAGGATGACGCTATGGCCCTGACCG

CTCTGATGATCCTGGAGGACCTGGGCGTGGACGCCGAGCTGCTCACCCTGATCGA

GGCTGCCTTCGGCGAGATCAGCTCCATCCACCTGCCCACCAAGACCAAGTTCAAG

TTCGGCGCTATGATGAAAAGCGGAATGTTCCTGACCCTGTTCGTGAACACCGTGA

TCAACATTGTGATCGCCAGCAGGGTGCTGCGGGAGAGGCTGACCGGCAGCCCCT

GCGCTGCCTTCATCGGCGACGACAACATCGTGAAGGGCGTGAAAAGCGACAAGC

TGATGGCCGACAGGTGCGCCACCTGGCTGAACATGGAGGTGAAGATCATCGACG

CCGTGGTGGGCGAGAAGGCCCCCTACTTCTGCGGCGGATTCATCCTGTGCGACAG

CGTGACCGGCACCGCCTGCAGGGTGGCCGACCCCCTGAAGAGGCTGTTCAAGCT

GGGCAAGCCACTGGCCGCTGACGATGAGCACGACGATGACAGGCGGAGGGCCCT

GCACGAGGAAAGCACCAGGTGGAACAGGGTGGGCATCCTGAGCGAGCTGTGCA

AGGCCGTGGAGAGCAGGTACGAGACCGTGGGCACCAGCATCATCGTGATGGCTA

TGACCACACTGGCCAGCTCCGTCAAGAGCTTCTCCTACCTGAGGGGGGCCCCTAT

AACTCTCTACGGCTAACCTGAATGGACTACGACATAGTCTAGTCCGCCAAGGCCG

CCACCATGTTTGTTTTTCTTGTTTTATTGCCACTAGTCTCTAGTCAGTGTGTTAATC

TTACAACCAGAACTCAATTACCCCCTGCATACACTAATTCTTTCACACGTGGTGT

TTATTACCCTGACAAAGTTTTCAGATCCTCAGTTTTACATTCAACTCAGGACTTGT

TCTTACCTTTCTTTTCCAATGTTACTTGGTTCCATGCTATACATGTCTCTGGGACC

AATGGTACTAAGAGGTTTGATAACCCTGTCCTACCATTTAATGATGGTGTTTATTT

TGCTTCCACTGAGAAGTCTAACATAATAAGAGGCTGGATTTTTGGTACTACTTTA

GATTCGAAGACCCAGTCCCTACTTATTGTTAATAACGCTACTAATGTTGTTATTAA

-continued

AGTCTGTGAATTTCAATTTTGTAATGATCCATTTTTGGGTGTTTATTACCACAAAA

ACAACAAAAGTTGGATGGAAAGTGAGTTCAGAGTTTATTCTAGTGCGAATAATT

GCACTTTTGAATATGTCTCTCAGCCTTTTCTTATGGACCTTGAAGGAAAACAGGG

TAATTTCAAAAATCTTAGGGAATTTGTGTTTAAGAATATTGATGGTTATTTTAAA

ATATATTCTAAGCACACGCCTATTAATTTAGTGCGTGATCTCCCTCAGGGTTTTC

GGCTTTAGAACCATTGGTAGATTTGCCAATAGGTATTAACATCACTAGGTTTCAA

ACTTTACTTGCTTTACATAGAAGTTATTTGACTCCTGGTGATTCTTCTTCAGGTTG

GACAGCTGGTGCTGCAGCTTATTATGTGGGTTATCTTCAACCTAGGACTTTTCTAT

TAAAATATAATGAAAATGGAACCATTACAGATGCTGTAGACTGTGCACTTGACC

CTCTCTCAGAAACAAAGTGTACGTTGAAATCCTTCACTGTAGAAAAAGGAATCTA

TCAAACTTCTAACTTTAGAGTCCAACCAACAGAATCTATTGTTAGATTTCCTAAT

ATTACAAACTTGTGCCCTTTTGGTGAAGTTTTTAACGCCACCAGATTTGCATCTGT

TTATGCTTGGAACAGGAAGAGAATCAGCAACTGTGTTGCTGATTATTCTGTCCTA

TATAATTCCGCATCATTTTCCACTTTTAAGTGTTATGGAGTGTCTCCTACTAAATT

AAATGATCTCTGCTTTACTAATGTCTATGCAGATTCATTTGTAATTAGAGGTGATG

AAGTCAGACAAATCGCTCCAGGGCAAACTGGAAAGATTGCTGATTATAATTATA

AATTACCAGATGATTTTACAGGCTGCGTTATAGCTTGGAATTCTAACAATCTTGA

TTCTAAGGTTGGTGGTAATTATAATTACCTGTATAGATTGTTTAGGAAGTCTAATC

TCAAACCTTTTGAGAGAGATATTTCAACTGAAATCTATCAGGCCGGTAGCACACC

TTGTAATGGTGTTGAAGGTTTTAATTGTTACTTTCCTTTACAATCATATGGTTTCC

AACCCACTAATGGTGTTGGTTACCAACCATACAGAGTAGTAGTACTTTCTTTTGA

ACTTCTACATGCACCAGCAACTGTTTGTGGACCTAAAAAGTCTACTAATTTGGTT

AAAAACAAATGTGTCAATTTCAACTTCAATGGTTTAACAGGCACAGGTGTTCTTA

CTGAGTCTAACAAAAAGTTTCTGCCTTTCCAACAATTTGGCAGAGACATTGCTGA

CACTACTGATGCTGTCCGTGATCCACAGACACTTGAGATTCTTGACATTACACCA

TGTTCTTTTGGTGGTGTCAGTGTTATAACACCAGGAACAAATACTTCTAACCAGG

TTGCTGTTCTTTATCAGGATGTTAACTGCACAGAAGTCCCTGTTGCTATTCATGCA

GATCAACTTACTCCTACTTGGCGTGTTTATTCTACAGGTTCTAATGTTTTTCAAAC

ACGTGCAGGCTGTTTAATAGGGGCTGAACATGTCAACAACTCATATGAGTGTGA

CATACCCATTGGTGCAGGTATATGCGCTAGTTATCAGACTCAGACTAATTCTCCT

CGGCGGGCACGTAGTGTAGCTAGTCAATCCATCATTGCCTACACTATGTCACTTG

GTGCAGAAAATTCAGTTGCTTACTCTAATAACTCTATTGCCATACCCACAAATTT

TACTATTAGTGTTACCACAGAAATTCTACCAGTGTCTATGACCAAGACATCAGTA

GATTGTACAATGTACATTTGTGGTGATTCAACTGAATGCAGCAATCTTTTGTTGC

AATATGGCAGTTTTTGTACACAATTAAACCGTGCTTTAACTGGAATAGCTGTTGA

ACAAGACAAAAACACCCAAGAAGTTTTTGCACAAGTCAAACAAATTTACAAAAC

ACCACCAATTAAAGATTTTGGTGGTTTTAATTTTTCACAAATATTACCAGATCCAT

CAAAACCAAGCAAGAGGTCATTTATTGAAGATCTACTTTTCAACAAAGTGACACT

TGCAGATGCTGGCTTCATCAAACAATATGGTGATTGCCTTGGTGATATTGCTGCT

AGAGACCTCATTTGTGCACAAAAGTTTAACGGCCTTACTGTTTTGCCACCTTTGCT

-continued

CACAGATGAAATGATTGCTCAATACACTTCTGCACTGTTAGCGGGTACAATCACT

TCTGGTTGGACCTTTGGTGCAGGTGCTGCATTACAAATACCATTTGCTATGCAAA

TGGCTTATAGGTTTAATGGTATTGGAGTTACACAGAATGTTCTCTATGAGAACCA

AAAATTGATTGCCAACCAATTTAATAGTGCTATTGGCAAAATTCAAGACTCACTT

TCTTCCACAGCAAGTGCACTTGGAAAACTTCAAGATGTGGTCAACCAAAATGCA

CAAGCTTTAAACACGCTTGTTAAACAACTTAGCTCCAATTTTGGTGCAATTTCAA

GTGTTTTAAATGATATCCTTTCACGTCTTGACAAAGTTGAGGCTGAAGTGCAAAT

TGATAGGTTGATCACAGGCAGACTTCAAAGTTTGCAGACATATGTGACTCAACA

ATTAATTAGAGCTGCAGAAATCAGAGCTTCTGCTAATCTTGCTGCTACTAAAATG

TCAGAGTGTGTACTTGGACAATCAAAAAGAGTTGATTTTTGTGGAAAGGGCTATC

ATCTTATGTCCTTCCCTCAGTCAGCACCTCATGGTGTAGTCTTCTTGCATGTGACT

TATGTCCCTGCACAAGAAAAGAACTTCACAACTGCTCCTGCCATTTGTCATGATG

GAAAAGCACACTTTCCTCGTGAAGGTGTCTTTGTTTCAAATGGCACACACTGGTT

TGTAACACAAAGGAATTTTTATGAACCACAAATCATTACTACAGACAACACATTT

GTGTCTGGTAACTGTGATGTTGTAATAGGAATTGTCAACAACACAGTTTATGATC

CTTTGCAACCTGAATTAGACTCATTCAAGGAGGAGTTAGATAAATATTTTAAGAA

TCATACATCACCAGATGTTGATTTAGGTGACATCTCTGGCATTAATGCTTCAGTTG

TAAACATTCAAAAAGAAATTGACCGCCTCAATGAGGTTGCCAAGAATTTAAATG

AATCTCTCATCGATCTCCAAGAACTTGGAAAGTATGAGCAGTATATAAAATGGCC

ATGGTACATTTGGCTAGGTTTTATAGCTGGCTTGATTGCCATAGTAATGGTGACA

ATTATGCTTTGCTGTATGACCAGTTGCTGTAGTTGTCTCAAGGGCTGTTGTTCTTG

TGGATCCTGCTGCAAATTTGATGAAGACGACTCTGAGCCAGTGCTCAAAGGAGT

CAAATTACATTACACATAAACTCGAGTATGTTACGTGCAAAGGTGATTGTCACCC

CCCGAAAGACCATATTGTGACACACCCTCAGTATCACGCCCAAACATTTACAGCC

GCGGTGTCAAAAACCGCGTGGACGTGGTTAACATCCCTGCTGGGAGGATCAGCC

GTAATTATTATAATTGGCTTGGTGCTGGCTACTATTGTGGCCATGTACGTGCTGAC

CAACCAGAAACATAATTGAATACAGCAGCAATTGGCAAGCTGCTTACATAGAAC

TCGCGGCGATTGGCATGCCGCCTTAAAATTTTTATTTTATTTTTTCTTTTCTTTTCC

GAATCGGATTTTGTTTTTAATATTTCAAAAAAAAAAAAAAAAAAAAAAAAAATCT

AGAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAA

SEQ ID NO: 125

ATGGGCGGCGCATGAGAGAAGCCCAGACCAATTACCTACCCAAAATGGAGAAA

GTTCACGTTGACATCGAGGAAGACAGCCCATTCCTCAGAGCTTTGCAGCGGAGCT

TCCCGCAGTTTGAGGTAGAAGCCAAGCAGGTCACTGATAATGACCATGCTAATG

CCAGAGCGTTTTCGCATCTGGCTTCAAAACTGATCGAAACGGAGGTGGACCCATC

CGACACGATCCTTGACATTGGAAGTGCGCCCGCCCGCAGAATGTATTCTAAGCAC

AAGTATCATTGTATCTGTCCGATGAGATGTGCGGAAGATCCGGACAGATTGTATA

AGTATGCAACTAAGCTGAAGAAAAACTGTAAGGAAATAACTGATAAGGAATTGG

ACAAGAAAATGAAGGAGCTGGCCGCCGTCATGAGCGACCCTGACCTGGAAACTG

AGACTATGTGCCTCCACGACGACGAGTCGTGTCGCTACGAAGGGCAAGTCGCTG

-continued

TTTACCAGGATGTATACGCCGTCGACGGCCCCACCAGCCTGTACCACCAGGCCAA

CAAGGGCGTGAGGGTGGCCTACTGGATCGGCTTCGACACCACACCCTTCATGTTC

AAGAACCTGGCCGGCGCCTACCCCAGCTACAGCACCAACTGGGCCGACGAGACC

GTGCTGACCGCCAGGAACATCGGCCTGTGCAGCAGCGACGTGATGGAGAGGAGC

CGGAGAGGCATGAGCATCCTGAGGAAGAAATACCTGAAGCCCAGCAACAACGT

GCTGTTCAGCGTGGGCAGCACCATCTACCACGAGAAGAGGGACCTGCTCAGGAG

CTGGCACCTGCCCAGCGTGTTCCACCTGAGGGGCAAGCAGAACTACACCTGCAG

GTGCGAGACCATCGTGAGCTGCGACGGCTACGTGGTGAAGAGGATCGCCATCAG

CCCCGGCCTGTACGGCAAGCCCAGCGGCTACGCCGCTACAATGCACAGGGAGGG

CTTCCTGTGCTGCAAGGTGACCGACACCCTGAACGGCGAGAGGGTGAGCTTCCC

CGTGTGCACCTACGTGCCCGCCACCCTGTGCGACCAGATGACCGGCATCCTGGCC

ACCGACGTGAGCGCCGACGACGCCCAGAAGCTGCTCGTGGGCCTGAACCAGAGG

ATCGTGGTCAACGGCAGGACCCAGAGGAACACCAACACAATGAAGAACTACCTG

CTGCCCGTGGTGGCCCAGGCTTTCGCCAGGTGGGCCAAGGAGTACAAGGAGGAC

CAGGAAGACGAGAGGCCCCTGGGCCTGAGGGACAGGCAGCTGGTGATGGGCTG

CTGCTGGGCCTTCAGGCGGCACAAGATCACCAGCATCTACAAGAGGCCCGACAC

CCAGACCATCATCAAGGTGAACAGCGACTTCCACAGCTTCGTGCTGCCCAGGATC

GGCAGCAACACCCTGGAGATCGGCCTGAGGACCCGGATCAGGAAGATGCTGGAG

GAACACAAGGAGCCCAGCCCACTGATCACCGCCGAGGACGTGCAGGAGGCCAA

GTGCGCTGCCGACGAGGCCAAGGAGGTGAGGGAGGCCGAGGAACTGAGGGCCG

CCCTGCCACCCCTGGCTGCCGACGTGGAGGAACCCACCCTGGAAGCCGACGTGG

ACCTGATGCTGCAGGAGGCCGGCGCCGGAAGCGTGGAGACACCCAGGGGCCTGA

TCAAGGTGACCAGCTACGACGGCGAGGACAAGATCGGCAGCTACGCCGTGCTGA

GCCCACAGGCCGTGCTGAAGTCCGAGAAGCTGAGCTGCATCCACCCACTGGCCG

AGCAGGTGATCGTGATCACCCACAGCGGCAGGAAGGGCAGGTACGCCGTGGAGC

CCTACCACGGCAAGGTGGTCGTGCCCGAGGGCCACGCCATCCCCGTGCAGGACT

TCCAGGCCCTGAGCGAGAGCGCCACCATCGTGTACAACGAGAGGGAGTTCGTGA

ACAGGTACCTGCACCATATCGCCACCCACGGCGGAGCCCTGAACACCGACGAGG

AATACTACAAGACCGTGAAGCCCAGCGAGCACGACGGCGAGTACCTGTACGACA

TCGACAGGAAGCAGTGCGTGAAGAAAGAGCTGGTGACCGGCCTGGGACTGACCG

GCGAGCTGGTGGACCCACCCTTCCACGAGTTCGCCTACGAGAGCCTGAGGACCA

GACCCGCCGCTCCCTACCAGGTGCCCACCATCGGCGTGTACGGCGTGCCCGGCA

GCGGAAAGAGCGGCATCATCAAGAGCGCCGTGACCAAGAAAGACCTGGTGGTC

AGCGCCAAGAAAGAGAACTGCGCCGAGATCATCAGGGACGTGAAGAAGATGAA

AGGCCTGGACGTGAACGCGCGCACCGTGGACAGCGTGCTGCTGAACGGCTGCAA

GCACCCCGTGGAGACCCTGTACATCGACGAGGCCTTCGCTTGCCACGCCGGCACC

CTGAGGGCCCTGATCGCCATCATCAGGCCCAAGAAAGCCGTGCTGTGCGGCGAC

CCCAAGCAGTGCGGCTTCTTCAACATGATGTGCCTGAAGGTGCACTTCAACCACG

AGATCTGCACCCAGGTGTTCCACAAGAGCATCAGCAGGCGGTGCACCAAGAGCG

TGACCAGCGTCGTGAGCACCCTGTTCTACGACAAGAAAATGAGGACCACCAACC

CCAAGGAGACCAAAATCGTGATCGACACCACAGGCAGCACCAAGCCCAAGCAG

-continued

GACGACCTGATCCTGACCTGCTTCAGGGGCTGGGTGAAGCAGCTGCAGATCGAC

TACAAGGGCAACGAGATCATGACCGCCGCTGCCAGCCAGGGCCTGACCAGGAAG

GGCGTGTACGCCGTGAGGTACAAGGTGAACGAGAACCCACTGTACGCTCCCACC

AGCGAGCACGTGAACGTGCTGCTGACCAGGACCGAGGACAGGATCGTGTGGAAG

ACCCTGGCCGGCGACCCCTGGATCAAGACCCTGACCGCCAAGTACCCCGGCAAC

TTCACCGCCACCATCGAAGAGTGGCAGGCCGAGCACGACGCCATCATGAGGCAC

ATCCTGGAGAGGCCCGACCCCACCGACGTGTTCCAGAACAAGGCCAACGTGTGC

TGGGCCAAGGCCCTGGTGCCCGTGCTGAAGACCGCCGGCATCGACATGACCACA

GAGCAGTGGAACACCGTGGACTACTTCGAGACCGACAAGGCCCACAGCGCCGAG

ATCGTGCTGAACCAGCTGTGCGTGAGGTTCTTCGGCCTGGACCTGGACAGCGGCC

TGTTCAGCGCCCCCACCGTGCCACTGAGCATCAGGAACAACCACTGGGACAACA

GCCCCAGCCCAAACATGTACGGCCTGAACAAGGAGGTGGTCAGGCAGCTGAGCA

GGCGGTACCCACAGCTGCCCAGGGCCGTGGCCACCGGCAGGGTGTACGACATGA

ACACCGGCACCCTGAGGAACTACGACCCCAGGATCAACCTGGTGCCCGTGAACA

GGCGGCTGCCCCACGCCCTGGTGCTGCACCACAACGAGCACCCACAGAGCGACT

TCAGCTCCTTCGTGAGCAAGCTGAAAGGCAGGACCGTGCTGGTCGTGGGCGAGA

AGCTGAGCGTGCCCGGCAAGATGGTGGACTGGCTGAGCGACAGGCCCGAGGCCA

CCTTCCGGGCCAGGCTGGACCTCGGCATCCCCGGCGACGTGCCCAAGTACGACA

TCATCTTCGTGAACGTCAGGACCCCATACAAGTACCACCATTACCAGCAGTGCGA

GGACCACGCCATCAAGCTGAGCATGCTGACCAAGAAGGCCTGCCTGCACCTGAA

CCCCGGAGGCACCTGCGTGAGCATCGGCTACGGCTACGCCGACAGGGCCAGCGA

GAGCATCATTGGCGCCATCGCCAGGCTGTTCAAGTTCAGCAGGGTGTGCAAACC

CAAGAGCAGCCTGGAGGAAACCGAGGTGCTGTTCGTGTTCATCGGCTACGACCG

GAAGGCCAGGACCCACAACCCCTACAAGCTGAGCAGCACCCTGACAAACATCTA

CACCGGCAGCAGGCTGCACGAGGCCGGCTGCGCCCCCAGCTACCACGTGGTCAG

GGGCGATATCGCCACCGCCACCGAGGGCGTGATCATCAACGCTGCCAACAGCAA

GGGCCAGCCCGGAGGCGGAGTGTGCGGCGCCCTGTACAAGAAGTTCCCCGAGAG

CTTCGACCTGCAGCCCATCGAGGTGGGCAAGGCCAGGCTGGTGAAGGGCGCCGC

TAAGCACATCATCCACGCCGTGGGCCCCAACTTCAACAAGGTGAGCGAGGTGGA

AGGCGACAAGCAGCTGGCCGAAGCCTACGAGAGCATCGCCAAGATCGTGAACG

ACAATAACTACAAGAGCGTGGCCATCCCACTGCTCAGCACCGGCATCTTCAGCG

GCAACAAGGACAGGCTGACCCAGAGCCTGAACCACCTGCTCACCGCCCTGGACA

CCACCGATGCCGACGTGGCCATCTACTGCAGGGACAAGAAGTGGGAGATGACCC

TGAAGGAGGCCGTGGCCAGGCGGGAGGCCGTGGAAGAGATCTGCATCAGCGAC

GACTCCAGCGTGACCGAGCCCGACGCCGAGCTGGTGAGGGTGCACCCCAAGAGC

TCCCTGGCCGGCAGGAAGGGCTACAGCACCAGCGACGGCAAGACCTTCAGCTAC

CTGGAGGGCACCAAGTTCCACCAGGCCGCTAAGGACATCGCCGAGATCAACGCT

ATGTGGCCCGTGGCCACCGAGGCCAACGAGCAGGTGTGCATGTACATCCTGGGC

GAGAGCATGTCCAGCATCAGGAGCAAGTGCCCCGTGGAGGAAAGCGAGGCCAG

CACACCACCCAGCACCCTGCCCTGCCTGTGCATCCACGCTATGACACCCGAGAGG

-continued

GTGCAGCGGCTGAAGGCCAGCAGGCCCGAGCAGATCACCGTGTGCAGCTCCTTC

CCACTGCCCAAGTACAGGATCACCGGCGTGCAGAAGATCCAGTGCAGCCAGCCC

ATCCTGTTCAGCCCAAAGGTGCCCGCCTACATCCACCCCAGGAAGTACCTGGTGG

AGACCCCACCCGTGGACGAGACACCCGAGCCAAGCGCCGAGAACCAGAGCACC

GAGGGCACACCCGAGCAGCCACCCCTGATCACCGAGGACGAGACAAGGACCCG

GACCCCAGAGCCCATCATTATCGAGGAAGAGGAAGAGGACAGCATCAGCCTGCT

GAGCGACGGCCCCACCCACCAGGTGCTGCAGGTGGAGGCCGACATCCACGGCCC

ACCCAGCGTGTCCAGCTCCAGCTGGAGCATCCCACACGCCAGCGACTTCGACGT

GGACAGCCTGAGCATCCTGGACACCCTGGAGGGCGCCAGCGTGACCTCCGGCGC

CACCAGCGCCGAGACCAACAGCTACTTCGCCAAGAGCATGGAGTTCCTGGCCAG

GCCCGTGCCAGCTCCCAGGACCGTGTTCAGGAACCCACCCCACCCAGCTCCCAG

GACCAGGACCCCAAGCCTGGCTCCCAGCAGGGCCTGCAGCAGGACCAGCCTGGT

GAGCACCCCACCCGGCGTGAACAGGGTGATCACCAGGGAGGAACTGGAGGCCCT

GACACCCAGCAGGACCCCCAGCAGGTCCGTGAGCAGGACTAGTCTGGTGTCCAA

CCCACCCGGCGTGAACAGGGTGATCACCAGGGAGGAATTCGAGGCCTTCGTGGC

CCAGCAACAGAGACGGTTCGACGCCGGCGCCTACATCTTCAGCAGCGACACCGG

CCAGGGACACCTGCAGCAAAAGAGCGTGAGGCAGACCGTGCTGAGCGAGGTGG

TGCTGGAGAGGACCGAGCTGGAAATCAGCTACGCCCCCAGGCTGGACCAGGAGA

AGGAGGAACTGCTCAGGAAGAAACTGCAGCTGAACCCCACCCCAGCCAACAGG

AGCAGGTACCAGAGCAGGAAGGTGGAGAACATGAAGGCCATCACCGCCAGGCG

GATCCTGCAGGGCCTGGGACACTACCTGAAGGCCGAGGGCAAGGTGGAGTGCTA

CAGGACCCTGCACCCCGTGCCACTGTACAGCTCCAGCGTGAACAGGGCCTTCTCC

AGCCCCAAGGTGGCCGTGGAGGCCTGCAACGCTATGCTGAAGGAGAACTTCCCC

ACCGTGGCCAGCTACTGCATCATCCCCGAGTACGACGCCTACCTGGACATGGTGG

ACGGCGCCAGCTGCTGCCTGGACACCGCCAGCTTCTGCCCCGCCAAGCTGAGGA

GCTTCCCCAAGAAACACAGCTACCTGGAGCCCACCATCAGGAGCGCCGTGCCCA

GCGCCATCCAGAACACCCTGCAGAACGTGCTGGCCGCTGCCACCAAGAGGAACT

GCAACGTGACCCAGATGAGGGAGCTGCCCGTGCTGGACAGCGCTGCCTTCAACG

TGGAGTGCTTCAAGAAATACGCCTGCAACAACGAGTACTGGGAGACCTTCAAGG

AGAACCCCATCAGGCTGACCGAAGAGAACGTGGTGAACTACATCACCAAGCTGA

AGGGCCCCAAGGCCGCTGCCCTGTTCGCTAAGACCCACAACCTGAACATGCTGC

AGGACATCCCAATGGACAGGTTCGTGATGGACCTGAAGAGGGACGTGAAGGTGA

CACCCGGCACCAAGCACACCGAGGAGAGGCCCAAGGTGCAGGTGATCCAGGCC

GCTGACCCACTGGCCACCGCCTACCTGTGCGGCATCCACAGGGAGCTGGTGAGG

CGGCTGAACGCCGTGCTGCTGCCCAACATCCACACCCTGTTCGACATGAGCGCCG

AGGACTTCGACGCCATCATCGCCGAGCACTTCCAGCCCGGCGACTGCGTGCTGG

AGACCGACATCGCCAGCTTCGACAAGAGCGAGGATGACGCTATGGCCCTGACCG

CTCTGATGATCCTGGAGGACCTGGGCGTGGACGCCGAGCTGCTCACCCTGATCGA

GGCTGCCTTCGGCGAGATCAGCTCCATCCACCTGCCCACCAAGACCAAGTTCAAG

TTCGGCGCTATGATGAAAAGCGGAATGTTCCTGACCCTGTTCGTGAACACCGTGA

TCAACATTGTGATCGCCAGCAGGGTGCTGCGGGAGAGGCTGACCGGCAGCCCCT

-continued

GCGCTGCCTTCATCGGCGACGACAACATCGTGAAGGGCGTGAAAAGCGACAAGC

TGATGGCCGACAGGTGCGCCACCTGGCTGAACATGGAGGTGAAGATCATCGACG

CCGTGGTGGGCGAGAAGGCCCCCTACTTCTGCGGCGGATTCATCCTGTGCGACAG

CGTGACCGGCACCGCCTGCAGGGTGGCCGACCCCCTGAAGAGGCTGTTCAAGCT

GGGCAAGCCACTGGCCGCTGACGATGAGCACGACGATGACAGGCGGAGGGCCCT

GCACGAGGAAAGCACCAGGTGGAACAGGGTGGGCATCCTGAGCGAGCTGTGCA

AGGCCGTGGAGAGCAGGTACGAGACCGTGGGCACCAGCATCATCGTGATGGCTA

TGACCACACTGGCCAGCTCCGTCAAGAGCTTCTCCTACCTGAGGGGGGCCCCTAT

AACTCTCTACGGCTAACCTGAATGGACTACGACATAGTCTAGTCCGCCAAGGCCG

CCACCATGTTCGTCTTCCTGGTCCTGCTGCCTCTGGTCTCCTCACAGTGCGTCAAT

CTGACAACTCGGACTCAGCTGCCACCTGCTTATACTAATAGCTTCACCAGAGGCG

TGTACTATCCTGACAAGGTGTTTAGAAGCTCCGTGCTGCACTCTACACAGGATCT

GTTTCTGCCATTCTTTAGCAACGTGACCTGGTTCCACGCCATCCACGTGAGCGGC

ACCAATGGCACAAAGCGGTTCGACAATCCCGTGCTGCCTTTTAACGATGGCGTGT

ACTTCGCCTCTACCGAGAAGTCCAACATCATCAGAGGCTGGATCTTTGGCACCAC

ACTGGACTCCAAGACACAGTCTCTGCTGATCGTGAACAATGCCACCAACGTGGTC

ATCAAGGTGTGCGAGTTCCAGTTTTGTAATGATCCCTTCCTGGGCGTGTACTATC

ACAAGAACAATAAGAGCTGGATGGAGTCCGAGTTTAGAGTGTATTCTAGCGCCA

ACAACTGCACATTTGAGTACGTGAGCCAGCCTTTCCTGATGGACCTGGAGGGCA

AGCAGGGCAATTTCAAGAACCTGAGGGAGTTCGTGTTTAAGAATATCGACGGCT

ACTTCAAAATCTACTCTAAGCACACCCCCATCAACCTGGTGCGCGACCTGCCTCA

GGGCTTCAGCGCCCTGGAGCCCCTGGTGGATCTGCCTATCGGCATCAACATCACC

CGGTTTCAGACACTGCTGGCCCTGCACAGAAGCTACCTGACACCCGGCGACTCCT

CTAGCGGATGGACCGCCGGCGCTGCCGCCTACTATGTGGGCTACCTCCAGCCCCG

GACCTTCCTGCTGAAGTACAACGAGAATGGCACCATCACAGACGCAGTGGATTG

CGCCCTGGACCCCCTGAGCGAGACAAAGTGTACACTGAAGTCCTTTACCGTGGA

GAAGGGCATCTATCAGACATCCAATTTCAGGGTGCAGCCAACCGAGTCTATCGT

GCGCTTTCCTAATATCACAAACCTGTGCCCATTTGGCGAGGTGTTCAACGCAACC

CGCTTCGCCAGCGTGTACGCCTGGAATAGGAAGCGGATCAGCAACTGCGTGGCC

GACTATAGCGTGCTGTACAACTCCGCCTCTTTCAGCACCTTTAAGTGCTATGGCG

TGTCCCCCACAAAGCTGAATGACCTGTGCTTTACCAACGTCTACGCCGATTCTTT

CGTGATCAGGGGCGACGAGGTGCGCCAGATCGCCCCCGGCCAGACAGGCAAGAT

CGCAGACTACAATTATAAGCTGCCAGACGATTTCACCGGCTGCGTGATCGCCTGG

AACAGCAACAATCTGGATTCCAAAGTGGGCGGCAACTACAATTATCTGTACCGG

CTGTTTAGAAAGAGCAATCTGAAGCCCTTCGAGAGGGACATCTCTACAGAAATC

TACCAGGCCGGCAGCACCCCTTGCAATGGCGTGGAGGGCTTTAACTGTTATTTCC

CACTCCAGTCCTACGGCTTCCAGCCCACAAACGGCGTGGGCTATCAGCCTTACCG

CGTGGTGGTGCTGAGCTTTGAGCTGCTGCACGCCCCAGCAACAGTGTGCGGCCCC

AAGAAGTCCACCAATCTGGTGAAGAACAAGTGCGTGAACTTCAACTTCAACGGC

CTGACCGGCACAGGCGTGCTGACCGAGTCCAACAAGAAGTTCCTGCCATTTCAG

-continued

CAGTTCGGCAGGGACATCGCAGATACCACAGACGCCGTGCGCGACCCACAGACC

CTGGAGATCCTGGACATCACACCCTGCTCTTTCGGCGGCGTGAGCGTGATCACAC

CCGGCACCAATACAAGCAACCAGGTGGCCGTGCTGTATCAGGACGTGAATTGTA

CCGAGGTGCCCGTGGCTATCCACGCCGATCAGCTGACCCCAACATGGCGGGTGT

ACAGCACCGGCTCCAACGTCTTCCAGACAAGAGCCGGATGCCTGATCGGAGCAG

AGCACGTGAACAATTCCTATGAGTGCGACATCCCAATCGGCGCCGGCATCTGTGC

CTCTTACCAGACCCAGACAAACTCTCCCAGACGGGCCCGGAGCGTGGCCTCCCA

GTCTATCATCGCCTATACCATGTCCCTGGGCGCCGAGAACAGCGTGGCCTACTCT

AACAATAGCATCGCCATCCCAACCAACTTCACAATCTCTGTGACCACAGAGATCC

TGCCCGTGTCCATGACCAAGACATCTGTGGACTGCACAATGTATATCTGTGGCGA

TTCTACCGAGTGCAGCAACCTGCTGCTCCAGTACGGCAGCTTTTGTACCCAGCTG

AATAGAGCCCTGACAGGCATCGCCGTGGAGCAGGATAAGAACACACAGGAGGT

GTTCGCCCAGGTGAAGCAAATCTACAAGACCCCCCCTATCAAGGACTTTGGCGG

CTTCAATTTTTCCCAGATCCTGCCTGATCCATCCAAGCCTTCTAAGCGGAGCTTTA

TCGAGGACCTGCTGTTCAACAAGGTGACCCTGGCCGATGCCGGCTTCATCAAGCA

GTATGGCGATTGCCTGGGCGACATCGCAGCCAGGGACCTGATCTGCGCCCAGAA

GTTTAATGGCCTGACCGTGCTGCCACCCCTGCTGACAGATGAGATGATCGCACAG

TACACAAGCGCCCTGCTGGCCGGCACCATCACATCCGGATGGACCTTCGGCGCA

GGAGCCGCCCTCCAGATCCCCTTTGCCATGCAGATGGCCTATAGGTTCAACGGCA

TCGGCGTGACCCAGAATGTGCTGTACGAGAACCAGAAGCTGATCGCCAATCAGT

TTAACTCCGCCATCGGCAAGATCCAGGACAGCCTGTCCTCTACAGCCAGCGCCCT

GGGCAAGCTCCAGGATGTGGTGAATCAGAACGCCCAGGCCCTGAATACCCTGGT

GAAGCAGCTGAGCAGCAACTTCGGCGCCATCTCTAGCGTGCTGAATGACATCCT

GAGCCGGCTGGACAAGGTGGAGGCAGAGGTGCAGATCGACCGGCTGATCACCG

GCCGGCTCCAGAGCCTCCAGACCTATGTGACACAGCAGCTGATCAGGGCCGCCG

AGATCAGGGCCAGCGCCAATCTGGCAGCAACCAAGATGTCCGAGTGCGTGCTGG

GCCAGTCTAAGAGAGTGGACTTTTGTGGCAAGGGCTATCACCTGATGTCCTTCCC

TCAGTCTGCCCCACACGGCGTGGTGTTTCTGCACGTGACCTACGTGCCCGCCCAG

GAGAAGAACTTCACCACAGCCCCTGCCATCTGCCACGATGGCAAGGCCCACTTTC

CAAGGGAGGGCGTGTTCGTGTCCAACGGCACCCACTGGTTTGTGACACAGCGCA

ATTTCTACGAGCCCCAGATCATCACCACAGACAACACCTTCGTGAGCGGCAACTG

TGACGTGGTCATCGGCATCGTGAACAATACCGTGTATGATCCACTCCAGCCCGAG

CTGGACAGCTTTAAGGAGGAGCTGGATAAGTATTTCAAGAATCACACCTCCCCTG

ACGTGGATCTGGGCGACATCAGCGGCATCAATGCCTCCGTGGTGAACATCCAGA

AGGAGATCGACCGCCTGAACGAGGTGGCTAAGAATCTGAACGAGAGCCTGATCG

ACCTCCAGGAGCTGGGCAAGTATGAGCAGTACATCAAGTGGCCCTGGTACATCT

GGCTGGGCTTCATCGCCGGCCTGATCGCCATCGTGATGGTGACCATCATGCTGTG

CTGTATGACATCCTGCTGTTCTTGCCTGAAGGGCTGCTGTAGCTGTGGCTCCTGCT

GTAAGTTTGACGAGGATGACTCTGAACCTGTGCTGAAGGGCGTGAAGCTGCATT

ACACCTAAACTCGAGTATGTTACGTGCAAAGGTGATTGTCACCCCCCGAAAGAC

CATATTGTGACACACCCTCAGTATCACGCCCAAACATTTACAGCCGCGGTGTCAA

-continued

AAACCGCGTGGACGTGGTTAACATCCCTGCTGGGAGGATCAGCCGTAATTATTAT

AATTGGCTTGGTGCTGGCTACTATTGTGGCCATGTACGTGCTGACCAACCAGAAA

CATAATTGAATACAGCAGCAATTGGCAAGCTGCTTACATAGAACTCGCGGCGAT

TGGCATGCCGCCTTAAAATTTTTATTTTATTTTTTCTTTTCTTTTCCGAATCGGATT

TTGTTTTTAATATTTCAAAAAAAAAAAAAAAAAAAAAAAAAAATCTAGAAAAAAAA

AAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAA

SEQ ID NO: 79

MEKVHVDIEEDSPFLRALQRSFPQFEVEAKQVTDNDHANARAFSHLASKLIETEVDP

SDTILDIGSAPARRMYSKHKYHCICPMRCAEDPDRLYKYATKLKKNCKEITDKELDK

KMKELAAVMSDPDLETETMCLHDDESCRYEGQVAVYQDVYAVDGPTSLYHQANK

GVRVAYWIGFDTTPFMFKNLAGAYPSYSTNWADETVLTARNIGLCSSDVMERSRRG

MSILRKKYLKPSNNVLFSVGSTIYHEKRDLLRSWHLPSVFHLRGKQNYTCRCETIVSC

DGYVVKRIAISPGLYGKPSGYAATMHREGFLCCKVTDTLNGERVSFPVCTYVPATLC

DQMTGILATDVSADDAQKLLVGLNQRIVVNGRTQRNTNTMKNYLLPVVAQAFARW

AKEYKEDQEDERPLGLRDRQLVMGCCWAFRRHKITSIYKRPDTQTIIKVNSDFHSFV

LPRIGSNTLEIGLRTRIRKMLEEHKEPSPLITAEDVQEAKCAADEAKEVREAEELRAA

LPPLAADVEEPTLEADVDLMLQEAGAGSVETPRGLIKVTSYDGEDKIGSYAVLSPQA

VLKSEKLSCIHPLAEQVIVITHSGRKGRYAVEPYHGKVVVPEGHAIPVQDFQALSESA

TIVYNEREFVNRYLHHIATHGGALNTDEEYYKTVKPSEHDGEYLYDIDRKQCVKKEL

VTGLGLTGELVDPPFHEFAYESLRTRPAAPYQVPTIGVYGVPGSGKSGIIKSAVTKKD

LVVSAKKENCAEIIRDVKKMKGLDVNARTVDSVLLNGCKHPVETLYIDEAFACHAG

TLRALIAIIRPKKAVLCGDPKQCGFFNMMCLKVHFNHEICTQVFHKSISRRCTKSVTS

VVSTLFYDKKMRTTNPKETKIVIDTTGSTKPKQDDLILTCFRGWVKQLQIDYKGNEI

MTAAASQGLTRKGVYAVRYKVNENPLYAPTSEHVNVLLTRTEDRIVWKTLAGDPW

IKTLTAKYPGNFTATIEEWQAEHDAIMRHILERPDPTDVFQNKANVCWAKALVPVL

KTAGIDMTTEQWNTVDYFETDKAHSAEIVLNQLCVRFFGLDLDSGLFSAPTVPLSIR

NNHWDNSPSPNMYGLNKEVVRQLSRRYPQLPRAVATGRVYDMNTGTLRNYDPRIN

LVPVNRRLPHALVLHHNEHPQSDFSSFVSKLKGRTVLVVGEKLSVPGKMVDWLSDR

PEATFRARLDLGIPGDVPKYDIIFVNVRTPYKYHHYQQCEDHAIKLSMLTKKACLHL

NPGGTCVSIGYGYADRASESIIGAIARLFKFSRVCKPKSSLEETEVLFVFIGYDRKART

HNPYKLSSTLTNIYTGSRLHEAGCAPSYHVVRGDIATATEGVIINAANSKGQPGGGV

CGALYKKFPESFDLQPIEVGKARLVKGAAKHIIHAVGPNFNKVSEVEGDKQLAEAYE

SIAKIVNDNNYKSVAIPLLSTGIFSGNKDRLTQSLNHLLTALDTTDADVAIYCRDKKW

EMTLKEAVARREAVEEICISDDSSVTEPDAELVRVHPKSSLAGRKGYSTSDGKTFSYL

EGTKFHQAAKDIAEINAMWPVATEANEQVCMYILGESMSSIRSKCPVEESEASTPPST

LPCLCIHAMTPERVQRLKASRPEQITVCSSFPLPKYRITGVQKIQCSQPILFSPKVPAYI

HPRKYLVETPPVDETPEPSAENQSTEGTPEQPPLITEDETRTRTPEPIIIEEEEEDSISLLS

DGPTHQVLQVEADIHGPPSVSSSSWSIPHASDFDVDSLSILDTLEGASVTSGATSAETN

SYFAKSMEFLARPVPAPRTVFRNPPHPAPRTRTPSLAPSRACSRTSLVSTPPGVNRVIT

REELEALTPSRTPSRSVSRTSLVSNPPGVNRVITREEFEAFVAQQQRRFDAGAYIFSSD

-continued

TGQGHLQQKSVRQTVLSEVVLERTELEISYAPRLDQEKEELLRKKLQLNPTPANRSR
YQSRKVENMKAITARRILQGLGHYLKAEGKVECYRTLHPVPLYSSSVNRAFSSPKVA
VEACNAMLKENFPTVASYCIIPEYDAYLDMVDGASCCLDTASFCPAKLRSFPKKHSY
LEPTIRSAVPSAIQNTLQNVLAAATKRNCNVTQMRELPVLDSAAFNVECFKKYACNN
EYWETFKENPIRLTEENVVNYITKLKGPKAAALFAKTHNLNMLQDIPMDRFVMDLK
RDVKVTPGTKHTEERPKVQVIQAADPLATAYLCGIHRELVRRLNAVLLPNIHTLFDM
SAEDFDAIIAEHFQPGDCVLETDIASFDKSEDDAMALTALMILEDLGVDAELLTLIEA
AFGEISSIHLPTKTKFKFGAMMKSGMFLTLFVNTVINIVIASRVLRERLTGSPCAAFIG
DDNIVKGVKSDKLMADRCATWLNMEVKIIDAVVGEKAPYFCGGFILCDSVTGTACR
VADPLKRLFKLGKPLAADDEHDDDRRRALHEESTRWNRVGILSELCKAVESRYETV
GTSIIVMAMTTLASSVKSFSYLRGAPITLYG

SEQ ID NO: 80

MPEKVHVDIEEDSPFLRALQRSFPQFEVEAKQVTDNDHANARAFSHLASKLIETEVD
PSDTILDIGSAPARRMYSKHKYHCICPMRCAEDPDRLYKYATKLKKNCKEITDKELD
KKMKELAAVMSDPDLETETMCLHDDESCRYEGQVAVYQDVYAVDGPTSLYHQAN
KGVRVAYWIGFDTTPFMFKNLAGAYPSYSTNWADETVLTARNIGLCSSDVMERSRR
GMSILRKKYLKPSNNVLFSVGSTIYHEKRDLLRSWHLPSVFHLRGKQNYTCRCETIVS
CDGYVVKRIAISPGLYGKPSGYAATMHREGFLCCKVTDTLNGERVSFPVCTYVPATL
CDQMTGILATDVSADDAQKLLVGLNQRIVVNGRTQRNTNTMKNYLLPVVAQAFAR
WAKEYKEDQEDERPLGLRDRQLVMGCCWAFRRHKITSIYKRPDTQTIIKVNSDFHSF
VLPRIGSNTLEIGLRTRIRKMLEEHKEPSPLITAEDVQEAKCAADEAKEVREAEELRA
ALPPLAADVEEPTLEADVDLMLQEAGAGSVETPRGLIKVTSYDGEDKIGSYAVLSPQ
AVLKSEKLSCIHPLAEQVIVITHSGRKGRYAVEPYHGKVVVPEGHAIPVQDFQALSES
ATIVYNEREFVNRYLHHIATHGGALNTDEEYYKTVKPSEHDGEYLYDIDRKQCVKK
ELVTGLGLTGELVDPPFHEFAYESLRTRPAAPYQVPTIGVYGVPGSGKSGIIKSAVTK
KDLVVSAKKENCAEIIRDVKKMKGLDVNARTVDSVLLNGCKHPVETLYIDEAFACH
AGTLRALIAIIRPKKAVLCGDPKQCGFFNMMCLKVHFNHEICTQVFHKSISRRCTKSV
TSVVSTLFYDKKMRTTNPKETKIVIDTTGSTKPKQDDLILTCFRGWVKQLQIDYKGN
EIMTAAASQGLTRKGVYAVRYKVNENPLYAPTSEHVNVLLTRTEDRIVWKTLAGDP
WIKTLTAKYPGNFTATIEEWQAEHDAIMRHILERPDPTDVFQNKANVCWAKALVPV
LKTAGIDMTTEQWNTVDYFETDKAHSAEIVLNQLCVRFFGLDLDSGLFSAPTVPLSIR
NNHWDNSPSPNMYGLNKEVVRQLSRRYPQLPRAVATGRVYDMNTGTLRNYDPRIN
LVPVNRRLPHALVLHHNEHPQSDFSSFVSKLKGRTVLVVGEKLSVPGKMVDWLSDR
PEATFRARLDLGIPGDVPKYDIIFVNVRTPYKYHHYQQCEDHAIKLSMLTKKACLHL
NPGGTCVSIGYGYADRASESIIGAIARLFKFSRVCKPKSSLEETEVLFVFIGYDRKART
HNPYKLSSTLTNIYTGSRLHEAGCAPSYHVVRGDIATATEGVIINAANSKGQPGGGV
CGALYKKFPESFDLQPIEVGKARLVKGAAKHIIHAVGPNFNKVSEVEGDKQLAEAYE
SIAKIVNDNNYKSVAIPLLSTGIFSGNKDRLTQSLNHLLTALDTTDADVAIYCRDKKW
EMTLKEAVARREAVEEICISDDSSVTEPDAELVRVHPKSSLAGRKGYSTSDGKTFSYL
EGTKFHQAAKDIAEINAMWPVATEANEQVCMYILGESMSSIRSKCPVEESEASTPPST
LPCLCIHAMTPERVQRLKASRPEQITVCSSFPLPKYRITGVQKIQCSQPILFSPKVPAYI

-continued

HPRKYLVETPPVDETPEPSAENQSTEGTPEQPPLITEDETRTRTPEPIIIEEEEEDSISLLS

DGPTHQVLQVEADIHGPPSVSSSSWSIPHASDFDVDSLSILDTLEGASVTSGATSAETN

SYFAKSMEFLARPVPAPRTVFRNPPHPAPRTRTPSLAPSRACSRTSLVSTPPGVNRVIT

REELEALTPSRTPSRSVSRTSLVSNPPGVNRVITREEFEAFVAQQQRRFDAGAYIFSSD

TGQGHLQQKSVRQTVLSEVVLERTELEISYAPRLDQEKEELLRKKLQLNPTPANRSR

YQSRKVENMKAITARRILQGLGHYLKAEGKVECYRTLHPVPLYSSSVNRAFSSPKVA

VEACNAMLKENFPTVASYCIIPEYDAYLDMVDGASCCLDTASFCPAKLRSFPKKHSY

LEPTIRSAVPSAIQNTLQNVLAAATKRNCNVTQMRELPVLDSAAFNVECFKKYACNN

EYWETFKENPIRLTEENVVNYITKLKGPKAAALFAKTHNLNMLQDIPMDRFVMDLK

RDVKVTPGTKHTEERPKVQVIQAADPLATAYLCGIHRELVRRLNAVLLPNIHTLFDM

SAEDFDAIIAEHFQPGDCVLETDIASFDKSEDDAMALTALMILEDLGVDAELLTLIEA

AFGEISSIHLPTKTKFKFGAMMKSGMFLTLFVNTVINIVIASRVLRERLTGSPCAAFIG

DDNIVKGVKSDKLMADRCATWLNMEVKIIDAVVGEKAPYFCGGFILCDSVTGTACR

VADPLKRLFKLGKPLAADDEHDDDRRRALHEESTRWNRVGILSELCKAVESRYETV

GTSIIVMAMTTLASSVKSFSYLRGAPITLYG

SEQ ID NO: 81

MEKVHVDIEEDSPFLRALQRSFPQFEVEAKQVTDNDHANARAFSHLASKLIETEVDP

SDTILDIGSAPARRMYSKHKYHCICPMRCAEDPDRLYKYATKLKKNCKEITDKELDK

KMKELAAVMSDPDLETETMCLHDDESCRYEGQVAVYQDVYAVDGPTSLYHQANK

GVRVAYWIGFDTTPFMFKNLAGAYPSYSTNWADETVLTARNIGLCSSDVMERSRRG

MSILRKKYLKPSNNVLFSVGSTIYHEKRDLLRSWHLPSVFHLRGKQNYTCRCETIVSC

DGYVVKRIAISPGLYGKPSGYAATMHREGFLCCKVTDTLNGERVSFPVCTYVPATLC

DQMTGILATDVSADDAQKLLVGLNQRIVVNGRTQRNTNTMKNYLLPVVAQAFARW

AKEYKEDQEDERPLGLRDRQLVMGCCWAFRRHKITSIYKRPDTQTIIKVNSDFHSFV

LPRIGSNTLEIGLRTRIRKMLEEHKEPSPLITAEDIQEAKCAADEAKEVREAEELRAAL

PPLAADFEEPTLEADVDLMLQEAGAGSVETPRGLIKVTSYAGEDKIGSYAVLSPQAV

LKSEKLSCIHPLAEQVIVITHSGRKGRYAVEPYHGKVVVPEGHAIPVQDFQALSESAT

IVYNEREFVNRYLHHIATHGGALNTDEEYYKTVKPSEHDGEYLYDIDRKQCVKKEL

VTGLGLTGELVDPPFHEFAYESLRTRPAAPYQVPTIGVYGVPGSGKSGIIKSAVTKKD

LVVSAKKENCAEIIRDVKKMKGLDVNARTVDSVLLNGCKHPVETLYIDEAFACHAG

TLRALIAIIRPKKAVLCGDPKQCGFFNMMCLKVHFNHEICTQVFHKSISRRCTKSVTS

VVSTLFYDKRMRTTNPKETKIVIDTTGSTKPKQDDLILTCFRGWVKQLQIDYKGNEI

MTAAASQGLTRKGVYAVRYKVNENPLYAPTSEHVNVLLTRTEDRIVWKTLAGDPW

IKILTAKYPGNFTATIEEWQAEHDAIMRHILERPDPTDVFQNKANVCWAKALVPVLK

TAGIDMTTEQWNTVDYFETDKAHSAEIVLNQLCVRFFGLDLDSGLFSAPTVPLSIRN

NHWDNSPSPNMYGLNKEVVRQLSRRYPQLPRAVATGRVYDMNTGTLRNYDPRINL

VPVNRRLPHALVLHHNEHPQSDFSSFVSKLKGRTVLVVGEKLSVPGKKVDWLSDQP

EATFRARLDLGIPGDVPKYDIVFINVRTPYKYHHYQQCEDHAIKLSMLTKKACLHLN

PGGTCVSIGYGYADRASESIIGAIARQFKFSRVCKPKSSHEETEVLFVFIGYDRKARTH

NPYKLSSTLTNIYTGSRLHEAGCAPSYHVVRGDIATATEGVIINAANSKGQPGGGVC

GALYKKFPESFDLQPIEVGKARLVKGAAKHIIHAVGPNFNKVSEVEGDKQLAEAYES

-continued

IAKIVNDNNYKSVAIPLLSTGIFSGNKDRLTQSLNHLLTALDTTDADVAIYCRDKKWE
MTLKEAVARREAVEEICISDDSSVTEPDAELVRVHPKSSLAGRKGYSTSDGKTFSYLE
GTKFHQAAKDIAEINAMWPVATEANEQVCMYILGESMSSIRSKCPVEESEASTPPSTL
PCLCIHAMTPERVQRLKASRPEQITVCSSFPLPKYRITGVQKIQCSQPILFSPKVPAYIH
PRKYLVETPPVEETPESPAENQSTEGTPEQPALVNVDATRTRMPEPIIIEEEEEDSISLL
SDGPTHQVLQVEADIHGSPSVSSSSWSIPHASDFDVDSLSILDTLDGASVTSGAVSAET
NSYFARSMEFRARPVPAPRTVFRNPPHPAPRTRTPPLAHSRASSRTSLVSTPPGVNRVI
TREELEALTPSRAPSRSASRTSLVSNPPGVNRVITREEFEAFVAQQQ*RFDAGAYIFSS
DTGQGHLQQKSVRQTVLSEVVLERTELEISYAPRLDQEKEELLRKKLQLNPTPANRS
RYQSRRVENMKAITARRILQGLGHYLKAEGKVECYRTLHPVPLYSSSVNRAFSSPKV
AVEACNAMLKENFPTVASYCIIPEYDAYLDMVDGASCCLDTASFCPAKLRSFPKKHS
YLEPTIRSAVPSAIQNTLQNVLAAATKRNCNVTQMRELPVLDSAAFNVECFKKYACN
NEYWETFKENPIRLTEENVVNYITKLKGPKAAALFAKTHNLNMLQDIPMDRFVMDL
KRDVKVTPGTKHTEERPKVQVIQAADPLATADLCGIHRELVRRLNAVLLPNIHTLFD
MSAEDFDAIIAEHFQPGDCVLETDIASFDKSEDDAMALTALMILEDLGVDAELLTLIE
AAFGEISSIHLPTKTKFKFGAMMKSGMFLTLFVNTVINIVIASRVLRERLTGSPCAAFI
GDDNIVKGVKSDKLMADRCATWLNMEVKIIDAVVGEKAPYFCGGFILCDSVTGTAC
RVADPLKRLFKLGKPLAVDDEHDDDRRRALHEESTRWNRVGILPELCKAVESRYET
VGTSIIVMAMTTLASSVKSFSYLRGAPITLYG*

SEQ ID NO: 126

AGGAAACTTAAGTCAACACAACATATACAAAACAAACGAATCTCAAGCAATCAA
GCATTCTACTTCTATTGCAGCAATTTAAATCATTTCTTTTAAAGCAAAAGCAATTT
TCTGAAAATTTTCACCATTTACGAACGATAGCCACCATGTTCGTCTTCCTGGTCCT
GCTGCCTCTGGTCTCCTCACAGTGCGTCAATCTGACAACTCGGACTCAGCTGCCA
CCTGCTTATACTAATAGCTTCACCAGAGGCGTGTACTATCCTGACAAGGTGTTTA
GAAGCTCCGTGCTGCACTCTACACAGGATCTGTTTCTGCCATTCTTTAGCAACGT
GACCTGGTTCCACGCCATCCACGTGAGCGGCACCAATGGCACAAAGCGGTTCGA
CAATCCCGTGCTGCCTTTTAACGATGGCGTGTACTTCGCCTCTACCGAGAAGTCC
AACATCATCAGAGGCTGGATCTTTGGCACCACACTGGACTCCAAGACACAGTCTC
TGCTGATCGTGAACAATGCCACCAACGTGGTCATCAAGGTGTGCGAGTTCCAGTT
TTGTAATGATCCCTTCCTGGGCGTGTACTATCACAAGAACAATAAGAGCTGGATG
GAGTCCGAGTTTAGAGTGTATTCTAGCGCCAACAACTGCACATTTGAGTACGTGA
GCCAGCCTTTCCTGATGGACCTGGAGGGCAAGCAGGGCAATTTCAAGAACCTGA
GGGAGTTCGTGTTTAAGAATATCGACGGCTACTTCAAAATCTACTCTAAGCACAC
CCCCATCAACCTGGTGCGCGACCTGCCTCAGGGCTTCAGCGCCCTGGAGCCCCTG
GTGGATCTGCCTATCGGCATCAACATCACCCGGTTTCAGACACTGCTGGCCCTGC
ACAGAAGCTACCTGACACCCGGCGACTCCTCTAGCGGATGGACCGCCGGCGCTG
CCGCCTACTATGTGGGCTACCTCCAGCCCCGGACCTTCCTGCTGAAGTACAACGA
GAATGGCACCATCACAGACGCAGTGGATTGCGCCCTGGACCCCCTGAGCGAGAC
AAAGTGTACACTGAAGTCCTTTACCGTGGAGAAGGGCATCTATCAGACATCCAA
TTTCAGGGTGCAGCCAACCGAGTCTATCGTGCGCTTTCCTAATATCACAAACCTG

-continued

TGCCCATTTGGCGAGGTGTTCAACGCAACCCGCTTCGCCAGCGTGTACGCCTGGA

ATAGGAAGCGGATCAGCAACTGCGTGGCCGACTATAGCGTGCTGTACAACTCCG

CCTCTTTCAGCACCTTTAAGTGCTATGGCGTGTCCCCCACAAAGCTGAATGACCT

GTGCTTTACCAACGTCTACGCCGATTCTTTCGTGATCAGGGGCGACGAGGTGCGC

CAGATCGCCCCCGGCCAGACAGGCAAGATCGCAGACTACAATTATAAGCTGCCA

GACGATTTCACCGGCTGCGTGATCGCCTGGAACAGCAACAATCTGGATTCCAAA

GTGGGCGGCAACTACAATTATCTGTACCGGCTGTTTAGAAAGAGCAATCTGAAG

CCCTTCGAGAGGGACATCTCTACAGAAATCTACCAGGCCGGCAGCACCCCTTGC

AATGGCGTGGAGGGCTTTAACTGTTATTTCCCACTCCAGTCCTACGGCTTCCAGC

CCACAAACGGCGTGGGCTATCAGCCTTACCGCGTGGTGGTGCTGAGCTTTGAGCT

GCTGCACGCCCCAGCAACAGTGTGCGGCCCCAAGAAGTCCACCAATCTGGTGAA

GAACAAGTGCGTGAACTTCAACTTCAACGGCCTGACCGGCACAGGCGTGCTGAC

CGAGTCCAACAAGAAGTTCCTGCCATTTCAGCAGTTCGGCAGGGACATCGCAGA

TACCACAGACGCCGTGCGCGACCCACAGACCCTGGAGATCCTGGACATCACACC

CTGCTCTTTCGGCGGCGTGAGCGTGATCACACCCGGCACCAATACAAGCAACCA

GGTGGCCGTGCTGTATCAGGACGTGAATTGTACCGAGGTGCCCGTGGCTATCCAC

GCCGATCAGCTGACCCCAACATGGCGGGTGTACAGCACCGGCTCCAACGTCTTCC

AGACAAGAGCCGGATGCCTGATCGGAGCAGAGCACGTGAACAATTCCTATGAGT

GCGACATCCCAATCGGCGCCGGCATCTGTGCCTCTTACCAGACCCAGACAAACTC

TCCCAGACGGGCCCGGAGCGTGGCCTCCCAGTCTATCATCGCCTATACCATGTCC

CTGGGCGCCGAGAACAGCGTGGCCTACTCTAACAATAGCATCGCCATCCCAACC

AACTTCACAATCTCTGTGACCACAGAGATCCTGCCCGTGTCCATGACCAAGACAT

CTGTGGACTGCACAATGTATATCTGTGGCGATTCTACCGAGTGCAGCAACCTGCT

GCTCCAGTACGGCAGCTTTTGTACCCAGCTGAATAGAGCCCTGACAGGCATCGCC

GTGGAGCAGGATAAGAACACACAGGAGGTGTTCGCCCAGGTGAAGCAAATCTAC

AAGACCCCCCCTATCAAGGACTTTGGCGGCTTCAATTTTTCCCAGATCCTGCCTG

ATCCATCCAAGCCTTCTAAGCGGAGCTTTATCGAGGACCTGCTGTTCAACAAGGT

GACCCTGGCCGATGCCGGCTTCATCAAGCAGTATGGCGATTGCCTGGGCGACATC

GCAGCCAGGGACCTGATCTGCGCCCAGAAGTTTAATGGCCTGACCGTGCTGCCA

CCCCTGCTGACAGATGAGATGATCGCACAGTACACAAGCGCCCTGCTGGCCGGC

ACCATCACATCCGGATGGACCTTCGGCGCAGGAGCCGCCCTCCAGATCCCCTTTG

CCATGCAGATGGCCTATAGGTTCAACGGCATCGGCGTGACCCAGAATGTGCTGT

ACGAGAACCAGAAGCTGATCGCCAATCAGTTTAACTCCGCCATCGGCAAGATCC

AGGACAGCCTGTCCTCTACAGCCAGCGCCCTGGGCAAGCTCCAGGATGTGGTGA

ATCAGAACGCCCAGGCCCTGAATACCCTGGTGAAGCAGCTGAGCAGCAACTTCG

GCGCCATCTCTAGCGTGCTGAATGACATCCTGAGCCGGCTGGACAAGGTGGAGG

CAGAGGTGCAGATCGACCGGCTGATCACCGGCCGGCTCCAGAGCCTCCAGACCT

ATGTGACACAGCAGCTGATCAGGGCCGCCGAGATCAGGGCCAGCGCCAATCTGG

CAGCAACCAAGATGTCCGAGTGCGTGCTGGGCCAGTCTAAGAGAGTGGACTTTT

GTGGCAAGGGCTATCACCTGATGTCCTTCCCTCAGTCTGCCCCACACGGCGTGGT

-continued

GTTTCTGCACGTGACCTACGTGCCCGCCCAGGAGAAGAACTTCACCACAGCCCCT

GCCATCTGCCACGATGGCAAGGCCCACTTTCCAAGGGAGGGCGTGTTCGTGTCCA

ACGGCACCCACTGGTTTGTGACACAGCGCAATTTCTACGAGCCCCAGATCATCAC

CACAGACAACACCTTCGTGAGCGGCAACTGTGACGTGGTCATCGGCATCGTGAA

CAATACCGTGTATGATCCACTCCAGCCCGAGCTGGACAGCTTTAAGGAGGAGCT

GGATAAGTATTTCAAGAATCACACCTCCCCTGACGTGGATCTGGGCGACATCAGC

GGCATCAATGCCTCCGTGGTGAACATCCAGAAGGAGATCGACCGCCTGAACGAG

GTGGCTAAGAATCTGAACGAGAGCCTGATCGACCTCCAGGAGCTGGGCAAGTAT

GAGCAGTACATCAAGTGGCCCTGGTACATCTGGCTGGGCTTCATCGCCGGCCTGA

TCGCCATCGTGATGGTGACCATCATGCTGTGCTGTATGACATCCTGCTGTTCTTGC

CTGAAGGGCTGCTGTAGCTGTGGCTCCTGCTGTAAGTTTGACGAGGATGACTCTG

AACCTGTGCTGAAGGGCGTGAAGCTGCATTACACCTAAACTCGAGCTAGTGACT

GACTAGGATCTGGTTACCACTAAACCAGCCTCAAGAACACCCGAATGGAGTCTC

TAAGCTACATAATACCAACTTACACTTACAAAATGTTGTCCCCCAAAATGTAGCC

ATTCGTATCTGCTCCTAATAAAAAGAAAGTTTCTTCACATTCTAGAAAAAAAAAA

AAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAA

SEQ ID NO: 82

AGGAAACTTAAGTCAACACAACATATACAAAACAAACGAATCTCAAGCAATCAA

GCATTCTACTTCTATTGCAGCAATTTAAATCATTTCTTTTAAAGCAAAAGCAATTT

TCTGAAAATTTTCACCATTTACGAACGATAGCCACC

SEQ ID NO: 83

ACTCGAGCTAGTGACTGACTAGGATCTGGTTACCACTAAACCAGCCTCAAGAAC

ACCCGAATGGAGTCTCTAAGCTACATAATACCAACTTACACTTACAAAATGTTGT

CCCCCAAAATGTAGCCATTCGTATCTGCTCCTAATAAAAAGAAAGTTTCTTCACA

TTCTAGAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAA

AA

SEQ ID NO: 1

GAGGAAACTT AAGAUGGG

SEQ ID NO: 2

GGAUGGG

SEQ ID NO: 3

GGAUAGG

SEQ ID NO: 4

GGAGAGG

SEQ ID NO: 58

GGGAUGGG

SEQ ID NO: 59

GAGAGG

SEQ ID NO: 60

GAGGG

SEQ ID NO: 61

GAGAUGGG

SEQ ID NO: 62

GAGUGG

-continued

SEQ ID NO: 63

GAGGGG

SEQ ID NO: 64

GAGUAGG

SEQ ID NO: 65

GAGUGGG (RNA sequence for a construct with two subgenomic promoters, Luc, and E3L)

SEQ ID NO: 127 atgggcggcgcatgagagaagcccagaccaattacctacccaaaatggagaaagttcacgttgacatcgaggaagacagcccatt
cctcagagctttgcagcggagcttcccgcagtttgaggtagaagccaagcaggtcactgataatgaccatgctaatgccagagcgtt
ttcgcatctggcttcaaaactgatcgaaacggaggtggacccatccgacacgatccttgacattggaagtgcgcccgcccgcagaat
gtattctaagcacaagtatcattgtatctgtccgatgagatgtgcggaagatccggacagattgtataagtatgcaactaagctgaa
gaaaaactgtaaggaaataactgataaggaattggacaagaaaatgaaggagctggccgccgtcatgagcgaccctgacctgga
aactgagactatgtgcctccacgacgacgagtcgtgtcgctacgaagggcaagtcgctgtttaccaggatgtatacgcCGTCGAC
GGCCCCACCAGCCTGTACCACCAGGCCAACAAGGGCGTGAGGGTGGCCTACTGGATCGGCTTCGAC
ACCACACCCTTCATGTTCAAGAACCTGGCCGGCGCCTACCCCAGCTACAGCACCAACTGGGCCGACG
AGACCGTGCTGACCGCCAGGAACATCGGCCTGTGCAGCAGCGACGTGATGGAGAGGAGCCGGAGA
GGCATGAGCATCCTGAGGAAGAAATACCTGAAGCCCAGCAACAACGTGCTGTTCAGCGTGGGCAGC
ACCATCTACCACGAGAAGAGGGACCTGCTCAGGAGCTGGCACCTGCCCAGCGTGTTCCACCTGAGG
GGCAAGCAGAACTACACCTGCAGGTGCGAGACCATCGTGAGCTGCGACGGCTACGTGGTGAAGAG
GATCGCCATCAGCCCCGGCCTGTACGGCAAGCCCAGCGGCTACGCCGCTACAATGCACAGGGAGGG
CTTCCTGTGCTGCAAGGTGACCGACACCCTGAACGGCGAGAGGGTGAGCTTCCCCGTGTGCACCTA
CGTGCCCGCCACCCTGTGCGACCAGATGACCGGCATCCTGGCCACCGACGTGAGCGCCGACGACGC
CCAGAAGCTGCTCGTGGGCCTGAACCAGAGGATCGTGGTCAACGGCAGGACCCAGAGGAACACCA
ACACAATGAAGAACTACCTGCTGCCCGTGGTGGCCCAGGCTTTCGCCAGGTGGGCCAAGGAGTACA
AGGAGGACCAGGAAGACGAGAGGCCCCTGGGCCTGAGGGACAGGCAGCTGGTGATGGGCTGCTG
CTGGGCCTTCAGGCGGCACAAGATCACCAGCATCTACAAGAGGCCCGACACCCAGACCATCATCAA
GGTGAACAGCGACTTCCACAGCTTCGTGCTGCCCAGGATCGGCAGCAACACCCTGGAGATCGGCCT
GAGGACCCGGATCAGGAAGATGCTGGAGGAACACAAGGAGCCCAGCCCACTGATCACCGCCGAGG
ACGTGCAGGAGGCCAAGTGCGCTGCCGACGAGGCCAAGGAGGTGAGGGAGGCCGAGGAACTGAG
GGCCGCCCTGCCACCCCTGGCTGCCGACGTGGAGGAACCCACCCTGGAAGCCGACGTGGACCTGAT
GCTGCAGGAGGCCGGCGCCGGAAGCGTGGAGACACCCAGGGGCCTGATCAAGGTGACCAGCTACG
ACGGCGAGGACAAGATCGGCAGCTACGCCGTGCTGAGCCCACAGGCCGTGCTGAAGTCCGAGAAG
CTGAGCTGCATCCACCCACTGGCCGAGCAGGTGATCGTGATCACCCACAGCGGCAGGAAGGGCAG
GTACGCCGTGGAGCCCTACCACGGCAAGGTGGTCGTGCCCGAGGGCCACGCCATCCCCGTGCAGGA
CTTCCAGGCCCTGAGCGAGAGCGCCACCATCGTGTACAACGAGAGGGAGTTCGTGAACAGGTACCT
GCACCATATCGCCACCCACGGCGGAGCCCTGAACACCGACGAGGAATACTACAAGACCGTGAAGCC
CAGCGAGCACGACGGCGAGTACCTGTACGACATCGACAGGAAGCAGTGCGTGAAGAAAGAGCTGG
TGACCGGCCTGGGACTGACCGGCGAGCTGGTGGACCCACCCTTCCACGAGTTCGCCTACGAGAGCC
TGAGGACCAGACCCGCCGCTCCCTACCAGGTGCCCACCATCGGCGTGTACGGCGTGCCCGGCAGCG
GAAAGAGCGGCATCATCAAGAGCGCCGTGACCAAGAAAGACCTGGTGGTCAGCGCCAAGAAAGAG
AACTGCGCCGAGATCATCAGGGACGTGAAGAAGATGAAAGGCCTGGACGTGAACGCGCGCACCGT
GGACAGCGTGCTGCTGAACGGCTGCAAGCACCCCGTGGAGACCCTGTACATCGACGAGGCCTTCGC -continued

TTGCCACGCCGGCACCCTGAGGGCCCTGATCGCCATCATCAGGCCCAAGAAAGCCGTGCTGTGCGG

CGACCCCAAGCAGTGCGGCTTCTTCAACATGATGTGCCTGAAGGTGCACTTCAACCACGAGATCTGC

ACCCAGGTGTTCCACAAGAGCATCAGCAGGCGGTGCACCAAGAGCGTGACCAGCGTCGTGAGCACC

CTGTTCTACGACAAGAAAATGAGGACCACCAACCCCAAGGAGACCAAAATCGTGATCGACACCACA

GGCAGCACCAAGCCCAAGCAGGACGACCTGATCCTGACCTGCTTCAGGGGCTGGGTGAAGCAGCTG

CAGATCGACTACAAGGGCAACGAGATCATGACCGCCGCTGCCAGCCAGGGCCTGACCAGGAAGGG

CGTGTACGCCGTGAGGTACAAGGTGAACGAGAACCCACTGTACGCTCCCACCAGCGAGCACGTGAA

CGTGCTGCTGACCAGGACCGAGGACAGGATCGTGTGGAAGACCCTGGCCGGCGACCCCTGGATCA

AGACCCTGACCGCCAAGTACCCCGGCAACTTCACCGCCACCATCGAAGAGTGGCAGGCCGAGCACG

ACGCCATCATGAGGCACATCCTGGAGAGGCCCGACCCCACCGACGTGTTCCAGAACAAGGCCAACG

TGTGCTGGGCCAAGGCCCTGGTGCCCGTGCTGAAGACCGCCGGCATCGACATGACCACAGAGCAGT

GGAACACCGTGGACTACTTCGAGACCGACAAGGCCCACAGCGCCGAGATCGTGCTGAACCAGCTGT

GCGTGAGGTTCTTCGGCCTGGACCTGGACAGCGGCCTGTTCAGCGCCCCCACCGTGCCACTGAGCAT

CAGGAACAACCACTGGGACAACAGCCCCAGCCCAAACATGTACGGCCTGAACAAGGAGGTGGTCA

GGCAGCTGAGCAGGCGGTACCCACAGCTGCCCAGGGCCGTGGCCACCGGCAGGGTGTACGACATG

AACACCGGCACCCTGAGGAACTACGACCCCAGGATCAACCTGGTGCCCGTGAACAGGCGGCTGCCC

CACGCCCTGGTGCTGCACCACAACGAGCACCCACAGAGCGACTTCAGCTCCTTCGTGAGCAAGCTGA

AAGGCAGGACCGTGCTGGTCGTGGGCGAGAAGCTGAGCGTGCCCGGCAAGATGGTGGACTGGCTG

AGCGACAGGCCCGAGGCCACCTTCCGGGCCAGGCTGGACCTCGGCATCCCCGGCGACGTGCCCAAG

TACGACATCATCTTCGTGAACGTCAGGACCCCATACAAGTACCACCATTACCAGCAGTGCGAGGACC

ACGCCATCAAGCTGAGCATGCTGACCAAGAAGGCCTGCCTGCACCTGAACCCCGGAGGCACCTGCG

TGAGCATCGGCTACGGCTACGCCGACAGGGCCAGCGAGAGCATCATTGGCGCCATCGCCAGGCTGT

TCAAGTTCAGCAGGGTGTGCAAACCCAAGAGCAGCCTGGAGGAAACCGAGGTGCTGTTCGTGTTCA

TCGGCTACGACCGGAAGGCCAGGACCCACAACCCCTACAAGCTGAGCAGCACCCTGACAAACATCT

ACACCGGCAGCAGGCTGCACGAGGCCGGCTGCGCCCCCAGCTACCACGTGGTCAGGGGCGATATC

GCCACCGCCACCGAGGGCGTGATCATCAACGCTGCCAACAGCAAGGGCCAGCCCGGAGGCGGAGT

GTGCGGCGCCCTGTACAAGAAGTTCCCCGAGAGCTTCGACCTGCAGCCCATCGAGGTGGGCAAGGC

CAGGCTGGTGAAGGGCGCCGCTAAGCACATCATCCACGCCGTGGGCCCCAACTTCAACAAGGTGAG

CGAGGTGGAAGGCGACAAGCAGCTGGCCGAAGCCTACGAGAGCATCGCCAAGATCGTGAACGACA

ATAACTACAAGAGCGTGGCCATCCCACTGCTCAGCACCGGCATCTTCAGCGGCAACAAGGACAGGC

TGACCCAGAGCCTGAACCACCTGCTCACCGCCCTGGACACCACCGATGCCGACGTGGCCATCTACTG

CAGGGACAAGAAGTGGGAGATGACCCTGAAGGAGGCCGTGGCCAGGCGGGAGGCCGTGGAAGAG

ATCTGCATCAGCGACGACTCCAGCGTGACCGAGCCCGACGCCGAGCTGGTGAGGGTGCACCCCAAG

AGCTCCCTGGCCGGCAGGAAGGGCTACAGCACCAGCGACGGCAAGACCTTCAGCTACCTGGAGGG

CACCAAGTTCCACCAGGCCGCTAAGGACATCGCCGAGATCAACGCTATGTGGCCCGTGGCCACCGA

GGCCAACGAGCAGGTGTGCATGTACATCCTGGGCGAGAGCATGTCCAGCATCAGGAGCAAGTGCCC

CGTGGAGGAAAGCGAGGCCAGCACACCACCCAGCACCCTGCCCTGCCTGTGCATCCACGCTATGAC

ACCCGAGAGGGTGCAGCGGCTGAAGGCCAGCAGGCCCGAGCAGATCACCGTGTGCAGCTCCTTCCC

ACTGCCCAAGTACAGGATCACCGGCGTGCAGAAGATCCAGTGCAGCCAGCCCATCCTGTTCAGCCCA

AAGGTGCCCGCCTACATCCACCCCAGGAAGTACCTGGTGGAGACCCCACCCGTGGACGAGACACCC

GAGCCAAGCGCCGAGAACCAGAGCACCGAGGGCACACCCGAGCAGCCACCCCTGATCACCGAGGA

-continued

CGAGACAAGGACCCGGACCCCAGAGCCCATCATTATCGAGGAAGAGGAAGAGGACAGCATCAGCC

TGCTGAGCGACGGCCCCACCCACCAGGTGCTGCAGGTGGAGGCCGACATCCACGGCCCACCCAGCG

TGTCCAGCTCCAGCTGGAGCATCCCACACGCCAGCGACTTCGACGTGGACAGCCTGAGCATCCTGG

ACACCCTGGAGGGCGCCAGCGTGACCTCCGGCGCCACCAGCGCCGAGACCAACAGCTACTTCGCCA

AGAGCATGGAGTTCCTGGCCAGGCCCGTGCCAGCTCCCAGGACCGTGTTCAGGAACCCACCCCACC

CAGCTCCCAGGACCAGGACCCCAAGCCTGGCTCCCAGCAGGGCCTGCAGCAGGACCAGCCTGGTGA

GCACCCCACCCGGCGTGAACAGGGTGATCACCAGGGAGGAACTGGAGGCCCTGACACCCAGCAGG

ACCCCCAGCAGGTCCGTGAGCAGGACTAGTCTGGTGTCCAACCCACCCGGCGTGAACAGGGTGATC

ACCAGGGAGGAATTCGAGGCCTTCGTGGCCCAGCAACAGAGACGGTTCGACGCCGGCGCCTACATC

TTCAGCAGCGACACCGGCCAGGGACACCTGCAGCAAAAGAGCGTGAGGCAGACCGTGCTGAGCGA

GGTGGTGCTGGAGAGGACCGAGCTGGAAATCAGCTACGCCCCCAGGCTGGACCAGGAGAAGGAG

GAACTGCTCAGGAAGAAACTGCAGCTGAACCCCACCCCAGCCAACAGGAGCAGGTACCAGAGCAG

GAAGGTGGAGAACATGAAGGCCATCACCGCCAGGCGGATCCTGCAGGGCCTGGGACACTACCTGA

AGGCCGAGGGCAAGGTGGAGTGCTACAGGACCCTGCACCCCGTGCCACTGTACAGCTCCAGCGTGA

ACAGGGCCTTCTCCAGCCCCAAGGTGGCCGTGGAGGCCTGCAACGCTATGCTGAAGGAGAACTTCC

CCACCGTGGCCAGCTACTGCATCATCCCCGAGTACGACGCCTACCTGGACATGGTGGACGGCGCCA

GCTGCTGCCTGGACACCGCCAGCTTCTGCCCCGCCAAGCTGAGGAGCTTCCCCAAGAAACACAGCTA

CCTGGAGCCCACCATCAGGAGCGCCGTGCCCAGCGCCATCCAGAACACCCTGCAGAACGTGCTGGC

CGCTGCCACCAAGAGGAACTGCAACGTGACCCAGATGAGGGAGCTGCCCGTGCTGGACAGCGCTG

CCTTCAACGTGGAGTGCTTCAAGAAATACGCCTGCAACAACGAGTACTGGGAGACCTTCAAGGAGA

ACCCCATCAGGCTGACCGAAGAGAACGTGGTGAACTACATCACCAAGCTGAAGGGCCCCAAGGCCG

CTGCCCTGTTCGCTAAGACCCACAACCTGAACATGCTGCAGGACATCCCAATGGACAGGTTCGTGAT

GGACCTGAAGAGGGACGTGAAGGTGACACCCGGCACCAAGCACACCGAGGAGAGGCCCAAGGTG

CAGGTGATCCAGGCCGCTGACCCACTGGCCACCGCCTACCTGTGCGGCATCCACAGGGAGCTGGTG

AGGCGGCTGAACGCCGTGCTGCTGCCCAACATCCACACCCTGTTCGACATGAGCGCCGAGGACTTC

GACGCCATCATCGCCGAGCACTTCCAGCCCGGCGACTGCGTGCTGGAGACCGACATCGCCAGCTTC

GACAAGAGCGAGGATGACGCTATGGCCCTGACCGCTCTGATGATCCTGGAGGACCTGGGCGTGGA

CGCCGAGCTGCTCACCCTGATCGAGGCTGCCTTCGGCGAGATCAGCTCCATCCACCTGCCCACCAAG

ACCAAGTTCAAGTTCGGCGCTATGATGAAAAGCGGAATGTTCCTGACCCTGTTCGTGAACACCGTGA

TCAACATTGTGATCGCCAGCAGGGTGCTGCGGGAGAGGCTGACCGGCAGCCCCTGCGCTGCCTTCA

TCGGCGACGACAACATCGTGAAGGGCGTGAAAAGCGACAAGCTGATGGCCGACAGGTGCGCCACC

TGGCTGAACATGGAGGTGAAGATCATCGACGCCGTGGTGGGCGAGAAGGCCCCCTACTTCTGCGGC

GGATTCATCCTGTGCGACAGCGTGACCGGCACCGCCTGCAGGGTGGCCGACCCCCTGAAGAGGCTG

TTCAAGCTGGGCAAGCCACTGGCCGCTGACGATGAGCACGACGATGACAGGCGGAGGGCCCTGCA

CGAGGAAAGCACCAGGTGGAACAGGGTGGGCATCCTGAGCGAGCTGTGCAAGGCCGTGGAGAGC

AGGTACGAGACCGTGGGCACCAGCATCATCGTGATGGCTATGACCACACTGGCCAGCTCCGTCAAG

AGCTTCTCCTACCTGAGGGGGGCCCCTATAACTCTCTACGGCTAACCTGAATGGACTACGACATAGT

CTAgccaccATGagcaagatctacatcgacgagcggagcaacgccgagatcgtgtgcgaggccatcaagaccatcggcatcga gggcgccaccgccgcccagctgaccaggcagctgaacatggagaagcgggaggtgaacaaggccctgtacgacctgcagaggag cgctatggtgtactccagcgacgacatccctccccggtggttcatgaccaccgaggccgacaagcccgacgccgacgctatggccg -continued acgtgatcatcgacgacgtgagcagggagaagtccatgagggaggaccacaagagcttcgacgacgtgatccccgccaagaaga tcatcgactggaagggcgccaaccccgtgaccgtgatcaacgagtactgccagatcaccaggagggactggagcttccggatcga gagcgtgggccccagcaacagccccaccttctacgcctgcgtggacatcgacggcagggtgttcgacaaggccgacggcaagagc aagcgggacgccaagaacaacgccgccaagctggccgtggacaagctgctgggctacgtgatcatccggttcTAAactcgagcta gtgactgactaggatctggttaccactaaaccagcctcaagaacacccgaatggagtctctaagctacataataccaacttacactt acaaaatgttgtcccccaaaatgtagccattcgtatctgctcctaataaaaagaaagtttcttcacattctagAGCTCCGTCAAG

AGCTTCTCCTACCTGAGGGGGGCCCCTATAACTCTCTACGGCTAACCTGAATGGACTACGACATAGT

CTAGCCACCATGGAAGATGCCAAAAACATTAAGAAGGGCCCAGCGCCATTCTACCCACTCGAAGAC

GGGACCGCCGGCGAGCAGCTGCACAAAGCCATGAAGCGCTACGCCCTGGTGCCCGGCACCATCGCC

TTTACCGACGCACATATCGAGGTGGACATTACCTACGCCGAGTACTTCGAGATGAGCGTTCGGCTGG

CAGAAGCTATGAAGCGCTATGGGCTGAATACAAACCATCGGATCGTGGTGTGCAGCGAGAATAGCT

TGCAGTTCTTCATGCCCGTGTTGGGTGCCCTGTTCATCGGTGTGGCTGTGGCCCCAGCTAACGACAT

CTACAACGAGCGCGAGCTGCTGAACAGCATGGGCATCAGCCAGCCCACCGTCGTATTCGTGAGCAA

GAAAGGGCTGCAAAAGATCCTCAACGTGCAAAAGAAGCTACCGATCATACAAAAGATCATCATCAT

GGATAGCAAGACCGACTACCAGGGCTTCCAAAGCATGTACACCTTCGTGACTTCCCATTTGCCACCC

GGCTTCAACGAGTACGACTTCGTGCCCGAGAGCTTCGACCGGGACAAAACCATCGCCCTGATCATGA

ACAGTAGTGGCAGTACCGGATTGCCCAAGGGCGTAGCCCTACCGCACCGCACCGCTTGTGTCCGATT

CAGTCATGCCCGCGACCCCATCTTCGGCAACCAGATCATCCCCGACACCGCTATCCTCAGCGTGGTG

CCATTTCACCACGGCTTCGGCATGTTCACCACGCTGGGCTACTTGATCTGCGGCTTTCGGGTCGTGCT

CATGTACCGCTTCGAGGAGGAGCTATTCTTGCGCAGCTTGCAAGACTATAAGATTCAATCTGCCCTG

CTGGTGCCCACACTATTTAGCTTCTTCGCTAAGAGCACTCTCATCGACAAGTACGACCTAAGCAACTT

GCACGAGATCGCCAGCGGCGGGGCGCCGCTCAGCAAGGAGGTAGGTGAGGCCGTGGCCAAACGC

TTCCACCTACCAGGCATCCGACAGGGCTACGGCCTGACAGAAACAACCAGCGCCATTCTGATCACCC

CCGAAGGGGACGACAAGCCTGGCGCAGTAGGCAAGGTGGTGCCCTTCTTCGAGGCTAAGGTGGTG

GACTTGGACACCGGTAAGACACTGGGTGTGAACCAGCGCGGCGAGCTGTGCGTCCGTGGCCCCATG

ATCATGAGCGGCTACGTTAACAACCCCGAGGCTACAAACGCTCTCATCGACAAGGACGGCTGGCTG

CACAGCGGCGACATCGCCTACTGGGACGAGGACGAGCACTTCTTCATCGTGGACCGGCTGAAGTCC

CTGATCAAATACAAGGGCTACCAGGTAGCCCCAGCCGAACTGGAGAGCATCCTGCTGCAACACCCC

AACATCTTCGACGCCGGGGTCGCCGGCCTGCCCGACGACGATGCCGGCGAGCTGCCCGCCGCAGTC

GTCGTGCTGGAACACGGTAAAACCATGACCGAGAAGGAGATCGTGGACTATGTGGCCAGCCAGGTT

ACAACCGCCAAGAAGCTGCGCGGTGGTGTTGTGTTCGTGGACGAGGTGCCTAAAGGACTGACCGG

CAAGTTGGACGCCCGCAAGATCCGCGAGATTCTCATTAAGGCCAAGAAGGGCGGCAAGATCGCCGT

GTAACTCGAGTATGTTACGTGCAAAGGTGATTGTCACCCCCCGAAAGACCATATTGTGACACACCCT

CAGTATCACGCCCAAACATTTACAGCCGCGGTGTCAAAAACCGCGTGGACGTGGTTAACATCCCTGC

TGGGAGGATCAGCCGTAATTATTATAATTGGCTTGGTGCTGGCTACTATTGTGGCCATGTACGTGCT

GACCAACCAGAAACATAATTGAATACAGCAGCAATTGGCAAGCTGCTTACATAGAACTCGCGGCGA

TTGGCATGCCGCCTTAAAATTTTTATTTTATTTTTTCTTTTCTTTTCCGAATCGGATTTTGTTTTTAATAT

TTCAAAAAAAAAAAAAAAAAAAAAAAAAATctagAAAAAAAAAAAAAAAAAAAAAAAAAAAAAAAAAA

AAAAAAAAAAAAAAAAAAAAAAAAAAAAAAAAAAAAAAAAAAAAAAAAaaaaaaaaaaaaaaaaaaaa

-continued (RNA sequence for STARR Fluc IRES-E3L)

SEQ ID NO: 128

AUGGGCGGCGCAUGAGAGAAGCCCAGACCAAUUACCUACCCAAAAUGGAGAAA

GUUCACGUUGACAUCGAGGAAGACAGCCCAUUCCUCAGAGCUUUGCAGCGGAG

CUUCCCGCAGUUUGAGGUAGAAGCCAAGCAGGUCACUGAUAAUGACCAUGCUA

AUGCCAGAGCGUUUUCGCAUCUGGCUUCAAAACUGAUCGAAACGGAGGUGGA

CCCAUCCGACACGAUCCUUGACAUUGGAAGUGCGCCCGCCCGCAGAAUGUAUU

CUAAGCACAAGUAUCAUUGUAUCUGUCCGAUGAGAUGUGCGGAAGAUCCGGA

CAGAUUGUAUAAGUAUGCAACUAAGCUGAAGAAAAACUGUAAGGAAAUAACU

GAUAAGGAAUUGGACAAGAAAAUGAAGGAGCUGGCCGCCGUCAUGAGCGACC

CUGACCUGGAAACUGAGACUAUGUGCCUCCACGACGACGAGUCGUGUCGCUAC

GAAGGGCAAGUCGCUGUUUACCAGGAUGUAUACGCCGUCGACGGCCCCACCAG

CCUGUACCACCAGGCCAACAAGGGCGUGAGGGUGGCCUACUGGAUCGGCUUCG

ACACCACACCCUUCAUGUUCAAGAACCUGGCCGGCGCCUACCCCAGCUACAGC

ACCAACUGGGCCGACGAGACCGUGCUGACCGCCAGGAACAUCGGCCUGUGCAG

CAGCGACGUGAUGGAGAGGAGCCGGAGAGGCAUGAGCAUCCUGAGGAAGAAA

UACCUGAAGCCCAGCAACAACGUGCUGUUCAGCGUGGGCAGCACCAUCUACCA

CGAGAAGAGGGACCUGCUCAGGAGCUGGCACCUGCCCAGCGUGUUCCACCUGA

GGGGCAAGCAGAACUACACCUGCAGGUGCGAGACCAUCGUGAGCUGCGACGGC

UACGUGGUGAAGAGGAUCGCCAUCAGCCCCGGCCUGUACGGCAAGCCCAGCGG

CUACGCCGCUACAAUGCACAGGGAGGGCUUCCUGUGCUGCAAGGUGACCGACA

CCCUGAACGGCGAGAGGGUGAGCUUCCCCGUGUGCACCUACGUGCCCGCCACC

CUGUGCGACCAGAUGACCGGCAUCCUGGCCACCGACGUGAGCGCCGACGACGC

CCAGAAGCUGCUCGUGGGCCUGAACCAGAGGAUCGUGGUCAACGGCAGGACCC

AGAGGAACACCAACACAAUGAAGAACUACCUGCUGCCCGUGGUGGCCCAGGCU

UUCGCCAGGUGGGCCAAGGAGUACAAGGAGGACCAGGAAGACGAGAGGCCCCU

GGGCCUGAGGGACAGGCAGCUGGUGAUGGGCUGCUGCUGGGCCUUCAGGCGGC

ACAAGAUCACCAGCAUCUACAAGAGGCCCGACACCCAGACCAUCAUCAAGGUG

AACAGCGACUUCCACAGCUUCGUGCUGCCCAGGAUCGGCAGCAACACCCUGGA

GAUCGGCCUGAGGACCCGGAUCAGGAAGAUGCUGGAGGAACACAAGGAGCCCA

GCCCACUGAUCACCGCCGAGGACGUGCAGGAGGCCAAGUGCGCUGCCGACGAG

GCCAAGGAGGUGAGGGAGGCCGAGGAACUGAGGGCCGCCCUGCCACCCCUGGC

UGCCGACGUGGAGGAACCCACCCUGGAAGCCGACGUGGACCUGAUGCUGCAGG

AGGCCGGCGCCGGAAGCGUGGAGACACCCAGGGGCCUGAUCAAGGUGACCAGC

UACGACGGCGAGGACAAGAUCGGCAGCUACGCCGUGCUGAGCCCACAGGCCGU

GCUGAAGUCCGAGAAGCUGAGCUGCAUCCACCCACUGGCCGAGCAGGUGAUCG

UGAUCACCCACAGCGGCAGGAAGGGCAGGUACGCCGUGGAGCCCUACCACGGC

AAGGUGGUCGUGCCCGAGGGCCACGCCAUCCCCGUGCAGGACUUCCAGGCCCU

GAGCGAGAGCGCCACCAUCGUGUACAACGAGAGGGAGUUCGUGAACAGGUACC

UGCACCAUAUCGCCACCCACGGCGGAGCCCUGAACACCGACGAGGAAUACUAC

AAGACCGUGAAGCCCAGCGAGCACGACGGCGAGUACCUGUACGACAUCGACAG

-continued

GAAGCAGUGCGUGAAGAAAGAGCUGGUGACCGGCCUGGGACUGACCGGCGAG

CUGGUGGACCCACCCUUCCACGAGUUCGCCUACGAGAGCCUGAGGACCAGACC

CGCCGCUCCCUACCAGGUGCCCACCAUCGGCGUGUACGGCGUGCCCGGCAGCG

GAAAGAGCGGCAUCAUCAAGAGCGCCGUGACCAAGAAAGACCUGGUGGUCAGC

GCCAAGAAAGAGAACUGCGCCGAGAUCAUCAGGGACGUGAAGAAGAUGAAAG

GCCUGGACGUGAACGCGCGCACCGUGGACAGCGUGCUGCUGAACGGCUGCAAG

CACCCCGUGGAGACCCUGUACAUCGACGAGGCCUUCGCUUGCCACGCCGGCAC

CCUGAGGGCCCUGAUCGCCAUCAUCAGGCCCAAGAAAGCCGUGCUGUGCGGCG

ACCCCAAGCAGUGCGGCUUCUUCAACAUGAUGUGCCUGAAGGUGCACUUCAAC

CACGAGAUCUGCACCCAGGUGUUCCACAAGAGCAUCAGCAGGCGGUGCACCAA

GAGCGUGACCAGCGUCGUGAGCACCCUGUUCUACGACAAGAAAAUGAGGACCA

CCAACCCCAAGGAGACCAAAAUCGUGAUCGACACCACAGGCAGCACCAAGCCC

AAGCAGGACGACCUGAUCCUGACCUGCUUCAGGGGCUGGGUGAAGCAGCUGCA

GAUCGACUACAAGGGCAACGAGAUCAUGACCGCCGCUGCCAGCCAGGGCCUGA

CCAGGAAGGGCGUGUACGCCGUGAGGUACAAGGUGAACGAGAACCCACUGUAC

GCUCCCACCAGCGAGCACGUGAACGUGCUGCUGACCAGGACCGAGGACAGGAU

CGUGUGGAAGACCCUGGCCGGCGACCCCUGGAUCAAGACCCUGACCGCCAAGU

ACCCCGGCAACUUCACCGCCACCAUCGAAGAGUGGCAGGCCGAGCACGACGCC

AUCAUGAGGCACAUCCUGGAGAGGCCCGACCCCACCGACGUGUUCCAGAACAA

GGCCAACGUGUGCUGGGCCAAGGCCCUGGUGCCCGUGCUGAAGACCGCCGGCA

UCGACAUGACCACAGAGCAGUGGAACACCGUGGACUACUUCGAGACCGACAAG

GCCCACAGCGCCGAGAUCGUGCUGAACCAGCUGUGCGUGAGGUUCUUCGGCCU

GGACCUGGACAGCGGCCUGUUCAGCGCCCCCACCGUGCCACUGAGCAUCAGGA

ACAACCACUGGGACAACAGCCCCAGCCCAAACAUGUACGGCCUGAACAAGGAG

GUGGUCAGGCAGCUGAGCAGGCGGUACCCACAGCUGCCCAGGGCCGUGGCCAC

CGGCAGGGUGUACGACAUGAACACCGGCACCCUGAGGAACUACGACCCCAGGA

UCAACCUGGUGCCCGUGAACAGGCGGCUGCCCCACGCCCUGGUGCUGCACCAC

AACGAGCACCCACAGAGCGACUUCAGCUCCUUCGUGAGCAAGCUGAAAGGCAG

GACCGUGCUGGUCGUGGGCGAGAAGCUGAGCGUGCCCGGCAAGAUGGUGGAC

UGGCUGAGCGACAGGCCCGAGGCCACCUUCCGGGCCAGGCUGGACCUCGGCAU

CCCCGGCGACGUGCCCAAGUACGACAUCAUCUUCGUGAACGUCAGGACCCCAU

ACAAGUACCACCAUUACCAGCAGUGCGAGGACCACGCCAUCAAGCUGAGCAUG

CUGACCAAGAAGGCCUGCCUGCACCUGAACCCCGGAGGCACCUGCGUGAGCAU

CGGCUACGGCUACGCCGACAGGGCCAGCGAGAGCAUCAUUGGCGCCAUCGCCA

GGCUGUUCAAGUUCAGCAGGGUGUGCAAACCCAAGAGCAGCCUGGAGGAAACC

GAGGUGCUGUUCGUGUUCAUCGGCUACGACCGGAAGGCCAGGACCCACAACCC

CUACAAGCUGAGCAGCACCCUGACAAACAUCUACACCGGCAGCAGGCUGCACG

AGGCCGGCUGCGCCCCCAGCUACCACGUGGUCAGGGGCGAUAUCGCCACCGCC

ACCGAGGGCGUGAUCAUCAACGCUGCCAACAGCAAGGGCCAGCCCGGAGGCGG

AGUGUGCGGCGCCCUGUACAAGAAGUUCCCCGAGAGCUUCGACCUGCAGCCCA

UCGAGGUGGGCAAGGCCAGGCUGGUGAAGGGCGCCGCUAAGCACAUCAUCCAC

-continued

GCCGUGGGCCCCAACUUCAACAAGGUGAGCGAGGUGGAAGGCGACAAGCAGCU

GGCCGAAGCCUACGAGAGCAUCGCCAAGAUCGUGAACGACAAUAACUACAAGA

GCGUGGCCAUCCCACUGCUCAGCACCGGCAUCUUCAGCGGCAACAAGGACAGG

CUGACCCAGAGCCUGAACCACCUGCUCACCGCCCUGGACACCACCGAUGCCGA

CGUGGCCAUCUACUGCAGGGACAAGAAGUGGGAGAUGACCCUGAAGGAGGCC

GUGGCCAGGCGGGAGGCCGUGGAAGAGAUCUGCAUCAGCGACGACUCCAGCGU

GACCGAGCCCGACGCCGAGCUGGUGAGGGUGCACCCCAAGAGCUCCCUGGCCG

GCAGGAAGGGCUACAGCACCAGCGACGGCAAGACCUUCAGCUACCUGGAGGGC

ACCAAGUUCCACCAGGCCGCUAAGGACAUCGCCGAGAUCAACGCUAUGUGGCC

CGUGGCCACCGAGGCCAACGAGCAGGUGUGCAUGUACAUCCUGGGCGAGAGCA

UGUCCAGCAUCAGGAGCAAGUGCCCCGUGGAGGAAAGCGAGGCCAGCACACCA

CCCAGCACCCUGCCCUGCCUGUGCAUCCACGCUAUGACACCCGAGAGGGUGCA

GCGGCUGAAGGCCAGCAGGCCCGAGCAGAUCACCGUGUGCAGCUCCUUCCCAC

UGCCCAAGUACAGGAUCACCGGCGUGCAGAAGAUCCAGUGCAGCCAGCCCAUC

CUGUUCAGCCCAAAGGUGCCCGCCUACAUCCACCCCAGGAAGUACCUGGUGGA

GACCCCACCCGUGGACGAGACACCCGAGCCAAGCGCCGAGAACCAGAGCACCG

AGGGCACACCCGAGCAGCCACCCCUGAUCACCGAGGACGAGACAAGGACCCGG

ACCCCAGAGCCCAUCAUUAUCGAGGAAGAGGAAGAGGACAGCAUCAGCCUGCU

GAGCGACGGCCCCACCCACCAGGUGCUGCAGGUGGAGGCCGACAUCCACGGCC

CACCCAGCGUGUCCAGCUCCAGCUGGAGCAUCCCACACGCCAGCGACUUCGAC

GUGGACAGCCUGAGCAUCCUGGACACCCUGGAGGGCGCCAGCGUGACCUCCGG

CGCCACCAGCGCCGAGACCAACAGCUACUUCGCCAAGAGCAUGGAGUUCCUGG

CCAGGCCCGUGCCAGCUCCCAGGACCGUGUUCAGGAACCCACCCCACCCAGCUC

CCAGGACCAGGACCCCAAGCCUGGCUCCCAGCAGGGCCUGCAGCAGGACCAGC

CUGGUGAGCACCCCACCCGGCGUGAACAGGGUGAUCACCAGGGAGGAACUGGA

GGCCCUGACACCCAGCAGGACCCCCAGCAGGUCCGUGAGCAGGACUAGUCUGG

UGUCCAACCCACCCGGCGUGAACAGGGUGAUCACCAGGGAGGAAUUCGAGGCC

UUCGUGGCCCAGCAACAGAGACGGUUCGACGCCGGCGCCUACAUCUUCAGCAG

CGACACCGGCCAGGGACACCUGCAGCAAAAGAGCGUGAGGCAGACCGUGCUGA

GCGAGGUGGUGCUGGAGAGGACCGAGCUGGAAAUCAGCUACGCCCCCAGGCUG

GACCAGGAGAAGGAGGAACUGCUCAGGAAGAAACUGCAGCUGAACCCCACCCC

AGCCAACAGGAGCAGGUACCAGAGCAGGAAGGUGGAGAACAUGAAGGCCAUC

ACCGCCAGGCGGAUCCUGCAGGGCCUGGGACACUACCUGAAGGCCGAGGGCAA

GGUGGAGUGCUACAGGACCCUGCACCCCGUGCCACUGUACAGCUCCAGCGUGA

ACAGGGCCUUCUCCAGCCCCAAGGUGGCCGUGGAGGCCUGCAACGCUAUGCUG

AAGGAGAACUUCCCCACCGUGGCCAGCUACUGCAUCAUCCCCGAGUACGACGC

CUACCUGGACAUGGUGGACGGCGCCAGCUGCUGCCUGGACACCGCCAGCUUCU

GCCCCGCCAAGCUGAGGAGCUUCCCCAAGAAACACAGCUACCUGGAGCCCACC

AUCAGGAGCGCCGUGCCCAGCGCCAUCCAGAACACCCUGCAGAACGUGCUGGC

CGCUGCCACCAAGAGGAACUGCAACGUGACCCAGAUGAGGGAGCUGCCCGUGC

-continued

UGGACAGCGCUGCCUUCAACGUGGAGUGCUUCAAGAAAUACGCCUGCAACAAC

GAGUACUGGGAGACCUUCAAGGAGAACCCCAUCAGGCUGACCGAAGAGAACGU

GGUGAACUACAUCACCAAGCUGAAGGGCCCCAAGGCCGCUGCCCUGUUCGCUA

AGACCCACAACCUGAACAUGCUGCAGGACAUCCCAAUGGACAGGUUCGUGAUG

GACCUGAAGAGGGACGUGAAGGUGACACCCGGCACCAAGCACACCGAGGAGAG

GCCCAAGGUGCAGGUGAUCCAGGCCGCUGACCCACUGGCCACCGCCUACCUGU

GCGGCAUCCACAGGGAGCUGGUGAGGCGGCUGAACGCCGUGCUGCUGCCCAAC

AUCCACACCCUGUUCGACAUGAGCGCCGAGGACUUCGACGCCAUCAUCGCCGA

GCACUUCCAGCCCGGCGACUGCGUGCUGGAGACCGACAUCGCCAGCUUCGACA

AGAGCGAGGAUGACGCUAUGGCCCUGACCGCUCUGAUGAUCCUGGAGGACCUG

GGCGUGGACGCCGAGCUGCUCACCCUGAUCGAGGCUGCCUUCGGCGAGAUCAG

CUCCAUCCACCUGCCCACCAAGACCAAGUUCAAGUUCGGCGCUAUGAUGAAAA

GCGGAAUGUUCCUGACCCUGUUCGUGAACACCGUGAUCAACAUUGUGAUCGCC

AGCAGGGUGCUGCGGGAGAGGCUGACCGGCAGCCCCUGCGCUGCCUUCAUCGG

CGACGACAACAUCGUGAAGGGCGUGAAAAGCGACAAGCUGAUGGCCGACAGG

UGCGCCACCUGGCUGAACAUGGAGGUGAAGAUCAUCGACGCCGUGGUGGGCGA

GAAGGCCCCCUACUUCUGCGGCGGAUUCAUCCUGUGCGACAGCGUGACCGGCA

CCGCCUGCAGGGUGGCCGACCCCCUGAAGAGGCUGUUCAAGCUGGGCAAGCCA

CUGGCCGCUGACGAUGAGCACGACGAUGACAGGCGGAGGGCCCUGCACGAGGA

AAGCACCAGGUGGAACAGGGUGGGCAUCCUGAGCGAGCUGUGCAAGGCCGUG

GAGAGCAGGUACGAGACCGUGGGCACCAGCAUCAUCGUGAUGGCUAUGACCAC

ACUGGCCAGCUCCGUCAAGAGCUUCUCCUACCUGAGGGGGGCCCCUAUAACUC

UCUACGGCUAACCUGAAUGGACUACGACAUAGUCUAGUCCGCCAAGGCCGCCA

CCAUGGAAGAUGCCAAAAACAUUAAGAAGGGCCCAGCGCCAUUCUACCCACUC

GAAGACGGGACCGCCGGCGAGCAGCUGCACAAAGCCAUGAAGCGCUACGCCCU

GGUGCCCGGCACCAUCGCCUUUACCGACGCACAUAUCGAGGUGGACAUUACCU

ACGCCGAGUACUUCGAGAUGAGCGUUCGGCUGGCAGAAGCUAUGAAGCGCUA

UGGGCUGAAUACAAACCAUCGGAUCGUGGUGUGCAGCGAGAAUAGCUUGCAG

UUCUUCAUGCCCGUGUUGGGUGCCCUGUUCAUCGGUGUGGCUGUGGCCCCAGC

UAACGACAUCUACAACGAGCGCGAGCUGCUGAACAGCAUGGGCAUCAGCCAGC

CCACCGUCGUAUUCGUGAGCAAGAAAGGGCUGCAAAAGAUCCUCAACGUGCAA

AAGAAGCUACCGAUCAUACAAAAGAUCAUCAUCAUGGAUAGCAAGACCGACU

ACCAGGGCUUCCAAAGCAUGUACACCUUCGUGACUUCCCAUUUGCCACCCGGC

UUCAACGAGUACGACUUCGUGCCCGAGAGCUUCGACCGGGACAAAACCAUCGC

CCUGAUCAUGAACAGUAGUGGCAGUACCGGAUUGCCCAAGGGCGUAGCCCUAC

CGCACCGCACCGCUUGUGUCCGAUUCAGUCAUGCCCGCGACCCCAUCUUCGGC

AACCAGAUCAUCCCCGACACCGCUAUCCUCAGCGUGGUGCCAUUUCACCACGG

CUUCGGCAUGUUCACCACGCUGGGCUACUUGAUCUGCGGCUUUCGGGUCGUGC

UCAUGUACCGCUUCGAGGAGGAGCUAUUCUUGCGCAGCUUGCAAGACUAUAA

GAUUCAAUCUGCCCUGCUGGUGCCCACACUAUUUAGCUUCUUCGCUAAGAGCA

CUCUCAUCGACAAGUACGACCUAAGCAACUUGCACGAGAUCGCCAGCGGCGGG

-continued

GCGCCGCUCAGCAAGGAGGUAGGUGAGGCCGUGGCCAAACGCUUCCACCUACC

AGGCAUCCGACAGGGCUACGGCCUGACAGAAACAACCAGCGCCAUUCUGAUCA

CCCCCGAAGGGGACGACAAGCCUGGCGCAGUAGGCAAGGUGGUGCCCUUCUUC

GAGGCUAAGGUGGUGGACUUGGACACCGGUAAGACACUGGGUGUGAACCAGC

GCGGCGAGCUGUGCGUCCGUGGCCCCAUGAUCAUGAGCGGCUACGUUAACAAC

CCCGAGGCUACAAACGCUCUCAUCGACAAGGACGGCUGGCUGCACAGCGGCGA

CAUCGCCUACUGGGACGAGGACGAGCACUUCUUCAUCGUGGACCGGCUGAAGU

CCCUGAUCAAAUACAAGGGCUACCAGGUAGCCCCAGCCGAACUGGAGAGCAUC

CUGCUGCAACACCCCAACAUCUUCGACGCCGGGGUCGCCGGCCUGCCCGACGA

CGAUGCCGGCGAGCUGCCCGCCGCAGUCGUCGUGCUGGAACACGGUAAAACCA

UGACCGAGAAGGAGAUCGUGGACUAUGUGGCCAGCCAGGUUACAACCGCCAAG

AAGCUGCGCGGUGGUGUUGUGUUCGUGGACGAGGUGCCUAAAGGACUGACCG

GCAAGUUGGACGCCCGCAAGAUCCGCGAGAUUCUCAUUAAGGCCAAGAAGGGC

GGCAAGAUCGCCGUGUAACUCGAGCCGGAAACGCAAUAGCCGAAAAACAAAAA

ACAAAAAAAACAAAAAAAAAACCAAAAAAACAAAACACAUUAAAACAGCCUG

UGGGUUGAUCCCACCCACAGGCCCAUUGGGCGCUAGCACUCUGGUAUCACGGU

ACCUUUGUGCGCCUGUUUUAUACCCCCUCCCCCAACUGUAACUUAGAAGUAAC

ACACACCGAUCAACAGUCAGCGUGGCACACCAGCCACGUUUUGAUCAAGCACU

UCUGUUACCCCGGACUGAGUAUCAAUAGACUGCUCACGCGGUUGAAGGAGAA

AGCGUUCGUUAUCCGGCCAACUACUUCGAAAAACCUAGUAACACCGUGGAAGU

UGCAGAGUGUUUCGCUCAGCACUACCCCAGUGUAGAUCAGGUCGAUGAGUCAC

CGCAUUCCCCACGGGCGACCGUGGCGGUGGCUGCGUUGGCGGCCUGCCCAUGG

GGAAACCCAUGGGACGCUCUAAUACAGACAUGGUGCGAAGAGUCUAUUGAGC

UAGUUGGUAGUCCUCCGGCCCCUGAAUGCGGCUAAUCCUAACUGCGGAGCACA

CACCCUCAAGCCAGAGGGCAGUGUGUCGUAACGGGCAACUCUGCAGCGGAACC

GACUACUUUGGGUGUCCGUGUUUCAUUUUAUUCCUAUACUGGCUGCUUAUGG

UGACAAUUGAGAGAUCGUUACCAUAUAGCUAUUGGAUUGGCCAUCCGGUGAC

UAAUAGAGCUAUUAUAUAUCCCUUUGUUGGGUUUAUACCACUUAGCUUGAAA

GAGGUUAAAACAUUACAAUUCAUUGUUAAGUUGAAUACAGCAAAAUGAGCAA

GAUCUACAUCGACGAGCGGAGCAACGCCGAGAUCGUGUGCGAGGCCAUCAAGA

CCAUCGGCAUCGAGGGCGCCACCGCCGCCCAGCUGACCAGGCAGCUGAACAUG

GAGAAGCGGGAGGUGAACAAGGCCCUGUACGACCUGCAGAGGAGCGCUAUGG

UGUACUCCAGCGACGACAUCCCUCCCCGGUGGUUCAUGACCACCGAGGCCGAC

AAGCCCGACGCCGACGCUAUGGCCGACGUGAUCAUCGACGACGUGAGCAGGGA

GAAGUCCAUGAGGGAGGACCACAAGAGCUUCGACGACGUGAUCCCCGCCAAGA

AGAUCAUCGACUGGAAGGGCGCCAACCCCGUGACCGUGAUCAACGAGUACUGC

CAGAUCACCAGGAGGGACUGGAGCUUCCGGAUCGAGAGCGUGGGCCCCAGCAA

CAGCCCCACCUUCUACGCCUGCGUGGACAUCGACGGCAGGGUGUUCGACAAGG

CCGACGGCAAGAGCAAGCGGGACGCCAAGAACAACGCCGCCAAGCUGGCCGUG

GACAAGCUGCUGGGCUACGUGAUCAUCCGGUUCUAAACGUAUGUUACGUGCA

-continued

AAGGUGAUUGUCACCCCCCGAAAGACCAUAUUGUGACACACCCUCAGUAUCAC

GCCCAAACAUUUACAGCCGCGGUGUCAAAAACCGCGUGGACGUGGUUAACAUC

CCUGCUGGGAGGAUCAGCCGUAAUUAUUAUAAUUGGCUUGGUGCUGGCUACU

AUUGUGGCCAUGUACGUGCUGACCAACCAGAAACAUAAUUGAAUACAGCAGC

AAUUGGCAAGCUGCUUACAUAGAACUCGCGGCGAUUGGCAUGCCGCCUUAAAA

UUUUUAUUUUAUUUUUUCUUUUCUUUUCCGAAUCGGAUUUUGUUUUUAAUAU

UUCAAAAAAAAAAAAAAAAAAAAAAAAAAAUCUAGAAAAAAAAAAAAAAAAAAA

AAAAAAAAAAAAAAAAAAAAAAAAAAAAAAAAAAAAAAAAAAAAAAAAAAAAA

AAAAAAAAAAAAAAAAAAAAAAAAAAAAA (RNA sequence for STARR Fluc IRES-E3L (short 3' UTR))

SEQ ID NO: 129

AUGGGCGGCGCAUGAGAGAAGCCCAGACCAAUUACCUACCCAAAAUGGAGAAA

GUUCACGUUGACAUCGAGGAAGACAGCCCAUUCCUCAGAGCUUUGCAGCGGAG

CUUCCCGCAGUUUGAGGUAGAAGCCAAGCAGGUCACUGAUAAUGACCAUGCUA

AUGCCAGAGCGUUUUCGCAUCUGGCUUCAAAACUGAUCGAAACGGAGGUGGA

CCCAUCCGACACGAUCCUUGACAUUGGAAGUGCGCCCGCCCGCAGAAUGUAUU

CUAAGCACAAGUAUCAUUGUAUCUGUCCGAUGAGAUGUGCGGAAGAUCCGGA

CAGAUUGUAUAAGUAUGCAACUAAGCUGAAGAAAAACUGUAAGGAAAUAACU

GAUAAGGAAUUGGACAAGAAAAUGAAGGAGCUGGCCGCCGUCAUGAGCGACC

CUGACCUGGAAACUGAGACUAUGUGCCUCCACGACGACGAGUCGUGUCGCUAC

GAAGGGCAAGUCGCUGUUUACCAGGAUGUAUACGCCGUCGACGGCCCCACCAG

CCUGUACCACCAGGCCAACAAGGGCGUGAGGGUGGCCUACUGGAUCGGCUUCG

ACACCACACCCUUCAUGUUCAAGAACCUGGCCGGCGCCUACCCCAGCUACAGC

ACCAACUGGGCCGACGAGACCGUGCUGACCGCCAGGAACAUCGGCCUGUGCAG

CAGCGACGUGAUGGAGAGGAGCCGGAGAGGCAUGAGCAUCCUGAGGAAGAAA

UACCUGAAGCCCAGCAACAACGUGCUGUUCAGCGUGGGCAGCACCAUCUACCA

CGAGAAGAGGGACCUGCUCAGGAGCUGGCACCUGCCCAGCGUGUUCCACCUGA

GGGGCAAGCAGAACUACACCUGCAGGUGCGAGACCAUCGUGAGCUGCGACGGC

UACGUGGUGAAGAGGAUCGCCAUCAGCCCCGGCCUGUACGGCAAGCCCAGCGG

CUACGCCGCUACAAUGCACAGGGAGGGCUUCCUGUGCUGCAAGGUGACCGACA

CCCUGAACGGCGAGAGGGUGAGCUUCCCCGUGUGCACCUACGUGCCCGCCACC

CUGUGCGACCAGAUGACCGGCAUCCUGGCCACCGACGUGAGCGCCGACGACGC

CCAGAAGCUGCUCGUGGGCCUGAACCAGAGGAUCGUGGUCAACGGCAGGACCC

AGAGGAACACCAACACAAUGAAGAACUACCUGCUGCCCGUGGUGGCCCAGGCU

UUCGCCAGGUGGGCCAAGGAGUACAAGGAGGACCAGGAAGACGAGAGGCCCCU

GGGCCUGAGGGACAGGCAGCUGGUGAUGGGCUGCUGCUGGGCCUUCAGGCGGC

ACAAGAUCACCAGCAUCUACAAGAGGCCCGACACCCAGACCAUCAUCAAGGUG

AACAGCGACUUCCACAGCUUCGUGCUGCCCAGGAUCGGCAGCAACACCCUGGA

GAUCGGCCUGAGGACCCGGAUCAGGAAGAUGCUGGAGGAACACAAGGAGCCCA

GCCCACUGAUCACCGCCGAGGACGUGCAGGAGGCCAAGUGCGCUGCCGACGAG

GCCAAGGAGGUGAGGGAGGCCGAGGAACUGAGGGCCGCCCUGCCACCCCUGGC

UGCCGACGUGGAGGAACCCACCCUGGAAGCCGACGUGGACCUGAUGCUGCAGG

-continued

AGGCCGGCGCCGGAAGCGUGGAGACACCCAGGGGCCUGAUCAAGGUGACCAGC
UACGACGGCGAGGACAAGAUCGGCAGCUACGCCGUGCUGAGCCCACAGGCCGU
GCUGAAGUCCGAGAAGCUGAGCUGCAUCCACCCACUGGCCGAGCAGGUGAUCG
UGAUCACCCACAGCGGCAGGAAGGGCAGGUACGCCGUGGAGCCCUACCACGGC
AAGGUGGUCGUGCCCGAGGGCCACGCCAUCCCCGUGCAGGACUUCCAGGCCCU
GAGCGAGAGCGCCACCAUCGUGUACAACGAGAGGGAGUUCGUGAACAGGUACC
UGCACCAUAUCGCCACCCACGGCGGAGCCCUGAACACCGACGAGGAAUACUAC
AAGACCGUGAAGCCCAGCGAGCACGACGGCGAGUACCUGUACGACAUCGACAG
GAAGCAGUGCGUGAAGAAAGAGCUGGUGACCGGCCUGGGACUGACCGGCGAG
CUGGUGGACCCACCCUUCCACGAGUUCGCCUACGAGAGCCUGAGGACCAGACC
CGCCGCUCCCUACCAGGUGCCCACCAUCGGCGUGUACGGCGUGCCCGGCAGCG
GAAAGAGCGGCAUCAUCAAGAGCGCCGUGACCAAGAAAGACCUGGUGGUCAGC
GCCAAGAAAGAGAACUGCGCCGAGAUCAUCAGGGACGUGAAGAAGAUGAAAG
GCCUGGACGUGAACGCGCGCACCGUGGACAGCGUGCUGCUGAACGGCUGCAAG
CACCCCGUGGAGACCCUGUACAUCGACGAGGCCUUCGCUUGCCACGCCGGCAC
CCUGAGGGCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCACUUCAAC
CACGAGAUCUGCACCCAGGUGUUCCACAAGAGCAUCAGCAGGCGGUGCACCAA
GAGCGUGACCAGCGUCGUGAGCACCCUGUUCUACGACAAGAAAAUGAGGACCA
CCAACCCCAAGGAGACCAAAAUCGUGAUCGACACCACAGGCAGCACCAAGCCC
AAGCAGGACGACCUGAUCCUGACCUGCUUCAGGGGCUGGGUGAAGCAGCUGCA
GAUCGACUACAAGGGCAACGAGAUCAUGACCGCCGCUGCCAGCCAGGGCCUGA
CCAGGAAGGGCGUGUACGCCGUGAGGUACAAGGUGAACGAGAACCCACUGUAC
GCUCCCACCAGCGAGCACGUGAACGUGCUGCUGACCAGGACCGAGGACAGGAU
CGUGUGGAAGACCCUGGCCGGCGACCCCUGGAUCAAGACCCUGACCGCCAAGU
ACCCCGGCAACUUCACCGCCACCAUCGAAGAGUGGCAGGCCGAGCACGACGCC
AUCAUGAGGCACAUCCUGGAGAGGCCCGACCCCACCGACGUGUUCCAGAACAA
GGCCAACGUGUGCUGGGCCAAGGCCCUGGUGCCCGUGCUGAAGACCGCCGGCA
UCGACAUGACCACAGAGCAGUGGAACACCGUGGACUACUUCGAGACCGACAAG
GCCCACAGCGCCGAGAUCGUGCUGAACCAGCUGUGCGUGAGGUUCUUCGGCCU
GGACCUGGACAGCGGCCUGUUCAGCGCCCCCACCGUGCCACUGAGCAUCAGGA
ACAACCACUGGGACAACAGCCCCAGCCCAAACAUGUACGGCCUGAACAAGGAG
GUGGUCAGGCAGCUGAGCAGGCGGUACCCACAGCUGCCCAGGGCCGUGGCCAC
CGGCAGGGUGUACGACAUGAACACCGGCACCCUGAGGAACUACGACCCCAGGA
UCAACCUGGUGCCCGUGAACAGGCGGCUGCCCCACGCCCUGGUGCUGCACCAC
AACGAGCACCCACAGAGCGACUUCAGCUCCUUCGUGAGCAAGCUGAAAGGCAG
GACCGUGCUGGUCGUGGGCGAGAAGCUGAGCGUGCCCGGCAAGAUGGUGGAC
UGGCUGAGCGACAGGCCCGAGGCCACCUUCCGGGCCAGGCUGGACCUCGGCAU
CCCCGGCGACGUGCCCAAGUACGACAUCAUCUUCGUGAACGUCAGGACCCCAU
ACAAGUACCACCAUUACCAGCAGUGCGAGGACCACGCCAUCAAGCUGAGCAUG

-continued
CUGACCAAGAAGGCCUGCCUGCACCUGAACCCCGGAGGCACCUGCGUGAGCAU
CGGCUACGGCUACGCCGACAGGGCCAGCGAGAGCAUCAUUGGCGCCAUCGCCA
GGCUGUUCAAGUUCAGCAGGGUGUGCAAACCCAAGAGCAGCCUGGAGGAAACC
GAGGUGCUGUUCGUGUUCAUCGGCUACGACCGGAAGGCCAGGACCCACAACCC
CUACAAGCUGAGCAGCACCCUGACAAACAUCUACACCGGCAGCAGGCUGCACG
AGGCCGGCUGCGCCCCCAGCUACCACGUGGUCAGGGGCGAUAUCGCCACCGCC
ACCGAGGGCGUGAUCAUCAACGCUGCCAACAGCAAGGGCCAGCCCGGAGGCGG
AGUGUGCGGCGCCCUGUACAAGAAGUUCCCCGAGAGCUUCGACCUGCAGCCCA
UCGAGGUGGGCAAGGCCAGGCUGGUGAAGGGCGCCGCUAAGCACAUCAUCCAC
GCCGUGGGCCCCAACUUCAACAAGGUGAGCGAGGUGGAAGGCGACAAGCAGCU
GGCCGAAGCCUACGAGAGCAUCGCCAAGAUCGUGAACGACAAUAACUACAAGA
GCGUGGCCAUCCCACUGCUCAGCACCGGCAUCUUCAGCGGCAACAAGGACAGG
CUGACCCAGAGCCUGAACCACCUGCUCACCGCCCUGGACACCACCGAUGCCGA
CGUGGCCAUCUACUGCAGGGACAAGAAGUGGGAGAUGACCCUGAAGGAGGCC
GUGGCCAGGCGGGAGGCCGUGGAAGAGAUCUGCAUCAGCGACGACUCCAGCGU
GACCGAGCCCGACGCCGAGCUGGUGAGGGUGCACCCCAAGAGCUCCCUGGCCG
GCAGGAAGGGCUACAGCACCAGCGACGGCAAGACCUUCAGCUACCUGGAGGGC
ACCAAGUUCCACCAGGCCGCUAAGGACAUCGCCGAGAUCAACGCUAUGUGGCC
CGUGGCCACCGAGGCCAACGAGCAGGUGUGCAUGUACAUCCUGGGCGAGAGCA
UGUCCAGCAUCAGGAGCAAGUGCCCCGUGGAGGAAAGCGAGGCCAGCACACCA
CCCAGCACCCUGCCCUGCCUGUGCAUCCACGCUAUGACACCCGAGAGGGUGCA
GCGGCUGAAGGCCAGCAGGCCCGAGCAGAUCACCGUGUGCAGCUCCUUCCCAC
UGCCCAAGUACAGGAUCACCGGCGUGCAGAAGAUCCAGUGCAGCCAGCCCAUC
CUGUUCAGCCCAAAGGUGCCCGCCUACAUCCACCCCAGGAAGUACCUGGUGGA
GACCCCACCCGUGGACGAGACACCCGAGCCAAGCGCCGAGAACCAGAGCACCG
AGGGCACACCCGAGCAGCCACCCCUGAUCACCGAGGACGAGACAAGGACCCGG
ACCCCAGAGCCCAUCAUUAUCGAGGAAGAGGAAGAGGACAGCAUCAGCCUGCU
GAGCGACGGCCCCACCCACCAGGUGCUGCAGGUGGAGGCCGACAUCCACGGCC
CACCCAGCGUGUCCAGCUCCAGCUGGAGCAUCCCACACGCCAGCGACUUCGAC
GUGGACAGCCUGAGCAUCCUGGACACCCUGGAGGGCGCCAGCGUGACCUCCGG
CGCCACCAGCGCCGAGACCAACAGCUACUUCGCCAAGAGCAUGGAGUUCCUGG
CCAGGCCCGUGCCAGCUCCCAGGACCGUGUUCAGGAACCCACCCCACCCAGCUC
CCAGGACCAGGACCCCAAGCCUGGCUCCCAGCAGGGCCUGCAGCAGGACCAGC
CUGGUGAGCACCCCACCCGGCGUGAACAGGGUGAUCACCAGGGAGGAACUGGA
GGCCCUGACACCCAGCAGGACCCCCAGCAGGUCCGUGAGCAGGACUAGUCUGG
UGUCCAACCCACCCGGCGUGAACAGGGUGAUCACCAGGGAGGAAUUCGAGGCC
UUCGUGGCCCAGCAACAGAGACGGUUCGACGCCGGCGCCUACAUCUUCAGCAG
CGACACCGGCCAGGGACACCUGCAGCAAAAGAGCGUGAGGCAGACCGUGCUGA
GCGAGGUGGUGCUGGAGAGGACCGAGCUGGAAAUCAGCUACGCCCCCAGGCUG
GACCAGGAGAAGGAGGAACUGCUCAGGAAGAAACUGCAGCUGAACCCCACCCC
AGCCAACAGGAGCAGGUACCAGAGCAGGAAGGUGGAGAACAUGAAGGCCAUC -continued

ACCGCCAGGCGGAUCCUGCAGGGCCUGGGACACUACCUGAAGGCCGAGGGCAA

GGUGGAGUGCUACAGGACCCUGCACCCCGUGCCACUGUACAGCUCCAGCGUGA

ACAGGGCCUUCUCCAGCCCCAAGGUGGCCGUGGAGGCCUGCAACGCUAUGCUG

AAGGAGAACUUCCCCACCGUGGCCAGCUACUGCAUCAUCCCCGAGUACGACGC

CUACCUGGACAUGGUGGACGGCGCCAGCUGCUGCCUGGACACCGCCAGCUUCU

GCCCCGCCAAGCUGAGGAGCUUCCCCAAGAAACACAGCUACCUGGAGCCCACC

AUCAGGAGCGCCGUGCCCAGCGCCAUCCAGAACACCCUGCAGAACGUGCUGGC

CGCUGCCACCAAGAGGAACUGCAACGUGACCCAGAUGAGGGAGCUGCCCGUGC

UGGACAGCGCUGCCUUCAACGUGGAGUGCUUCAAGAAAUACGCCUGCAACAAC

GAGUACUGGGAGACCUUCAAGGAGAACCCCAUCAGGCUGACCGAAGAGAACGU

GGUGAACUACAUCACCAAGCUGAAGGGCCCCAAGGCCGCUGCCCUGUUCGCUA

AGACCCACAACCUGAACAUGCUGCAGGACAUCCCAAUGGACAGGUUCGUGAUG

GACCUGAAGAGGGACGUGAAGGUGACACCCGGCACCAAGCACACCGAGGAGAG

GCCCAAGGUGCAGGUGAUCCAGGCCGCUGACCCACUGGCCACCGCCUACCUGU

GCGGCAUCCACAGGGAGCUGGUGAGGCGGCUGAACGCCGUGCUGCUGCCCAAC

AUCCACACCCUGUUCGACAUGAGCGCCGAGGACUUCGACGCCAUCAUCGCCGA

GCACUUCCAGCCCGGCGACUGCGUGCUGGAGACCGACAUCGCCAGCUUCGACA

AGAGCGAGGAUGACGCUAUGGCCCUGACCGCUCUGAUGAUCCUGGAGGACCUG

GGCGUGGACGCCGAGCUGCUCACCCUGAUCGAGGCUGCCUUCGGCGAGAUCAG

CUCCAUCCACCUGCCCACCAAGACCAAGUUCAAGUUCGGCGCUAUGAUGAAAA

GCGGAAUGUUCCUGACCCUGUUCGUGAACACCGUGAUCAACAUUGUGAUCGCC

AGCAGGGUGCUGCGGGAGAGGCUGACCGGCAGCCCCUGCGCUGCCUUCAUCGG

CGACGACAACAUCGUGAAGGGCGUGAAAAGCGACAAGCUGAUGGCCGACAGG

UGCGCCACCUGGCUGAACAUGGAGGUGAAGAUCAUCGACGCCGUGGUGGGCGA

GAAGGCCCCCUACUUCUGCGGCGGAUUCAUCCUGUGCGACAGCGUGACCGGCA

CCGCCUGCAGGGUGGCCGACCCCCUGAAGAGGCUGUUCAAGCUGGGCAAGCCA

CUGGCCGCUGACGAUGAGCACGACGAUGACAGGCGGAGGGCCCUGCACGAGGA

AAGCACCAGGUGGAACAGGGUGGGCAUCCUGAGCGAGCUGUGCAAGGCCGUG

GAGAGCAGGUACGAGACCGUGGGCACCAGCAUCAUCGUGAUGGCUAUGACCAC

ACUGGCCAGCUCCGUCAAGAGCUUCUCCUACCUGAGGGGGGCCCCUAUAACUC

UCUACGGCUAACCUGAAUGGACUACGACAUAGUCUAGUCCGCCAAGGCCGCCA

CCAUGGAAGAUGCCAAAAACAUUAAGAAGGGCCCAGCGCCAUUCUACCCACUC

GAAGACGGGACCGCCGGCGAGCAGCUGCACAAAGCCAUGAAGCGCUACGCCCU

GGUGCCCGGCACCAUCGCCUUUACCGACGCACAUAUCGAGGUGGACAUUACCU

ACGCCGAGUACUUCGAGAUGAGCGUUCGGCUGGCAGAAGCUAUGAAGCGCUA

UGGGCUGAAUACAAACCAUCGGAUCGUGGUGUGCAGCGAGAAUAGCUUGCAG

UUCUUCAUGCCCGUGUUGGGUGCCCUGUUCAUCGGUGUGGCUGUGGCCCCAGC

UAACGACAUCUACAACGAGCGCGAGCUGCUGAACAGCAUGGGCAUCAGCCAGC

CCACCGUCGUAUUCGUGAGCAAGAAAGGGCUGCAAAAGAUCCUCAACGUGCAA

AAGAAGCUACCGAUCAUACAAAAGAUCAUCAUCAUGGAUAGCAAGACCGACU

-continued

ACCAGGGCUUCCAAAGCAUGUACACCUUCGUGACUUCCCAUUUGCCACCCGGC
UUCAACGAGUACGACUUCGUGCCCGAGAGCUUCGACCGGGACAAAACCAUCGC
CCUGAUCAUGAACAGUAGUGGCAGUACCGGAUUGCCCAAGGGCGUAGCCCUAC
CGCACCGCACCGCUUGUGUCCGAUUCAGUCAUGCCCGCGACCCCAUCUUCGGC
AACCAGAUCAUCCCCGACACCGCUAUCCUCAGCGUGGUGCCAUUUCACCACGG
CUUCGGCAUGUUCACCACGCUGGGCUACUUGAUCUGCGGCUUUCGGGUCGUGC
UCAUGUACCGCUUCGAGGAGGAGCUAUUCUUGCGCAGCUUGCAAGACUAUAA
GAUUCAAUCUGCCCUGCUGGUGCCCACACUAUUUAGCUUCUUCGCUAAGAGCA
CUCUCAUCGACAAGUACGACCUAAGCAACUUGCACGAGAUCGCCAGCGGGGG
GCGCCGCUCAGCAAGGAGGUAGGUGAGGCCGUGGCCAAACGCUUCCACCUACC
AGGCAUCCGACAGGGCUACGGCCUGACAGAAACAACCAGCGCCAUUCUGAUCA
CCCCCGAAGGGGACGACAAGCCUGGCGCAGUAGGCAAGGUGGUGCCCUUCUUC
GAGGCUAAGGUGGUGGACUUGGACACCGGUAAGACACUGGGUGUGAACCAGC
GCGGCGAGCUGUGCGUCCGUGGCCCCAUGAUCAUGAGCGGCUACGUUAACAAC
CCCGAGGCUACAAACGCUCUCAUCGACAAGGACGGCUGGCUGCACAGCGGCGA
CAUCGCCUACUGGGACGAGGACGAGCACUUCUUCAUCGUGGACCGGCUGAAGU
CCCUGAUCAAAUACAAGGGCUACCAGGUAGCCCCAGCCGAACUGGAGAGCAUC
CUGCUGCAACACCCCAACAUCUUCGACGCCGGGGUCGCCGGCCUGCCCGACGA
CGAUGCCGGCGAGCUGCCCGCCGCAGUCGUCGUGCUGGAACACGGUAAAACCA
UGACCGAGAAGGAGAUCGUGGACUAUGUGGCCAGCCAGGUUACAACCGCCAAG
AAGCUGCGCGGUGGUGUUGUGUUCGUGGACGAGGUGCCUAAAGGACUGACCG
GCAAGUUGGACGCCCGCAAGAUCCGCGAGAUUCUCAUUAAGGCCAAGAAGGGC
GGCAAGAUCGCCGUGUAACUCGAGCCGGAAACGCAAUAGCCGAAAAACAAAAA
ACAAAAAAAACAAAAAAAAAACCAAAAAAACAAAACACAUUAAAACAGCCUG
UGGGUUGAUCCCACCCACAGGCCCAUUGGGCGCUAGCACUCUGGUAUCACGGU
ACCUUUGUGCGCCUGUUUUAUACCCCCUCCCCCAACUGUAACUUAGAAGUAAC
ACACACCGAUCAACAGUCAGCGUGGCACACCAGCCACGUUUUGAUCAAGCACU
UCUGUUACCCCGGACUGAGUAUCAAUAGACUGCUCACGCGGUUGAAGGAGAA
AGCGUUCGUUAUCCGGCCAACUACUUCGAAAAACCUAGUAACACCGUGGAAGU
UGCAGAGUGUUUCGCUCAGCACUACCCCAGUGUAGAUCAGGUCGAUGAGUCAC
CGCAUUCCCCACGGGCGACCGUGGCGGUGGCUGCGUUGGCGGCCUGCCCAUGG
GGAAACCCAUGGGACGCUCUAAUACAGACAUGGUGCGAAGAGUCUAUUGAGC
UAGUUGGUAGUCCUCCGGCCCCUGAAUGCGGCUAAUCCUAACUGCGGAGCACA
CACCCUCAAGCCAGAGGGCAGUGUGUCGUAACGGGCAACUCUGCAGCGGAACC
GACUACUUUGGGUGUCCGUGUUUCAUUUUAUUCCUAUACUGGCUGCUUAUGG
UGACAAUUGAGAGAUCGUUACCAUAUAGCUAUUGGAUUGGCCAUCCGGUGAC
UAAUAGAGCUAUUAUAUAUCCCUUUGUUGGGUUUAUACCACUUAGCUUGAAA
GAGGUUAAAACAUUACAAUUCAUUGUUAAGUUGAAUACAGCAAAAUGAGCAA
GAUCUACAUCGACGAGCGGAGCAACGCCGAGAUCGUGUGCGAGGCCAUCAAGA
CCAUCGGCAUCGAGGGCGCCACCGCCGCCCAGCUGACCAGGCAGCUGAACAUG
GAGAAGCGGGAGGUGAACAAGGCCCUGUACGACCUGCAGAGGAGCGCUAUGG

-continued

UGUACUCCAGCGACGACAUCCCUCCCCGGUGGUUCAUGACCACCGAGGCCGAC

AAGCCCGACGCCGACGCUAUGGCCGACGUGAUCAUCGACGACGUGAGCAGGGA

GAAGUCCAUGAGGGAGGACCACAAGAGCUUCGACGACGUGAUCCCCGCCAAGA

AGAUCAUCGACUGGAAGGGCGCCAACCCCGUGACCGUGAUCAACGAGUACUGC

CAGAUCACCAGGAGGGACUGGAGCUUCCGGAUCGAGAGCGUGGGCCCCAGCAA

CAGCCCCACCUUCUACGCCUGCGUGGACAUCGACGGCAGGGUGUUCGACAAGG

CCGACGGCAAGAGCAAGCGGGACGCCAAGAACAACGCCGCCAAGCUGGCCGUG

GACAAGCUGCUGGGCUACGUGAUCAUCCGGUUCUAAACAAUUGGCAAGCUGCU

UACAUAGAACUCGCGGCGAUUGGCAUGCCGCCUUAAAAUUUUUAUUUUAUUU

UUUCUUUUCUUUUCCGAAUCGGAUUUUGUUUUUAAUAUUUCAAAAAAAAAAA

AAAAAAAAAAAAAAUCUAGAAAAAAAAAAAAAAAAAAAAAAAAAAAAAAAAA

AAAAAAAAAAAAAAAAAAAAAAAAAAAAAAAAAAAAAAAAAAAAAAAAAAAA

AAAAAAAAAAAAAAA

TABLE 8

| SEQ ID NO | Description |
|---|---|
| SEQ ID NO: 72 | nsP1-4 ORF, codon-optimized |
| SEQ ID NO: 73 | 5' UTR |
| SEQ ID NO: 74 | 5' UTR |
| SEQ ID NO: 75 | 5' UTR |
| SEQ ID NO: 76 | 3' UTR |
| SEQ ID NO: 121 | SARS-CoV-2 spike glycoprotein (non-codon optimized nucleic acid) |
| SEQ ID NO: 122 | SARS-CoV-2 spike glycoprotein (codon-optimized nucleic acid) |
| SEQ ID NO: 123 | SARS-CoV-2 spike glycoprotein (wild-type protein) |
| SEQ ID NO: 77 | Intergenic region between nsP1-4 ORF and antigenic protein ORF |
| SEQ ID NO: 78 | Replicon sequence comprising SEQ ID NO: 72, SEQ ID NO: 73, SEQ ID NO: 76, and SEQ ID NO: 77 |
| SEQ ID NO: 124 | Replicon sequence comprising SEQ ID NO: 72, SEQ ID NO: 73, SEQ ID NO: 76, SEQ ID NO: 121, and SEQ ID NO: 77 |
| SEQ ID NO: 125 | Replicon sequence comprising SEQ ID NO: 72, SEQ ID NO: 73, SEQ ID NO: 76, SEQ ID NO: 122, and SEQ ID NO: 77 (ARCT-021; aka "STARR ™ SARS-CoV-2 RNA) |
| SEQ ID NO: 79 | nsP1-4 protein sequence |
| SEQ ID NO: 80 | nsP1-4 protein sequence |
| SEQ ID NO: 81 | nsP1-4 protein sequence |
| SEQ ID NO: 126 | mRNA encoding SARS-CoV-2 glycoprotein |
| SEQ ID NO: 82 | 5' UTR (TEV) |
| SEQ ID NO: 83 | 3' UTR (Xbg) |

Example 10

This example describes characterization of self-replicating (STARR™) technology using firefly luciferase transgene expression.

In vitro transcripts were formulated with lipid nanoparticles (LNP) at a concentration of 0.1 mg/ml, and injected intramuscularly in both legs of female BALB/C mice (n=3) at a dose of 5 ug per leg. Expression of firefly luciferase (FLuc) was measured by IVIS Lumina LT Series III (PerkinElmer) by administering 100 ul of 1.5 mg Xenolight D-luciferin (PerkinElmer) in PBS via intraperitoneal injection ~10 min prior to the measurement. Six data points per group of mice were obtained at each time point (FIGS. 18A-18D).

Figure 18A:
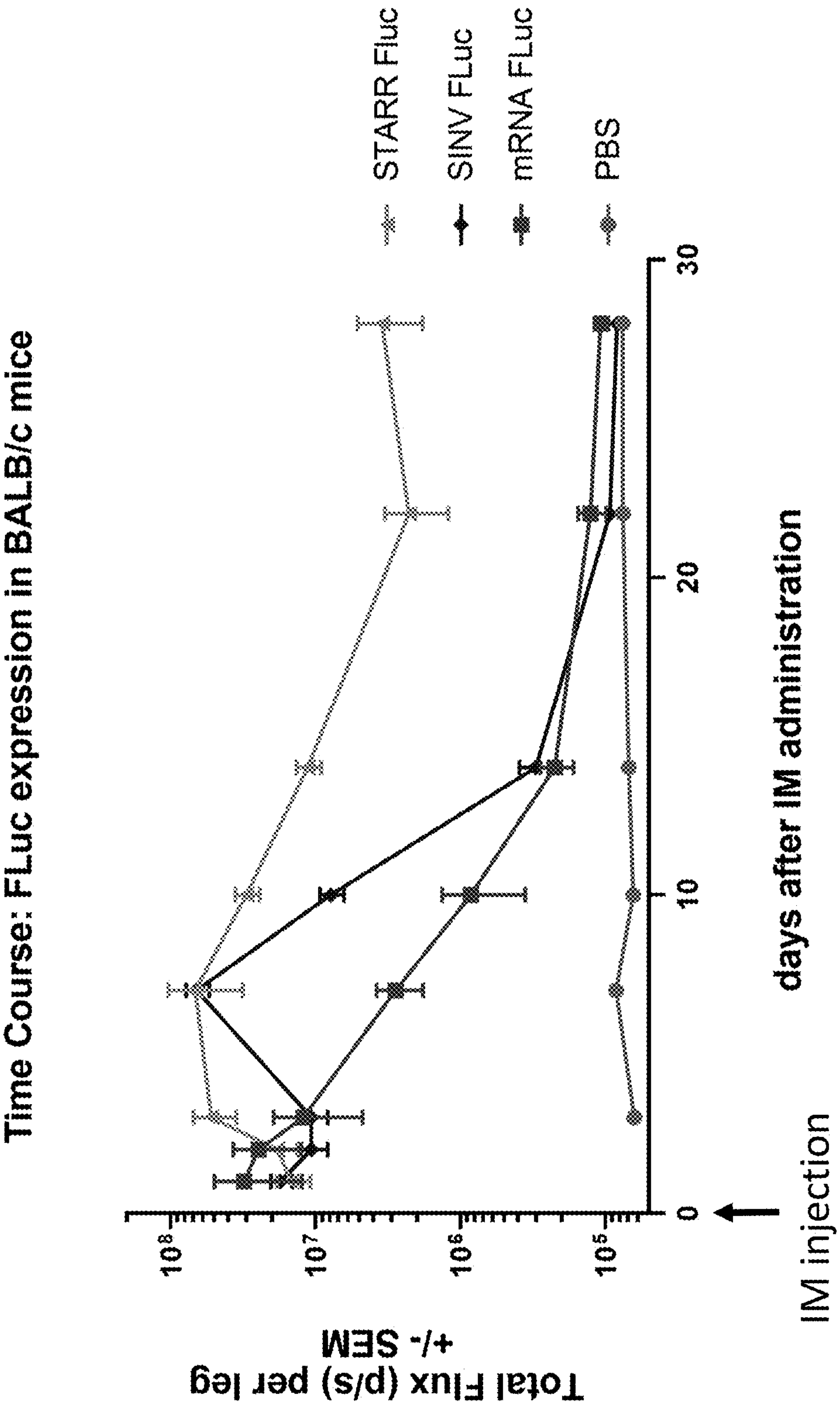
FIGS. 18A-18D shows characterization of STARR™ technology with firefly luciferase transgene expression. (18A) Firefly luciferase (FLuc) expression from STARR™ Fluc, SINV FLuc, and mRNA FLuc was monitored up to day 28 by In Vivo Imaging System (IVIS). The average of total flux (p/s) from 6 injection sites in a mouse group was plotted at each time point with a standard error of mean, SEM. (18B) IVIS picture of three mice (6 injection sites) per group on day 14 is shown for each group that was administered with the test article labeled below the picture. (18C) Luciferase expression from mice that were intramuscularly injected with STARR™ FLuc was monitored by IVIS up to 63 days post administration. (18D) Effect of prior administration of replicon backbone was examined for STARR™ (upper panel) and SINV (lower panel). Replicon encoding FLuc was IM injected at 7 days post dose of replicon with homologous backbone with an irrelevant gene/sequence (labeled STARR™ irr or SINV irr) at day 0. As a reference, a mouse group with PBS administration at day 0 was included in each of STARR™ and SINV group.
Figure 18B:
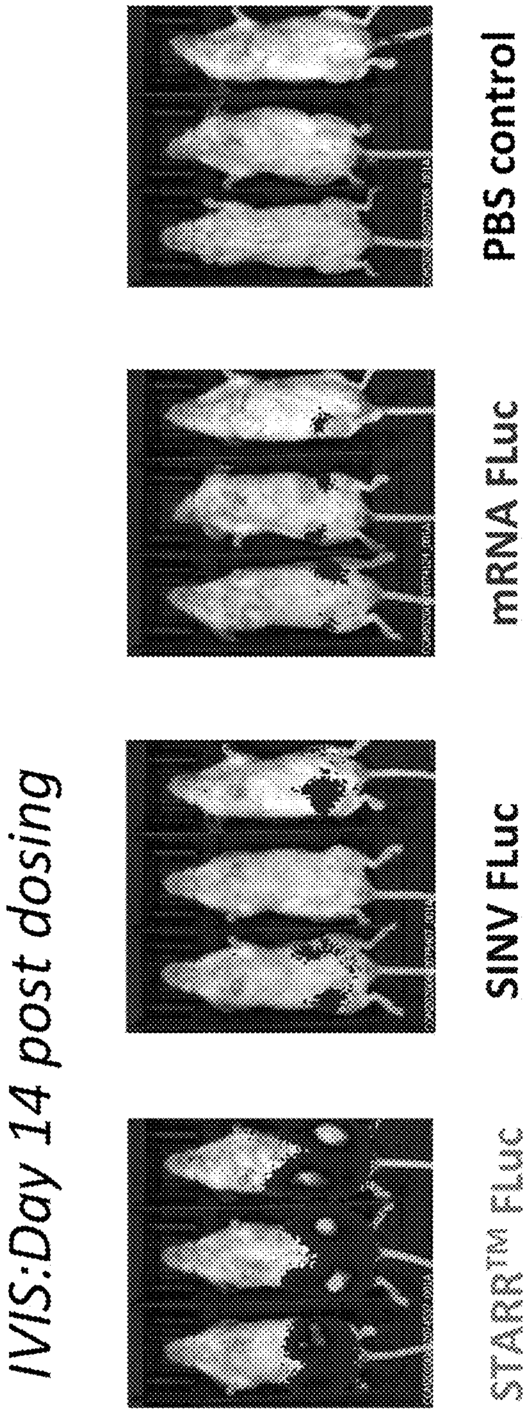
Figure 18C:
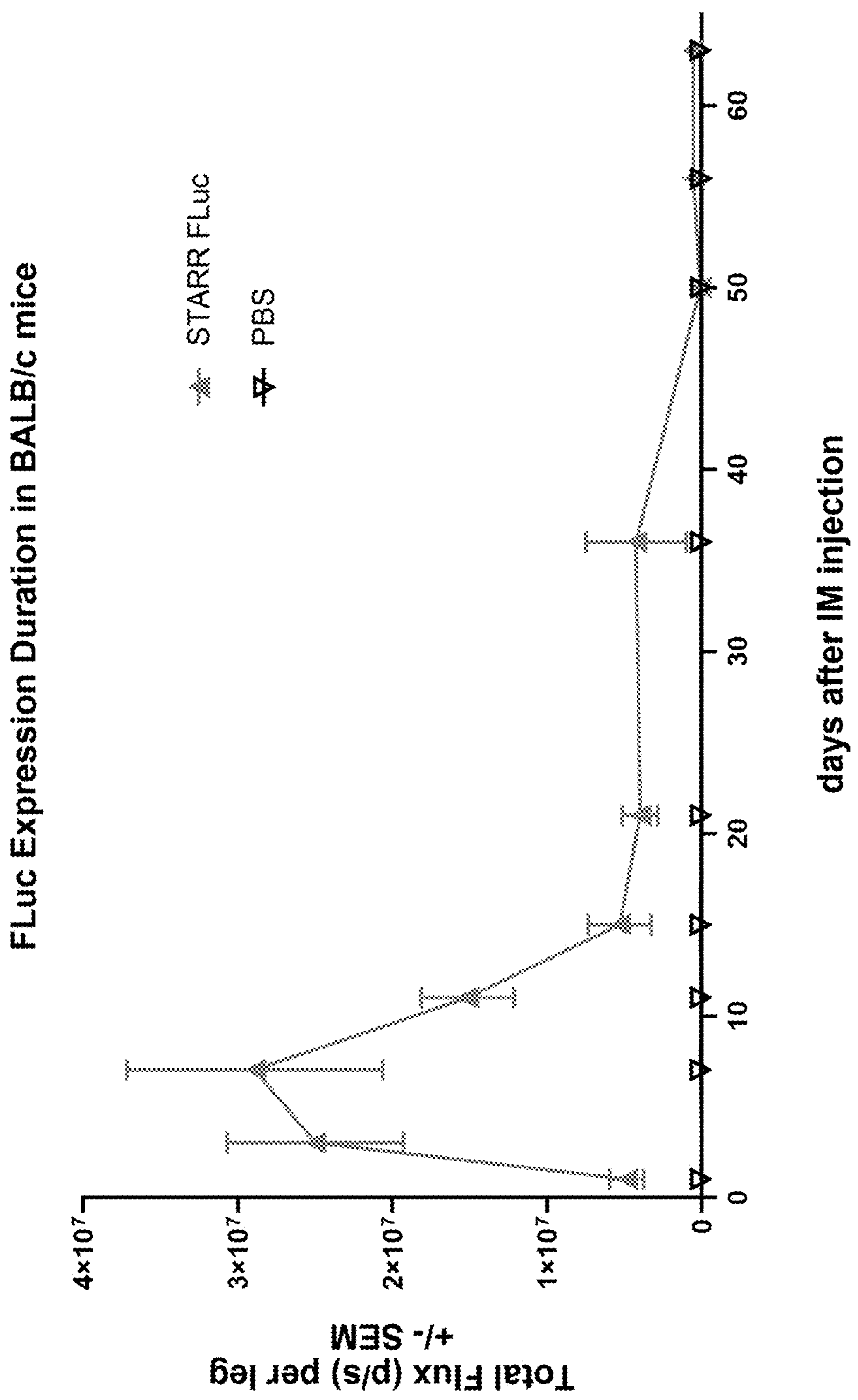
Figure 18D:
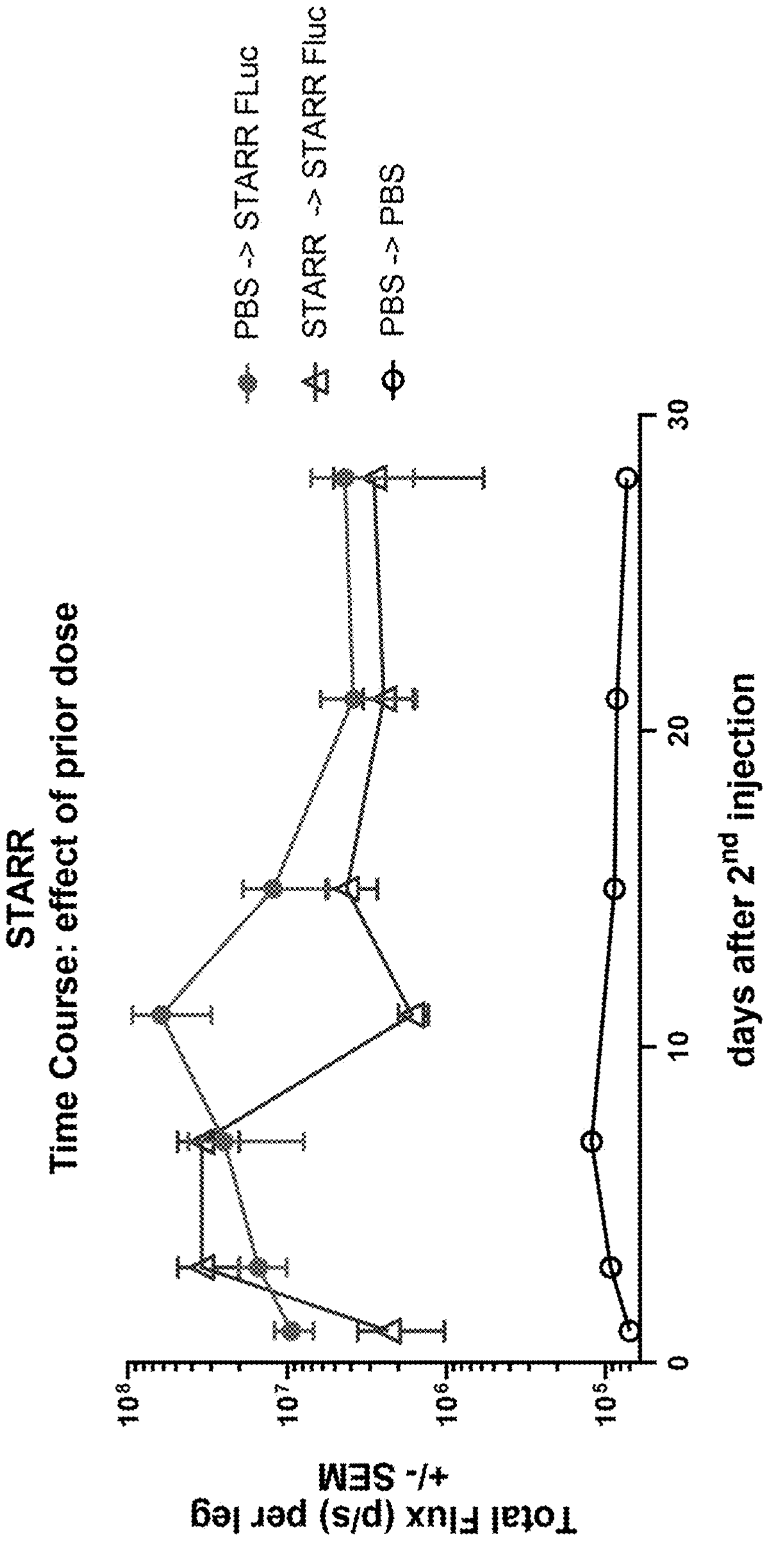
Figure 18D:
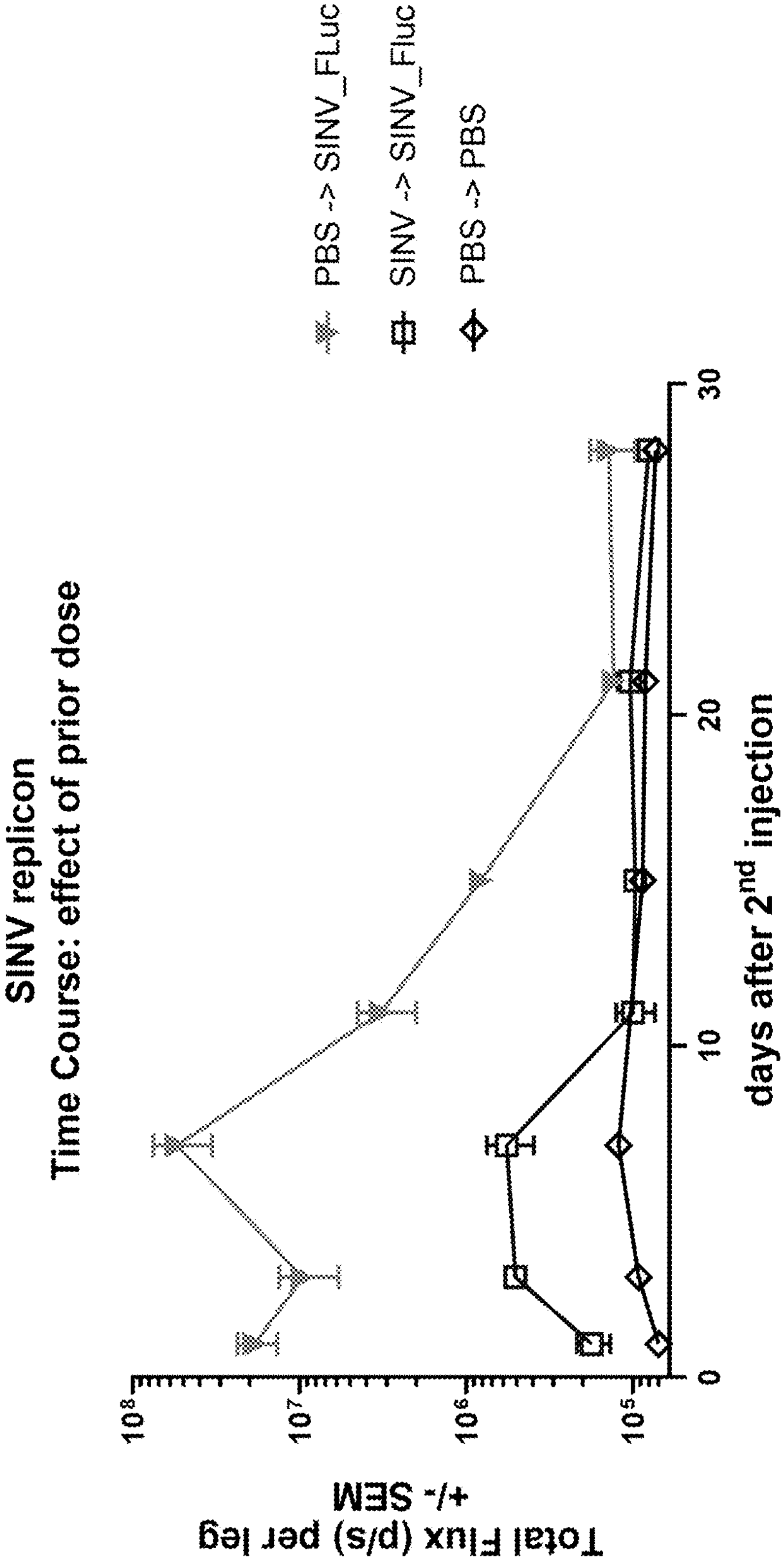

Firefly luciferase (FLuc) expression was monitored from STARR™ Fluc, SINV FLuc, and mRNA FLuc up to day 28 by In Vivo Imaging System (IVIS). Enhanced levels and durations of transgene expression from STARR™ were observed. The expression from STARR™ Fluc peaked around day 3 to 7 and declined until day 22. Fluc expression from SINV FLuc also peaked on day 10, however, the expression was reduced at a significantly faster rate than STARR™ FLuc. Additionally, the expression on day 3 was significantly lower than STARR™ FLuc. FLuc expression from the conventional mRNA backbone was highest at day 1, the earliest time point in this study, and declined at a slightly faster rate than that of STARR™-Fluc (FIG. 18A). FIG. 18B shows that at 14 days post dosing, FLuc expression from STARR™ FLuc was higher than the other groups by about two orders of magnitude. FIG. 18D shows that the effect of the STARR™ backbone remained minimal throughout the experimental period (up to day 28), while prior administration of SINV replicon backbone resulted in a reduction of FLuc transgene expression by ~2 orders of magnitude.

Figure 19:
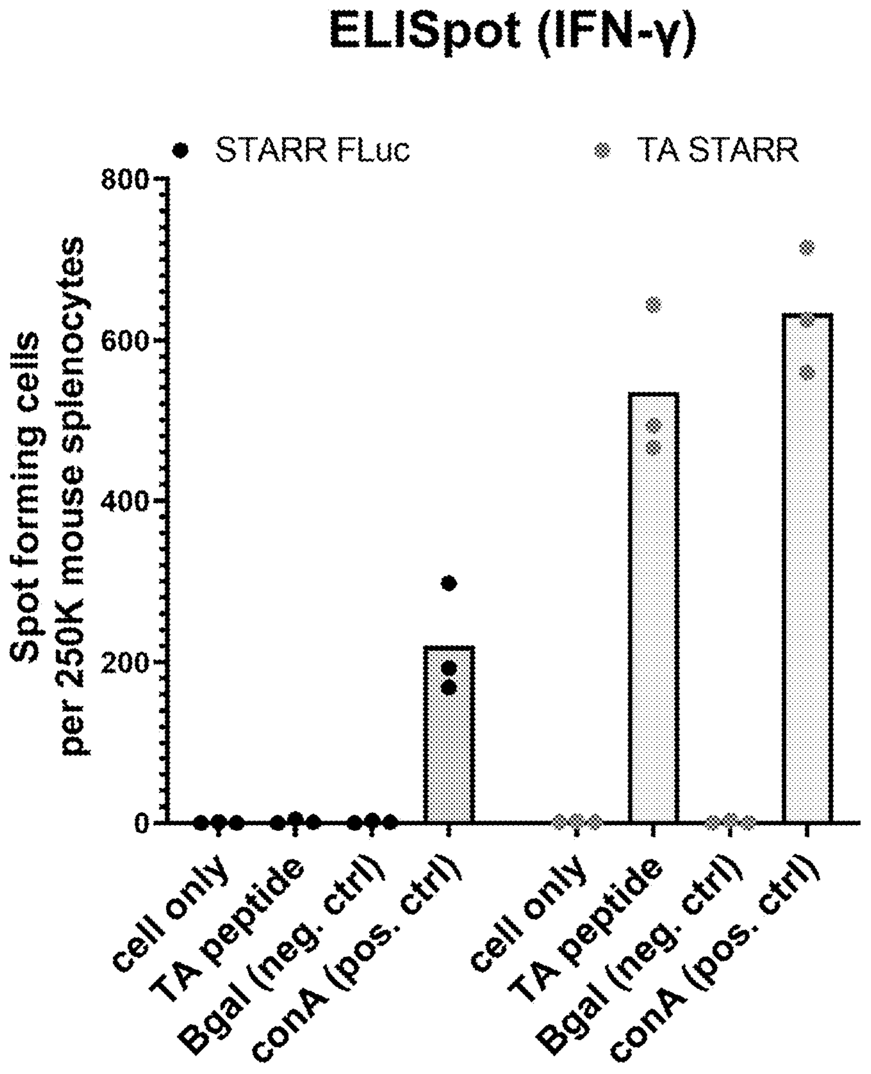
FIG. 19 shows that STARR™ elicits antigen-specific IFN-gamma response. Enzyme-linked immune absorbent spot ELISpot was used to count the number of splenocytes that were specifically stimulated by an antigen peptide of the same amino acid sequence encoded in TA STARR™. Neither no peptide (cell only) nor irrelevant peptide (Bgal) did not elicit significant IFN-gamma from splenocytes from mice vaccinated with STARR™ FLuc or TA STARR™. Stimulation with AH1-A5 peptide resulted in the detection of IFN-gamma-producing cells specifically from the mice that were vaccinated with TASTARR™. Concanavalin A (ConA) was used as a positive control of IFN-gamma production.
Figure 20A:
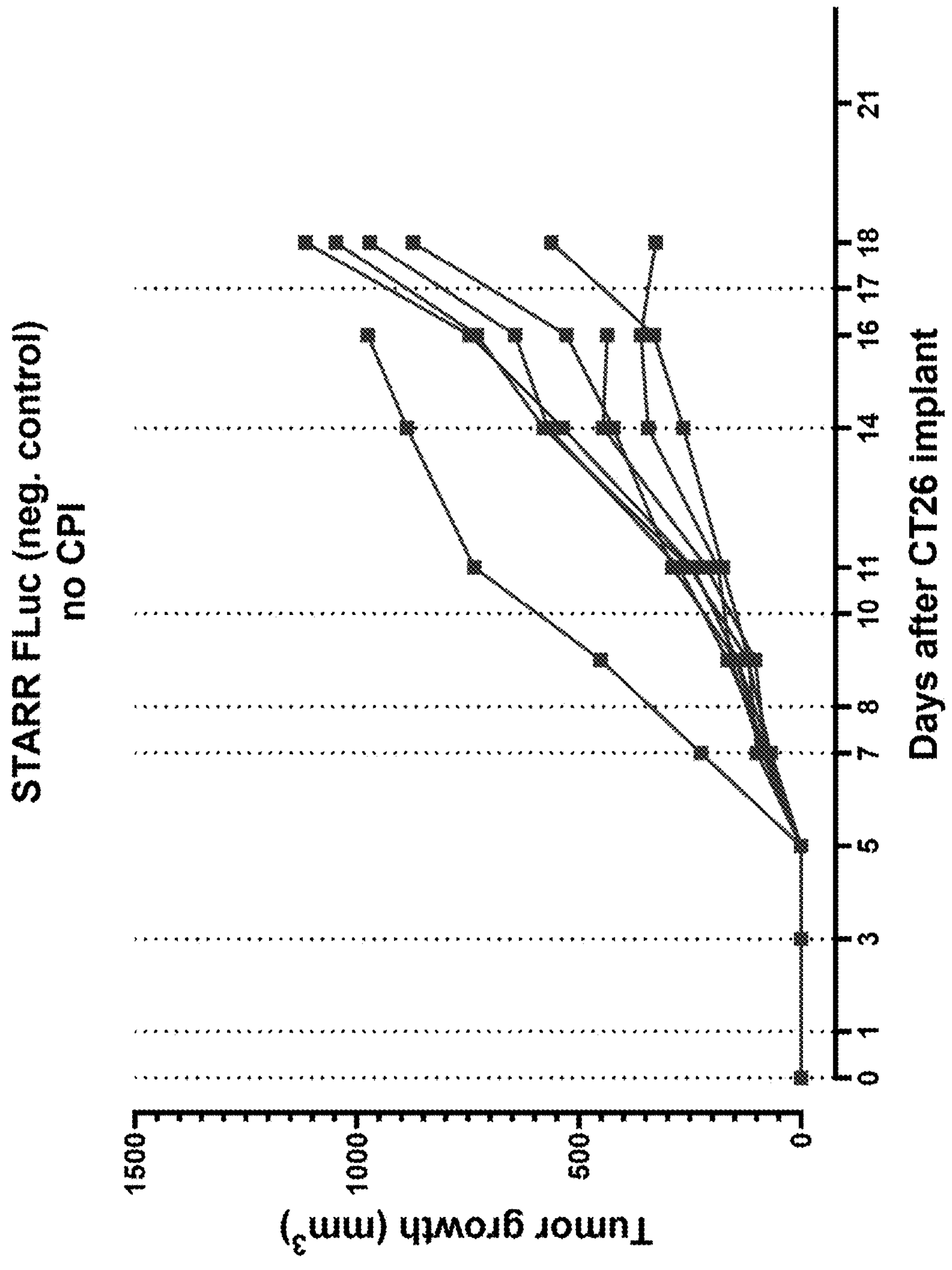
FIGS. 20A-20F illustrate reduced tumor growth rate by TA STARR™ vaccination in a CT26 syngeneic mouse model. CT26 murine colorectal carcinoma cells ($5\times10^5$) were subcutaneously implanted in 10-week old female BALB/c mice (n=8 per group). On days 1 and 8, the mice were vaccinated with STARR™ FLuc, a negative control, or TA STARR™, which encodes AH1A5 epitope. Tumor growth was monitored in mice vaccinated with (20A) STARR™ FLuc without checkpoint inhibitor treatment; (20B) STARR™ FLuc with a combination anti-PD1/PDL1 treatment; (20C) STARR™ FLuc with a combination anti-CTLA4 treatment; (20D) STARR™ vaccine without checkpoint inhibitor treatment; (20E) STARR™ vaccine with a combination treatment of anti-PD1 and anti-PDL1; and (20F) STARR™ vaccine with a combination treatment of anti-CTLA4. The individual tumor growth curves from a mouse group that were administered with STARR™ FLuc and TA STARR™ are shown in upper and lower panels, respectively.
Figure 20B:
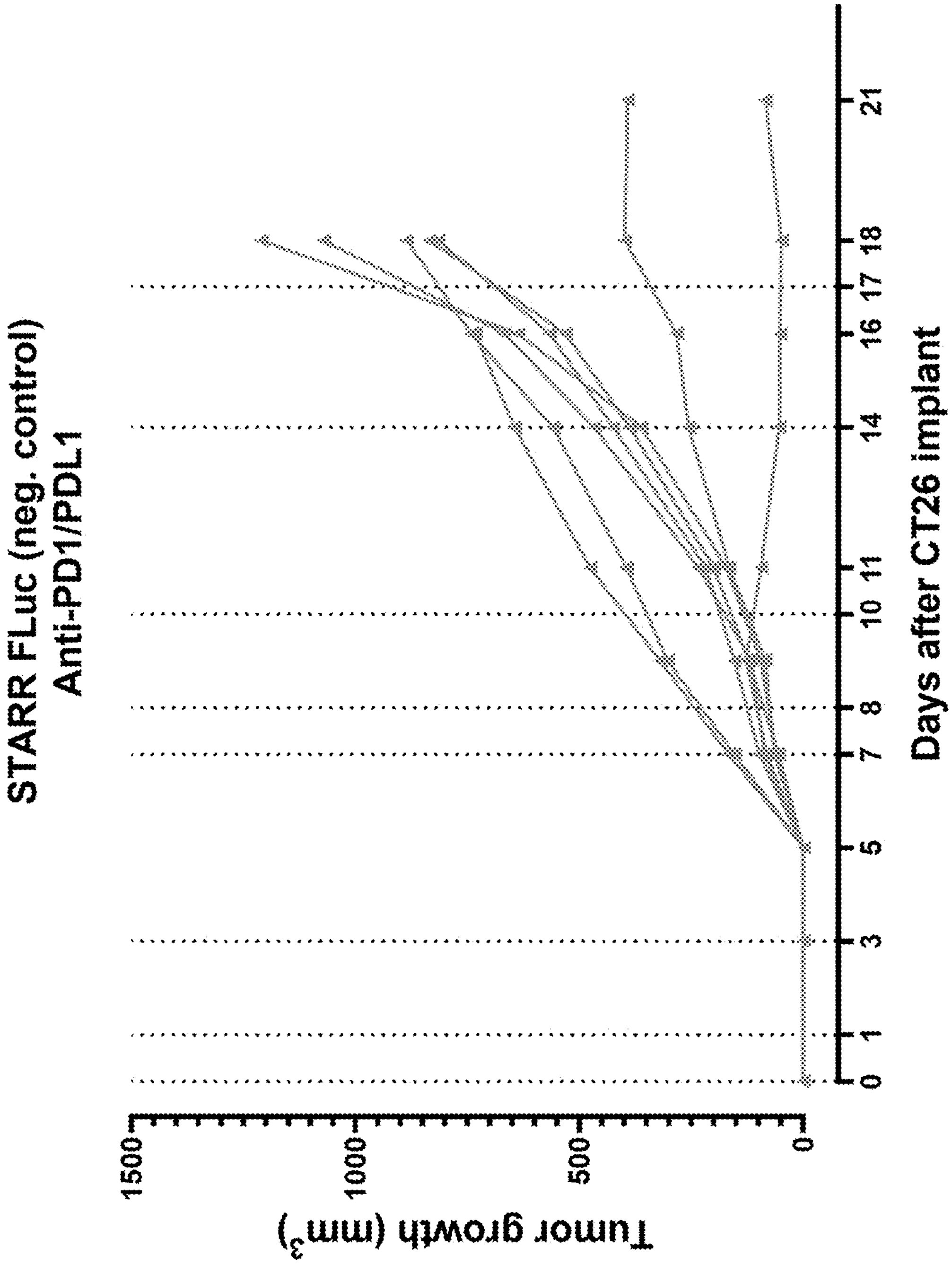
Figure 20C:
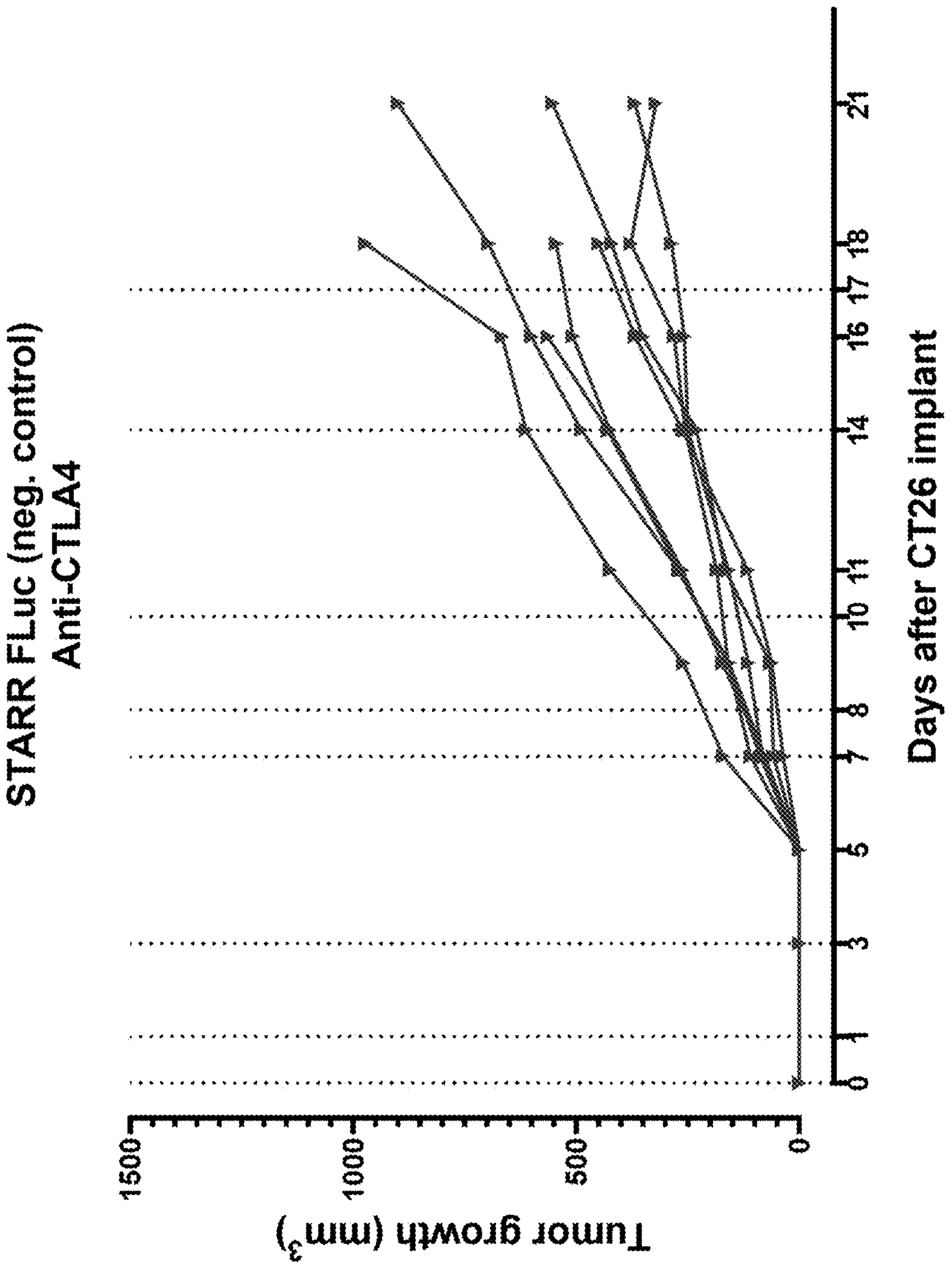
Figure 20D:
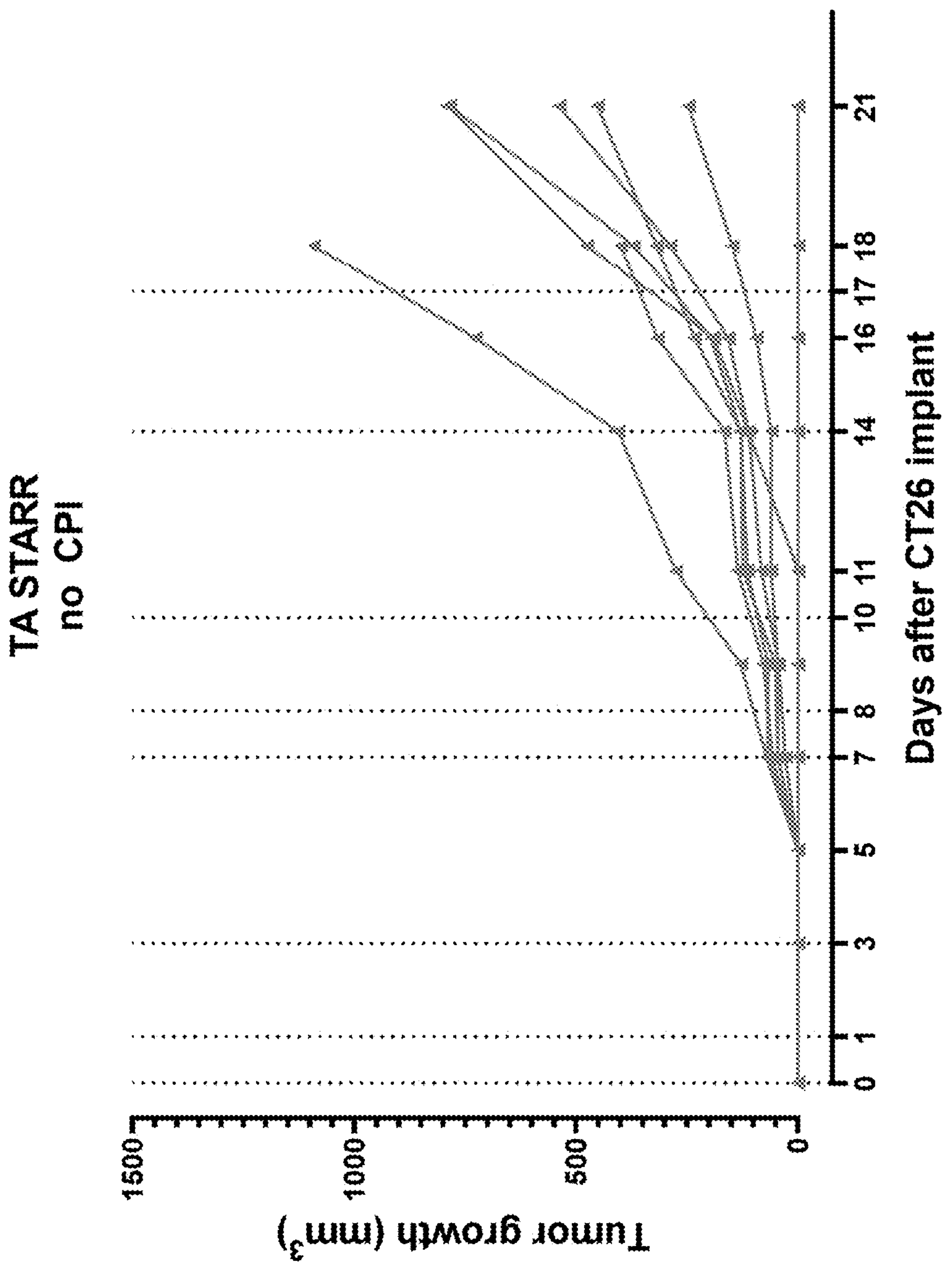
Figure 20E:
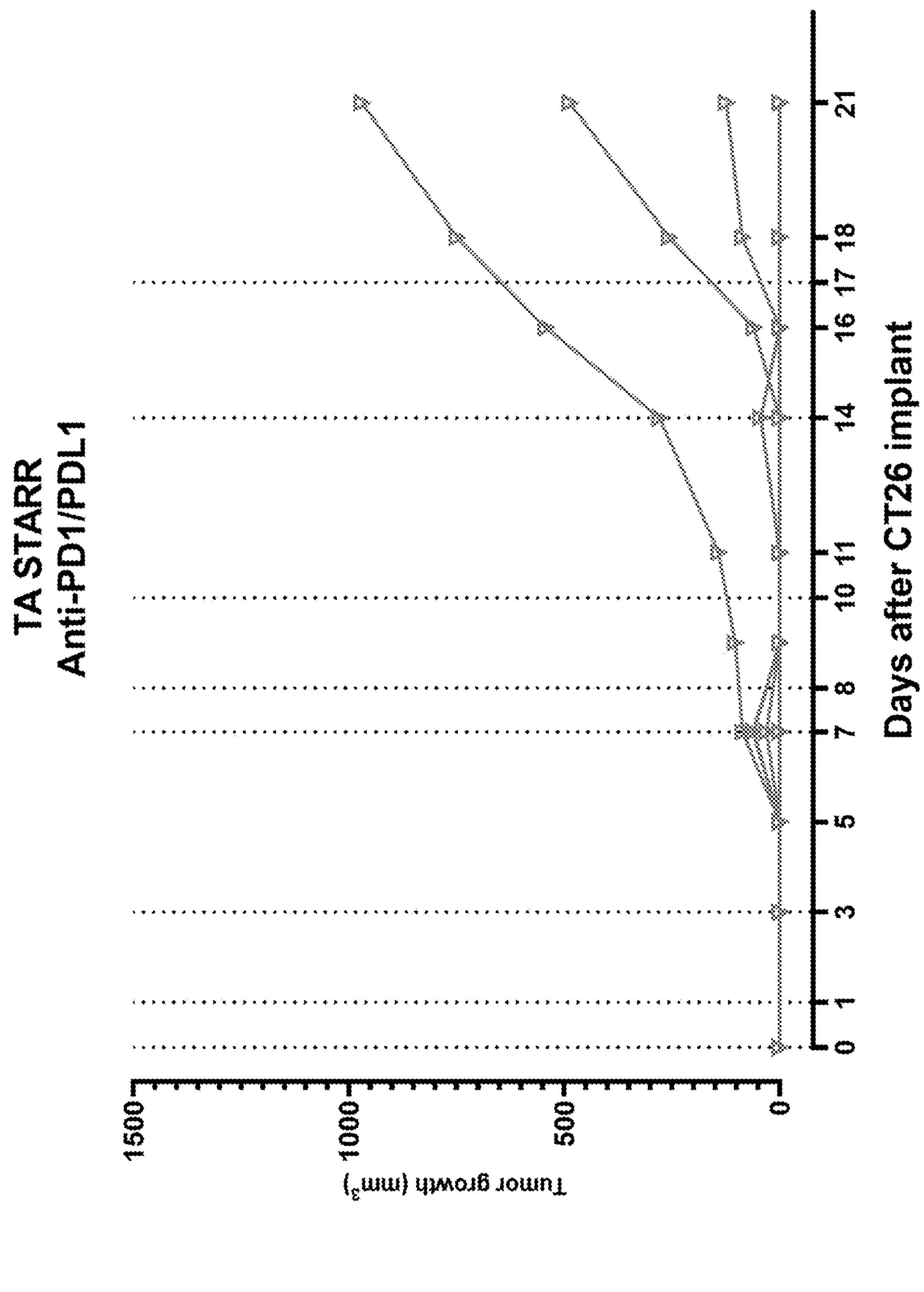
Figure 20F:
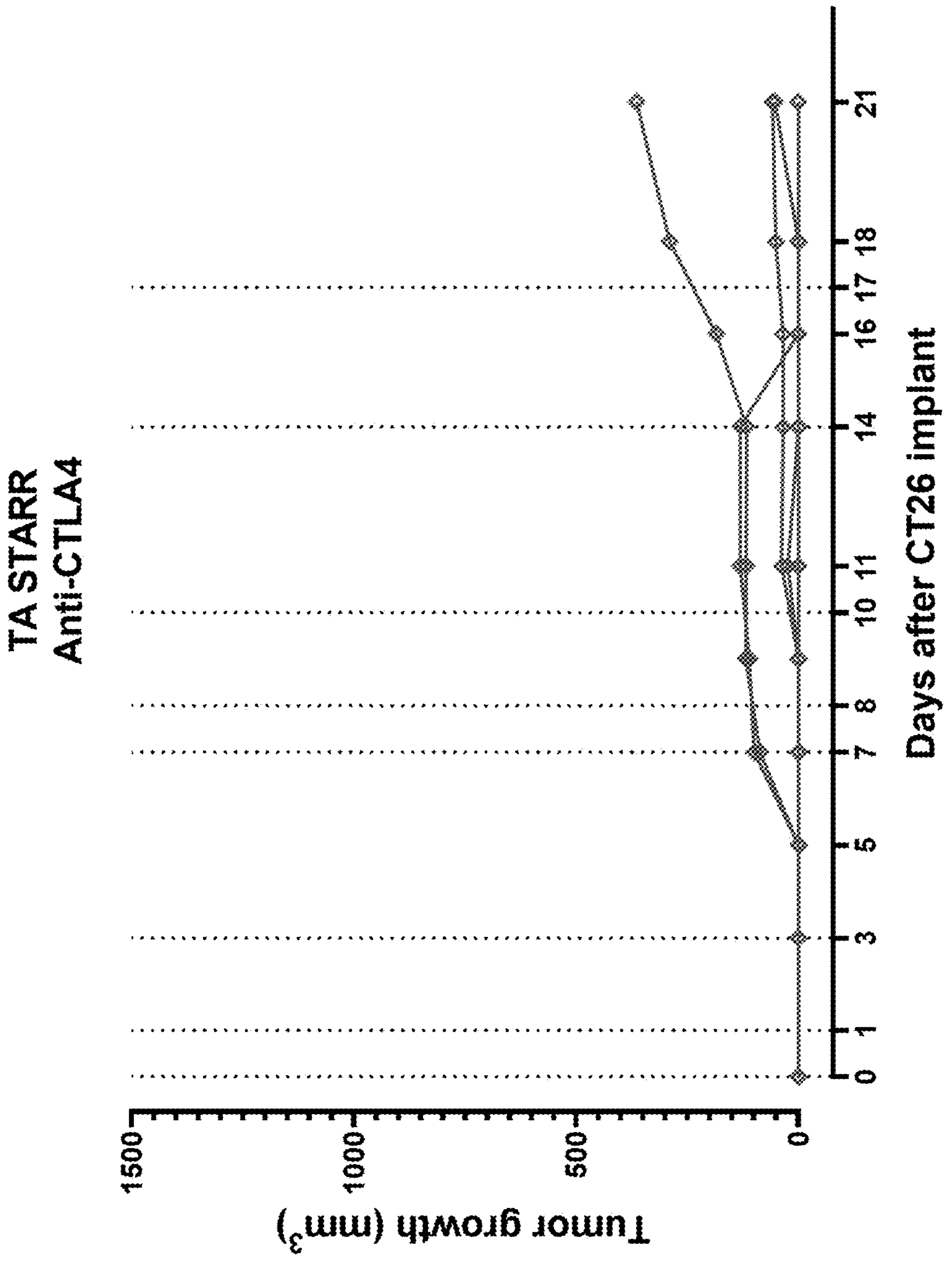

A cancer vaccine substrate, TA STARR™, was constructed next with the STARR™ backbone that encodes AH1A5 epitope from gp70, an envelope glycoprotein of endogenous Murine leukemia virus. AH1 (SPSYVYHQF) (SEQ ID NO:110) is an H-2Ld-restricted antigen of gp70423-431, which is expressed in tumor cells such as the CT26 colorectal cancer cell line, but not expressed in most of the normal tissues. AH1-A5 is a mutated sequence with SPSYAYHQF (SEQ ID NO:111) (the mutation underlined) with enhanced affinity to the T cell receptor (Slansky, et al., 2000, Immunity 13: 529-538). The open reading frame of the TA STARR™ subgenomic RNA contains a cassette with a signal peptide from the HLA class I antigen, gp70 sequence containing AH1A5 epitope, ovalbumin epitope (OVA323-339), and MHC class I trafficking signal (Kreiter, et al. 2008, J Immunol 180: 309-318). Three female BALB/c mice were intramuscularly injected with 10 ug of LNP formulated STARR™ transcripts, STARR™ FLuc or TA STARR™, on day 0 and day 7. On day 16, the spleens were harvested and the splenocytes were isolated. Splenocytes (2.5×105 cells) were incubated with or without AH1A5 (SPSYAYHQF) (SEQ ID NO:111), beta-gal peptide (TPH- PARIGL) (SEQ ID NO: 112) at 1 ug/ml, and 1× Concanavalin A (Life Technologies). ELISpot detecting murine IFN-gamma (ImmunoSpot) was performed according to the manufacturer's instructions. As can be seen in FIG. 19, TA STARR™ elicited antigen-specific IFN-gamma responses.

Figure 21:
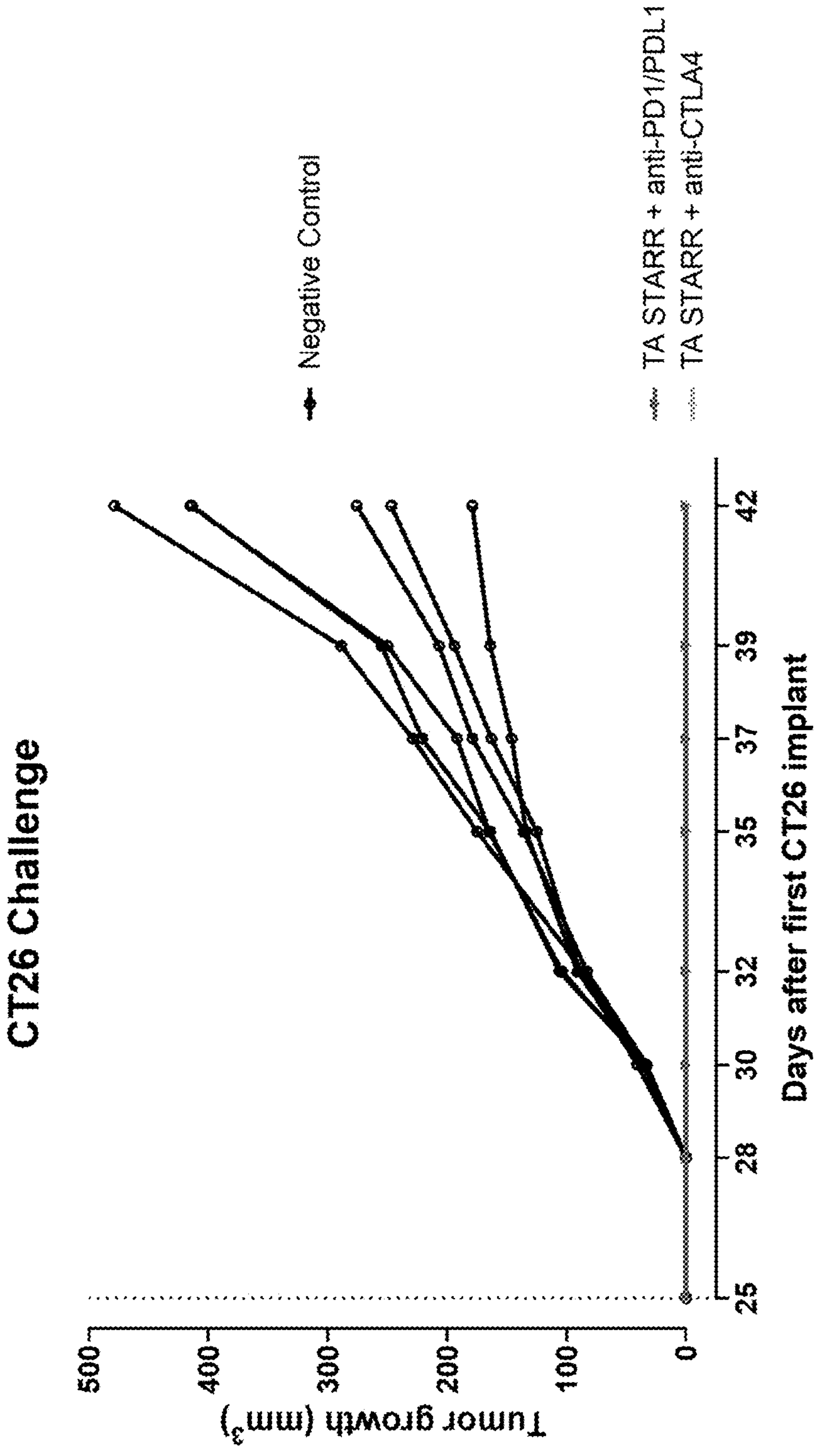
FIG. 21 illustrates prolonged protection by combination treatment of TA STARR™ Vaccine with checkpoint inhibitors. Mice that were treated with TA STARR™ combined with anti-PD1/PDL1 or anti-CTLA4 were found to be resistant to tumor growth following the CT26 challenge at day 25 to 42. Naïve mice were used as a control for the CT26 tumor growth.

BALB/c mice, 10 week-old female, were subcutaneously implanted in the right flank with 5×105 cells of CT26 cells in PBS. A day later, LNP-formulated STARR™ RNA was injected intramuscularly in the left leg at a dose of 10 ug in 100 ul. The mice were administered another booster shot on day 8 with the same dose. For a group with combination treatment of anti-mouse PD1 (RMP1-14, BioXCell) and anti-mouse PDL1 (10F.9G2, BioXcell), the combined checkpoint inhibitor (100 ug each) was administered via intraperitoneal injection in the right quadrant twice weekly for two weeks starting on day 3. For a group with the treatment of anti-mouse CTLA4 (9H10, BioxCell), 200 ug of the checkpoint inhibitor was administered in the same manner but starting on day 7. Five mice of the group with the combo treatment of TA STARR™ vaccine and the checkpoint inhibitors remained tumor-free on day 25, and were further challenged by subcutaneous implantation of CT26 (5×105 cells) in the right flank where the implantation site was slightly above the first implantation site. Naïve mice were used as a control group. The tumor growth was monitored for another 17 days (i.e. up to day 42 since the first CT26 implantation) before euthanization. FIGS. 20A-20F illustrates reduced tumor growth resulting from TA STARR™ vaccination and FIG. 21 shows prolonged protection resulting from treatment with the TA STARR™ vaccine in combination with checkpoint inhibitors.

Figure 22A:
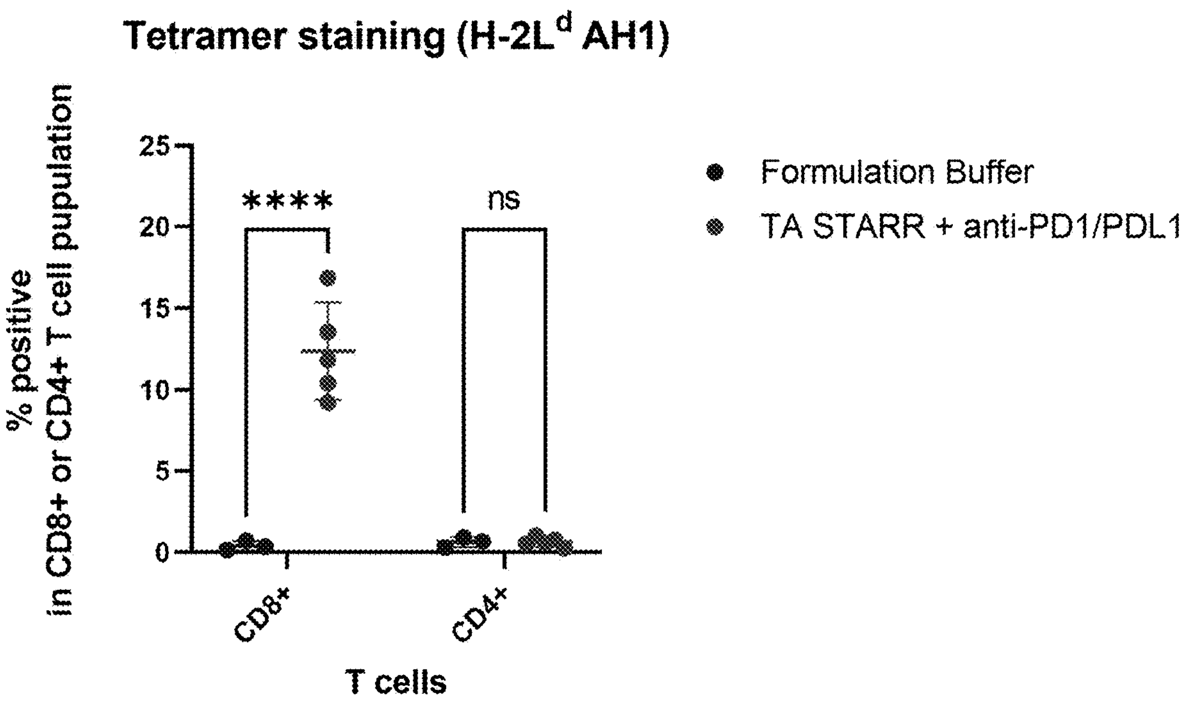
FIGS. 22A-22C show results from AH1-tetramer staining of CD8+ T-cells in the form of (22A) a graph and (22B and 22C) plots. Splenocytes from the mice group with combination treatment of TA STARR™ and anti-PD1/PDL1 at day 42 were stained with AH1 (H-2Ld)-tetramer. The staining was specific to CD8+ T cells from the mouse group with TA STARR™ treatment, and the population represented 9-17% of total CD8+ T cells from the splenocytes.
Figure 22B:
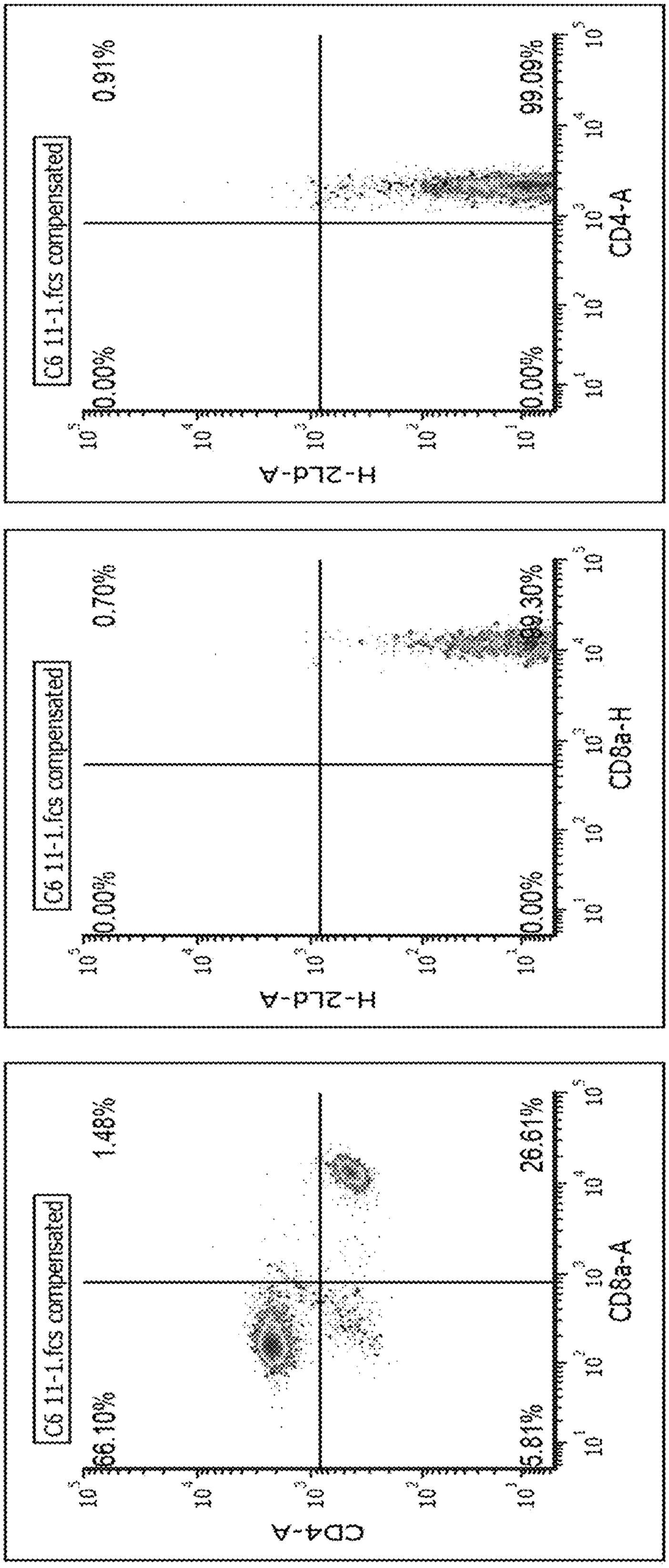
Figure 22C:
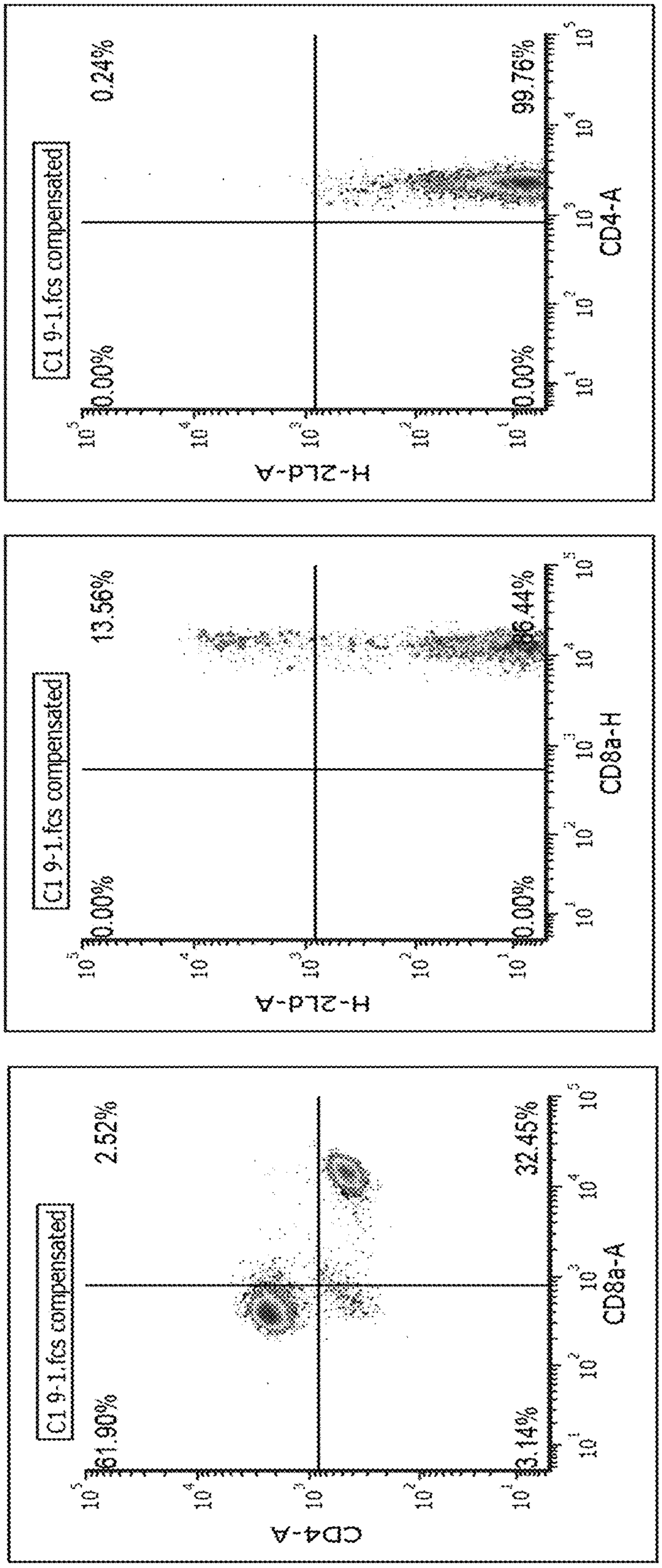

Splenocytes from the combination treatment group with TA STARR™ and anti-PD1/PDL1 were harvested for tetramer staining with AH1 peptide. Splenocytes from the control group with the LNP formulation buffer with the same dosing schedule were used as a negative control. The splenocytes (2×106 cells) were incubated with AH1 (H-2Ld)-tetramer (MBL) followed by appropriate fluorescent-labeled antibodies (Alexa Fluor 488 anti-CD8a (53-6.7), Pacific Orange anti-CD4 (RM4-5), and Pacific Blue anti-mouse CD3ε (145-2C11), eBioscience) and DRAQ7 (Invitrogen) by following the manufacture's recommendation, and 500K events were analyzed by ZE5 Cell Analyzer (Bio-Rad). Results are shown in FIGS. 22A-22C.

TABLE 9

| Transgene ORF nucleotide sequence | | | |
|---|---|---|---|
| mARM # | RNA back bone | Transgene | Sequence |
| 2809 (SEQ ID NO: 84) | STARR ™ | Fluc | AUGGAAGAUGCCAAAAACAUUAAGAAGGGCCCAGCGCCAUUCUACC<br>CACUCGAAGACGGGACCGCCGGCGAGCAGCUGCACAAAGCCAUGAA<br>GCGCUACGCCCUGGUGCCCGGCACCAUCGCCUUUACCGACGCACAU<br>AUCGAGGUGGACAUUACCUACGCCGAGUACUUCGAGAUGAGCGUUC<br>GGCUGGCAGAAGCUAUGAAGCGCUAUGGGCUGAAUACAAACCAUCG<br>GAUCGUGGUGUGCAGCGAGAAUAGCUUGCAGUUCUUCAUGCCCGUG<br>UUGGGUGCCCUGUUCAUCGGUGUGGCUGUGGCCCCAGCUAACGACA<br>UCUACAACGAGCGCGAGCUGCUGAACAGCAUGGGCAUCAGCCAGCC<br>CACCGUCGUAUUCGUGAGCAAGAAAGGGCUGCAAAAGAUCCUCAAC<br>GUGCAAAAGAAGCUACCGAUCAUACAAAAGAUCAUCAUCAUGGAUA<br>GCAAGACCGACUACCAGGGCUUCCAAAGCAUGUACACCUUCGUGAC<br>UUCCCAUUUGCCACCCGGCUUCAACGAGUACGACUUCGUGCCCGAG<br>AGCUUCGACCGGGACAAAACCAUCGCCCUGAUCAUGAACAGUAGUG<br>GCAGUACCGGAUUGCCCAAGGGCGUAGCCCUACCGCACCGCACCGC<br>UUGUGUCCGAUUCAGUCAUGCCCGCGACCCCAUCUUCGGCAACCAG<br>AUCAUCCCCGACACCGCUAUCCUCAGCGUGGUGCCAUUUCACCACG<br>GCUUCGGCAUGUUCACCACGCUGGGCUACUUGAUCUGCGGCUUUCG<br>GGUCGUGCUCAUGUACCGCUUCGAGGAGGAGCUAUUCUUGCGCAGC<br>UUGCAAGACUAUAAGAUUCAAUCUGCCCUGCUGGUGCCCACACUAU<br>UUAGCUUCUUCGCUAAGAGCACUCUCAUCGACAAGUACGACCUAAG<br>CAACUUGCACGAGAUCGCCAGCGGCGGGGCGCCGCUCAGCAAGGAG<br>GUAGGUGAGGCCGUGGCCAAACGCUUCCACCUACCAGGCAUCCGAC<br>AGGGCUACGGCCUGACAGAAACAACCAGCGCCAUUCUGAUCACCCC<br>CGAAGGGGACGACAAGCCUGGCGCAGUAGGCAAGGUGGUGCCCUUC<br>UUCGAGGCUAAGGUGGUGGACUUGGACACCGGUAAGACACUGGGUG<br>UGAACCAGCGCGGCGAGCUGUGCGUCCGUGGCCCCAUGAUCAUGAG<br>CGGCUACGUUAACAACCCCGAGGCUACAAACGCUCUCAUCGACAAG<br>GACGGCUGGCUGCACAGCGGCGACAUCGCCUACUGGGACGAGGACG<br>AGCACUUCUUCAUCGUGGACCGGCUGAAGUCCCUGAUCAAAUACAA<br>GGGCUACCAGGUAGCCCCAGCCGAACUGGAGAGCAUCCUGCUGCAA<br>CACCCCAACAUCUUCGACGCCGGGGUCGCCGGCCUGCCCGACGACG<br>AUGCCGGCGAGCUGCCCGCCGCAGUCGUCGUGCUGGAACACGGUAA<br>AACCAUGACCGAGAAGGAGAUCGUGGACUAUGUGGCCAGCCAGGUU<br>ACAACCGCCAAGAAGCUGCGCGGUGGUGUUGUGUUCGUGGACGAGG<br>UGCCUAAAGGACUGACCGGCAAGUUGGACGCCCGCAAGAUCCGCGA<br>GAUUCUCAUUAAGGCCAAGAAGGGCGGCAAGAUCGCCGUGUAA |
| 2842 (SEQ ID NO: 85) | SINV replicon | Fluc | AUGGAAGAUGCCAAAAACAUUAAGAAGGGCCCAGCGCCAUUCUACC<br>CACUCGAAGACGGGACCGCCGGCGAGCAGCUGCACAAAGCCAUGAA<br>GCGCUACGCCCUGGUGCCCGGCACCAUCGCCUUUACCGACGCACAU<br>AUCGAGGUGGACAUUACCUACGCCGAGUACUUCGAGAUGAGCGUUC<br>GGCUGGCAGAAGCUAUGAAGCGCUAUGGGCUGAAUACAAACCAUCG<br>GAUCGUGGUGUGCAGCGAGAAUAGCUUGCAGUUCUUCAUGCCCGUG<br>UUGGGUGCCCUGUUCAUCGGUGUGGCUGUGGCCCCAGCUAACGACA<br>UCUACAACGAGCGCGAGCUGCUGAACAGCAUGGGCAUCAGCCAGCC<br>CACCGUCGUAUUCGUGAGCAAGAAAGGGCUGCAAAAGAUCCUCAAC |

TABLE 9-continued

| | | | |
|---|---|---|---|
| | | | GUGCAAAAGAAGCUACCGAUCAUACAAAAGAUCAUCAUCAUGGAUA<br>GCAAGACCGACUACCAGGGCUUCCAAAGCAUGUACACCUUCGUGAC<br>UUCCCAUUUGCCACCCGGCUUCAACGAGUACGACUUCGUGCCCGAG<br>AGCUUCGACCGGGACAAAACCAUCGCCCUGAUCAUGAACAGUAGUG<br>GCAGUACCGGAUUGCCCAAGGGCGUAGCCCUACCGCACCGCACCGC<br>UUGUGUCCGAUUCAGUCAUGCCCGCGACCCCAUCUUCGGCAACCAG<br>AUCAUCCCCGACACCGCUAUCCUCAGCGUGGUGCCAUUUCACCACG<br>GCUUCGGCAUGUUCACCACGCUGGGCUACUUGAUCUGCGGCUUUCG<br>GGUCGUGCUCAUGUACCGCUUCGAGGAGGAGCUAUUCUUGCGCAGC<br>UUGCAAGACUAUAAGAUUCAAUCUGCCCUGCUGGUGCCCACACUAU<br>UUAGCUUCUUCGCUAAGAGCACUCUCAUCGACAAGUACGACCUAAG<br>CAACUUGCACGAGAUCGCCAGCGGCGGGGCGCCGCUCAGCAAGGAG<br>GUAGGUGAGGCCGUGGCCAAACGCUUCCACCUACCAGGCAUCCGAC<br>AGGGCUACGGCCUGACAGAAACAACCAGCGCCAUUCUGAUCACCCC<br>CGAAGGGGACGACAAGCCUGGCGCAGUAGGCAAGGUGGUGCCCUUC<br>UUCGAGGCUAAGGUGGUGGACUUGGACACCGGUAAGACACUGGGUG<br>UGAACCAGCGCGGCGAGCUGUGCGUCCGUGGCCCCAUGAUCAUGAG<br>CGGCUACGUUAACAACCCCGAGGCUACAAACGCUCUCAUCGACAAG<br>GACGGCUGGCUGCACAGCGGCGACAUCGCCUACUGGGACGAGGACG<br>AGCACUUCUUCAUCGUGGACCGGCUGAAGUCCCUGAUCAAAUACAA<br>GGGCUACCAGGUAGCCCCAGCCGAACUGGAGAGCAUCCUGCUGCAA<br>CACCCCAACAUCUUCGACGCCGGGGUCGCCGGCCUGCCCGACGACG<br>AUGCCGGCGAGCUGCCCGCCGCAGUCGUCGUGCUGGAACACGGUAA<br>AACCAUGACCGAGAAGGAGAUCGUGGACUAUGUGGCCAGCCAGGUU<br>ACAACCGCCAAGAAGCUGCGCGGUGGUGUUGUGUUCGUGGACGAGG<br>UGCCUAAAGGACUGACCGGCAAGUUGGACGCCCGCAAGAUCCGCGA<br>GAUUCUCAUUAAGGCCAAGAAGGGCGGCAAGAUCGCCGUGUAA |
| 1782 (SEQ ID NO: 86) | mRNA (TEV-XbG) | Fluc | AUGGAAGAUGCCAAAAACAUUAAGAAGGGCCCAGCGCCAUUCUACC<br>CACUCGAAGACGGGACCGCCGGCGAGCAGCUGCACAAAGCCAUGAA<br>GCGCUACGCCCUGGUGCCCGGCACCAUCGCCUUUACCGACGCACAU<br>AUCGAGGUGGACAUUACCUACGCCGAGUACUUCGAGAUGAGCGUUC<br>GGCUGGCAGAAGCUAUGAAGCGCUAUGGGCUGAAUACAAACCAUCG<br>GAUCGUGGUGUGCAGCGAGAAUAGCUUGCAGUUCUUCAUGCCCGUG<br>UUGGGUGCCCUGUUCAUCGGUGUGGCUGUGGCCCCAGCUAACGACA<br>UCUACAACGAGCGCGAGCUGCUGAACAGCAUGGGCAUCAGCCAGCC<br>CACCGUCGUAUUCGUGAGCAAGAAAGGGCUGCAAAAGAUCCUCAAC<br>GUGCAAAAGAAGCUACCGAUCAUACAAAAGAUCAUCAUCAUGGAUA<br>GCAAGACCGACUACCAGGGCUUCCAAAGCAUGUACACCUUCGUGAC<br>UUCCCAUUUGCCACCCGGCUUCAACGAGUACGACUUCGUGCCCGAG<br>AGCUUCGACCGGGACAAAACCAUCGCCCUGAUCAUGAACAGUAGUG<br>GCAGUACCGGAUUGCCCAAGGGCGUAGCCCUACCGCACCGCACCGC<br>UUGUGUCCGAUUCAGUCAUGCCCGCGACCCCAUCUUCGGCAACCAG<br>AUCAUCCCCGACACCGCUAUCCUCAGCGUGGUGCCAUUUCACCACG<br>GCUUCGGCAUGUUCACCACGCUGGGCUACUUGAUCUGCGGCUUUCG<br>GGUCGUGCUCAUGUACCGCUUCGAGGAGGAGCUAUUCUUGCGCAGC<br>UUGCAAGACUAUAAGAUUCAAUCUGCCCUGCUGGUGCCCACACUAU<br>UUAGCUUCUUCGCUAAGAGCACUCUCAUCGACAAGUACGACCUAAG<br>CAACUUGCACGAGAUCGCCAGCGGCGGGGCGCCGCUCAGCAAGGAG<br>GUAGGUGAGGCCGUGGCCAAACGCUUCCACCUACCAGGCAUCCGAC<br>AGGGCUACGGCCUGACAGAAACAACCAGCGCCAUUCUGAUCACCCC<br>CGAAGGGGACGACAAGCCUGGCGCAGUAGGCAAGGUGGUGCCCUUC<br>UUCGAGGCUAAGGUGGUGGACUUGGACACCGGUAAGACACUGGGUG<br>UGAACCAGCGCGGCGAGCUGUGCGUCCGUGGCCCCAUGAUCAUGAG<br>CGGCUACGUUAACAACCCCGAGGCUACAAACGCUCUCAUCGACAAG<br>GACGGCUGGCUGCACAGCGGCGACAUCGCCUACUGGGACGAGGACG<br>AGCACUUCUUCAUCGUGGACCGGCUGAAGUCCCUGAUCAAAUACAA<br>GGGCUACCAGGUAGCCCCAGCCGAACUGGAGAGCAUCCUGCUGCAA<br>CACCCCAACAUCUUCGACGCCGGGGUCGCCGGCCUGCCCGACGACG<br>AUGCCGGCGAGCUGCCCGCCGCAGUCGUCGUGCUGGAACACGGUAA<br>AACCAUGACCGAGAAGGAGAUCGUGGACUAUGUGGCCAGCCAGGUU<br>ACAACCGCCAAGAAGCUGCGCGGUGGUGUUGUGUUCGUGGACGAGG<br>UGCCUAAAGGACUGACCGGCAAGUUGGACGCCCGCAAGAUCCGCGA<br>GAUUCUCAUUAAGGCCAAGAAGGGCGGCAAGAUCGCCGUGUAA |
| 2847 (SEQ ID NO: 87) | STARR ™ | KRAS epitope wt | AUGAAGUUGGUGGUUGUGGGGGCCGGGGGUGUUGGCAAAAGCGCCC<br>UUACAAUUUGA |
| 2862 (SEQ ID NO: 88) | SINV replicon | Empty | AUGGAUCCUAGACGCUACGCCCCAAUGAUCCGACCAGCAAAACUCG<br>AUGUACUUCCGAGGAACUGA |

TABLE 9-continued

| | | | |
|---|---|---|---|
| 3060 (SEQ ID NO: 89) | STARR ™ | Signal peptide-gp70 with AH1A5-MITD | AUGAGAGUGACAGCCCCUAGAACCUUACUGCUUCUGCUUUGGGGAGCUGUUGCUCUGACAGAGACAUGGGCUGGAUCUCUGAGCGAGGUGACCGGCCAGGGCCUGUGCAUCGGCGCCGUGCCCAAGACCCACCAGGUGCUGUGCAACACCACCCAGAAGACCAGCGACGGCAGCUACUACCUGGCCGCUCCCACCGGCACCACCUGGGCCUGCAGCACCGGCCUGACCCCUUGCAUCAGCACCACCAUCCUGAACCUGACCACCGACUACUGCGUGCUGGUGGAGCUGUGGCCCAGGGUGACCUACCACAGCCCCAGCUACGCCUACCACCAGUUCGAGAGGAGGGCCAAGUACAAGAGGGAGCCCGUGAGCCUGACCCUGGCCCUGCUGCUGGGCGGCCUGACAAUGGGCGGCAUCGCCGCCGGCGUGGGCACCGGCACCACCGCCCUGGUGGCCACCCAGCAGUUCCAGCAGCUGCAGGCCGCCAUGCACGACGACCUGAAGGAGGUGGAGAAGUCCAUCACCAACCUGGAGAAGUCCCUGACCAGCCUGAGCGAGGUGGUGCUGCAGAACAGGAGGGGCCUGGACCUGCUGUUCCUGAAGGAGGGCGGCCUGUGCGCCGCCCUGAAGGAGGAGUGCUGCCUGUACGCCGACCACACCGGCCUGGUGAUCGUGGGCAUUGUCGCUGGCCUGGCCGUCCUCGCCGUGGUGGUGAUUGGAGCUGUGGUCGCAGCUGUUAUGUGCAGAAGAAAGUCAUCCGGCGGAAAGGGAGGCUCCUACUCUCAGGCUGCUUCUGCUACAGUGCCUAGAGCUCUUAUGUGUUUAUCUCAGCUGUAA |
| 3061 (SEQ ID NO: 90) | STARR ™ | Signal peptide-AH1A5 OVA-MITD | AUGAGAGUGACAGCCCCUAGAACCUUACUGCUUCUGCUUUGGGGAGCUGUUGCUCUGACAGAGACAUGGGCUGGAUCUUACCACAGCCCCAGCUACGCCUACCACCAGUUCGAGAGGGGGGGAGGAGGCUCCGGGGGAGGAGGCUCCCUGAAGAUCAGCCAGGCCGUGCACGCCGCCCACGCCGAGAUCAACGAGGCCGGCCGGGAGGUGAUCGUGGGCAUUGUCGCUGGCCUGGCCGUCCUCGCCGUGGUGGUGAUUGGAGCUGUGGUCGCAGCUGUUAUGUGCAGAAGAAAGUCAUCCGGCGGAAAGGGAGGCUCCUACUCUCAGGCUGCUUCUGCUACAGUGCCUAGAGCUCUUAUGUGUUUAUCUCAGCUGUAA |
| 3076 (SEQ ID NO: 91) | STARR ™ | Signal peptide-gp70 with AH1A5-MITD-FLAG | AUGAGAGUGACAGCCCCUAGAACCUUACUGCUUCUGCUUUGGGGAGCUGUUGCUCUGACAGAGACAUGGGCUGGAUCUCUGAGCGAGGUGACCGGCCAGGGCCUGUGCAUCGGCGCCGUGCCCAAGACCCACCAGGUGCUGUGCAACACCACCCAGAAGACCAGCGACGGCAGCUACUACCUGGCCGCUCCCACCGGCACCACCUGGGCCUGCAGCACCGGCCUGACCCCUUGCAUCAGCACCACCAUCCUGAACCUGACCACCGACUACUGCGUGCUGGUGGAGCUGUGGCCCAGGGUGACCUACCACAGCCCCAGCUACGCCUACCACCAGUUCGAGAGGAGGGCCAAGUACAAGAGGGAGCCCGUGAGCCUGACCCUGGCCCUGCUGCUGGGCGGCCUGACAAUGGGCGGCAUCGCCGCCGGCGUGGGCACCGGCACCACCGCCCUGGUGGCCACCCAGCAGUUCCAGCAGCUGCAGGCCGCCAUGCACGACGACCUGAAGGAGGUGGAGAAGUCCAUCACCAACCUGGAGAAGUCCCUGACCAGCCUGAGCGAGGUGGUGCUGCAGAACAGGAGGGGCCUGGACCUGCUGUUCCUGAAGGAGGGCGGCCUGUGCGCCGCCCUGAAGGAGGAGUGCUGCCUGUACGCCGACCACACCGGCCUGGUGAUCGUGGGCAUUGUCGCUGGCCUGGCCGUCCUCGCCGUGGUGGUGAUUGGAGCUGUGGUCGCAGCUGUUAUGUGCAGAAGAAAGUCAUCCGGCGGAAAGGGAGGCUCCUACUCUCAGGCUGCUUCUGCUACAGUGCCUAGAGCUCUUAUGUGUUUAUCUCAGCUGGGCGGCGGAGGCAGCGACUACAAGGACGACGAUGACAAGUAA |
| 3068 (SEQ ID NO: 92) | STARR | Signal peptide-AH1A5 OVA-MITD-FLAG | AUGAGAGUGACAGCCCCUAGAACCUUACUGCUUCUGCUUUGGGGAGCUGUUGCUCUGACAGAGACAUGGGCUGGAUCUUACCACAGCCCCAGCUACGCCUACCACCAGUUCGAGAGGGGGGGAGGAGGCUCCGGGGGAGGAGGCUCCCUGAAGAUCAGCCAGGCCGUGCACGCCGCCCACGCCGAGAUCAACGAGGCCGGCCGGGAGGUGAUCGUGGGCAUUGUCGCUGGCCUGGCCGUCCUCGCCGUGGUGGUGAUUGGAGCUGUGGUCGCAGCUGUUAUGUGCAGAAGAAAGUCAUCCGGCGGAAAGGGAGGCUCCUACUCUCAGGCUGCUUCUGCUACAGUGCCUAGAGCUCUUAUGUGUUUAUCUCAGCUGGGCGGCGGAGGCAGCGACUACAAGGACGACGAUGACAAGUAA |

Transgene ORF amino acid sequence

| mARM # | transgene description | Sequence |
|---|---|---|
| 2809, 2842, 1782 (SEQ ID NO: 93) | Fluc | MEDAKNIKKGPAPFYPLEDGTAGEQLHKAMKRYALVPGTIAFTDAHIEVDITYAEYFEMSVRLAEAMKRYGLNTNHRIVVCSENSLQFFMPVLGALFIGVAVAPANDIYNERELLNSMGISQPTVVFVSKKGLQKILNVQKKLPIIQKIIIMDSKTDYQGFQSMYTFVTSHLPPGFNEYDFVPESFDRDKTIALIMNSSGSTGLPKGVALPHRTACVRFSHARDPIFGNQIIPDTAILSVVPFHHGFGMFTTLGYLICGFRVVLMYRFEEELFLRSLQDYKIQSALLVPTLFSFFAKSTLIDKYDLSNLHEIASGGAPLSKEVGEAVAKRFHLPGIRQGYGLTETTSAILITPEGDDKPGAVGKVVPFFEAKVVDLDTGKTLGVNQRGELCVRGPMIMSGYVNNPEATNALIDKDGWLHSGDIAYWDEDEHFFIVDRLKSLIKYKGYQVAPAELESILLQHPNIFDAGVAGLPDDDAGELPAAVVVLEHGKTMTEKEIVDYVASQVTTAKKLRGGVVFVDEVPKGLTGKLDARKIREILIKAKKGGKIAV* |

TABLE 9-continued

| | | |
|---|---|---|
| 2847 (SEQ ID NO: 94) | KRAS epitope wt | MKLVVVGAGGVGKSALTI* |
| 2862 (SEQ ID NO: 95) | Empty | MDPRRYAPMIRPAKLDVLPRN* |
| 3060 (SEQ ID NO: 96) | Signal peptide-gp70 with AH1A5-MITD | MRVTAPRTLLLLLWGAVALTETWAGSLSEVTGQGLCIGAVPKTHQV<br>LCNTTQKTSDGSYYLAAPTGTTWACSTGLTPCISTTILNLTTDYCV<br>LVELWPRVTYHSPSYAYHQFERRAKYKREPVSLTLALLLGGLTMGG<br>IAAGVGTGTTALVATQQFQQLQAAMHDDLKEVEKSITNLEKSLTSL<br>SEVVLQNRRGLDLLFLKEGGLCAALKEECCLYADHTGLVIVGIVAG<br>LAVLAVVVIGAVVAAVMCRRKSSGGKGGSYSQAASATVPRALMCLS<br>QL* |
| 3061 (SEQ ID NO: 97) | Signal peptide-AH1A5 OVA-MITD | MRVTAPRTLLLLLWGAVALTETWAGSYHSPSYAYHQFERGGGGSGG<br>GGSLKISQAVHAAHAEINEAGREVIVGIVAGLAVLAVVVIGAVVAA<br>VMCRRKSSGGKGGSYSQAASATVPRALMCLSQL* |
| 3076 (SEQ ID NO: 98) | Signal peptide-gp70 with AH1A5-MITD-FLAG | MRVTAPRTLLLLLWGAVALTETWAGSLSEVTGQGLCIGAVPKTHQV<br>LCNTTQKTSDGSYYLAAPTGTTWACSTGLTPCISTTILNLTTDYCV<br>LVELWPRVTYHSPSYAYHQFERRAKYKREPVSLTLALLLGGLTMGG<br>IAAGVGTGTTALVATQQFQQLQAAMHDDLKEVEKSITNLEKSLTSL<br>SEVVLQNRRGLDLLFLKEGGLCAALKEECCLYADHTGLVIVGIVAG<br>LAVLAVVVIGAVVAAVMCRRKSSGGKGGSYSQAASATVPRALMCLS<br>QLGGGGSDYKDDDDK* |
| 3068 (SEQ NO: 99) | Signal peptide-AH1A5 OVA-MITD-FLAG | MRVTAPRTLLLLLWGAVALTETWAGSYHSPSYAYHQFERGGGGSGG<br>GGSLKISQAVHAAHAEINEAGREVIVGIVAGLAVLAVVVIGAVVAA<br>VMCRRKSSGGKGGSYSQAASATVPRALMCLSQLGGGGSDYKDDDDK<br>* |

whole RNA sequence

| mARM # | brief name | Sequence |
|---|---|---|
| 2809 (SEQ ID NO: 100) | STARR ™ 2809 Fluc | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGGAGAGGCAUGAGCAUCCUGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGAGCUUCCCCGUGUGCACCUACGUGCCCGCCACCCUG<br>UGCGACCAGAUGACCGGCAUCCUGGCCACCGACGUGAGCGCCGACG<br>ACGCCCAGAAGCUGCUCGUGGGCCUGAACCAGAGGAUCGUGGUCAA<br>CGGCAGGACCCAGAGGAACACCAACACAAUGAAGAACUACCUGCUG<br>CCCGUGGUGGCCCAGGCUUUCGCCAGGUGGGCCAAGGAGUACAAGG<br>AGGACCAGGAAGACGAGAGGCCCCUGGGCCUGAGGGACAGGCAGCU<br>GGUGAUGGGCUGCUGCUGGGCCUUCAGGCGGCACAAGAUCACCAGC<br>AUCUACAAGAGGCCCGACACCCAGACCAUCAUCAAGGUGAACAGCG<br>ACUUCCACAGCUUCGUGCUGCCCAGGAUCGGCAGCAACACCCUGGA<br>GAUCGGCCUGAGGACCCGGAUCAGGAAGAUGCUGGAGGAACACAAG<br>GAGCCCAGCCCACUGAUCACCGCCGAGGACGUGCAGGAGGCCAAGU<br>GCGCUGCCGACGAGGCCAAGGAGGUGAGGGAGGCCGAGGAACUGAG<br>GGCCGCCCUGCCACCCCUGGCUGCCGACGUGGAGGAACCCACCCUG<br>GAAGCCGACGUGGACCUGAUGCUGCAGGAGGCCGGCGCCGGAAGCG<br>UGGAGACACCCAGGGGCCUGAUCAAGGUGACCAGCUACGACGGCGA<br>GGACAAGAUCGGCAGCUACGCCGUGCUGAGCCCACAGGCCGUGCUG |

TABLE 9-continued

AAGUCCGAGAAGCUGAGCUGCAUCCACCCACUGGCCGAGCAGGUGA
UCGUGAUCACCCACAGCGGCAGGAAGGGCAGGUACGCCGUGGAGCC
CUACCACGGCAAGGUGGUCGUGCCCGAGGGCCACGCCAUCCCCGUG
CAGGACUUCCAGGCCCUGAGCGAGAGCGCCACCAUCGUGUACAACG
AGAGGGAGUUCGUGAACAGGUACCUGCACCAUAUCGCCACCCACGG
CGGAGCCCUGAACACCGACGAGGAAUACUACAAGACCGUGAAGCCC
AGCGAGCACGACGGCGAGUACCUGUACGACAUCGACAGGAAGCAGU
GCGUGAAGAAAGAGCUGGUGACCGGCCUGGGACUGACCGGCGAGCU
GGUGGACCCACCCUUCCACGAGUUCGCCUACGAGAGCCUGAGGACC
AGACCCGCCGCUCCCUACCAGGUGCCCACCAUCGGCGUGUACGGCG
UGCCCGGCAGCGGAAAGAGCGGCAUCAUCAAGAGCGCCGUGACCAA
GAAAGACCUGGUGGUCAGCGCCAAGAAAGAGAACUGCGCCGAGAUC
AUCAGGGACGUGAAGAAGAUGAAAGGCCUGGACGUGAACGCGCGCA
CCGUGGACAGCGUGCUGCUGAACGGCUGCAAGCACCCCGUGGAGAC
CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU

TABLE 9-continued

| |
|---|
| CAGGAACCCACCCCACCCAGCUCCCAGGACCAGGACCCCAAGCCUG<br>GCUCCCAGCAGGGCCUGCAGCAGGACCAGCCUGGUGAGCACCCCAC<br>CCGGCGUGAACAGGGUGAUCACCAGGGAGGAACUGGAGGCCCUGAC<br>ACCCAGCAGGACCCCCAGCAGGUCCGUGAGCAGGACUAGUCUGGUG<br>UCCAACCCACCCGGCGUGAACAGGGUGAUCACCAGGGAGGAAUUCG<br>AGGCCUUCGUGGCCCAGCAACAGAGACGGUUCGACGCCGGCGCCUA<br>CAUCUUCAGCAGCGACACCGGCCAGGGACACCUGCAGCAAAAGAGC<br>GUGAGGCAGACCGUGCUGAGCGAGGUGGUGCUGGAGAGGACCGAGC<br>UGGAAAUCAGCUACGCCCCCAGGCUGGACCAGGAGAAGGAGGAACU<br>GCUCAGGAAGAAACUGCAGCUGAACCCCACCCCAGCCAACAGGAGC<br>AGGUACCAGAGCAGGAAGGUGGAGAACAUGAAGGCCAUCACCGCCA<br>GGCGGAUCCUGCAGGGCCUGGGACACUACCUGAAGGCCGAGGGCAA<br>GGUGGAGUGCUACAGGACCCUGCACCCCGUGCCACUGUACAGCUCC<br>AGCGUGAACAGGGCCUUCUCCAGCCCCAAGGUGGCCGUGGAGGCCU<br>GCAACGCUAUGCUGAAGGAGAACUUCCCCACCGUGGCCAGCUACUG<br>CAUCAUCCCCGAGUACGACGCCUACCUGGACAUGGUGGACGGCGCC<br>AGCUGCUGCCUGGACACCGCCAGCUUCUGCCCCGCCAAGCUGAGGA<br>GCUUCCCCAAGAAACACAGCUACCUGGAGCCCACCAUCAGGAGCGC<br>CGUGCCCAGCGCCAUCCAGAACACCCUGCAGAACGUGCUGGCCGCU<br>GCCACCAAGAGGAACUGCAACGUGACCCAGAUGAGGGAGCUGCCCG<br>UGCUGGACAGCGCUGCCUUCAACGUGGAGUGCUUCAAGAAAUACGC<br>CUGCAACAACGAGUACUGGGAGACCUUCAAGGAGAACCCCAUCAGG<br>CUGACCGAAGAGAACGUGGUGAACUACAUCACCAAGCUGAAGGGCC<br>CCAAGGCCGCUGCCCUGUUCGCUAAGACCCACAACCUGAACAUGCU<br>GCAGGACAUCCCAAUGGACAGGUUCGUGAUGGACCUGAAGAGGGAC<br>GUGAAGGUGACACCCGGCACCAAGCACACCGAGGAGAGGCCCAAGG<br>UGCAGGUGAUCCAGGCCGCUGACCCACUGGCCACCGCCUACCUGUG<br>CGGCAUCCACAGGGAGCUGGUGAGGCGGCUGAACGCCGUGCUGCUG<br>CCCAACAUCCACACCCUGUUCGACAUGAGCGCCGAGGACUUCGACG<br>CCAUCAUCGCCGAGCACUUCCAGCCCGGCGACUGCGUGCUGGAGAC<br>CGACAUCGCCAGCUUCGACAAGAGCGAGGAUGACGCUAUGGCCCUG<br>ACCGCUCUGAUGAUCCUGGAGGACCUGGGCGUGGACGCCGAGCUGC<br>UCACCCUGAUCGAGGCUGCCUUCGGCGAGAUCAGCUCCAUCCACCU<br>GCCCACCAAGACCAAGUUCAAGUUCGGCGCUAUGAUGAAAAGCGGA<br>AUGUUCCUGACCCUGUUCGUGAACACCGUGAUCAACAUUGUGAUCG<br>CCAGCAGGGUGCUGCGGGAGAGGCUGACCGGCAGCCCCUGCGCUGC<br>CUUCAUCGGCGACGACAACAUCGUGAAGGGCGUGAAAAGCGACAAG<br>CUGAUGGCCGACAGGUGCGCCACCUGGCUGAACAUGGAGGUGAAGA<br>UCAUCGACGCCGUGGUGGGCGAGAAGGCCCCCUACUUCUGCGGCGG<br>AUUCAUCCUGUGCGACAGCGUGACCGGCACCGCCUGCAGGGUGGCC<br>GACCCCCUGAAGAGGCUGUUCAAGCUGGGCAAGCCACUGGCCGCUG<br>ACGAUGAGCACGACGAUGACAGGCGGAGGGCCCUGCACGAGGAAAG<br>CACCAGGUGGAACAGGGUGGGCAUCCUGAGCGAGCUGUGCAAGGCC<br>GUGGAGAGCAGGUACGAGACCGUGGGCACCAGCAUCAUCGUGAUGG<br>CUAUGACCACACUGGCCAGCUCCGUCAAGAGCUUCUCCUACCUGAG<br>GGGGGCCCCUAUAACUCUCUACGGCUAACCUGAAUGGACUACGACA<br>UAGUCUAGUCCGCCAAGGCCGCCACCAUGGAAGAUGCCAAAAACAU<br>UAAGAAGGGCCCAGCGCCAUUCUACCCACUCGAAGACGGGACCGCC<br>GGCGAGCAGCUGCACAAAGCCAUGAAGCGCUACGCCCUGGUGCCCG<br>GCACCAUCGCCUUUACCGACGCACAUAUCGAGGUGGACAUUACCUA<br>CGCCGAGUACUUCGAGAUGAGCGUUCGGCUGGCAGAAGCUAUGAAG<br>CGCUAUGGGCUGAAUACAAACCAUCGGAUCGUGGUGUGCAGCGAGA<br>AUAGCUUGCAGUUCUUCAUGCCCGUGUUGGGUGCCCUGUUCAUCGG<br>UGUGGCUGUGGCCCCAGCUAACGACAUCUACAACGAGCGCGAGCUG<br>CUGAACAGCAUGGGCAUCAGCCAGCCCACCGUCGUAUUCGUGAGCA<br>AGAAAGGGCUGCAAAAGAUCCUCAACGUGCAAAAGAAGCUACCGAU<br>CAUACAAAAGAUCAUCAUCAUGGAUAGCAAGACCGACUACCAGGGC<br>UUCCAAAGCAUGUACACCUUCGUGACUUCCCAUUUGCCACCCGGCU<br>UCAACGAGUACGACUUCGUGCCCGAGAGCUUCGACCGGGACAAAAC<br>CAUCGCCCUGAUCAUGAACAGUAGUGGCAGUACCGGAUUGCCCAAG<br>GGCGUAGCCCUACCGCACCGCACCGCUUGUGUCCGAUUCAGUCAUG<br>CCCGCGACCCCAUCUUCGGCAACCAGAUCAUCCCCGACACCGCUAU<br>CCUCAGCGUGGUGCCAUUUCACCACGGCUUCGGCAUGUUCACCACG<br>CUGGGCUACUUGAUCUGCGGCUUUCGGGUCGUGCUCAUGUACCGCU<br>UCGAGGAGGAGCUAUUCUUGCGCAGCUUGCAAGACUAUAAGAUUCA<br>AUCUGCCCUGCUGGUGCCCACACUAUUUAGCUUCUUCGCUAAGAGC<br>ACUCUCAUCGACAAGUACGACCUAAGCAACUUGCACGAGAUCGCCA<br>GCGGCGGGGCGCCGCUCAGCAAGGAGGUAGGUGAGGCCGUGGCCAA<br>ACGCUUCCACCUACCAGGCAUCCGACAGGGCUACGGCCUGACAGAA<br>ACAACCAGCGCCAUUCUGAUCACCCCCGAAGGGGACGACAAGCCUG<br>GCGCAGUAGGCAAGGUGGUGCCCUUCUUCGAGGCUAAGGUGGUGGA<br>CUUGGACACCGGUAAGACACUGGGUGUGAACCAGCGCGGCGAGCUG<br>UGCGUCCGUGGCCCCAUGAUCAUGAGCGGCUACGUUAACAACCCCG<br>AGGCUACAAACGCUCUCAUCGACAAGGACGGCUGGCUGCACAGCGG<br>CGACAUCGCCUACUGGGACGAGGACGAGCACUUCUUCAUCGUGGAC<br>CGGCUGAAGUCCCUGAUCAAAUACAAGGGCUACCAGGUAGCCCCAG<br>CCGAACUGGAGAGCAUCCUGCUGCAACACCCCAACAUCUUCGACGC<br>CGGGGUCGCCGGCCUGCCCGACGACGAUGCCGGCGAGCUGCCCGCC<br>GCAGUCGUCGUGCUGGAACACGGUAAAACCAUGACCGAGAAGGAGA<br>UCGUGGACUAUGUGGCCAGCCAGGUUACAACCGCCAAGAAGCUGCG |

TABLE 9-continued

| | | | |
|---|---|---|---|
| | | | CGGUGGUGUUGUGUUCGUGGACGAGGUGCCUAAAGGACUGACCGGC<br>AAGUUGGACGCCCGCAAGAUCCGCGAGAUUCUCAUUAAGGCCAAGA<br>AGGGCGGCAAGAUCGCCGUGUAACUCGAGUAUGUUACGUGCAAAGG<br>UGAUUGUCACCCCCCGAAAGACCAUAUUGUGACACACCCUCAGUAU<br>CACGCCCAAACAUUUACAGCCGCGGUGUCAAAAACCGCGUGGACGU<br>GGUUAACAUCCCUGCUGGGAGGAUCAGCCGUAAUUAUUAUAAUUGG<br>CUUGGUGCUGGCUACUAUUGUGGCCAUGUACGUGCUGACCAACCAG<br>AAACAUAAUUGAAUACAGCAGCAAUUGGCAAGCUGCUUACAUAGAA<br>CUCGCGGCGAUUGGCAUGCCGCCUUAAAAUUUUUAUUUUAUUUUUU<br>CUUUUCUUUUCCGAAUCGGAUUUUGUUUUUAAUAUUUCAAAAAAAA<br>AAAAAAAAAAAAAAAAAUCUAGAAAAAAAAAAAAAAAAAAAAAAAAAA<br>AAAAAAAAAAAAAAAAAAAAAAAAAAAAAAAAAAAAAAAAAAAAAAAA<br>AAAAAAAAAAAAAAAAAAAAAAAAAAAAAAA |
| 2842 (SEQ ID NO: 101) | SINV Fluc | 2842 | AUUGACGGCGUAGUACACACUAUUGAAUCAAACAGCCGACCAAUUG<br>CACUACCAUCACAAUGGAGAAGCCAGUAGUAAACGUAGACGUAGAC<br>CCCCAGAGUCCGUUUGUCGUGCAACUGCAAAAAAGCUUCCCGCAAU<br>UUGAGGUAGUAGCACAGCAGGUCACUCCAAAUGACCAUGCUAAUGC<br>CAGAGCAUUUUCGCAUCUGGCCAGUAAACUAAUCGAGCUGGAGGUU<br>CCUACCACAGCGACGAUCUUGGACAUAGGCAGCGCACCGGCUCGUA<br>GAAUGUUUUCCGAGCACCAGUAUCAUUGUGUCUGCCCCAUGCGUAG<br>UCCAGAAGACCCGGACCGCAUGAUGAAAUAUGCCAGUAAACUGGCG<br>GAAAAAGCGUGCAAGAUUACAAACAAGAACUUGCAUGAGAAGAUUA<br>AGGAUCUCCGGACCGUACUUGAUACGCCGGAUGCUGAAACACCAUC<br>GCUCUGCUUUCACAACGAUGUUACCUGCAACAUGCGUGCCGAAUAU<br>UCCGUCAUGCAGGACGUGUAUAUCAACGCUCCCGGAACUAUCUAUC<br>AUCAGGCUAUGAAAGGCGUGCGGACCCUGUACUGGAUUGGCUUCGA<br>CACCACCCAGUUCAUGUUCUCGGCUAUGGCAGGUUCGUACCCUGCG<br>UACAACACCAACUGGGCCGACGAGAAAGUCCUUGAAGCGCGUAACA<br>UCGGACUUUGCAGCACAAAGCUGAGUGAAGGUAGGACAGGAAAAUU<br>GUCGAUAAUGAGGAAGAAGGAGUUGAAGCCCGGGUCGCGGGUUUAU<br>UUCUCCGUAGGAUCGACACUUUAUCCAGAACACAGAGCCAGCUUGC<br>AGAGCUGGCAUCUUCCAUCGGUGUUCCACUUGAAUGGAAAGCAGUC<br>GUACACUUGCCGCUGUGAUACAGUGGUGAGUUGCGAAGGCUACGUA<br>GUGAAGAAAAUCACCAUCAGUCCCGGGAUCACGGGAGAAACCGUGG<br>GAUACGCGGUUACACACAAUAGCGAGGGCUUCUUGCUAUGCAAAGU<br>UACUGACACAGUAAAAGGAGAACGGGUAUCGUUCCCUGUGUGCACG<br>UACAUCCCGGCCACCAUAUGCGAUCAGAUGACUGGUAUAAUGGCCA<br>CGGAUAUAUCACCUGACGAUGCACAAAAACUUCUGGUUGGGCUCAA<br>CCAGCGAAUUGUCAUUAACGGUAGGACUAACAGGAACACCAACACC<br>AUGCAAAAUUACCUUCUGCCGAUCAUAGCACAAGGGUUCAGCAAAU<br>GGGCUAAGGAGCGCAAGGAUGAUCUUGAUAACGAGAAAAUGCUGGG<br>UACUAGAGAACGCAAGCUUACGUAUGGCUGCUUGUGGGCGUUUCGC<br>ACUAAGAAAGUACAUUCGUUUUAUCGCCCACCUGGAACGCAGACCU<br>GCGUAAAAGUCCCAGCCUCUUUUAGCGCUUUUCCCAUGUCGUCCGU<br>AUGGACGACCUCUUUGCCCAUGUCGCUGAGGCAGAAAUUGAAACUG<br>GCAUUGCAACCAAAGAAGGAGGAAAAACUGCUGCAGGUCUCGGAGG<br>AAUUAGUCAUGGAGGCCAAGGCUGCUUUUGAGGAUGCUCAGGAGGA<br>AGCCAGAGCGGAGAAGCUCCGAGAAGCACUUCCACCAUUAGUGGCA<br>GACAAAGGCAUCGAGGCAGCCGCAGAAGUUGUCUGCGAAGUGGAGG<br>GGCUCCAGGCGGACAUCGGAGCAGCAUUAGUUGAAACCCCGCGCGG<br>UCACGUAAGGAUAAUACCUCAAGCAAAUGACCGUAUGAUCGGACAG<br>UAUAUCGUUGUCUCGCCAAACUCUGUGCUGAAGAAUGCCAAACUCG<br>CACCAGCGCACCCGCUAGCAGAUCAGGUUAAGAUCAUAACACACUC<br>CGGAAGAUCAGGAAGGUACGCGGUCGAACCAUACGACGCUAAAGUA<br>CUGAUGCCAGCAGGAGGUGCCGUACCAUGGCCAGAAUUCCUAGCAC<br>UGAGUGAGAGCGCCACGUUAGUGUACAACGAAAGAGAGUUUGUGAA<br>CCGCAAACUAUACCACAUUGCCAUGCAUGGCCCCGCCAAGAAUACA<br>GAAGAGGAGCAGUACAAGGUUACAAAGGCAGAGCUUGCAGAAACAG<br>AGUACGUGUUUGACGUGGACAAGAAGCGUUGCGUUAAGAAGGAAGA<br>AGCCUCAGGUCUGGUCCUCUCGGGAGAACUGACCAACCCUCCCUAU<br>CAUGAGCUAGCUCUGGAGGGACUGAAGACCCGACCUGCGGUCCCGU<br>ACAAGGUCGAAACAAUAGGAGUGAUAGGCACACCGGGGUCGGGCAA<br>GUCAGCUAUUAUCAAGUCAACUGUCACGGCACGAGAUCUUGUUACC<br>AGCGGAAAGAAAGAAAAUUGUCGCGAAAUUGAGGCCGACGUGCUAA<br>GACUGAGGGGUAUGCAGAUUACGUCGAAGACAGUAGAUUCGGUUAU<br>GCUCAACGGAUGCCACAAAGCCGUAGAAGUGCUGUACGUUGACGAA<br>GCGUUCGCGUGCCACGCAGGAGCACUACUUGCCUUGAUUGCUAUCG<br>UCAGGCCCCGCAAGAAGGUAGUACUAUGCGGAGACCCCAUGCAAUG<br>CGGAUUCUUCAACAUGAUGCAACUAAAGGUACAUUUCAAUCACCCU<br>GAAAAAGACAUAUGCACCAAGACAUUCUACAAGUAUAUCUCCCGGC<br>GUUGCACACAGCCAGUUACAGCUAUUGUAUCGACACUGCAUUACGA<br>UGGAAAGAUGAAAACCACGAACCCGUGCAAGAAGAACAUUGAAAUC<br>GAUAUUACAGGGGCCACAAAGCCGAAGCCAGGGGAUAUCAUCCUGA<br>CAUGUUUCCGCGGGUGGGUUAAGCAAUUGCAAAUCGACUAUCCCGG<br>ACAUGAAGUAAUGACAGCCGCGGCCUCACAAGGGCUAACCAGAAAA<br>GGAGUGUAUGCCGUCCGGCAAAAAGUCAAUGAAAACCCACUGUACG<br>CGAUCACAUCAGAGCAUGUGAACGUGUUGCUCACCCGCACUGAGGA<br>CAGGCUAGUGUGGAAAACCUUGCAGGGCGACCCAUGGAUUAAGCAG<br>CUCACUAACAUACCUAAAGGAAACUUUCAGGCUACUAUAGAGGACU |

TABLE 9-continued

GGGAAGCUGAACACAAGGGAAUAAUUGCUGCAAUAAACAGCCCCAC
UCCCCGUGCCAAUCCGUUCAGCUGCAAGACCAACGUUUGCUGGGCG
AAAGCAUUGGAACCGAUACUAGCCACGGCCGGUAUCGUACUUACCG
GUUGCCAGUGGAGCGAACUGUUCCCACAGUUUGCGGAUGACAAACC
ACAUUCGGCCAUUUACGCCUUAGACGUAAUUUGCAUUAAGUUUUUC
GGCAUGGACUUGACAAGCGGACUGUUUUCUAAACAGAGCAUCCCAC
UAACGUACCAUCCCGCCGAUUCAGCGAGGCCGGUAGCUCAUUGGGA
CAACAGCCCAGGAACCCGCAAGUAUGGGUACGAUCACGCCAUUGCC
GCCGAACUCUCCCGUAGAUUUCCGGUGUUCCAGCUAGCUGGGAAGG
GCACACAACUUGAUUUGCAGACGGGGAGAACCAGAGUUAUCUCUGC
ACAGCAUAACCUGGUCCCGGUGAACCGCAAUCUUCCUCACGCCUUA
GUCCCCGAGUACAAGGAGAAGCAACCCGGCCCGGUCGAAAAAUUCU
UGAACCAGUUCAAACACCACUCAGUACUUGUGGUAUCAGAGGAAAA
AAUUGAAGCUCCCCGUAAGAGAAUCGAAUGGAUCGCCCCGAUUGGC
AUAGCCGGUGCAGAUAAGAACUACAACCUGGCUUUCGGGUUUCCGC
CGCAGGCACGGUACGACCUGGUGUUCAUCAACAUUGGAACUAAAUA
CAGAAACCACCACUUUCAGCAGUGCGAAGACCAUGCGGCGACCUUA
AAAACCCUUUCGCGUUCGGCCCUGAAUUGCCUUAACCCAGGAGGCA
CCCUCGUGGUGAAGUCCUAUGGCUACGCCGACCGCAACAGUGAGGA
CGUAGUCACCGCUCUUGCCAGAAAGUUUGUCAGGGUGUCUGCAGCG
AGACCAGAUUGUGUCUCAAGCAAUACAGAAAUGUACCUGAUUUUCC
GACAACUAGACAACAGCCGUACACGGCAAUUCACCCCGCACCAUCU
GAAUUGCGUGAUUUCGUCCGUGUAUGAGGGUACAAGAGAUGGAGUU
GGAGCCGCGCCGUCAUACCGCACCAAAAGGGAGAAUAUUGCUGACU
GUCAAGAGGAAGCAGUUGUCAACGCAGCCAAUCCGCUGGGUAGACC
AGGCGAAGGAGUCUGCCGUGCCAUCUAUAAACGUUGGCCGACCAGU
UUUACCGAUUCAGCCACGGAGACAGGCACCGCAAGAAUGACUGUGU
GCCUAGGAAAGAAAGUGAUCCACGCGGUCGGCCCUGAUUUCCGGAA
GCACCCAGAAGCAGAAGCCUUGAAAUUGCUACAAAACGCCUACCAU
GCAGUGGCAGACUUAGUAAAUGAACAUAACAUCAAGUCUGUCGCCA
UUCCACUGCUAUCUACAGGCAUUUACGCAGCCGGAAAAGACCGCCU
UGAAGUAUCACUUAACUGCUUGACAACCGCGCUAGACAGAACUGAC
GCGGACGUAACCAUCUAUUGCCUGGAUAAGAAGUGGAAGGAAAGAA
UCGACGCGGCACUCCAACUUAAGGAGUCUGUAACAGAGCUGAAGGA
UGAAGAUAUGGAGAUCGACGAUGAGUUAGUAUGGAUCCAUCCAGAC
AGUUGCUUGAAGGGAAGAAAGGGAUUCAGUACUACAAAAGGAAAAU
UGUAUUCGUACUUCGAAGGCACCAAAUUCCAUCAAGCAGCAAAAGA
CAUGGCGGAGAUAAAGGUCCUGUUCCCUAAUGACCAGGAAAGUAAU
GAACAACUGUGUGCCUACAUAUUGGGUGAGACCAUGGAAGCAAUCC
GCGAAAAGUGCCCGGUCGACCAUAACCCGUCGUCUAGCCCGCCCAA
AACGUUGCCGUGCCUUUGCAUGUAUGCCAUGACGCCAGAAAGGGUC
CACAGACUUAGAAGCAAUAACGUCAAAGAAGUUACAGUAUGCUCCU
CCACCCCCCUUCCUAAGCACAAAAUUAAGAAUGUUCAGAAGGUUCA
GUGCACGAAAGUAGUCCUGUUUAAUCCGCACACUCCCGCAUUCGUU
CCCGCCCGUAAGUACAUAGAAGUGCCAGAACAGCCUACCGCUCCUC
CUGCACAGGCCGAGGAGGCCCCCGAAGUUGUAGCGACACCGUCACC
AUCUACAGCUGAUAACACCUCGCUUGAUGUCACAGACAUCUCACUG
GAUAUGGAUGACAGUAGCGAAGGCUCACUUUUUUCGAGCUUUAGCG
GAUCGGACAACUCUAUUACUAGUAUGGACAGUUGGUCGUCAGGACC
UAGUUCACUAGAGAUAGUAGACCGAAGGCAGGUGGUGGUGGCUGAC
GUUCAUGCCGUCCAAGAGCCUGCCCCUAUUCCACCGCCAAGGCUAA
AGAAGAUGGCCCGCCUGGCAGCGGCAAGAAAAGAGCCCACUCCACC
GGCAAGCAAUAGCUCUGAGUCCCUCCACCUCUCUUUUGGUGGGGUA
UCCAUGUCCCUCGGAUCAAUUUUCGACGGAGAGACGGCCCGCCAGG
CAGCGGUACAACCCCUGGCAACAGGCCCCACGGAUGUGCCUAUGUC
UUUCGGAUCGUUUUCCGACGGAGAGAUUGAUGAGCUGAGCCGCAGA
GUAACUGAGUCCGAACCCGUCCUGUUUGGAUCAUUUGAACCGGGCG
AAGUGAACUCAAUUAUAUCGUCCCGAUCAGCCGUAUCUUUUCCUCU
ACGCAAGCAGAGACGUAGACGCAGGAGCAGGAGGACUGAAUACUGA
CUAACCGGGGUAGGUGGGUACAUAUUUUCGACGGACACAGGCCCUG
GGCACUUGCAAAAGAAGUCCGUUCUGCAGAACCAGCUUACAGAACC
GACCUUGGAGCGCAAUGUCCUGGAAAGAAUUCAUGCCCCGGUGCUC
GACACGUCGAAAGAGGAACAACUCAAACUCAGGUACCAGAUGAUGC
CCACCGAAGCCAACAAAAGUAGGUACCAGUCUCGUAAAGUAGAAAA
UCAGAAAGCCAUAACCACUGAGCGACUACUGUCAGGACUACGACUG
UAUAACUCUGCCACAGAUCAGCCAGAAUGCUAUAAGAUCACCUAUC
CGAAACCAUUGUACUCCAGUAGCGUACCGGCGAACUACUCCGAUCC
ACAGUUCGCUGUAGCUGUCUGUAACAACUAUCUGCAUGAGAACUAU
CCGACAGUAGCAUCUUAUCAGAUUACUGACGAGUACGAUGCUUACU
UGGAUAUGGUAGACGGGACAGUCGCCUGCCUGGACACUGCAACCUU
CUGCCCCGCUAAGCUUAGAAGUUACCCGAAAAAACAUGAGUAUAGA
GCCCCGAAUAUCCGCAGUGCGGUUCCAUCAGCGAUGCAGAACACGC
UACAAAAUGUGCUCAUUGCCGCAACUAAAAGAAAUUGCAACGUCAC
GCAGAUGCGUGAACUGCCAACACUGGACUCAGCGACAUUCAAUGUC
GAAUGCUUUCGAAAAUAUGCAUGUAAUGACGAGUAUUGGGAGGAGU
UCGCUCGGAAGCCAAUUAGGAUUACCACUGAGUUUGUCACCGCAUA
UGUAGCUAGACUGAAAGGCCCUAAGGCCGCCGCACUAUUUGCAAAG
ACGUAUAAUUUGGUCCCAUUGCAAGAAGUGCCUAUGGAUAGAUUCG
UCAUGGACAUGAAAAGAGACGUGAAAGUUACACCAGGCACGAAACA
CACAGAAGAAAGACCGAAAGUACAAGUGAUACAAGCCGCAGAACCC

TABLE 9-continued

| | | | |
|---|---|---|---|
| | | | CUGGCGACUGCUUACUUAUGCGGGAUUCACCGGGAAUUAGUGCGUA<br>GGCUUACGGCCGUCUUGCUUCCAAACAUUCACACGCUUUUUGACAU<br>GUCGGCGGAGGAUUUUGAUGCAAUCAUAGCAGAACACUUCAAGCAA<br>GGCGACCCGGUACUGGAGACGGAUAUCGCAUCAUUCGACAAAAGCC<br>AAGACGACGCUAUGGCGUUAACCGGUCUGAUGAUCUUGGAGGACCU<br>GGGUGUGGAUCAACCACUACUCGACUUGAUCGAGUGCGCCUUUGGA<br>GAAAUAUCAUCCACCCAUCUACCUACGGGUACUCGUUUUAAAUUCG<br>GGGCGAUGAUGAAAUCCGGAAUGUUCCUCACACUUUUUGUCAACAC<br>AGUUUUGAAUGUCGUUAUCGCCAGCAGAGUACUAGAGGAGCGGCUU<br>AAAACGUCCAGAUGUGCAGCGUUCAUUGGCGACGACAACAUCAUAC<br>AUGGAGUAGUAUCUGACAAAGAAAUGGCUGAGAGGUGCGCCACCUG<br>GCUCAACAUGGAGGUUAAGAUCAUCGACGCAGUCAUCGGUGAGAGA<br>CCACCUUACUUCUGCGGCGGAUUUAUCUUGCAAGAUUCGGUUACUU<br>CCACAGCGUGCCGCGUGGCGGAUCCCCUGAAAAGGCUGUUUAAGUU<br>GGGUAAACCGCUCCCAGCCGACGACGAGCAAGACGAAGACAGAAGA<br>CGCGCUCUGCUAGAUGAAACAAAGGCGUGGUUUAGAGUAGGUAUAA<br>CAGGCACUUUAGCAGUGGCCGUGACGACCCGGUAUGAGGUAGACAA<br>UAUUACACCUGUCCUACUGGCAUUGAGAACUUUUGCCCAGAGCAAA<br>AGAGCAUUCCAAGCCAUCAGAGGGGAAAUAAAGCAUCUCUACGGUG<br>GUCCUAAAUAGUCAGCAUAGUACAUUUCAUCUGACUAAUACUACAA<br>CACCACCACCAUGGAAGAUGCCAAAAACAUUAAGAAGGGCCCAGCG<br>CCAUUCUACCCACUCGAAGACGGGACCGCCGGCGAGCAGCUGCACA<br>AAGCCAUGAAGCGCUACGCCCUGGUGCCCGGCACCAUCGCCUUUAC<br>CGACGCACAUAUCGAGGUGGACAUUACCUACGCCGAGUACUUCGAG<br>AUGAGCGUUCGGCUGGCAGAAGCUAUGAAGCGCUAUGGGCUGAAUA<br>CAAACCAUCGGAUCGUGGUGUGCAGCGAGAAUAGCUUGCAGUUCUU<br>CAUGCCCGUGUUGGGUGCCCUGUUCAUCGGUGUGGCUGUGGCCCCA<br>GCUAACGACAUCUACAACGAGCGCGAGCUGCUGAACAGCAUGGGCA<br>UCAGCCAGCCCACCGUCGUAUUCGUGAGCAAGAAAGGGCUGCAAAA<br>GAUCCUCAACGUGCAAAAGAAGCUACCGAUCAUACAAAAGAUCAUC<br>AUCAUGGAUAGCAAGACCGACUACCAGGGCUUCCAAAGCAUGUACA<br>CCUUCGUGACUUCCCAUUUGCCACCCGGCUUCAACGAGUACGACUU<br>CGUGCCCGAGAGCUUCGACCGGGACAAAACCAUCGCCCUGAUCAUG<br>AACAGUAGUGGCAGUACCGGAUUGCCCAAGGGCGUAGCCCUACCGC<br>ACCGCACCGCUUGUGUCCGAUUCAGUCAUGCCCGCGACCCCAUCUU<br>CGGCAACCAGAUCAUCCCCGACACCGCUAUCCUCAGCGUGGUGCCA<br>UUUCACCACGGCUUCGGCAUGUUCACCACGCUGGGCUACUUGAUCU<br>GCGGCUUUCGGGUCGUGCUCAUGUACCGCUUCGAGGAGGAGCUAUU<br>CUUGCGCAGCUUGCAAGACUAUAAGAUUCAAUCUGCCCUGCUGGUG<br>CCCACACUAUUUAGCUUCUUCGCUAAGAGCACUCUCAUCGACAAGU<br>ACGACCUAAGCAACUUGCACGAGAUCGCCAGCGGCGGGGCGCCGCU<br>CAGCAAGGAGGUAGGUGAGGCCGUGGCCAAACGCUUCCACCUACCA<br>GGCAUCCGACAGGGCUACGGCCUGACAGAAACAACCAGCGCCAUUC<br>UGAUCACCCCCGAAGGGGACGACAAGCCUGGCGCAGUAGGCAAGGU<br>GGUGCCCUUCUUCGAGGCUAAGGUGGUGGACUUGGACACCGGUAAG<br>ACACUGGGUGUGAACCAGCGCGGCGAGCUGUGCGUCCGUGGCCCCA<br>UGAUCAUGAGCGGCUACGUUAACAACCCCGAGGCUACAAACGCUCU<br>CAUCGACAAGGACGGCUGGCUGCACAGCGGCGACAUCGCCUACUGG<br>GACGAGGACGAGCACUUCUUCAUCGUGGACCGGCUGAAGUCCCUGA<br>UCAAAUACAAGGGCUACCAGGUAGCCCCAGCCGAACUGGAGAGCAU<br>CCUGCUGCAACACCCCAACAUCUUCGACGCCGGGGUCGCCGGCCUG<br>CCCGACGACGAUGCCGGCGAGCUGCCCGCCGCAGUCGUCGUGCUGG<br>AACACGGUAAAACCAUGACCGAGAAGGAGAUCGUGGACUAUGUGGC<br>CAGCCAGGUUACAACCGCCAAGAAGCUGCGCGGUGGUGUUGUGUUC<br>GUGGACGAGGUGCCUAAAGGACUGACCGGCAAGUUGGACGCCCGCA<br>AGAUCCGCGAGAUUCUCAUUAAGGCCAAGAAGGGCGGCAAGAUCGC<br>CGUGUAAACGCGUGCUAGACCAUGGAUCCUAGACGCUACGCCCCAA<br>UGAUCCGACCAGCAAAACUCGAUGUACUUCCGAGGAACUGAUGUGC<br>AUAAUGCAUCAGGCUGGUACAUUAGAUCCCCGCUUACCGCGGGCAA<br>UAUAGCAACACUAAAAACUCGAUGUACUUCCGAGGAAGCGCAGUGC<br>AUAAUGCUGCGCAGUGUUGCCACAUAACCACUAUAUUAACCAUUUA<br>UCUAGCGGACGCCAAAAACUCAAUGUAUUUCUGAGGAAGCGUGGUG<br>CAUAAUGCCACGCAGCGUCUGCAUAACUUUUAUUAUUUCUUUUAUU<br>AAUCAACAAAAUUUGUUUUUAACAUUUCAAAAAAAAAAAAAAAAAAAA<br>AAAAAAAAUCUAGAAAAAAAAAAAAAAAAAAAAAAAAAAAAAAAAAAA<br>AAAAAAAAAAAAAAAAAAAAAAAAAAAAAAAAAAAAAAAAAAAAAAAA<br>AAAAAAAAAAAAAAAAAAAAAA |
| 1782 (SEQ ID NO: 102) | mRNA Fluc | 1782 | AGGAAACUUAAGUCAACACAACAUAUACAAAACAAACGAAUCUCAA<br>GCAAUCAAGCAUUCUACUUCUAUUGCAGCAAUUUAAAUCAUUUCUU<br>UUAAAGCAAAAGCAAUUUUCUGAAAAUUUUCACCAUUUACGAACGA<br>UAGCCAUGGAAGAUGCCAAAAACAUUAAGAAGGGCCCAGCGCCAUU<br>CUACCCACUCGAAGACGGGACCGCCGGCGAGCAGCUGCACAAAGCC<br>AUGAAGCGCUACGCCCUGGUGCCCGGCACCAUCGCCUUUACCGACG<br>CACAUAUCGAGGUGGACAUUACCUACGCCGAGUACUUCGAGAUGAG<br>CGUUCGGCUGGCAGAAGCUAUGAAGCGCUAUGGGCUGAAUACAAAC<br>CAUCGGAUCGUGGUGUGCAGCGAGAAUAGCUUGCAGUUCUUCAUGC<br>CCGUGUUGGGUGCCCUGUUCAUCGGUGUGGCUGUGGCCCCAGCUAA<br>CGACAUCUACAACGAGCGCGAGCUGCUGAACAGCAUGGGCAUCAGC<br>CAGCCCACCGUCGUAUUCGUGAGCAAGAAAGGGCUGCAAAAGAUCC |

TABLE 9-continued

| | | |
|---|---|---|
| | | UCAACGUGCAAAAGAAGCUACCGAUCAUACAAAAGAUCAUCAUCAU<br>GGAUAGCAAGACCGACUACCAGGGCUUCCAAAGCAUGUACACCUUC<br>GUGACUUCCCAUUUGCCACCCGGCUUCAACGAGUACGACUUCGUGC<br>CCGAGAGCUUCGACCGGGACAAAACCAUCGCCCUGAUCAUGAACAG<br>UAGUGGCAGUACCGGAUUGCCCAAGGGCGUAGCCCUACCGCACCGC<br>ACCGCUUGUGUCCGAUUCAGUCAUGCCCGCGACCCCAUCUUCGGCA<br>ACCAGAUCAUCCCCGACACCGCUAUCCUCAGCGUGGUGCCAUUUCA<br>CCACGGCUUCGGCAUGUUCACCACGCUGGGCUACUUGAUCUGCGGC<br>UUUCGGGUCGUGCUCAUGUACCGCUUCGAGGAGGAGCUAUUCUUGC<br>GCAGCUUGCAAGACUAUAAGAUUCAAUCUGCCCUGCUGGUGCCCAC<br>ACUAUUUAGCUUCUUCGCUAAGAGCACUCUCAUCGACAAGUACGAC<br>CUAAGCAACUUGCACGAGAUCGCCAGCGGCGGGGCGCCGCUCAGCA<br>AGGAGGUAGGUGAGGCCGUGGCCAAACGCUUCCACCUACCAGGCAU<br>CCGACAGGGCUACGGCCUGACAGAAACAACCAGCGCCAUUCUGAUC<br>ACCCCCGAAGGGGACGACAAGCCUGGCGCAGUAGGCAAGGUGGUGC<br>CCUUCUUCGAGGCUAAGGUGGUGGACUUGGACACCGGUAAGACACU<br>GGGUGUGAACCAGCGCGGCGAGCUGUGCGUCCGUGGCCCCAUGAUC<br>AUGAGCGGCUACGUUAACAACCCCGAGGCUACAAACGCUCUCAUCG<br>ACAAGGACGGCUGGCUGCACAGCGGCGACAUCGCCUACUGGGACGA<br>GGACGAGCACUUCUUCAUCGUGGACCGGCUGAAGUCCCUGAUCAAA<br>UACAAGGGCUACCAGGUAGCCCCAGCCGAACUGGAGAGCAUCCUGC<br>UGCAACACCCCAACAUCUUCGACGCCGGGGUCGCCGGCCUGCCCGA<br>CGACGAUGCCGGCGAGCUGCCCGCCGCAGUCGUCGUGCUGGAACAC<br>GGUAAAACCAUGACCGAGAAGGAGAUCGUGGACUAUGUGGCCAGCC<br>AGGUUACAACCGCCAAGAAGCUGCGCGGUGGUGUUGUGUUCGUGGA<br>CGAGGUGCCUAAAGGACUGACCGGCAAGUUGGACGCCCGCAAGAUC<br>CGCGAGAUUCUCAUUAAGGCCAAGAAGGGCGGCAAGAUCGCCGUGU<br>AACUCGAGCUAGUGACUGACUAGGAUCUGGUUACCACUAAACCAGC<br>CUCAAGAACACCCGAAUGGAGUCUCUAAGCUACAUAAUACCAACUU<br>ACACUUACAAAAUGUUGUCCCCCAAAAUGUAGCCAUUCGUAUCUGC<br>UCCUAAUAAAAAGAAAGUUUCUUCACAUUCUAGAAAAAAAAAAAAA<br>AAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAA<br>AAAAAAAAAAAAAAAA |
| 2847 (SEQ ID NO: 103) | STARR ™ 2847 KRAS wt | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGGAGAGGCAUGAGCAUCCUGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGAGCUUCCCCGUGUGCACCUACGUGCCCGCCACCCUG<br>UGCGACCAGAUGACCGGCAUCCUGGCCACCGACGUGAGCGCCGACG<br>ACGCCCAGAAGCUGCUCGUGGGCCUGAACCAGAGGAUCGUGGUCAA<br>CGGCAGGACCCAGAGGAACACCAACACAAUGAAGAACUACCUGCUG<br>CCCGUGGUGGCCCAGGCUUUCGCCAGGUGGGCCAAGGAGUACAAGG<br>AGGACCAGGAAGACGAGAGGCCCCUGGGCCUGAGGGACAGGCAGCU<br>GGUGAUGGGCUGCUGCUGGGCCUUCAGGCGGCACAAGAUCACCAGC<br>AUCUACAAGAGGCCCGACACCCAGACCAUCAUCAAGGUGAACAGCG<br>ACUUCCACAGCUUCGUGCUGCCCAGGAUCGGCAGCAACACCCUGGA<br>GAUCGGCCUGAGGACCCGGAUCAGGAAGAUGCUGGAGGAACACAAG<br>GAGCCCAGCCCACUGAUCACCGCCGAGGACGUGCAGGAGGCCAAGU<br>GCGCUGCCGACGAGGCCAAGGAGGUGAGGGAGGCCGAGGAACUGAG<br>GGCCGCCCUGCCACCCCUGGCUGCCGACGUGGAGGAACCCACCCUG<br>GAAGCCGACGUGGACCUGAUGCUGCAGGAGGCCGGCGCCGGAAGCG<br>UGGAGACACCCAGGGGCCUGAUCAAGGUGACCAGCUACGACGGCGA<br>GGACAAGAUCGGCAGCUACGCCGUGCUGAGCCCACAGGCCGUGCUG<br>AAGUCCGAGAAGCUGAGCUGCAUCCACCCACUGGCCGAGCAGGUGA<br>UCGUGAUCACCCACAGCGGCAGGAAGGGCAGGUACGCCGUGGAGCC<br>CUACCACGGCAAGGUGGUCGUGCCCGAGGGCCACGCCAUCCCCGUG<br>CAGGACUUCCAGGCCCUGAGCGAGAGCGCCACCAUCGUGUACAACG<br>AGAGGGAGUUCGUGAACAGGUACCUGCACCAUAUCGCCACCCACGG<br>CGGAGCCCUGAACACCGACGAGGAAUACUACAAGACCGUGAAGCCC<br>AGCGAGCACGACGGCGAGUACCUGUACGACAUCGACAGGAAGCAGU |

TABLE 9-continued

GCGUGAAGAAAGAGCUGGUGACCGGCCUGGGACUGACCGGCGAGCU
GGUGGACCCACCCUUCCACGAGUUCGCCUACGAGAGCCUGAGGACC
AGACCCGCCGCUCCCUACCAGGUGCCCACCAUCGGCGUGUACGGCG
UGCCCGGCAGCGGAAAGAGCGGCAUCAUCAAGAGCGCCGUGACCAA
GAAAGACCUGGUGGUCAGCGCCAAGAAAGAGAACUGCGCCGAGAUC
AUCAGGGACGUGAAGAAGAUGAAAGGCCUGGACGUGAACGCGCGCA
CCGUGGACAGCGUGCUGCUGAACGGCUGCAAGCACCCCGUGGAGAC
CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC

TABLE 9-continued

| | | | |
|---|---|---|---|
| | | | GUGAGGCAGACCGUGCUGAGCGAGGUGGUGCUGGAGAGGACCGAGC<br>UGGAAAUCAGCUACGCCCCCAGGCUGGACCAGGAGAAGGAGGAACU<br>GCUCAGGAAGAAACUGCAGCUGAACCCCACCCCAGCCAACAGGAGC<br>AGGUACCAGAGCAGGAAGGUGGAGAACAUGAAGGCCAUCACCGCCA<br>GGCGGAUCCUGCAGGGCCUGGGACACUACCUGAAGGCCGAGGGCAA<br>GGUGGAGUGCUACAGGACCCUGCACCCCGUGCCACUGUACAGCUCC<br>AGCGUGAACAGGGCCUUCUCCAGCCCCAAGGUGGCCGUGGAGGCCU<br>GCAACGCUAUGCUGAAGGAGAACUUCCCCACCGUGGCCAGCUACUG<br>CAUCAUCCCCGAGUACGACGCCUACCUGGACAUGGUGGACGGCGCC<br>AGCUGCUGCCUGGACACCGCCAGCUUCUGCCCCGCCAAGCUGAGGA<br>GCUUCCCCAAGAAACACAGCUACCUGGAGCCCACCAUCAGGAGCGC<br>CGUGCCCAGCGCCAUCCAGAACACCCUGCAGAACGUGCUGGCCGCU<br>GCCACCAAGAGGAACUGCAACGUGACCCAGAUGAGGGAGCUGCCCG<br>UGCUGGACAGCGCUGCCUUCAACGUGGAGUGCUUCAAGAAAUACGC<br>CUGCAACAACGAGUACUGGGAGACCUUCAAGGAGAACCCCAUCAGG<br>CUGACCGAAGAGAACGUGGUGAACUACAUCACCAAGCUGAAGGGCC<br>CCAAGGCCGCUGCCCUGUUCGCUAAGACCCACAACCUGAACAUGCU<br>GCAGGACAUCCCAAUGGACAGGUUCGUGAUGGACCUGAAGAGGGAC<br>GUGAAGGUGACACCCGGCACCAAGCACACCGAGGAGAGGCCCAAGG<br>UGCAGGUGAUCCAGGCCGCUGACCCACUGGCCACCGCCUACCUGUG<br>CGGCAUCCACAGGGAGCUGGUGAGGCGGCUGAACGCCGUGCUGCUG<br>CCCAACAUCCACACCCUGUUCGACAUGAGCGCCGAGGACUUCGACG<br>CCAUCAUCGCCGAGCACUUCCAGCCCGGCGACUGCGUGCUGGAGAC<br>CGACAUCGCCAGCUUCGACAAGAGCGAGGAUGACGCUAUGGCCCUG<br>ACCGCUCUGAUGAUCCUGGAGGACCUGGGCGUGGACGCCGAGCUGC<br>UCACCCUGAUCGAGGCUGCCUUCGGCGAGAUCAGCUCCAUCCACCU<br>GCCCACCAAGACCAAGUUCAAGUUCGGCGCUAUGAUGAAAAGCGGA<br>AUGUUCCUGACCCUGUUCGUGAACACCGUGAUCAACAUUGUGAUCG<br>CCAGCAGGGUGCUGCGGGAGAGGCUGACCGGCAGCCCCUGCGCUGC<br>CUUCAUCGGCGACGACAACAUCGUGAAGGGCGUGAAAAGCGACAAG<br>CUGAUGGCCGACAGGUGCGCCACCUGGCUGAACAUGGAGGUGAAGA<br>UCAUCGACGCCGUGGUGGGCGAGAAGGCCCCCUACUUCUGCGGCGG<br>AUUCAUCCUGUGCGACAGCGUGACCGGCACCGCCUGCAGGGUGGCC<br>GACCCCCUGAAGAGGCUGUUCAAGCUGGGCAAGCCACUGGCCGCUG<br>ACGAUGAGCACGACGAUGACAGGCGGAGGGCCCUGCACGAGGAAAG<br>CACCAGGUGGAACAGGGUGGGCAUCCUGAGCGAGCUGUGCAAGGCC<br>GUGGAGAGCAGGUACGAGACCGUGGGCACCAGCAUCAUCGUGAUGG<br>CUAUGACCACACUGGCCAGCUCCGUCAAGAGCUUCUCCUACCUGAG<br>GGGGGCCCCUAUAACUCUCUACGGCUAACCUGAAUGGACUACGACA<br>UAGUCUAGUCCGCCAAGGCCGCCACCCAUGAAGUUGGUGGUUGUGG<br>GGGCCGGGGGUGUUGGCAAAAGCGCCCUUACAAUUUGACUCGAGUA<br>UGUUACGUGCAAAGGUGAUUGUCACCCCCCGAAAGACCAUAUUGUG<br>ACACACCCUCAGUAUCACGCCCAAACAUUUACAGCCGCGGUGUCAA<br>AAACCGCGUGGACGUGGUUAACAUCCCUGCUGGGAGGAUCAGCCGU<br>AAUUAUUAUAAUUGGCUUGGUGCUGGCUACUAUUGUGGCCAUGUAC<br>GUGCUGACCAACCAGAAACAUAAUUGAAUACAGCAGCAAUUGGCAA<br>GCUGCUUACAUAGAACUCGCGGCGAUUGGCAUGCCGCCUUAAAAUU<br>UUUAUUUUAUUUUUUCUUUUCUUUUCCGAAUCGGAUUUUGUUUUUA<br>AUAUUUCAAAAAAAAAAAAAAAAAAAAAAAAUCUAGAAAAAAAAAA<br>AAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAA |
| 2862 (SEQ ID NO: 104) | SINV empty | 2862 | AUUGACGGCGUAGUACACACUAUUGAAUCAAACAGCCGACCAAUUG<br>CACUACCAUCACAAUGGAGAAGCCAGUAGUAAACGUAGACGUAGAC<br>CCCCAGAGUCCGUUUGUCGUGCAACUGCAAAAAAGCUUCCCGCAAU<br>UUGAGGUAGUAGCACAGCAGGUCACUCCAAAUGACCAUGCUAAUGC<br>CAGAGCAUUUUCGCAUCUGGCCAGUAAACUAAUCGAGCUGGAGGUU<br>CCUACCACAGCGACGAUCUUGGACAUAGGCAGCGCACCGGCUCGUA<br>GAAUGUUUUCCGAGCACCAGUAUCAUUGUGUCUGCCCCAUGCGUAG<br>UCCAGAAGACCCGGACCGCAUGAUGAAAUAUGCCAGUAAACUGGCG<br>GAAAAAGCGUGCAAGAUUACAAACAAGAACUUGCAUGAGAAGAUUA<br>AGGAUCUCCGGACCGUACUUGAUACGCCGGAUGCUGAAACACCAUC<br>GCUCUGCUUUCACAACGAUGUUACCUGCAACAUGCGUGCCGAAUAU<br>UCCGUCAUGCAGGACGUGUAUAUCAACGCUCCCGGAACUAUCUAUC<br>AUCAGGCUAUGAAAGGCGUGCGGACCCUGUACUGGAUUGGCUUCGA<br>CACCACCCAGUUCAUGUUCUCGGCUAUGGCAGGUUCGUACCCUGCG<br>UACAACACCAACUGGGCCGACGAGAAAGUCCUUGAAGCGCGUAACA<br>UCGGACUUUGCAGCACAAAGCUGAGUGAAGGUAGGACAGGAAAAUU<br>GUCGAUAAUGAGGAAGAAGGAGUUGAAGCCCGGGUCGCGGUUUAU<br>UUCUCCGUAGGAUCGACACUUUAUCCAGAACACAGAGCCAGCUUGC<br>AGAGCUGGCAUCUUCCAUCGGUGUUCCACUUGAAUGGAAAGCAGUC<br>GUACACUUGCCGCUGUGAUACAGUGGUGAGUUGCGAAGGCUACGUA<br>GUGAAGAAAAUCACCAUCAGUCCCGGGAUCACGGGAGAAACCGUGG<br>GAUACGCGGUUACACACAAUAGCGAGGGCUUCUUGCUAUGCAAAGU<br>UACUGACACAGUAAAAGGAGAACGGGUAUCGUUCCCUGUGUGCACG<br>UACAUCCCGGCCACCAUAUGCGAUCAGAUGACUGGUAUAAUGGCCA<br>CGGAUAUAUCACCUGACGAUGCACAAAAACUUCUGGUUGGGCUCAA<br>CCAGCGAAUUGUCAUUAACGGUAGGACUAACAGGAACACCAACACC<br>AUGCAAAAUUACCUUCUGCCGAUCAUAGCACAAGGGUUCAGCAAAU<br>GGGCUAAGGAGCGCAAGGAUGAUCUUGAUAACGAGAAAAUGCUGGG |

TABLE 9-continued

UACUAGAGAACGCAAGCUUACGUAUGGCUGCUUGUGGGCGUUUCGC
ACUAAGAAAGUACAUUCGUUUUAUCGCCCACCUGGAACGCAGACCU
GCGUAAAAGUCCCAGCCUCUUUUAGCGCUUUUCCCAUGUCGUCCGU
AUGGACGACCUCUUUGCCCAUGUCGCUGAGGCAGAAAUUGAAACUG
GCAUUGCAACCAAAGAAGGAGGAAAAACUGCUGCAGGUCUCGGAGG
AAUUAGUCAUGGAGGCCAAGGCUGCUUUUGAGGAUGCUCAGGAGGA
AGCCAGAGCGGAGAAGCUCCGAGAAGCACUUCCACCAUUAGUGGCA
GACAAAGGCAUCGAGGCAGCCGCAGAAGUUGUCUGCGAAGUGGAGG
GGCUCCAGGCGGACAUCGGAGCAGCAUUAGUUGAAACCCCGCGCGG
UCACGUAAGGAUAAUACCUCAAGCAAAUGACCGUAUGAUCGGACAG
UAUAUCGUUGUCUCGCCAAACUCUGUGCUGAAGAAUGCCAAACUCG
CACCAGCGCACCCGCUAGCAGAUCAGGUUAAGAUCAUAACACACUC
CGGAAGAUCAGGAAGGUACGCGGUCGAACCAUACGACGCUAAAGUA
CUGAUGCCAGCAGGAGGUGCCGUACCAUGGCCAGAAUUCCUAGCAC
UGAGUGAGAGCGCCACGUUAGUGUACAACGAAAGAGAGUUUGUGAA
CCGCAAACUAUACCACAUUGCCAUGCAUGGCCCCGCCAAGAAUACA
GAAGAGGAGCAGUACAAGGUUACAAAGGCAGAGCUUGCAGAAACAG
AGUACGUGUUUGACGUGGACAAGAAGCGUUGCGUUAAGAAGGAAGA
AGCCUCAGGUCUGGUCCUCUCGGGAGAACUGACCAACCCUCCCUAU
CAUGAGCUAGCUCUGGAGGGACUGAAGACCCGACCUGCGGUCCCGU
ACAAGGUCGAAACAAUAGGAGUGAUAGGCACACCGGGGUCGGGCAA
GUCAGCUAUUAUCAAGUCAACUGUCACGGCACGAGAUCUUGUUACC
AGCGGAAAGAAAGAAAAUUGUCGCGAAAUUGAGGCCGACGUGCUAA
GACUGAGGGGUAUGCAGAUUACGUCGAAGACAGUAGAUUCGGUUAU
GCUCAACGGAUGCCACAAAGCCGUAGAAGUGCUGUACGUUGACGAA
GCGUUCGCGUGCCACGCAGGAGCACUACUUGCCUUGAUUGCUAUCG
UCAGGCCCCGCAAGAAGGUAGUACUAUGCGGAGACCCCAUGCAAUG
CGGAUUCUUCAACAUGAUGCAACUAAAGGUACAUUUCAAUCACCCU
GAAAAAGACAUAUGCACCAAGACAUUCUACAAGUAUAUCUCCCGGC
GUUGCACACAGCCAGUUACAGCUAUUGUAUCGACACUGCAUUACGA
UGGAAAGAUGAAAACCACGAACCCGUGCAAGAAGAACAUUGAAAUC
GAUAUUACAGGGGCCACAAAGCCGAAGCCAGGGGAUAUCAUCCUGA
CAUGUUUCCGCGGGUGGGUUAAGCAAUUGCAAAUCGACUAUCCCGG
ACAUGAAGUAAUGACAGCCGCGGCCUCACAAGGGCUAACCAGAAAA
GGAGUGUAUGCCGUCCGGCAAAAAGUCAAUGAAAACCCACUGUACG
CGAUCACAUCAGAGCAUGUGAACGUGUUGCUCACCCGCACUGAGGA
CAGGCUAGUGUGGAAAACCUUGCAGGGCGACCCAUGGAUUAAGCAG
CUCACUAACAUACCUAAAGGAAACUUUCAGGCUACUAUAGAGGACU
GGGAAGCUGAACACAAGGGAAUAAUUGCUGCAAUAAACAGCCCCAC
UCCCCGUGCCAAUCCGUUCAGCUGCAAGACCAACGUUUGCUGGGCG
AAAGCAUUGGAACCGAUACUAGCCACGGCCGGUAUCGUACUUACCG
GUUGCCAGUGGAGCGAACUGUUCCCACAGUUUGCGGAUGACAAACC
ACAUUCGGCCAUUUACGCCUUAGACGUAAUUUGCAUUAAGUUUUUC
GGCAUGGACUUGACAAGCGGACUGUUUUCUAAACAGAGCAUCCCAC
UAACGUACCAUCCCGCCGAUUCAGCGAGGCCGGUAGCUCAUUGGGA
CAACAGCCCAGGAACCCGCAAGUAUGGGUACGAUCACGCCAUUGCC
GCCGAACUCUCCCGUAGAUUUCCGGUGUUCCAGCUAGCUGGGAAGG
GCACACAACUUGAUUUGCAGACGGGGAGAACCAGAGUUAUCUCUGC
ACAGCAUAACCUGGUCCCGGUGAACCGCAAUCUUCCUCACGCCUUA
GUCCCCGAGUACAAGGAGAAGCAACCCGGCCCGGUCGAAAAAUUCU
UGAACCAGUUCAAACACCACUCAGUACUUGUGGUAUCAGAGGAAAA
AAUUGAAGCUCCCCGUAAGAGAAUCGAAUGGAUCGCCCCGAUUGGC
AUAGCCGGUGCAGAUAAGAACUACAACCUGGCUUUCGGGUUUCCGC
CGCAGGCACGGUACGACCUGGUGUUCAUCAACAUUGGAACUAAAUA
CAGAAACCACCACUUUCAGCAGUGCGAAGACCAUGCGGCGACCUUA
AAAACCCUUUCGCGUUCGGCCCUGAAUUGCCUUAACCCAGGAGGCA
CCCUCGUGGUGAAGUCCUAUGGCUACGCCGACCGCAACAGUGAGGA
CGUAGUCACCGCUCUUGCCAGAAAGUUUGUCAGGGUGUCUGCAGCG
AGACCAGAUUGUGUCUCAAGCAAUACAGAAAUGUACCUGAUUUUCC
GACAACUAGACAACAGCCGUACACGGCAAUUCACCCCGCACCAUCU
GAAUUGCGUGAUUUCGUCCGUGUAUGAGGGUACAAGAGAUGGAGUU
GGAGCCGCGCCGUCAUACCGCACCAAAAGGGAGAAUAUUGCUGACU
GUCAAGAGGAAGCAGUUGUCAACGCAGCCAAUCCGCUGGGUAGACC
AGGCGAAGGAGUCUGCCGUGCCAUCUAUAAACGUUGGCCGACCAGU
UUUACCGAUUCAGCCACGGAGACAGGCACCGCAAGAAUGACUGUGU
GCCUAGGAAAGAAAGUGAUCCACGCGGUCGGCCCUGAUUUCCGGAA
GCACCCAGAAGCAGAAGCCUUGAAAUUGCUACAAAACGCCUACCAU
GCAGUGGCAGACUUAGUAAAUGAACAUAACAUCAAGUCUGUCGCCA
UUCCACUGCUAUCUACAGGCAUUUACGCAGCCGGAAAAGACCGCCU
UGAAGUAUCACUUAACUGCUUGACAACCGCGCUAGACAGAACUGAC
GCGGACGUAACCAUCUAUUGCCUGGAUAAGAAGUGGAAGGAAAGAA
UCGACGCGGCACUCCAACUUAAGGAGUCUGUAACAGAGCUGAAGGA
UGAAGAUAUGGAGAUCGACGAUGAGUUAGUAUGGAUCCAUCCAGAC
AGUUGCUUGAAGGGAAGAAAGGGAUUCAGUACUACAAAAGGAAAAU
UGUAUUCGUACUUCGAAGGCACCAAAUUCCAUCAAGCAGCAAAAGA
CAUGGCGGAGAUAAAGGUCCUGUUCCCUAAUGACCAGGAAAGUAAU
GAACAACUGUGUGCCUACAUAUUGGGUGAGACCAUGGAAGCAAUCC
GCGAAAAGUGCCCGGUCGACCAUAACCCGUCGUCUAGCCCGCCCAA
AACGUUGCCGUGCCUUUGCAUGUAUGCCAUGACGCCAGAAAGGGUC
CACAGACUUAGAAGCAAUAACGUCAAAGAAGUUACAGUAUGCUCCU

TABLE 9-continued

| | | |
|---|---|---|
| | | CCACCCCCCUUCCUAAGCACAAAAUUAAGAAUGUUCAGAAGGUUCA<br>GUGCACGAAAGUAGUCCUGUUUAAUCCGCACACUCCCGCAUUCGUU<br>CCCGCCCGUAAGUACAUAGAAGUGCCAGAACAGCCUACCGCUCCUC<br>CUGCACAGGCCGAGGAGGCCCCCGAAGUUGUAGCGACACCGUCACC<br>AUCUACAGCUGAUAACACCUCGCUUGAUGUCACAGACAUCUCACUG<br>GAUAUGGAUGACAGUAGCGAAGGCUCACUUUUUUCGAGCUUUAGCG<br>GAUCGGACAACUCUAUUACUAGUAUGGACAGUUGGUCGUCAGGACC<br>UAGUUCACUAGAGAUAGUAGACCGAAGGCAGGUGGUGGUGGCUGAC<br>GUUCAUGCCGUCCAAGAGCCUGCCCCUAUUCCACCGCCAAGGCUAA<br>AGAAGAUGGCCCGCCUGGCAGCGGCAAGAAAAGAGCCCACUCCACC<br>GGCAAGCAAUAGCUCUGAGUCCCUCCACCUCUCUUUUGGUGGGGUA<br>UCCAUGUCCCUCGGAUCAAUUUUCGACGGAGAGACGGCCCGCCAGG<br>CAGCGGUACAACCCCUGGCAACAGGCCCCACGGAUGUGCCUAUGUC<br>UUUCGGAUCGUUUUCCGACGGAGAGAUUGAUGAGCUGAGCCGCAGA<br>GUAACUGAGUCCGAACCCGUCCUGUUUGGAUCAUUUGAACCGGGCG<br>AAGUGAACUCAAUUAUAUCGUCCCGAUCAGCCGUAUCUUUUCCUCU<br>ACGCAAGCAGAGACGUAGACGCAGGAGCAGGAGGACUGAAUACUGA<br>CUAACCGGGGUAGGUGGGUACAUAUUUUCGACGGACACAGGCCCUG<br>GGCACUUGCAAAAGAAGUCCGUUCUGCAGAACCAGCUUACAGAACC<br>GACCUUGGAGCGCAAUGUCCUGGAAAGAAUUCAUGCCCCGGUGCUC<br>GACACGUCGAAAGAGGAACAACUCAAACUCAGGUACCAGAUGAUGC<br>CCACCGAAGCCAACAAAAGUAGGUACCAGUCUCGUAAAGUAGAAAA<br>UCAGAAAGCCAUAACCACUGAGCGACUACUGUCAGGACUACGACUG<br>UAUAACUCUGCCACAGAUCAGCCAGAAUGCUAUAAGAUCACCUAUC<br>CGAAACCAUUGUACUCCAGUAGCGUACCGGCGAACUACUCCGAUCC<br>ACAGUUCGCUGUAGCUGUCUGUAACAACUAUCUGCAUGAGAACUAU<br>CCGACAGUAGCAUCUUAUCAGAUUACUGACGAGUACGAUGCUUACU<br>UGGAUAUGGUAGACGGGACAGUCGCCUGCCUGGACACUGCAACCUU<br>CUGCCCCGCUAAGCUUAGAAGUUACCCGAAAAAACAUGAGUAUAGA<br>GCCCCGAAUAUCCGCAGUGCGGUUCCAUCAGCGAUGCAGAACACGC<br>UACAAAAUGUGCUCAUUGCCGCAACUAAAAGAAAUUGCAACGUCAC<br>GCAGAUGCGUGAACUGCCAACACUGGACUCAGCGACAUUCAAUGUC<br>GAAUGCUUUCGAAAAUAUGCAUGUAAUGACGAGUAUUGGGAGGAGU<br>UCGCUCGGAAGCCAAUUAGGAUUACCACUGAGUUUGUCACCGCAUA<br>UGUAGCUAGACUGAAAGGCCCUAAGGCCGCCGCACUAUUUGCAAAG<br>ACGUAUAAUUUGGUCCCAUUGCAAGAAGUGCCUAUGGAUAGAUUCG<br>UCAUGGACAUGAAAAGAGACGUGAAAGUUACACCAGGCACGAAACA<br>CACAGAAGAAAGACCGAAAGUACAAGUGAUACAAGCCGCAGAACCC<br>CUGGCGACUGCUUACUUAUGCGGGAUUCACCGGGAAUUAGUGCGUA<br>GGCUUACGGCCGUCUUGCUUCCAAACAUUCACACGCUUUUUGACAU<br>GUCGGCGGAGGAUUUUGAUGCAAUCAUAGCAGAACACUUCAAGCAA<br>GGCGACCCGGUACUGGAGACGGAUAUCGCAUCAUUCGACAAAAGCC<br>AAGACGACGCUAUGGCGUUAACCGGUCUGAUGAUCUUGGAGGACCU<br>GGGUGUGGAUCAACCACUACUCGACUUGAUCGAGUGCGCCUUUGGA<br>GAAAUAUCAUCCACCCAUCUACCUACGGGUACUCGUUUUAAAUUCG<br>GGGCGAUGAUGAAAUCCGGAAUGUUCCUCACACUUUUUGUCAACAC<br>AGUUUUGAAUGUCGUUAUCGCCAGCAGAGUACUAGAGGAGCGGCUU<br>AAAACGUCCAGAUGUGCAGCGUUCAUUGGCGACGACAACAUCAUAC<br>AUGGAGUAGUAUCUGACAAAGAAAUGGCUGAGAGGUGCGCCACCUG<br>GCUCAACAUGGAGGUUAAGAUCAUCGACGCAGUCAUCGGUGAGAGA<br>CCACCUUACUUCUGCGGCGGAUUUAUCUUGCAAGAUUCGGUUACUU<br>CCACAGCGUGCCGCGUGGCGGAUCCCCUGAAAAGGCUGUUUAAGUU<br>GGGUAAACCGCUCCCAGCCGACGACGAGCAAGACGAAGACAGAAGA<br>CGCGCUCUGCUAGAUGAAACAAAGGCGUGGUUUAGAGUAGGUAUAA<br>CAGGCACUUUAGCAGUGGCCGUGACGACCCGGUAUGAGGUAGACAA<br>UAUUACACCUGUCCUACUGGCAUUGAGAACUUUUGCCCAGAGCAAA<br>AGAGCAUUCCAAGCCAUCAGAGGGGAAAUAAAGCAUCUCUACGGUG<br>GUCCUAAAUAGUCAGCAUAGUACAUUUCAUCUGACUAAUACUACAA<br>CACCACCACCACGCGUGCUAGACCAUGGAUCCUAGACGCUACGCCC<br>CAAUGAUCCGACCAGCAAAACUCGAUGUACUUCCGAGGAACUGAUG<br>UGCAUAAUGCAUCAGGCUGGUACAUUAGAUCCCCGCUUACCGCGGG<br>CAAUAUAGCAACACUAAAAACUCGAUGUACUUCCGAGGAAGCGCAG<br>UGCAUAAUGCUGCGCAGUGUUGCCACAUAACCACUAUAUUAACCAU<br>UUAUCUAGCGGACGCCAAAAACUCAAUGUAUUUCUGAGGAAGCGUG<br>GUGCAUAAUGCCACGCAGCGUCUGCAUAACUUUUAUUAUUUCUUUU<br>AUUAAUCAACAAAAUUUUGUUUUUAACAUUUCAAAAAAAAAAAAAAAA<br>AAAAAAAAAAAAUCUAGAAAAAAAAAAAAAAAAAAAAAAAAAAAAAAA<br>AAAAAAAAAAAAAAAAAAAAAAAAAAAAAAAAAAAAAAAAAAAAAAAA<br>AAAAAAAAAAAAAAAAAAAAAAAAA |
| 3060 (SEQ ID NO: 105) | STARR ™ 3060 gp70 | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA |

TABLE 9-continued

GUCGUGUCGCUACGAAGGGCAAGUCGCUGUUUACCAGGAUGUAUAC
GCCGUCGACGGCCCCACCAGCCUGUACCACCAGGCCAACAAGGGCG
UGAGGGUGGCCUACUGGAUCGGCUUCGACACCACACCCUUCAUGUU
CAAGAACCUGGCCGGCGCCUACCCCAGCUACAGCACCAACUGGGCC
GACGAGACCGUGCUGACCGCCAGGAACAUCGGCCUGUGCAGCAGCG
ACGUGAUGGAGAGGAGCCGGAGAGGCAUGAGCAUCCUGAGGAAGAA
AUACCUGAAGCCCAGCAACAACGUGCUGUUCAGCGUGGGCAGCACC
AUCUACCACGAGAAGAGGGACCUGCUCAGGAGCUGGCACCUGCCCA
GCGUGUUCCACCUGAGGGGCAAGCAGAACUACACCUGCAGGUGCGA
GACCAUCGUGAGCUGCGACGGCUACGUGGUGAAGAGGAUCGCCAUC
AGCCCCGGCCUGUACGGCAAGCCCAGCGGCUACGCCGCUACAAUGC
ACAGGGAGGGCUUCCUGUGCUGCAAGGUGACCGACACCCUGAACGG
CGAGAGGGUGAGCUUCCCCGUGUGCACCUACGUGCCCGCCACCCUG
UGCGACCAGAUGACCGGCAUCCUGGCCACCGACGUGAGCGCCGACG
ACGCCCAGAAGCUGCUCGUGGGCCUGAACCAGAGGAUCGUGGUCAA
CGGCAGGACCCAGAGGAACACCAACACAAUGAAGAACUACCUGCUG
CCCGUGGUGGCCCAGGCUUUCGCCAGGUGGGCCAAGGAGUACAAGG
AGGACCAGGAAGACGAGAGGCCCCUGGGCCUGAGGGACAGGCAGCU
GGUGAUGGGCUGCUGCUGGGCCUUCAGGCGGCACAAGAUCACCAGC
AUCUACAAGAGGCCCGACACCCAGACCAUCAUCAAGGUGAACAGCG
ACUUCCACAGCUUCGUGCUGCCCAGGAUCGGCAGCAACACCCUGGA
GAUCGGCCUGAGGACCCGGAUCAGGAAGAUGCUGGAGGAACACAAG
GAGCCCAGCCCACUGAUCACCGCCGAGGACGUGCAGGAGGCCAAGU
GCGCUGCCGACGAGGCCAAGGAGGUGAGGGAGGCCGAGGAACUGAG
GGCCGCCCUGCCACCCCUGGCUGCCGACGUGGAGGAACCCACCCUG
GAAGCCGACGUGGACCUGAUGCUGCAGGAGGCCGGCGCCGGAAGCG
UGGAGACACCCAGGGGCCUGAUCAAGGUGACCAGCUACGACGGCGA
GGACAAGAUCGGCAGCUACGCCGUGCUGAGCCCACAGGCCGUGCUG
AAGUCCGAGAAGCUGAGCUGCAUCCACCCACUGGCCGAGCAGGUGA
UCGUGAUCACCCACAGCGGCAGGAAGGGCAGGUACGCCGUGGAGCC
CUACCACGGCAAGGUGGUCGUGCCCGAGGGCCACGCCAUCCCCGUG
CAGGACUUCCAGGCCCUGAGCGAGAGCGCCACCAUCGUGUACAACG
AGAGGGAGUUCGUGAACAGGUACCUGCACCAUAUCGCCACCCACGG
CGGAGCCCUGAACACCGACGAGGAAUACUACAAGACCGUGAAGCCC
AGCGAGCACGACGGCGAGUACCUGUACGACAUCGACAGGAAGCAGU
GCGUGAAGAAAGAGCUGGUGACCGGCCUGGGACUGACCGGCGAGCU
GGUGGACCCACCCUUCCACGAGUUCGCCUACGAGAGCCUGAGGACC
AGACCCGCCGCUCCCUACCAGGUGCCCACCAUCGGCGUGUACGGCG
UGCCCGGCAGCGGAAAGAGCGGCAUCAUCAAGAGCGCCGUGACCAA
GAAAGACCUGGUGGUCAGCGCCAAGAAAGAGAACUGCGCCGAGAUC
AUCAGGGACGUGAAGAAGAUGAAAGGCCUGGACGUGAACGCGCGCA
CCGUGGACAGCGUGCUGCUGAACGGCUGCAAGCACCCCGUGGAGAC
CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC

TABLE 9-continued

UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCCGAGUACGACGCCUACCUGGACAUGGUGGACGGCGCC
AGCUGCUGCCUGGACACCGCCAGCUUCUGCCCCGCCAAGCUGAGGA
GCUUCCCCAAGAAACACAGCUACCUGGAGCCCACCAUCAGGAGCGC
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACGUGGAGUGCUUCAAGAAAUACGC
CUGCAACAACGAGUACUGGGAGACCUUCAAGGAGAACCCCAUCAGG
CUGACCGAAGAGAACGUGGUGAACUACAUCACCAAGCUGAAGGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
GUGAAGGUGACACCCGGCACCAAGCACACCGAGGAGAGGCCCAAGG
UGCAGGUGAUCCAGGCCGCUGACCCACUGGCCACCGCCUACCUGUG
CGGCAUCCACAGGGAGCUGGUGAGGCGGCUGAACGCCGUGCUGCUG
CCCAACAUCCACACCCUGUUCGACAUGAGCGCCGAGGACUUCGACG
CCAUCAUCGCCGAGCACUUCCAGCCCGGCGACUGCGUGCUGGAGAC
CGACAUCGCCAGCUUCGACAAGAGCGAGGAUGACGCUAUGGCCCUG
ACCGCUCUGAUGAUCCUGGAGGACCUGGGCGUGGACGCCGAGCUGC
UCACCCUGAUCGAGGCUGCCUUCGGCGAGAUCAGCUCCAUCCACCU
GCCCACCAAGACCAAGUUCAAGUUCGGCGCUAUGAUGAAAAGCGGA
AUGUUCCUGACCCUGUUCGUGAACACCGUGAUCAACAUUGUGAUCG
CCAGCAGGGUGCUGCGGGAGAGGCUGACCGGCAGCCCCUGCGCUGC
CUUCAUCGGCGACGACAACAUCGUGAAGGGCGUGAAAAGCGACAAG
CUGAUGGCCGACAGGUGCGCCACCUGGCUGAACAUGGAGGUGAAGA
UCAUCGACGCCGUGGUGGGCGAGAAGGCCCCCUACUUCUGCGGCGG
AUUCAUCCUGUGCGACAGCGUGACCGGCACCGCCUGCAGGGUGGCC
GACCCCCUGAAGAGGCUGUUCAAGCUGGGCAAGCCACUGGCCGCUG
ACGAUGAGCACGACGAUGACAGGCGGAGGGCCCUGCACGAGGAAAG
CACCAGGUGGAACAGGGUGGGCAUCCUGAGCGAGCUGUGCAAGGCC
GUGGAGAGCAGGUACGAGACCGUGGGCACCAGCAUCAUCGUGAUGG
CUAUGACCACACUGGCCAGCUCCGUCAAGAGCUUCUCCUACCUGAG
GGGGGCCCCUAUAACUCUCUACGGCUAACCUGAAUGGACUACGACA
UAGUCUAGUCCGCCAAGGCCGCCACCAUGAGAGUGACAGCCCCUAG
AACCUUACUGCUUCUGCUUUGGGGAGCUGUUGCUCUGACAGAGACA
UGGGCUGGAUCUCUGAGCGAGGUGACCGGCCAGGGCCUGUGCAUCG
GCGCCGUGCCCAAGACCCACCAGGUGCUGUGCAACACCACCCAGAA
GACCAGCGACGGCAGCUACUACCUGGCCGCUCCCACCGGCACCACC
UGGGCCUGCAGCACCGGCCUGACCCCUUGCAUCAGCACCACCAUCC

TABLE 9-continued

| | | |
|---|---|---|
| | | UGAACCUGACCACCGACUACUGCGUGCUGGUGGAGCUGUGGCCCAG<br>GGUGACCUACCACAGCCCCAGCUACGCCUACCACCAGUUCGAGAGG<br>AGGGCCAAGUACAAGAGGGAGCCCGUGAGCCUGACCCUGGCCCUGC<br>UGCUGGGCGGCCUGACAAUGGGCGGCAUCGCCGCCGGCGUGGGCAC<br>CGGCACCACCGCCCUGGUGGCCACCCAGCAGUUCCAGCAGCUGCAG<br>GCCGCCAUGCACGACGACCUGAAGGAGGUGGAGAAGUCCAUCACCA<br>ACCUGGAGAAGUCCCUGACCAGCCUGAGCGAGGUGGUGCUGCAGAA<br>CAGGAGGGGCCUGGACCUGCUGUUCCUGAAGGAGGGCGGCCUGUGC<br>GCCGCCCUGAAGGAGGAGUGCUGCCUGUACGCCGACCACACCGGCC<br>UGGUGAUCGUGGGCAUUGUCGCUGGCCUGGCCGUCCUCGCCGUGGU<br>GGUGAUUGGAGCUGUGGUCGCAGCUGUUAUGUGCAGAAGAAAGUCA<br>UCCGGCGGAAAGGGAGGCUCCUACUCUCAGGCUGCUUCUGCUACAG<br>UGCCUAGAGCUCUUAUGUGUUUAUCUCAGCUGUAAACUCGAGUAUG<br>UUACGUGCAAAGGUGAUUGUCACCCCCCGAAAGACCAUAUUGUGAC<br>ACACCCUCAGUAUCACGCCCAAACAUUUACAGCCGCGGUGUCAAAA<br>ACCGCGUGGACGUGGUUAACAUCCCUGCUGGGAGGAUCAGCCGUAA<br>UUAUUAUAAUUGGCUUGGUGCUGGCUACUAUUGUGGCCAUGUACGU<br>GCUGACCAACCAGAAACAUAAUUGAAUACAGCAGCAAUUGGCAAGC<br>UGCUUACAUAGAACUCGCGGCGAUUGGCAUGCCGCCUUAAAAUUUU<br>UAUUUUAUUUUUUCUUUUCUUUUCCGAAUCGGAUUUUGUUUUUAAU<br>AUUUCAAAAAAAAAAAAAAAAAAAAAAAAUCUAGAAAAAAAAAAAA<br>AAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAA |
| 3061 (SEQ ID NO: 106) | STARR ™ 3061 AH1A5 | AUGGGCGGCGCAUGAGAGAAGCCCAGACCAAUUACCUACCCAAA<br>AUGGAGAAAGUUCACGUUGACAUCGAGGAAGACAGCCCAUUCCU<br>CAGAGCUUUGCAGCGGAGCUUCCCGCAGUUUGAGGUAGAAGCCA<br>AGCAGGUCACUGAUAAUGACCAUGCUAAUGCCAGAGCGUUUUCG<br>CAUCUGGCUUCAAAACUGAUCGAAACGGAGGUGGACCCAUCCGA<br>CACGAUCCUUGACAUUGGAAGUGCGCCCGCCCGCAGAAUGUAUU<br>CUAAGCACAAGUAUCAUUGUAUCUGUCCGAUGAGAUGUGCGGAA<br>GAUCCGGACAGAUUGUAUAAGUAUGCAACUAAGCUGAAGAAAAA<br>CUGUAAGGAAAUAACUGAUAAGGAAUUGGACAAGAAAAUGAAGG<br>AGCUGGCCGCCGUCAUGAGCGACCCUGACCUGGAAACUGAGACU<br>AUGUGCCUCCACGACGACGAGUCGUGUCGCUACGAAGGGCAAGU<br>CGCUGUUUACCAGGAUGUAUACGCCGUCGACGGCCCCACCAGCC<br>UGUACCACCAGGCCAACAAGGGCGUGAGGGUGGCCUACUGGAUC<br>GGCUUCGACACCACACCCUUCAUGUUCAAGAACCUGGCCGGCGC<br>CUACCCCAGCUACAGCACCAACUGGGCCGACGAGACCGUGCUGA<br>CCGCCAGGAACAUCGGCCUGUGCAGCAGCGACGUGAUGGAGAGG<br>AGCCGGAGAGGCAUGAGCAUCCUGAGGAAGAAAUACCUGAAGCC<br>CAGCAACAACGUGCUGUUCAGCGUGGGCAGCACCAUCUACCACG<br>AGAAGAGGGACCUGCUCAGGAGCUGGCACCUGCCCAGCGUGUUC<br>CACCUGAGGGGCAAGCAGAACUACACCUGCAGGUGCGAGACCAU<br>CGUGAGCUGCGACGGCUACGUGGUGAAGAGGAUCGCCAUCAGCC<br>CCGGCCUGUACGGCAAGCCCAGCGGCUACGCCGCUACAAUGCAC<br>AGGGAGGGCUUCCUGUGCUGCAAGGUGACCGACACCCUGAACGG<br>CGAGAGGGUGAGCUUCCCCGUGUGCACCUACGUGCCCGCCACCC<br>UGUGCGACCAGAUGACCGGCAUCCUGGCCACCGACGUGAGCGCC<br>GACGACGCCCAGAAGCUGCUCGUGGGCCUGAACCAGAGGAUCGU<br>GGUCAACGGCAGGACCCAGAGGAACACCAACACAAUGAAGAACU<br>ACCUGCUGCCCGUGGUGGCCCAGGCUUUCGCCAGGUGGGCCAAG<br>GAGUACAAGGAGGACCAGGAAGACGAGAGGCCCCUGGGCCUGAG<br>GGACAGGCAGCUGGUGAUGGGCUGCUGCUGGGCCUUCAGGCGGC<br>ACAAGAUCACCAGCAUCUACAAGAGGCCCGACACCCAGACCAUC<br>AUCAAGGUGAACAGCGACUUCCACAGCUUCGUGCUGCCCAGGAU<br>CGGCAGCAACACCCUGGAGAUCGGCCUGAGGACCCGGAUCAGGA<br>AGAUGCUGGAGGAACACAAGGAGCCCAGCCCACUGAUCACCGCC<br>GAGGACGUGCAGGAGGCCAAGUGCGCUGCCGACGAGGCCAAGGA<br>GGUGAGGGAGGCCGAGGAACUGAGGGCCGCCCUGCCACCCCUGG<br>CUGCCGACGUGGAGGAACCCACCCUGGAAGCCGACGUGGACCUG<br>AUGCUGCAGGAGGCCGGCGCCGGAAGCGUGGAGACACCCAGGGG<br>CCUGAUCAAGGUGACCAGCUACGACGGCGAGGACAAGAUCGGCA<br>GCUACGCCGUGCUGAGCCCACAGGCCGUGCUGAAGUCCGAGAAG<br>CUGAGCUGCAUCCACCCACUGGCCGAGCAGGUGAUCGUGAUCAC<br>CCACAGCGGCAGGAAGGGCAGGUACGCCGUGGAGCCCUACCACG<br>GCAAGGUGGUCGUGCCCGAGGGCCACGCCAUCCCCGUGCAGGAC<br>UUCCAGGCCCUGAGCGAGAGCGCCACCAUCGUGUACAACGAGAG<br>GGAGUUCGUGAACAGGUACCUGCACCAUAUCGCCACCCACGGCG<br>GAGCCCUGAACACCGACGAGGAAUACUACAAGACCGUGAAGCCC<br>AGCGAGCACGACGGCGAGUACCUGUACGACAUCGACAGGAAGCA<br>GUGCGUGAAGAAAGAGCUGGUGACCGGCCUGGGACUGACCGGCG<br>AGCUGGUGGACCCACCCUUCCACGAGUUCGCCUACGAGAGCCUG<br>AGGACCAGACCCGCCGCUCCCUACCAGGUGCCCACCAUCGGCGU<br>GUACGGCGUGCCCGGCAGCGGAAAGAGCGGCAUCAUCAAGAGCG<br>CCGUGACCAAGAAAGACCUGGUGGUCAGCGCCAAGAAAGAGAAC<br>UGCGCCGAGAUCAUCAGGGACGUGAAGAAGAUGAAAGGCCUGGA<br>CGUGAACGCGCGCACCGUGGACAGCGUGCUGCUGAACGGCUGCA<br>AGCACCCCGUGGAGACCCUGUACAUCGACGAGGCCUUCGCUUGC<br>CACGCCGGCACCCUGAGGGCCCUGAUCGCCAUCAUCAGGCCCAA |

TABLE 9-continued

GAAAGCCGUGCUGUGCGGCGACCCCAAGCAGUGCGGCUUCUUCA
ACAUGAUGUGCCUGAAGGUGCACUUCAACCACGAGAUCUGCACC
CAGGUGUUCCACAAGAGCAUCAGCAGGCGGUGCACCAAGAGCGU
GACCAGCGUCGUGAGCACCCUGUUCUACGACAAGAAAAUGAGGA
CCACCAACCCCAAGGAGACCAAAAUCGUGAUCGACACCACAGGC
AGCACCAAGCCCAAGCAGGACGACCUGAUCCUGACCUGCUUCAG
GGGCUGGGUGAAGCAGCUGCAGAUCGACUACAAGGGCAACGAGA
UCAUGACCGCCGCUGCCAGCCAGGGCCUGACCAGGAAGGGCGUG
UACGCCGUGAGGUACAAGGUGAACGAGAACCCACUGUACGCUCC
CACCAGCGAGCACGUGAACGUGCUGCUGACCAGGACCGAGGACA
GGAUCGUGUGGAAGACCCUGGCCGGCGACCCCUGGAUCAAGACC
CUGACCGCCAAGUACCCCGGCAACUUCACCGCCACCAUCGAAGA
GUGGCAGGCCGAGCACGACGCCAUCAUGAGGCACAUCCUGGAGA
GGCCCGACCCCACCGACGUGUUCCAGAACAAGGCCAACGUGUGC
UGGGCCAAGGCCCUGGUGCCCGUGCUGAAGACCGCCGGCAUCGA
CAUGACCACAGAGCAGUGGAACACCGUGGACUACUUCGAGACCG
ACAAGGCCCACAGCGCCGAGAUCGUGCUGAACCAGCUGUGCGUG
AGGUUCUUCGGCCUGGACCUGGACAGCGGCCUGUUCAGCGCCCC
CACCGUGCCACUGAGCAUCAGGAACAACCACUGGGACAACAGCC
CCAGCCCAAACAUGUACGGCCUGAACAAGGAGGUGGUCAGGCAG
CUGAGCAGGCGGUACCCACAGCUGCCCAGGGCCGUGGCCACCGG
CAGGGUGUACGACAUGAACACCGGCACCCUGAGGAACUACGACC
CCAGGAUCAACCUGGUGCCCGUGAACAGGCGGCUGCCCCACGCC
CUGGUGCUGCACCACAACGAGCACCCACAGAGCGACUUCAGCUC
CUUCGUGAGCAAGCUGAAAGGCAGGACCGUGCUGGUCGUGGGCG
AGAAGCUGAGCGUGCCCGGCAAGAUGGUGGACUGGCUGAGCGAC
AGGCCCGAGGCCACCUUCCGGGCCAGGCUGGACCUCGGCAUCCC
CGGCGACGUGCCCAAGUACGACAUCAUCUUCGUGAACGUCAGGA
CCCCAUACAAGUACCACCAUUACCAGCAGUGCGAGGACCACGCC
AUCAAGCUGAGCAUGCUGACCAAGAAGGCCUGCCUGCACCUGAA
CCCCGGAGGCACCUGCGUGAGCAUCGGCUACGGCUACGCCGACA
GGGCCAGCGAGAGCAUCAUUGGCGCCAUCGCCAGGCUGUUCAAG
UUCAGCAGGGUGUGCAAACCCAAGAGCAGCCUGGAGGAAACCGA
GGUGCUGUUCGUGUUCAUCGGCUACGACCGGAAGGCCAGGACCC
ACAACCCCUACAAGCUGAGCAGCACCCUGACAAACAUCUACACC
GGCAGCAGGCUGCACGAGGCCGGCUGCGCCCCCAGCUACCACGU
GGUCAGGGGCGAUAUCGCCACCGCCACCGAGGGCGUGAUCAUCA
ACGCUGCCAACAGCAAGGGCCAGCCCGGAGGCGGAGUGUGCGGC
GCCCUGUACAAGAAGUUCCCCGAGAGCUUCGACCUGCAGCCCAU
CGAGGUGGGCAAGGCCAGGCUGGUGAAGGGCGCCGCUAAGCACA
UCAUCCACGCCGUGGGCCCCAACUUCAACAAGGUGAGCGAGGUG
GAAGGCGACAAGCAGCUGGCCGAAGCCUACGAGAGCAUCGCCAA
GAUCGUGAACGACAAUAACUACAAGAGCGUGGCCAUCCCACUGC
UCAGCACCGGCAUCUUCAGCGGCAACAAGGACAGGCUGACCCAG
AGCCUGAACCACCUGCUCACCGCCCUGGACACCACCGAUGCCGA
CGUGGCCAUCUACUGCAGGGACAAGAAGUGGGAGAUGACCCUGA
AGGAGGCCGUGGCCAGGCGGGAGGCCGUGGAAGAGAUCUGCAUC
AGCGACGACUCCAGCGUGACCGAGCCCGACGCCGAGCUGGUGAG
GGUGCACCCCAAGAGCUCCCUGGCCGGCAGGAAGGGCUACAGCA
CCAGCGACGGCAAGACCUUCAGCUACCUGGAGGGCACCAAGUUC
CACCAGGCCGCUAAGGACAUCGCCGAGAUCAACGCUAUGUGGCC
CGUGGCCACCGAGGCCAACGAGCAGGUGUGCAUGUACAUCCUGG
GCGAGAGCAUGUCCAGCAUCAGGAGCAAGUGCCCCGUGGAGGAA
AGCGAGGCCAGCACACCACCCAGCACCCUGCCCUGCCUGUGCAU
CCACGCUAUGACACCCGAGAGGGUGCAGCGGCUGAAGGCCAGCA
GGCCCGAGCAGAUCACCGUGUGCAGCUCCUUCCCACUGCCCAAG
UACAGGAUCACCGGCGUGCAGAAGAUCCAGUGCAGCCAGCCCAU
CCUGUUCAGCCCAAAGGUGCCCGCCUACAUCCACCCCAGGAAGU
ACCUGGUGGAGACCCCACCCGUGGACGAGACACCCGAGCCAAGC
GCCGAGAACCAGAGCACCGAGGGCACACCCGAGCAGCCACCCCU
GAUCACCGAGGACGAGACAAGGACCCGGACCCCAGAGCCCAUCA
UUAUCGAGGAAGAGGAAGAGGACAGCAUCAGCCUGCUGAGCGAC
GGCCCCACCCACCAGGUGCUGCAGGUGGAGGCCGACAUCCACGG
CCCACCCAGCGUGUCCAGCUCCAGCUGGAGCAUCCCACACGCCA
GCGACUUCGACGUGGACAGCCUGAGCAUCCUGGACACCCUGGAG
GGCGCCAGCGUGACCUCCGGCGCCACCAGCGCCGAGACCAACAG
CUACUUCGCCAAGAGCAUGGAGUUCCUGGCCAGGCCCGUGCCAG
CUCCCAGGACCGUGUUCAGGAACCCACCCCACCCAGCUCCCAGG
ACCAGGACCCCAAGCCUGGCUCCCAGCAGGGCCUGCAGCAGGAC
CAGCCUGGUGAGCACCCCACCCGGCGUGAACAGGGUGAUCACCA
GGGAGGAACUGGAGGCCCUGACACCCAGCAGGACCCCCAGCAGG
UCCGUGAGCAGGACUAGUCUGGUGUCCAACCCACCCGGCGUGAA
CAGGGUGAUCACCAGGGAGGAAUUCGAGGCCUUCGUGGCCCAGC
AACAGAGACGGUUCGACGCCGGCGCCUACAUCUUCAGCAGCGAC
ACCGGCCAGGGACACCUGCAGCAAAAGAGCGUGAGGCAGACCGU
GCUGAGCGAGGUGGUGCUGGAGAGGACCGAGCUGGAAAUCAGCU
ACGCCCCCAGGCUGGACCAGGAGAAGGAGGAACUGCUCAGGAAG
AAACUGCAGCUGAACCCCACCCCAGCCAACAGGAGCAGGUACCA
GAGCAGGAAGGUGGAGAACAUGAAGGCCAUCACCGCCAGGCGGA
UCCUGCAGGGCCUGGGACACUACCUGAAGGCCGAGGGCAAGGUG

TABLE 9-continued

| | | |
|---|---|---|
| | | GAGUGCUACAGGACCCUGCACCCCGUGCCACUGUACAGCUCCAG<br>CGUGAACAGGGCCUUCUCCAGCCCCAAGGUGGCCGUGGAGGCCU<br>GCAACGCUAUGCUGAAGGAGAACUUCCCCACCGUGGCCAGCUAC<br>UGCAUCAUCCCCGAGUACGACGCCUACCUGGACAUGGUGGACGG<br>CGCCAGCUGCUGCCUGGACACCGCCAGCUUCUGCCCCGCCAAGC<br>UGAGGAGCUUCCCCAAGAAACACAGCUACCUGGAGCCCACCAUC<br>AGGAGCGCCGUGCCCAGCGCCAUCCAGAACACCCUGCAGAACGU<br>GCUGGCCGCUGCCACCAAGAGGAACUGCAACGUGACCCAGAUGA<br>GGGAGCUGCCCGUGCUGGACAGCGCUGCCUUCAACGUGGAGUGC<br>UUCAAGAAAUACGCCUGCAACAACGAGUACUGGGAGACCUUCAA<br>GGAGAACCCCAUCAGGCUGACCGAAGAGAACGUGGUGAACUACA<br>UCACCAAGCUGAAGGGCCCCAAGGCCGCUGCCCUGUUCGCUAAG<br>ACCCACAACCUGAACAUGCUGCAGGACAUCCCAAUGGACAGGUU<br>CGUGAUGGACCUGAAGAGGGACGUGAAGGUGACACCCGGCACCA<br>AGCACACCGAGGAGAGGCCCAAGGUGCAGGUGAUCCAGGCCGCU<br>GACCCACUGGCCACCGCCUACCUGUGCGGCAUCCACAGGGAGCU<br>GGUGAGGCGGCUGAACGCCGUGCUGCUGCCCAACAUCCACACCC<br>UGUUCGACAUGAGCGCCGAGGACUUCGACGCCAUCAUCGCCGAG<br>CACUUCCAGCCCGGCGACUGCGUGCUGGAGACCGACAUCGCCAG<br>CUUCGACAAGAGCGAGGAUGACGCUAUGGCCCUGACCGCUCUGA<br>UGAUCCUGGAGGACCUGGGCGUGGACGCCGAGCUGCUCACCCUG<br>AUCGAGGCUGCCUUCGGCGAGAUCAGCUCCAUCCACCUGCCCAC<br>CAAGACCAAGUUCAAGUUCGGCGCUAUGAUGAAAAGCGGAAUGU<br>UCCUGACCCUGUUCGUGAACACCGUGAUCAACAUUGUGAUCGCC<br>AGCAGGGUGCUGCGGGAGAGGCUGACCGGCAGCCCCUGCGCUGC<br>CUUCAUCGGCGACGACAACAUCGUGAAGGGCGUGAAAAGCGACA<br>AGCUGAUGGCCGACAGGUGCGCCACCUGGCUGAACAUGGAGGUG<br>AAGAUCAUCGACGCCGUGGUGGGCGAGAAGGCCCCCUACUUCUG<br>CGGCGGAUUCAUCCUGUGCGACAGCGUGACCGGCACCGCCUGCA<br>GGGUGGCCGACCCCCUGAAGAGGCUGUUCAAGCUGGGCAAGCCA<br>CUGGCCGCUGACGAUGAGCACGACGAUGACAGGCGGAGGGCCCU<br>GCACGAGGAAAGCACCAGGUGGAACAGGGUGGGCAUCCUGAGCG<br>AGCUGUGCAAGGCCGUGGAGAGCAGGUACGAGACCGUGGGCACC<br>AGCAUCAUCGUGAUGGCUAUGACCACACUGGCCAGCUCCGUCAA<br>GAGCUUCUCCUACCUGAGGGGGGCCCCUAUAACUCUCUACGGCU<br>AACCUGAAUGGACUACGACAUAGUCUAGUCCGCCAAGGCCGCCA<br>CCAUGAGAGUGACAGCCCCUAGAACCUUACUGCUUCUGCUUUGG<br>GGAGCUGUUGCUCUGACAGAGACAUGGGCUGGAUCUUACCACAG<br>CCCCAGCUACGCCUACCACCAGUUCGAGAGGGGGGGAGGAGGCU<br>CCGGGGGAGGAGGCUCCCUGAAGAUCAGCCAGGCCGUGCACGCC<br>GCCCACGCCGAGAUCAACGAGGCCGGCCGGGAGGUGAUCGUGGG<br>CAUUGUCGCUGGCCUGGCCGUCCUCGCCGUGGUGGUGAUUGGAG<br>CUGUGGUCGCAGCUGUUAUGUGCAGAAGAAAGUCAUCCGGCGGA<br>AAGGGAGGCUCCUACUCUCAGGCUGCUUCUGCUACAGUGCCUAG<br>AGCUCUUAUGUGUUUAUCUCAGCUGUAAACUCGAGUAUGUUACG<br>UGCAAAGGUGAUUGUCACCCCCCGAAAGACCAUAUUGUGACACA<br>CCCUCAGUAUCACGCCCAAACAUUUACAGCCGCGGUGUCAAAAA<br>CCGCGUGGACGUGGUUAACAUCCCUGCUGGGAGGAUCAGCCGUA<br>AUUAUUAUAAUUGGCUUGGUGCUGGCUACUAUUGUGGCCAUGUA<br>CGUGCUGACCAACCAGAAACAUAAUUGAAUACAGCAGCAAUUGG<br>CAAGCUGCUUACAUAGAACUCGCGGCGAUUGGCAUGCCGCCUUA<br>AAAUUUUUAUUUUAUUUUUUCUUUUCUUUUCCGAAUCGGAUUUU<br>GUUUUUAAUAUUUCAAAAAAAAAAAAAAAAAAAAAAAAAUCUAG<br>AAAAAAAAAAAAAAAAAAAAAAAAAAAAAAAAAAAAAAAAAAAA<br>AAAAAAAAAAAAAAAAAAAAAAAAAAAAAAAAAAAAAAAAAAAA<br>AAAAAAAAAAAA |
| 3067 (SEQ ID NO: 107) | STARR ™ 3067 gp70-FLAG | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGGAGAGGCAUGAGCAUCCUGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGAGCUUCCCCGUGUGCACCUACGUGCCCGCCACCCUG |

TABLE 9-continued

UGCGACCAGAUGACCGGCAUCCUGGCCACCGACGUGAGCGCCGACG
ACGCCCAGAAGCUGCUCGUGGGCCUGAACCAGAGGAUCGUGGUCAA
CGGCAGGACCCAGAGGAACACCAACACAAUGAAGAACUACCUGCUG
CCCGUGGUGGCCCAGGCUUUCGCCAGGUGGGCCAAGGAGUACAAGG
AGGACCAGGAAGACGAGAGGCCCCUGGGCCUGAGGGACAGGCAGCU
GGUGAUGGGCUGCUGCUGGGCCUUCAGGCGGCACAAGAUCACCAGC
AUCUACAAGAGGCCCGACACCCAGACCAUCAUCAAGGUGAACAGCG
ACUUCCACAGCUUCGUGCUGCCCAGGAUCGGCAGCAACACCCUGGA
GAUCGGCCUGAGGACCCGGAUCAGGAAGAUGCUGGAGGAACACAAG
GAGCCCAGCCCACUGAUCACCGCCGAGGACGUGCAGGAGGCCAAGU
GCGCUGCCGACGAGGCCAAGGAGGUGAGGGAGGCCGAGGAACUGAG
GGCCGCCCUGCCACCCCUGGCUGCCGACGUGGAGGAACCCACCCUG
GAAGCCGACGUGGACCUGAUGCUGCAGGAGGCCGGCGCCGGAAGCG
UGGAGACACCCAGGGGCCUGAUCAAGGUGACCAGCUACGACGGCGA
GGACAAGAUCGGCAGCUACGCCGUGCUGAGCCCACAGGCCGUGCUG
AAGUCCGAGAAGCUGAGCUGCAUCCACCCACUGGCCGAGCAGGUGA
UCGUGAUCACCCACAGCGGCAGGAAGGGCAGGUACGCCGUGGAGCC
CUACCACGGCAAGGUGGUCGUGCCCGAGGGCCACGCCAUCCCCGUG
CAGGACUUCCAGGCCCUGAGCGAGAGCGCCACCAUCGUGUACAACG
AGAGGGAGUUCGUGAACAGGUACCUGCACCAUAUCGCCACCCACGG
CGGAGCCCUGAACACCGACGAGGAAUACUACAAGACCGUGAAGCCC
AGCGAGCACGACGGCGAGUACCUGUACGACAUCGACAGGAAGCAGU
GCGUGAAGAAAGAGCUGGUGACCGGCCUGGGACUGACCGGCGAGCU
GGUGGACCCACCCUUCCACGAGUUCGCCUACGAGAGCCUGAGGACC
AGACCCGCCGCUCCCUACCAGGUGCCCACCAUCGGCGUGUACGGCG
UGCCCGGCAGCGGAAAGAGCGGCAUCAUCAAGAGCGCCGUGACCAA
GAAAGACCUGGUGGUCAGCGCCAAGAAAGAGAACUGCGCCGAGAUC
AUCAGGGACGUGAAGAAGAUGAAAGGCCUGGACGUGAACGCGCGCA
CCGUGGACAGCGUGCUGCUGAACGGCUGCAAGCACCCCGUGGAGAC
CCUGUACAUCGACGAGGCCUUCGCUUGCCACGCCGGCACCCUGAGG
GCCCUGAUCGCCAUCAUCAGGCCCAAGAAAGCCGUGCUGUGCGGCG
ACCCCAAGCAGUGCGGCUUCUUCAACAUGAUGUGCCUGAAGGUGCA
CUUCAACCACGAGAUCUGCACCCAGGUGUUCCACAAGAGCAUCAGC
AGGCGGUGCACCAAGAGCGUGACCAGCGUCGUGAGCACCCUGUUCU
ACGACAAGAAAAUGAGGACCACCAACCCCAAGGAGACCAAAAUCGU
GAUCGACACCACAGGCAGCACCAAGCCCAAGCAGGACGACCUGAUC
CUGACCUGCUUCAGGGGCUGGGUGAAGCAGCUGCAGAUCGACUACA
AGGGCAACGAGAUCAUGACCGCCGCUGCCAGCCAGGGCCUGACCAG
GAAGGGCGUGUACGCCGUGAGGUACAAGGUGAACGAGAACCCACUG
UACGCUCCCACCAGCGAGCACGUGAACGUGCUGCUGACCAGGACCG
AGGACAGGAUCGUGUGGAAGACCCUGGCCGGCGACCCCUGGAUCAA
GACCCUGACCGCCAAGUACCCCGGCAACUUCACCGCCACCAUCGAA
GAGUGGCAGGCCGAGCACGACGCCAUCAUGAGGCACAUCCUGGAGA
GGCCCGACCCCACCGACGUGUUCCAGAACAAGGCCAACGUGUGCUG
GGCCAAGGCCCUGGUGCCCGUGCUGAAGACCGCCGGCAUCGACAUG
ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACCAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG

TABLE 9-continued

CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCCGAGUACGACGCCUACCUGGACAUGGUGGACGGCGCC
AGCUGCUGCCUGGACACCGCCAGCUUCUGCCCCGCCAAGCUGAGGA
GCUUCCCCAAGAAACACAGCUACCUGGAGCCCACCAUCAGGAGCGC
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACGUGGAGUGCUUCAAGAAAUACGC
CUGCAACAACGAGUACUGGGAGACCUUCAAGGAGAACCCCAUCAGG
CUGACCGAAGAGAACGUGGUGAACUACAUCACCAAGCUGAAGGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
GUGAAGGUGACACCCGGCACCAAGCACACCGAGGAGAGGCCCAAGG
UGCAGGUGAUCCAGGCCGCUGACCCACUGGCCACCGCCUACCUGUG
CGGCAUCCACAGGGAGCUGGUGAGGCGGCUGAACGCCGUGCUGCUG
CCCAACAUCCACACCCUGUUCGACAUGAGCGCCGAGGACUUCGACG
CCAUCAUCGCCGAGCACUUCCAGCCCGGCGACUGCGUGCUGGAGAC
CGACAUCGCCAGCUUCGACAAGAGCGAGGAUGACGCUAUGGCCCUG
ACCGCUCUGAUGAUCCUGGAGGACCUGGGCGUGGACGCCGAGCUGC
UCACCCUGAUCGAGGCUGCCUUCGGCGAGAUCAGCUCCAUCCACCU
GCCCACCAAGACCAAGUUCAAGUUCGGCGCUAUGAUGAAAAGCGGA
AUGUUCCUGACCCUGUUCGUGAACACCGUGAUCAACAUUGUGAUCG
CCAGCAGGGUGCUGCGGGAGAGGCUGACCGGCAGCCCCUGCGCUGC
CUUCAUCGGCGACGACAACAUCGUGAAGGGCGUGAAAAGCGACAAG
CUGAUGGCCGACAGGUGCGCCACCUGGCUGAACAUGGAGGUGAAGA
UCAUCGACGCCGUGGUGGGCGAGAAGGCCCCCUACUUCUGCGGCGG
AUUCAUCCUGUGCGACAGCGUGACCGGCACCGCCUGCAGGGUGGCC
GACCCCCUGAAGAGGCUGUUCAAGCUGGGCAAGCCACUGGCCGCUG
ACGAUGAGCACGACGAUGACAGGCGGAGGGCCCUGCACGAGGAAAG
CACCAGGUGGAACAGGGUGGGCAUCCUGAGCGAGCUGUGCAAGGCC
GUGGAGAGCAGGUACGAGACCGUGGGCACCAGCAUCAUCGUGAUGG
CUAUGACCACACUGGCCAGCUCCGUCAAGAGCUUCUCCUACCUGAG
GGGGGCCCCUAUAACUCUCUACGGCUAACCUGAAUGGACUACGACA
UAGUCUAGUCCGCCAAGGCCGCCACCAUGAGAGUGACAGCCCCUAG
AACCUUACUGCUUCUGCUUUGGGGAGCUGUUGCUCUGACAGAGACA
UGGGCUGGAUCUCUGAGCGAGGUGACCGGCCAGGGCCUGUGCAUCG
GCGCCGUGCCCAAGACCCACCAGGUGCUGUGCAACACCACCCAGAA
GACCAGCGACGGCAGCUACUACCUGGCCGCUCCCACCGGCACCACC
UGGGCCUGCAGCACCGGCCUGACCCCUUGCAUCAGCACCACCAUCC
UGAACCUGACCACCGACUACUGCGUGCUGGUGGAGCUGUGGCCCAG
GGUGACCUACCACAGCCCCAGCUACGCCUACCACCAGUUCGAGAGG
AGGGCCAAGUACAAGAGGGAGCCCGUGAGCCUGACCCUGGCCCUGC
UGCUGGGCGGCCUGACAAUGGGCGGCAUCGCCGCCGGCGUGGGCAC
CGGCACCACCGCCCUGGUGGCCACCCAGCAGUUCCAGCAGCUGCAG
GCCGCCAUGCACGACGACCUGAAGGAGGUGGAGAAGUCCAUCACCA
ACCUGGAGAAGUCCCUGACCAGCCUGAGCGAGGUGGUGCUGCAGAA
CAGGAGGGGCCUGGACCUGCUGUUCCUGAAGGAGGGCGGCCUGUGC
GCCGCCCUGAAGGAGGAGUGCUGCCUGUACGCCGACCACACCGGCC
UGGUGAUCGUGGGCAUUGUCGCUGGCCUGGCCGUCCUCGCCGUGGU
GGUGAUUGGAGCUGUGGUCGCAGCUGUUAUGUGCAGAAGAAAGUCA
UCCGGCGGAAAGGGAGGCUCCUACUCUCAGGCUGCUUCUGCUACAG
UGCCUAGAGCUCUUAUGUGUUUAUCUCAGCUGGGCGGCGGAGGCAG

TABLE 9-continued

| | | |
|---|---|---|
| | | CGACUACAAGGACGACGAUGACAAGUAAACUCGAGUAUGUUACGUG<br>CAAAGGUGAUUGUCACCCCCCGAAAGACCAUAUUGUGACACACCCU<br>CAGUAUCACGCCCAAACAUUUACAGCCGCGGUGUCAAAAACCGCGU<br>GGACGUGGUUAACAUCCCUGCUGGGAGGAUCAGCCGUAAUUAUUAU<br>AAUUGGCUUGGUGCUGGCUACUAUUGUGGCCAUGUACGUGCUGACC<br>AACCAGAAACAUAAUUGAAUACAGCAGCAAUUGGCAAGCUGCUUAC<br>AUAGAACUCGCGGCGAUUGGCAUGCCGCCUUAAAAUUUUUAUUUUA<br>UUUUUUCUUUUCUUUUCCGAAUCGGAUUUUGUUUUUAAUAUUUCAA<br>AAAAAAAAAAAAAAAAAAAAAAAAUCUAGAAAAAAAAAAAAAAAAAA<br>AAAAAAAAAAAAAAAAAAAAAAAAAAAAAAAAAAAAAAAAAAAAAAA<br>AAAAAAAAAAAAAAAAAAAAAAAAAAAAAAAAAAAAA |
| 3068 (SEQ ID NO: 108) | STARR ™ 3068 AH1A 5-FLAG | AUGGGCGGCGCAUGAGAGAAGCCCAGACCAAUUACCUACCCAAAAU<br>GGAGAAAGUUCACGUUGACAUCGAGGAAGACAGCCCAUUCCUCAGA<br>GCUUUGCAGCGGAGCUUCCCGCAGUUUGAGGUAGAAGCCAAGCAGG<br>UCACUGAUAAUGACCAUGCUAAUGCCAGAGCGUUUUCGCAUCUGGC<br>UUCAAAACUGAUCGAAACGGAGGUGGACCCAUCCGACACGAUCCUU<br>GACAUUGGAAGUGCGCCCGCCCGCAGAAUGUAUUCUAAGCACAAGU<br>AUCAUUGUAUCUGUCCGAUGAGAUGUGCGGAAGAUCCGGACAGAUU<br>GUAUAAGUAUGCAACUAAGCUGAAGAAAAACUGUAAGGAAAUAACU<br>GAUAAGGAAUUGGACAAGAAAAUGAAGGAGCUGGCCGCCGUCAUGA<br>GCGACCCUGACCUGGAAACUGAGACUAUGUGCCUCCACGACGACGA<br>GUCGUGUCGCUACGAAGGGCAAGUCGCUGUUUACCAGGAUGUAUAC<br>GCCGUCGACGGCCCCACCAGCCUGUACCACCAGGCCAACAAGGGCG<br>UGAGGGUGGCCUACUGGAUCGGCUUCGACACCACACCCUUCAUGUU<br>CAAGAACCUGGCCGGCGCCUACCCCAGCUACAGCACCAACUGGGCC<br>GACGAGACCGUGCUGACCGCCAGGAACAUCGGCCUGUGCAGCAGCG<br>ACGUGAUGGAGAGGAGCCGGAGAGGCAUGAGCAUCCUGAGGAAGAA<br>AUACCUGAAGCCCAGCAACAACGUGCUGUUCAGCGUGGGCAGCACC<br>AUCUACCACGAGAAGAGGGACCUGCUCAGGAGCUGGCACCUGCCCA<br>GCGUGUUCCACCUGAGGGGCAAGCAGAACUACACCUGCAGGUGCGA<br>GACCAUCGUGAGCUGCGACGGCUACGUGGUGAAGAGGAUCGCCAUC<br>AGCCCCGGCCUGUACGGCAAGCCCAGCGGCUACGCCGCUACAAUGC<br>ACAGGGAGGGCUUCCUGUGCUGCAAGGUGACCGACACCCUGAACGG<br>CGAGAGGGUGAGCUUCCCCGUGUGCACCUACGUGCCCGCCACCCUG<br>UGCGACCAGAUGACCGGCAUCCUGGCCACCGACGUGAGCGCCGACG<br>ACGCCCAGAAGCUGCUCGUGGGCCUGAACCAGAGGAUCGUGGUCAA<br>CGGCAGGACCCAGAGGAACACCAACACAAUGAAGAACUACCUGCUG<br>CCCGUGGUGGCCCAGGCUUUCGCCAGGUGGGCCAAGGAGUACAAGG<br>AGGACCAGGAAGACGAGAGGCCCCUGGGCCUGAGGGACAGGCAGCU<br>GGUGAUGGGCUGCUGCUGGGCCUUCAGGCGGCACAAGAUCACCAGC<br>AUCUACAAGAGGCCCGACACCCAGACCAUCAUCAAGGUGAACAGCG<br>ACUUCCACAGCUUCGUGCUGCCCAGGAUCGGCAGCAACACCCUGGA<br>GAUCGGCCUGAGGACCCGGAUCAGGAAGAUGCUGGAGGAACACAAG<br>GAGCCCAGCCCACUGAUCACCGCCGAGGACGUGCAGGAGGCCAAGU<br>GCGCUGCCGACGAGGCCAAGGAGGUGAGGGAGGCCGAGGAACUGAG<br>GGCCGCCCUGCCACCCCUGGCUGCCGACGUGGAGGAACCCACCCUG<br>GAAGCCGACGUGGACCUGAUGCUGCAGGAGGCCGGCGCCGGAAGCG<br>UGGAGACACCCAGGGGCCUGAUCAAGGUGACCAGCUACGACGGCGA<br>GGACAAGAUCGGCAGCUACGCCGUGCUGAGCCCACAGGCCGUGCUG<br>AAGUCCGAGAAGCUGAGCUGCAUCCACCCACUGGCCGAGCAGGUGA<br>UCGUGAUCACCCACAGCGGCAGGAAGGGCAGGUACGCCGUGGAGCC<br>CUACCACGGCAAGGUGGUCGUGCCCGAGGGCCACGCCAUCCCCGUG<br>CAGGACUUCCAGGCCCUGAGCGAGAGCGCCACCAUCGUGUACAACG<br>AGAGGGAGUUCGUGAACAGGUACCUGCACCAUAUCGCCACCCACGG<br>CGGAGCCCUGAACACCGACGAGGAAUACUACAAGACCGUGAAGCCC<br>AGCGAGCACGACGGCGAGUACCUGUACGACAUCGACAGGAAGCAGU<br>GCGUGAAGAAAGAGCUGGUGACCGGCCUGGGACUGACCGGCGAGCU<br>GGUGGACCCACCCUUCCACGAGUUCGCCUACGAGAGCCUGAGGACC<br>AGACCCGCCGCUCCCUACCAGGUGCCCACCAUCGGCGUGUACGGCG<br>UGCCCGGCAGCGGAAAGAGCGGCAUCAUCAAGAGCGCCGUGACCAA<br>GAAAGACCUGGUGGUCAGCGCCAAGAAAGAGAACUGCGCCGAGAUC<br>AUCAGGGACGUGAAGAAGAUGAAAGGCCUGGACGUGAACGCGCGCA<br>CCGUGGACAGCGUGCUGCUGAACGGCUGCAAGCACCCCGUGGAGAC<br>CCUGUACAUCGACGAGGCCUUCGCUUGCCACGCCGGCACCCUGAGG<br>GCCCUGAUCGCCAUCAUCAGGCCCAAGAAAGCCGUGCUGUGCGGCG<br>ACCCCAAGCAGUGCGGCUUCUUCAACAUGAUGUGCCUGAAGGUGCA<br>CUUCAACCACGAGAUCUGCACCCAGGUGUUCCACAAGAGCAUCAGC<br>AGGCGGUGCACCAAGAGCGUGACCAGCGUCGUGAGCACCCUGUUCU<br>ACGACAAGAAAAUGAGGACCACCAACCCCAAGGAGACCAAAAUCGU<br>GAUCGACACCACAGGCAGCACCAAGCCCAAGCAGGACGACCUGAUC<br>CUGACCUGCUUCAGGGGCUGGGUGAAGCAGCUGCAGAUCGACUACA<br>AGGGCAACGAGAUCAUGACCGCCGCUGCCAGCCAGGGCCUGACCAG<br>GAAGGGCGUGUACGCCGUGAGGUACAAGGUGAACGAGAACCCACUG<br>UACGCUCCCACCAGCGAGCACGUGAACGUGCUGCUGACCAGGACCG<br>AGGACAGGAUCGUGUGGAAGACCCUGGCCGGCGACCCCUGGAUCAA<br>GACCCUGACCGCCAAGUACCCCGGCAACUUCACCGCCACCAUCGAA<br>GAGUGGCAGGCCGAGCACGACGCCAUCAUGAGGCACAUCCUGGAGA<br>GGCCCGACCCCACCGACGUGUUCCAGAACAAGGCCAACGUGUGCUG<br>GGCCAAGGCCCUGGUGCCCGUGCUGAAGACCGCCGGCAUCGACAUG |

TABLE 9-continued

ACCACAGAGCAGUGGAACACCGUGGACUACUUCGAGACCGACAAGG
CCCACAGCGCCGAGAUCGUGCUGAACCAGCUGUGCGUGAGGUUCUU
CGGCCUGGACCUGGACAGCGGCCUGUUCAGCGCCCCCACCGUGCCA
CUGAGCAUCAGGAACAACCACUGGGACAACAGCCCCAGCCCAAACA
UGUACGGCCUGAACAAGGAGGUGGUCAGGCAGCUGAGCAGGCGGUA
CCCACAGCUGCCCAGGGCCGUGGCCACCGGCAGGGUGUACGACAUG
AACACCGGCACCCUGAGGAACUACGACCCCAGGAUCAACCUGGUGC
CCGUGAACAGGCGGCUGCCCCACGCCCUGGUGCUGCACCACAACGA
GCACCCACAGAGCGACUUCAGCUCCUUCGUGAGCAAGCUGAAAGGC
AGGACCGUGCUGGUCGUGGGCGAGAAGCUGAGCGUGCCCGGCAAGA
UGGUGGACUGGCUGAGCGACAGGCCCGAGGCCACCUUCCGGGCCAG
GCUGGACCUCGGCAUCCCCGGCGACGUGCCCAAGUACGACAUCAUC
UUCGUGAACGUCAGGACCCCAUACAAGUACCACCAUUACCAGCAGU
GCGAGGACCACGCCAUCAAGCUGAGCAUGCUGACCAAGAAGGCCUG
CCUGCACCUGAACCCCGGAGGCACCUGCGUGAGCAUCGGCUACGGC
UACGCCGACAGGGCCAGCGAGAGCAUCAUUGGCGCCAUCGCCAGGC
UGUUCAAGUUCAGCAGGGUGUGCAAACCCAAGAGCAGCCUGGAGGA
AACCGAGGUGCUGUUCGUGUUCAUCGGCUACGACCGGAAGGCCAGG
ACCCACAACCCCUACAAGCUGAGCAGCACCCUGACAAACAUCUACA
CCGGCAGCAGGCUGCACGAGGCCGGCUGCGCCCCCAGCUACCACGU
GGUCAGGGGCGAUAUCGCCACCGCCACCGAGGGCGUGAUCAUCAAC
GCUGCCAACAGCAAGGGCCAGCCCGGAGGCGGAGUGUGCGGCGCCC
UGUACAAGAAGUUCCCCGAGAGCUUCGACCUGCAGCCCAUCGAGGU
GGGCAAGGCCAGGCUGGUGAAGGGCGCCGCUAAGCACAUCAUCCAC
GCCGUGGGCCCCAACUUCAACAAGGUGAGCGAGGUGGAAGGCGACA
AGCAGCUGGCCGAAGCCUACGAGAGCAUCGCCAAGAUCGUGAACGA
CAAUAACUACAAGAGCGUGGCCAUCCCACUGCUCAGCACCGGCAUC
UUCAGCGGCAACAAGGACAGGCUGACCCAGAGCCUGAACCACCUGC
UCACCGCCCUGGACACCACCGAUGCCGACGUGGCCAUCUACUGCAG
GGACAAGAAGUGGGAGAUGACCCUGAAGGAGGCCGUGGCCAGGCGG
GAGGCCGUGGAAGAGAUCUGCAUCAGCGACGACUCCAGCGUGACCG
AGCCCGACGCCGAGCUGGUGAGGGUGCACCCCAAGAGCUCCCUGGC
CGGCAGGAAGGGCUACAGCACCAGCGACGGCAAGACCUUCAGCUAC
CUGGAGGGCACCAAGUUCCACCAGGCCGCUAAGGACAUCGCCGAGA
UCAACGCUAUGUGGCCCGUGGCCACCGAGGCCAACGAGCAGGUGUG
CAUGUACAUCCUGGGCGAGAGCAUGUCCAGCAUCAGGAGCAAGUGC
CCCGUGGAGGAAAGCGAGGCCAGCACACCACCCAGCACCCUGCCCU
GCCUGUGCAUCCACGCUAUGACACCCGAGAGGGUGCAGCGGCUGAA
GGCCAGCAGGCCCGAGCAGAUCACCGUGUGCAGCUCCUUCCCACUG
CCCAAGUACAGGAUCACCGGCGUGCAGAAGAUCCAGUGCAGCCAGC
CCAUCCUGUUCAGCCCAAAGGUGCCCGCCUACAUCCACCCCAGGAA
GUACCUGGUGGAGACCCCACCCGUGGACGAGACACCCGAGCCAAGC
GCCGAGAACCAGAGCACCGAGGGCACACCCGAGCAGCCACCCCUGA
UCACCGAGGACGAGACAAGGACCCGGACCCCAGAGCCCAUCAUUAU
CGAGGAAGAGGAAGAGGACAGCAUCAGCCUGCUGAGCGACGGCCCC
ACCCACCAGGUGCUGCAGGUGGAGGCCGACAUCCACGGCCCACCCA
GCGUGUCCAGCUCCAGCUGGAGCAUCCCACACGCCAGCGACUUCGA
CGUGGACAGCCUGAGCAUCCUGGACACCCUGGAGGGCGCCAGCGUG
ACCUCCGGCGCCACCAGCGCCGAGACCAACAGCUACUUCGCCAAGA
GCAUGGAGUUCCUGGCCAGGCCCGUGCCAGCUCCCAGGACCGUGUU
CAGGAACCCACCCCACCCAGCUCCCAGGACCAGGACCCCAAGCCUG
GCUCCCAGCAGGGCCUGCAGCAGGACCAGCCUGGUGAGCACCCCAC
CCGGCGUGAACAGGGUGAUCACCAGGGAGGAACUGGAGGCCCUGAC
ACCCAGCAGGACCCCCAGCAGGUCCGUGAGCAGGACUAGUCUGGUG
UCCAACCCACCCGGCGUGAACAGGGUGAUCACCAGGGAGGAAUUCG
AGGCCUUCGUGGCCCAGCAACAGAGACGGUUCGACGCCGGCGCCUA
CAUCUUCAGCAGCGACACCGGCCAGGGACACCUGCAGCAAAAGAGC
GUGAGGCAGACCGUGCUGAGCGAGGUGGUGCUGGAGAGGACCGAGC
UGGAAAUCAGCUACGCCCCCAGGCUGGACCAGGAGAAGGAGGAACU
GCUCAGGAAGAAACUGCAGCUGAACCCCACCCCAGCCAACAGGAGC
AGGUACCAGAGCAGGAAGGUGGAGAACAUGAAGGCCAUCACCGCCA
GGCGGAUCCUGCAGGGCCUGGGACACUACCUGAAGGCCGAGGGCAA
GGUGGAGUGCUACAGGACCCUGCACCCCGUGCCACUGUACAGCUCC
AGCGUGAACAGGGCCUUCUCCAGCCCCAAGGUGGCCGUGGAGGCCU
GCAACGCUAUGCUGAAGGAGAACUUCCCCACCGUGGCCAGCUACUG
CAUCAUCCCCGAGUACGACGCCUACCUGGACAUGGUGGACGGCGCC
AGCUGCUGCCUGGACACCGCCAGCUUCUGCCCCGCCAAGCUGAGGA
GCUUCCCCAAGAAACACAGCUACCUGGAGCCCACCAUCAGGAGCGC
CGUGCCCAGCGCCAUCCAGAACACCCUGCAGAACGUGCUGGCCGCU
GCCACCAAGAGGAACUGCAACGUGACCCAGAUGAGGGAGCUGCCCG
UGCUGGACAGCGCUGCCUUCAACGUGGAGUGCUUCAAGAAAUACGC
CUGCAACAACGAGUACUGGGAGACCUUCAAGGAGAACCCCAUCAGG
CUGACCGAAGAGAACGUGGUGAACUACAUCACCAAGCUGAAGGGCC
CCAAGGCCGCUGCCCUGUUCGCUAAGACCCACAACCUGAACAUGCU
GCAGGACAUCCCAAUGGACAGGUUCGUGAUGGACCUGAAGAGGGAC
GUGAAGGUGACACCCGGCACCAAGCACACCGAGGAGAGGCCCAAGG
UGCAGGUGAUCCAGGCCGCUGACCCACUGGCCACCGCCUACCUGUG
CGGCAUCCACAGGGAGCUGGUGAGGCGGCUGAACGCCGUGCUGCUG
CCCAACAUCCACACCCUGUUCGACAUGAGCGCCGAGGACUUCGACG
CCAUCAUCGCCGAGCACUUCCAGCCCGGCGACUGCGUGCUGGAGAC

TABLE 9-continued

| | | |
|---|---|---|
| | | CGACAUCGCCAGCUUCGACAAGAGCGAGGAUGACGCUAUGGCCCUG<br>ACCGCUCUGAUGAUCCUGGAGGACCUGGGCGUGGACGCCGAGCUGC<br>UCACCCUGAUCGAGGCUGCCUUCGGCGAGAUCAGCUCCAUCCACCU<br>GCCCACCAAGACCAAGUUCAAGUUCGGCGCUAUGAUGAAAAGCGGA<br>AUGUUCCUGACCCUGUUCGUGAACACCGUGAUCAACAUUGUGAUCG<br>CCAGCAGGGUGCUGCGGGAGAGGCUGACCGGCAGCCCCUGCGCUGC<br>CUUCAUCGGCGACGACAACAUCGUGAAGGGCGUGAAAAGCGACAAG<br>CUGAUGGCCGACAGGUGCGCCACCUGGCUGAACAUGGAGGUGAAGA<br>UCAUCGACGCCGUGGUGGGCGAGAAGGCCCCCUACUUCUGCGGCGG<br>AUUCAUCCUGUGCGACAGCGUGACCGGCACCGCCUGCAGGGUGGCC<br>GACCCCCUGAAGAGGCUGUUCAAGCUGGGCAAGCCACUGGCCGCUG<br>ACGAUGAGCACGACGAUGACAGGCGGAGGGCCCUGCACGAGGAAAG<br>CACCAGGUGGAACAGGGUGGGCAUCCUGAGCGAGCUGUGCAAGGCC<br>GUGGAGAGCAGGUACGAGACCGUGGGCACCAGCAUCAUCGUGAUGG<br>CUAUGACCACACUGGCCAGCUCCGUCAAGAGCUUCUCCUACCUGAG<br>GGGGGCCCCUAUAACUCUCUACGGCUAACCUGAAUGGACUACGACA<br>UAGUCUAGUCCGCCAAGGCCGCCACCAUGAGAGUGACAGCCCCUAG<br>AACCUUACUGCUUCUGCUUUGGGGAGCUGUUGCUCUGACAGAGACA<br>UGGGCUGGAUCUUACCACAGCCCCAGCUACGCCUACCACCAGUUCG<br>AGAGGGGGGGAGGAGGCUCCGGGGGAGGAGGCUCCCUGAAGAUCAG<br>CCAGGCCGUGCACGCCGCCCACGCCGAGAUCAACGAGGCCGGCCGG<br>GAGGUGAUCGUGGGCAUUGUCGCUGGCCUGGCCGUCCUCGCCGUGG<br>UGGUGAUUGGAGCUGUGGUCGCAGCUGUUAUGUGCAGAAGAAAGUC<br>AUCCGGCGGAAAGGGAGGCUCCUACUCUCAGGCUGCUUCUGCUACA<br>GUGCCUAGAGCUCUUAUGUGUUUAUCUCAGCUGGGCGGCGGAGGCA<br>GCGACUACAAGGACGACGAUGACAAGUAAACUCGAGUAUGUUACGU<br>GCAAAGGUGAUUGUCACCCCCCGAAAGACCAUAUUGUGACACACCC<br>UCAGUAUCACGCCCAAACAUUUACAGCCGCGGUGUCAAAAACCGCG<br>UGGACGUGGUUAACAUCCCUGCUGGGAGGAUCAGCCGUAAUUAUUA<br>UAAUUGGCUUGGUGCUGGCUACUAUUGUGGCCAUGUACGUGCUGAC<br>CAACCAGAAACAUAAUUGAAUACAGCAGCAAUUGGCAAGCUGCUUA<br>CAUAGAACUCGCGGCGAUUGGCAUGCCGCCUUAAAAUUUUUAUUUU<br>AUUUUUUCUUUUCUUUUCCGAAUCGGAUUUUGUUUUUAAUAUUUCA<br>AAAAAAAAAAAAAAAAAAAAAAAAAUCUAGAAAAAAAAAAAAAAAAA<br>AAAAAAAAAAAAAAAAAAAAAAAAAAAAAAAAAAAAAAAAAAAAAAA<br>AAAAAAAAAAAAAAAAAAAAAAAAAAAAAAAAAAAAAA |

non structural protein of SINV

| mARM # | | |
|---|---|---|
| 2842 and 2862 (SEQ ID NO: 109) | SINV nsP1-4 AA | MEKPVVNVDVDPQSPFVVQLQKSFPQFEVVAQQVTPNDHANARAFS<br>HLASKLIELEVPTTATILDIGSAPARRMFSEHQYHCVCPMRSPEDP<br>DRMMKYASKLAEKACKITNKNLHEKIKDLRTVLDTPDAETPSLCFH<br>NDVTCNMRAEYSVMQDVYINAPGTIYHQAMKGVRTLYWIGFDTTQF<br>MFSAMAGSYPAYNTNWADEKVLEARNIGLCSTKLSEGRTGKLSIMR<br>KKELKPGSRVYFSVGSTLYPEHRASLQSWHLPSVFHLNGKQSYTCR<br>CDTVVSCEGYVVKKITISPGITGETVGYAVTHNSEGFLLCKVTDTV<br>KGERVSFPVCTYIPATICDQMTGIMATDISPDDAQKLLVGLNQRIV<br>INGRTNRNTNTMQNYLLPIIAQGFSKWAKERKDDLDNEKMLGTRER<br>KLTYGCLWAFRTKKVHSFYRPPGTQTCVKVPASFSAFPMSSVWTTS<br>LPMSLRQKLKLALQPKKEEKLLQVSEELVMEAKAAFEDAQEEARAE<br>KLREALPPLVADKGIEAAAEVVCEVEGLQADIGAALVETPRGHVRI<br>IPQANDRMIGQYIVVSPNSVLKNAKLAPAHPLADQVKIITHSGRSG<br>RYAVEPYDAKVLMPAGGAVPWPEFLALSESATLVYNEREFVNRKLY<br>HIAMHGPAKNTEEEQYKVTKAELAETEYVFDVDKKRCVKKEEASGL<br>VLSGELTNPPYHELALEGLKTRPAVPYKVETIGVIGTPGSGKSAII<br>KSTVTARDLVTSGKKENCREIEADVLRLRGMQITSKTVDSVMLNGC<br>HKAVEVLYVDEAFACHAGALLALIAIVRPRKKVVLCGDPMQCGFFN<br>MMQLKVHFNHPEKDICTKTFYKYISRRCTQPVTAIVSTLHYDGKMK<br>TTNPCKKNIEIDITGATKPKPGDIILTCFRGWVKQLQIDYPGHEVM<br>TAAASQGLTRKGVYAVRQKVNENPLYAITSEHVNVLLTRTEDRLVW<br>KTLQGDPWIKQLTNIPKGNFQATIEDWEAEHKGIIAAINSPTPRAN<br>PFSCKTNVCWAKALEPILATAGIVLTGCQWSELFPQFADDKPHSAI<br>YALDVICIKFFGMDLTSGLFSKQSIPLTYHPADSARPVAHWDNSPG<br>TRKYGYDHAIAAELSRRFPVFQLAGKGTQLDLQTGRTRVISAQHNL<br>VPVNRNLPHALVPEYKEKQPGPVEKFLNQFKHHSVLVVSEEKIEAP<br>RKRIEWIAPIGIAGADKNYNLAFGFPPQARYDLVFINIGTKYRNHH<br>FQQCEDHAATLKTLSRSALNCLNPGGTLVVKSYGYADRNSEDVVTA<br>LARKFVRVSAARPDCVSSNTEMYLIFRQLDNSRTRQFTPHHLNCVI<br>SSVYEGTRDGVGAAPSYRTKRENIADCQEEAVVNAANPLGRPGEGV<br>CRAIYKRWPTSFTDSATETGTARMTVCLGKKVIHAVGPDFRKHPEA<br>EALKLLQNAYHAVADLVNEHNIKSVAIPLLSTGIYAAGKDRLEVSL<br>NCLTTALDRTDADVTIYCLDKKWKERIDAALQLKESVTELKDEDME<br>IDDELVWIHPDSCLKGRKGFSTTKGKLYSYFEGTKFHQAAKDMAEI<br>KVLFPNDQESNEQLCAYILGETMEAIREKCPVDHNPSSSPPKTLPC<br>LCMYAMTPERVHRLRSNNVKEVTVCSSTPLPKHKIKNVQKVQCTKV<br>VLFNPHTPAFVPARKYIEVPEQPTAPPAQAEEAPEVVATPSPSTAD<br>NTSLDVTDISLDMDDSSEGSLFSSFSGSDNSITSMDSWSSGPSSLE |

TABLE 9-continued

| | |
|---|---|
| | IVDRRQVVVADVHAVQEPAPIPPPRLKKMARLAAARKEPTPPASNS<br>SESLHLSFGGVSMSLGSIFDGETARQAAVQPLATGPTDVPMSFGSF<br>SDGEIDELSRRVTESEPVLFGSFEPGEVNSIISSRSAVSFPLRKQR<br>RRRRSRRTEY*LTGVGGYIFSTDTGPGHLQKKSVLQNQLTEPTLER<br>NVLERIHAPVLDTSKEEQLKLRYQMMPTEANKSRYQSRKVENQKAI<br>TTERLLSGLRLYNSATDQPECYKITYPKPLYSSSVPANYSDPQFAV<br>AVCNNYLHENYPTVASYQITDEYDAYLDMVDGTVACLDTATFCPAK<br>LRSYPKKHEYRAPNIRSAVPSAMQNTLQNVLIAATKRNCNVTQMRE<br>LPTLDSATFNVECFRKYACNDEYWEEFARKPIRITTEFVTAYVARL<br>KGPKAAALFAKTYNLVPLQEVPMDRFVMDMKRDVKVTPGTKHTEER<br>PKVQVIQAAEPLATAYICGIHRELVRRLTAVLLPNIHTLFDMSAED<br>FDAIIAEHFKQGDPVLETDIASFDKSQDDAMALTGLMILEDLGVDQ<br>PLLDLIECAFGEISSTHLPTGTRFKFGAMMKSGMFLTLFVNTVLNV<br>VIASRVLEERLKTSRCAAFIGDDNIIHGVVSDKEMAERCATWLNME<br>VKIIDAVIGERPPYFCGGFILQDSVTSTACRVADPLKRLFKLGKPL<br>PADDEQDEDRRRALLDETKAWFRVGITGTLAVAVTTRYEVDNITPV<br>LLALRTFAQSKRAFQAIRGEIKHLYGGPK |

Example 11

This example describes analysis of the immunogenicity of influenza hemagglutinin (HA) expressed from self-replicating RNA or mRNA.

Self-replicating RNA and mRNA vaccine constructs were designed to encode the full-length hemagglutinin (HA) protein from influenza virus A/California/07/2009 (H1N1) (SEQ ID NO:113 and 114). As described above for Example 1, the mRNA vaccine construct encoding HA included a tobacco etch virus (TEV) 5' UTR and a Xenopus beta-globin (Xbg) 3' UTR. Both self-replicating RNA (SEQ ID NO:56; entire RNA mARM3039) and mRNA vaccine constructs (SEQ ID NO:116; entire RNA sequence mARM3038) were encapsulated in the same lipid nanoparticle (LNP) composition that included four lipid excipients (an ionizable cationic lipid, 1,2-distearoyl-sn-glycero-3-phosphocholine (DSPC), cholesterol, and PEG2000-DMG) dispersed in HEPES buffer (pH 8.0) containing sodium chloride and the cryoprotectants sucrose and glycerol. The N:P ratio of complexing lipid and RNA was approximately 9:1. The ionizable cationic lipid had the following structure:

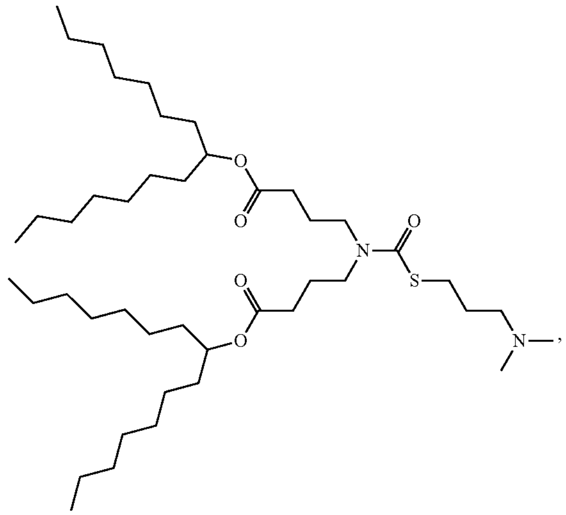 [SMILES: CCCCCCCC(CCCCCCC)OC(=O)CCCN(CCCC(=O)OC(CCCCCCC)CCCCCCC)C(=O)SCCCN(C)C]

Five female, 8-10 week old Balb/c mice were injected intramuscularly with 2 mg of mRNA or self-replicating RNA encoding HA. Mice were bled on days 14, 28, 42, and 56, followed by hemagglutination inhibition (HAI) assay using serially diluted sera. The reciprocal of the highest dilution of serum that caused inhibition of hemagglutination was considered the HAI titer, with a titer of 1/40 being protective against influenza virus infection and four-fold higher titers than baseline indicating seroconversion.

Figure 23:
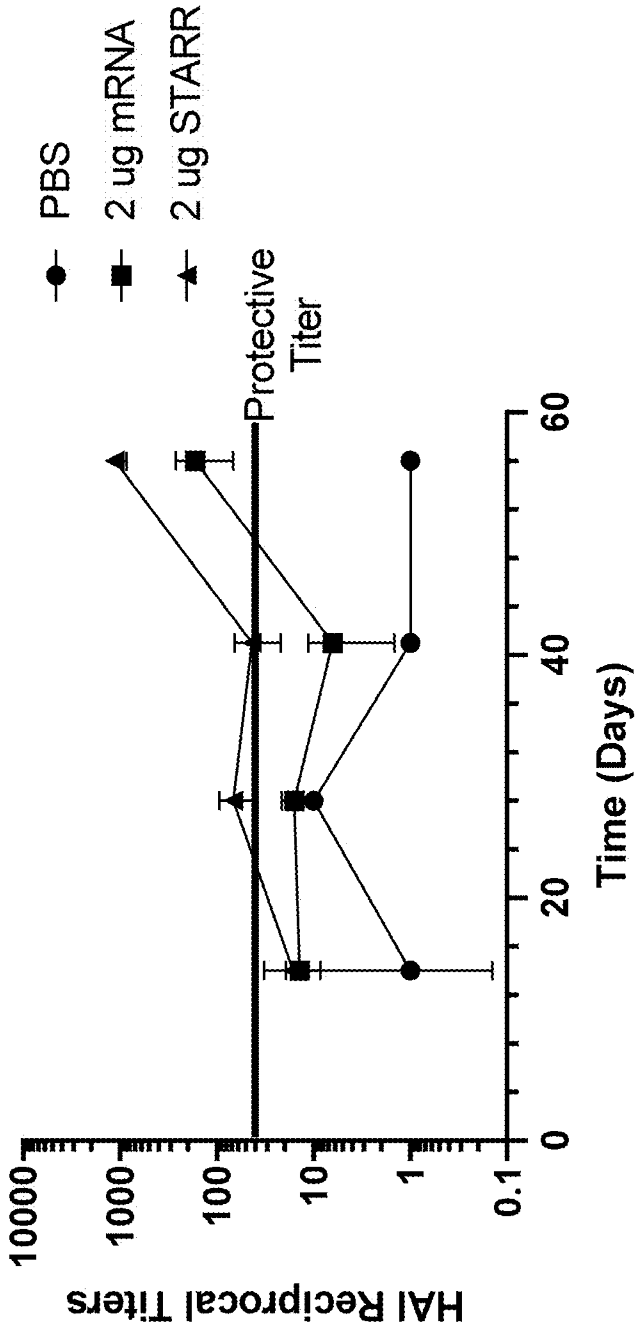
FIG. 23 shows HAI titers obtained for self-replicating RNA (STARR™) and mRNA constructs encoding the hemagglutinin of influenza virus A/California/07/2009 (H1N1).

Results in FIG. 23 show that greater HAI titers were obtained with self-replicating RNA encoding HA as compared to mRNA encoding HA. HAI titers for the self-replicating RNA construct encoding HA were greater than HAI titers for the mRNA encoding HA at all time points beginning at day 28. In addition, protective HAI titers were seen for the self-replicating RNA construct encoding HA beginning at day 28 that were maintained for at least 56 days. By contrast, mRNA encoding HA showed protective HAI titers only at day 56 that were lower than HAI titers seen for the self-replicating RNA HA construct. At all other time points, HAI titers for the mRNA construct encoding HA were below the protective titer threshold, with an HAI titer that was comparable to injection with PBS control at day 28.

These results show that the self-replicating RNA construct encoding HA elicited protective HA antibody titers, with greater HAI titers as compared to the mRNA construct encoding HA.

Example 12

This example describes dsRNA production and luciferase expression for self-replicating RNA.

Several self-replicating RNA systems from different alphaviruses were tested for expression in vitro using either green fluorescent protein (GFP) or firefly luciferase (Luc) as reporter genes. Initial transfection of cells with increasing amounts of self-replicating RNA resulted in expression of reporter genes at a lower dose compared to mRNA. However, as the amount of input self-replicating RNA increased, detectable expression of the reporter gene decreased.

Self-replicating RNA produces double stranded RNA (dsRNA) as an intermediate in the amplification process. Overproduction of dsRNA can suppress translation. To evaluate the effect of dsRNA production on transgene expression, dsRNA and the expression of reporter gene luciferase were measured simultaneously. HEK293 cells were transfected with 2 μg of replicon A (SEQ ID NO:115; entire RNA sequence mARM2826) or replicon B (SEQ ID NO:100, entire RNA sequence mARM2809) self-replicating RNA, or mRNA expressing Luc (SEQ ID NO:102, entire mRNA sequence mARM1782) using a commercial RNA transfection reagent. Untransfected cells (UTC) served as a control. dsRNA production (FIG. 24A) was quantified using immunohistochemical staining for dsRNA, followed by fluorescence quantification using a fluorescence scanner 24 hours after transfection. Luciferase expression (FIG. 24B) was assayed by measuring bioluminescence in parallel.

Figure 15A:
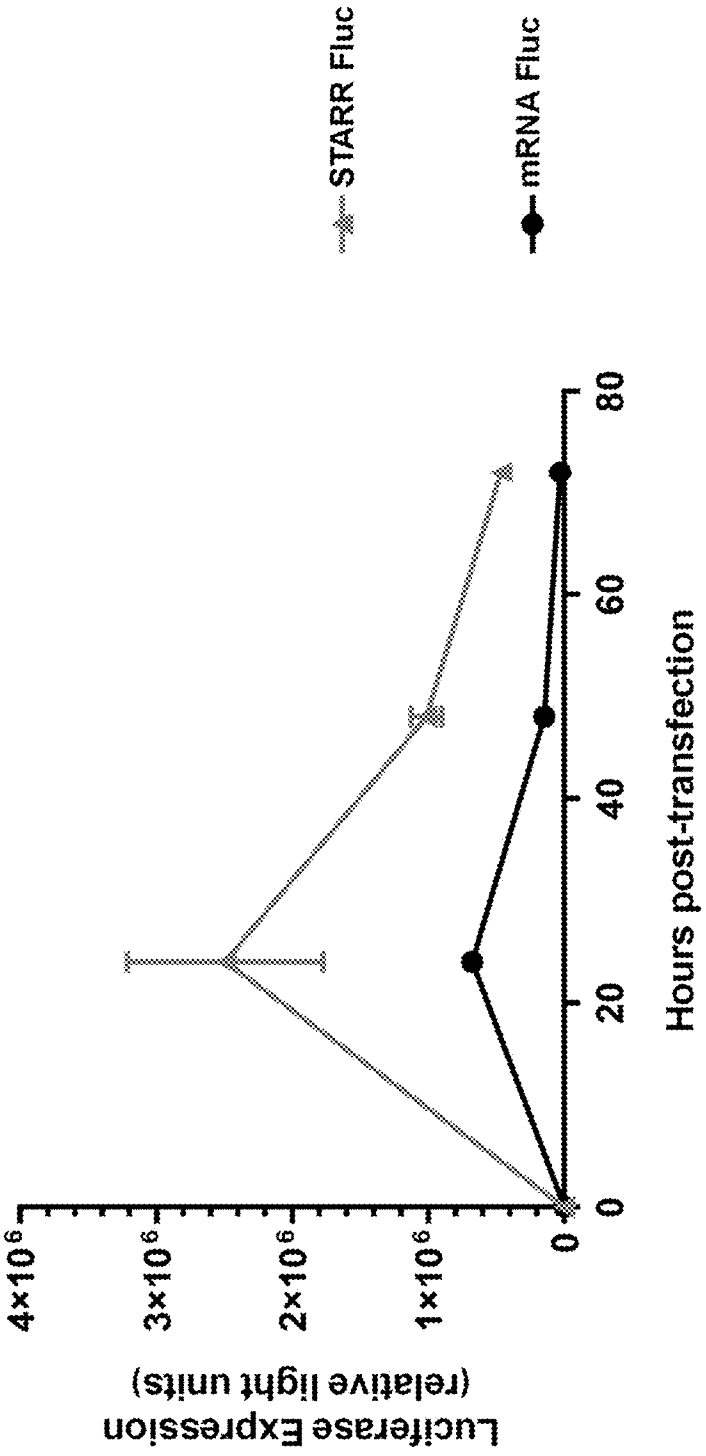
FIGS. 15A-15C show duration of luciferase reporter gene expression for self-replicating (replicon) RNA (STARR™), such as (15A) STARR™ FLuc, (15B) STARR™ FLuc IRES-E3L, and (15C) STARR™ FLuc IRES E3L (short 3' UTR) as compared to mRNA.
Figure 15B:
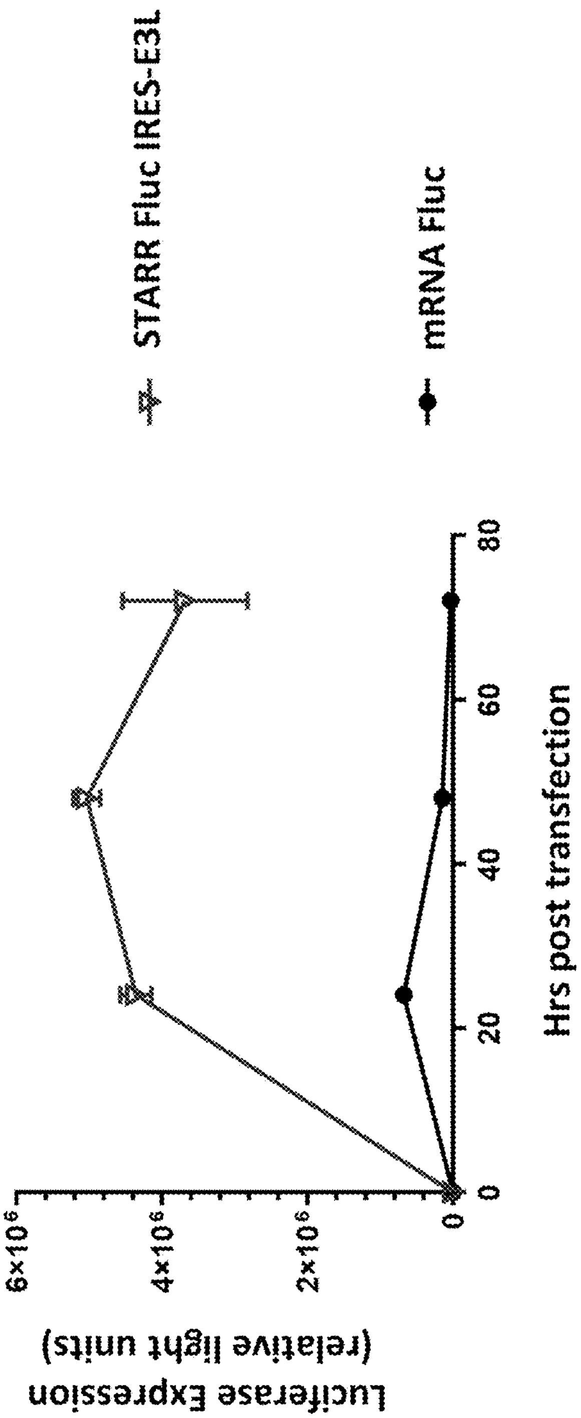
Figure 15C:
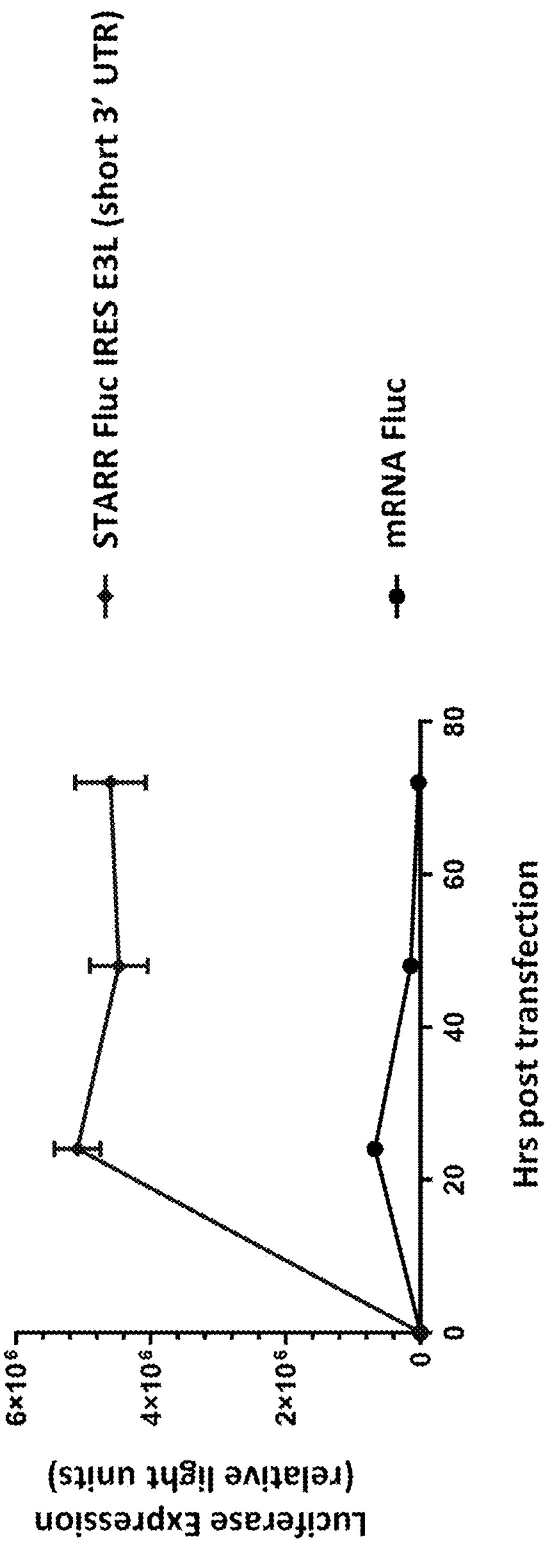
Figure 16A:
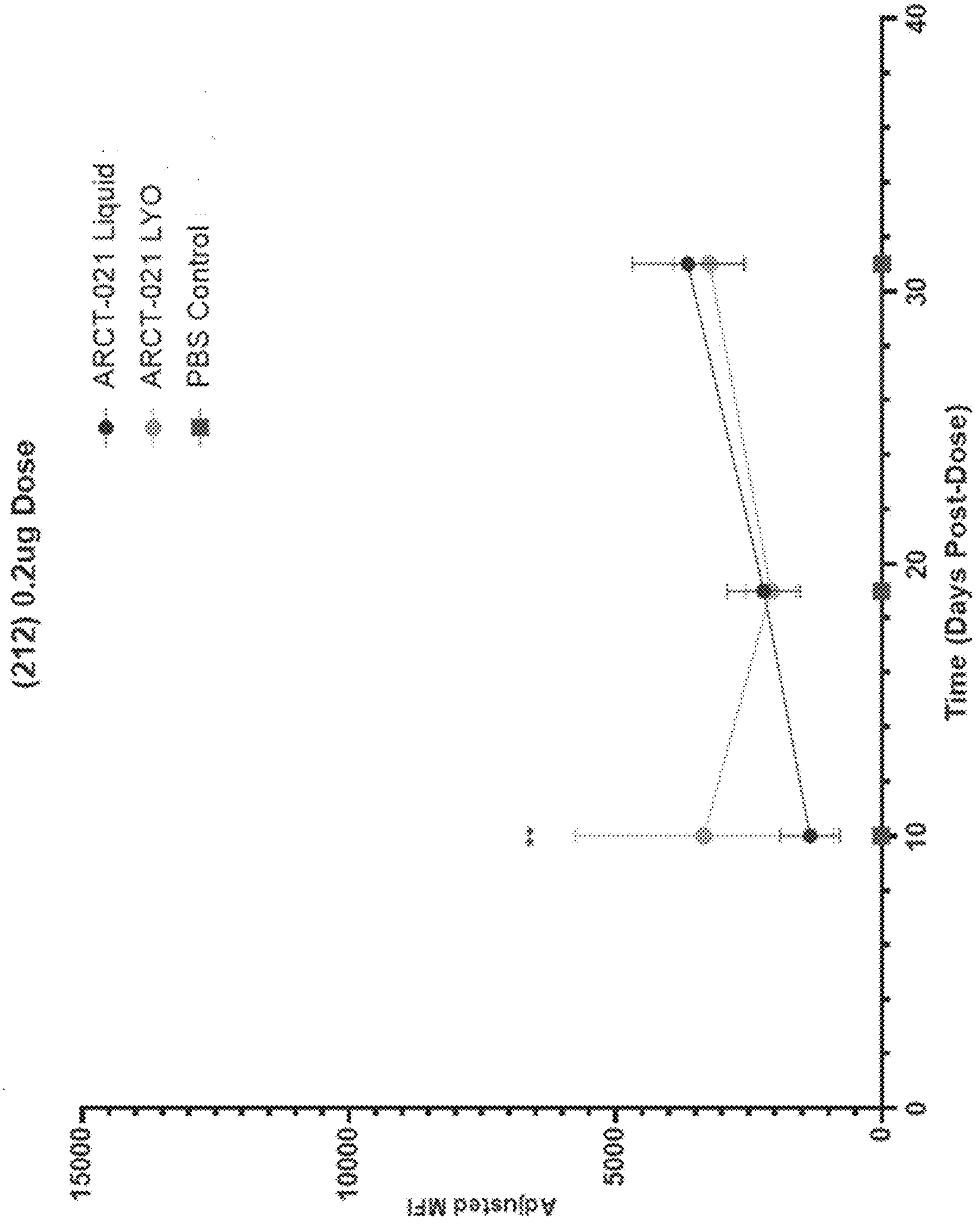
FIG. 16A-16D show results of Luminex Assay for anti-SARS-Cov-2 Spike Glycoprotein IgG in two pre-clinical studies. BALB/c mice were vaccinated with increasing RNA doses of self-replicating RNA (SEQ ID NO:125) formulated as lyophilized lipid nanoparticles (LYO-LNP) and liquid (frozen) lipid nanoparticles (Liquid-LNP). (16A) First Study 0.2 μg, (16B) First Study 2 μg, (16C) Second Study 0.2 μg, and (16D) Second Study 2 μg. Blood was collected and processed to serum at various times post-vaccination and evaluated for anti-SARS-CoV-2 spike glycoprotein IgG. Two way ANOVA, Tukey's multiple comparison post-test compared LYO-LNP to Liquid-LNP where * $p<0.0332$,  $p<0.0021$, * $p<0.0002$, **** $p<0.0001$.
Figure 16B:
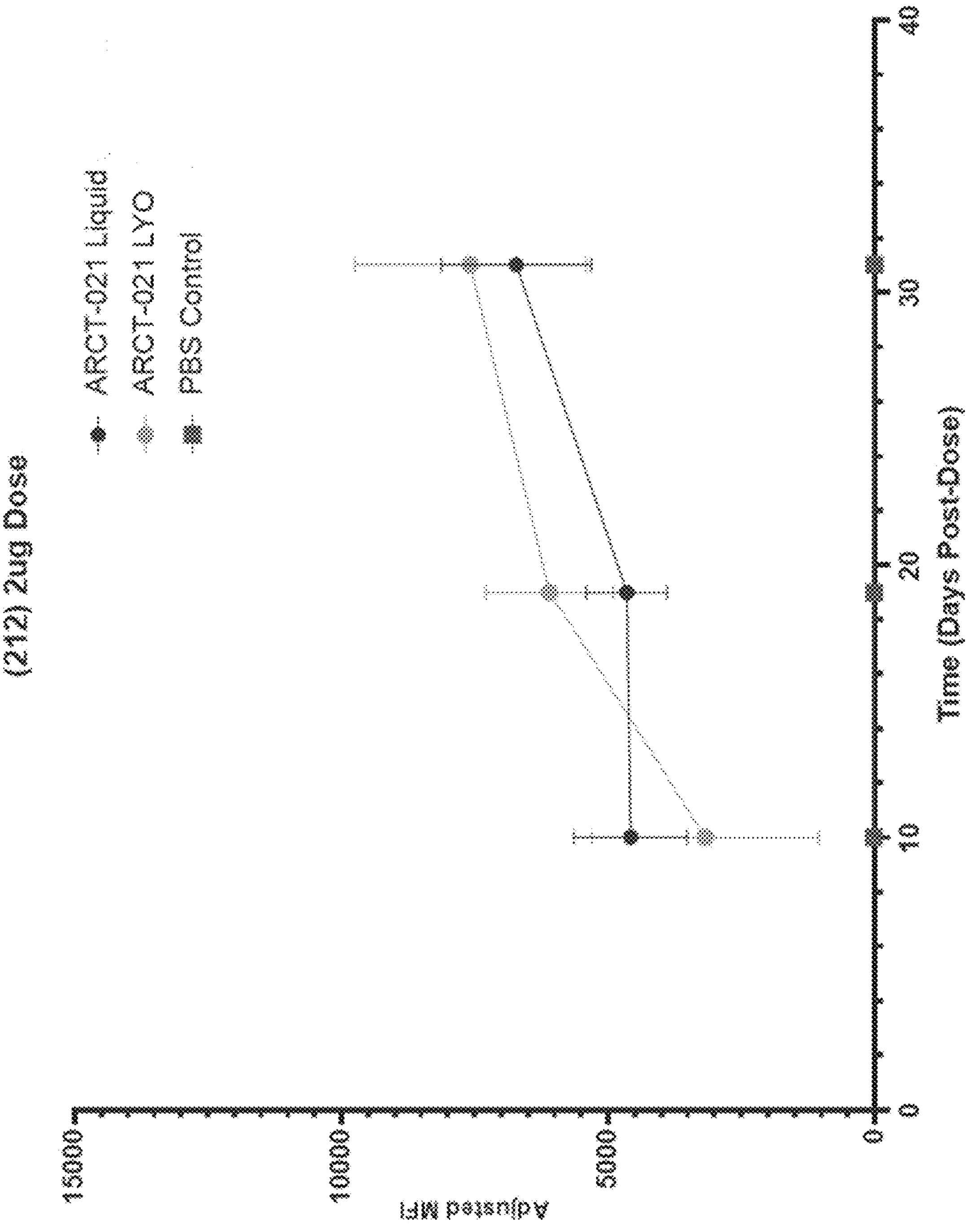
Figure 16C:
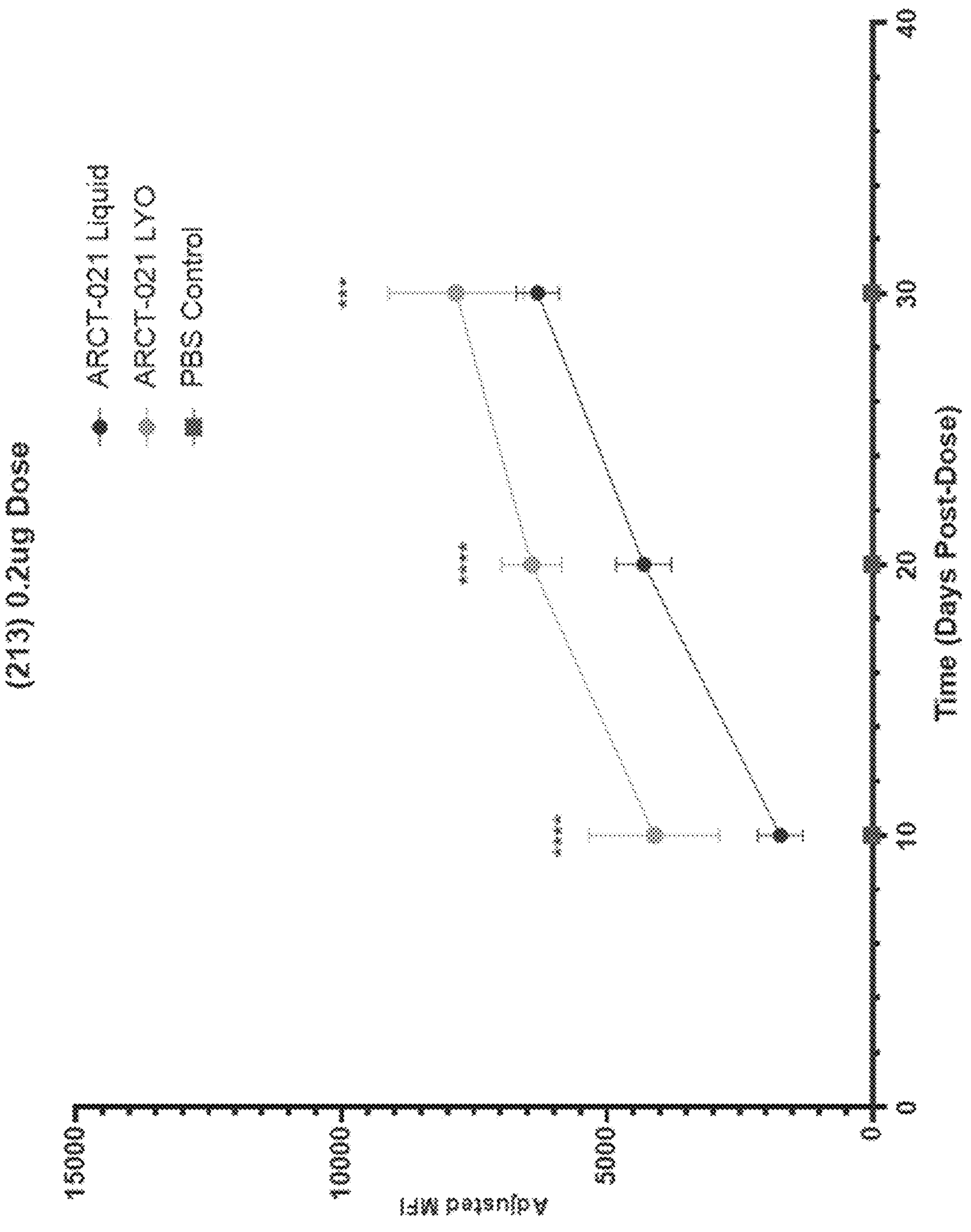
Figure 16D:
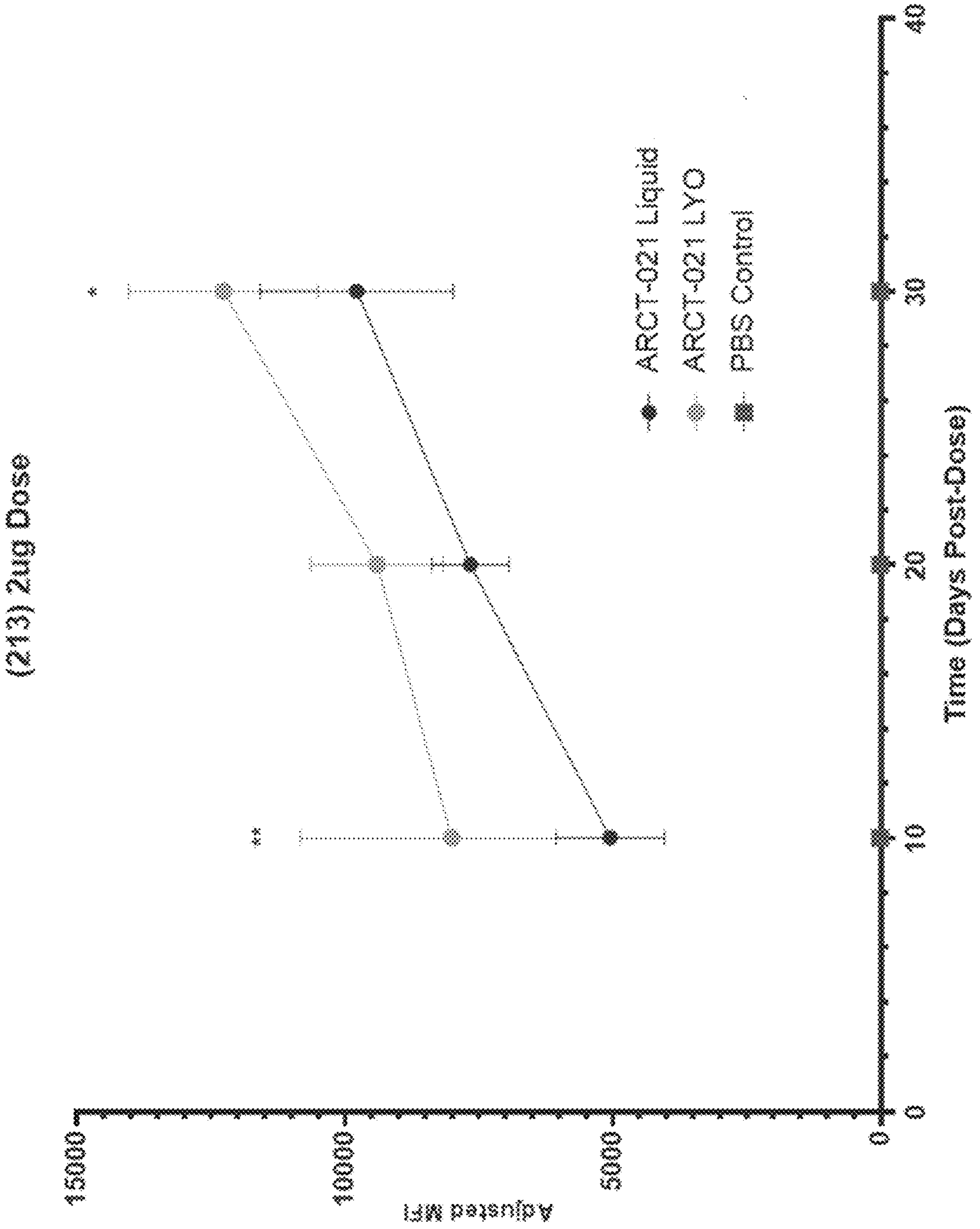
Figure 24A:
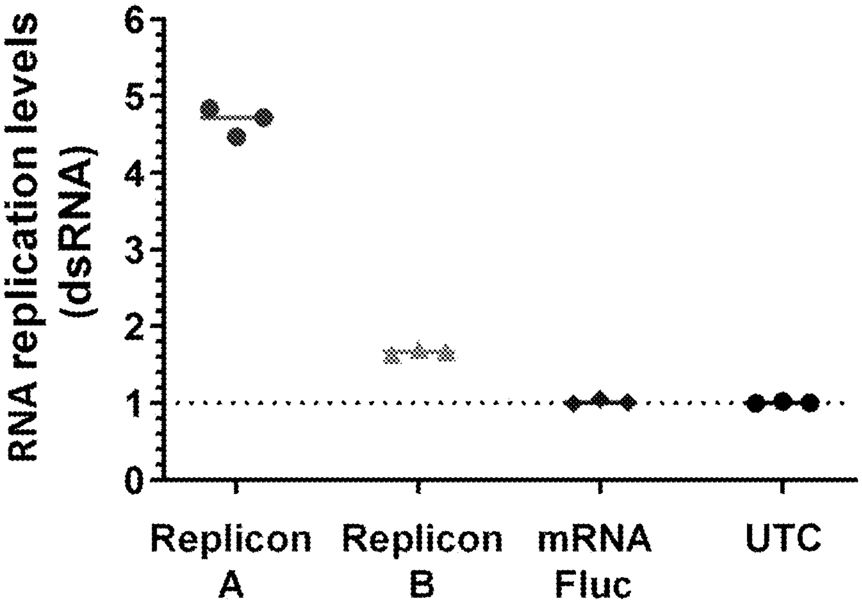
FIGS. 24A-24B show RNA replication levels (FIG. 24A) and luciferase reporter gene expression levels (FIG. 24B) for the indicated self-replicating (replicon) RNAs as compared to mRNA.
Figure 24B:
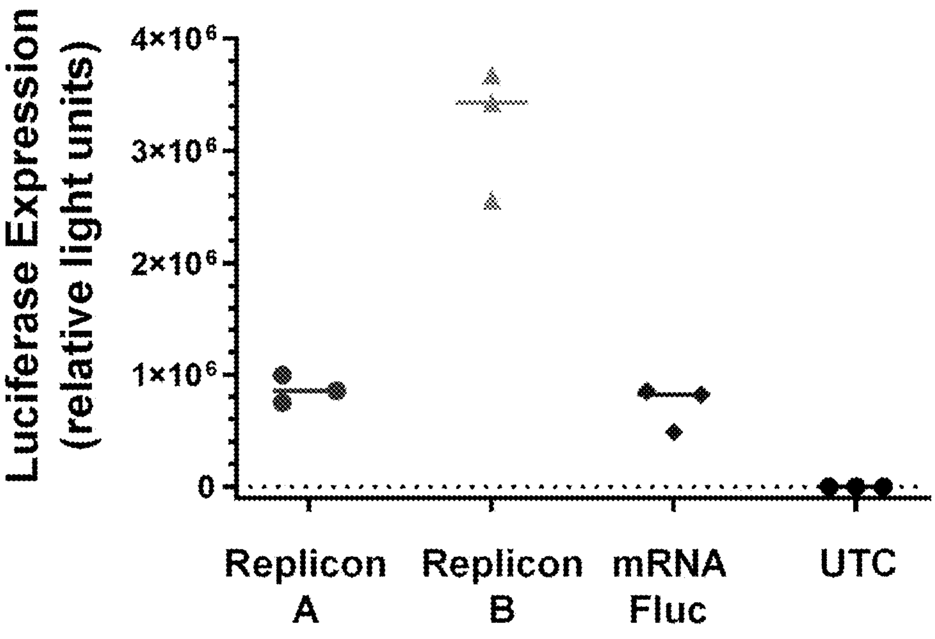

Replicon A produced a 3-fold higher level of dsRNA than replicon B 24 hrs after transfection (FIG. 24A). However, replicon B produced a 2.4-fold higher expression level of luciferase compared to replicon A. Furthermore, the level of luciferase expression from replicon A was equivalent to that observed for mRNA. Thus, even though replicon A had the ability to amplify the amount of replicon RNA and transcribed mRNA encoding luciferase, translation of the amplified mRNA was inhibited, consistent with overproduction of dsRNA inhibiting translation. Furthermore, higher levels of luciferase gene expression were seen for replicon RNA as compared to mRNA at 24, 48, and 72 hours after transfection of HEK293 cells (FIG. 15A). Self-replicating RNA with an expression cassette that included a luciferase reporter gene followed by an IRES and E3L also showed robust luciferase expression (FIGS. 15B, 15C; SEQ ID NOs: 128 and 129). Luciferase expression was also seen for a self-replicating RNA that expressed E3L from a first subgenomic promoter and a luciferase reporter gene from a second subgenomic promoter located 3' of the E3L open reading frame (not shown). Thus, not only did replicon RNA produce higher levels of luciferase gene expression compared to mRNA, but replicon RNA also showed increased duration of expression over a 72-hr period.

Example 13

This example describes immunogenicity of liquid and lyophilized self-replicating RNA formulations. Immunogenicity of self-replicating RNA (SEQ ID NO: 125) formulated as a lyophilized lipid nanoparticle (LYO-LNP) was tested in BALB/c mice in two separate preclinical studies and compared with the liquid (frozen) LNP formulation (Liquid-LNP). Each study included the use of a PBS dosing group as a negative control and a Liquid dosing group (Liquid-LNP) as a positive control. Both LYO-LNP and Liquid-LNP formulations were dosed at 0.2 and 2 μg. There were n=5 animals per dose group in each study. Test formulations were administered intramuscularly (IM) and serum was collected at various timepoints (Days 10, 19, 31 for the first study and Days 10, 20, 30 for the second study) post-immunization to measure the production of anti-SARS-CoV-2 spike protein IgG using a Luminex bead fluorescent assay.

Figure 17A:
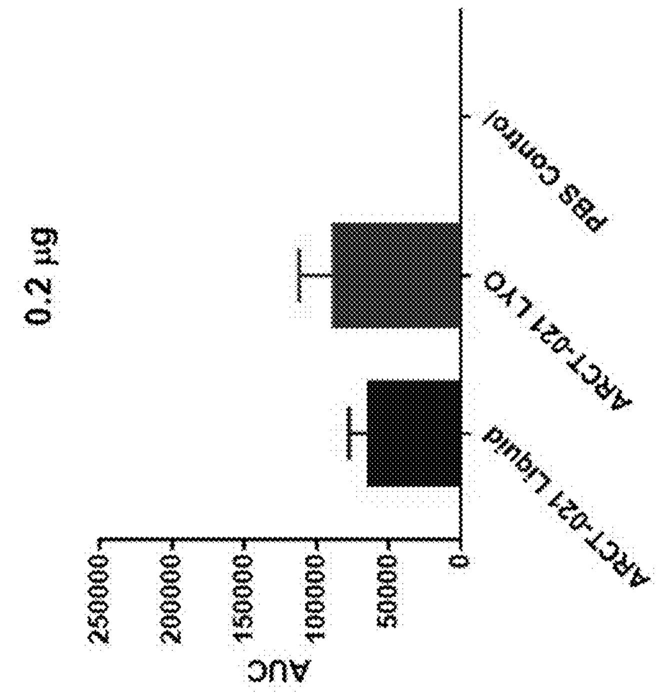
FIGS. 17A-17B show the Area Under the Curve (AUC) Analysis for anti-SARS-Cov-2 Spike Glycoprotein IgG (First and Second Study combined data). IgG assay results were combined from two studies to evaluate self-replicating RNA (SEQ ID NO:125) formulated as lyophilized lipid nanoparticles (LYO-LNP) and liquid (frozen) lipid nanoparticles (Liquid-LNP) at (17A) 0.2 μg, and (17B) 2 μg. N=10/group. First Study Day 19 and 31 results were combined with Second Study Day 20 and 30 results, respectively, and an Area Under the Curve (AUC) analysis was performed. One way ANOVA, Sidak's multiple comparison post-test compared LYO-LNP to Liquid-LNP and resulted in no statistical differences.
Figure 17B:
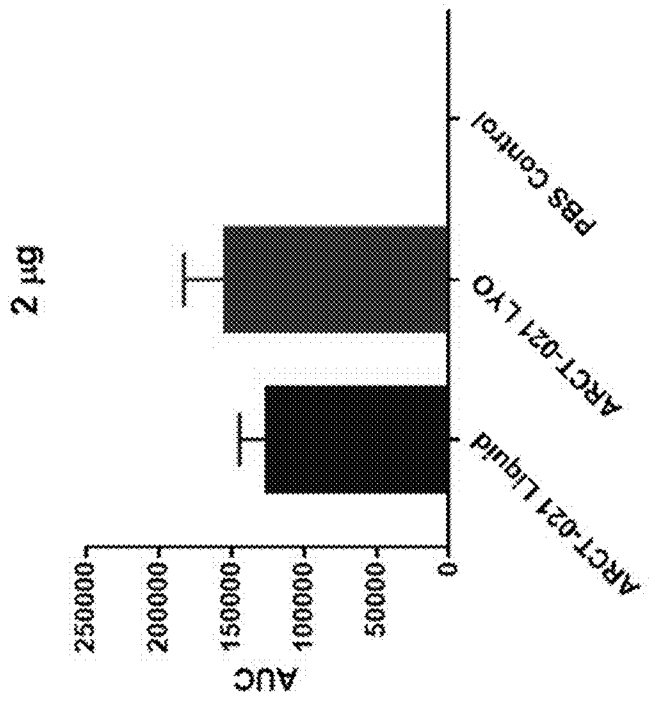

In both studies, anti-SARS-CoV-2 spike protein IgGs were detected in serum in a time- and dose-dependent manner for both Liquid-LNP and LYO-LNP formulations, whereas PBS injection did not elicit an immunogenic response (FIG. 16A-16D). There was no statistical difference in immunogenicity seen between Liquid-LNP and LYO-LNP dose groups in the first study, whereas LYO-LNP produced statistically different and greater IgG than Liquid-LNP in the second study. Without being limited by theory, under-powering (n=5/group) of these two separate studies may have contributed to the statistical differences in immunogenicity results observed in the two studies. In combining the results of both studies, no statistically significant differences were observed between Liquid-LNP and LYO-LNP formulations at the 0.2 and 2 μg dose levels (FIG. 17A, 17B). Taken together, the results of these studies demonstrate that the immunogenicity of the liquid and lyophilized formulations were comparable.

In summary, the liquid and lyophilized formulations of the self-replicating RNA vaccine (SEQ ID NO:125) showed comparable immunogenicity. The vaccine can induce effective, adaptive humoral (neutralizing antibodies) and cellular (CD8+) immune responses targeting the SARS-CoV-2 S glycoprotein. The vaccine also elicits induction of anti-spike glycoprotein antibodies (IgG) levels that are higher than a conventional mRNA vaccine and also induces production of IgG antibodies at a faster rate than a conventional mRNA vaccine. It continues to produce increasing levels of IgG up to 50 days post vaccination whereas the conventional mRNA vaccine plateaus by day 10 post vaccination. It produces an RNA dose-dependent increase in CD8+ T lymphocytes and a balanced, Th1 dominant CD4+ T helper cell immune response with no skew towards a Th2 response.

Any and all references and citations to other documents, such as patents, patent applications, patent publications, journals, books, papers, web contents, that have been made throughout this disclosure are hereby incorporated herein in their entirety for all purposes.

Although the invention has been described with reference to the above examples, it will be understood that modifications and variations are encompassed within the spirit and scope of the invention. Accordingly, the invention is limited only by the following claims.

Example 14

Lyophilization of Self-Replicating RNA-Lipid Nanoparticle Formulation Materials and Methods Generally The processes conducted in this example were conducted using lipid nanoparticle compositions that were manufactured according to well-known processes, for example, those described in U.S. application Ser. No. 16/823,212, the contents of which are incorporated by reference for the specific purpose of teaching lipid nanoparticle manufacturing processes. The lipid nanoparticle compositions and the lyophilized products were characterized for several properties. The materials and methods for these characterization processes as well as a general method of manufacturing the lipid nanoparticle compositions that were used for lyophilization experiments are provided in this example.

Lipid Nanoparticle Manufacture

Lipid nanoparticle formulations used in this example were manufactured by mixing lipids (ionizable cationic lipid (ATX-126):helper lipid:cholesterol:PEG-lipid) in ethanol with RNA dissolved in citrate buffer. The mixed material was instantaneously diluted with Phosphate Buffer. Ethanol was removed by dialysis against phosphate buffer using regenerated cellulose membrane (100 kD MWCO) or by tangential flow filtration (TFF) using modified polyethersulfone (mPES) hollow fiber membranes (100 kD MWCO). Once the ethanol was completely removed, the buffer was exchanged with HEPES (4-(2-hydroxyethyl)-1-piperazineethanesulfonic acid) buffer containing 10-300 (for example, 40-60) mM NaCl and 5-15% sucrose, pH 7.3. The formulation was concentrated followed by 0.2 μm filtration using PES filters. The RNA concentration in the formulation was then measured by RiboGreen fluorimetric assay, and the concentration was adjusted to a final desired concentration by diluting with HEPES buffer containing 10-100 (for example 40-60) mM NaCl, 0-15% sucrose, pH 7.2-8.5 containing glycerol. If not used immediately for further studies, the final formulation was then filtered through a 0.2 μm filter and filled into glass vials, stoppered, capped and placed at −70±5° C. The lipid nanoparticles formulations were characterized for their pH and osmolality. Lipid Content and RNA content were measured by high performance liquid chromatography (HPLC), and mRNA integrity by was measured by fragment analyzer.

Dynamic Light Scattering (DLS)

The average particle size (z) and polydispersity index (PDI) of lipid nanoparticle formulations used in the Examples was measured by dynamic light scattering on a Malvern Zetasizer Nano ZS (United Kingdom).

RiboGreen Assay

The encapsulation efficiency of the lipid nanoparticle formulations was characterized using the RiboGreen fluorometric assay. RiboGreen is a proprietary fluorescent dye (Molecular Probes/Invitrogen a division of Life Technologies, now part of Thermo Fisher Scientific of Eugene, Oregon, United States) that is used in the detection and quantification of nucleic acids, including both RNA and DNA. In its free form, RiboGreen exhibits little fluorescence and possesses a negligible absorbance signature. When bound to nucleic acids, the dye fluoresces with an intensity that is several orders of magnitude greater than the unbound form. The fluorescence can be then be detected by a sensor (fluorimeter) and the nucleic acid can be quantified.

Lyophilization Process

Self-Replicating RNAs (aka Replicon RNA) are typically larger than the average mRNA, and tests were designed to determine whether self-replicating RNA lipid nanoparticle formulations could be successfully lyophilized. The quality of lyophilized lipid nanoparticle formulations was assessed by analyzing the formulations post-lyophilization and comparing this to the lipid nanoparticle formulation prior to lyophilization as well as after a conventional freeze/thaw cycle (i.e., frozen at ~−70° C. then allowed to thaw at room temperature).

The analysis of the lipid nanoparticle formulations included the analysis of particle size and polydispersity (PDI) and encapsulation efficiency (% Encap). The particle size post-lyophilization was compared to the particle size pre-lyophilization and the difference can be reported as a delta (6). The various compositions tested were screened as to whether a threshold of properties was met including minimal particle size increase (6<10 nm), the maintenance of PDI (<0.2), and maintenance of high encapsulation efficiency (>85%).

The lipid nanoparticle formulations were prepared as described above, with self-replicating RNA (SEQ ID NO: 125). The resulting lipid nanoparticle formulation was then processed with a buffer exchange to form a prelyophilization suspension having a concentration of 0.05 to 2.0 mg/mL self-replicating RNA, 0.01 to 0.05 M potassium sorbate, 0.01 to 0.10% w/v Poloxamer 188 (Kolliphor®), 14 to 18% w/v sucrose, 25 to 75 mM NaCl, and 15 to 25 mM pH 8.0 Tris buffer. The prelyophilization formulation was then lyophilized in a Millrock Revo Freeze Dryer (Model No. RV85S4), using aliquots of 2.0 mL of suspension and the lyophilization cycle provided in Table 10 below. The lyophilized formulations of this example were then applied to the studies of Example 13 above as "LYO-LNP".

TABLE 10

Lyophilization Cycle for Self-Replicating RNA-Lipid Nanoparticle Formulation
Freeze drying cycle

| Step | shelf temperature (° C., ±2° C.) | step duration (h:min) | chamber vacuum (mbar) |
|---|---|---|---|
| Initial Freezing | −50 | 4:00 | atmosphere |
| Evacuation | −50 | 00:30-01:45 | from atmosph. pressure to 0.05 |
| Primary drying (ramp down) | −50 → 0 | 63:00 | 0.05 |
| Secondary drying (ramp up) | 0 → +25 | 39:30 | 0.05 |
| Backfill with $N_2$ and stoppering | 25 | 00:10-00:20 | 700 ± 50 |
| Aeration with air | 5 | 00:10-00:20 | atmosphere |

The lyophilized particles prepared following the methods described above were reconstituted in 2 mL of water and characterized using DLS and RiboGreen. The results provided in Table 11 below show that the lyophilized compositions were found to produce lyophilized lipid nanoparticle formulations with adequate size, polydispersity, and delta values (~5.3 nm) upon reconstitution.

TABLE 11

Self-Replicating RNA-Lipid Nanoparticle Characteristics
Pre- and Post-LYO

| | Average Particle Size (nm) | PDI | encap (%) |
|---|---|---|---|
| Pre-LYO | 76.3 | 0.129 | 97 |
| Post-LYO | 81.6 | 0.152 | 93 |

What is claimed is:

1. A nucleic acid molecule comprising:

(i) a first polynucleotide encoding one or more viral replication proteins, wherein the first polynucleotide is codon-optimized as compared to a wild-type polynucleotide encoding the one or more viral replication proteins, and wherein the first polynucleotide comprises a sequence having at least 80% identity to the sequence of SEQ ID NO:72; and (ii) a second polynucleotide comprising a transgene encoding an antigenic protein or a fragment thereof, wherein the antigenic protein is a coronavirus protein encoded by a sequence having at least 90% identity to the sequence of SEQ ID NO: 122.

2. The nucleic acid molecule of claim 1, further comprising a 5' untranslated region (UTR), wherein the 5' UTR comprises an alphavirus 5' UTR sequence.

3. The nucleic acid molecule of claim 2, wherein the 5' UTR comprises a sequence of SEQ ID NO:73, SEQ ID NO:74, or SEQ ID NO:75.

4. The nucleic acid molecule of claim 1, further comprising a 3' untranslated region (UTR), wherein the 3' UTR comprises an alphavirus 3' UTR sequence.

5. The nucleic acid molecule of claim 4, wherein the 3' UTR comprises a poly-A sequence.

6. The nucleic acid molecule of claim 1, wherein the first polynucleotide is located 5' of the second polynucleotide.

7. The nucleic acid molecule of claim 6, further comprising an intergenic region located between the first polynucleotide and the second polynucleotide.

8. The nucleic acid molecule of claim 7, wherein the intergenic region comprises a sequence having at least 85% identity to a sequence of SEQ ID NO:77.

9. The nucleic acid molecule of claim 1, wherein the nucleic acid molecule is (a) a DNA molecule; or (b) an RNA molecule, wherein T is substituted with U.

10. The nucleic acid molecule of claim 9, wherein the DNA molecule further comprises a promoter located 5' of the 5' UTR, wherein the promoter is a T7 promoter, a T3 promoter, or an SP6 promoter.

11. The nucleic acid molecule of claim 9, wherein the RNA molecule is a self-replicating RNA molecule.

12. The nucleic acid molecule of claim 9, wherein the RNA molecule further comprises a 5' cap having a Cap 1 structure, a Cap 1 ($^{m6}$A) structure, a Cap 2 structure, or a Cap 0 structure.

13. A composition comprising the nucleic acid molecule of claim 1 and a lipid formulation selected from a lipoplex, a liposome, a lipid nanoparticle, a polymer-based carrier, an exosome, a lamellar body, a micelle, and an emulsion.

14. The composition of claim 13, wherein the lipid formulation is a lipid nanoparticle.

15. The composition of claim 13, wherein the lipid formulation comprises an ionizable cationic lipid.

16. The composition of claim 15, wherein the ionizable cationic lipid has a structure of Formula I:

(I)

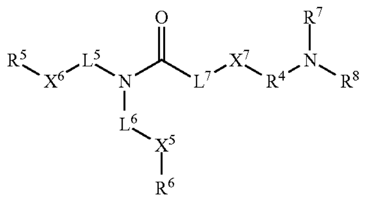

or a pharmaceutically acceptable salt or solvate thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl; $L^5$ and $L^6$ are each independently selected from the group consisting of a linear $C_1$-$C_{20}$ alkyl and $C_2$-$C_{20}$ alkenyl; X5 is —C(O)O—, whereby —C(O)O—R6 is formed or —OC(O)— whereby —OC(O)—$R^6$ is formed; $X^6$ is —C(O)O— whereby —C(O)O—$R^5$ is formed or —OC(O)— whereby —OC(O)—$R^5$ is formed; $X^7$ is S or O; $L^7$ is absent or lower alkyl; $R^4$ is a linear or branched $C_1$-$C_6$ alkyl; and $R^7$ and $R^8$ are each independently selected from the group consisting of a hydrogen and a linear or branched $C_1$-$C_6$ alkyl.

17. The composition of claim 15, wherein the ionizable cationic lipid has a structure of:

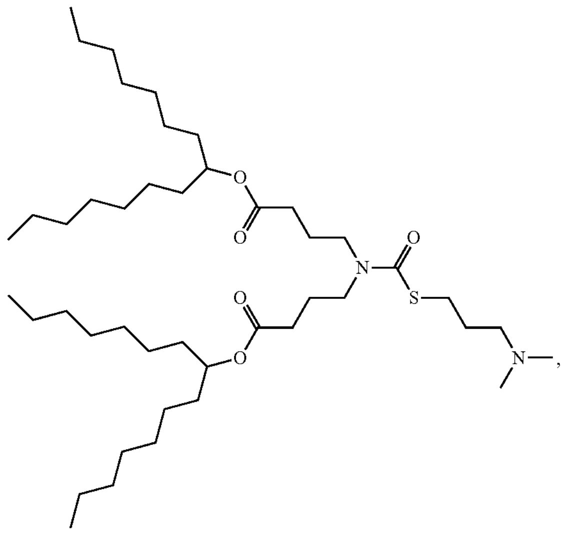

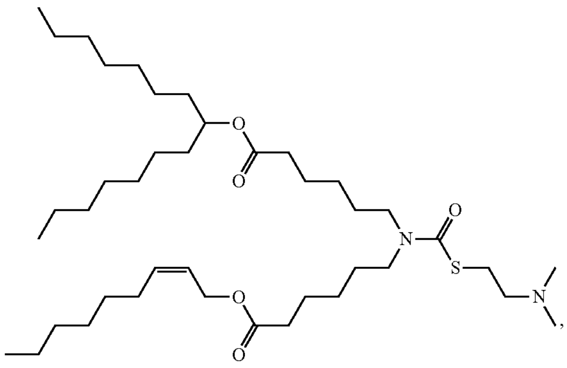

-continued

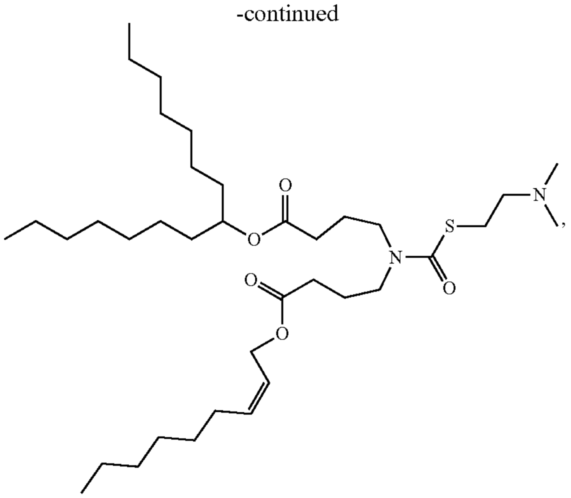

or a pharmaceutically acceptable salt thereof.

18. The composition of claim 13, wherein the lipid formulation encapsulates the nucleic acid molecule or is complexed to the nucleic acid molecule.

19. The composition of claim 13, wherein the lipid formulation comprises (a) a helper lipid;

(b) a phospholipid;

(c) a polyethylene glycol (PEG)-lipid conjugate; or (d) any combination thereof.

20. The composition of claim 19, wherein the phospholipid is selected from dioleoylphosphatidyl ethanolamine (DOPE), dimyristoylphosphatidyl choline (DMPC), distearoylphosphatidyl choline (DSPC), dimyristoylphosphatidyl glycerol (DMPG), dipalmitoyl phosphatidylcholine (DPPC), and phosphatidylcholine (PC).

21. The composition of claim 13, wherein the lipid portion of the lipid formulation comprises about 40 mol % to about 60 mol % of the ionizable cationic lipid, about 4 mol % to about 16 mol % DSPC, about 30 mol % to about 47 mol % cholesterol, and about 0.5 mol % to about 3 mol % PEG2000-DMG.

22. The composition of claim 13, wherein the composition has a total lipid: nucleic acid molecule weight ratio of about 50:1 to about 10:1.

23. The composition of claim 13, wherein the composition comprises (a) a HEPES or TRIS buffer at a pH of about 7.0 to about 8.5;

(b) a HEPES or TRIS buffer at a concentration of about 7 mg/mL to about 15 mg/ml;

(c) about 2.0 mg/mL to about 4.0 mg/mL of NaCl;

(d) one or more cryoprotectants;

(e) one or more cryoprotectants selected from sucrose, glycerol, or a combination of sucrose and glycerol; or (f) any combination thereof.

24. The composition of claim 13, wherein the composition is a lyophilized composition.

25. The composition of claim 24, wherein the lyophilized composition comprises one or more lyoprotectants.

26. The composition of claim 24, wherein the lyophilized composition comprises a poloxamer, potassium sorbate, sucrose, or any combination thereof.

27. The composition of claim 24, wherein the lyophilized composition comprises (a) about 0.01 to about 1.0% w/w of the nucleic acid molecule;

(b) about 1.0 to about 5.0% w/w lipids;

(c) about 0.5 to about 2.5% w/w of TRIS buffer;

(d) about 0.75 to about 2.75% w/w of NaCl;

(e) about 85 to about 95% w/w of a sugar;

(f) about 0.01 to about 1.0% w/w of a poloxamer;

(g) about 1.0 to about 5.0% w/w of potassium sorbate; or (h) any combination thereof.

28. A method of administering the composition of claim 13 to a subject in need thereof, wherein the composition is lyophilized and is reconstituted prior to administration.

29. A method of preventing or ameliorating COVID-19, comprising administering the composition of claim 13 to a subject in need thereof.

30. A method of administering a booster dose to a vaccinated subject, comprising administering the composition of claim 13 to a subject who was previously vaccinated against coronavirus.

31. The method of claim 29, wherein the composition is administered at a dosage of about 0.01 ug to about 1,000 ug of nucleic acid.

32. A method of inducing an immune response against a coronavirus in a subject comprising:

administering to the subject an effective amount of a nucleic acid molecule of claim 1.

33. A method of inducing an immune response against a coronavirus in a subject comprising:

administering to the subject an effective amount of a composition of claim 13.

* * * * *